United States Patent
Li et al.

(10) Patent No.: US 11,597,701 B2
(45) Date of Patent: Mar. 7, 2023

(54) INTEGRIN LIGANDS AND USES THEREOF

(71) Applicant: Arrowhead Pharmaceuticals, Inc., Pasadena, CA (US)

(72) Inventors: Zhen Li, Westfield, NJ (US); Xiaokai Li, Middleton, WI (US); Erik W. Bush, Verona, WI (US); Rui Zhu, San Diego, CA (US); Dongxu Shu, Madison, WI (US); Jonathan Benson, Stoughton, WI (US); Patrick Shao, Fanwood, NJ (US); Matthew Fowler-Watters, Madison, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 16/759,610

(22) PCT Filed: Oct. 31, 2018

(86) PCT No.: PCT/US2018/058471
§ 371 (c)(1),
(2) Date: Apr. 27, 2020

(87) PCT Pub. No.: WO2019/089765
PCT Pub. Date: May 9, 2019

(65) Prior Publication Data
US 2020/0369613 A1 Nov. 26, 2020

Related U.S. Application Data

(60) Provisional application No. 62/679,549, filed on Jun. 1, 2018, provisional application No. 62/646,739, filed on Mar. 22, 2018, provisional application No. 62/580,398, filed on Nov. 1, 2017.

(51) Int. Cl.
| | | |
|---|---|---|
| *C07H 21/04* | (2006.01) | |
| *C07D 213/74* | (2006.01) | |
| *C07D 409/12* | (2006.01) | |
| *C07D 413/12* | (2006.01) | |
| *A61K 47/54* | (2017.01) | |
| *A61K 47/56* | (2017.01) | |
| *A61K 47/60* | (2017.01) | |
| *C12N 15/11* | (2006.01) | |
| *C12N 15/113* | (2010.01) | |

(52) U.S. Cl.
CPC .......... *C07D 213/74* (2013.01); *A61K 47/545* (2017.08); *A61K 47/56* (2017.08); *A61K 47/60* (2017.08); *C07D 409/12* (2013.01); *C07D 413/12* (2013.01); *C12N 15/111* (2013.01); *C12N 15/1138* (2013.01); *C12N 2310/3513* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 6,326,403 B1 | 12/2001 | Holzemann et al. |
| 6,576,637 B1 | 6/2003 | Holzemann et al. |
| 8,507,659 B2 | 8/2013 | Ooya et al. |
| 2003/0171304 A1 | 9/2003 | Holzeman |
| 2008/0213249 A1 | 9/2008 | Sinha et al. |
| 2011/0003858 A1 | 1/2011 | Bergstrom et al. |
| 2015/0125392 A1 | 5/2015 | Howard et al. |
| 2015/0179823 A1 | 6/2015 | Kurita |
| 2016/0009806 A1 | 1/2016 | Ryan et al. |

(Continued)

FOREIGN PATENT DOCUMENTS

| | | |
|---|---|---|
| NO | 2008006102 A2 | 1/2008 |
| WO | 2001000660 A1 | 1/2001 |

(Continued)

OTHER PUBLICATIONS

Marinelli, Luciana, et al. "Human integrin αvβ5: Homology modeling and ligand binding." Journal of medicinal chemistry 47.17 (2004): 4166-4177.*
Supplementary Partial European Search Report for corresponding European Application No. 18873120 dated Mar. 24, 2021.
Barden S. et al.; "Adhesion of Several Cell Lines to Helicobacter pylori CagL Is Mediated by Integrin αVβ6 via an RGDLXXL Motif"; Journal of Molecular Biology; vol. 427; 1304-1315; 2015.
Butler, et al.; "The Use of Maleic Anhydride for the Reversible Blocking of Amino Groups in Polypeptide Chains"; Biochem. J.; pp. 679-689; 1969.
Conibear, Anne C., et al.; "Arginine side-chain modification that occurs during copper-catalysed azide-alkyne click reactions resembles an advanced glycation end product"; Organic & Biomolecular Chemistry; vol. 14; 2016; 6205-6211.

(Continued)

*Primary Examiner* — Kimberly Chong
(74) *Attorney, Agent, or Firm* — Paul VanderVelde; Robert M. Teigen; Meibo Chen

(57) ABSTRACT

Synthetic αvβ6 integrin ligands of Formula I having serum stability and affinity for integrin αvβ6, which is a receptor expressed in a variety of cell types, are described. The described ligands are useful for delivering cargo molecules, such as RNAi agents or other oligonucleotide-based compounds, to cells that express integrin αvβ6, and thereby facilitating the uptake of the cargo molecules into these cells. Compositions that include αvβ6 integrin ligands and methods of use are also described.

(Formula I)

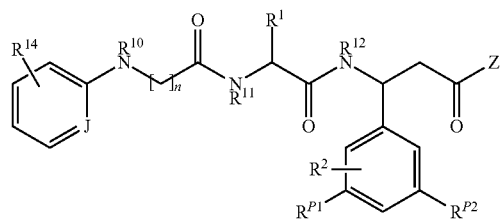

24 Claims, No Drawings

Specification includes a Sequence Listing.

(56) References Cited

U.S. PATENT DOCUMENTS

2016/0272971 A1 9/2016 Almeida et al.
2016/0348107 A1 12/2016 Wong et al.

FOREIGN PATENT DOCUMENTS

| WO | 2006020768 A2 | 2/2006 |
|---|---|---|
| WO | 2007039728 A2 | 4/2007 |
| WO | 2008152131 A2 | 12/2008 |
| WO | 2015160770 A1 | 10/2015 |
| WO | 2015179823 A2 | 11/2015 |
| WO | 2018027106 A2 | 2/2018 |

OTHER PUBLICATIONS

Dicara D. et al.; "Structure-Function Analysis of Arg-Gly-Asp Helix Motifs in αvβ6 Integrin Ligands"; Journal of Biological Chemistry; vol. 282:(13); 9657-9665; 2007.
Di Leva F. et al.; "From a Helix to a Small Cycle: Metadynamics-Inspired αvβ6 Integrin Selective Ligands"; Angewandte Chemie International Edition; vol. 57; 1-6; 2018.
Dong X. et al.; "Structural determinants of integrin β-subunit specificity for latent TGF-β"; Nature Structural & Molecular Biology; vol. 21:(12); 1091-1097; 2014.
Elayadi A. et al., "A Peptide Selected by Biopanning Identifies the Integrin αvβ6 as a Prognostic Biomarker for Nonsmall Cell Lung Cancer"; Cancer Research; vol. 67:(12); 5889-5895; 2007.
Färber S. et al.; "Therapeutic Radiopharmaceuticals Targeting Integrin αvβ6"; American Chemical Society Omega; vol. 3; 2428-2436; 2018.
Goodman, et al.; "Nanomolar Small Molecule Inhibitors for αvβ6, αvβ5, and αvβ3 Integrins"; J. Med. Chem.; 45; 1045-1051; 2002.
Gray B. et al.; "A Liposomal Drug Platform Overrides Peptide Ligand Targeting to a Cancer Biomarker, Irrespective of Ligand Affinity or Density"; PLOS ONE; vol. 8:(8); 1-19; 2013.
Gray B. et al.; "From Phage Display to Nanoparticle Delivery: Functionalizing Liposomes with Multivalent Peptides Improves Targeting to a Cancer Biomarker"; Bionconjugate Chemistry; vol. 24:(1); 85-96; 2013.
Guthi J. et al.; "MRI-Visible Micellar Nanomedicine for Targeted Drug Delivery to Lung Cancer Cells"; Molecular Pharmaceutics; vol. 7:(1); 32-40; 2010.
Hackel B. et al.; "18F-Fluorobenzoate-Labeled Cystine Knot Peptides for PET Imaging of Integrin αvβ6"; The Journal of Nuclear Medicine; vol. 54; 1101-1105; 2013.
Hausner S. et al.; "Use of a Peptide Derived from Foot-and-Mouth Disease Virus for the Noninvasive Imaging of Human Cancer: Generation and Evaluation of 4-[18F]Fluorobenzoyl A20FMDV2 for In vivo Imaging of Integrin αvβ 6 Expression with Positron Emission Tomography"; Cancer Research; vol. 67:(16); 7833-7840; 2007.
Hausner S. et al.; "Targeted In vivo Imaging of Integrin αvβ6 with an Improved Radiotracer and Its Relevance in a Pancreatic Tumor Model"; Cancer Research; vol. 69:(14); 5843-5850; 2009.
Hausner S. et al.; "Preclinical development and first-in-human imaging of the integrin αvβ6 with [18F]αvβ6-Binding Peptide in metastatic carcinoma."; Clinical Cancer Research; vol. 25:(4); 1206-1215; 2018.
Hu L. et al.; "Characterization and Evaluation of 64Cu-Labeled A20FMDV2 Conjugates for Imaging the Integrin αvβ6"; Molecular Imaging Biology; vol. 16:(4); 567-577; 2014.
John A. et al.; "Preclinical SPECT/CT Imaging of αvβ6 Integrins for Molecular Stratification of Idiopathic Pulmonary Fibrosis"; The Journal of Nuclear Medicine; vol. 54:(12); 2146-2152; 2013.
Kapp T. et al.; "A Comprehensive Evaluation of the Activity and Selectivity Profile of Ligands for RGD-binding Integrins"; Nature Scientific Reports; vol. 7; 1-13; 2017.
Kimura R. et al.; "Pharmacokinetically Stabilized Cystine Knot Peptides That Bind Alpha-v-Beta-6 Integrin with Single-Digit Nanomolar Affinities for Detection of Pancreatic Cancer"; Clinical Cancer Research; vol. 18:(3); 839-849; 2012.
Kimura R. et al.; "Evaluation of integrin αvβ6 cystine knot PET tracers to detect cancer and idiopathic pulmonary fibrosis"; Nature Communications; vol. 10:(1); 1-17; 2019.
Kraft S. et al.; "Definition of an Unexpected Ligand Recognition Motif for αvβ6 Integrin"; The Journal of Biological Chemistry; vol. 274:(4); 1979-1988; 1999.
Leung K.; "4-[18F]Fluorobenzoyl-NAVPNLRGDLQVLAQKVART"; Molecular Imaging & Contrast Agent Database; 2008.
Li S. et al.; "Synthesis and characterization of a high-affinity αvβ6-specific ligand for in vitro and in vivo applications"; Molecular Cancer Therapy; vol. 8:(5); 1239-1249; 2009.
Li S. et al.; "Synthesis and biological evaluation of a peptide-paclitaxel conjugate which targets the integrin αvβ6"; Bioorganic & Medicinal Chemistry; vol. 19; 5480-5489; 2011.
Liu H. et al.; "Molecular imaging of integrin αvβ6 expression in living subjects"; American Journal of Nuclear Medicine & Molecular Imaging; vol. 4:(4); 333-345; 2014.
Lukey P. et al.; "Clinical quantification of the integrin αvβ6 by [18F]FB-A20FMDV2 positron emission tomography in healthy and fibrotic human lung (PETAL Study)"; European Journal of Nuclear Medicine and Molecular Imaging; vol. 1-13; 2019.
Maltsev O. et al.; "Stable Peptides Instead of Stapled Peptides: Highly Potent αvβ6—Selective Integrin Ligands"; Angewandte Chemie International Edition; vol. 55; 1535-1593; 2016.
McGuire M. et al.; "Identification and Characterization of a Suite of Tumor Targeting Peptides for Non-Small Cell Lung Cancer"; Nature Scientific Reports; vol. 4; 1-11; 2014.
Nieberler M. et al.; "Fluorescence imaging of invasive head and neck carcinoma cells with integrin _v_6—targeting RGD-peptides: an approach to a fluorescence-assisted intraoperative cytological assessment of bony resection margins"; Journal of Oral and Maxillofacial Surgery; vol. 56; 962-978; 2018.
Nothelfer E. et al.; "Identification and Characterization of a Peptide with Affinity to Head and Neck Cancer"; The Journal of Nuclear Medicine; vol. 50; 426-434; 2009.
Notni J. et al.; "In Vivo PET Imaging of the Cancer Integrin αvβ6 Using 68Ga-Labeled Cyclic RGD Nonapeptides"; The Journal of Nuclear Medicine; vol. 58:(4); 671-677; 2017.
Singh A. et al.; "Dimerization of a Phage-Display Selected Peptide for Imaging of αvβ6—Integrin: Two Approaches to the Multivalent Effect"; Theranostics; vol. 4:(7); 745-760; 2014.
Shunzi, Li et al.; "Synthesis and biological evaluation of a peptidepaclitaxel conjugate which targets the integrin αvβ6"; Biorganic & Medicinal Chemistry; vol. 19; 2011; 5480-5489.
Slack R. et al.; "Pharmacological Characterization of the αvβ6 Integrin Binding and Internalization Kinetics of the Foot-and-Mouth Disease Virus Derived Peptide A20FMDV2"; Pharmacology; vol. 97; 114-125; 2015.
Uusi-Kerttula H. et al.; "Pseudotyped αvβ6 integrin-targeted adenovirus vectors for ovarian cancer therapies"; Oncotarget; vol. 7:(19); 27926-27937; 2016.
White B. et al.; "ImmunoPET Imaging of αvβ6 Expression Using an Engineered Anti-αvβ6 Cys-diabody Site-Specifically Radiolabeled with Cu-64: Considerations for Optimal Imaging with Antibody Fragments"; Molecular Imaging and Biology; vol. 20; 103-113; 2018.
International Search Report and Written Opinion for corresponding International Application No. PCT/US2018/058471 dated Feb. 7, 2019.
Goswami, R. et al.; "Chemically Programmed Antibodies Targeting Multiple Alpha(v) Integrins and Their Effects on Tumor-Related Functions in Vitro"; Bioconjugate Chemistry; vol. 22; p. 1535-1544; Jul. 20, 2011.
CAS Registry No. 442137-98-6, entered Aug. 2, 2002, American Chemical Society.
CAS Registry No. 442138-55-8, entered Aug. 2, 2002, American Chemical Society.
CAS Registry No. 444053-20-7, entered Aug. 16, 2002, American Chemical Society.

* cited by examiner

INTEGRIN LIGANDS AND USES THEREOF

CROSS REFERENCE TO RELATED APPLICATIONS

This application is a U.S. National Phase Application under 35 U.S.C. § 371 of International Patent Application No. PCT/US18/58471 which claims priority from U.S. Provisional Patent Application Ser. No. 62/679,549, filed on Jun. 1, 2018, U.S. Provisional Patent Application Ser. No. 62/646,739, filed on Mar. 22, 2018, and U.S. Provisional Patent Application Ser. No. 62/580,398, filed on Nov. 1, 2017, the contents of each of which are incorporated herein by reference in their entirety.

BACKGROUND

Integrin alpha-v beta-6 ($\alpha v\beta 6$), which is expressed in various cell types including epithelial cells, is a receptor for the latency-associated peptide (LAP) of TGF-$\beta$ and for the extracellular matrix (ECM) proteins fibronectin, vitronectin, and tenascin. Although barely detectable in normal healthy adult epithelia, $\alpha v\beta 6$ integrin is upregulated during wound healing and in different cancers (e.g., colon, ovarian, endometrial, and gastric cancer), and often associates with poor cancer prognosis. It has been shown that $\alpha v\beta 6$ integrin can promote cell invasion and migration in metastasis, and inhibit apoptosis. $\alpha v\beta 6$ integrin may also regulate expression of matrix metalloproteases (MMPs) and activate TGF-$\beta 1$. There is increasing evidence, primarily from in vitro studies, that suggest that $\alpha v\beta 6$ integrin may promote carcinoma progression. Thus, integrin $\alpha v\beta 6$ is attractive as a tumor biomarker and potential therapeutic target in view of, among other things, its role in expression of matrix metalloproteases (MMPs) and activation of TGF-$\beta 1$.

The in vivo delivery of therapeutically effective compounds, such as drug compounds, to the desired cells and/or tissues, continues to be a general challenge for the development of drug products. There continues to exist a need for stable and effective targeting ligands that are able to selectively target cells or tissues, which can be employed to facilitate the targeted delivery of cargo molecules (e.g., a therapeutically active compound or ingredient) to specific cells or tissues. Indeed, there is a general need for targeting ligands that can be conjugated to one or more cargo molecules of choice, such as one or more drug products or other payloads, to facilitate the delivery of the cargo molecules to desired cells or tissues in vivo. Moreover, there exists a need for compounds that target integrin alpha-v beta-6, which are suitable to be conjugated to cargo molecules, to deliver the cargo molecules to cells expressing integrin alpha-v beta-6, in vivo. With respect to specific cargo molecules, such as therapeutic oligonucleotide-based compounds (e.g., an antisense oligonucleotides or an RNAi agents), there exists a need for targeting ligands that are able to target integrin alpha-v beta-6 that can be conjugated to oligonucleotide-based compounds to deliver the therapeutic to cells and/or tissues expressing integrin alpha-v beta-6, and facilitate the entry of the therapeutic into the cell through receptor-mediated endocytosis, pinocytosis, or by other means.

SUMMARY

Described herein are novel, synthetic $\alpha v\beta 6$ integrin ligands (also referred to herein as $\alpha v\beta 6$ ligands). The $\alpha v\beta 6$ integrin ligands disclosed herein are stable in serum and have affinity for, and can bind with specificity to, $\alpha v\beta 6$ integrins. The $\alpha v\beta 6$ integrin ligands can be conjugated to cargo molecules to facilitate the delivery of the cargo molecule to desired cells or tissues that express $\alpha v\beta 6$ integrin, such as to epithelial cells.

Also disclosed herein are methods of delivery of a cargo molecule to a tissue and/or cell expressing $\alpha v\beta 6$ integrin in vivo, wherein the methods including administering to a subject one or more $\alpha v\beta 6$ integrin ligands disclosed herein that have been conjugated to one or more cargo molecules. Further disclosed are methods of treatment of a subject having a disease, symptom, or disorder for which the delivery of a therapeutic cargo molecule (e.g., an active pharmaceutical ingredient) to a cell expressing $\alpha v\beta 6$ integrin is capable of treating the subject, wherein the methods include administering to a subject one or more $\alpha v\beta 6$ integrin ligands disclosed herein that have been conjugated to one or more therapeutic cargo molecules.

In some embodiments, described herein are methods of inhibiting expression of a target gene in a cell, wherein the methods include administering to the cell an effective amount of one or more $\alpha v\beta 6$ integrin ligands that have been conjugated to one or more oligonucleotide-based compounds (e.g., an oligonucleotide-based therapeutic) capable of inhibiting expression of a target gene in a cell, such as an RNAi agent. In some embodiments, described herein are methods of inhibiting expression of a target gene in a cell of a subject, wherein the subject is administered an effective amount of one or more $\alpha v\beta 6$ integrin ligands that have been conjugated to one or more oligonucleotide-based compounds capable of inhibiting expression of a target gene in a cell, such as an RNAi agent.

Further described herein are compositions that include $\alpha v\beta 6$ integrin ligands. The compositions described herein can be pharmaceutical compositions that include one or more $\alpha v\beta 6$ integrin ligands disclosed herein conjugated to one or more therapeutic substances, such as an RNAi agent or other cargo molecule.

In some embodiments, described herein are methods of treatment of a subject having a disease or disorder mediated at least in part by expression of a target gene, wherein the methods including administering to a subject in need thereof an effective amount of a pharmaceutical composition, wherein the pharmaceutical composition includes one or more $\alpha v\beta 6$ integrin ligands disclosed herein conjugated to one or more oligonucleotide-based compounds, such as an RNAi agent.

In a first aspect, this disclosure provides synthetic $\alpha v\beta 6$ integrin ligands.

In some embodiments, an $\alpha v\beta 6$ integrin ligand disclosed herein includes the structure of the following formula:

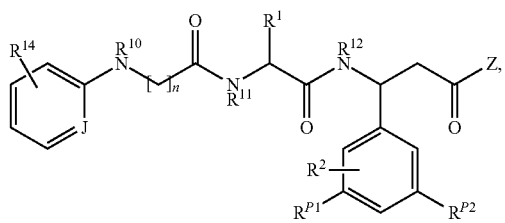

(Formula I)

or a pharmaceutically acceptable salt thereof,
wherein,
n is an integer from 0 to 7;

J is C—H or N;

Z is $OR^{13}$, $N(R^{13})_2$ or $SR^{13}$;

$R^1$ is H, optionally substituted $C_1$-$C_6$ alkyl, OH, COOH, $CON(R^5)_2$, $OR^6$, or $R^1$ comprises a cargo molecule, wherein each $R^5$ is independently H or $C_1$-$C_6$ alkyl, and $R^6$ is H or $C_1$-$C_6$ alkyl;

$R^2$, $R^{P1}$ and $R^{P2}$ are each independently H, halo, optionally substituted cycloalkylene, optionally substituted arylene, optionally substituted heterocycloalkylene, or optionally substituted heteroarylene, or $R^2$, $R^{P1}$ and $R^{P2}$ may comprise a cargo molecule;

$R^{10}$ is H or optionally substituted alkyl;

$R^{11}$ is H or optionally substituted alkyl, or $R^{11}$ and $R^1$ together with the atoms to which they are attached form an optionally substituted heterocycle;

$R^{12}$ is H or optionally substituted alkyl;

each $R^{13}$ is independently H, optionally substituted alkyl, or $R^{13}$ comprises a cargo molecule;

$R^{14}$ is optionally substituted alkyl; and wherein at least one of $R^1$, $R^2$, $R^{13}$, $R^{P1}$ and $R^{P2}$ comprises a cargo molecule.

In some embodiments, an αvβ6 integrin ligand disclosed herein can be conjugated to one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30) cargo molecules (e.g., any of the cargo molecules described herein or known in the art).

In some embodiments, more than one αvβ6 integrin ligand disclosed herein (e.g., 2, 3, 4, 5, 6, 7, 8, or 1 to 8, 1 to 7, 1 to 6, 1 to 5, 1 to 4, 1 to 3, 1 to 2, 2 to 8, 2 to 7, 2 to 6, 2 to 5, 2 to 4, 2 to 3, 3 to 8, 3 to 7, 3 to 6, 3 to 5, 3 to 4, 4 to 8, 4 to 7, 4 to 6, or 4 to 5 αvβ6 integrin ligands) can be conjugated to one cargo molecule (e.g., any of the cargo molecules described herein or known in the art).

In another aspect, this disclosure provides compositions that include one or more of the αvβ6 integrin ligands described herein. For example, in some embodiments, compositions comprising one or more αvβ6 integrin ligands disclosed herein include one or more oligonucleotide-based compound(s), such as one or more RNAi agent(s), to be delivered to a cell in vivo. In some embodiments, described herein are compositions for delivering an RNAi agent to a cell in vivo, wherein the RNAi agent is linked to one or more αvβ6 integrin ligands.

Compositions that include one or more αvβ6 integrin ligands are described. In some embodiments, a composition comprises a pharmaceutically acceptable excipient. In some embodiments, a composition that includes one or more αvβ6 integrin ligands comprises one or more other pharmaceutical substances or pharmaceutically active ingredients or compounds. In some embodiments, medicaments that include one or more αvβ6 integrin ligands are described herein.

Compositions that include one or more αvβ6 integrin ligands disclosed herein conjugated to one or more cargo molecules can facilitate the delivery of the cargo molecule in vivo or in vitro to cells that express integrin αvβ6. For example, compositions that include one or more αvβ6 integrin ligands disclosed herein can deliver cargo molecules, such as oligonucleotide-based compounds, in vivo or in vitro, to type I and II alveolar epithelial cells, goblet cells, secretory epithelial cells, ciliated epithelial cells, corneal and conjunctival epithelial cells, dermal epithelial cells, cholangiocytes, enterocytes, ductal epithelial cells, glandular epithelial cells, and epithelial tumors (carcinomas).

In another aspect, the present disclosure provides methods comprising the use of one or more αvβ6 integrin ligands and/or compositions as described herein and, if desired, bringing the disclosed αvβ6 integrin ligands and/or compositions into a form suitable for administration as a pharmaceutical product. In other embodiments, the disclosure provides methods for the manufacture of the ligands and compositions, e.g., medicaments, described herein.

Compositions that include one or more αvβ6 integrin ligands can be administered to subjects in vivo using routes of administration known in the art to be suitable for such administration in view of the cargo molecule sought to be administered, including, for example, inhaled (aerosol or dry powder formulations), intranasal, subcutaneous, intravenous, intraperitoneal, intradermal, transdermal, oral, sublingual, topical, or intratumoral administration. In some embodiments, the compositions that include one or more αvβ6 integrin ligands may be administered for systemic delivery, for example, by intravenous or subcutaneous administration. In some embodiments, the compositions that include one or more αvβ6 integrin ligands may be administered for localized delivery, for example, by inhaled delivery via dry powder inhaler or nebulizer. In some embodiments, the compositions that include one or more αvβ6 integrin ligands may be administered for localized delivery by topical administration.

In some embodiments, disclosed herein are methods for delivering one or more desired cargo molecule(s) to a type I alveolar epithelial cell in vivo, wherein the methods include administering to the subject one or more αvβ6 integrin ligands conjugated to the one or more cargo molecule.

In some embodiments, disclosed herein are methods for delivering one or more desired cargo molecule(s) to a type II alveolar epithelial cell in vivo, wherein the methods include administering to the subject one or more αvβ6 integrin ligands conjugated to the one or more cargo molecule.

In some embodiments, disclosed herein are methods for delivering one or more desired cargo molecule(s) to a goblet cell in vivo, wherein the methods include administering to the subject one or more αvβ6 integrin ligands conjugated to the one or more cargo molecule.

In some embodiments, disclosed herein are methods for delivering one or more desired cargo molecule(s) to a secretory epithelial cell in vivo, wherein the methods include administering to the subject one or more αvβ6 integrin ligands conjugated to the one or more cargo molecule.

In some embodiments, disclosed herein are methods for delivering one or more desired cargo molecule(s) to a ciliated epithelial cell in vivo, wherein the methods include administering to the subject one or more αvβ6 integrin ligands conjugated to the one or more cargo molecule.

In some embodiments, disclosed herein are methods for delivering one or more desired cargo molecule(s) to a corneal epithelial cell in vivo, wherein the methods include administering to the subject one or more αvβ6 integrin ligands conjugated to the one or more cargo molecule.

In some embodiments, disclosed herein are methods for delivering one or more desired cargo molecule(s) to a conjunctival epithelial cell in vivo, wherein the methods include administering to the subject one or more αvβ6 integrin ligands conjugated to the one or more cargo molecule.

In some embodiments, disclosed herein are methods for delivering one or more desired cargo molecule(s) to a dermal epithelial cell in vivo, wherein the methods include administering to the subject one or more αvβ6 integrin ligands conjugated to the one or more cargo molecule.

In some embodiments, disclosed herein are methods for delivering one or more desired cargo molecule(s) to a cholangiocyte in vivo, wherein the methods include administering to the subject one or more αvβ6 integrin ligands conjugated to the one or more cargo molecule.

In some embodiments, disclosed herein are methods for delivering one or more desired cargo molecule(s) to an enterocyte in vivo, wherein the methods include administering to the subject one or more αvβ6 integrin ligands conjugated to the one or more cargo molecule.

In some embodiments, disclosed herein are methods for delivering one or more desired cargo molecule(s) to a ductal epithelial cell in vivo, wherein the methods include administering to the subject one or more αvβ6 integrin ligands conjugated to the one or more cargo molecule.

In some embodiments, disclosed herein are methods for delivering one or more desired cargo molecule(s) to a glandular epithelial cell in vivo, wherein the methods include administering to the subject one or more αvβ6 integrin ligands conjugated to the one or more cargo molecule.

In some embodiments, disclosed herein are methods for delivering one or more desired cargo molecule(s) to an epithelial tumor (carcinoma) in vivo, wherein the methods include administering to the subject one or more αvβ6 integrin ligands conjugated to the one or more cargo molecules.

In some embodiments, disclosed herein are methods of delivering an oligonucleotide-based compound to a type I alveolar epithelial cell in vivo, wherein the methods include administering to the subject one or more αvβ6 integrin ligands conjugated to the one or more oligonucleotide-based compounds. In some embodiments, disclosed herein are methods of delivering an RNAi agent to a type I alveolar epithelial cell in vivo, wherein the methods include administering to the subject one or more αvβ6 integrin ligands conjugated to the one or more RNAi agents. In some embodiments, disclosed herein are methods of inhibiting the expression of a target gene in a type I alveolar epithelial cell in vivo, wherein the methods include administering to the subject an RNAi agent conjugated to one or more ligands having affinity for αvβ6 integrin.

In some embodiments, disclosed herein are methods of delivering an oligonucleotide-based compound to a type II alveolar epithelial cell in vivo, wherein the methods include administering to the subject one or more αvβ6 integrin ligands conjugated to the one or more oligonucleotide-based compounds. In some embodiments, disclosed herein are methods of delivering an RNAi agent to a type II alveolar epithelial cell in vivo, wherein the methods include administering to the subject one or more αvβ6 integrin ligands conjugated to the one or more RNAi agents. In some embodiments, disclosed herein are methods of inhibiting the expression of a target gene in a type II alveolar epithelial cell in vivo, wherein the methods include administering to the subject an RNAi agent conjugated to one or more ligands having affinity for αvβ6 integrin.

In some embodiments, disclosed herein are methods of delivering an oligonucleotide-based compound to a goblet cell in vivo, wherein the methods include administering to the subject one or more αvβ6 integrin ligands conjugated to the one or more oligonucleotide-based compounds. In some embodiments, disclosed herein are methods of delivering an RNAi agent to a goblet cell in vivo, wherein the methods include administering to the subject one or more αvβ6 integrin ligands conjugated to the one or more RNAi agents. In some embodiments, disclosed herein are methods of inhibiting the expression of a target gene in a goblet cell in vivo, wherein the methods include administering to the subject an RNAi agent conjugated to one or more ligands having affinity for αvβ6 integrin.

In some embodiments, disclosed herein are methods of delivering an oligonucleotide-based compound to a secretory epithelial cell in vivo, wherein the methods include administering to the subject one or more αvβ6 integrin ligands conjugated to the one or more oligonucleotide-based compounds. In some embodiments, disclosed herein are methods of delivering an RNAi agent to a secretory epithelial cell in vivo, wherein the methods include administering to the subject one or more αvβ6 integrin ligands conjugated to the one or more RNAi agents. In some embodiments, disclosed herein are methods of inhibiting the expression of a target gene in a secretory epithelial cell in vivo, wherein the methods include administering to the subject an RNAi agent conjugated to one or more ligands having affinity for αvβ6 integrin.

In some embodiments, disclosed herein are methods of delivering an oligonucleotide-based compound to a ciliated epithelial cell in vivo, wherein the methods include administering to the subject one or more αvβ6 integrin ligands conjugated to the one or more oligonucleotide-based compounds. In some embodiments, disclosed herein are methods of delivering an RNAi agent to a ciliated epithelial cell in vivo, wherein the methods include administering to the subject one or more αvβ6 integrin ligands conjugated to the one or more RNAi agents. In some embodiments, disclosed herein are methods of inhibiting the expression of a target gene in a ciliated epithelial cell in vivo, wherein the methods include administering to the subject an RNAi agent conjugated to one or more ligands having affinity for αvβ6 integrin.

In some embodiments, disclosed herein are methods of delivering an oligonucleotide-based compound to a corneal epithelial cell in vivo, wherein the methods include administering to the subject one or more αvβ6 integrin ligands conjugated to the one or more oligonucleotide-based compounds. In some embodiments, disclosed herein are methods of delivering an RNAi agent to a corneal epithelial cell in vivo, wherein the methods include administering to the subject one or more αvβ6 integrin ligands conjugated to the one or more RNAi agents. In some embodiments, disclosed herein are methods of inhibiting the expression of a target gene in a corneal epithelial cell in vivo, wherein the methods include administering to the subject an RNAi agent conjugated to one or more ligands having affinity for αvβ6 integrin.

In some embodiments, disclosed herein are methods of delivering an oligonucleotide-based compound to a conjunctival epithelial cell in vivo, wherein the methods include administering to the subject one or more αvβ6 integrin ligands conjugated to the one or more oligonucleotide-based compounds. In some embodiments, disclosed herein are methods of delivering an RNAi agent to a conjunctival epithelial cell in vivo, wherein the methods include administering to the subject one or more αvβ6 integrin ligands conjugated to the one or more RNAi agents. In some embodiments, disclosed herein are methods of inhibiting the expression of a target gene in a conjunctival epithelial cell in vivo, wherein the methods include administering to the subject an RNAi agent conjugated to one or more ligands having affinity for αvβ6 integrin.

In some embodiments, disclosed herein are methods of delivering an oligonucleotide-based compound to a dermal epithelial cell in vivo, wherein the methods include administering to the subject one or more αvβ6 integrin ligands conjugated to the one or more oligonucleotide-based compounds. In some embodiments, disclosed herein are methods of delivering an RNAi agent to a dermal epithelial cell in vivo, wherein the methods include administering to the subject one or more αvβ6 integrin ligands conjugated to the one or more RNAi agents. In some embodiments, disclosed herein are methods of inhibiting the expression of a target gene in a dermal epithelial cell in vivo, wherein the methods include administering to the subject an RNAi agent conjugated to one or more ligands having affinity for αvβ6 integrin.

In some embodiments, disclosed herein are methods of delivering an oligonucleotide-based compound to a cholangiocyte in vivo, wherein the methods include administering to the subject one or more αvβ6 integrin ligands conjugated to the one or more oligonucleotide-based compounds. In some embodiments, disclosed herein are methods of delivering an RNAi agent to a cholangiocyte in vivo, wherein the methods include administering to the subject one or more αvβ6 integrin ligands conjugated to the one or more RNAi agents. In some embodiments, disclosed herein are methods of inhibiting the expression of a target gene in a cholangiocyte in vivo, wherein the methods include administering to the subject an RNAi agent conjugated to one or more ligands having affinity for αvβ6 integrin.

In some embodiments, disclosed herein are methods of delivering an oligonucleotide-based compound to an enterocyte in vivo, wherein the methods include administering to the subject one or more αvβ6 integrin ligands conjugated to the one or more oligonucleotide-based compounds. In some embodiments, disclosed herein are methods of delivering an RNAi agent to an enterocyte in vivo, wherein the methods include administering to the subject one or more αvβ6 integrin ligands conjugated to the one or more RNAi agents. In some embodiments, disclosed herein are methods of inhibiting the expression of a target gene in an enterocyte in vivo, wherein the methods include administering to the subject an RNAi agent conjugated to one or more ligands having affinity for αvβ6 integrin.

In some embodiments, disclosed herein are methods of delivering an oligonucleotide-based compound to a ductal epithelial cell in vivo, wherein the methods include administering to the subject one or more αvβ6 integrin ligands conjugated to the one or more oligonucleotide-based compounds. In some embodiments, disclosed herein are methods of delivering an RNAi agent to a ductal epithelial cell in vivo, wherein the methods include administering to the subject one or more αvβ6 integrin ligands conjugated to the one or more RNAi agents. In some embodiments, disclosed herein are methods of inhibiting the expression of a target gene in a ductal epithelial cell in vivo, wherein the methods include administering to the subject an RNAi agent conjugated to one or more ligands having affinity for αvβ6 integrin.

In some embodiments, disclosed herein are methods of delivering an oligonucleotide-based compound to a glandular epithelial cell in vivo, wherein the methods include administering to the subject one or more αvβ6 integrin ligands conjugated to the one or more oligonucleotide-based compounds. In some embodiments, disclosed herein are methods of delivering an RNAi agent to a glandular epithelial cell in vivo, wherein the methods include administering to the subject one or more αvβ6 integrin ligands conjugated to the one or more RNAi agents. In some embodiments, disclosed herein are methods of inhibiting the expression of a target gene in a glandular epithelial cell in vivo, wherein the methods include administering to the subject an RNAi agent conjugated to one or more ligands having affinity for αvβ6 integrin.

In some embodiments, disclosed herein are methods of delivering an oligonucleotide-based compound to an epithelial tumor (carcinoma) in vivo, wherein the methods include administering to the subject one or more αvβ6 integrin ligands conjugated to the one or more oligonucleotide-based compounds. In some embodiments, disclosed herein are methods of delivering an RNAi agent to an epithelial tumor (carcinoma) in vivo, wherein the methods include administering to the subject one or more αvβ6 integrin ligands conjugated to the one or more RNAi agents. In some embodiments, disclosed herein are methods of inhibiting the expression of a target gene in an epithelial tumor (carcinoma) in vivo, wherein the methods include administering to the subject an RNAi agent conjugated to one or more ligands having affinity for αvβ6 integrin.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects, features, aspects, and advantages of the invention will be apparent from the following detailed description and from the claims.

DETAILED DESCRIPTION

αvβ6 Integrin Ligands

Described herein are synthetic αvβ6 integrin ligands having serum stability and affinity for integrin αvβ6. The αvβ6 integrin ligands can be used to target cells that express integrin αvβ6 in vitro, in situ, ex vivo, and/or in vivo. In some embodiments, the αvβ6 integrin ligands disclosed herein can be conjugated to one or more cargo molecules to preferentially direct and target the cargo molecules to cells that express integrin αvβ6 in vitro, in situ, ex vivo, and/or in vivo. In some embodiments, the cargo molecules include or consist of pharmaceutically active compounds. In some embodiments, the cargo molecules include or consist of oligonucleotide-based compounds, such as RNAi agents. In some embodiments, the αvβ6 integrin ligands disclosed herein are conjugated to cargo molecules to direct the cargo molecules to epithelial cells in vivo.

In a first aspect, this disclosure provides synthetic αvβ6 integrin ligands.

In some embodiments, an αvβ6 integrin ligand disclosed herein includes the structure of the following formula:

(Formula I)

or a pharmaceutically acceptable salt thereof,
wherein,
n is an integer from 0 to 7;
J is C—H or N;
Z is $OR^{13}$, $N(R^{13})_2$ or $SR^{13}$;
$R^1$ is H, optionally substituted $C_1$-$C_6$ alkyl, OH, COOH, $CON(R^5)_2$, $OR^6$, or $R^1$ comprises a cargo molecule, wherein each $R^5$ is independently H or $C_1$-$C_6$ alkyl, and $R^6$ is H or $C_1$-$C_6$ alkyl;
$R^2$, $R^{P1}$ and $R^{P2}$ are each independently H, halo, optionally substituted cycloalkylene, optionally substituted arylene, optionally substituted heterocycloalkylene, or optionally substituted heteroarylene, or $R^2$, $R^{P1}$ and $R^{P2}$ may comprise a cargo molecule;
$R^{10}$ is H or optionally substituted alkyl;
$R^{11}$ is H or optionally substituted alkyl, or $R^{11}$ and $R^1$ together with the atoms to which they are attached form an optionally substituted heterocycle;
$R^{12}$ is H or optionally substituted alkyl;
each $R^{13}$ is independently H, optionally substituted alkyl, or $R^{13}$ comprises a cargo molecule;
$R^{14}$ is optionally substituted alkyl; and
wherein at least one of $R^1$, $R^2$, $R^{13}$, $R^{P1}$ and $R^{P2}$ comprises a cargo molecule.

In some embodiments, n=3 in Formula I. In some embodiments, n=4 in Formula I.

In some embodiments of Formula I, $R^2$ is napthylene. In some embodiments of Formula I, $R^2$ is substituted napthylene and $R^2$ also comprises a cargo molecule.

In some embodiments an αvβ6 integrin ligand disclosed herein includes the structure of the following formula:

(Formula II)

or a pharmaceutically acceptable salt thereof,
wherein,
n is an integer from 0 to 7 (i.e., n is 0, 1, 2, 3, 4, 5, 6, or 7);
J is C—H or N;
$R^1$ is H, $C_1$-$C_6$ alkyl, $CH(R^3)(R^4)$, OH, COOH, $CH_2CH_2CH_2NH_2$, $CONHR^5$, $OR^6$, wherein $R^3$ is H or $C_1$-$C_6$ alkyl, $R^4$ is H, $C_1$-$C_6$ alkyl, $R^5$ is H or $C_1$-$C_6$ alkyl, and $R^6$ is H or $C_1$-$C_6$ alkyl;

$R^2$ is optionally substituted cycloalkylene, optionally substituted arylene, optionally substituted heterocycloalkylene, or optionally substituted heteroarylene,
$R^{10}$ is H or optionally substituted alkyl;
$R^{11}$ is H or optionally substituted alkyl, or $R^{11}$ and $R^1$ together with the atoms to which they are attached form an optionally substituted heterocycle;
$R^{12}$ is H or optionally substituted alkyl;
$R^{13}$ is H or optionally substituted alkyl;
$R^{14}$ is optionally substituted alkyl;
wherein at least one of $R^1$ or $R^2$ includes a cargo molecule.

In some embodiments, n=3 in Formula II. In some embodiments, n=4 in Formula II.

In some embodiments, an αvβ6 integrin ligand disclosed herein includes the structure of the following formula:

(Formula III)

or a pharmaceutically acceptable salt thereof,
wherein,
n is an integer from 1 to 7 (i.e., n is 1, 2, 3, 4, 5, 6, or 7);
$R^7$ includes one or more cargo molecules; and
$R^8$ is one or more optionally substituted divalent cyclic moieties having 2, 3, 4, 5, 6, 7, 8, 9, or 10 carbon atoms, such as cycloalkyl (e.g., cyclopropyl, cyclobutyl, cyclopentyl, cyclohexyl, or cycloheptyl), cycloalkenyl (e.g., cyclopentenyl, cyclobutenyl, cyclopentenyl, cyclohexenyl, or cycloheptenyl), aryl (e.g., phenyl), heteroaryl (e.g., pyridyl, pyrimidinyl, pyridazinyl, pyrrole, pyrazole, imidazole, thiophene, benzothiophene, thiazole, benzothiazole, furan, oxazole, isoxazole, benzofuran, indole, indazole, benzimidazole, oxadiazole, 1,2,3-triazole, 1,2,4-triazole, tetrazole, quinolinyl, isoquinolinyl, or quinoxalinyl), or heterocyclyl (e.g., tetrahydrofuran, tetrahydropyran, piperidine, pyrrolidine, dioxane, or dioxolane).

In some embodiments, n=3 in Formula III. In some embodiments, n=4 in Formula III.

In some embodiments, an αvβ6 integrin ligand disclosed herein includes the structure of the following formula:

(Formula IV)

or a pharmaceutically acceptable salt thereof, wherein, n is an integer from 1 to 7 (i.e., n is 1, 2, 3, 4, 5, 6, or 7); and $R^9$ includes one or more cargo molecules.

In some embodiments, n=3 in Formula IV. In some embodiments, n=4 in Formula IV.

In another aspect, the invention provides integrin targeting ligand precursor of the structure:

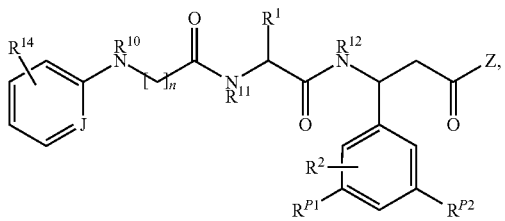

(Formula Ib)

or a pharmaceutically acceptable salt thereof, wherein, n is an integer from 0 to 7;

J is C—H or N;

Z is $OR^{13}$, $N(R^{13})_2$ or $SR^{13}$.

$R^1$ is H, optionally substituted $C_1$-$C_6$ alkyl, OH, COOH, $CON(R^5)_2$, $OR^6$, or $R^1$ comprises a linking group conjugated to a reactive group, wherein each R is independently H or $C_1$-$C_6$ alkyl, and $R^6$ is H or $C_1$-$C_6$ alkyl;

$R^2$, $R^{P1}$ and $R^{P2}$ are each independently H, halo, optionally substituted cycloalkylene, optionally substituted arylene, optionally substituted heterocycloalkylene, or optionally substituted heteroarylene, or $R^2$, $R^{P1}$ and $R^{P2}$ may comprise a linking group conjugated to a reactive group;

$R^{10}$ is H or optionally substituted alkyl;

$R^{11}$ is H or optionally substituted alkyl, or $R^{11}$ and $R^1$ together with the atoms to which they are attached form an optionally substituted heterocycle;

$R^{12}$ is H or optionally substituted alkyl;

each $R^{13}$ is independently H, optionally substituted alkyl, or $R^{13}$ comprises a linking group conjugated to a reactive group;

$R^{14}$ is optionally substituted alkyl; and wherein at least one of $R^1$, $R^2$, $R^{13}$, $R^{P1}$ and $R^{P2}$ comprises a linking group conjugated to a reactive group.

In some embodiments, an αvβ6 integrin ligand disclosed herein can be conjugated to one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30) cargo molecules (e.g., any of the cargo molecules described herein or known in the art).

In some embodiments, more than one αvβ6 integrin ligand disclosed herein (e.g., 2, 3, 4, 5, 6, 7, 8, or 1 to 8, 1 to 7, 1 to 6, 1 to 5, 1 to 4, 1 to 3, 1 to 2, 2 to 8, 2 to 7, 2 to 6, 2 to 5, 2 to 4, 2 to 3, 3 to 8, 3 to 7, 3 to 6, 3 to 5, 3 to 4, 4 to 8, 4 to 7, 4 to 6, or 4 to 5 αvβ6 integrin ligands) can be conjugated to one cargo molecule (e.g., any of the cargo molecules described herein or known in the art).

In some embodiments, the αvβ6 integrin ligands disclosed herein are optionally conjugated to one or more cargo molecules via a linking group, such as, for example, a polyethylene glycol (PEG) group.

In some embodiments, the αvβ6 integrin ligands disclosed herein are optionally conjugated to one or more cargo molecules via a scaffold that includes at least one attachment point for each ligand and at least one attachment point for each cargo molecule. In some embodiments, the αvβ6 integrin ligands comprise, consist of, or consist essentially of, one cargo molecule. In some embodiments, the αvβ6 integrin ligands comprise, consist of, or consist essentially of, more than one cargo molecule.

In some embodiments, the αvβ6 integrin ligand comprises, consists of, or consists essentially of, any of Structure 1, Structure 2, Structure 5, Structure 5.1, Structure 5.2, Structure 6, Structure 6.1, Structure 6.2, Structure 6.3, Structure 6.4, Structure 7, Structure 8, Structure 9, Structure 10, Structure 11, Structure 12, Structure 13, Structure 14, Structure 15, Structure 16, Structure 17, Structure 18, Structure 19, Structure 20, Structure 22, Structure 23, Structure 24, Structure 25, Structure 27, Structure 29, Structure 30, Structure 31, Structure 32, Structure 33, Structure 34, Structure 35, Structure 36, or Structure 37, each as disclosed herein.

Any of the αvβ6 integrin ligands disclosed herein can be linked to a cargo molecule, a reactive group, and/or a protected reactive group. A reactive group can be used to facilitate conjugation of the αvβ6 integrin ligand to a cargo molecule. The αvβ6 integrin ligands disclosed herein can increase targeting of a cargo molecule to an αvβ6 integrin or to a cell expressing an αvβ6 integrin. A cargo molecule can be, but is not limited to, a pharmaceutically active ingredient or compound, a prodrug, or another substance with known therapeutic or diagnostic benefit. In some embodiments, a cargo molecule can be, but is not limited to, a small molecule, an antibody, an antibody fragment, an immunoglobulin, a monoclonal antibody, a label or marker, a lipid, a natural or modified oligonucleotide-based compound (e.g., an antisense oligonucleotide or an RNAi agent), a natural or modified nucleic acid, a peptide, an aptamer, a polymer, a polyamine, a protein, a toxin, a vitamin, a polyethylene glycol, a hapten, a digoxigenin, a biotin, a radioactive atom or molecule, or a fluorophore. In some embodiments, a cargo molecule includes a pharmaceutically active ingredient or a prodrug. In some embodiments, a cargo molecule includes an oligonucleotide-based compound as a pharmaceutically active ingredient. In some embodiments, a cargo molecule includes an RNAi agent as a pharmaceutically active ingredient.

As used herein, the term "alkyl" refers to a saturated aliphatic hydrocarbon group, straight chain or branched, having from 1 to 10 carbon atoms unless otherwise specified. For example, "$C_1$-$C_6$ alkyl" includes alkyl groups having 1, 2, 3, 4, 5, or 6 carbons in a linear or branched arrangement. Non-limiting examples of alkyl groups include methyl, ethyl, iso-propyl, tert-butyl, n-hexyl. As used herein, the term "aminoalkyl" refers to an alkyl group as defined above, substituted at any position with one or more amino groups as permitted by normal valency. The amino groups may be unsubstituted, monosubstituted, or di-substituted. Non-limiting examples of aninoalkyl groups include aninomethyl, dimethylaminomethyl, and 2-aminoprop-1-yl.

As used herein, the term "cycloalkyl" means a saturated or unsaturated nonaromatic hydrocarbon ring group having from 3 to 14 carbon atoms, unless otherwise specified. Non-limiting examples of cycloalkyl groups include, but are not limited to, cyclopropyl, methyl-cyclopropyl, 2,2-dimethyl-cyclobutyl, 2-ethyl-cyclopentyl, and cyclohexyl.

Cycloalkyls may include multiple spiro- or fused rings. Cycloalkyl groups are optionally mono-, di-, tri-, tetra-, or penta-substituted on any position as permitted by normal valency.

As used herein, the term "cycloalkylene" refers to a divalent radical of a cycloalkyl group as described herein. Cycloalkylene is a subset of cycloalkyl, referring to the same residues as cycloalkyl, but having two points of substitution. Examples of cycloalkylene include cyclopropylene,

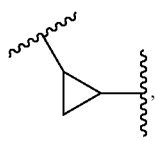

1,4-cyclohexylene,

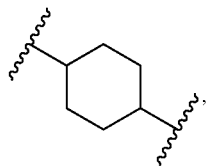 [SMILES: *C1CCC(*)CC1]

and 1,5-cyclooxylene

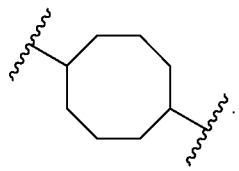 [SMILES: *C1CCCC(*)CCC1]

Cycloalkylene groups are optionally mono-, di-, tri-, tetra-, or penta-substituted on any position as permitted by normal valency. Cycloalkylene groups may mono-, di-, or tri-cyclic.

As used herein, the term "alkenyl" refers to a non-aromatic hydrocarbon radical, straight, or branched, containing at least one carbon-carbon double bond, and having from 2 to 10 carbon atoms unless otherwise specified. Up to five carbon-carbon double bonds may be present in such groups. For example, "$C_2$-$C_6$" alkenyl is defined as an alkenyl radical having from 2 to 6 carbon atoms. Examples of alkenyl groups include, but are not limited to, ethenyl, propenyl, butenyl, and cyclohexenyl. The straight, branched, or cyclic portion of the alkenyl group may contain double bonds and is optionally mono-, di-, tri-, tetra-, or penta-substituted on any position as permitted by normal valency. The term "cycloalkenyl" means a monocyclic hydrocarbon group having the specified number of carbon atoms and at least one carbon-carbon double bond.

As used herein, the term "alkynyl" refers to a hydrocarbon radical, straight or branched, containing from 2 to 10 carbon atoms, unless otherwise specified, and containing at least one carbon-carbon triple bond. Up to 5 carbon-carbon triple bonds may be present. Thus, "$C_2$-$C_6$ alkynyl" means an alkynyl radical having from 2 to 6 carbon atoms. Examples of alkynyl groups include, but are not limited to, ethynyl, 2-propynyl, and 2-butynyl. The straight or branched portion of the alkynyl group may be optionally mono-, di-, tri-, tetra-, or penta-substituted on any position as permitted by normal valency.

As used herein, "alkoxyl" or "alkoxy" refers to —O-alkyl radical having the indicated number of carbon atoms. For example, $C_{1-6}$ alkoxy is intended to include $C_1$, $C_2$, $C_3$, $C_4$, $C_5$, and $C_6$ alkoxy groups. For example, $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "keto" refers to any alkyl, alkenyl, alkynyl, cycloalkyl, cycloalkenyl, heterocyclyl, heteroaryl, or aryl group as defined herein attached through a carbonyl bridge. Examples of keto groups include, but are not limited to, alkanoyl (e.g., acetyl, propionyl, butanoyl, pentanoyl, or hexanoyl), alkenoyl (e.g., acryloyl) alkynoyl (e.g., ethynoyl, propynoyl, butynoyl, pentynoyl, or hexynoyl), aryloyl (e.g., benzoyl), heteroaryloyl (e.g., pyrroloyl, imidazoloyl, quinolinoyl, or pyridinoyl).

As used herein, "alkoxycarbonyl" refers to any alkoxy group as defined above attached through a carbonyl bridge (i.e., —C(O)O-alkyl). Examples of alkoxycarbonyl groups include, but are not limited to, methoxycarbonyl, ethoxycarbonyl, iso-propoxycarbonyl, n-propoxycarbonyl, t-butoxycarbonyl, benzyloxycarbonyl, or n-pentoxycarbonyl.

As used herein, "aryloxycarbonyl" refers to any aryl group as defined herein attached through an oxycarbonyl bridge (i.e., —C(O)O-aryl). Examples of aryloxycarbonyl groups include, but are not limited to, phenoxycarbonyl and naphthyloxycarbonyl.

As used herein, "heteroaryloxycarbonyl" refers to any heteroaryl group as defined herein attached through an oxycarbonyl bridge (i.e., —C(O)O-heteroaryl). Examples of heteroaryloxycarbonyl groups include, but are not limited to, 2-pyridyloxycarbonyl, 2-oxazolyloxycarbonyl, 4-thiazolyloxycarbonyl, or pyrimidinyloxycarbonyl.

As used herein, "aryl" or "aromatic" means any stable monocyclic or polycyclic carbon ring of up to 6 atoms in each ring, wherein at least one ring is aromatic. Examples of aryl groups include, but are not limited to, phenyl, naphthyl, anthracenyl, tetrahydronaphthyl, indanyl, and biphenyl. In cases where the aryl substituent is bicyclic and one ring is non-aromatic, it is understood that attachment is via the aromatic ring. Aryl groups are optionally mono-, di-, tri-, tetra-, or penta-substituted on any position as permitted by normal valency.

As used herein, the term "arylene" refers to a divalent radical of an aryl group as described herein. Arylene is a subset of aryl, referring to the same residues as aryl, but having two points of substitution. Examples of arylene include phenylene, which refers to a divalent phenyl group. Arylene groups are optionally mono-, di-, tri-, tetra-, or penta-substituted on any position as permitted by normal valency.

As used herein, the term "halo" refers to a halogen radical. For instance, "halo" may refer to a fluorine (F), chlorine (Cl), bromine (Br), or an iodine (I) radical.

As used herein, the term "heteroaryl" represents a stable monocyclic or polycyclic ring of up to 7 atoms in each ring, wherein at least one ring is aromatic and contains from 1 to 4 heteroatoms selected from the group consisting of O, N, and S. Examples of heteroaryl groups include, but are not limited to, acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, and tetrahydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring. Heteroaryl groups are optionally mono-, di-, tri-, tetra- or penta-substituted on any position as permitted by normal valency.

As used herein, the term "heteroarylene" refers to a divalent radical of a heteroaryl group as described herein. Heteroarylene is a subset of heteroaryl, referring to the same residues as heteroaryl, but having two points of substitution. Examples of heteroaryl include pyridinylene, pyrimidinylene, and pyrrolylene. Heteroarylene groups are optionally mono-, di-, tri-, tetra-, or penta-substituted on any position as permitted by normal valency.

As used herein, the term "heterocycle," "heterocyclic," or "heterocyclyl" means a 3- to 14-membered aromatic or nonaromatic heterocycle containing from 1 to 4 heteroatoms selected from the group consisting of O, N, and S, including polycyclic groups. As used herein, the term "heterocyclic" is also considered to be synonymous with the terms "heterocycle" and "heterocyclyl" and is understood as also having the same definitions set forth herein. "Heterocyclyl" includes the above mentioned heteroaryls, as well as dihydro and tetrahydro analogs thereof. Examples of heterocyclyl groups include, but are not limited to, azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyridinonyl, pyrinidyl, pyrimidinonyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydrooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom. Heterocyclyl groups are optionally mono-, di-, tri-, tetra-, or penta-substituted on any position as permitted by normal valency.

As used herein, the term "heterocycloalkyl" means a 3- to 14-membered nonaromatic heterocycle containing from to 4 heteroatoms selected from the group consisting of O, N, and S, including polycyclic groups. Examples of heterocyclyl groups include, but are not limited to, azetidinyl, oxopiperazinyl, oxopyrrolidinyl, oxomorpholinyl, oxetanyl, pyranyl, pyridinonyl, pyrimidinonyl, tetrahydropyranyl, tetrahydrofuranyl, tetrahydrothiopyranyl, tetrahydroisoquinolinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, dioxidothiomorpholinyl, and tetrahydrothienyl, and N-oxides thereof. Attachment of a heterocycloalkyl substituent can occur via a carbon atom or via a heteroatom. Heterocyclyl groups are optionally mono-, di-, tri-, tetra-, or penta-substituted on any position as permitted by normal valency.

As used herein, the term "heterocycloalkylene" refers to a divalent radical of a heterocycloalkyl group as described herein. Heterocycloalkylene is a subset of heterocycloalkyl, referring to the same residues as heterocycloalkyl, but having two points of substitution. Examples of heterocycloalkylene include piperidinylene, azetidinylene, and tetrahydrofuranylene. Heterocycloalkylene groups are optionally mono-, di-, tri-, tetra-, or penta-substituted on any position as permitted by normal valency.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means that delivering the RNAi agent to the cell in a manner that enables the RNAi agent to have the expected biological activity, e.g., sequence-specific inhibition of gene expression.

Unless stated otherwise, use of the symbol

as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center." When the compounds described herein contain olefinic double bonds or other centers of geometric asymmetry for which the isomeric structure is not specifically defined, it is intended that the compounds can include both E and Z geometric isomers individually or in a mixture. The compounds of Formula I or their pharmaceutically acceptable salts, for example, are meant to include all possible isomers, as well as their racemic and optically pure forms. Likewise, unless expressly stated otherwise, all tautomeric forms are also intended to be included.

As used herein, a linking group is one or more atoms that connects one molecule or portion of a molecule to another to second molecule or second portion of a molecule. In the art, the terms linking group and spacers are sometimes used interchangeably. Similarly, as used in the art, the term scaffold is sometimes used interchangeably with a linking group. In some embodiments, a linking group can include a peptide-cleavable linking group. In some embodiments, a linking group can include or consist of the peptide phenylalanine-citrulline-phenylalanine-proline. In some embodiments, a linking group can include or consist of a PEG group.

As used herein, the term "linked" when referring to the connection between two molecules means that two molecules are joined by a covalent bond or that two molecules are associated via noncovalent bonds (e.g., hydrogen bonds or ionic bonds). In some examples, where the term "linked" refers to the association between two molecules via noncovalent bonds, the association between the two different molecules has a $K_D$ of less than $1\times10^{-4}$ M (e.g., less than $1\times10^{-5}$ M, less than $1\times10^{-6}$ M, or less than $1\times10^{-7}$ M) in physiologically acceptable buffer (e.g., phosphate buffered saline). Unless stated, the term linked as used herein may refer to the connection between a first compound and a second compound either with or without any intervening atoms or groups of atoms.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the pH of the environment, as would be readily understood by the person of ordinary skill in the art.

Structures may be depicted as having a bond "floating" over a ring structure to indicate binding to any carbon or heteroatom on the ring as permitted by valency. For example, the structure

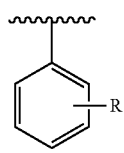

indicates that R may replace any hydrogen atom at any of the five available positions on the ring. "Floating" bonds may also be used in bicyclic structures to indicate a bond to any position on either ring of the bicycle as permitted by valency. In the case of bicycles, the bond will be shown "floating" over both rings, for example,

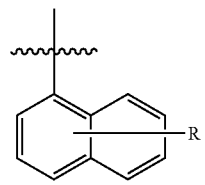

indicates that R may replace any hydrogen atom at any of the seven available positions on the ring.

As used in a claim herein, the phrase "consisting of" excludes any element, step, or ingredient not specified in the claim. hen used in a claim herein, the phrase "consisting essentially of" limits the scope of a claim to the specified materials or steps and those that do not materially affect the basic and novel characteristic(s) of the claimed invention.

Described herein is the use of the described αvβ6 integrin ligands to target and deliver a cargo molecule to a cell that expresses αvβ6 integrin. The cargo molecule can be delivered to a cell in vitro, in situ, ex vivo, or in vivo.

In some embodiments of Formula Ib, the linking group is a PEG group containing 2-20 ethylene glycol units.

In some embodiments of Formula Ib, the reactive group is an azide.

In some embodiments, the αv6 integrin ligand have structures that include, consist of, or consist essentially of any of the structures represented by the following:

(Structure 1)

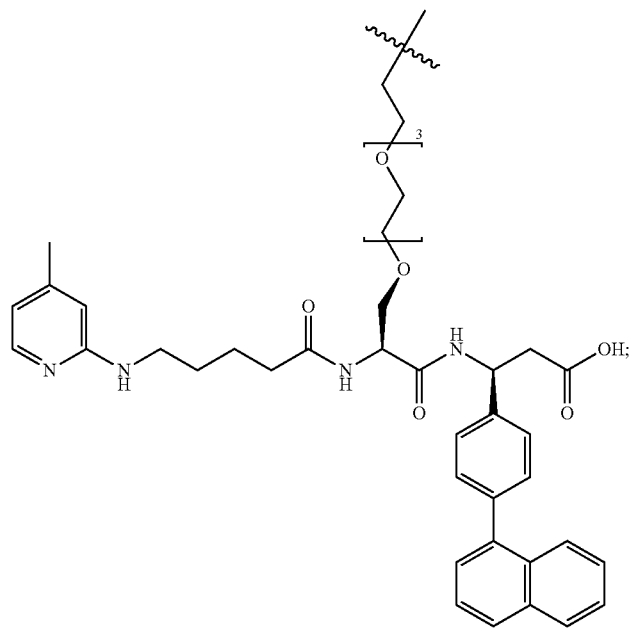

(Structure 2)
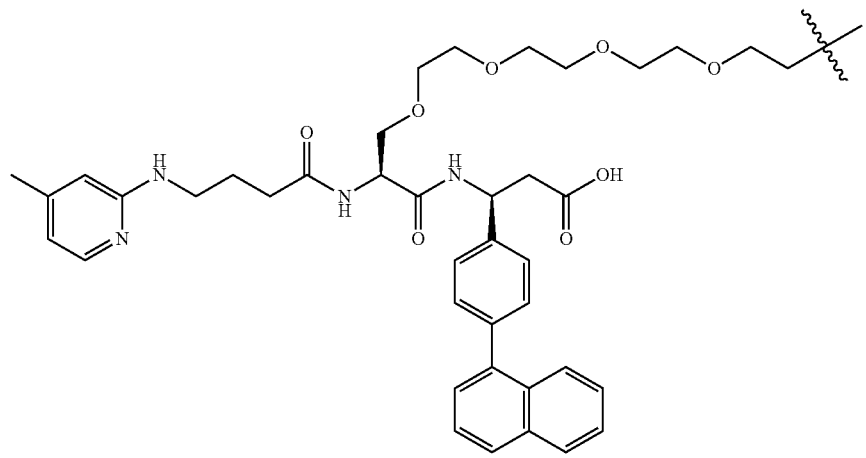
;
(Structure 5)
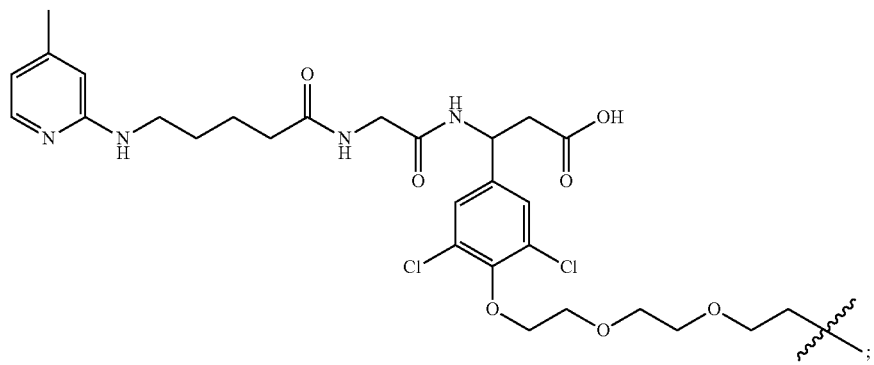
;
(Structure 5.1)
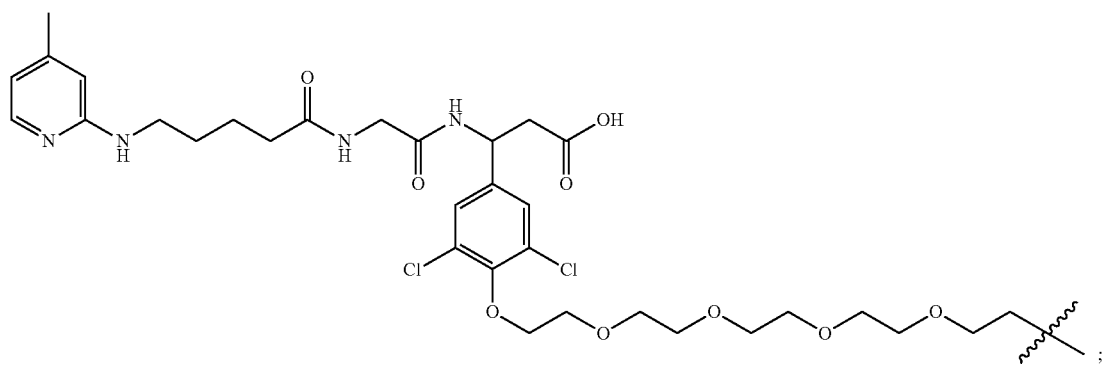
;
(Structure 5.2)
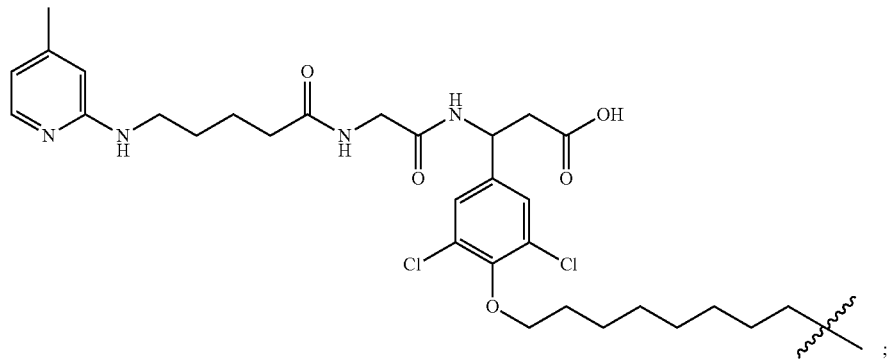
;

-continued
(Structure 6)
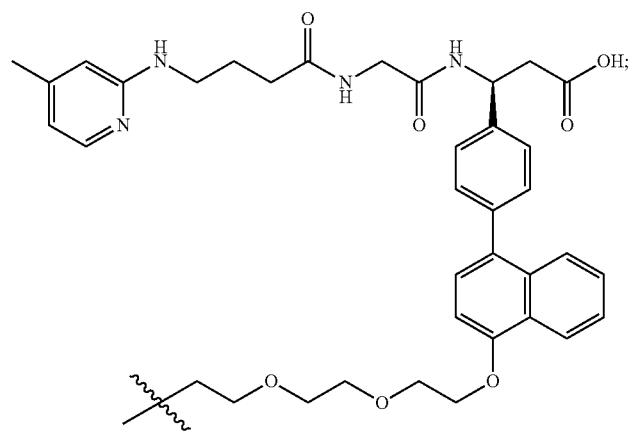
(Structure 6.1)
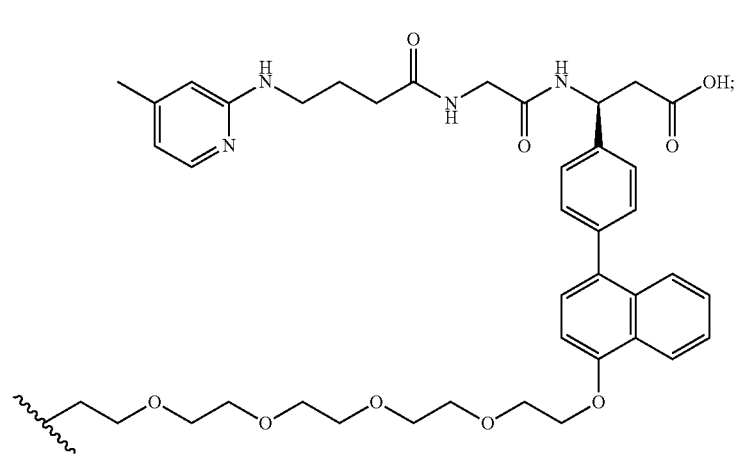
(Structure 6.2
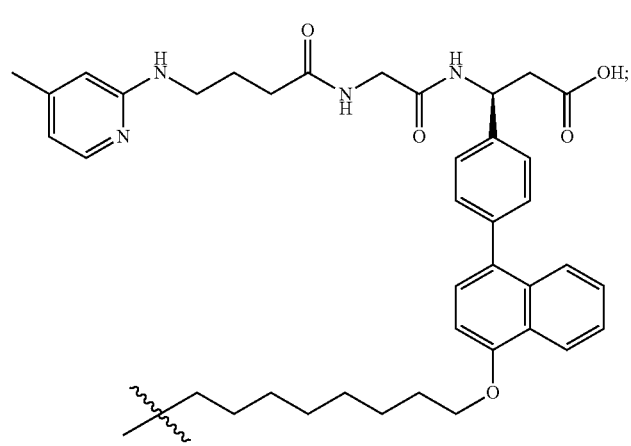

(Structure 6.3)
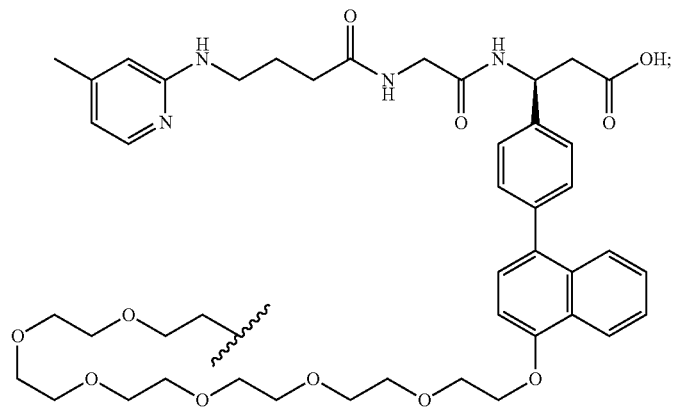
(Structure 6.4)
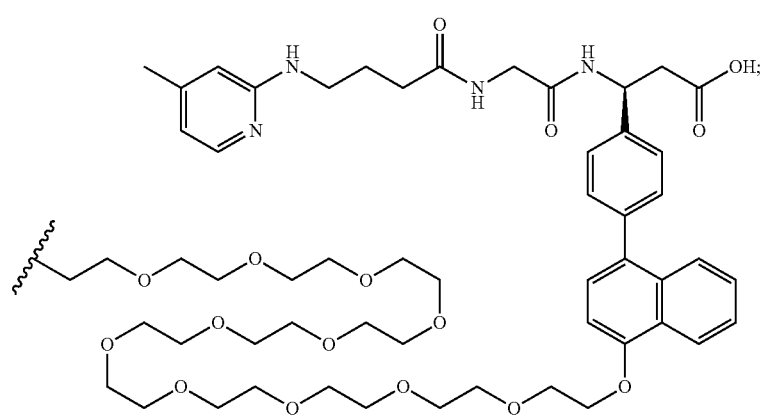
(Structure 7)
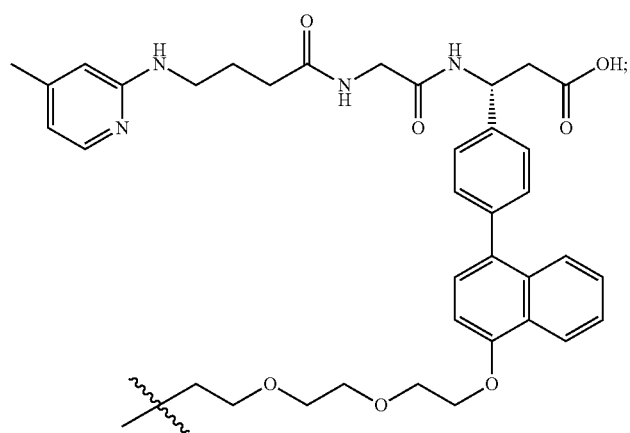

(Structure 8)
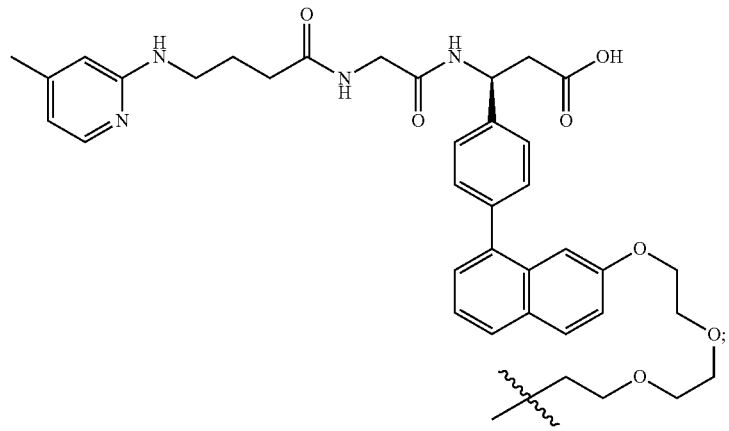
(Structure 9)
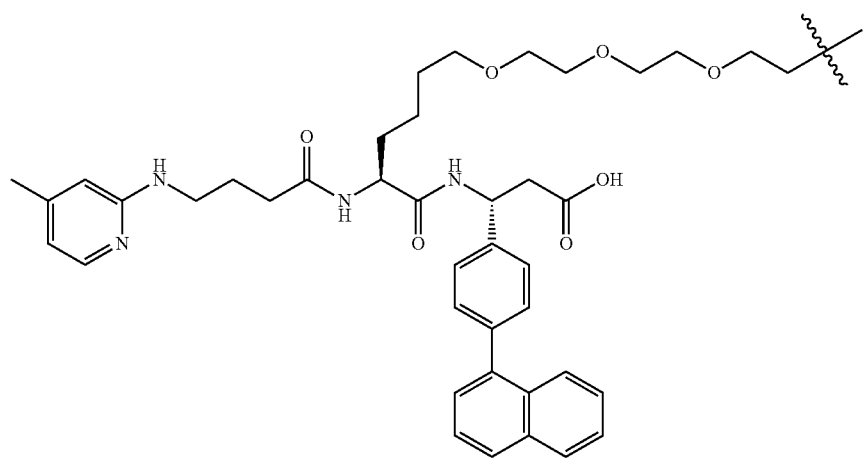
;
(Structure 10)
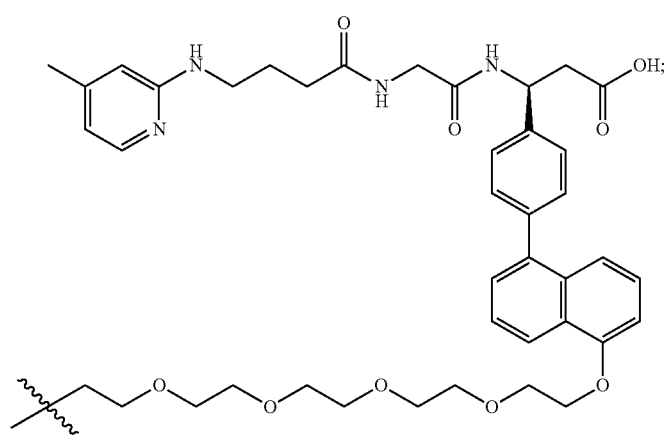

-continued
(Structure 11)
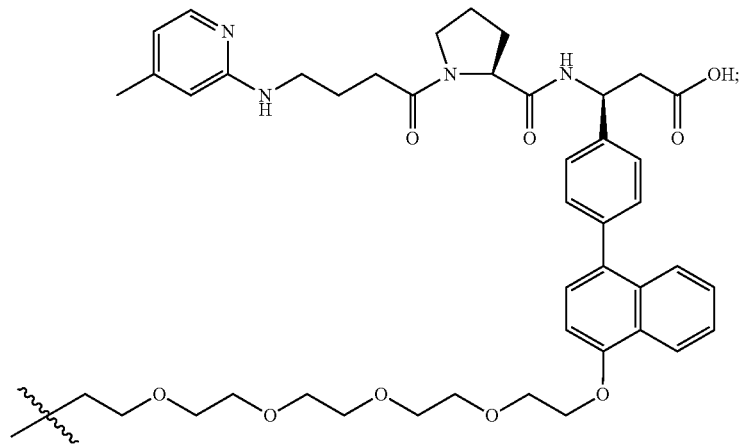
(Structure 12)
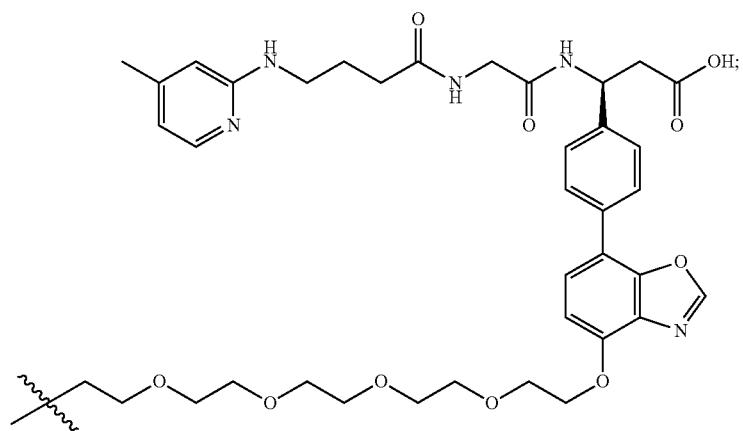
(Structure 13)
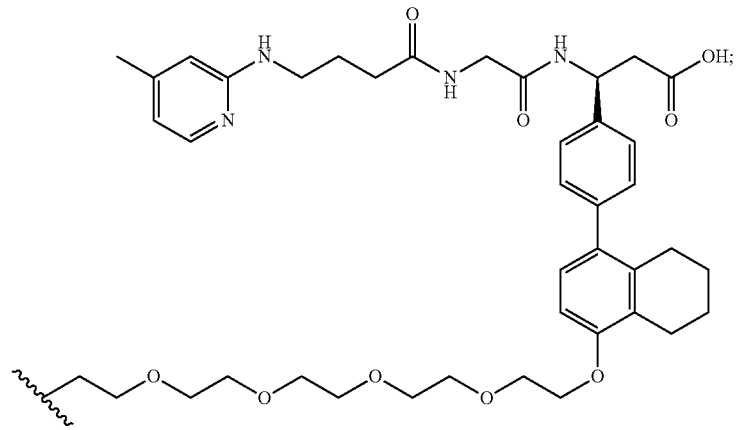

(Structure 14)
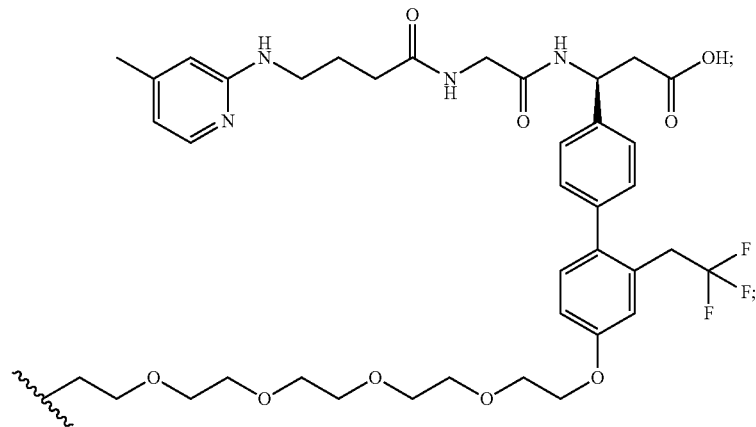
(Structure 15)
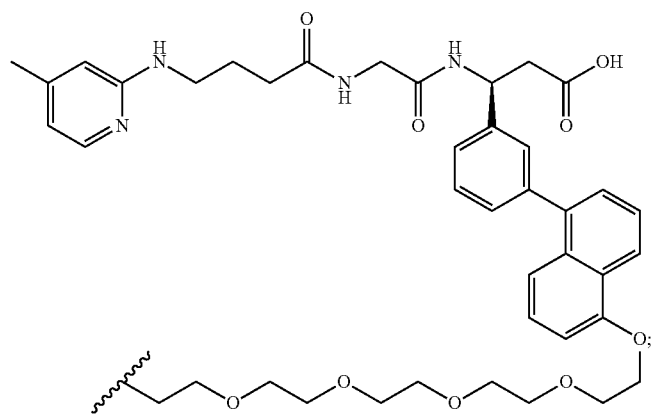
(Structure 16)
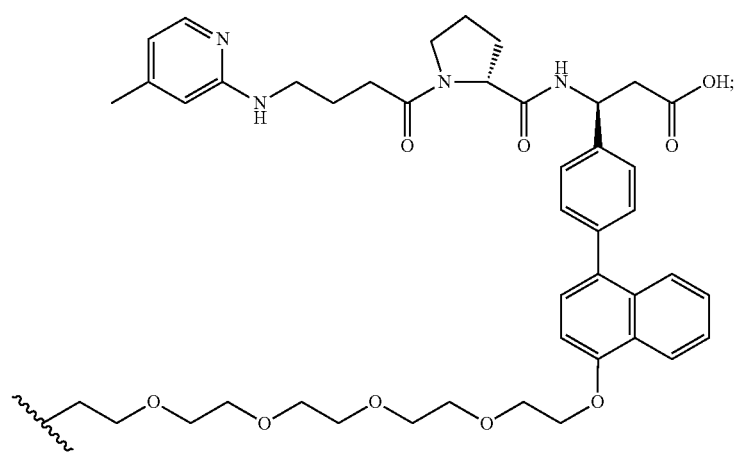

(Structure 17)
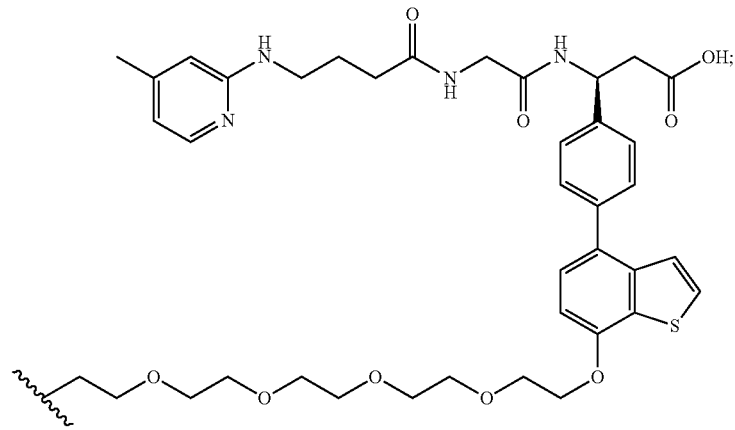
(Structure 18)
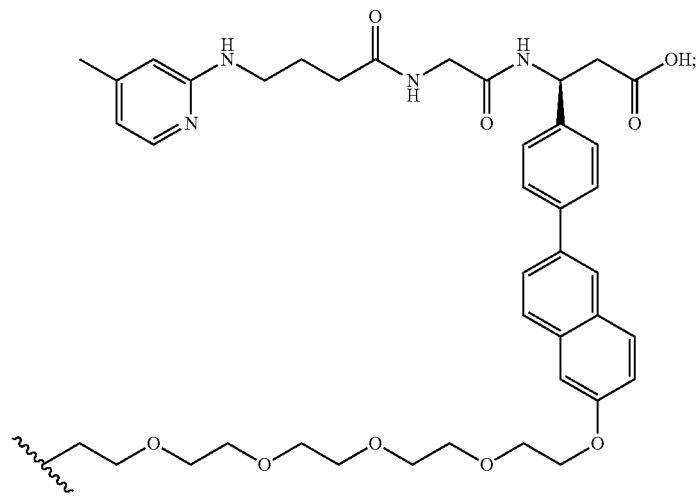
(Structure 19)
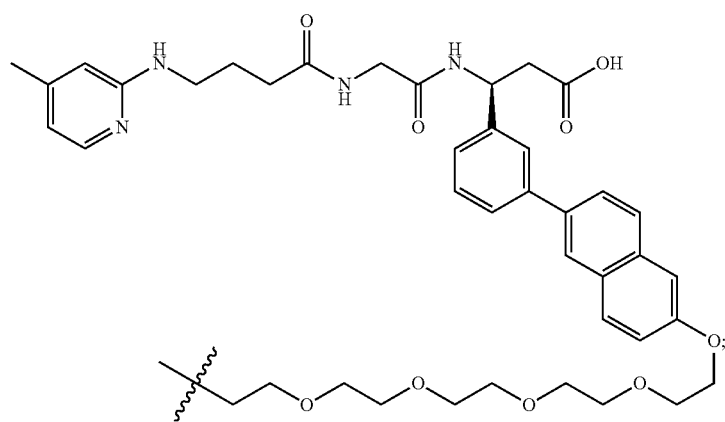

-continued
(Structure 20)
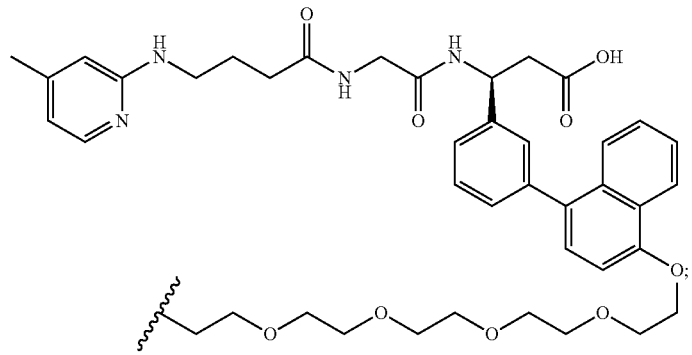
(Structure 22)
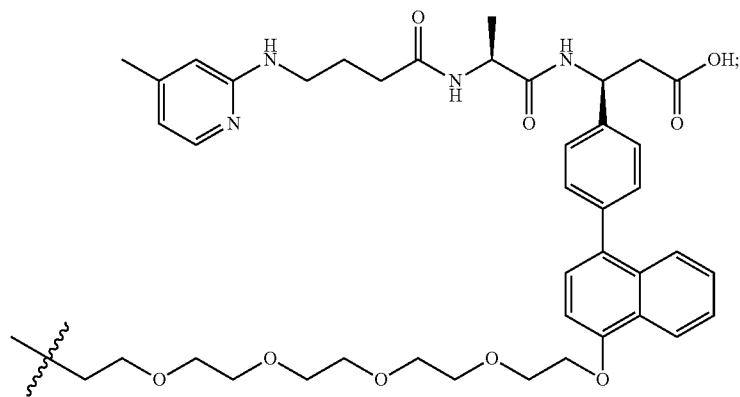
(Structure 23)
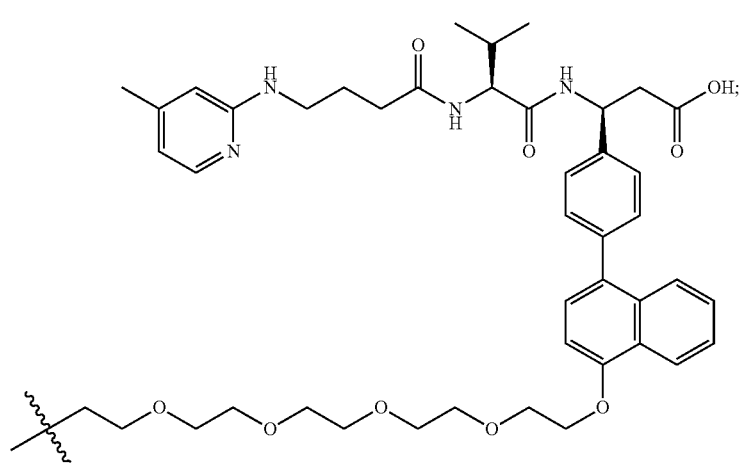

-continued
(Structure 24)
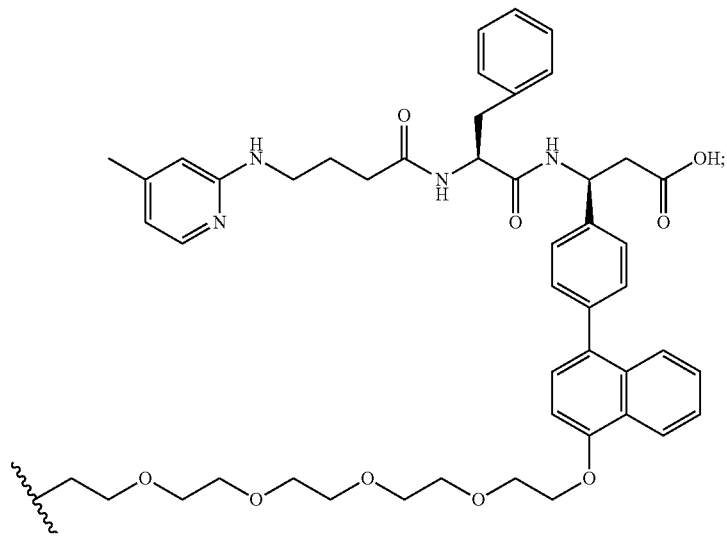
(Structure 25)
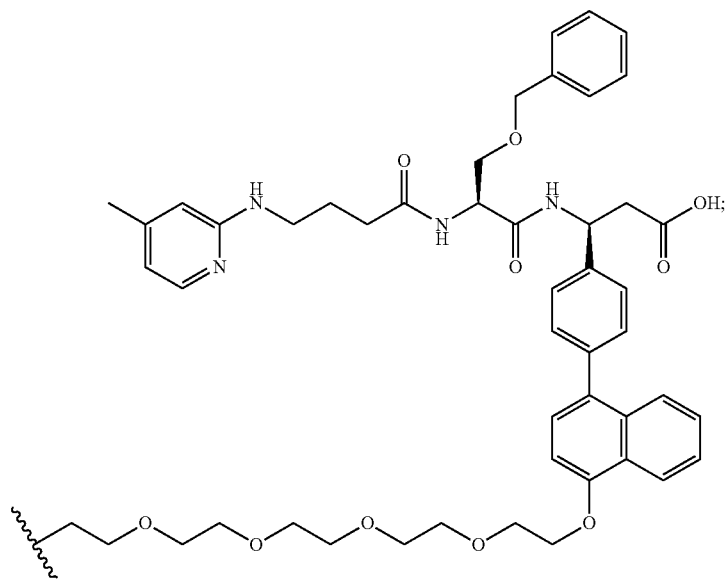
(Structure 27)
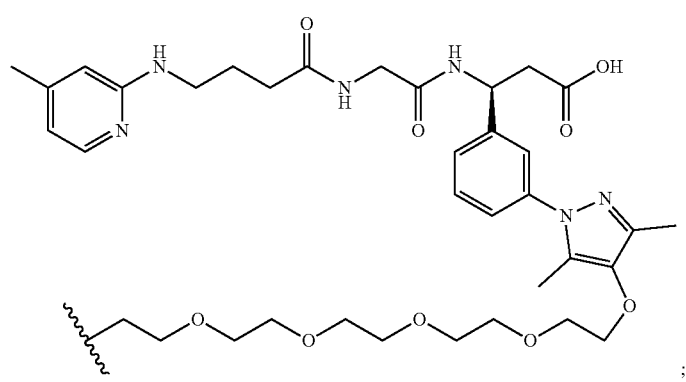

(Structure 29)
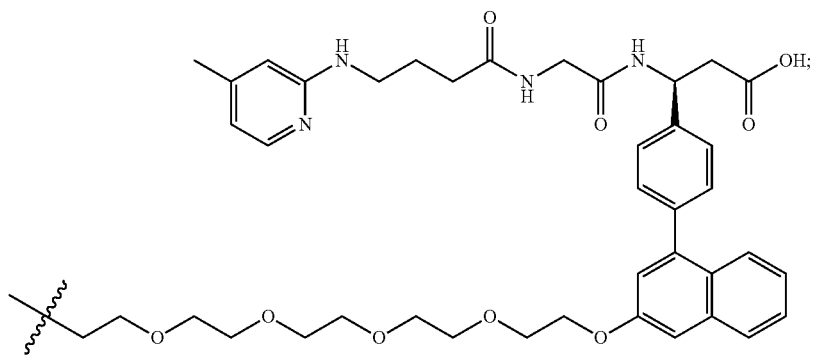
(Structure 30)
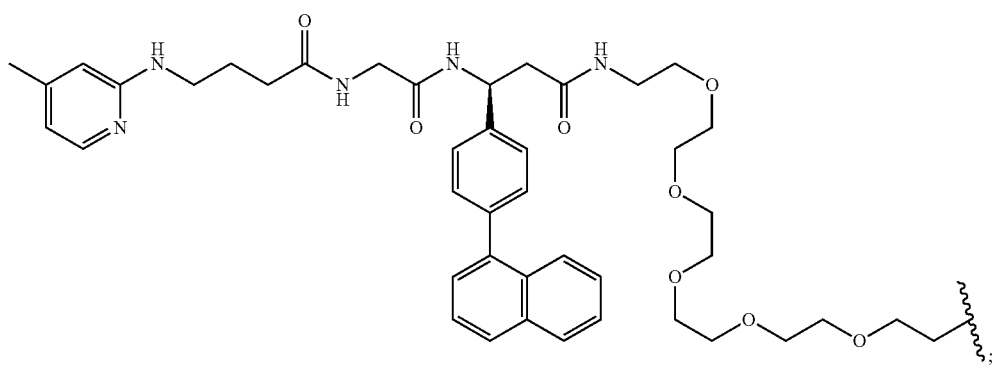
(Structure 31)
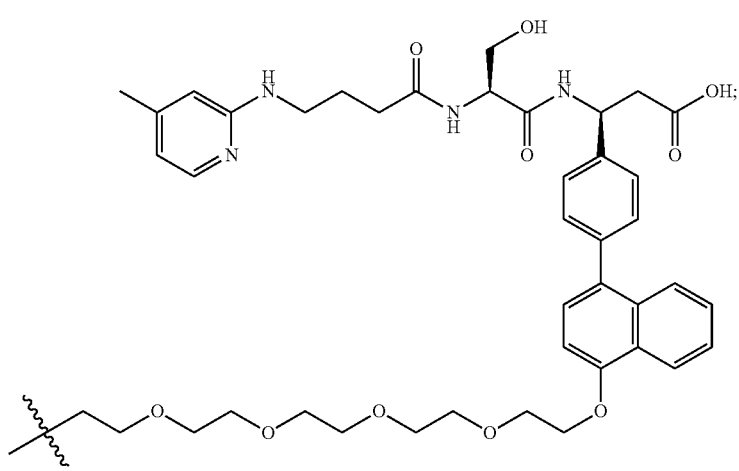

(Structure 32)
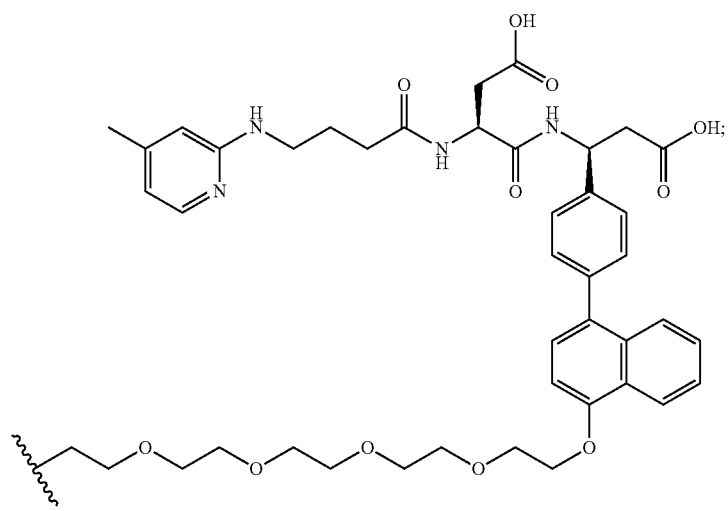
(Structure 33)
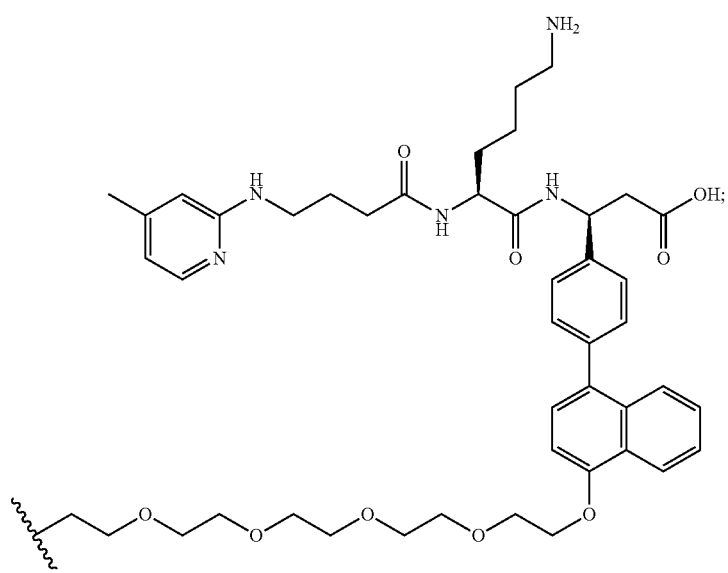

(Structure 34)
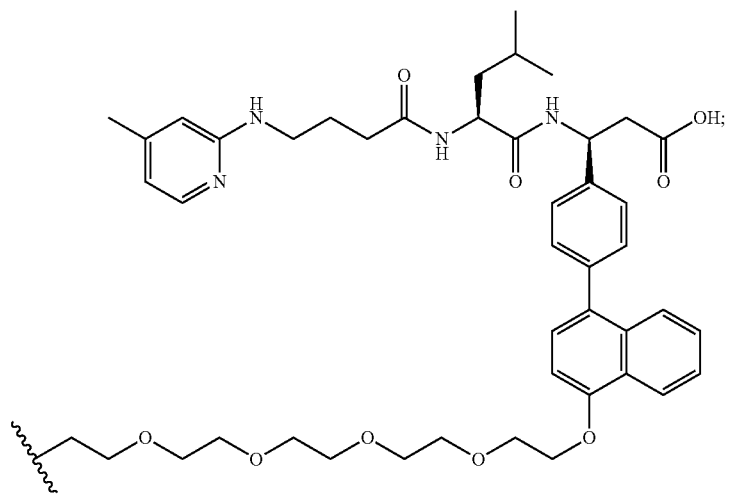
(Structure 35)
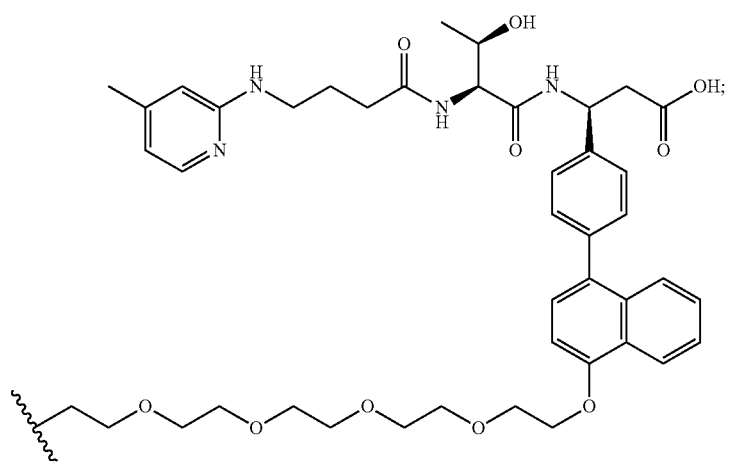

(Structure 36)

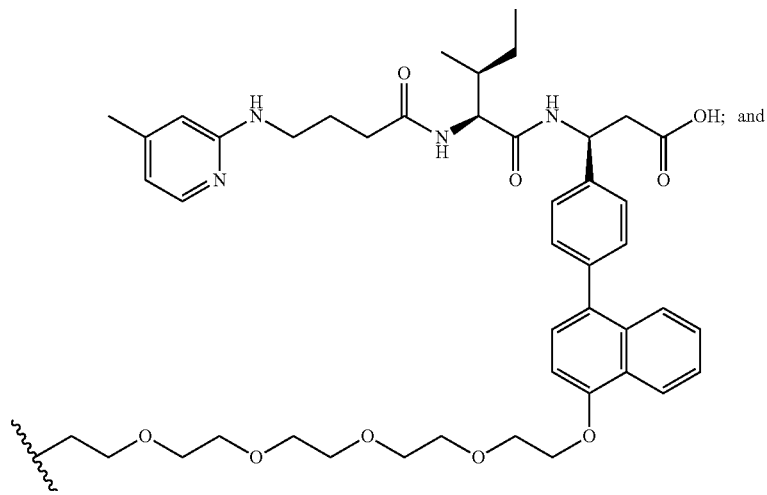

and (Structure 37)

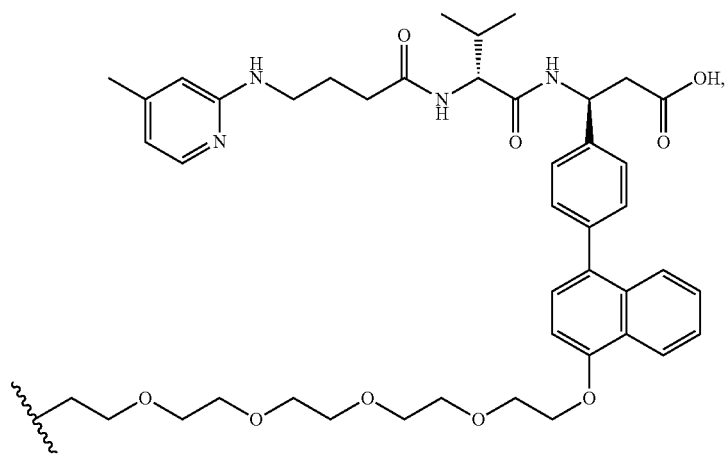

or pharmaceutically acceptable salts thereof, wherein ⸾ indicates the point of attachment to a moiety comprising a cargo molecule.

In some embodiments, an αvβ6 integrin ligand disclosed herein can be conjugated to one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30) cargo molecules (e.g., any of the cargo molecules described herein or known in the art).

In some embodiments, more than one αvβ6 integrin ligand disclosed herein (e.g., 2, 3, 4, 5, 6, 7, 8, or 1 to 8, 1 to 7, 1 to 6, 1 to 5, 1 to 4, 1 to 3, 1 to 2, 2 to 8, 2 to 7, 2 to 6, 2 to 5, 2 to 4, 2 to 3, 3 to 8, 3 to 7, 3 to 6, 3 to 5, 3 to 4, 4 to 8, 4 to 7, 4 to 6, or 4 to 5 αvβ6 integrin ligands) can be conjugated to one cargo molecule (e.g., any of the cargo molecules described herein or known in the art).

In some embodiments, the αvβ6 integrin ligands disclosed herein are optionally conjugated to one or more cargo molecules via a linking group, such as, for example, a polyethylene glycol (PEG) group.

In some embodiments, the αvβ6 integrin ligands disclosed herein are optionally conjugated to one or more cargo molecules via a scaffold that includes at least one attachment point for each ligand and at least one attachment point for each cargo molecule. In some embodiments, the αvβ6 integrin ligands comprise, consist of, or consist essentially of, one cargo molecule. In some embodiments, the αvβ6 integrin ligands comprise, consist of, or consist essentially of, more than one cargo molecule.

In some embodiments, the αvβ6 integrin ligand comprises, consists of, or consists essentially of, any of Structure 1, Structure 2, Structure 5, Structure 5.1, Structure 5.2, Structure 6, Structure 6.1, Structure 6.2, Structure 6.3, Structure 6.4, Structure 7, Structure 8, Structure 9, Structure 10, Structure 11, Structure 12, Structure 13, Structure 14, Structure 15, Structure 16, Structure 17, Structure 18, Structure 19, Structure 20, Structure 22, Structure 23, Structure 24, Structure 25, Structure 27, Structure 29, Structure 30, Structure 31, Structure 32, Structure 33, Structure 34, Structure 35, Structure 36, or Structure 37, each as disclosed herein.

Any of the αvβ6 integrin ligands disclosed herein can be linked to a cargo molecule, a reactive group, and/or a protected reactive group. A reactive group can be used to facilitate conjugation of the αvβ6 integrin ligand to a cargo molecule. The αvβ6 integrin ligands disclosed herein can increase targeting of a cargo molecule to an αvβ6 integrin or to a cell expressing an αvβ6 integrin. A cargo molecule can be, but is not limited to, a pharmaceutically active ingredient or compound, a prodrug, or another substance with known therapeutic benefit. In some embodiments, a cargo molecule can be, but is not limited to, a small molecule, an antibody, an antibody fragment, an immunoglobulin, a monoclonal antibody, a label or marker, a lipid, a natural or modified oligonucleotide-based compound (e.g., an antisense oligonucleotide or an RNAi agent), a natural or modified nucleic acid, a peptide, an aptamer, a polymer, a polyamine, a protein, a toxin, a vitamin, a polyethylene glycol, a hapten, a digoxigenin, a biotin, a radioactive atom or molecule, or a fluorophore. In some embodiments, a cargo molecule includes a pharmaceutically active ingredient or a prodrug. In some embodiments, a cargo molecule includes an oligonucleotide-based compound as a pharmaceutically active ingredient. In some embodiments, a cargo molecule includes an RNAi agent as a pharmaceutically active ingredient.

In one aspect, the invention provides for a structure comprising an αvβ6 integrin ligand as described herein, a linking group, and a scaffold, wherein the scaffold is bound to a cargo molecule. In some embodiments, the structure may comprise the ligand in monodentate form. In some embodiments, the structure may comprise the ligand in bidentate form. In some embodiments, the structure may comprise the ligand in tridentate form. In some embodiments, the structure may comprise the ligand in tetradentate form.

In some embodiments, an αvβ6 integrin ligand disclosed herein comprises the following structure:

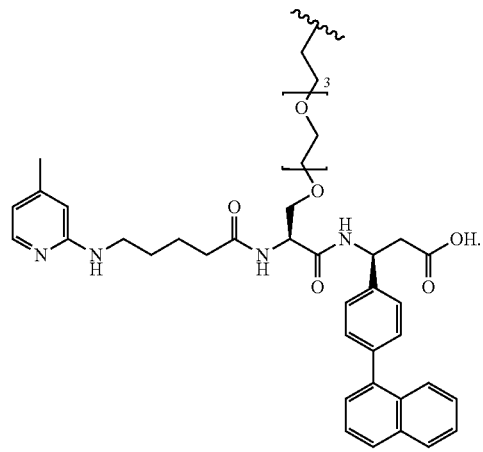

(Structure 1)

In some embodiments, the αvβ6 integrin ligand of Structure 1 is linked to one or more cargo molecules (e.g., RNAi agent(s)).

In some embodiments, an αvβ6 integrin ligand can be synthesized to include a reactive group, a protected reactive group, or a cargo molecule, and comprises the following structure:

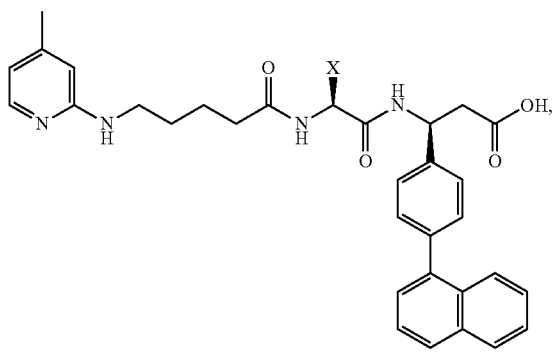

(Structure 1a)

wherein X includes a reactive group, a protected reactive group, or a cargo molecule (e.g., an RNAi agent).

In some embodiments, an αvβ6 integrin ligand can be synthesized to include a polyethylene glycol (PEG)-azide reactive group, and comprises the following structure:

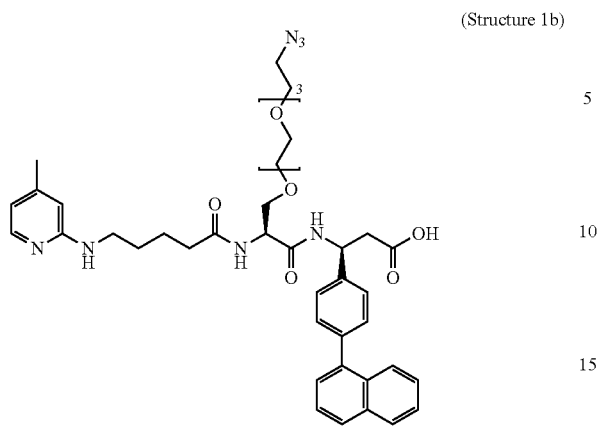

(Structure 1b)

In some embodiments, an αvβ6 integrin ligand disclosed herein comprises the following structure:

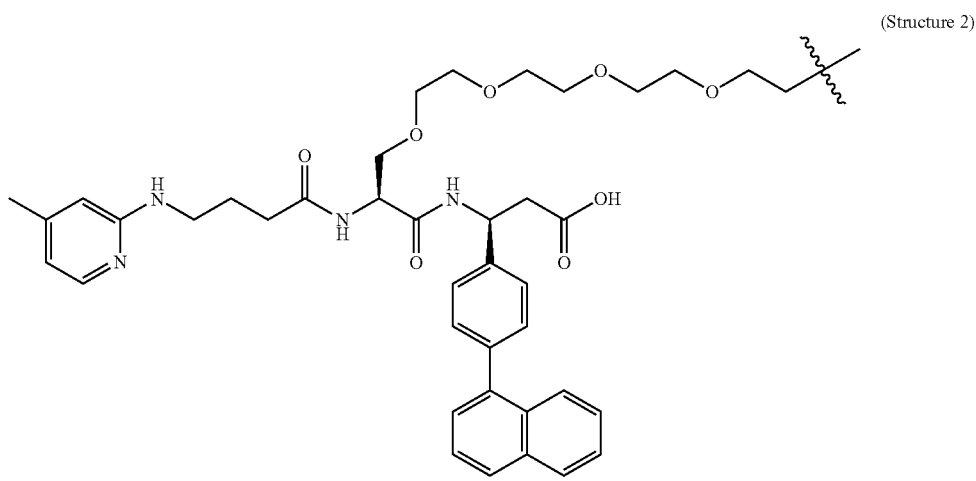 [SMILES: *CCOCCOCCOCCOC[C@H](NC(=O)CCCNc1cc(C)ccn1)C(=O)N[C@@H](CC(=O)O)c1ccc(-c2cccc3ccccc23)cc1]

(Structure 2)

In some embodiments, the αvβ6 integrin ligand of Structure 2 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

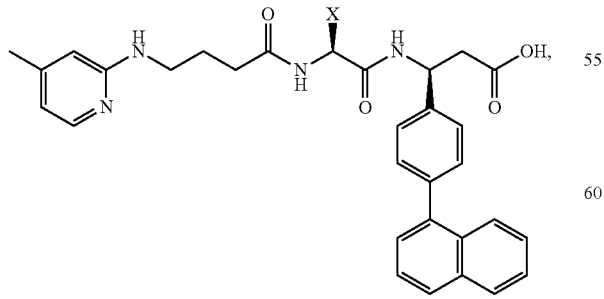

(Structure 2a)

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

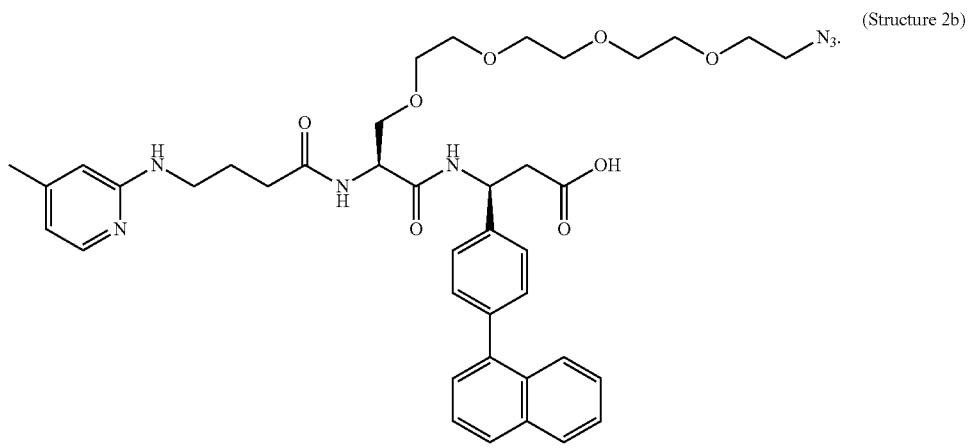 [SMILES: Cc1ccnc(NCCCC(=O)N[C@@H](COCCOCCOCCOCCN=[N+]=[N-])C(=O)N[C@@H](CC(=O)O)c2ccc(-c3cccc4ccccc34)cc2)c1]
(Structure 2b)

In some embodiments, the αvβ6 integrin ligand can be synthesized to include a polyethylene glycol (PEG)-azide reactive group, and comprises the following structure:

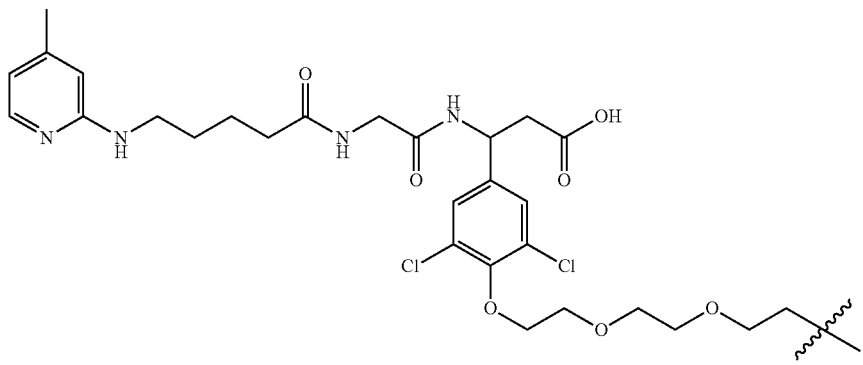
(Structure 5)

In some embodiments, the αvβ6 integrin ligand of Structure 5 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

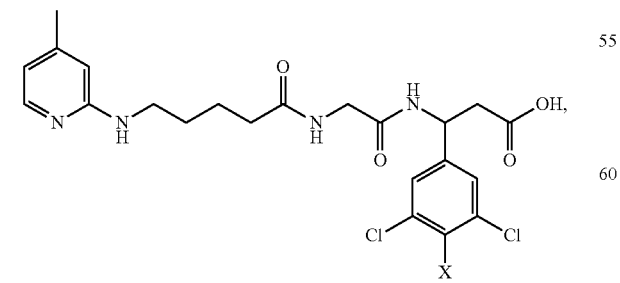
(Structure 5a)

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 5b)

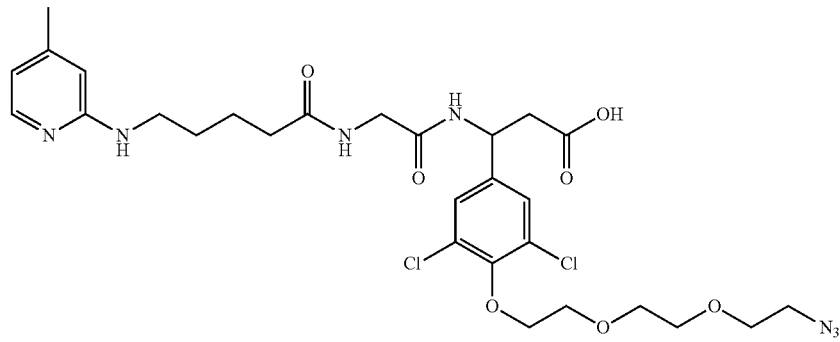

In some embodiments, an αvβ6 integrin ligand disclosed herein comprises the following structure:

(Structure 5.1)

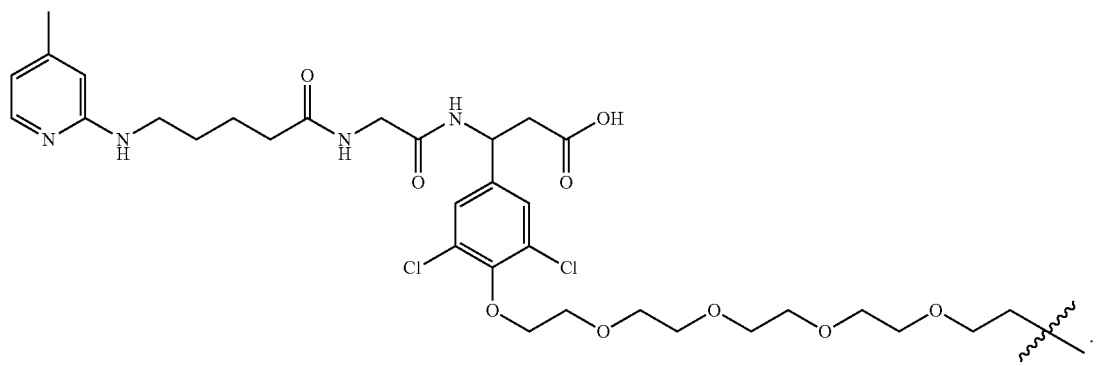

In the embodiments, the length of the PEG in the PEG-azide reactive group may be varied. In some embodiments, the αvβ6 integrin ligands of Structure 5.1 can be synthesized to include a polyethylene glycol (PEG)-azide reactive group and comprises the following structure:

(Structure 5.1b)

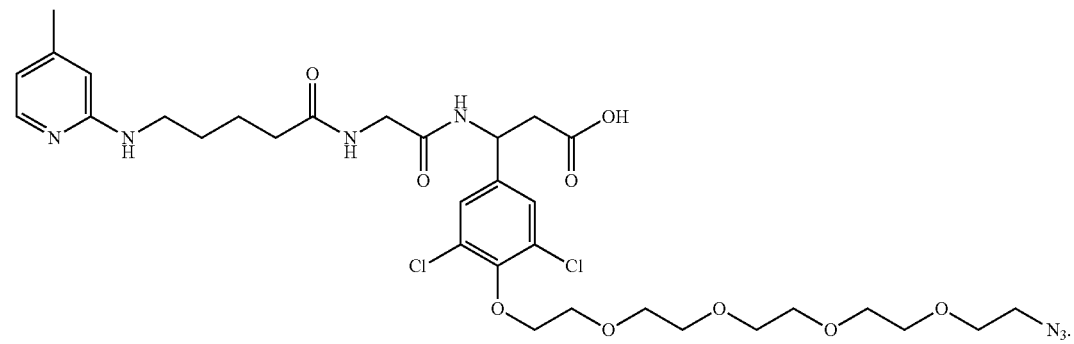

A reactive group (or protected reactive group) can be used to facilitate the conjugation of the αvβ6 integrin ligand to a molecule of interest, e.g., to a cargo molecule (either directly or via one or more scaffolds and/or linker).

In some embodiments, an αvβ6 integrin ligand disclosed herein comprises the following structure:

(Structure 5.2)

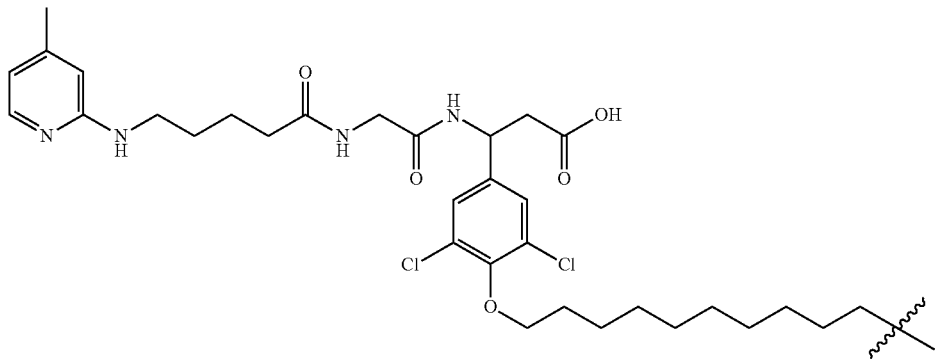

In some embodiments, the αvβ6 integrin ligand of Structure 5.2 is linked to one or more cargo molecules (e.g., RNAi agent(s)).

In some embodiments, a PEG-azide reactive group may be replaced with an alkyl-azide reactive group. In some embodiments, the αvβ6 integrin ligand can be synthesized to include an alkyl-azide reactive group and comprises the following structure:

(Structure 5.2b)

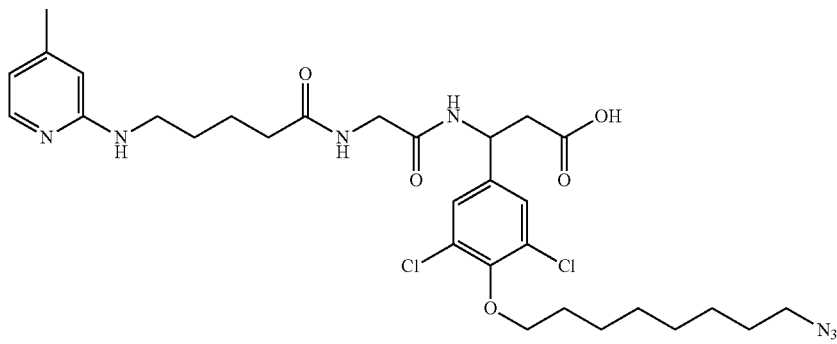

In some embodiments, an αvβ6 integrin ligand disclosed herein comprises the following structure:

(Structure 6)

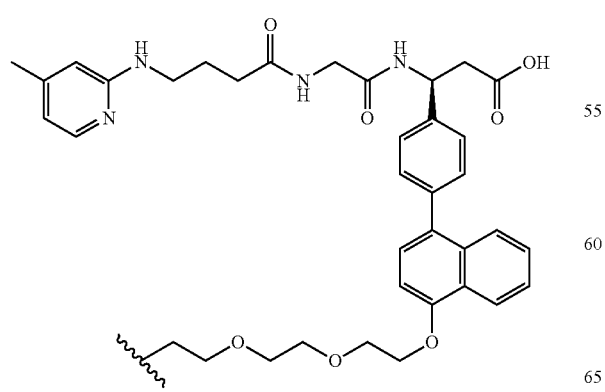

In some embodiments, the αvβ6 integrin ligand of Structure 6 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 6a)

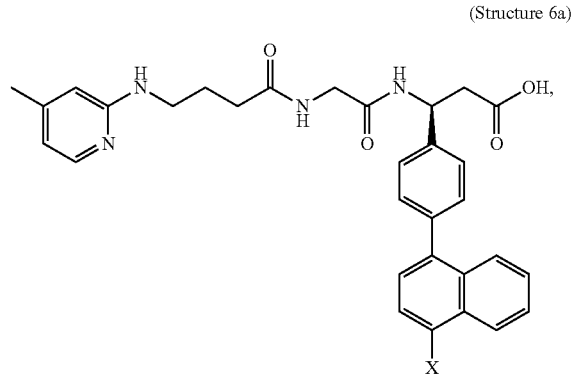

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 6b)

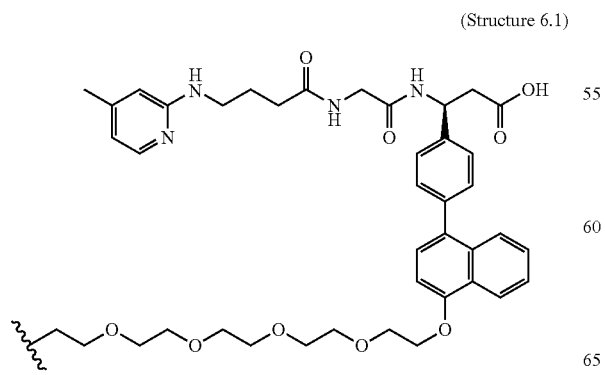

In some embodiments, an αvβ6 integrin ligand disclosed herein comprises the following structure:

(Structure 6.1)

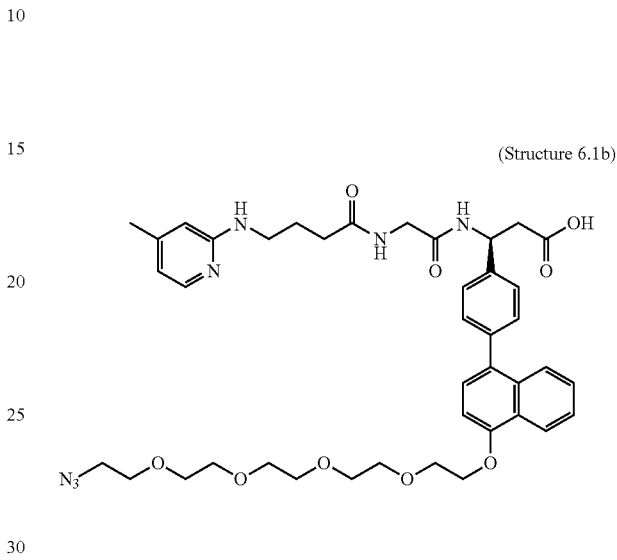

In some embodiments, the αvβ6 integrin ligand of Structure 6.1 is linked to one or more cargo molecules (e.g., RNAi agent(s)).

In the embodiments, the length of the PEG in the PEG-azide reactive group may be varied. In some embodiments, the αvβ6 integrin ligands can be synthesized to include a polyethylene glycol (PEG)-azide reactive group, and comprises the following structure:

(Structure 6.1b)

A reactive group (or protected reactive group) can be used to facilitate the conjugation of the αvβ6 integrin ligand to a molecule of interest, e.g., to a cargo molecule (either directly or via one or more scaffolds and/or linker).

In some embodiments, an αvβ6 integrin ligand disclosed herein comprises the following structure:

(Structure 6.2)

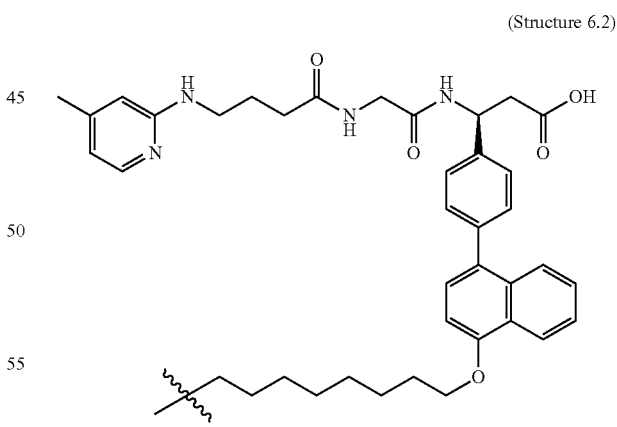

In some embodiments, the αvβ6 integrin ligand of Structure 6.2 is linked to one or more cargo molecules (e.g., RNAi agent(s)).

In some embodiments, a PEG-azide reactive group may be replaced with an alkyl-azide reactive group. In some embodiments, the αvβ6 integrin ligand can be synthesized to include an alkyl-azide reactive group, and comprises the following structure:

(Structure 6.2b)

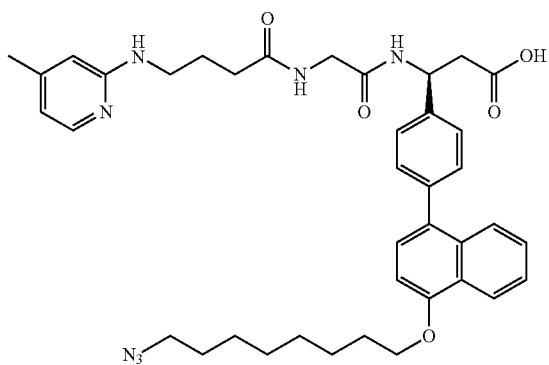

A reactive group (or protected reactive group) can be used to facilitate the conjugation of the αvβ6 integrin ligand to a molecule of interest, e.g., to a cargo molecule (either directly or via one or more scaffolds and/or linker).

In some embodiments, an αvβ6 integrin ligand disclosed herein comprises the following structure:

(Structure 6.3)

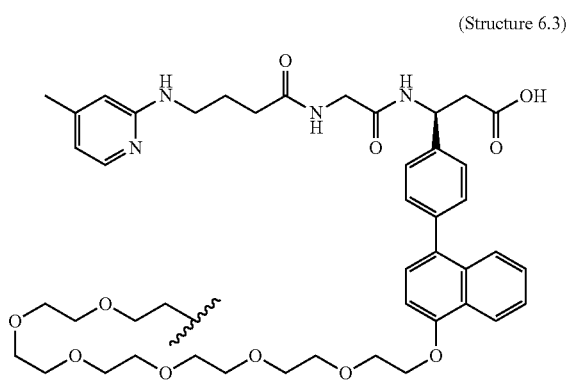 [SMILES: *CCOCCOCCOCCOCCOCCOCCOc1ccc(-c2ccc([C@H](CC(=O)O)NC(=O)CNC(=O)CCCNc3cc(C)ccn3)cc2)c2ccccc12]

In some embodiments, the αvβ6 integrin ligand of Structure 6.3 is linked to one or more cargo molecules (e.g., RNAi agent(s)).

In some embodiments, the αvβ6 integrin ligand can be synthesized to include a reactive group, a protected reactive group, or a cargo molecule. In some embodiments, the αvβ6 integrin ligands can be synthesized to include an azide reactive group and comprises the following structure:

(Structure 6.3b)

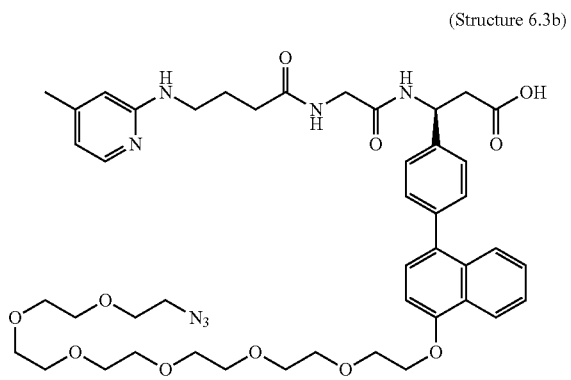 [SMILES: Cc1ccnc(NCCCC(=O)NCC(=O)N[C@@H](CC(=O)O)c2ccc(-c3ccc(OCCOCCOCCOCCOCCOCCOCCN=[N+]=[N-])c4ccccc34)cc2)c1]

In some embodiments, an αvβ6 integrin ligand disclosed herein comprises the following structure:

(Structure 6.4)

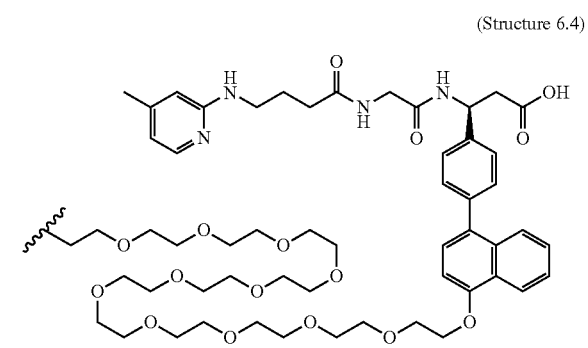 [SMILES: *CCOCCOCCOCCOCCOCCOCCOCCOCCOCCOCCOCCOc1ccc(-c2ccc([C@H](CC(=O)O)NC(=O)CNC(=O)CCCNc3cc(C)ccn3)cc2)c2ccccc12]

In some embodiments, the αvβ6 integrin ligand of Structure 6.4 is linked to one or more cargo molecules (e.g., RNAi agent(s)).

In some embodiments, the αvβ6 integrin ligand can be synthesized to include an azide reactive group and comprises the following structure:

(Structure 6.4b)

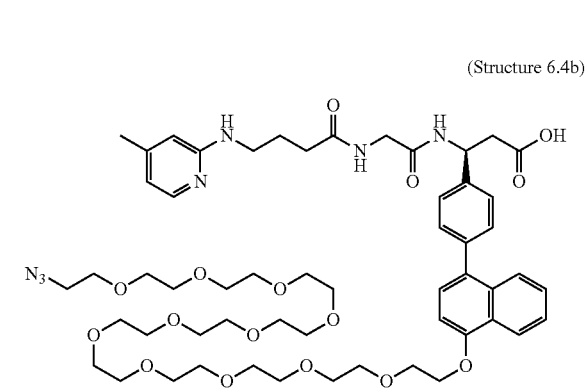 [SMILES: Cc1ccnc(NCCCC(=O)NCC(=O)N[C@@H](CC(=O)O)c2ccc(-c3ccc(OCCOCCOCCOCCOCCOCCOCCOCCOCCOCCOCCOCCN=[N+]=[N-])c4ccccc34)cc2)c1]

In some embodiments, an αvβ6 integrin ligand disclosed herein comprises the following structure:

(Structure 7)

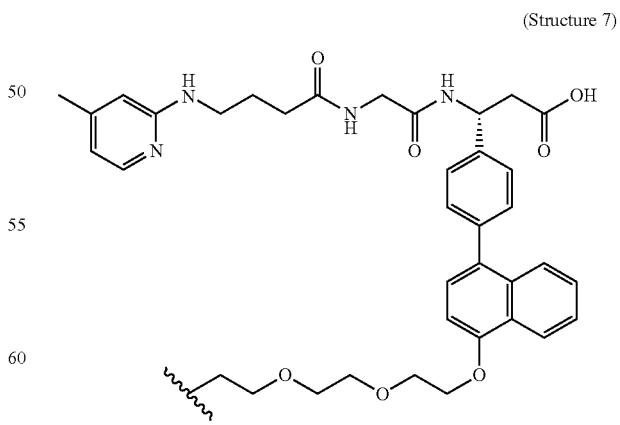

In some embodiments, the αvβ6 integrin ligand of Structure 7 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 7a)

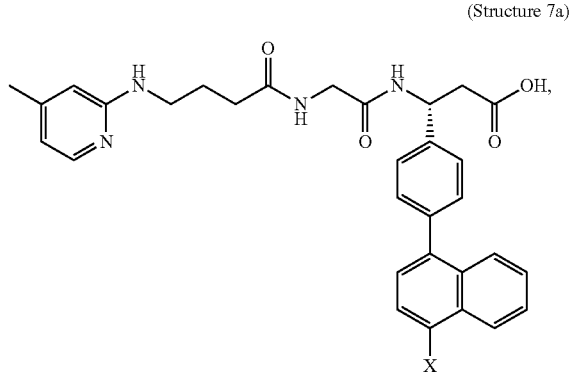

wherein X includes a reactive group, a protected reactive group, or a cargo molecule (e.g., an RNAi agent).

In some embodiments, the αvβ6 integrin ligand can be synthesized to include a PEG-azide reactive group, and comprises the following structure:

(Structure 7b)

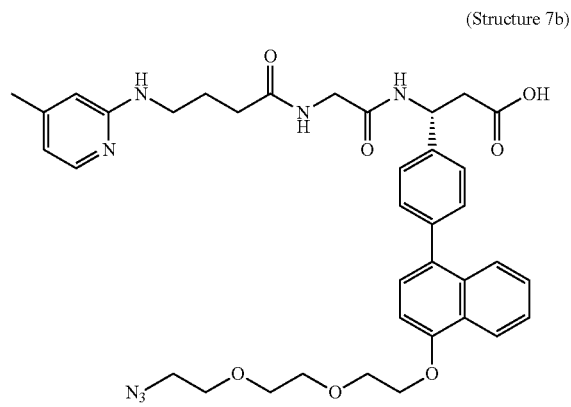 [SMILES: Cc1ccnc(NCCCC(=O)NCC(=O)N[C@H](CC(=O)O)c2ccc(-c3ccc(OCCOCCOCCN=[N+]=[N-])c4ccccc34)cc2)c1]

In some embodiments, an αvβ6 integrin ligand disclosed herein comprises the following structure:

(Structure 8)

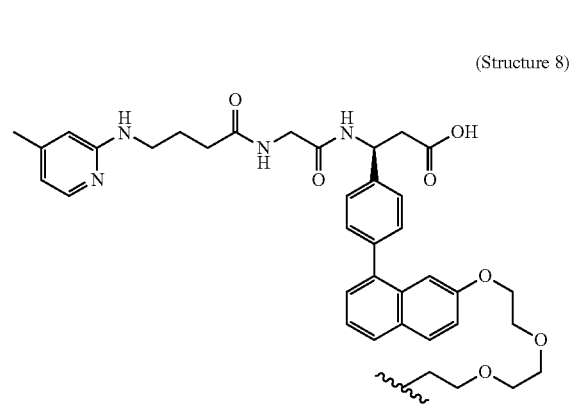 [SMILES: *CCOCCOCCOc1ccc2cccc(-c3ccc([C@H](CC(=O)O)NC(=O)CNC(=O)CCCNc4cc(C)ccn4)cc3)c2c1]

In some embodiments, the αvβ6 integrin ligand of Structure 8 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 8a)

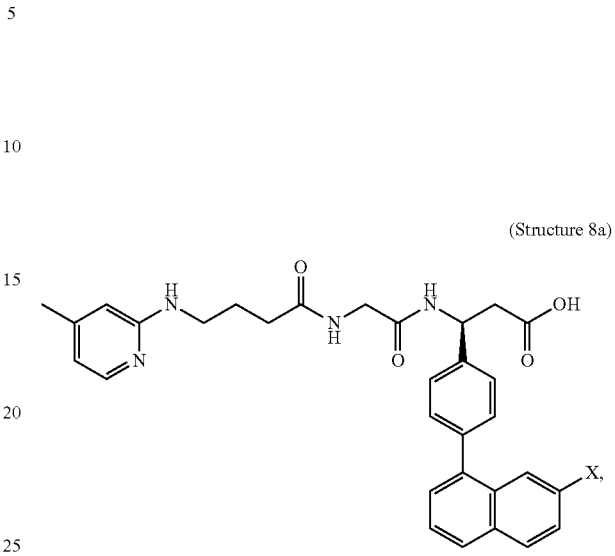

wherein X includes a reactive group, a protected reactive group, or a cargo molecule (e.g., an RNAi agent).

In some embodiments, the αvβ6 integrin ligand can be synthesized to include a PEG-azide reactive group, and comprises the following structure:

(Structure 8b)

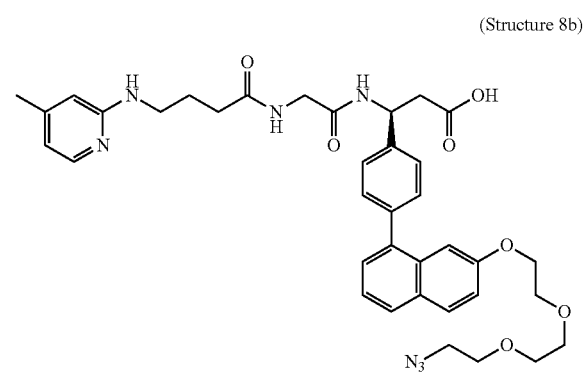 [SMILES: Cc1ccnc(NCCCC(=O)NCC(=O)N[C@@H](CC(=O)O)c2ccc(-c3cccc4ccc(OCCOCCOCCN=[N+]=[N-])cc34)cc2)c1]

In some embodiments, an αvβ6 integrin ligand disclosed herein comprises the following structure:

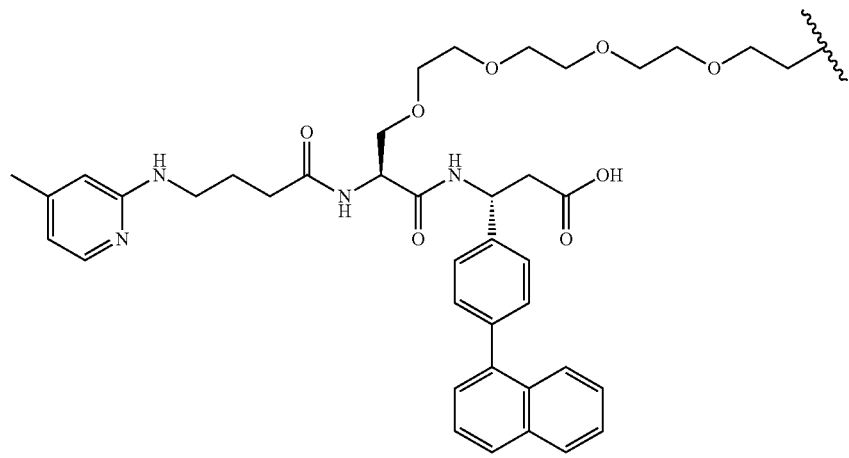
(Structure 9)

In some embodiments, the αvβ6 integrin ligand of Structure 9 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 9a)

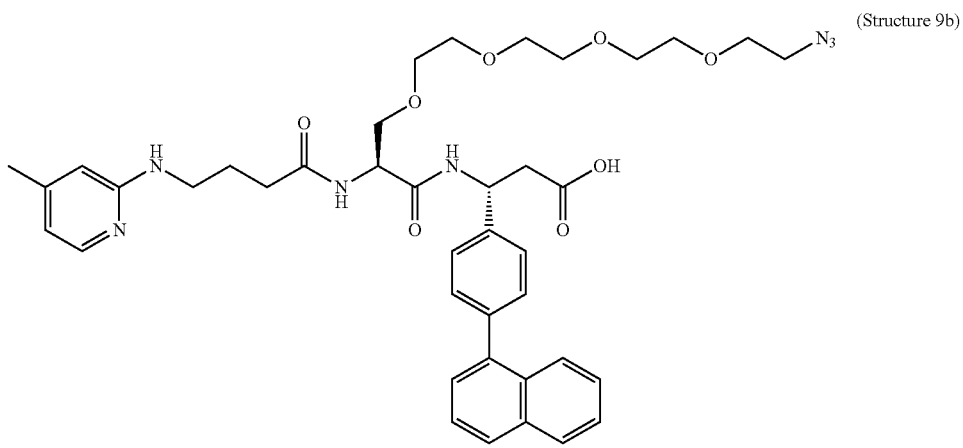 [SMILES: Cc1ccnc(NCCCC(=O)N[C@@H](COCCOCCOCCOCCN=[N+]=[N-])C(=O)N[C@H](CC(=O)O)c2ccc(-c3cccc4ccccc34)cc2)c1]

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 9b)

In some embodiments, an αvβ6 integrin ligand disclosed herein comprises the following structure:

(Structure 10)

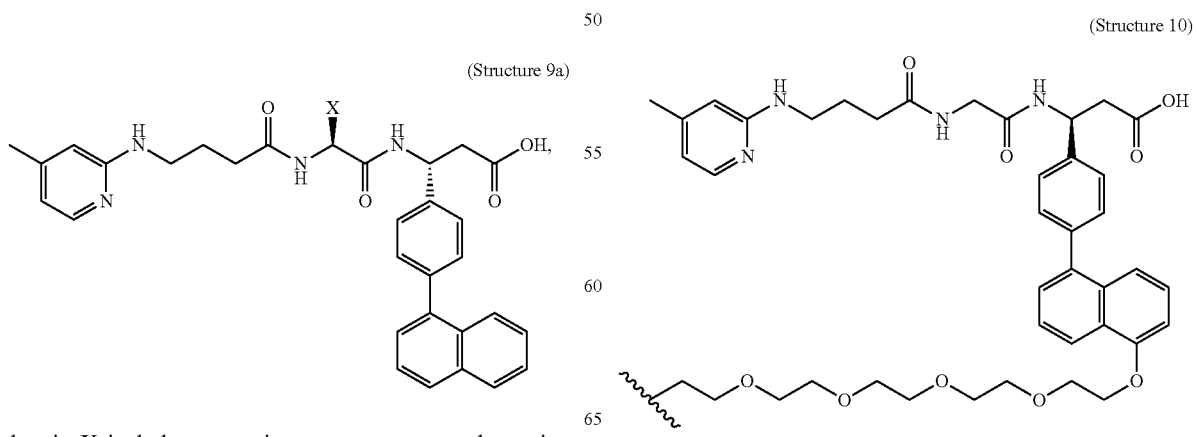

In some embodiments, the αvβ6 integrin ligand of Structure 10 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 10a)

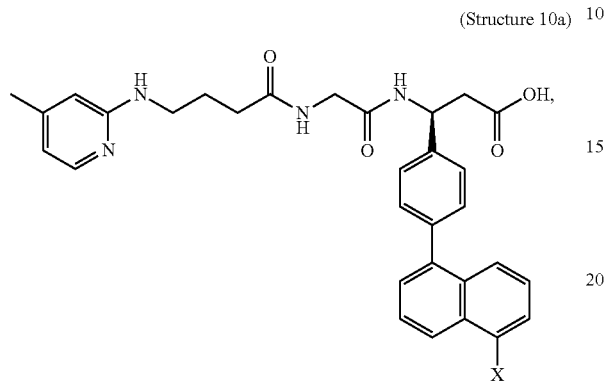

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 10b)

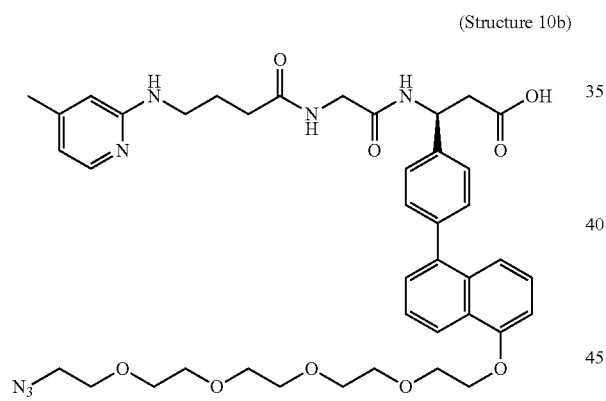

In some embodiments, an αvβ6 integrin ligand disclosed herein comprises the following structure:

(Structure 11)

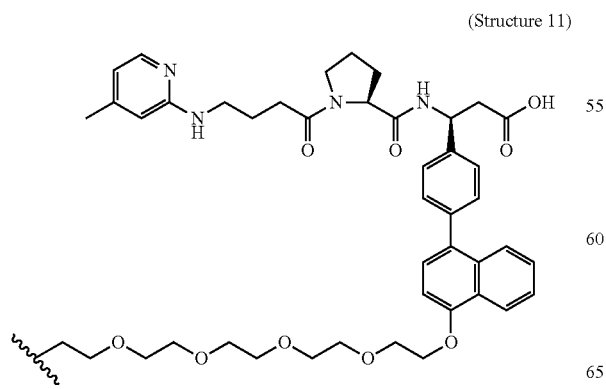

In some embodiments, the αvβ6 integrin ligand of Structure 11 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 11a)

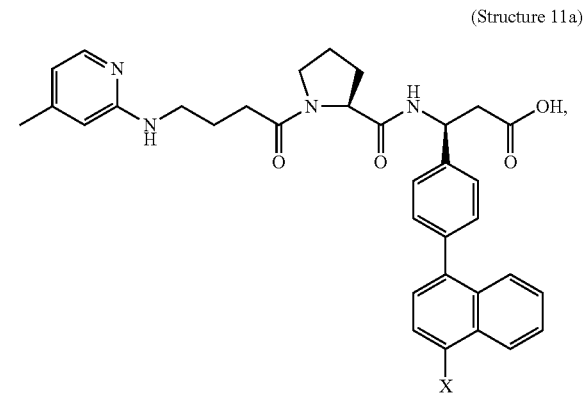

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 11b)

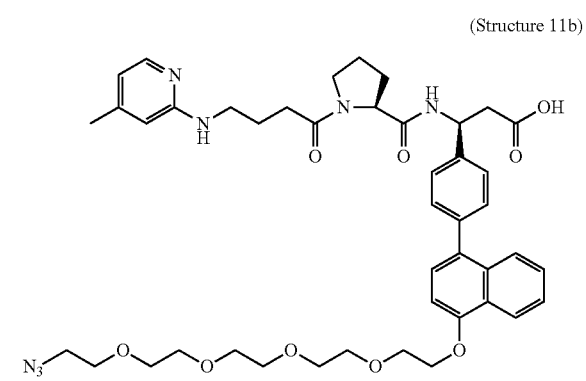 [SMILES: Cc1ccnc(NCCCC(=O)N2CCC[C@H]2C(=O)N[C@@H](CC(=O)O)c2ccc(-c3ccc(OCCOCCOCCOCCOCCN=[N+]=[N-])c4ccccc34)cc2)c1]

In some embodiments, an αvβ6 integrin ligand disclosed herein comprises the following structure:

(Structure 12)

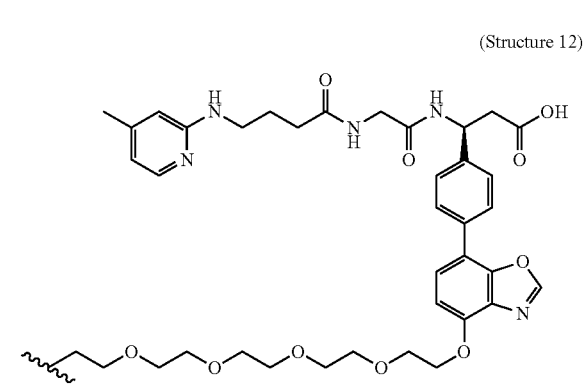 [SMILES: *CCOCCOCCOCCOCCOc1ccc(-c2ccc([C@H](CC(=O)O)NC(=O)CNC(=O)CCCNc3cc(C)ccn3)cc2)c2ocnc12]

In some embodiments, the αvβ6 integrin ligand of Structure 12 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 12a)

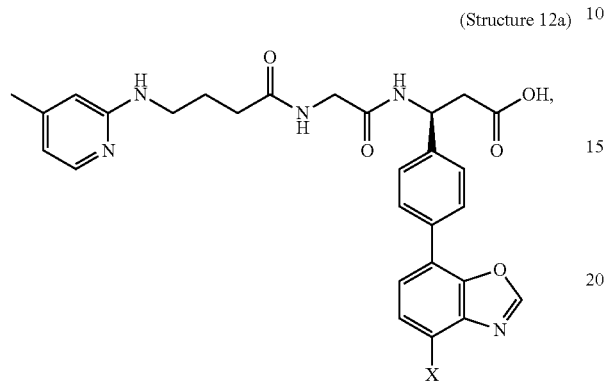

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 12b)

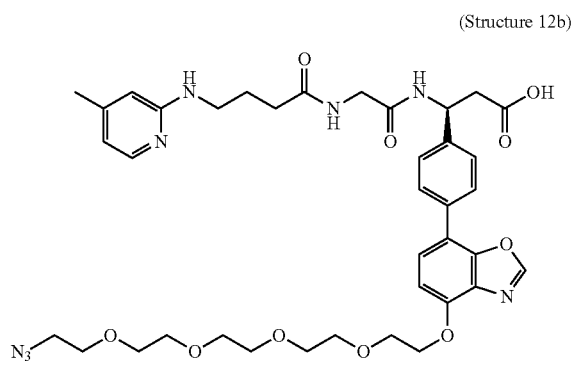 [SMILES: Cc1ccnc(NCCCC(=O)NCC(=O)N[C@@H](CC(=O)O)c2ccc(-c3ccc(OCCOCCOCCOCCOCCN=[N+]=[N-])c4ncoc34)cc2)c1]

In some embodiments, an αvβ6 integrin ligand disclosed herein comprises the following structure:

(Structure 13)

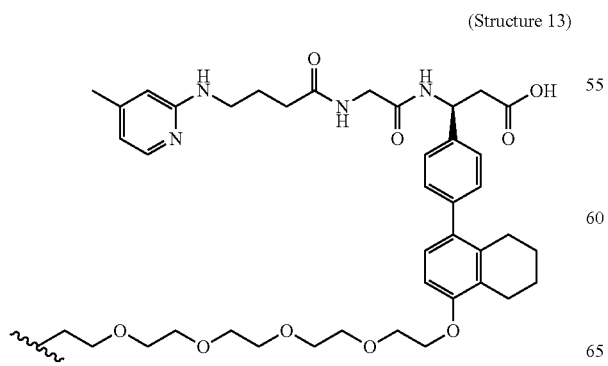

In some embodiments, the αvβ6 integrin ligand of Structure 13 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 13a)

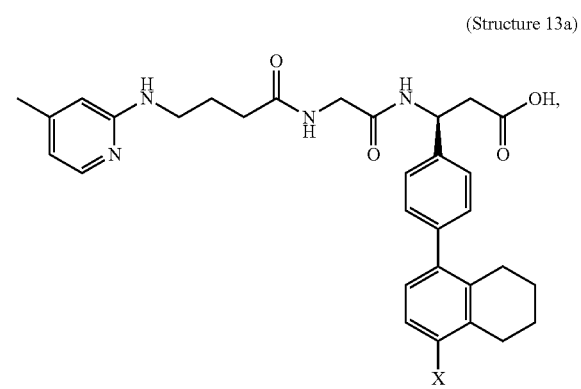

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 13b)

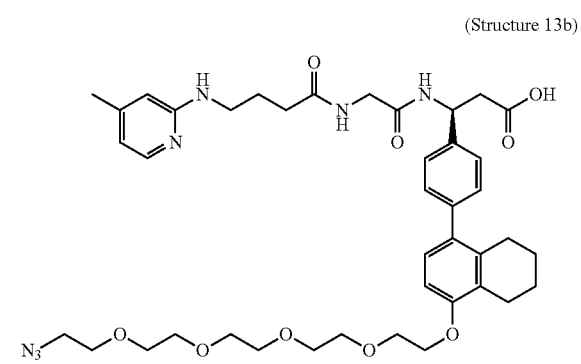 [SMILES: Cc1ccnc(NCCCC(=O)NCC(=O)N[C@@H](CC(=O)O)c2ccc(-c3ccc(OCCOCCOCCOCCOCCN=[N+]=[N-])c4c3CCCC4)cc2)c1]

In some embodiments, an αvβ6 integrin ligand disclosed herein comprises the following structure:

(Structure 14)

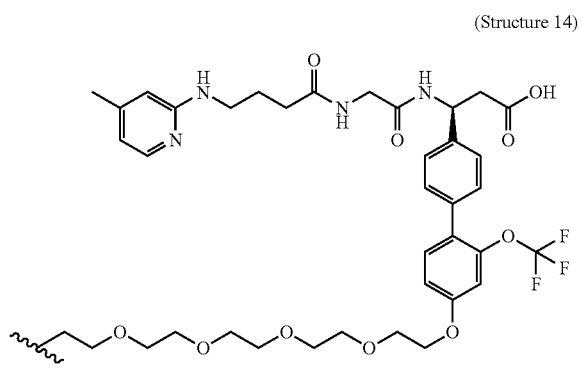 [SMILES: *CCOCCOCCOCCOCCOc1ccc(-c2ccc([C@H](CC(=O)O)NC(=O)CNC(=O)CCCNc3cc(C)ccn3)cc2)c(OC(F)(F)F)c1]

In some embodiments, the αvβ6 integrin ligand of Structure 14 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 14a)

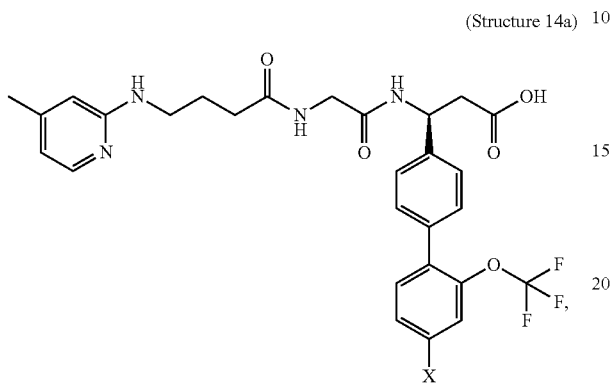

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 14b)

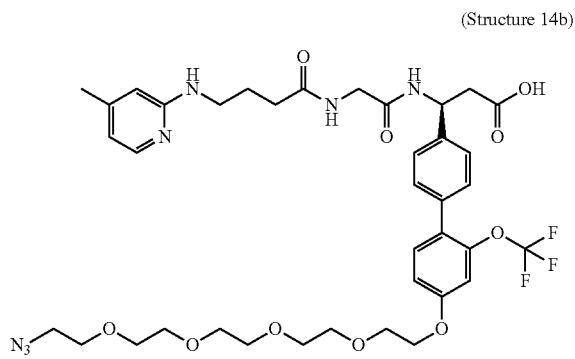 [SMILES: Cc1ccnc(NCCCC(=O)NCC(=O)N[C@@H](CC(=O)O)c2ccc(-c3ccc(OCCOCCOCCOCCOCCN=[N+]=[N-])cc3OC(F)(F)F)cc2)c1]

In some embodiments, an αvβ6 integrin ligand disclosed herein comprises the following structure:

(Structure 15)

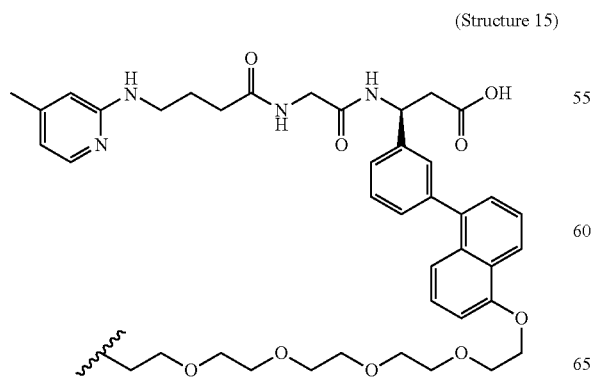

In some embodiments, the αvβ6 integrin ligand of Structure 15 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 15a)

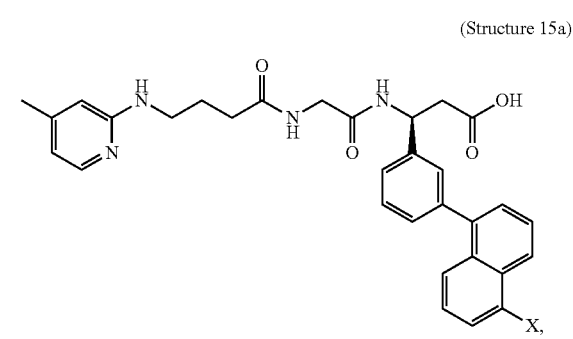

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 15b)

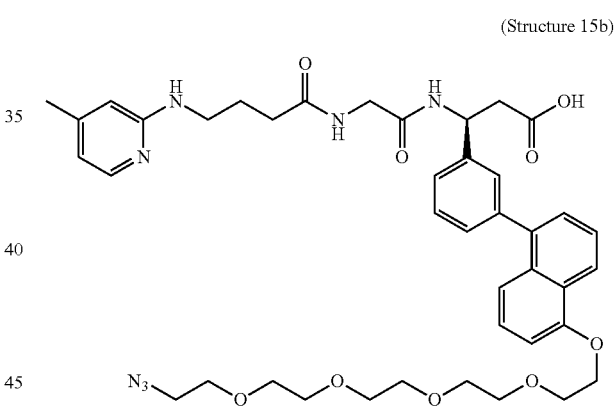

In some embodiments, an αvβ6 integrin ligand disclosed herein comprises the following structure:

(Structure 16)

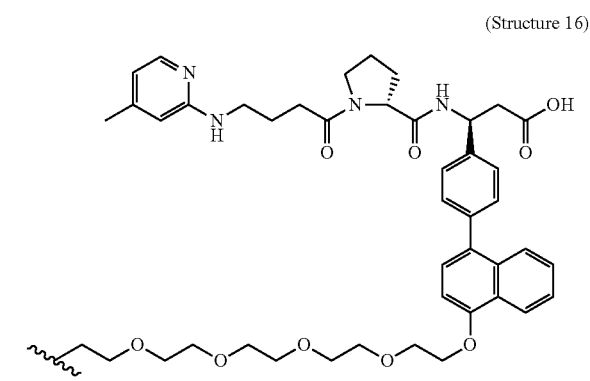 [SMILES: *CCOCCOCCOCCOCCOc1ccc(-c2ccc([C@H](CC(=O)O)NC(=O)[C@H]3CCCN3C(=O)CCCNc3cc(C)ccn3)cc2)c2ccccc12]

In some embodiments, the αvβ6 integrin ligand of Structure 16 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 16a)

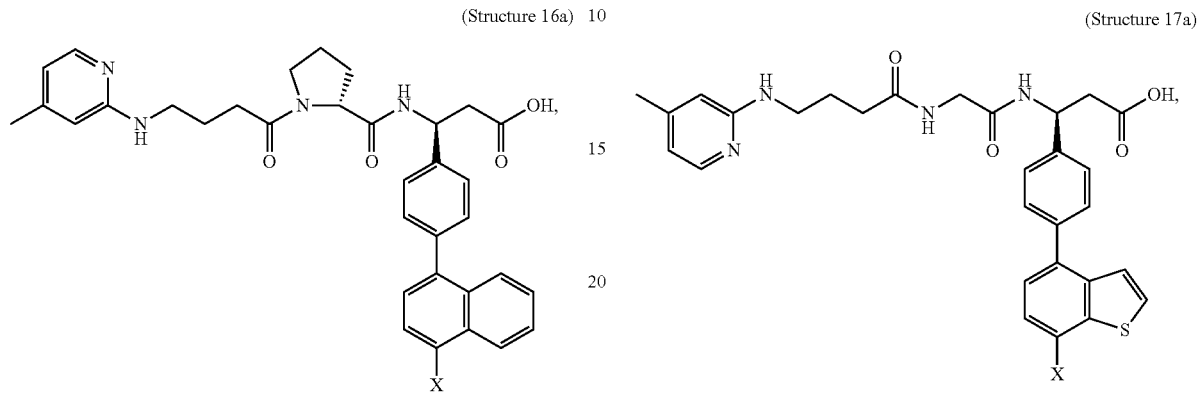

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 16b)

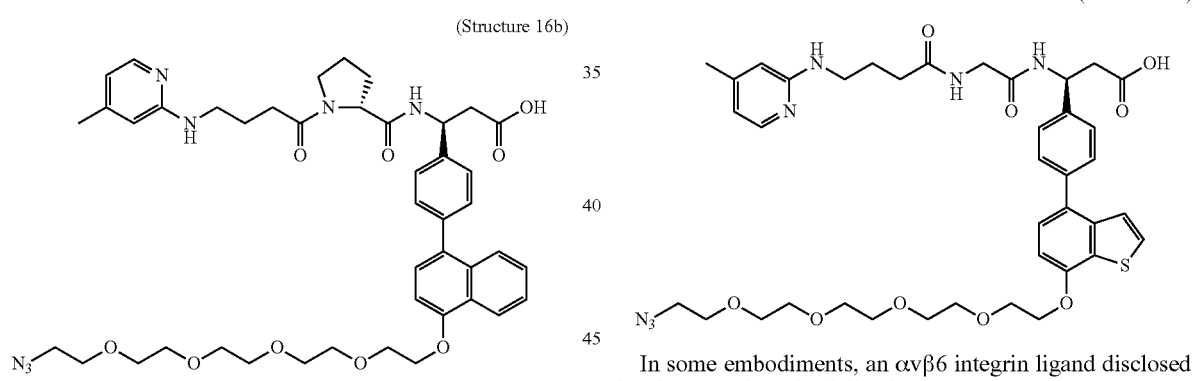

In some embodiments, an αvβ6 integrin ligand disclosed herein comprises the following structure:

(Structure 17)

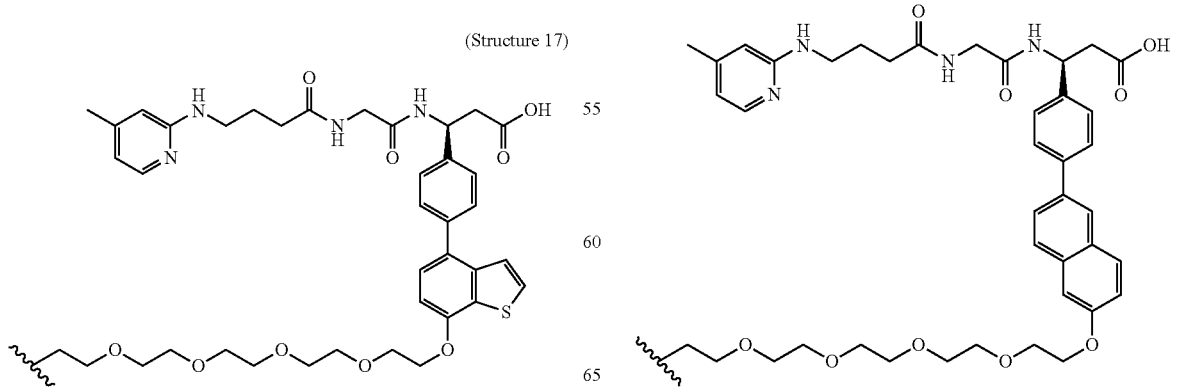

In some embodiments, the αvβ6 integrin ligand of Structure 17 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 17a)

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 17b)

In some embodiments, an αvβ6 integrin ligand disclosed herein comprises the following structure:

(Structure 18)

In some embodiments, the αvβ6 integrin ligand of Structure 18 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 18a)

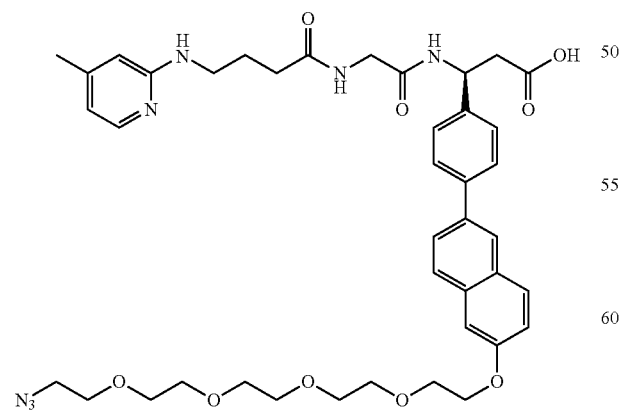

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 18b)

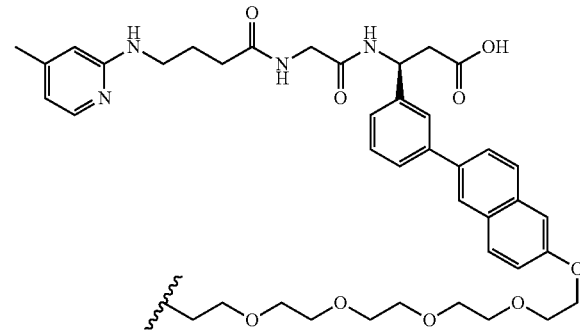

In some embodiments, an αvβ6 integrin ligand disclosed herein comprises the following structure:

(Structure 19)

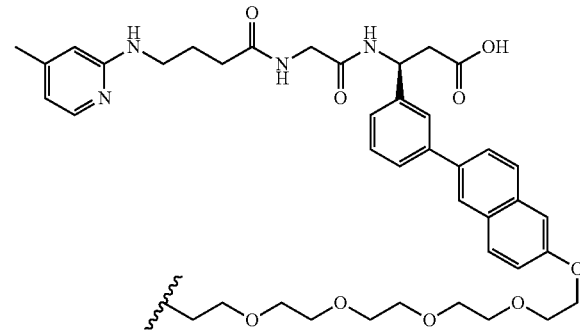

In some embodiments, the αvβ6 integrin ligand of Structure 19 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 19a)

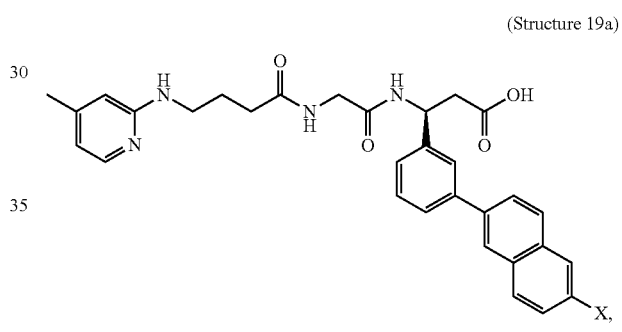

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 19b)

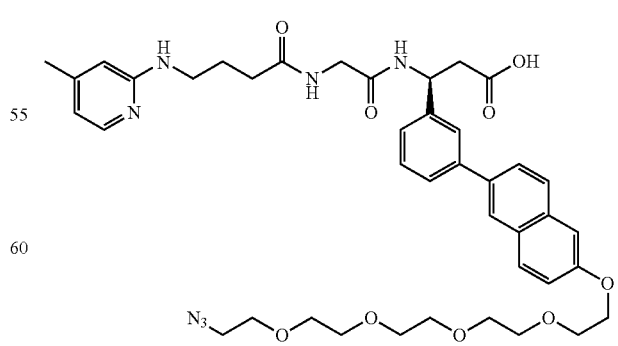

In some embodiments, an αvβ6 integrin ligand disclosed herein comprises the following structure:

(Structure 20)

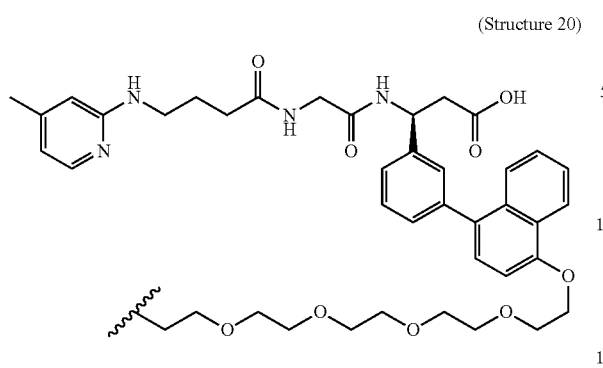

In some embodiments, the αvβ6 integrin ligand of Structure 20 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 20a)

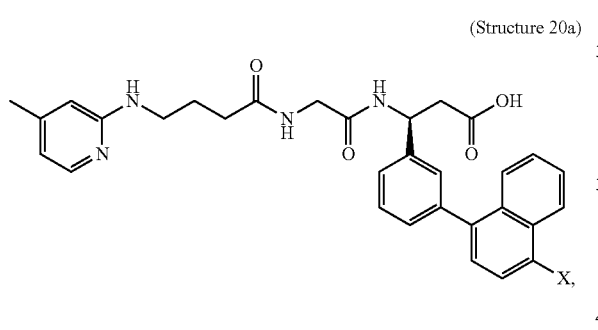

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 20b)

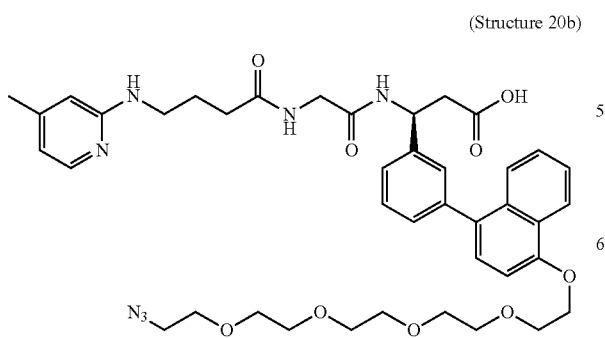

In some embodiments, an αvβ6 integrin ligand disclosed herein comprises the following structure:

(Structure 22)

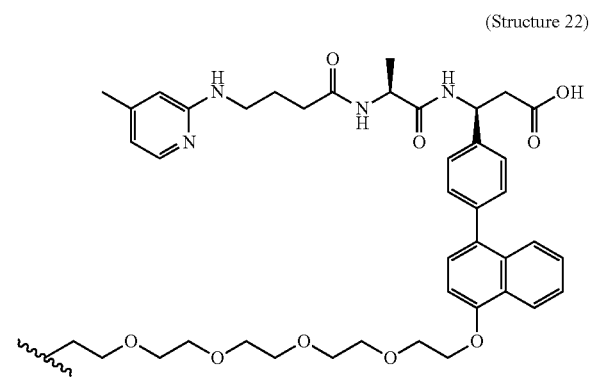 [SMILES: *CCOCCOCCOCCOCCOc1ccc(-c2ccc([C@H](CC(=O)O)NC(=O)[C@H](C)NC(=O)CCCNc3cc(C)ccn3)cc2)c2ccccc12]

In some embodiments, the αvβ6 integrin ligand of Structure 22 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 22a)

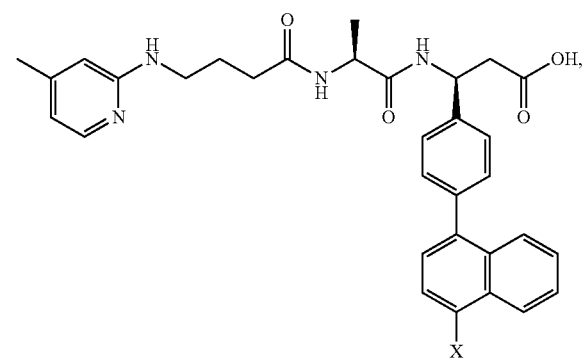

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 22b)

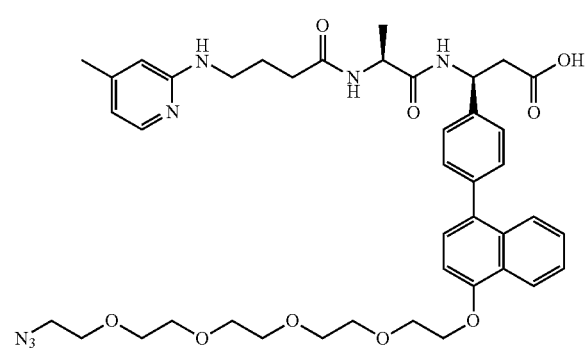

In some embodiments, an αvβ6 integrin ligand disclosed herein comprises the following structure:

(Structure 23)

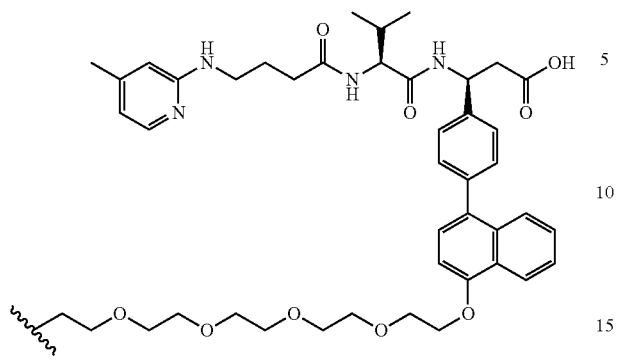

In some embodiments, the αvβ6 integrin ligand of Structure 23 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 23a)

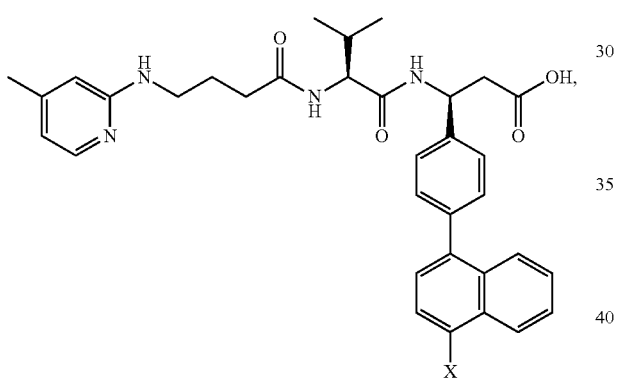

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 23b)

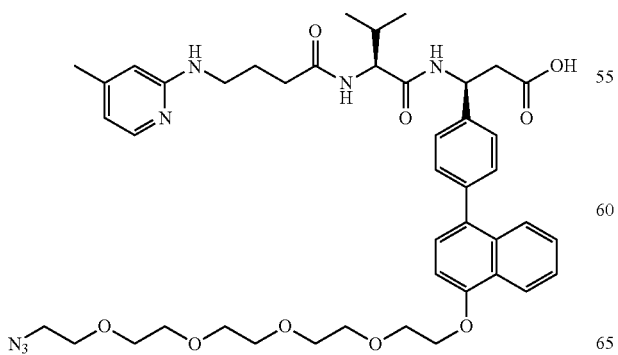

In some embodiments, an αvβ6 integrin ligand disclosed herein comprises the following structure:

(Structure 24)

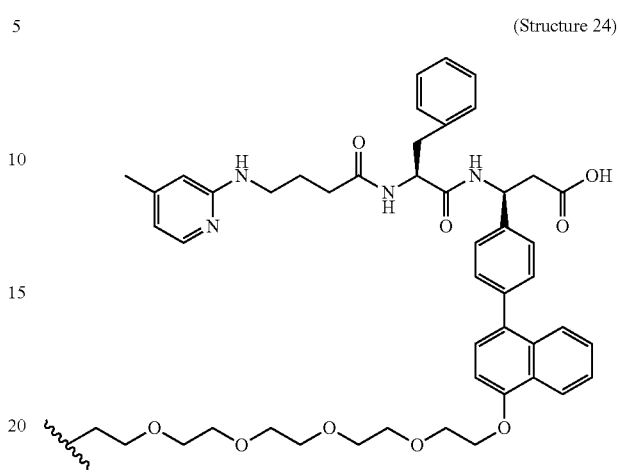

In some embodiments, the αvβ6 integrin ligand of Structure 24 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 24a)

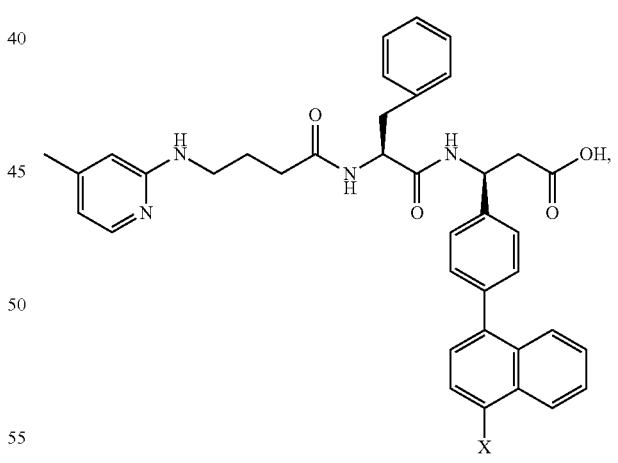

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 24b)

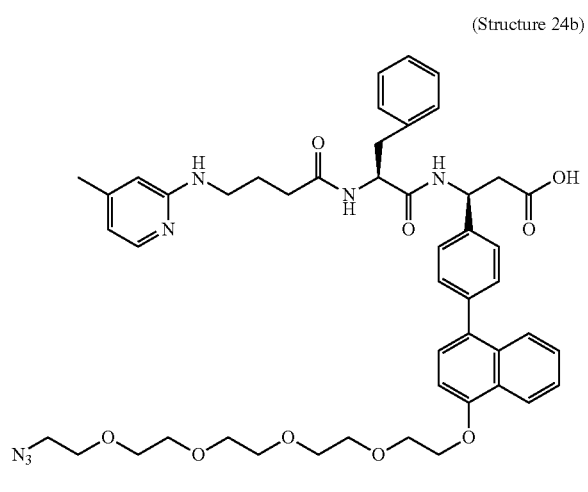 [SMILES: Cc1ccnc(NCCCC(=O)N[C@@H](Cc2ccccc2)C(=O)N[C@@H](CC(=O)O)c2ccc(-c3ccc(OCCOCCOCCOCCOCCN=[N+]=[N-])c4ccccc34)cc2)c1]

In some embodiments, an αvβ6 integrin ligand disclosed herein comprises the following structure:

(Structure 25)

(Structure 25a)

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 25b)

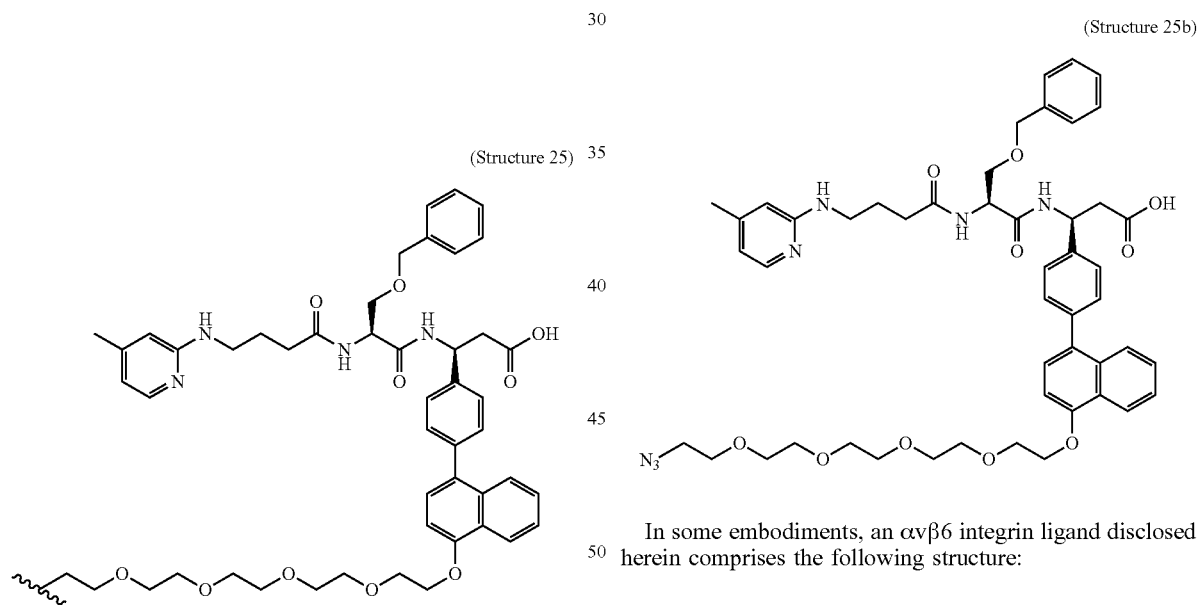

In some embodiments, an αvβ6 integrin ligand disclosed herein comprises the following structure:

(Structure 27)

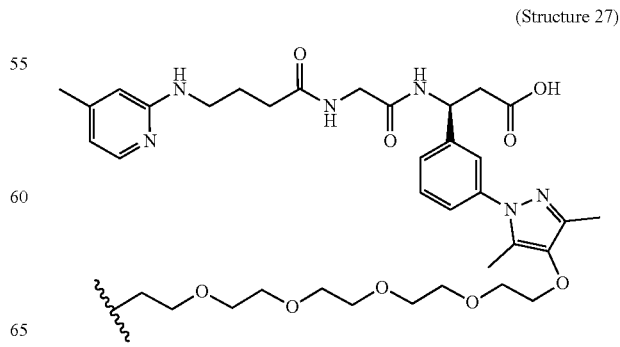

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 27a)

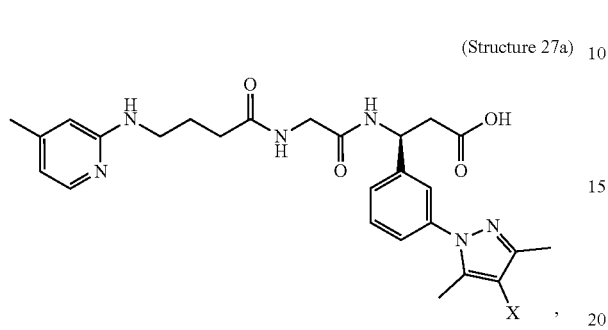

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 27b)

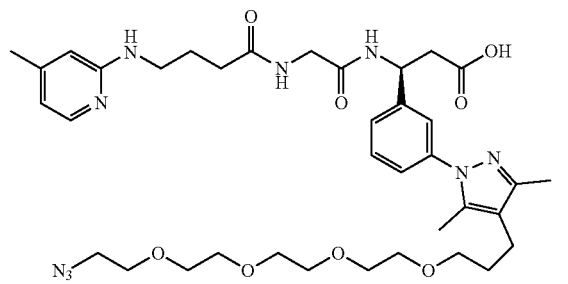

In some embodiments, an αvβ6 integrin ligand disclosed herein comprises the following structure:

In some embodiments, an αvβ6 integrin ligand disclosed herein comprises the following structure:

(Structure 29)

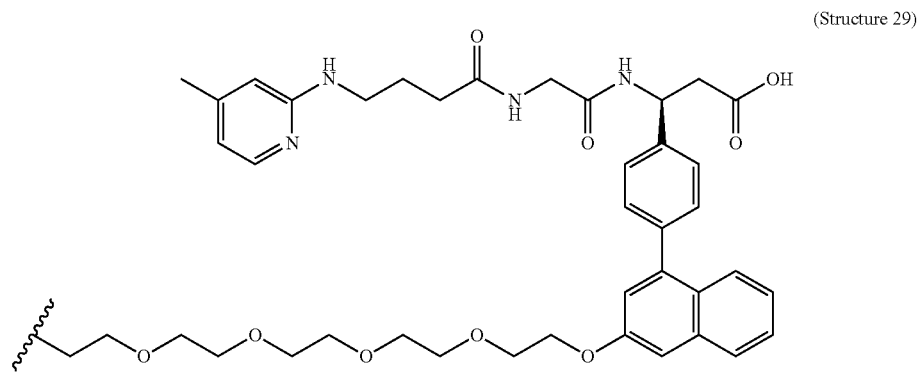 [SMILES: *CCOCCOCCOCCOCCOc1cc(-c2ccc([C@H](CC(=O)O)NC(=O)CNC(=O)CCCNc3cc(C)ccn3)cc2)c2ccccc2c1]

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 29a)

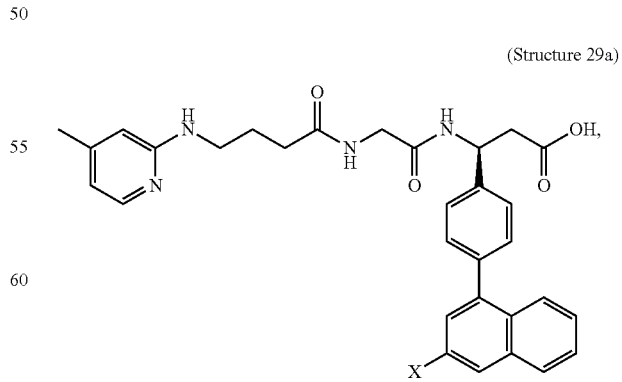

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

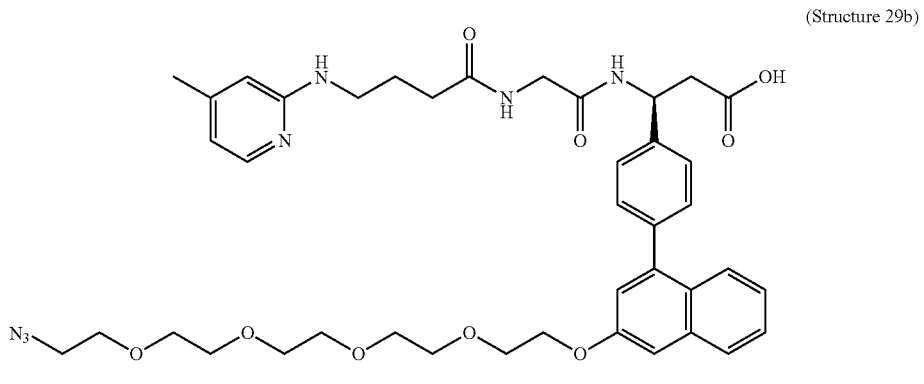 [SMILES: Cc1ccnc(NCCCC(=O)NCC(=O)N[C@@H](CC(=O)O)c2ccc(-c3cc(OCCOCCOCCOCCOCCN=[N+]=[N-])cc4ccccc34)cc2)c1]

(Structure 29b)

In some embodiments, an αvβ6 integrin ligand disclosed herein comprises the following structure:

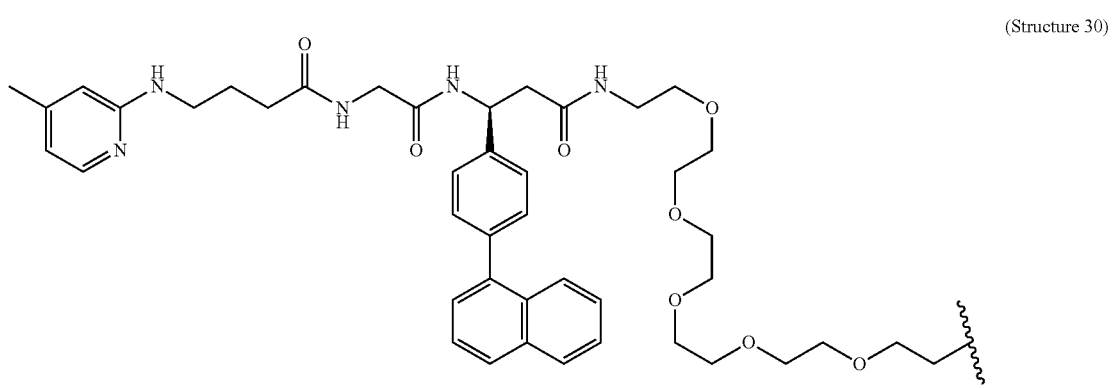 [SMILES: *CCOCCOCCOCCOCCOCCNC(=O)C[C@H](NC(=O)CNC(=O)CCCNc1cc(C)ccn1)c1ccc(-c2cccc3ccccc23)cc1]

(Structure 30)

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

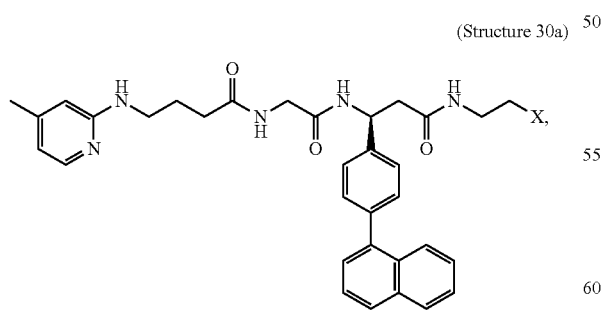

(Structure 30a)

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 30b)

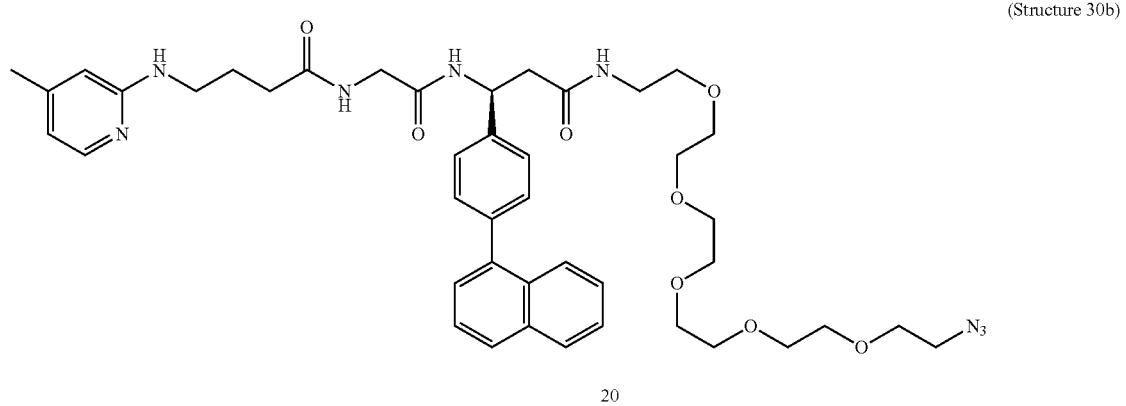

In some embodiments, an αvβ6 integrin ligand disclosed herein comprises the following structure:

(Structure 31)

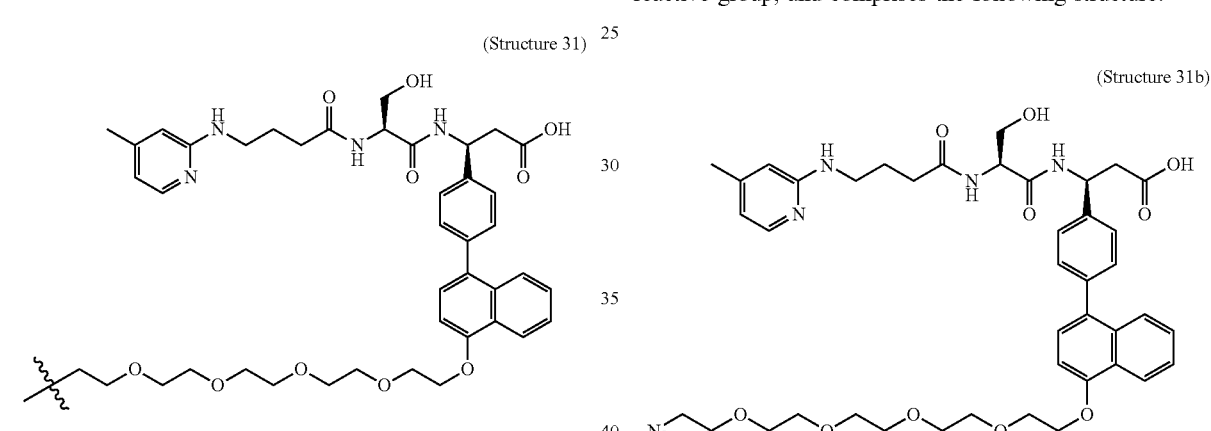

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 31a)

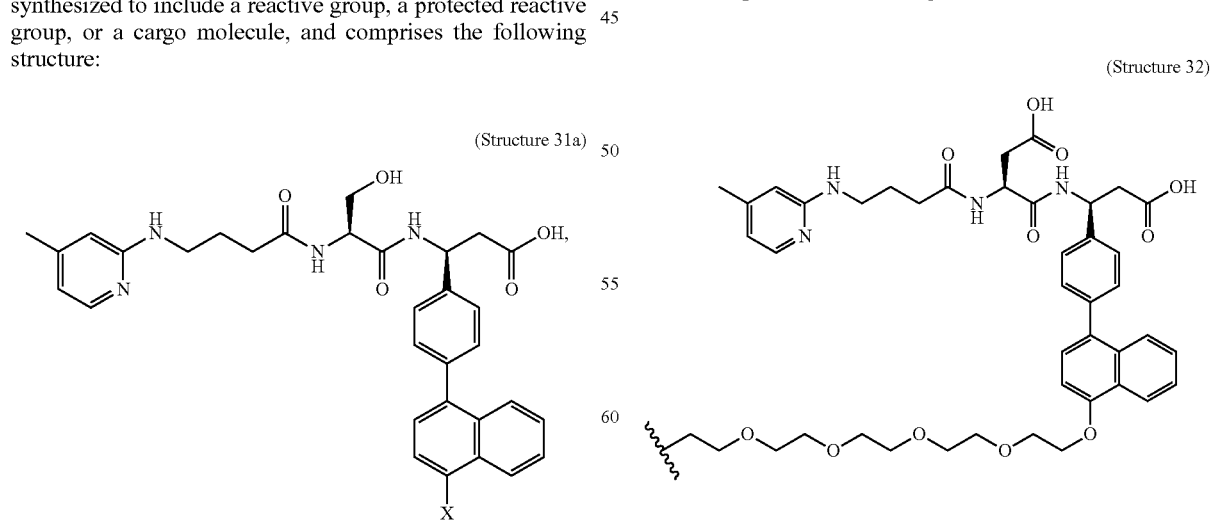

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 31b)

In some embodiments, an αvβ6 integrin ligand disclosed herein comprises the following structure:

(Structure 32)

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 32a)

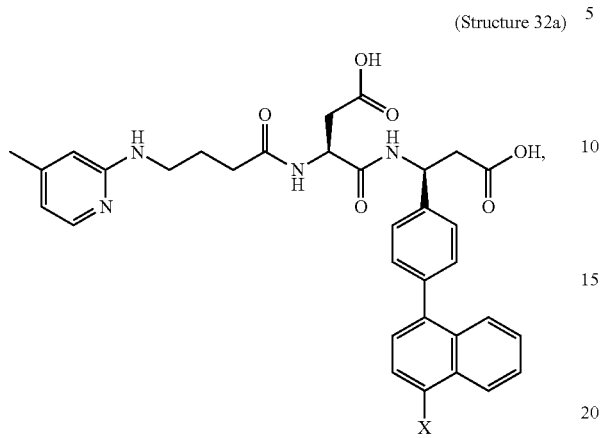

wherein X includes a reactive group, a protected reactive group, or a cargo molecule (e.g., an RNAi agent).

In some embodiments, the αvβ6 integrin ligand can be synthesized to include a polyethylene glycol (PEG-azide reactive group, and comprises the following structure:

(Structure 32b)

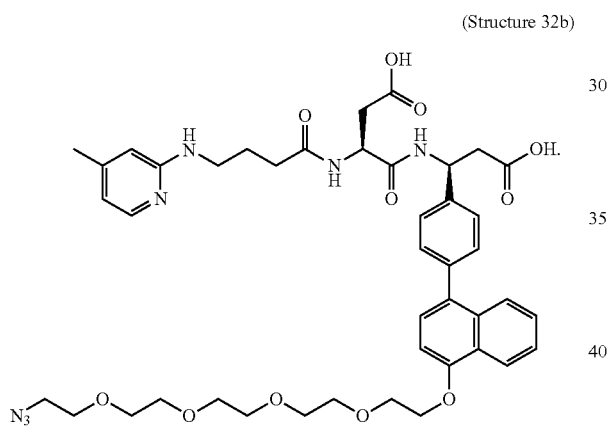

In some embodiments, an αvβ6 integrin ligand disclosed herein comprises the following structure:

(Structure 33)

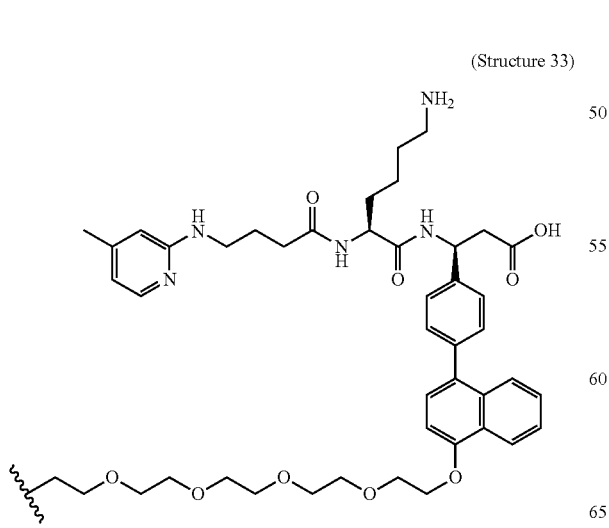

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 33a)

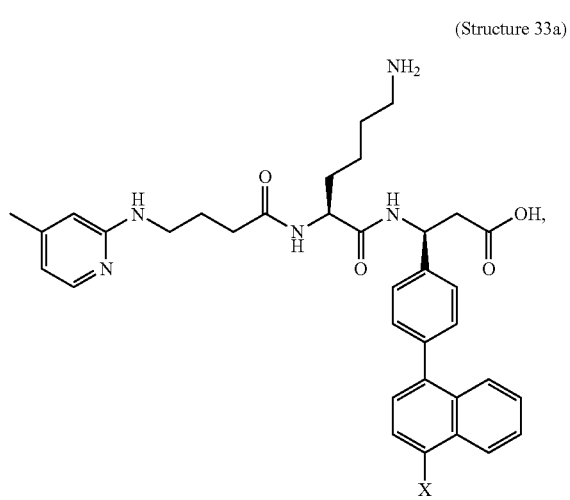

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 33b)

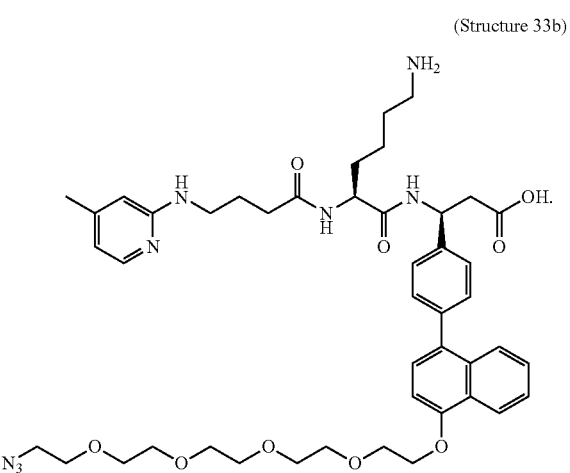 [SMILES: Cc1ccnc(NCCCC(=O)N[C@@H](CCCCN)C(=O)N[C@@H](CC(=O)O)c2ccc(-c3ccc(OCCOCCOCCOCCOCCN=[N+]=[N-])c4ccccc34)cc2)c1]

In some embodiments, an αvβ6 integrin ligand disclosed herein comprises the following structure:

(Structure 34)

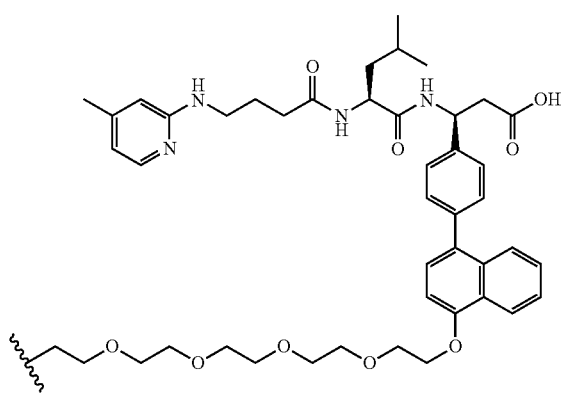

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 34a)

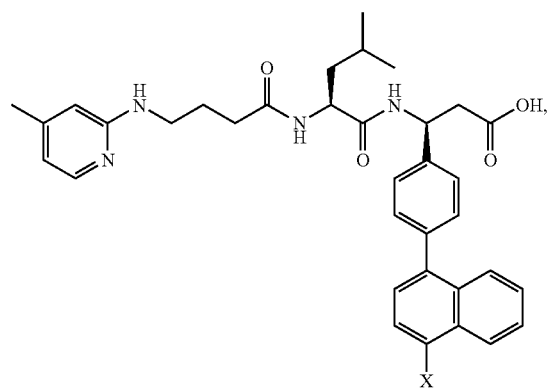

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 34b)

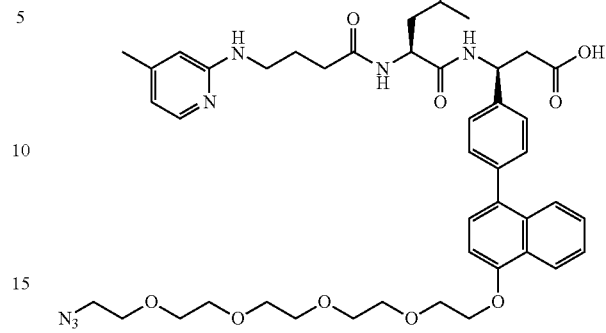

In some embodiments, an αvβ6 integrin ligand disclosed herein comprises the following structure:

(Structure 35)

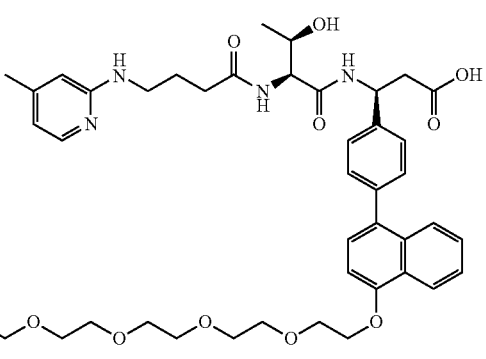

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 35a)

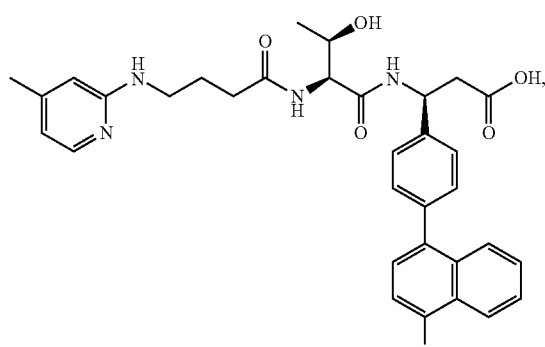

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 35b)

In some embodiments, an αvβ6 integrin ligand disclosed herein comprises the following structure:

(Structure 36)

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

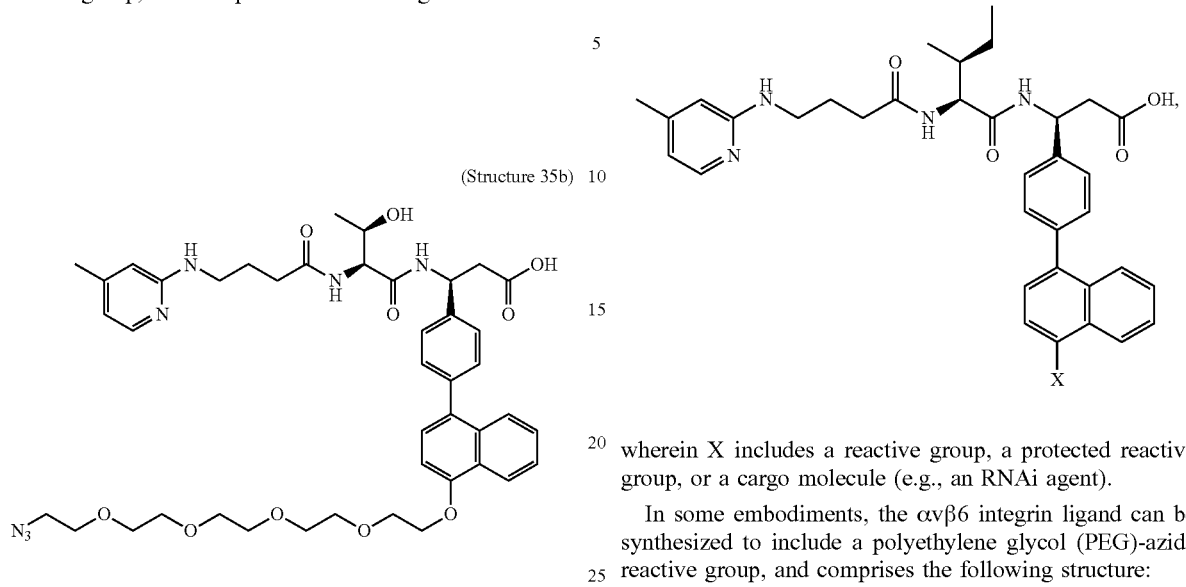

(Structure 36a)

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 36b)

In some embodiments, an αvβ6 integrin ligand disclosed herein comprises the following structure:

(Structure 37)

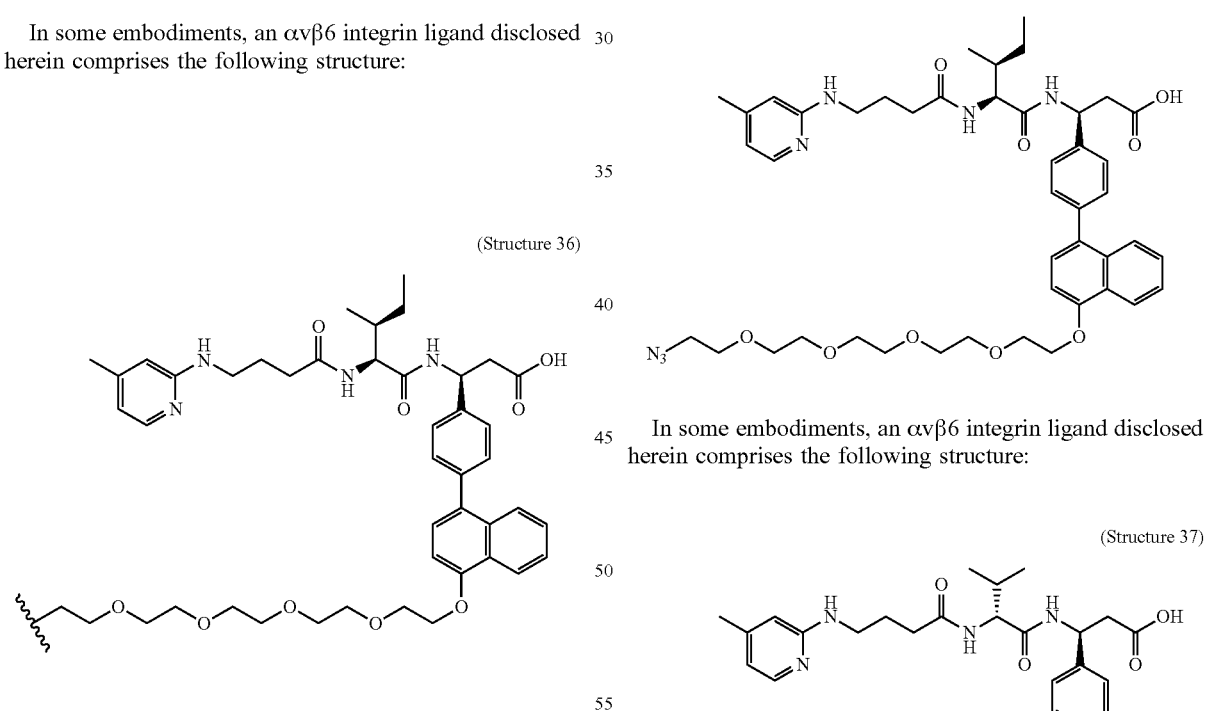

In some embodiments, the αvβ6 integrin ligand of Structure 25 is linked to one or more cargo molecules (e.g., RNAi agent(s)).

In some embodiments, the αvβ6 integrin ligand can be synthesized to include a reactive group, a protected reactive group, or a cargo molecule, and comprises the following structure:

(Structure 37a)

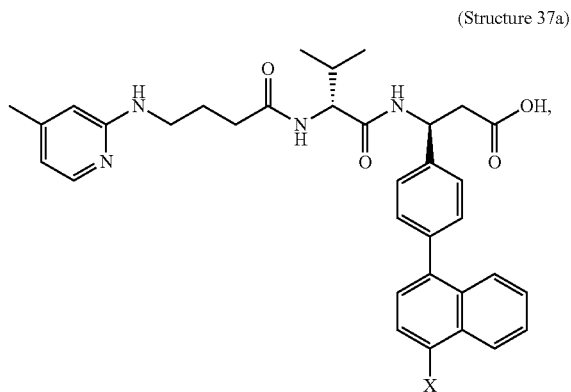

wherein X includes a reactive group, a protected reactive group, or a cargo molecule (e.g., an RNAi agent).

In some embodiments, the αvβ6 integrin ligand can be synthesized to include a polyethylene glycol (PEG)-azide reactive group, and comprises the following structure:

(Structure 37b)

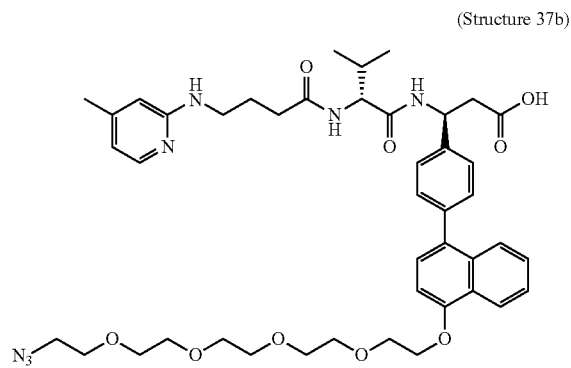 [SMILES: Cc1ccnc(NCCCC(=O)N[C@@H](C(=O)N[C@@H](CC(=O)O)c2ccc(-c3ccc(OCCOCCOCCOCCOCCN=[N+]=[N-])c4ccccc34)cc2)C(C)C)c1]

The reactive group as disclosed in any of Structure 1a, Structure 1b, Structure 2a, Structure 2b, Structure 5a, Structure 5b, Structure 6a, Structure 6b, Structure 7a, Structure 7b, Structure 8a, Structure 8b, Structure 9a, Structure 9b, Structure 10a, Structure 10b, Structure 11a, Structure 11b, Structure 12a, Structure 12b, Structure 13a, Structure 13b, Structure 14a, Structure 14b, Structure 15a, Structure 15b, Structure 16a, Structure 16b, Structure 17a, Structure 17b, Structure 18a, Structure 18b, Structure 19a, Structure 19b, Structure 20a, Structure 20b, Structure 22a, Structure 22b, Structure 23a, Structure 23b, Structure 24a, Structure 24b, Structure 25a, Structure 25b, Structure 27a, Structure 27b, Structure 29a, Structure 29b, Structure 30a, Structure 30b, Structure 31a, Structure 31b, Structure 32a, Structure 32b, Structure 33a, Structure 33b, Structure 34a, Structure 34b, Structure 35a, Structure 35b, Structure 36a, Structure 36b, Structure 37a, or Structure 37b can be used to attach the αvβ6 integrin ligand to a molecule of interest, i.e., to a cargo molecule such as an RNAi agent. The cargo molecule can be any molecule that is desired to be targeted to an αvβ6 integrin-expressing cell.

Multidentate αvβ6 Integrin Ligands and Scaffolds

As disclosed herein, in some embodiments, one or more αvβ6 integrin ligands may be linked to one or more cargo molecules. In some embodiments, only one αvβ6 integrin ligand is conjugated to a cargo molecule (referred to herein as a "monodentate" or "monovalent" ligand). In some embodiments, two αvβ6 integrin ligands are conjugated to a cargo molecule (referred to herein as a "bidentate" or "divalent" ligand). In some embodiments, three αvβ6 integrin ligands are conjugated to a cargo molecule (referred to herein as a "tridentate" or "trivalent" ligand). In some embodiments, four αvβ6 integrin ligands are conjugated to a cargo molecule (referred to herein as a "tetradentate" or "tetravalent" ligand). In some embodiments, more than four αvβ6 integrin ligands are conjugated to a cargo molecule.

In some embodiments, where only one αvβ6 integrin ligand is conjugated to a cargo molecule (referred to herein as a "monodentate" ligand), the αvβ6 integrin ligand may be conjugated directly to the cargo molecule. In some embodiments, an αvβ6 integrin ligand disclosed herein can be conjugated to a cargo molecule via a scaffold or other linker structure.

In some embodiments, the αvβ6 integrin ligands disclosed herein include one or more scaffolds. Scaffolds, also sometimes referred to in the art as linking groups or linkers, can be used to facilitate the linkage of one or more cargo molecules to one or more αvβ6 integrin ligands disclosed herein. Useful scaffolds compatible with the ligands disclosed herein are generally known in the art. Non-limiting examples of scaffolds that can be used with the αvβ6 integrin ligands disclosed herein include, but are not limited to polymers and polyamino acids (e.g., bis-glutamic acid, poly-L-lysine, etc.). In some embodiments, scaffolds may include cysteine linkers or groups, DBCO-PEG$_{1-24}$-NHS, Propargyl-PEG$_{1-24}$-NHS, and/or multidentate DBCO and/or propargyl moieties.

In some embodiments, the scaffold used for linking one or more αvβ6 integrin ligands disclosed herein to one or more cargo molecules has the following structure:

(Scaffold 1)

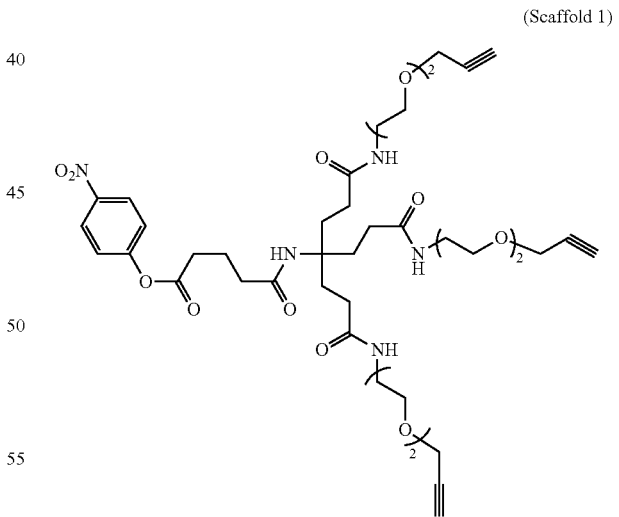

The use of Scaffold 1, for example, facilitates efficient conjugation with both the αvβ6 integrin ligand monomers and the one or more cargo molecules. Scaffold 1 includes an amine reactive p-nitrophenol (also called 4-nitrophenol) ester, an amide linkage, and three of PEG$_2$ units, as well as terminal alkynes. The 4-nitrophenol ester can be conjugated with the primary amine on a cargo molecule, such as the primary amine on an RNA trigger formulated with a terminal amine group (e.g., NH$_2$—C$_6$), through amide formation. The terminal alkyne can be conjugated with azido modified ligands (both peptides and small molecules) through copper-catalyzed click chemistry.

In some embodiments, the cargo molecule is an RNAi agent. In some embodiments, Scaffold 1 may be attached to the terminal end of an RNAi agent, such as to the 5' terminal end of the sense strand of an RNAi agent. For example, the 5' terminal end of the sense strand of an RNAi agent may be modified to include a $C_6$ amine (—$C_6$—$NH_2$) attached to the 5' end of the 5' terminal nucleotide of the RNAi agent. An RNAi agent having such a $C_6$ amine modification (or another other modification resulting in a terminal amine) may be readily conjugated to Scaffold 1, as shown in by the representation in the following structure:

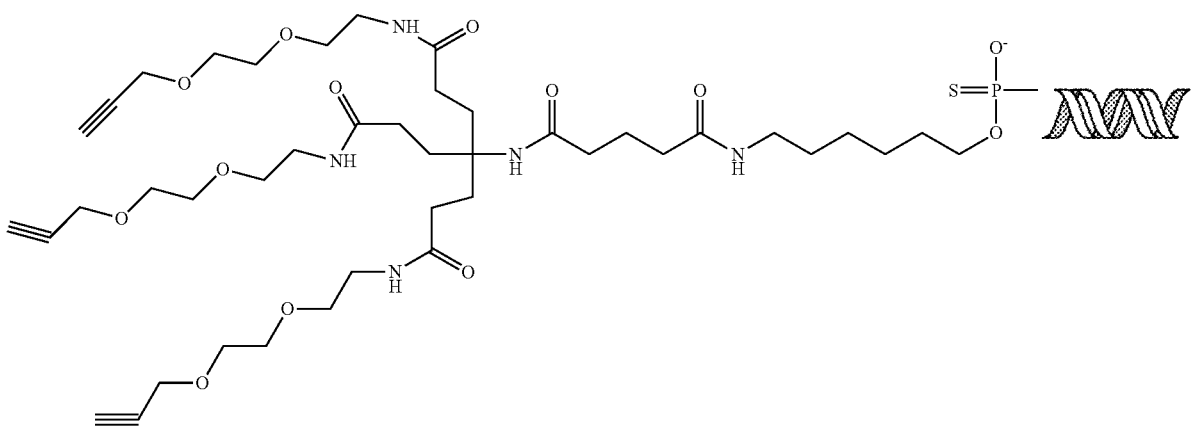 [SMILES: C#CCOCCOCCNC(=O)CCC(CCC(=O)NCCOCCOCC#C)(CCC(=O)NCCOCCOCC#C)NC(=O)CCCC(=O)NCCCCCCOP(C)([O-])=S]

(Structure 380), wherein ⁣⁣⁣⁣ indicates an RNAi agent. The alkyne groups of Structure 380, above, may then be conjugated to the αvβ6 integrin ligands disclosed herein to form tridentate αvβ6 integrin ligands.

In some embodiments, a scaffold may be synthesized using DBCO (dibenzocyclooctyne), which can be represented by the following structure:

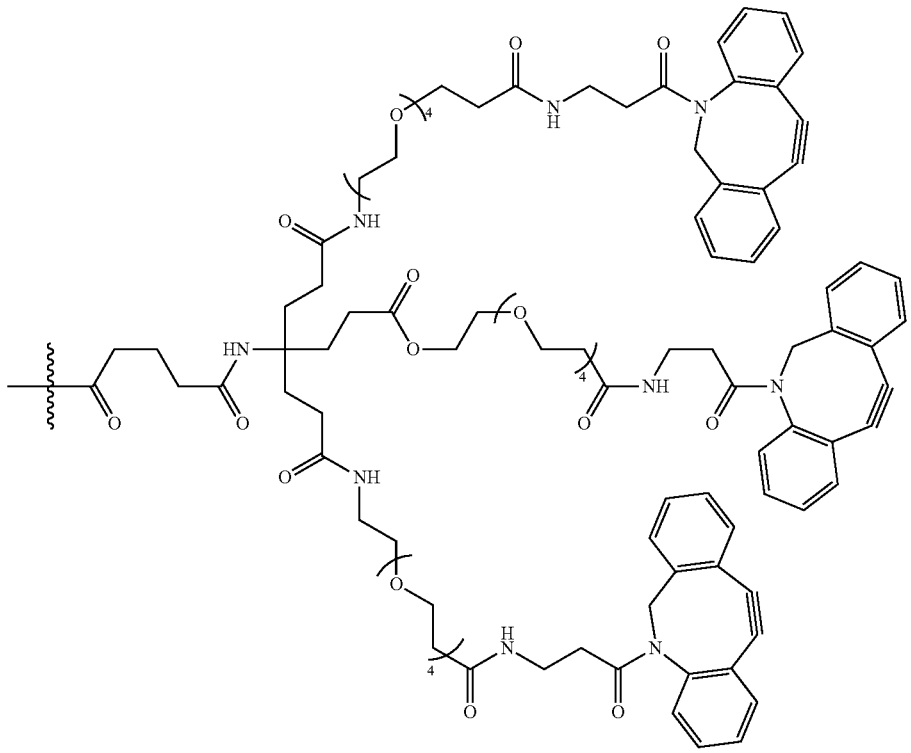

wherein ⁞ indicates attachment to a reactive group or a moiety comprising cargo molecule.

In some embodiments, triazole groups are formed between the RNAi agent and the αvβ6 integrin ligands disclosed herein, as shown in the following general structure:

In some embodiments, an αvβ6 integrin ligand disclosed herein comprises Structure 2 in a tridentate form, and can be represented by the following structure:
(Structure 700)
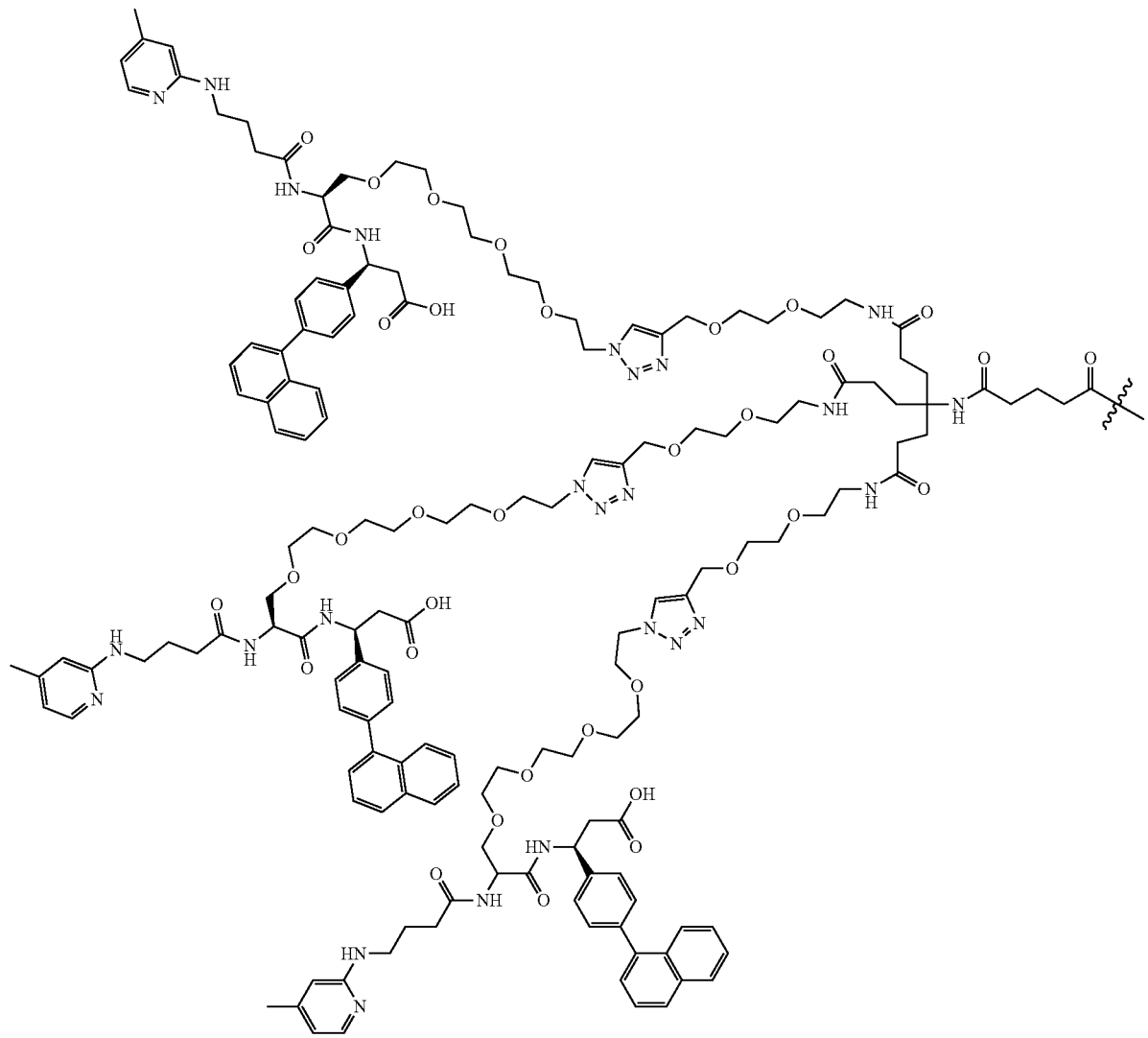

In some embodiments, an αvβ6 integrin ligand disclosed herein comprises Structure 6.1 in a tridentate form, and can be represented by the following structure:
(Structure 701)
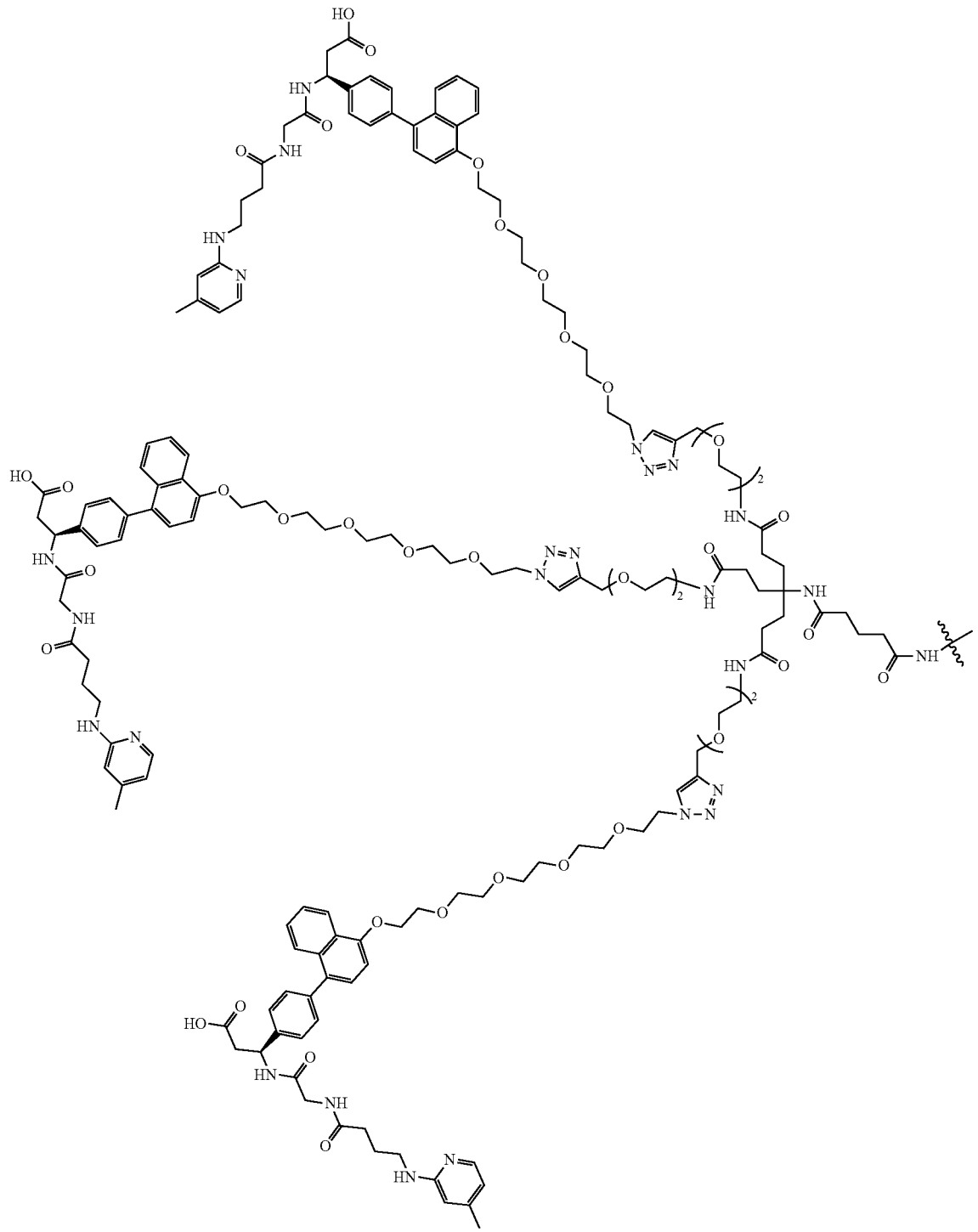

In some embodiments, an αvβ6 integrin ligand disclosed herein comprises Structure 6.1 in a tridentate form, and can be represented by the following structure:
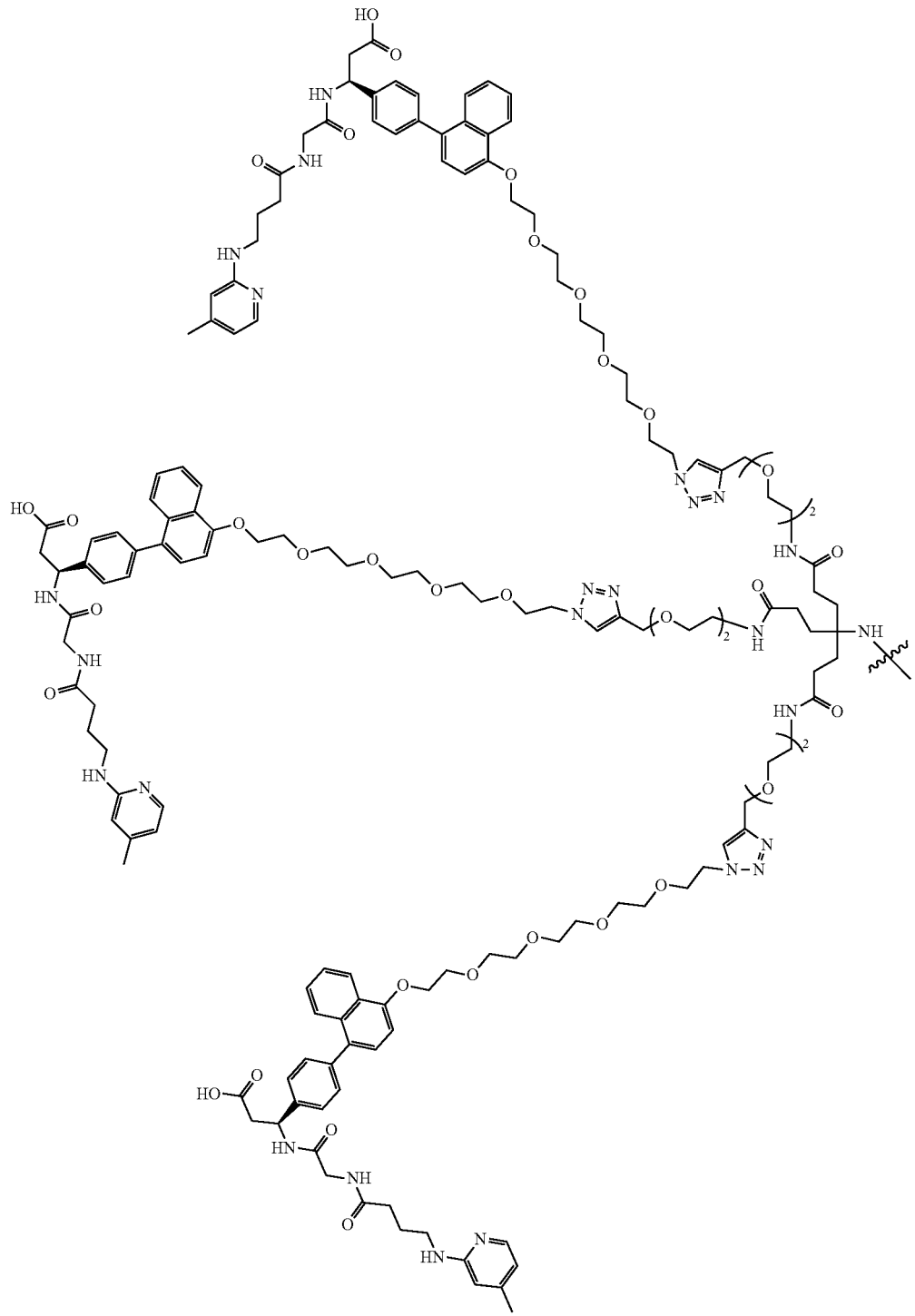
(Structure 701a)

In some embodiments, an αvβ6 integrin ligand disclosed herein comprises Structure 6.1 in a tridentate form that includes a glutaric linker, and can be represented by the following structure:
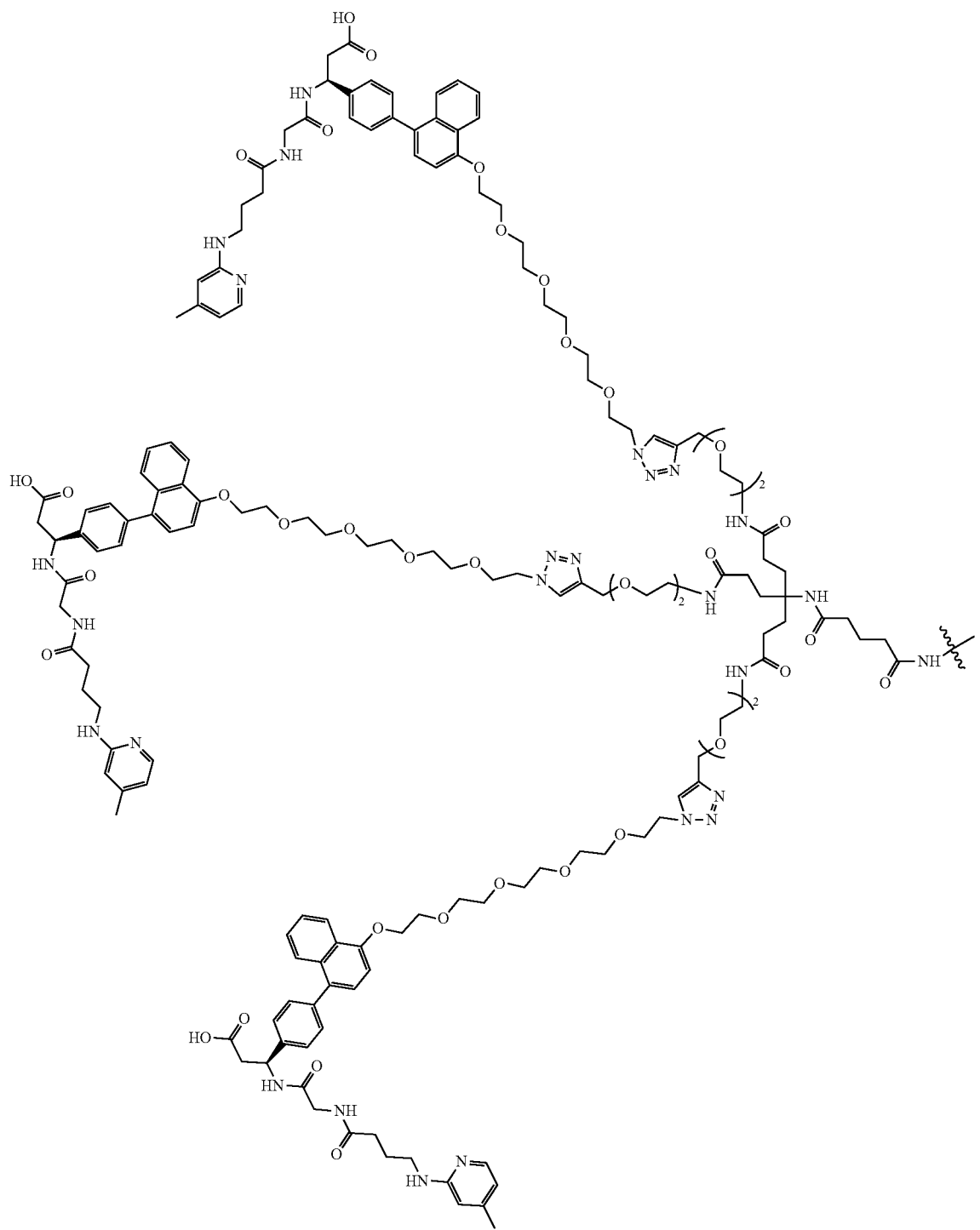
(Structure 701b)

In some embodiments, an αvβ6 integrin ligand disclosed herein comprises Structure 6.1 in a tridentate form conjugated to an RNAi agent, and may be represented by the following structure:
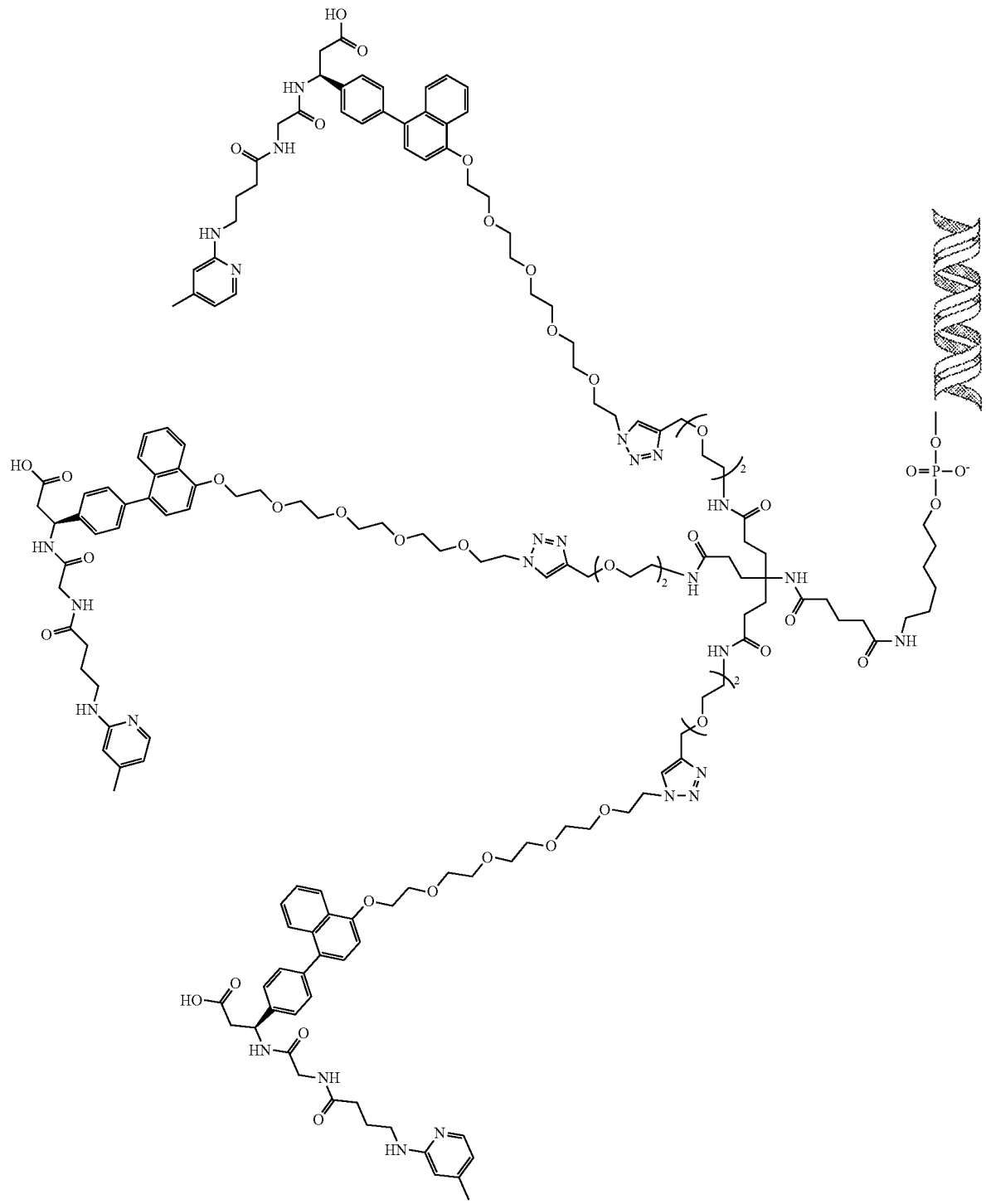

(Structure 701c), wherein ∿∿∿ indicates an RNAi agent.
In some embodiments, an αvβ6 integrin ligand disclosed herein comprises Structure 6.1 in a tridentate form, and may be represented by the following structure:
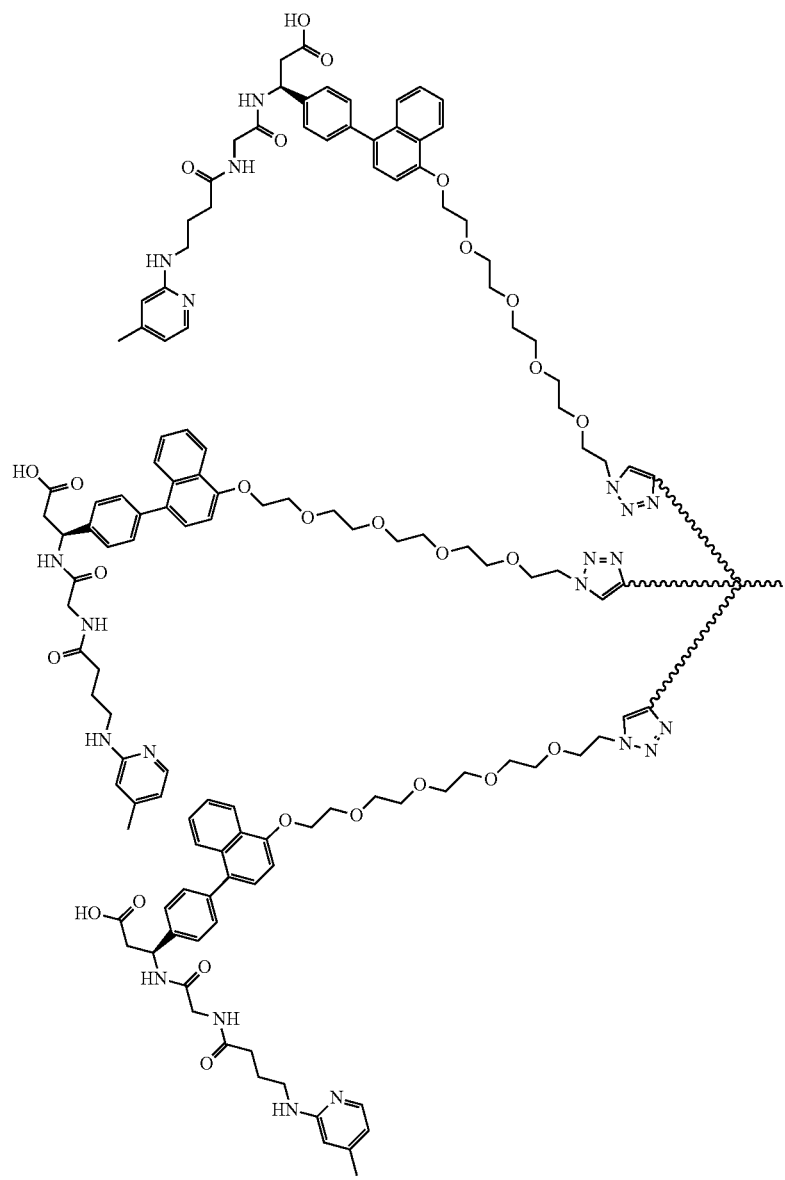
(Structure 701d), wherein ∿∿∿∿∿ indicates any suitable scaffold that can be used to link a ligand and a cargo molecule.

In some embodiments, an αvβ6 integrin ligand disclosed herein comprises Structure 6.1 in a tridentate form conjugated to an RNAi agent, and may be represented by the following structure:

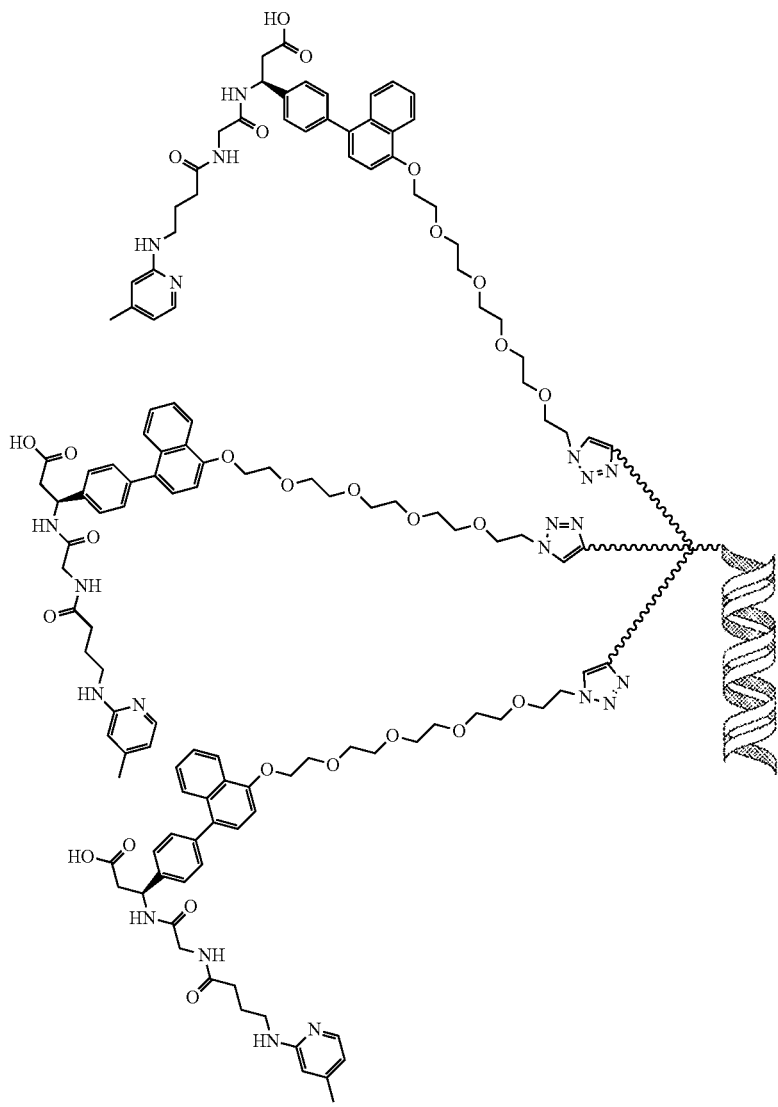

(Structure 701e), wherein ~~~~~~ vindicates any suitable scaffold that can be used to link a ligand and a RNAi agent, and 🧬 indicates a RNAi agent Reactive Groups and Protected Reactive Groups Reactive groups are well known in the art and provide for formation of covalent linkages between two molecules or reactants. Suitable reactive groups for use in the scope of the inventions herein include, but are not limited to: amino groups, amide groups, carboxylic acid groups, azides, alkynes, propargyl groups, BCN (biclclo[6.1.0]nonyne, DBCO (dibenzocyclooctyne) thiols, maleimide groups, aminooxy groups, N-hydroxysuccinimide (NHS) or other activated ester (for example, PNP, TFP, PFP), bromo groups, aldehydes, carbonates, tosylates, tetrazines, trans-cyclooctene (TCO), hydrazides, hydroxyl groups, disulfides, and orthopyridyl disulfide groups.

Incorporation of reactive groups can facilitate conjugation of an αvβ6 integrin ligand disclosed herein to a cargo molecule. Conjugation reactions are well known in the art and provide for formation of covalent linkages between two molecules or reactants. Suitable conjugation reactions for use in the scope of the inventions herein include, but are not limited to, amide coupling reaction, Michael addition reaction, hydrazone formation reaction and click chemistry cycloaddition reaction.

In some embodiments, the αvβ6 integrin targeting ligands disclosed herein are synthesized as a tetrafluorophenyl (TFP) ester, which can be displaced by a reactive amino group to attach a cargo molecule. In some embodiments, the integrin targeting ligands disclosed herein are synthesized as an azide, which can be conjugated to a propargyl or DBCO group, for example, via click chemistry cycloaddition reaction, to attach a cargo molecule.

Protected reactive groups are also commonly used in the art. A protecting group provides temporary chemical transformation of a reactive group into a group that does not react under conditions where the non-protected group reacts, e.g, to provide chemo-selectivity in a subsequent chemical reaction. Suitable protected reactive groups for use in the scope of the inventions herein include, but are not limited to, BOC groups (t-butoxycarbonyl), Fmoc (9-fluorenylmethoxycarbonyl), carboxybenzyl (CBZ) groups, benzyl esters, and PBF (2,2,4,6,7-pentamethyldihydrobenzofuran-5-sulfonyl).

Cargo Molecules (Including RNAi Agents)

A cargo molecule is any molecule which, when detached from the αvβ6 integrin ligands described herein, would have a desirable effect on a cell comprising an αvβ6 integrin receptor. A cargo molecule can be, but is not limited to, a pharmaceutical ingredient, a drug product, a prodrug, a substance with a known therapeutic benefit, a small molecule, an antibody, an antibody fragment, an immunoglobulin, a monoclonal antibody, a label or marker, a lipid, a natural or modified nucleic acid or polynucleotide, a peptide, a polymer, a polyamine, a protein, an aptamer, a toxin, a vitamin, a PEG, a hapten, a digoxigenin, a biotin, a radioactive atom or molecule, or a fluorophore. In some embodiments, one or more cargo molecules (e.g., the same or different cargo molecules) are linked to one or more αvβ6 integrin ligands to target the cargo molecules to a cell expressing an αvβ6 integrin.

In some embodiments, the one or more cargo molecules is a pharmaceutical ingredient or pharmaceutical composition. In some embodiments, the one or more cargo molecules is an oligonucleotide-based compound. As used herein, an "oligonucleotide-based compound" is a nucleotide sequence containing about 10-50 (e.g., 10 to 48, 10 to 46, 10 to 44, 10 to 42, 10 to 40, 10 to 38, 10 to 36, 10 to 34, 10 to 32, 10 to 30, 10 to 28, 10 to 26, 10 to 24, 10 to 22, 10 to 20, 10 to 18, 10 to 16, 10 to 14, 10 to 12, 12 to 50, 12 to 48, 12 to 46, 12 to 44, 12 to 42, 12 to 40, 12 to 38, 12 to 36, 12 to 34, 12 to 32, 12 to 30, 12 to 28, 12 to 26, 12 to 24, 12 to 22, 12 to 20, 12 to 18, 12 to 16, 12 to 14, 14 to 50, 14 to 48, 14 to 46, 14 to 44, 14 to 42, 14 to 40, 14 to 38, 14 to 36, 14 to 34, 14 to 32, 14 to 30, 14 to 28, 14 to 26, 14 to 24, 14 to 22, 14 to 20, 14 to 18, 14 to 16, 16 to 50, 16 to 48, 16 to 46, 16 to 44, 16 to 42, 16 to 40, 16 to 38, 16 to 36, 16 to 34, 16 to 32, 16 to 30, 16 to 28, 16 to 26, 16 to 24, 16 to 22, 16 to 20, 16 to 18, 18 to 50, 18 to 48, 18 to 46, 18 to 44, 18 to 42, 18 to 40, 18 to 38, 18 to 36, 18 to 34, 18 to 32, 18 to 30, 18 to 28, 18 to 26, 18 to 24, 18 to 22, 18 to 20, 20 to 50, 20 to 48, 20 to 46, 20 to 44, 20 to 42, 20 to 40, 20 to 38, 20 to 36, 20 to 34, 20 to 32, 20 to 30, 20 to 28, 20 to 26, 20 to 24, 20 to 22, 22 to 50, 22 to 48, 22 to 46, 22 to 44, 22 to 42, 22 to 40, 22 to 38, 22 to 36, 22 to 34, 22 to 32, 22 to 30, 22 to 28, 22 to 26, 22 to 24, 24 to 50, 24 to 48, 24 to 46, 24 to 44, 24 to 42, 24 to 40, 24 to 38, 24 to 36, 24 to 34, 24 to 32, 24 to 30, 24 to 28, 24 to 26, 26 to 50, 26 to 48, 26 to 46, 26 to 44, 26 to 42, 26 to 40, 26 to 38, 26 to 36, 26 to 34, 26 to 32, 26 to 30, 26 to 28, 28 to 50, 28 to 48, 28 to 46, 28 to 44, 28 to 42, 28 to 40, 28 to 38, 28 to 36, 28 to 34, 28 to 32, to 28 to 30, 30 to 50, 30 to 48, 30 to 46, 30 to 44, 30 to 42, 30 to 40, 30 to 38, 30 to 36, 30 to 34, 30 to 32, 32 to 50, 32 to 48, 32 to 46, 32 to 44, 32 to 42, 32 to 40, 32 to 38, 32 to 36, 32 to 34, 34 to 50, 34 to 48, 34 to 46, 34 to 44, 34 to 42, 34 to 40, 34 to 38, 34 to 36, 36 to 50, 36 to 48, 36 to 46, 36 to 44, 36 to 42, 36 to 40, 36 to 38, 38 to 50, 38 to 48, 38 to 46, 38 to 44, 38 to 42, 38 to 40, 40 to 50, 40 to 48, 40 to 46, 40 to 44, 40 to 42, 42 to 50, 42 to 48, 42 to 46, 42 to 44, 44 to 50, 44 to 48, 44 to 46, 46 to 50, 46 to 48, or 48 to 50) nucleotides or nucleotide base pairs. In some embodiments, an oligonucleotide-based compound has a nucleobase sequence that is at least partially complementary to a coding sequence in an expressed target nucleic acid or target gene within a cell. In some embodiments, the oligonucleotide-based compounds, upon delivery to a cell expressing a gene, are able to inhibit the expression of the underlying gene, and are referred to herein as "expression-inhibiting oligonucleotide-based compounds." The gene expression can be inhibited in vitro or in vivo.

"Oligonucleotide-based compounds" include, but are not limited to: single-stranded oligonucleotides, single-stranded antisense oligonucleotides, short interfering RNAs (siRNAs), double-strand RNAs (dsRNA), micro RNAs (miRNAs), short hairpin RNAs (shRNA), ribozymes, interfering RNA molecules, and dicer substrates. In some embodiments, an oligonucleotide-based compound is a single-stranded oligonucleotide, such as an antisense oligonucleotide. In some embodiments, an oligonucleotide-based compound is a double-stranded oligonucleotide. In some embodiments, an oligonucleotide-based compound is a double-stranded oligonucleotide that is an RNAi agent.

In some embodiments, the one or more cargo molecules is/are an "RNAi agent," which as defined herein is a composition that contains an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double-strand RNAs (dsRNA), micro RNAs (miRNAs), short hairpin RNAs (shRNA), and dicer substrates. The antisense strand of the RNAi agents described herein is at least partially complementary to the mRNA being targeted. RNAi agents can include one or more modified nucleotides and/or one or more non-phosphodiester linkages.

Typically, RNAi agents can be comprised of at least a sense strand (also referred to as a passenger strand) that includes a first sequence, and an antisense strand (also referred to as a guide strand) that includes a second sequence. The length of an RNAi agent sense and antisense strands can each be 16 to 49 nucleotides in length. In some embodiments, the sense and antisense strands of an RNAi agent are independently 17 to 26 nucleotides in length. In some embodiments, the sense and antisense strands are independently 19 to 26 nucleotides in length. In some embodiments, the sense and antisense strands are independently 21 to 26 nucleotides in length. In some embodiments, the sense and antisense strands are independently 21 to 24 nucleotides in length. The sense and antisense strands can be either the same length or different lengths. The RNAi agents include an antisense strand sequence that is at least partially complementary to a sequence in the target gene, and upon delivery to a cell expressing the target, an RNAi agent may inhibit the expression of one or more target genes in vivo or in vitro.

Oligonucleotide-based compounds generally, and RNAi agents specifically, may be comprised of modified nucleotides and/or one or more non-phosphodiester linkages. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides include, but are not limited to, deoxyribonucleotides, nucleotide mimics, abasic nucleotides, 2'-modified nucleotides, 3' to 3' linkages (inverted) nucleotides, non-natural base-comprising nucleotides, bridged nucleotides, peptide nucleic acids, 2',3'-seco nucleotide mimics (unlocked nucleobase analogues, locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e. a nucleotide with a group other than a hydroxyl group at the 2' position of the five-membered sugar ring) include, but are not limited to, 2'-O-methyl nucleotides, 2'-deoxy-2'-fluoro nucleotides, 2'-deoxy nucleotides, 2'-methoxyethyl (2'-O-2-methoxylethyl) nucleotides, 2'-amino nucleotides, and 2'-alkyl nucleotides.

Moreover, one or more nucleotides of an oligonucleotide-based compound, such as an RNAi agent, may be linked by non-standard linkages or backbones (i.e., modified internucleoside linkages or modified backbones). A modified internucleoside linkage may be a non-phosphate-containing covalent internucleoside linkage. Modified internucleoside linkages or backbones include, but are not limited to, 5'-phosphorothioate groups, chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'.

It is not necessary for all positions in a given compound to be uniformly modified. Conversely, more than one modification may be incorporated in a single oligonucleotide-based compound or even in a single nucleotide thereof.

In some embodiments, the cargo molecule is an RNAi agent for inhibiting alpha ENaC gene expression. The cargo molecule may be an RNAi agent described in International Patent Application No. PCT/US18/40874, which is herein incorporated by reference in its entirety.

The RNAi agent sense strands and antisense strands may be synthesized and/or modified by methods known in the art. For example, the disclosure of RNAi agents directed to the inhibition of alpha-ENaC expression may be found, for example, in International Patent Application Publication No. WO 2008/152131, which is incorporated by reference herein in its entirety. Additional disclosures related to RNAi agents may be found, for example, in the disclosure of modifications may be found, for example, in International Patent Application No. PCT/US2017/0455446 to Arrowhead Pharmaceuticals, Inc., which also is incorporated by reference herein in its entirety. In some embodiments, the one or more cargo molecule(s) can include or consist of a PEG moiety that can acts as a pharmacokinetic (PK) modulator. In some embodiments, the one or more cargo molecules can include a PEG moiety having about 20-900 ethylene oxide ($CH_2$—$CH_2$—O) units (e.g., 20 to 850, 20 to 800, 20 to 750, 20 to 700, 20 to 650, 20 to 600, 20 to 550, 20 to 500, 20 to 450, 20 to 400, 20 to 350, 20 to 300, 20 to 250, 20 to 200, 20 to 150, 20 to 100, 20 to 75, 20 to 50, 100 to 850, 100 to 800, 100 to 750, 100 to 700, 100 to 650, 100 to 600, 100 to 550, 100 to 500, 100 to 450, 100 to 400, 100 to 350, 100 to 300, 100 to 250, 100 to 200, 100 to 150, 200 to 850, 200 to 800, 200 to 750, 200 to 700, 200 to 650, 200 to 600, 200 to 550, 200 to 500, 200 to 450, 200 to 400, 200 to 350, 200 to 300, 200 to 250, 250 to 900, 250 to 850, 250 to 800, 250 to 750, 250 to 700, 250 to 650, 250 to 600, 250 to 550, 250 to 500, 250 to 450, 250 to 400, 250 to 350, 250 to 300, 300 to 900, 300 to 850, 300 to 800, 300 to 750, 300 to 700, 300 to 650, 300 to 600, 300 to 550, 300 to 500, 300 to 450, 300 to 400, 300 to 350, 350 to 900, 350 to 850, 350 to 800, 350 to 750, 350 to 700, 350 to 650, 350 to 600, 350 to 550, 350 to 500, 350 to 450, 350 to 400, 400 to 900, 400 to 850, 400 to 800, 400 to 750, 400 to 700, 400 to 650, 400 to 600, 400 to 550, 400 to 500, 400 to 450, 450 to 900, 450 to 850, 450 to 800, 450 to 750, 450 to 700, 450 to 650, 450 to 600, 450 to 550, 450 to 500, 500 to 900, 500 to 850, 500 to 800, 500 to 750, 500 to 700, 500 to 650, 500 to 600, 500 to 550, 550 to 900, 550 to 850, 550 to 800, 550 to 750, 550 to 700, 550 to 650, 550 to 600, 600 to 900, 600 to 850, 600 to 800, 600 to 750, 600 to 700, 600 to 650, 650 to 900, 650 to 850, 650 to 800, 650 to 750, 650 to 700, 700 to 900, 700 to 850, 700 to 800, 700 to 750, 750 to 900, 750 to 850, 750 to 800, 800 to 900, 850 to 900, or 850 to 900 ethylene oxide units). In some embodiments, the one or more cargo molecule(s) consist of a PEG moiety having approximately 455 ethylene oxide units (about 20 kilodalton (kDa) molecular weight). In some embodiments, a PEG moiety has a molecular weight of about 2 kilodaltons. In some embodiments, a PEG moiety has a molecular weight of about 20 kilodaltons. In some embodiments, a PEG moiety has a molecular weight of about 40 kilodaltons. The PEG moieties described herein may be linear or branched. The PEG moieties may be discrete (monodispersed) or non-discrete (polydispersed). PEG moieties for use as a PK enhancing cargo molecule may be purchase commercially. In some embodiments, the one or more cargo molecule(s) include a PEG moiety that can act as a PK modulator or enhancer, as well as a different cargo molecule, such as a pharmaceutically active ingredient or compound.

The described αvβ6 integrin ligands include salts or solvates thereof. Solvates of an αvβ6 integrin ligand is taken to mean adductions of inert solvent molecules onto the αvβ6 integrin ligand which form owing to their mutual attractive force. Solvates are, for example, mono- or dihydrates or addition compounds with alcohols, such as, for example, with methanol or ethanol.

Free amino groups or free hydroxyl groups can be provided as substituents of αvβ6 integrin ligands with corresponding protecting groups.

The αvβ6 integrin ligands also include, e.g., derivatives, i.e., αvβ6 integrin ligands modified with, for example, alkyl or acyl groups, sugars or oligopeptides, which are cleaved either in vitro or in an organism.

In some embodiments, an αvβ6 integrin ligand disclosed herein facilitates the delivery of a cargo molecule into the cytosol of a cell presenting an αvβ6 integrin on its surface, either through ligand-mediated endocytosis, pinocytosis, or by other means. In some embodiments, an αvβ6 integrin ligand disclosed herein facilitates the delivery of a cargo molecule to the plasma membrane of a cell presenting an αvβ6 integrin.

Pharmaceutical Compositions

In some embodiments, the present disclosure provides pharmaceutical compositions that include, consist of, or consist essentially of, one or more of the αvβ6 integrin ligands disclosed herein.

As used herein, a "pharmaceutical composition" comprises a pharmacologically effective amount of an Active Pharmaceutical Ingredient (API), and optionally one or more pharmaceutically acceptable excipients. Pharmaceutically acceptable excipients (excipients) are substances other than the Active Pharmaceutical ingredient (API, therapeutic product) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

The pharmaceutical compositions described herein can contain other additional components commonly found in pharmaceutical compositions. In some embodiments, the additional component is a pharmaceutically-active material. Pharmaceutically-active materials include, but are not limited to: anti-pruritics, astringents, local anesthetics, or anti-inflammatory agents (e.g., antihistamine, diphenhydramine, etc.), small molecule drug, antibody, antibody fragment, aptamers, and/or vaccine.

The pharmaceutical compositions may also contain preserving agents, solubilizing agents, stabilizing agents, wetting agents, emulsifiers, sweeteners, colorants, odorants, salts for the variation of osmotic pressure, buffers, coating agents, or antioxidants. They may also contain other agent with a known therapeutic benefit.

The pharmaceutical compositions can be administered in a number of ways depending upon whether local or systemic treatment is desired and upon the area to be treated. Administration can be made by any way commonly known in the art, such as, but not limited to, topical (e.g., by a transdermal patch), pulmonary (e.g., by inhalation or insufflation of powders or aerosols, including by nebulizer, intratracheal, intranasal), epidermal, transdermal, oral or parenteral. Parenteral administration includes, but is not limited to, intravenous, intraarterial, subcutaneous, intraperitoneal or intramuscular injection or infusion; subdermal (e.g., via an implanted device), intracranial, intraparenchymal, intrathecal, and intraventricular, administration. In some embodiments, the pharmaceutical compositions described herein are administered by subcutaneous injection. The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels, or solutions; or parenterally, for example using injectable solutions.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of any of the ligands described herein that can be in microcrystalline form, for example, in the form of an aqueous microcrystalline suspension. Liposomal formulations or biodegradable polymer systems can also be used to present any of the ligands described herein for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). As used herein, "pharmacologically effective amount," "therapeutically effective amount," or simply "effective amount" refers to that amount of an the pharmaceutically active agent to produce a pharmacological, therapeutic or preventive result.

Medicaments containing an αvβ6 integrin ligand are also an object of the present invention, as are processes for the manufacture of such medicaments, which processes comprise bringing one or more compounds containing a αvβ6 integrin ligand, and, if desired, one or more other substances with a known therapeutic benefit, into a pharmaceutically acceptable form.

The described αvβ6 integrin ligands and pharmaceutical compositions comprising αvβ6 integrin ligands disclosed herein may be packaged or included in a kit, container, pack, or dispenser. The αvβ6 integrin ligands and pharmaceutical compositions comprising the αvβ6 integrin ligands may be packaged in pre-filled syringes or vials.

Cells, Tissues, and Non-Human Organisms

Cells, tissues, and non-human organisms that include at least one of the αvβ6 integrin ligands described herein is contemplated. The cell, tissue, or non-human organism is made by delivering the αvβ6 integrin ligand to the cell, tissue, or non-human organism by any means available in the art. In some embodiments, the cell is a mammalian cell, including, but not limited to, a human cell.

Targeting Groups, Linking Groups, Pharmacokinetic (PK) Modulators, and Delivery Vehicles In some embodiments, an αvβ6 ligand is conjugated to one or more non-nucleotide groups including, but not limited to, a linking group, a pharmacokinetic (PK) modulator, a delivery polymer, or a delivery vehicle. The non-nucleotide group can enhance targeting, delivery, or attachment of the cargo molecule. Examples of targeting groups and linking groups are provided in Table 6. The non-nucleotide group can be covalently linked to the 3' and/or 5' end of either the sense strand and/or the antisense strand. In embodiments where the cargo molecule is an RNAi agent, the RNAi agent contains a non-nucleotide group linked to the 3' and/or 5' end of the sense strand. In some embodiments, a non-nucleotide group is linked to the 5' end of an RNAi agent sense strand. An αvβ6 ligand can be linked directly or indirectly to the cargo molecule via a linker/linking group. In some embodiments, a αvβ6 ligand is linked to the cargo molecule via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the conjugate. In some embodiments, a non-nucleotide group enhances endocytosis of the RNAi agent.

Targeting groups or targeting moieties enhance the pharmacokinetic or biodistribution properties of a cargo molecule to which they are attached to improve cell-specific (including, in some cases, organ specific) distribution and cell-specific (or organ specific) uptake of the cargo molecule. In some embodiments, a targeting group may comprise an αvβ6 ligand as described herein. In some embodiments, a targeting group comprises a linker. In some embodiments, a targeting group comprises a PK modulator. In some embodiments, an αvβ6 ligand is linked to a cargo molecule using a linker, such as a PEG linker or one, two, or three abasic and/or ribitol (abasic ribose) residues, which in some instances can serve as linkers.

Cargo molecules can be synthesized having a reactive group, such as an amino group (also referred to herein as an amine). In embodiments where the cargo molecule is an RNAi agent, the reactive group may be linked at the 5'-terminus and/or the 3'-terminus. The reactive group can be used subsequently to attach an αvβ6 ligand using methods typical in the art.

For example, in some embodiments, an RNAi agent is synthesized having an $NH_2$—$C_6$ group at the 5'-terminus of the sense strand of the RNAi agent. The terminal amino group subsequently can be reacted to form a conjugate with, for example, a group that includes an αvβ6 integrin targeting ligand. In some embodiments, an RNAi agent is synthesized having one or more alkyne groups at the 5'-terminus of the sense strand of the RNAi agent. The terminal alkyne group (s) can subsequently be reacted to form a conjugate with, for example, a group that includes an αvβ6 integrin targeting ligand.

In some embodiments, a linking group is conjugated to the αvβ6 ligand. The linking group facilitates covalent linkage of the αvβ6 ligand to a cargo molecule, pharmacokinetic modulator, delivery polymer, or delivery vehicle. Examples of linking groups, include, but are not limited to: Alk-SMPT-C6, Alk-SS-C6, DBCO-TEG, Me-Alk-SS-C6, and C6-SS-Alk-Me, reactive groups such a primary amines and alkynes, alkyl groups, abasic residues/nucleotides, amino acids, tri-alkyne functionalized groups, ribitol, and/or PEG groups.

A linker or linking group is a connection between two atoms that links one chemical group (such as an RNAi agent) or segment of interest to another chemical group (such as an αvβ6 ligand, pharmacokinetic modulator, or delivery polymer) or segment of interest via one or more covalent bonds. A labile linkage contains a labile bond. A linkage can optionally include a spacer that increases the distance between the two joined atoms. A spacer may further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some embodiments, αvβ6 ligands are linked to cargo molecules without the use of an additional linker. In some embodiments, the αvβ6 ligand is designed having a linker readily present to facilitate the linkage to a cargo molecule. In some embodiments, when two or more RNAi agents are included in a composition, the two or more RNAi agents can be linked to their respective targeting groups using the same linkers. In some embodiments, when two or more RNAi agents are included in a composition, the two or more RNAi agents are linked to their respective targeting groups using different linkers.

Examples of certain linking groups are provided in Table A.

TABLE A

Structures Representing Various Linking Groups

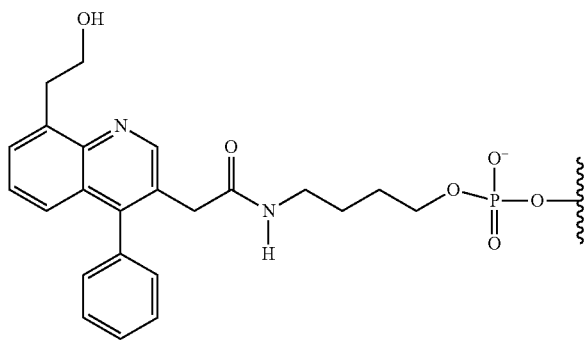

(PAZ)

When positioned at the 3' terminal end of oligonucleotide:

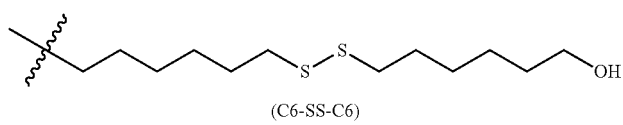 [SMILES: *CCCCCCSSCCCCCCO]

(C6-SS-C6)

When positioned internally in oligonucleotide:

linkage towards 5' end of oligonucleotide        linkage towards 3' end of oligonucleotide

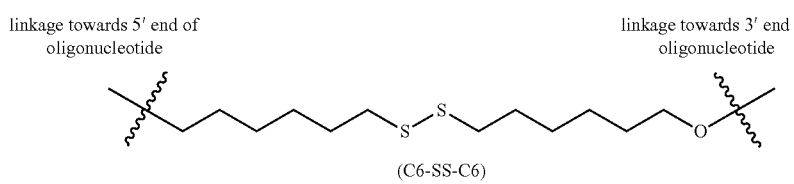

(C6-SS-C6)

When positioned at the 3' terminal end of oligonucleotide:

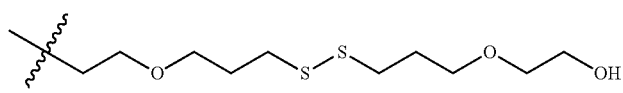 [SMILES: *CCOCCCSSCCCOCCO]

When positioned internally in oligonucleotide:

linkage towards 5' end of oligonucleotide        linkage towards 3' end of oligonucleotide

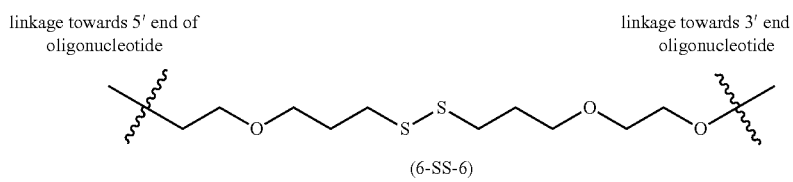

(6-SS-6)

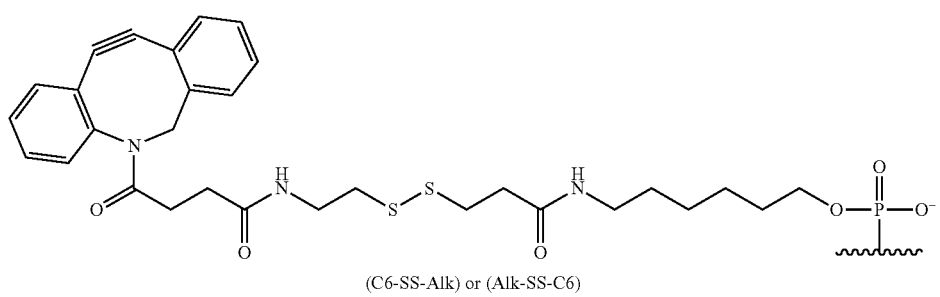 [SMILES: *P(=O)([O-])OCCCCCCNC(=O)CCSSCCNC(=O)CCC(=O)N1Cc2ccccc2C#Cc2ccccc21]

(C6-SS-Alk) or (Alk-SS-C6)

TABLE A-continued
Structures Representing Various Linking Groups
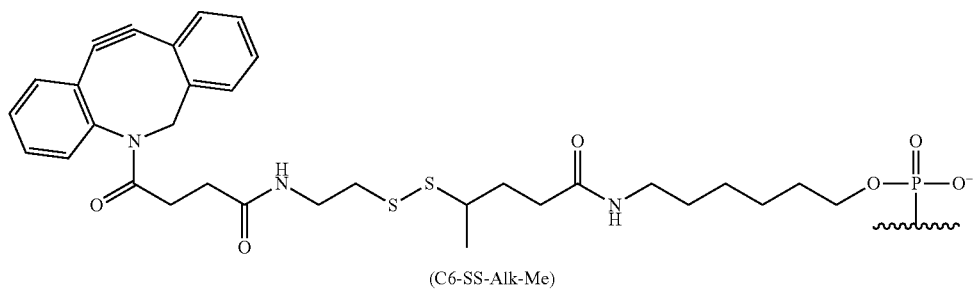 [SMILES: *P(=O)([O-])OCCCCCCNC(=O)CCC(C)SSCCNC(=O)CCC(=O)N1Cc2ccccc2C#Cc2ccccc21]
(C6-SS-Alk-Me)
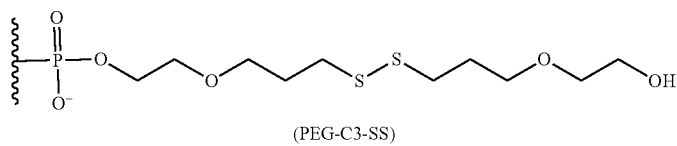 [SMILES: *P(=O)([O-])OCCOCCCSSCCCOCCO]
(PEG-C3-SS)
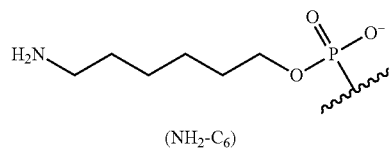
(NH₂-C₆)
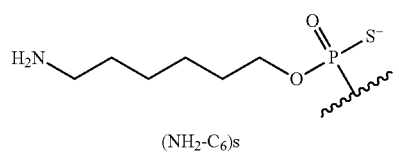 [SMILES: *P(=O)([S-])OCCCCCCN ; "(NH2-C6)s"]
(NH₂-C₆)s
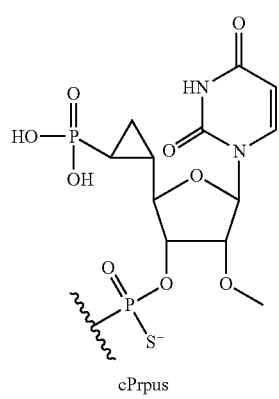 [SMILES: *P(=O)([S-])OC1C(C2CC2P(=O)(O)O)OC(n2ccc(=O)[nH]c2=O)C1OC]
cPrpus
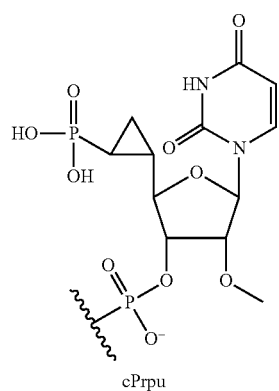 [SMILES: *P(=O)([O-])OC1C(C2CC2P(=O)(O)O)OC(n2ccc(=O)[nH]c2=O)C1OC]
cPrpu TABLE A-continued
Structures Representing Various Linking Groups
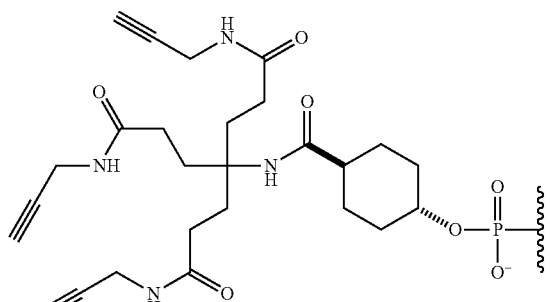
(TriAlk1)
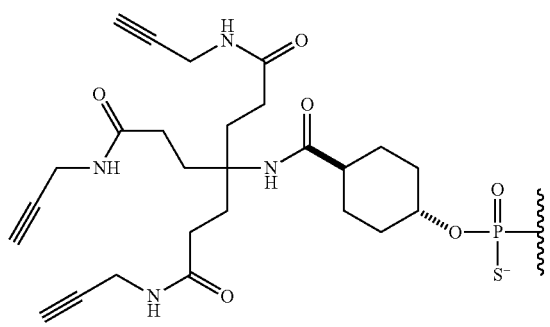
(TriAlk1)s
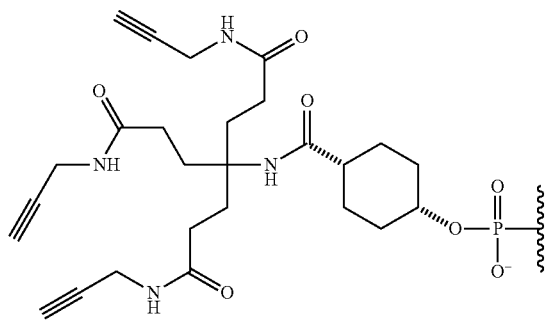
(TriAlk2)
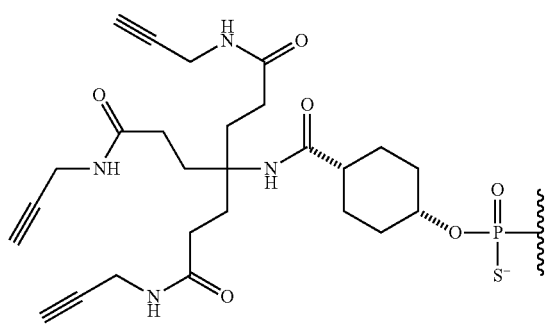
(TriAlk2)s TABLE A-continued
Structures Representing Various Linking Groups
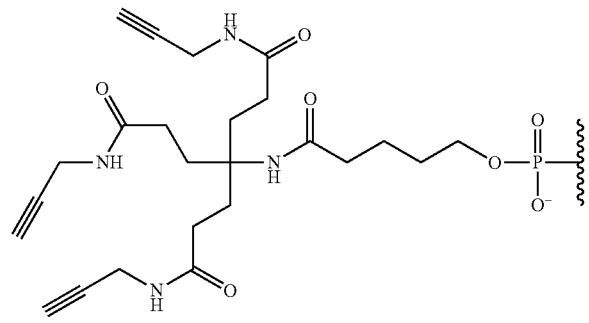
(TriAlk3)
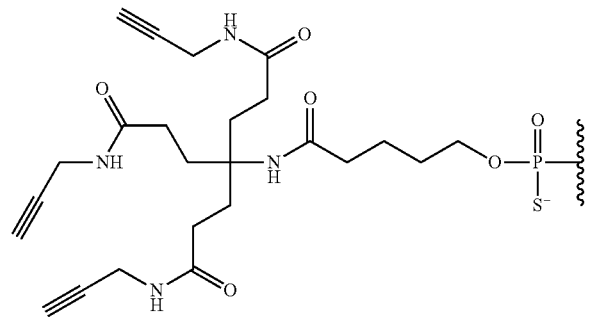
(TriAlk3)s
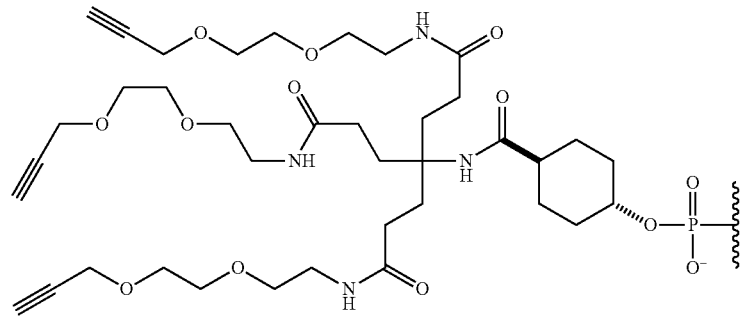
(TriAlk4)
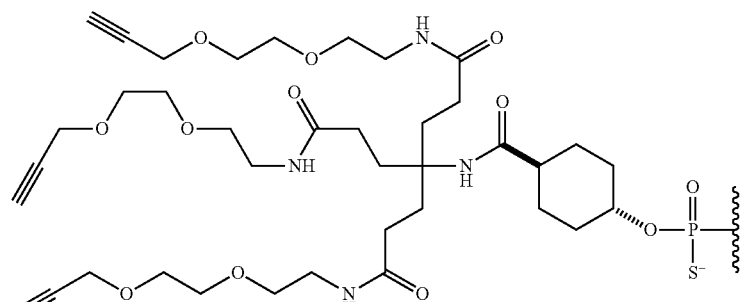
(TriAlk4)s TABLE A-continued
Structures Representing Various Linking Groups
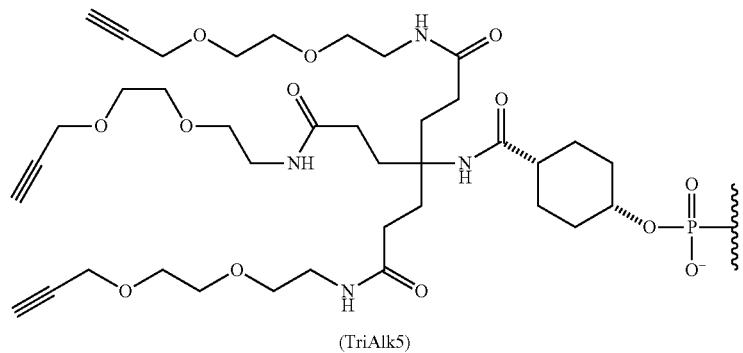
(TriAlk5)
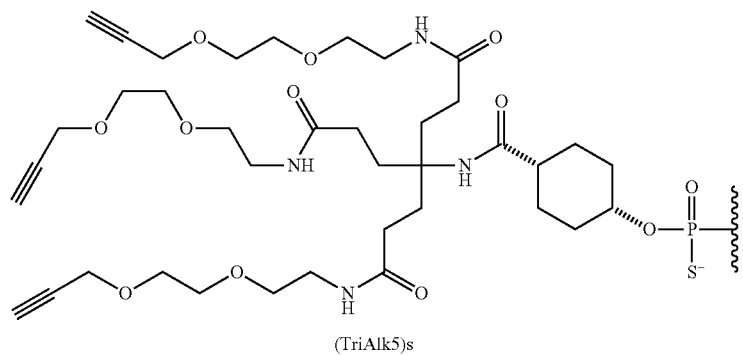
(TriAlk5)s
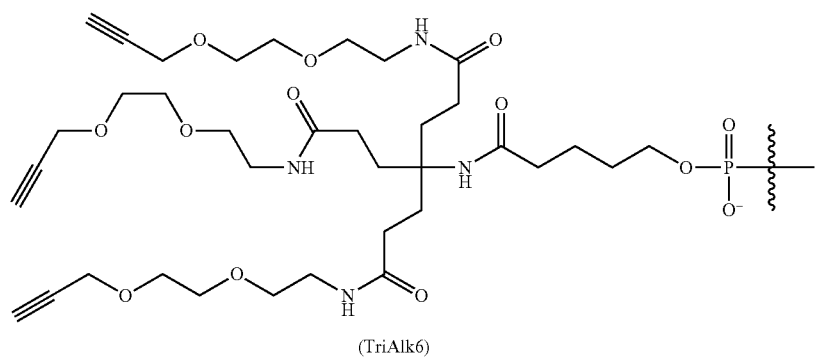 [SMILES: *P(=O)([O-])OCCCCC(=O)NC(CCC(=O)NCCOCCOCC#C)(CCC(=O)NCCOCCOCC#C)CCC(=O)NCCOCCOCC#C]
(TriAlk6)
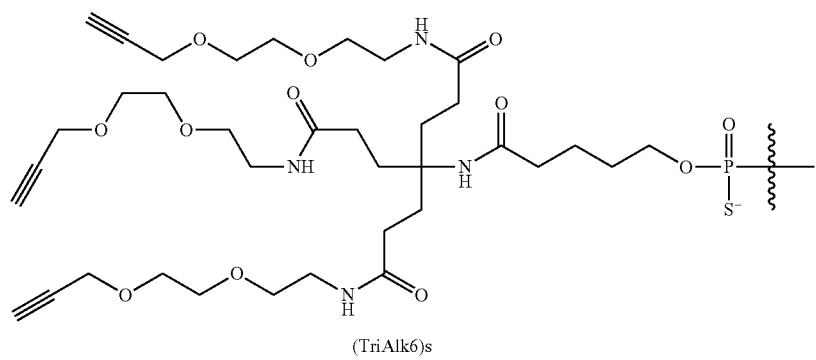 [SMILES: *P(=O)([S-])OCCCCC(=O)NC(CCC(=O)NCCOCCOCC#C)(CCC(=O)NCCOCCOCC#C)CCC(=O)NCCOCCOCC#C]
(TriAlk6)s TABLE A-continued
Structures Representing Various Linking Groups
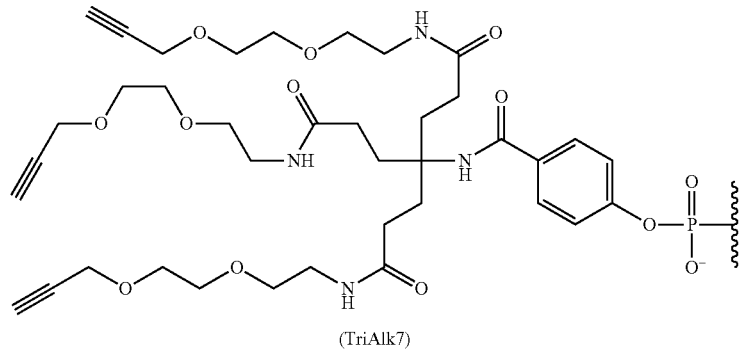
(TriAlk7)
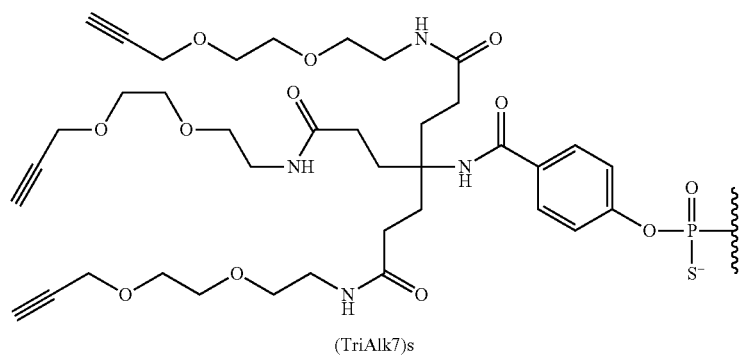 [SMILES: *P(=O)([S-])Oc1ccc(C(=O)NC(CCC(=O)NCCOCCOCC#C)(CCC(=O)NCCOCCOCC#C)CCC(=O)NCCOCCOCC#C)cc1]
(TriAlk7)s
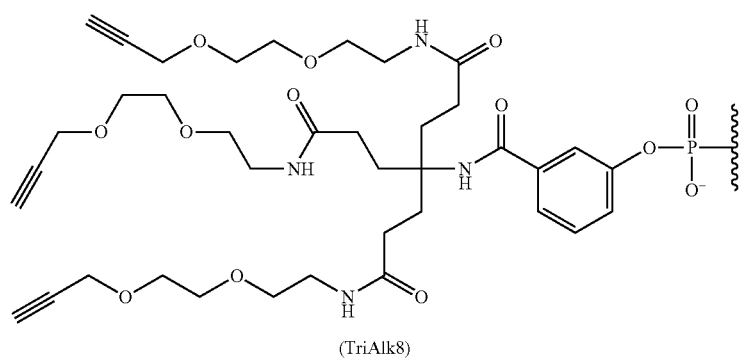 [SMILES: *P(=O)([O-])Oc1cccc(C(=O)NC(CCC(=O)NCCOCCOCC#C)(CCC(=O)NCCOCCOCC#C)CCC(=O)NCCOCCOCC#C)c1]
(TriAlk8)
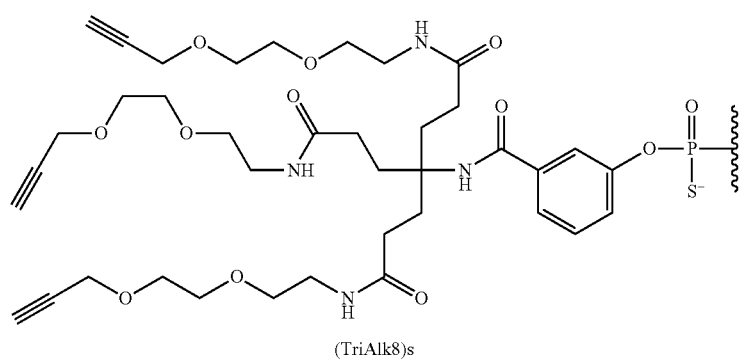 [SMILES: *P(=O)([S-])Oc1cccc(C(=O)NC(CCC(=O)NCCOCCOCC#C)(CCC(=O)NCCOCCOCC#C)CCC(=O)NCCOCCOCC#C)c1]
(TriAlk8)s TABLE A-continued
Structures Representing Various Linking Groups
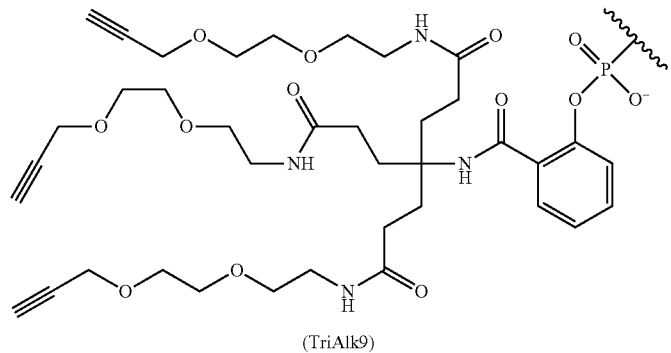 [SMILES: *P(=O)([O-])Oc1ccccc1C(=O)NC(CCC(=O)NCCOCCOCC#C)(CCC(=O)NCCOCCOCC#C)CCC(=O)NCCOCCOCC#C]
(TriAlk9)
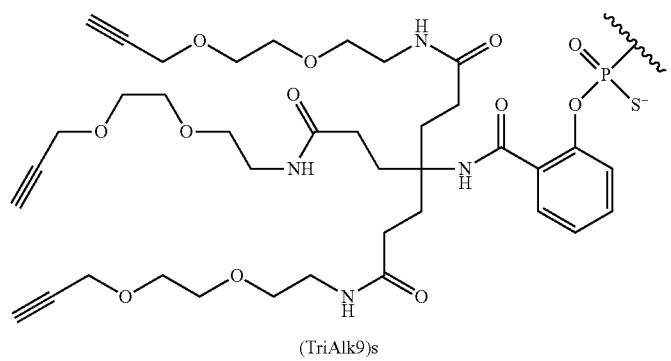 [SMILES: *P(=O)([S-])Oc1ccccc1C(=O)NC(CCC(=O)NCCOCCOCC#C)(CCC(=O)NCCOCCOCC#C)CCC(=O)NCCOCCOCC#C]
(TriAlk9)s
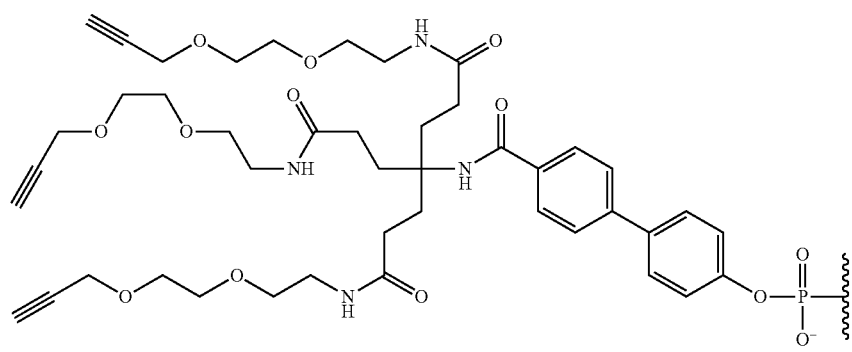
(TriAlk10)
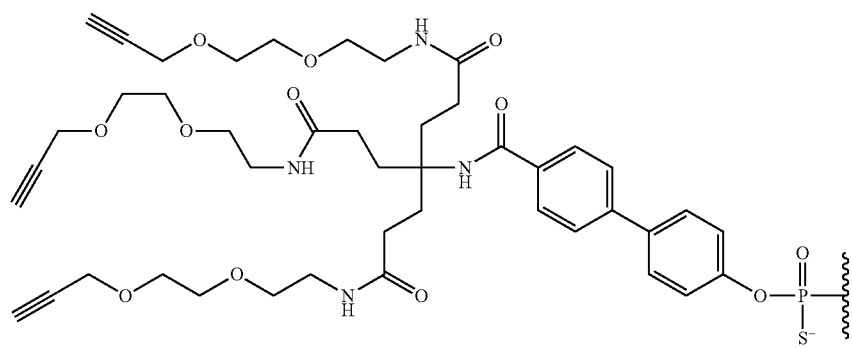
(TriAlk10)s TABLE A-continued
Structures Representing Various Linking Groups
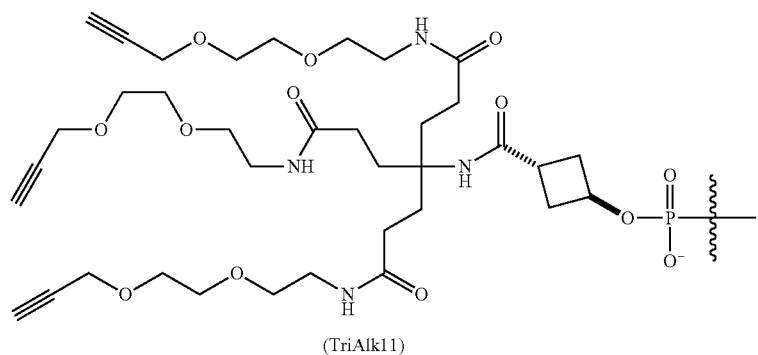
(TriAlk11)
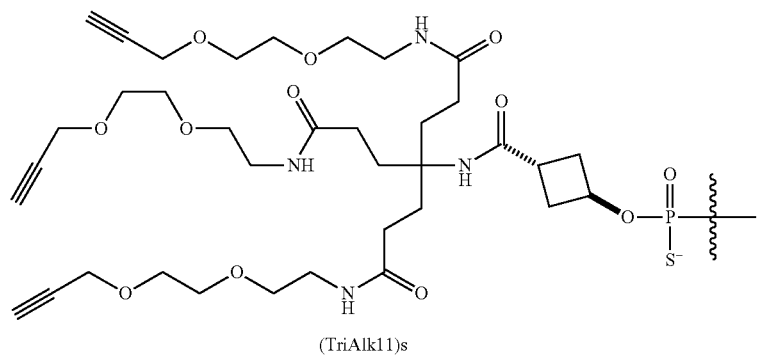
(TriAlk11)s
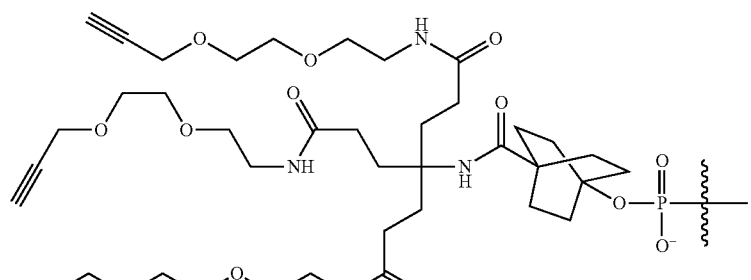
(TriAlk12)
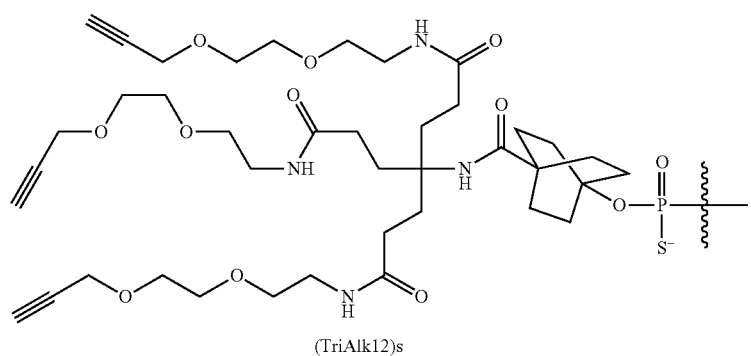 [SMILES: *P(=O)([O-])OC12CCC(C(=O)NC(CCC(=O)NCCOCCOCC#C)(CCC(=O)NCCOCCOCC#C)CCC(=O)NCCOCCOCC#C)(CC1)CC2]
(TriAlk12)s TABLE A-continued Structures Representing Various Linking Groups

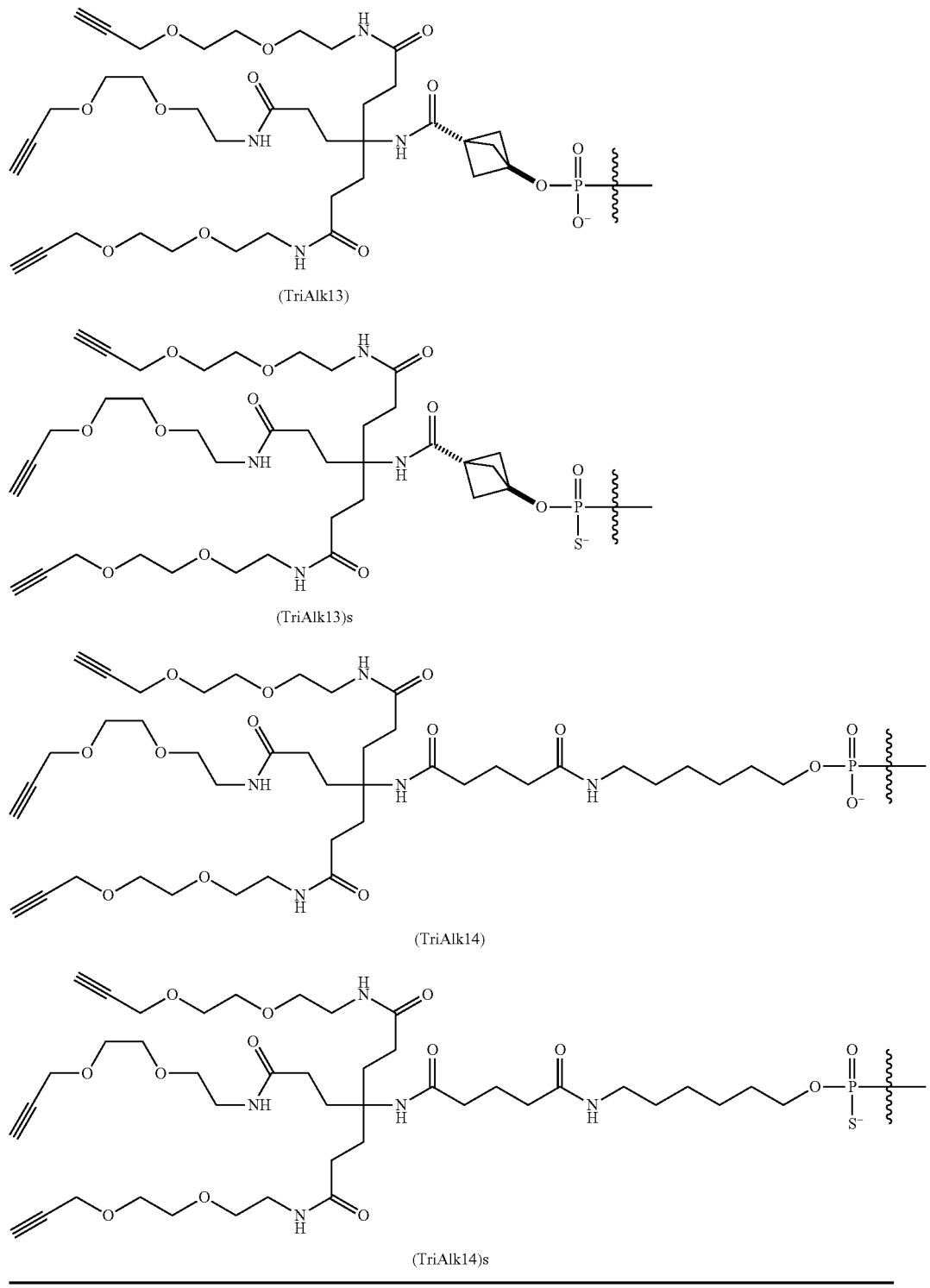

(TriAlk13)

(TriAlk13)s (TriAlk14)

(TriAlk14)s wherein ⸹ indicates the point of attachment to a cargo molecule.

Alternatively, other linking groups known in the art may be used.

The above provided embodiments and items are now illustrated with the following, non-limiting examples.

EXAMPLES

The following examples are not limiting and are intended to illustrate certain embodiments disclosed herein.

Example 1. Synthesis of αvβ6 Integrin Ligands

Some of the abbreviations used in the following experimental details of the synthesis of the examples are defined as follows: h or hr=hour(s); min=minute(s); mol=mole(s); mmol=millimole(s); M=molar; M=micromolar; g=gram(s); g=microgram(s); rt or RT=room temperature; L=liter(s); mL=milliliter(s); wt=weight; $Et_2O$=diethyl ether; THF=tetrahydrofuran; DMSO=dimethyl sulfoxide; EtOAc=ethyl acetate; $Et_3N$ or TEA=triethylamine; i-$Pr_2NEt$ or DIPEA or DIEA=diisopropylethylamine; $CH_2Cl_2$ or DCM=methylene chloride; $CHCl_3$=chloroform; $CDCl_3$=deuterated chloroform; $CCl_4$=carbon tetrachloride; MeOH=methanol; EtOH=ethanol; DMF=dimethylformamide; BOC=t-butoxycarbonyl; CBZ=benzyloxycarbonyl; TBS=t-butyldimethylsilyl; TBSCl or TBDMSCl=t-butyldimethylsilyl chloride; TFA=trifluoroacetic acid; DMAP=4-dimethylaminopyridine; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; HCl=hydrogen chloride or hydrochloric acid; NMM=N-methylmorpholine; $H_2$=hydrogen gas; KF=potassium fluoride; EDC-HCl=N-(3-Dimethylaminopropyl)-N'-ethylcarbodiimide hydrochloride; MTBE=methyl-tert-butyl ether; Ar=argon; $N_2$=nitrogen; RT=retention time.

Chemical names for structures 1-37 were automatically generated using ChemDraw® software.

Synthesis of Structure 1b ((14S,17S)-1-azido-14-(5-((4-methylpyridin-2-yl)amino)pentanamido)-17-(4-(naphthalen-1-yl)phenyl)-15-oxo-3,6,9,12-tetraoxa-16-azanonadecan-19-oic Acid)

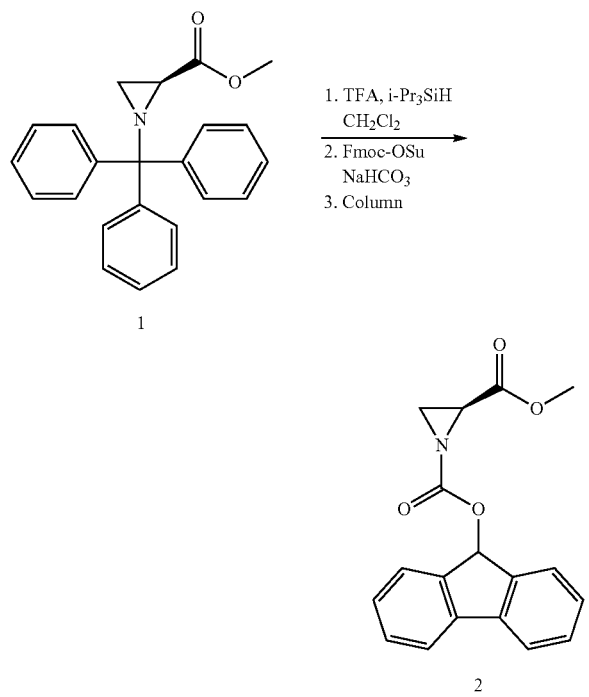

Compound 1 (Methyl (S)-(−)-1-tritylaziridine-2-carboxylate (4.204 g, 12.24 mmol, 1.0 equiv.) and triisopropylsilane (3.877 g, 5.02 mL, 24.48 mmol, 2 equiv.) were dissolved in DCM (40 mL), the solution was cooled to 0° C., and then TFA (8.5 eq) was added dropwise. The solution remained for 1 hour at 0° C. The reaction was monitored by TLC Hexane:Ethyl Acetate (8:2). The solution was dried to yield a mixture of white precipitate and light yellow oil. Hexanes (40 mL) were added and heated gently over heat gun until all white precipitate dissolved. The addition of hexanes resulted in two layers, a clear upper layer and an oil layer. The hexane layer was poured off and the oil layer was retained. The hexanes addition was repeated and once again poured off. The oil was allowed to dry. The aziridine (1.06 g, 10.5 mmol) was dissolved in THF/$H_2O$ (2/1) 60 mL total. Fmoc-OSu (5.312 g, 15.75 mmol, 1.5 eq) and $NaHCO_3$ (2.646 g, 31.5 mmol, 3 eq to keep pH=8.5) were added to the mixture at room temp and allowed to react overnight. The reaction was monitored by TLC, Hexane:Ethyl Acetate 8:2. The mixture was concentrated until all the THF was removed, then diluted with ethyl acetate (350 mL) and $H_2O$ (25 mL). The layers were separated, and the organics washed with $H_2O$ (40 mL). The organics were then washed with pH 3-4 water (2×40 mL), then $H_2O$ (40 mL), then saturated aq. NaCl solution (40 mL). The organic phase was dried over $Na_2SO_4$, filtered, and concentrated. The product was purified on silica column 10%-20% ethyl acetate in hexanes.

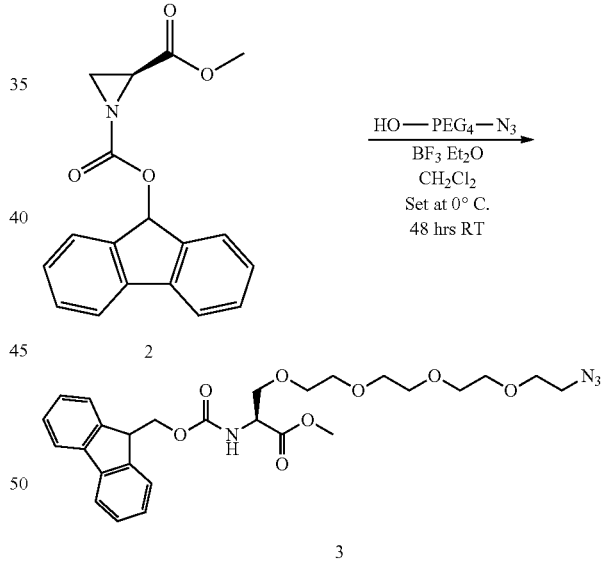

Compound 2 (Fmoc-aziridine) (1.46 g, 4.52 mmol) and HO-$PEG_4$-$N_3$ (1.983 g, 9.04 mmol, 2 eq) were dissolved in DCM. The mixture was cooled to 0° C. Boron trifluoride diethyl etherate (12 drops) was added dropwise. The mixture was stirred at RT for 48 hours. The reaction was monitored by TLC, DCM with 5% MeOH. The reaction was quenched with $NH_4Cl$ saturated solution (5 mL), diluted with DCM (60 mL) and washed with $H_2O$ (3×20 mL), saturated aq. NaCl solution (20 mL), dried over $Na_2SO_4$, filtered, and concentrated. The product was purified on a silica column, 40%-60% ethyl acetate in hexanes.

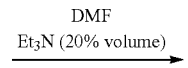

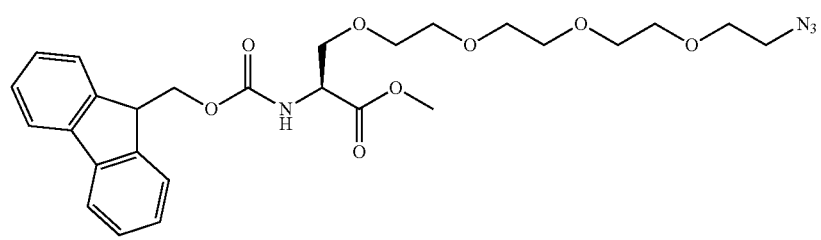

3

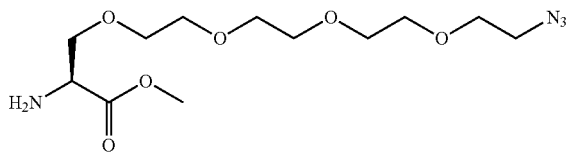

4

Compound 3 was dissolved in a solution of 20% triethylamine in DMF. The reaction was monitored by TLC. The product was concentrated.

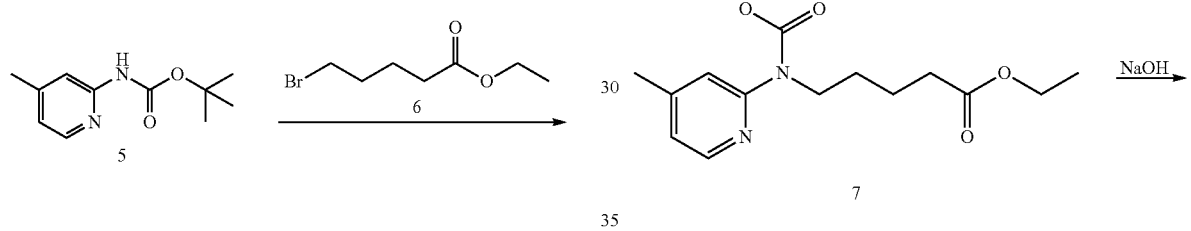

Compound 5 (tert-Butyl(4-methylpyridin-2-yl)carbamate) (0.501 g, 2.406 mmol, 1.0 equiv.) was dissolved in DMF (17 mL). To the mixture was added NaH (0.116 mg, 3.01 mmol, 1.25 eq, 60% dispersion in mineral oil) at room temperature. The mixture stirred for 10 min, then ethyl 5-bromovalerate (0.798 g, 3.82 mmol, 0.604 mL) was added. After 3 hours the reaction was quenched with ethanol (18 mL) and concentrated. The product was dissolved in DCM (50 mL) and washed with saturated aq. NaCl solution (50 mL), dried over $Na_2SO_4$, filtered and concentrated. The product was purified on silica column, gradient 0-5% methanol in DCM.

Compound 7 (0.80 g, 2.378 mmol) was dissolved in 100 mL of acetone:0.1 M NaOH (1:1), and the reaction was monitored by TLC (5% ethyl acetate in hexane). The organics were concentrated, and the mixture was acidified to pH 3-4 with 0.3 M citric acid (40 mL). The product was extracted with DCM (3×75 mL). The organics were pooled, dried over $Na_2SO_4$, filtered and concentrated. The product was used without further purification.

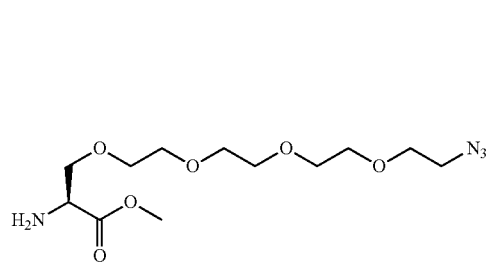

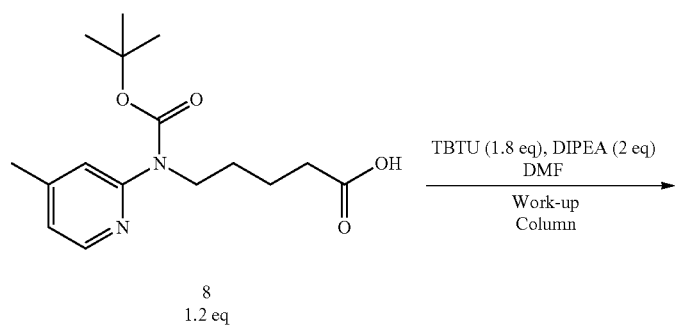

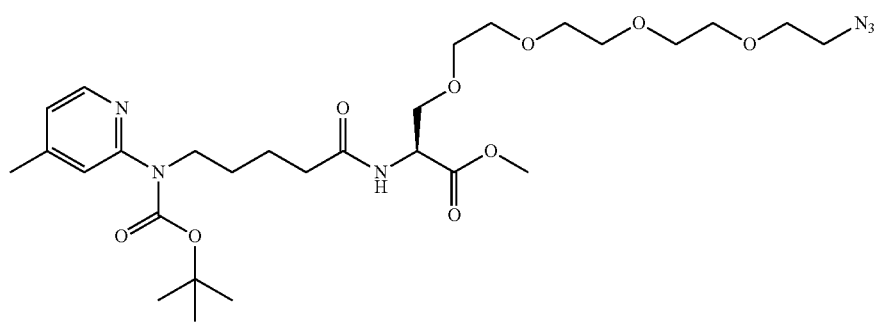

Compound 4 was dissolved (0.340 g, 1.104 mmol) in DMF (10 mL). To the solution was added TBTU (0.531 g, 1.655 mmol) and diisopropylethylamine (0.320 mL, 1.839 mmol). Then compound 8 was added (0.295 g, 0.9197 mmol). The reaction was monitored by LC-MS and TLC (DCM with 5% MeOH). The reaction was complete in 2 hours. The product was concentrated and dissolved in ethyl acetate (150 mL), and washed with pH 3-4 H$_2$O (2×12 mL). Then the product was washed with H$_2$O (2×12 mL), saturated aq. NaHCO$_3$ solution (12 mL), then saturated aq. NaCl solution (12 mL). The organic phase was dried over Na$_2$SO$_4$, filtered and concentrated. The product was purified on silica column, hexanes 20% in ethyl acetate to 100% ethyl acetate.

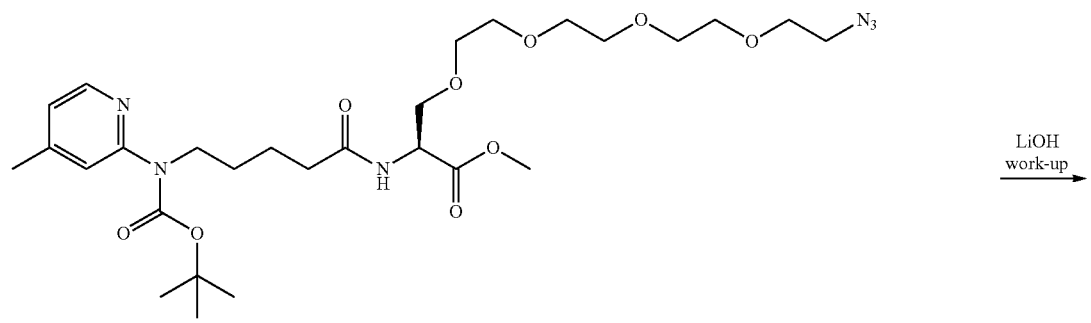

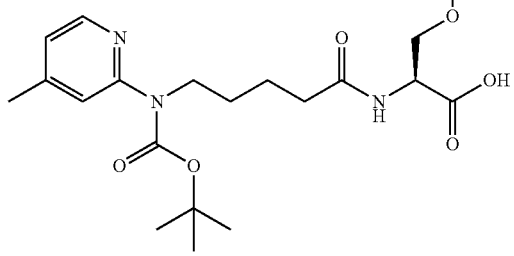

10

Compound 9 was dissolved (0.330 g, 0.540 mmol) in 10 mL of MeOH:dioxane [1:1] and 1 M LiOH solution (10 mL) The mixture was stirred at rt for 2 hr, monitored by LC-MS and TLC (EtOAc). The organics were concentrated away, and the mixture was diluted with H₂O (5 mL) and acidified to pH 4. The product was extracted with ethyl acetate (2×50 mL). The organics were pooled, washed with saturated aq. NaCl solution (10 mL), dried over Na₂SO₄, filtered and concentrated. The product was used without further purification.

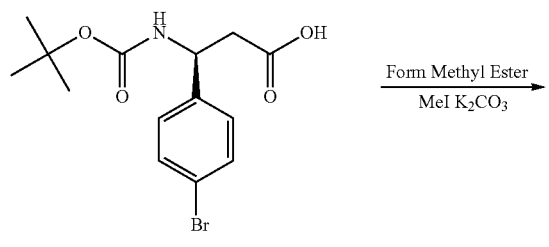

11

Form Methyl Ester
MeI K₂CO₃
→

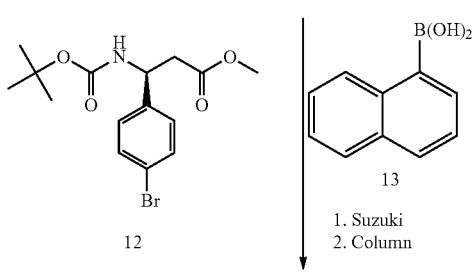

12

B(OH)₂

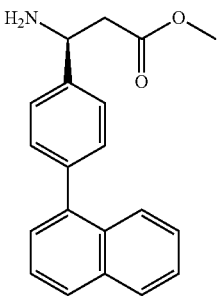

13

1. Suzuki
2. Column

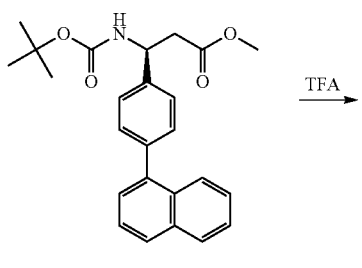

14

TFA →

-continued

H₂N

15

Compound 11 ((S)-3-(4-Bromophenyl)-3-((tert-butoxycarbonyl)amino)-propionic acid) (2.0 g, 5.81 mmol) was dissolved in DMF (40 mL). To the mixture was added K₂CO₃ (1.2 g, 8.72 mmol). Then iodomethane (1.65 g, 11.62 mmol, 0.72 mL) was added. The reaction was monitored by TLC (hexane:ethyl acetate (7:3)). Upon completion, the mixture was cooled to 0° C. and H₂O (20 mL) and MTBE (40 mL) were added. The product was extracted with MTBE (4×40 mL). The combined organic phase was washed with saturated aq. NaHCO₃ (40 mL) then H₂O (4×40 mL). The mixture was dried over Na₂SO₄, filtered and concentrated.

To dried product compound 12 (1.0 g, 2.7915 mmol) was added compound 13 (1-Naphthalene Boronic Acid (0.960 g, 5.583 mmol, 2 eq)). To the mixture was added [1,1'-Bis(diphenylphosphino)ferrocene]dichloropalladium(II) or Pd(dppf)Cl₂ (0.0817 g, 0.1117 mmol, 0.4 eq) along with Na₂CO₃ (0.888 g, 8.375 mmol, 3 eq). Next, 1,4-dioxane (5 mL) and H₂O (0.2 mL) were added, and the mixture was stirred at 100° C. for 4 hr. The reaction was monitored by TLC (hexane:ethyl acetate (7:3)). The product was purified by silica chromatography, gradient 0% to 50% ethyl acetate in hexanes.

Compound 14 (0.200 g, 0.493 mmol) was dissolved in DCM (2.5 mL), then TFA (0.45 mL) was added. The reaction was monitored by TLC, (DCM:methanol (9:1)). Upon completion, the reaction mixture was concentrated. The residue was dissolved in DCM (4 mL) and washed with saturated aq. NaHCO₃ solution (2×2 mL) then saturated aq. NaCl solution (2×2 mL). The organic phase was dried over Na₂SO₄, filtered and concentrated. The product was used without further purification.

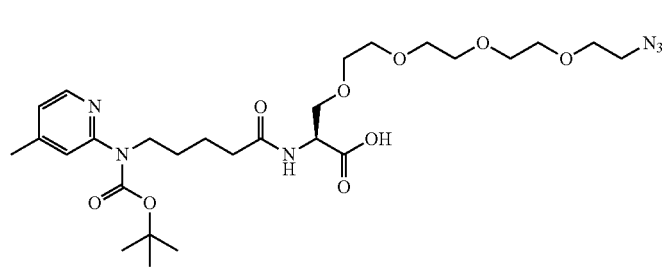

10

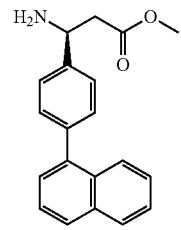

15 (1 eq)

TBTU (1.5 eq), DIPEA (2 eq)
DMF
——————————→
Work-up Column

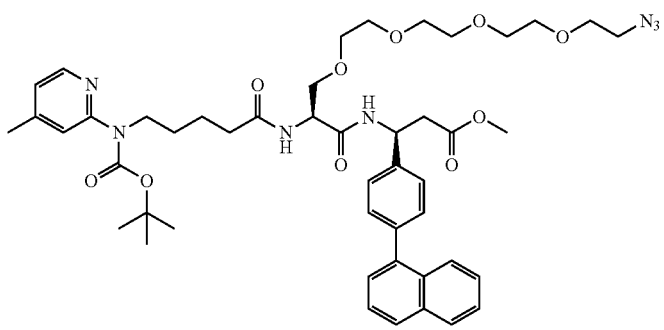

16

Compound 10 (0.3224 g, 0.54 mmol) was dissolved in DMF (7 mL). To the mixture was added TBTU (0.236 g, 0.735 mmol) and diisopropylethylamine (0.170 mL, 0.98 mmol). Then compound 15 was added (0.1496 g, 0.49 mmol). The reaction was stirred at RT for 2 hours. The reaction was monitored by LC-MS. The mixture was concentrated, and the residue was dissolved in ethyl acetate (90 mL), and washed with pH 3-4 $H_2O$ (3×10 mL). The product was washed with $H_2O$ (2×10 mL), saturated aq. $NaHCO_3$ solution (10 mL), and then saturated aq. NaCl solution (1×10 mL). The organic phase was dried over $Na_2SO_4$, filtered and concentrated. The product was purified by silica chromatography using DCM, gradient to 5% MeOH.

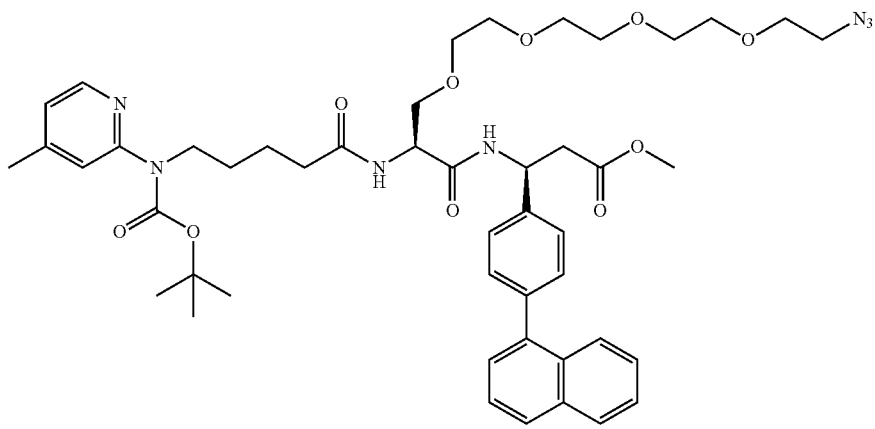

16

1. LiOH
2. TFA
——————→

-continued

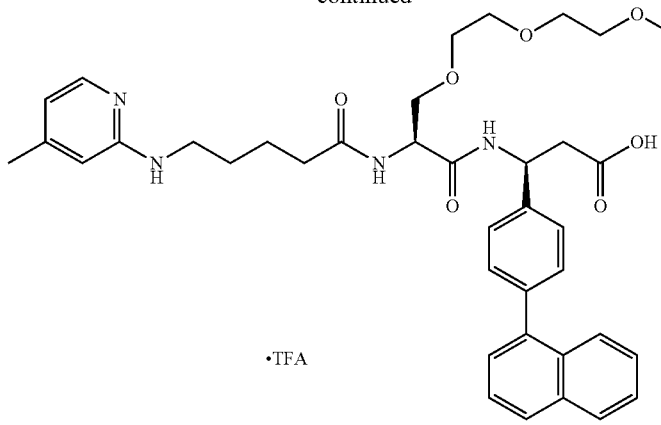

Structure 1b

A Compound 16 was dissolved (0.250 g, 0.2828 mmol) in MeOH:dioxane [1:1] (4 mL) and 1 M LiOH (4 mL) The mixture was stirred at RT for 2 hr. The organics were concentrated away, and the residue was diluted with $H_2O$ (3 mL) and acidified to pH 4. The product was extracted with ethyl acetate (3×20 mL). The organics were pooled and washed with saturated aq. NaCl solution (10 mL). The product was dried over $Na_2SO_4$. The product was dissolved (0.200 g, 0.2299 mmol) in 2 mL DCM:TFA [25:75] and stirred at RT for 2 hours. To the mixture was added toluene (4 mL). The mixture was concentrated, then coevaporated with acetonitrile (2×4 mL). The product was purified by HPLC, gradient 35% ACN to 50% over 30 minutes, 0.1% TFA buffer.=>[M+H]+ calculated for $C_{41}H_{51}N_7O_8$: 769.90, found: 770.45; $^1$H NMR (400 MHz, DMSO) δ 8.64 (d, 1H), 8.07 (d, 1H), 8.00 (d, 1H), 7.95 (d, 1H), 7.78 (t, 2H), 7.60-7.40 (m, 8H), 6.80 (s, 1H), 6.67 (d, 1H), 5.31 (q, 1H), 4.55 (m, 1H), 3.62-3.45 (m, 18H), 3.40 (t, 2H), 3.25 (m, 2H), 2.80 (dd, 2H), 2.30 (s, 3H), 2.20 (t, 2H), 1.55 (m, 4H).

Synthesis of Structure 2b ((14S,17S)-1-azido-14-(4-((4-methylpyridin-2-yl)amino)butanamido)-17-(4-(naphthalen-1-yl)phenyl)-15-oxo-3,6,9,12-tetraoxa-16-azanonadecan-19-oic Acid)

Compound 5 (tert-Butyl(4-methylpyridin-2-yl)carbamate) (0.501 g, 2.406 mmol, 1 equiv.) was dissolved in DMF (17 mL). To the mixture was added NaH (0.116 mg, 3.01 mmol, 1.25 eq, 60% dispersion in oil) The mixture stirred for 10 min before adding Compound 20 (Ethyl 4-Bromobutyrate (0.745 g, 3.82 mmol, 0.547 mL)) (Sigma 167118). After 3 hours the reaction was quenched with ethanol (18 mL) and concentrated. The concentrate was dissolved in DCM (50 mL) and washed with saturated aq. NaCl solution (1×50 mL), dried over $Na_2SO_4$, filtered and concentrated. The product was purified on silica column, gradient 0-5% Methanol in DCM.

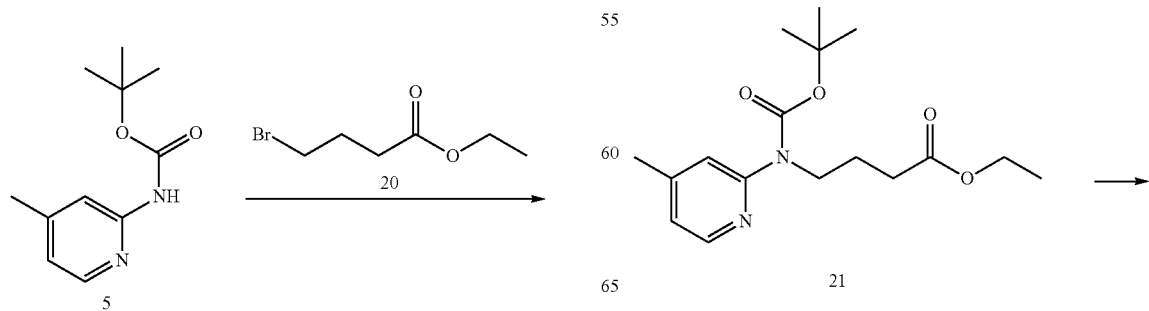

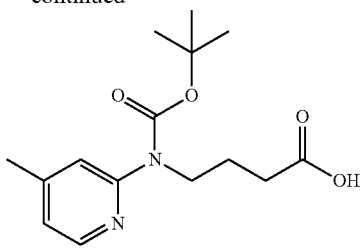

22

Compound 21 was dissolved (0.80 g, 2.378 mmol) in 100 mL of Acetone:0.1 M NaOH [1:1]. The reaction was monitored by TLC (5% ethyl acetate in hexane). The organics were concentrated away, and the residue was acidified to pH 3-4 with 0.3 M Citric Acid (40 mL). The product was extracted with DCM (3×75 mL). The organics were pooled, dried over Na₂SO₄, filtered and concentrated. The product was used without further purification

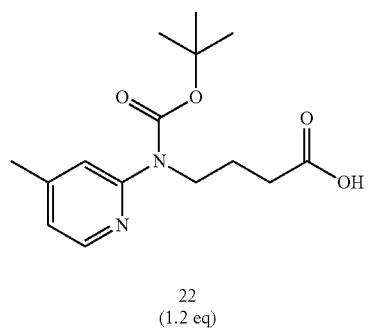

22
(1.2 eq)

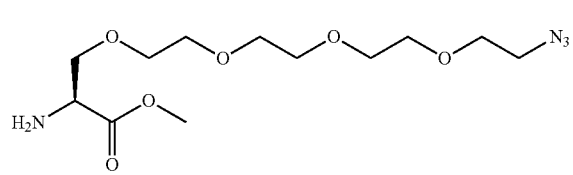

10

TBTU (1.8 eq), DIPEA (2 eq) DMF
Work-up Column
→

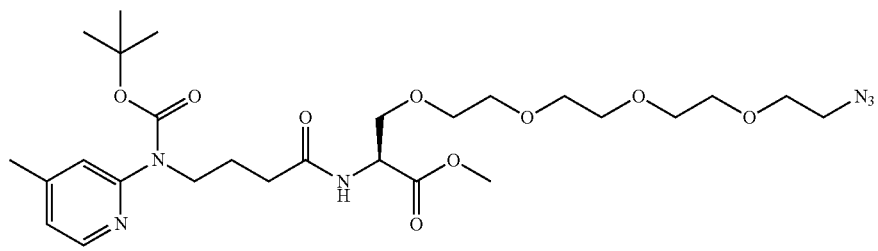

23

Compound 22 was dissolved (0.340 g, 1.104 mmol) in DMF (10 mL). To the mixture was added TBTU (0.531 g, 1.655 mmol) and diisopropylethylamine (0.320 mL, 1.839 mmol). Then Compound 10 (0.295 g, 0.9197 mmol) was added. The reaction was monitored by LC-MS and TLC (DCM with 5% MeOH). The reaction was complete in 2 hr. The mixture was concentrated, dissolved in ethyl acetate (150 mL), and washed with pH 3-4 H₂O (2×12 mL). The mixture was then washed with H₂O (2×12 mL), saturated aq. NaHCO₃ solution (12 mL), then saturated aq. NaCl solution (12 mL). The organic phase was dried over Na₂SO₄, filtered and concentrated. The product was purified on silica column, Hexanes 20% in ethyl acetate to 100% ethyl acetate.

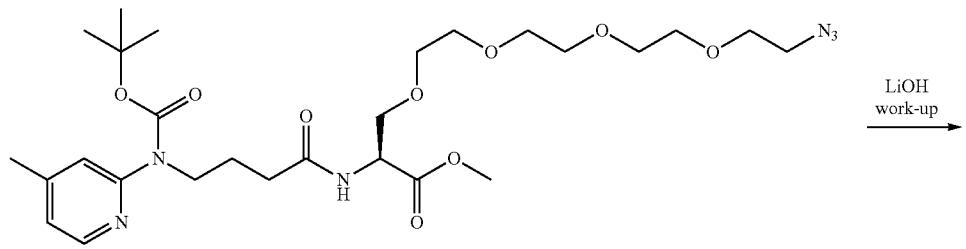

23

LiOH
work-up
→

-continued

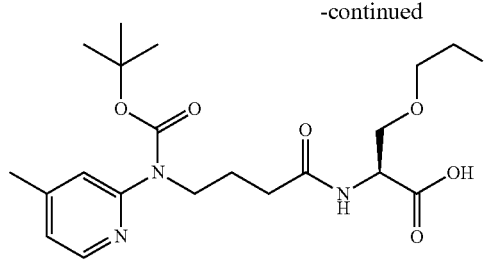

24

Compound 23 was dissolved (0.330 g, 0.540 mmol) in 10 mL of MeOH:Dioxane [1:1] and 1 M LiOH (10 mL) The mixture was stirred at room temperature for 2 hours and monitored by LC-MS and TLC (100% EtOAc). The organics were concentrated, and the residue was diluted with H₂O (5 mL), and acidified to pH 4. The product was extracted with ethyl acetate (2×50 mL). The combined organic phase was washed with saturated aq. NaCl solution (1×10 mL). The organic phase was dried over Na₂SO₄, filtered and concentrated. The product was used without further purification.

Compound 24 was dissolved (0.3224 g, 0.54 mmol) in DMF (7 mL). To the mixture was added TBTU (0.236 g, 0.735 mmol) and diisopropylethylamine (0.170 mL, 0.98 mmol). Compound 15 was then added (0.1496 g, 0.49 mmol). The mixture was stirred at room temperature for 2 hours. The reaction was monitored by LC-MS. The mixture was concentrated, and the residue was dissolved in ethyl acetate (90 mL) and washed with pH 3-4 H₂O (3×10 mL). The concentrate was washed with H₂O (2×10 mL), saturated aq. NaHCO₃ solution (10 mL), and then saturated aq. NaCl solution (10 mL). The organic phase was dried over Na₂SO₄, filtered and concentrated. The product was purified on silica column, DCM, gradient to 5% MeOH.

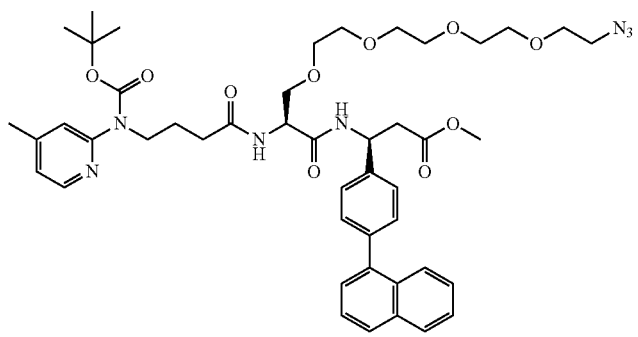

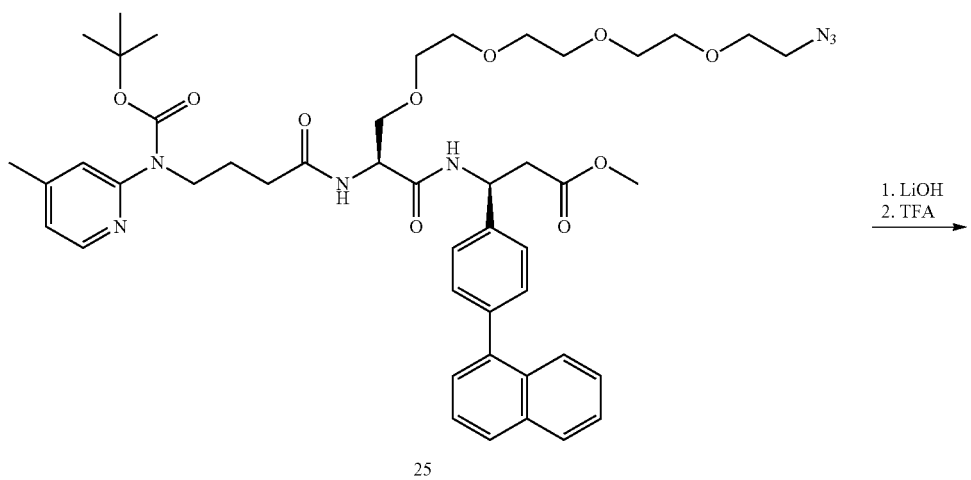

25

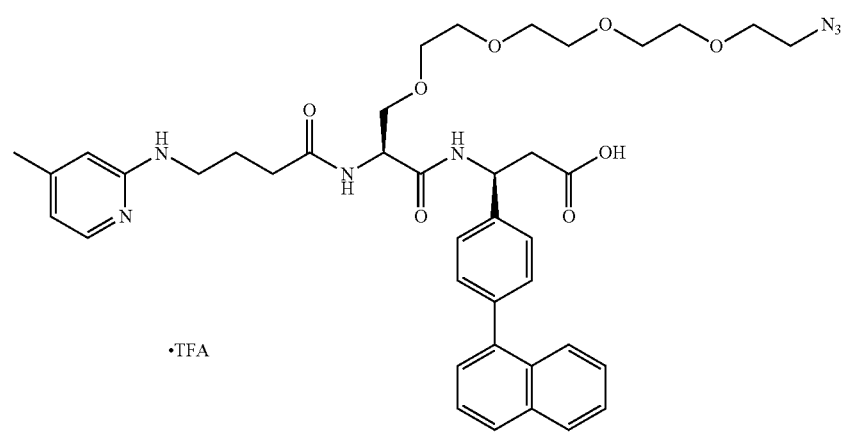

•TFA

Structure 2b

Compound 25 was dissolved (0.250 g, 0.2828 mmol) in MeOH:Dioxane [1:1] (4 mL) and 1 M LiOH (4 mL). The mixture was stirred at room temperature for 2 hr, monitored by LC-MS. The organics were concentrated, and the residue was diluted with H$_2$O (3 mL) and acidified to pH 4. The product was extracted with ethyl acetate (3×20 mL). The organics were pooled and washed with saturated aq. NaCl solution (1×10 mL). The organic phase was dried over Na$_2$SO$_4$ and concentrated. The residue was dissolved (0.200 g, 0.2299 mmol) in 2 mL DCM/TFA (25/75) and stirred at RT for 2 hours while monitored by LC-MS. Toluene (4 mL) was added, and the mixture was concentrated. Then acetonitrile (2×4 mL) was added, and the mixture was concentrated. The product was purified on HPLC, gradient 35% ACN to 50% over 30 minutes, 0.1% TFA buffer. [M+H]+ calculated for C$_{40}$H$_{49}$N$_7$O$_8$: 755.87, found: 756.32; $^1$H NMR (400 MHz, DMSO) δ 8.64 (t, 1H), 8.17-8.10 (m, 1H), 8.00 (d, 1H), 7.95 (d, 1H), 7.80 (d, 1H), 7.75 (m, 1H), 7.60-7.40 (m, 8H), 6.8 (s, 1H), 6.67 (d, 1H), 5.31 (q, 1H), 4.55 (m, 1H), 3.62-3.45 (m, 18H), 3.40 (t, 2H), 3.25 (m, 2H), 2.80 (dd, 2H), 2.30 (s, 3H), 2.26 (t, 2H), 1.80 (m, 2H).

Synthesis of Structure 5b, 5.1b, and 5.2b

Structure 5b (3-(4-(2-(2-(2-azidoethoxy)ethoxy)ethoxy)-3,5-dichlorophenyl)-3-(2-(5-((4-methylpyridin-2-yl)amino)pentanamido)acetamido)propanoic Acid)

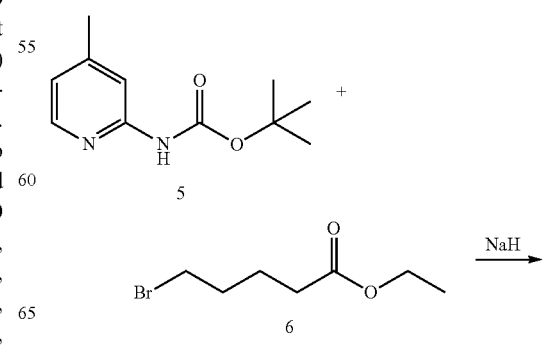

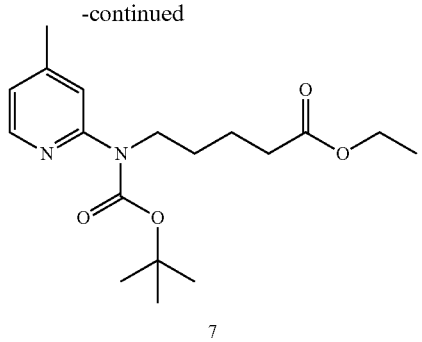

7

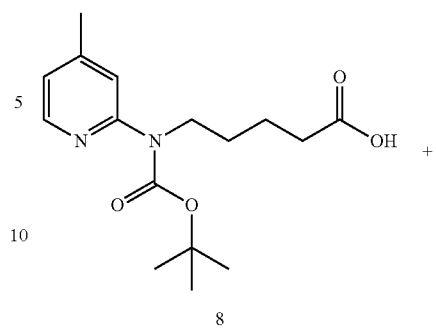

8

To a solution of Compound 5 (0.98 g, 4.70 mmol, 1 equiv.) in dry DMF (10 mL) was added NaH (0.226 g, 5.647 mmol, 1.2 equiv., 60% oil dispersion) portion-wise at 0° C. under $N_2$ atmosphere. The reaction mixture was kept at 0° C. for 30 min followed by the addition of compound 6 (1.18 mL, 5.647 mmol, 1.2 equiv.) at the same temperature. After additional stirring at 0° C. for 30 min the mixture was allowed to warm to room temperature. After stirring at room temperature for 1 hour, the reaction was quenched by saturated $NH_4Cl$ aqueous solution. The aqueous phase was extracted with ethyl acetate (3×20 mL) and the organic layer was combined, dried over $Na_2SO_4$, and concentrated. The product was separated by CombiFlash® using silica gel as the stationary phase. LC-MS: [M+H]+ 337.20, found 337.39.

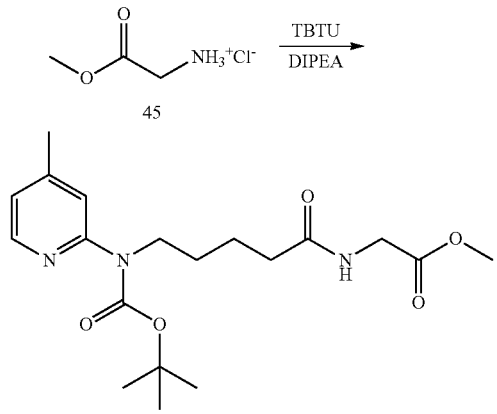

46

To a solution of Compound 8 (1.163 g, 3.77 mmol, 1 equiv.), Compound 45 (568 mg, 4.52 mmol, 1.2 equiv.), and TBTU (1.453 g, 4.52 mmol, 1.2 equiv.) in anhydrous DMF (10 mL) was added diisopropylethylamine (1.97 mL, 11.31 mmol, 3 equiv.) at 0° C. The reaction mixture was warmed to room temperature and stirred 3 hours. The reaction was quenched by saturated $NaHCO_3$ solution (20 mL). The aqueous layer was extracted with ethyl acetate (3×10 mL), and the organic phase was combined, dried over anhydrous $Na_2SO_4$, and concentrated. The product was separated by CombiFlash® using silica gel as the stationary phase. LC-MS: calculated [M+H]+ 380.21, found 380.51.

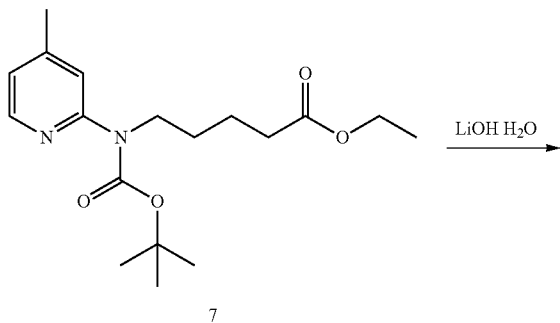

7

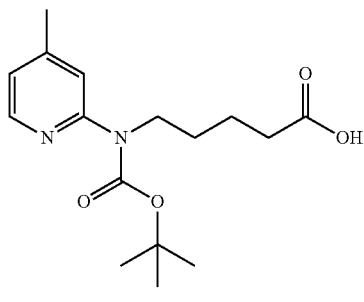

8

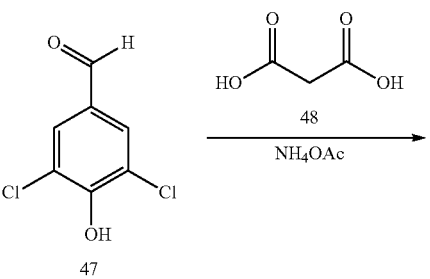

47

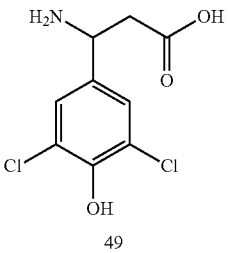

49

To a solution of compound 7 (1.347 g, 4.00 mmol, 1 equiv.) in THF (5 mL) and $H_2O$ (5 mL) was added lithium hydroxide monohydrate (0.505 g, 12.01 mmol, 5 equiv.) portion-wise at 0° C. The reaction mixture was warmed to room temperature. After stirring at room temperature for 1 h, the reaction mixture was acidified by HCl (6 N) to pH 4.0. The aqueous phase was extracted with ethyl acetate (3×20 mL) and the organic layer was combined, dried over $Na_2SO_4$, and concentrated. LC-MS: [M+H]+ 309.17, found 309.39.

To a solution of compound 47 (1.0 g, 5.23 mmol, 1 equiv.) and malonic acid (1.09 g, 10.47 mmol, 2 equiv.) in ethanol (10 mL) was added ammonium acetate (0.807 mg, 10.47 mmol, 2.0 equiv.) at room temperature. The reaction mixture was stirred at reflux overnight. The solid was filtered and washed with cold ethanol. The product was used directly for further steps without further purification. LC-MS: calculated [M+H]+ 250.00, found 250.16.

To a suspension of compound 49 (0.531 g, 2.12 mmol, 1 equiv.) in anhydrous methanol (10 mL) was added thionyl chloride (308 uL, 4.24 mmol, 2.0 equiv.) on ice bath. The reaction was warmed to room temperature and stirred overnight. The solvent was removed under reduced pressure and the product was directly used without further purification. LC-MS: calculated [M+H]+ 264.01, found 264.20.

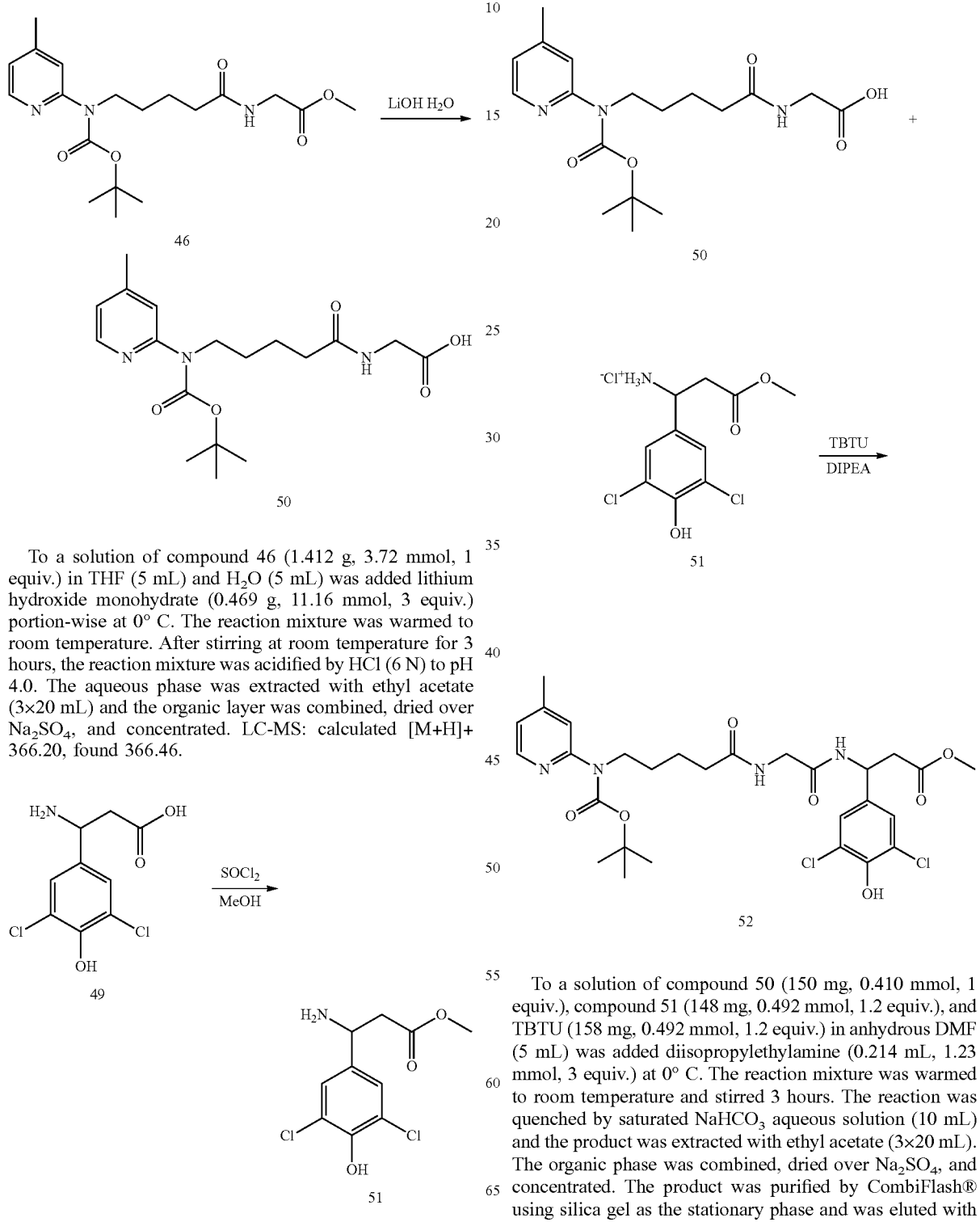

To a solution of compound 46 (1.412 g, 3.72 mmol, 1 equiv.) in THF (5 mL) and H₂O (5 mL) was added lithium hydroxide monohydrate (0.469 g, 11.16 mmol, 3 equiv.) portion-wise at 0° C. The reaction mixture was warmed to room temperature. After stirring at room temperature for 3 hours, the reaction mixture was acidified by HCl (6 N) to pH 4.0. The aqueous phase was extracted with ethyl acetate (3×20 mL) and the organic layer was combined, dried over Na₂SO₄, and concentrated. LC-MS: calculated [M+H]+ 366.20, found 366.46.

To a solution of compound 50 (150 mg, 0.410 mmol, 1 equiv.), compound 51 (148 mg, 0.492 mmol, 1.2 equiv.), and TBTU (158 mg, 0.492 mmol, 1.2 equiv.) in anhydrous DMF (5 mL) was added diisopropylethylamine (0.214 mL, 1.23 mmol, 3 equiv.) at 0° C. The reaction mixture was warmed to room temperature and stirred 3 hours. The reaction was quenched by saturated NaHCO₃ aqueous solution (10 mL) and the product was extracted with ethyl acetate (3×20 mL). The organic phase was combined, dried over Na₂SO₄, and concentrated. The product was purified by CombiFlash® using silica gel as the stationary phase and was eluted with 2-4% methanol in DCM.

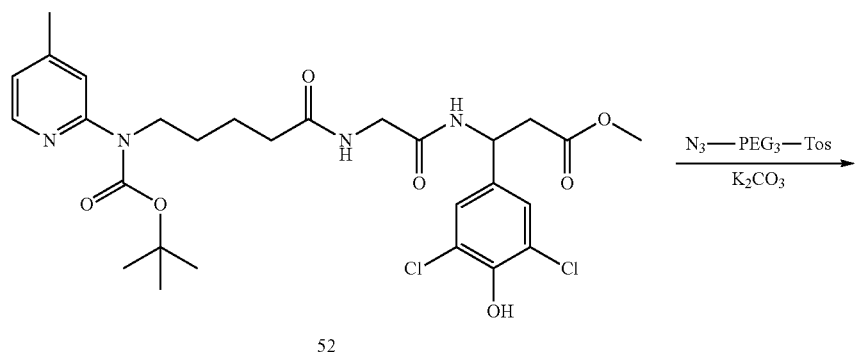

52

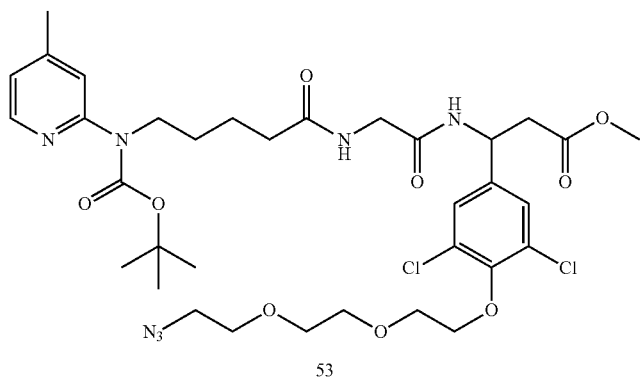

53

To a solution of compound 52 (80 mg, 0.130 mmol, 1 equiv.) and azido-PEG$_3$-OTs (86 mg, 0.262 mmol, 2 equiv.) in anhydrous DMF (2 mL) was added K$_2$CO$_3$ (36 mg, 0.262 mmol, 2 equiv.) at 0° C. The reaction mixture was stirred for 1 hr at 80° C. The solvent was removed by rotary evaporator. The product was purified by CombiFlash® using silica gel as the stationary phase and was eluted with 24% methanol in DCM. LC-MS: calculated [M+H]+ 768.28, found 769.

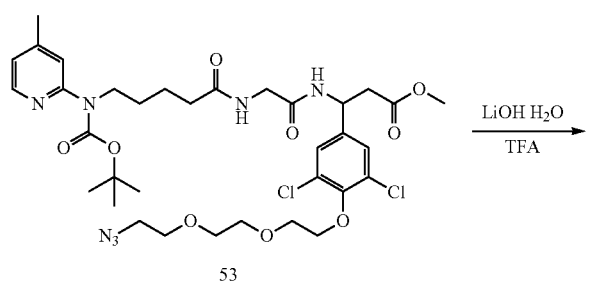

53

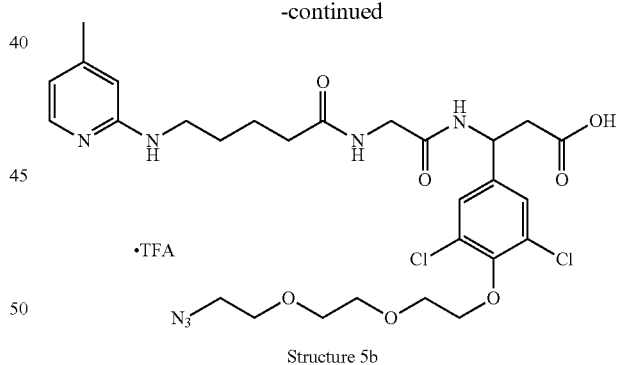

Structure 5b

To a solution of compound 53 (58 mg, 0.0755 mmol, 1.0 equiv.) in THF (2 mL) and water (2 mL) was added lithium hydroxide monohydrate (10 mg, 0.226 mmol, 3.0 equiv.) at room temperature. The mixture was stirred at room temperature for another 2 hours. The pH was adjusted to 3.0 by HCl (6N) and the aqueous phase was extracted with EtOAc (3×10 mL). The organic phase was combined, dried over Na$_2$SO$_4$, and concentrated. TFA (0.25 mL) and DCM (0.75 mL) was added into the residue and the mixture was stirred at room temperature for another 1 hour. The solvent was removed by rotary evaporator. LC-MS: calculated [M+H]+ 654.21, found 655.

Structure 5.1b (3-(4-((14-azido-3,6,9,12-tetraoxatetradecyl)oxy)-3,5-dichlorophenyl)-3-(2-(5-((4-methylpyridin-2-yl)amino)pentanamido)acetamido)propanoic Acid)

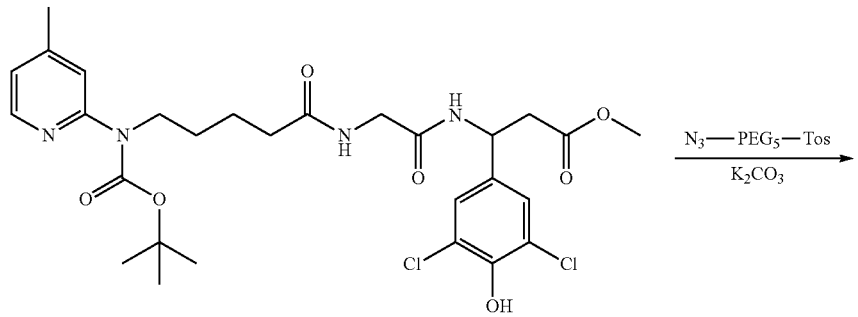

52

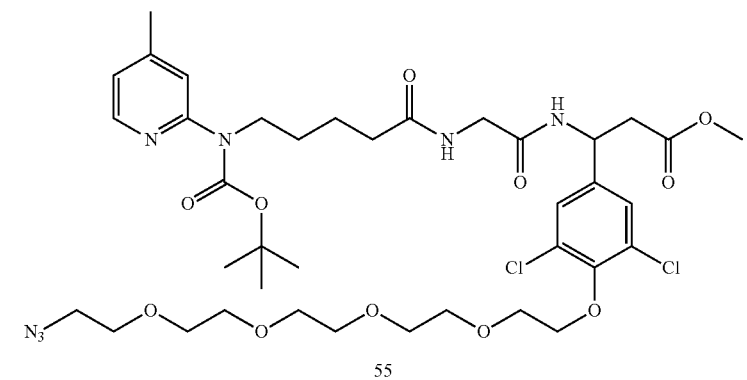

55

To a solution of compound 52 (100 mg, 0.163 mmol, 1 equiv.) and azido-PEG$_5$-OTs (205 mg, 0.491 mmol, 3 equiv.) in anhydrous DMF (2 mL) was added K$_2$CO$_3$ (68 mg, 0.491 mmol, 2 equiv.) at 0° C. The reaction mixture was stirred for 1 hour at 80° C. The solvent was removed by rotary evaporator. The product was purified by CombiFlash® using silica gel as the stationary phase and was eluted with 2-3% methanol in DCM. LC-MS: calculated [M+H]+ 856.33, found 857.07.

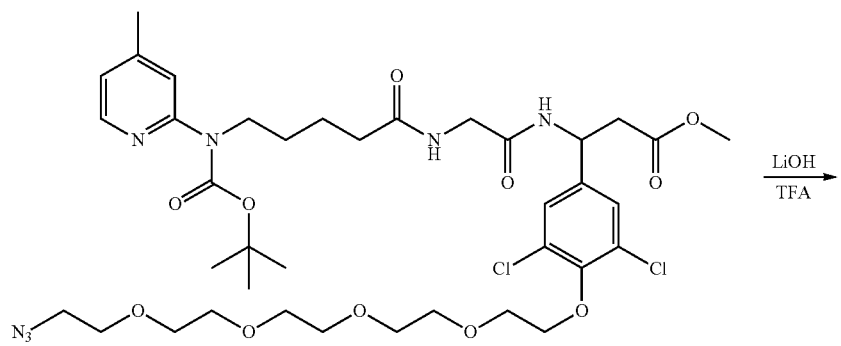

55

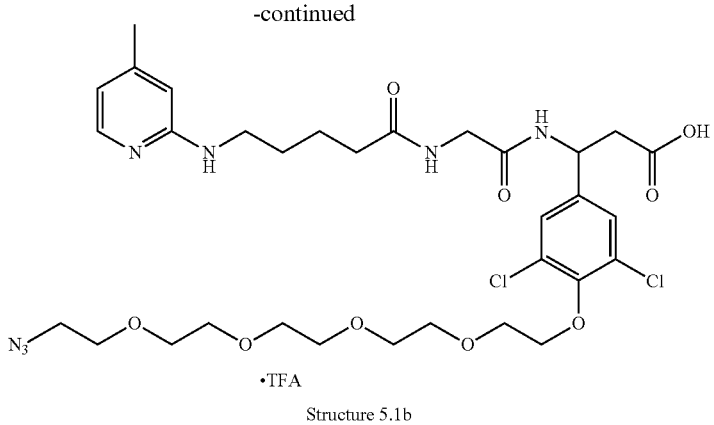

·TFA

Structure 5.1b

To a solution of compound 55 (119 mg, 0.139 mmol, 1.0 equiv.) in THF (4 mL) and water (4 mL) was added lithium hydroxide (10 mg, 0.417 mmol, 3.0 equiv.) at room temperature. The mixture was stirred at room temperature for another 1 hr. The pH was adjusted to 3.0 by HCl (6N) and the aqueous phase was extracted with EtOAc (3×10 mL). The organic phase was combined, dried over Na₂SO₄, and concentrated. TFA (2 mL) and DCM (2 mL) was added into the residue and the mixture was stirred at room temperature for another 3 hours. The solvent was removed by rotary evaporator. LC-MS: calculated [M+H]+ 742.27, found 743.02.

Structure 5.2b (3-(4-((8-azidooctyl)oxy)-3,5-dichlorophenyl)-3-(2-(5-(((4-methylpyridin-2-yl)amino)pentanamido)acetamido)propanoic Acid)

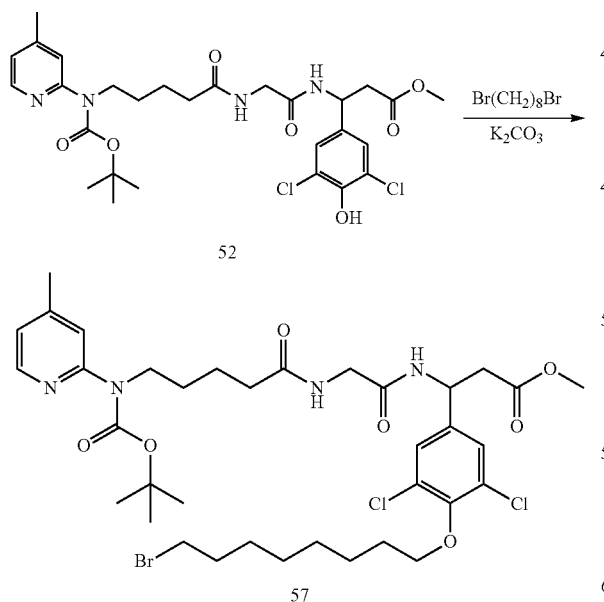

To a solution of compound 52 (89 mg, 0.14 mmol, 1 equiv.) and 1,8-dibromooctane (80 uL, 0.436 mmol, 3 equiv.) in acetone (2 mL) was added K₂CO₃ (60 mg, 0.436 mmol, 3 equiv.) at room temperature. The reaction mixture was stirred for 6 hours at 55° C. The reaction was quenched by saturated NaHCO₃ solution and the aqueous layer was extracted with ethyl acetate (3×10 mL). The organic phase was combined, dried over Na₂SO₄, and concentrated. LC-MS: calculated [M+H]+ 801.23, found 801.98.

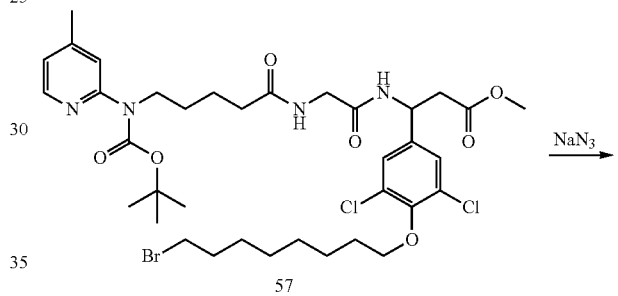

To a solution of compound 57 (97 mg, 0.114 mmol, 1 equiv.) in anhydrous DMF (2 mL) was added sodium azide (15 mg, 0.229 mmol, 2 equiv.) at room temperature. The reaction mixture was stirred for 2 hours at 80° C. The reaction was quenched by water and the aqueous layer was extracted with ethyl acetate (3×10 mL). The organic phase was combined, dried over Na₂SO₄, and concentrated. The product was used directly without further purification. LC-MS: calculated [M+H]+ 764.32, found 765.07.

165

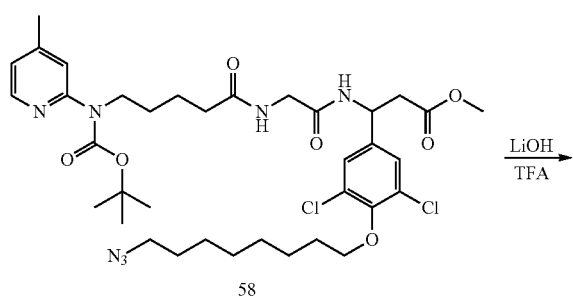

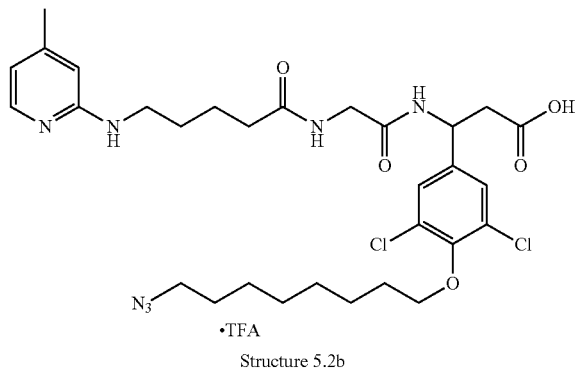

·TFA
Structure 5.2b

To a solution of compound 58 (78 mg, 0.101 mmol, 1.0 equiv.) in THF (2 mL) and water (2 mL) was added lithium hydroxide (7 mg, 0.304 mmol, 3.0 equiv.) at room temperature. The mixture was stirred at room temperature for another 1 hr. The pH was adjusted to 3.0 by HCl (6N) and the aqueous phase was extracted with EtOAc (3×10 mL). The organic phase was combined, dried over Na$_2$SO$_4$, and concentrated. TFA (2 mL) and DCM (2 mL) was added into the residue and the mixture was stirred at room temperature for another 3 hr. The solvent was removed by rotary evaporator. LC-MS: calculated [M+H]+ 650.25, found 650.83.

Synthesis of Structure 6b, 6.1b, 6.2b, 6.3b, and 6.4b

Structure 6b ((S)-3-(4-(4-(2-(2-(2-azidoethoxy)ethoxy)ethoxy)naphthalen-1-yl)phenyl)-3-(2-(4-((4-methylpyridin-2-yl)amino)butanamido)acetamido)propanoic Acid)

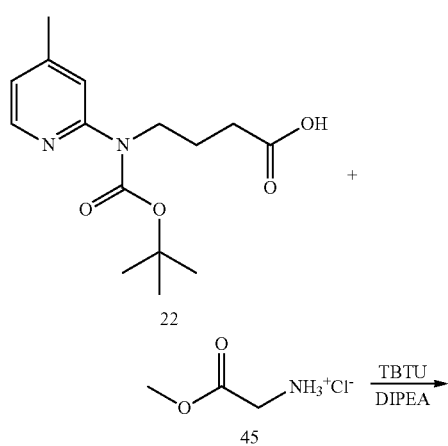

166

-continued

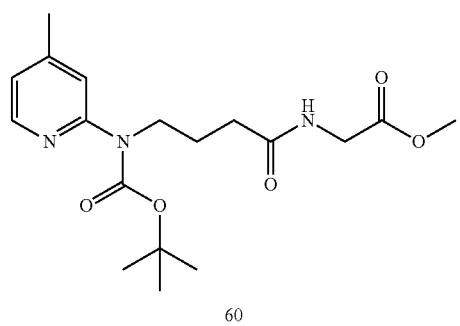

60

To a solution of Compound 22 (1.1 g, 3.95 mmol, 1 equiv.), Compound 45 (595 mg, 4.74 mmol, 1.2 equiv.), and TBTU (1.52 g, 4.74 mmol, 1.2 equiv.) in anhydrous DMF (10 mL) was added diisopropylethylamine (2.06 mL, 11.85 mmol, 3 equiv.) at 0° C. The reaction mixture was warmed to room temperature and stirred 3 hours. The reaction was quenched by saturated NaHCO$_3$ solution (10 mL). The aqueous phase was extracted with ethyl acetate (3×10 mL) and the organic phase was combined, dried over anhydrous Na$_2$SO$_4$, and concentrated. The product was separated by CombiFlash® using silica gel as the stationary phase. LC-MS: calculated [M+H]+ 366.20, found 367.

To a solution of compound 61 (2 g, 8.96 mmol, 1 equiv.), and compound 62 (2.13 mL, 17.93 mmol, 2 equiv.) in anhydrous DMF (10 mL) was added K$_2$CO$_3$ (2.48 g, 17.93 mmol, 2 equiv.) at 0° C. The reaction mixture was warmed to room temperature and stirred overnight. The reaction was quenched by water (10 mL). The aqueous phase was extracted with ethyl acetate (3×10 mL) and the organic phase was combined, dried over anhydrous Na$_2$SO$_4$, and concentrated. The product was separated by CombiFlash® using silica gel as the stationary phase.

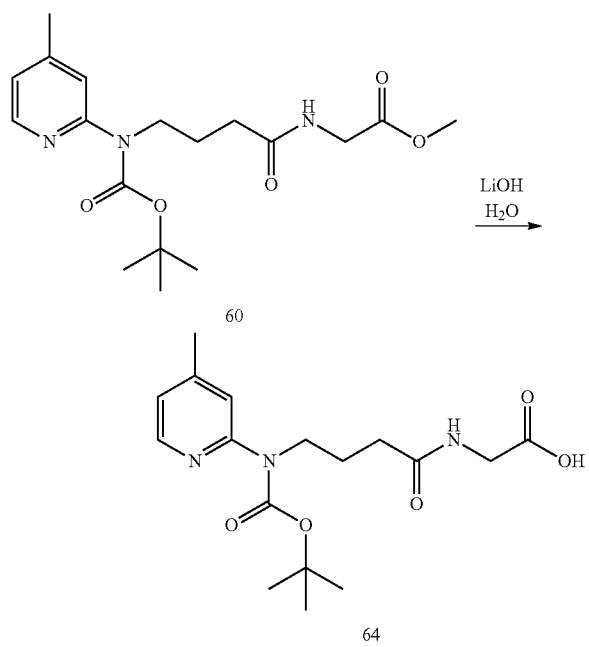

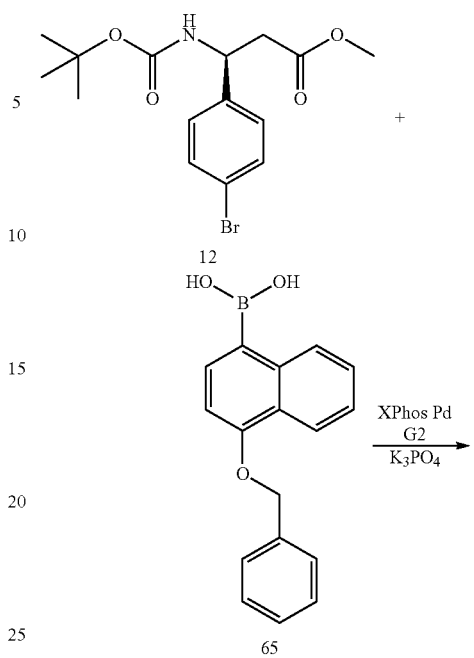

To a solution of compound 60 (1.77 g, 4.84 mmol, 1 equiv.) in THF (5 mL) and H₂O (5 mL) was added lithium hydroxide monohydrate (0.61 g, 14.53 mmol, 3 equiv.) portion-wise at 0° C. The reaction mixture was warmed to room temperature. After stirring at room temperature for 3 hours, the reaction mixture was acidified by HCl (6 N) to pH 3.0. The aqueous phase was extracted with ethyl acetate (3×20 mL) and the organic layer was combined, dried over Na₂SO₄, and concentrated. LC-MS: calculated [M+H]+ 352.18, found 352.

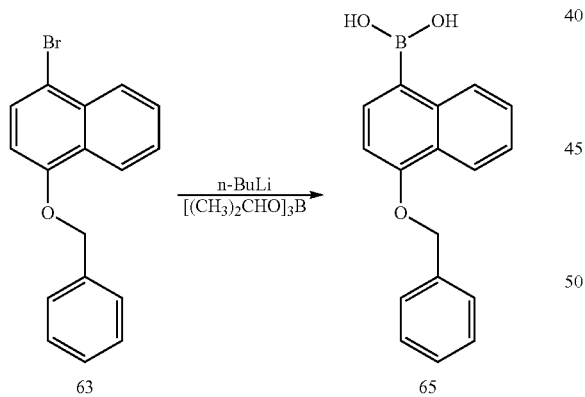

To a solution of compound 63 (1.88 g, 6.0 mmol, 1.0 equiv.) in anhydrous THF (20 mL) was added n-BuLi in hexane (3.6 mL, 9.0 mmol, 1.5 equiv.) drop-wise at −78° C. The reaction was kept at −78° C. for another 1 hour. Triisopropylborate (2.08 mL, 9.0 mmol, 1.5 equiv.) was then added into the mixture at −78° C. The reaction was then warmed up to room temperature and stirred for another 1 hour. The reaction was quenched by saturated NH₄Cl solution (20 mL) and the pH was adjusted to 3. The aqueous phase was extracted with EtOAc (3×20 mL) and the organic phase was combined, dried over Na₂SO₄, and concentrated.

Compound 12 (300 mg, 0.837 mmol, 1.0 equiv.), Compound 65 (349 mg, 1.256 mmol, 1.5 equiv.), XPhos Pd G2 (13 mg, 0.0167 mmol, 0.02 equiv.), and K₃PO₄ (355 mg, 1.675 mmol, 2.0 equiv.) were mixed in a round-bottom flask. The flask was sealed with a screw-cap septum, and then evacuated and backfilled with nitrogen (this process was repeated a total of 3 times). Then, THF (8 mL) and water (2 mL) were added via syringe. The mixture was bubbled with nitrogen for 20 min and the reaction was kept at room temperature for overnight. The reaction was quenched with water (10 mL), and the aqueous phase was extracted with ethyl acetate (3×10 mL). The organic phase was dried over Na₂SO₄, concentrated, and purified via CombiFlash® using silica gel as the stationary phase and was eluted with 15% EtOAc in hexane. LC-MS: calculated [M+H]+ 512.24, found 512.56.

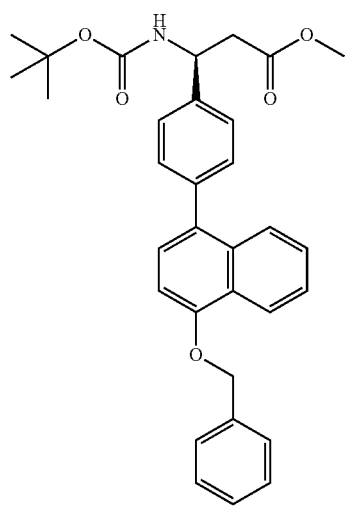

66

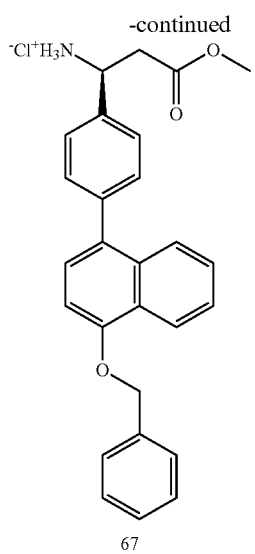

67

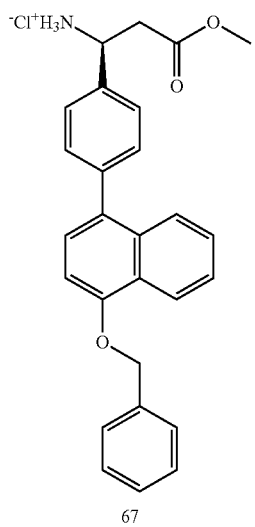

67

Compound 66 (858 mg, 1.677 mmol, 1.0 equiv.) was cooled by ice bath. HCl in dioxane (8.4 mL, 33.54 mmol, 20 equiv.) was added into the flask. The reaction was warmed to room temperature and stirred for another 1 hr. The solvent was removed by rotary evaporator and the product was directly used without further purification. LC-MS: calculated [M+H]+ 412.18, found 412.46.

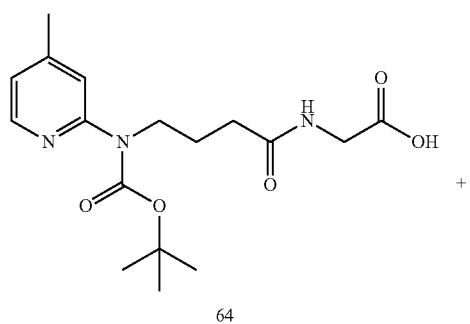

64

68

To a solution of compound 64 (500 mg, 1.423 mmol, 1 equiv.), compound 67 (669 mg, 1.494 mmol, 1.05 equiv.), and TBTU (548 mg, 0.492 mmol, 1.2 equiv.) in anhydrous DMF (15 mL) was added diisopropylethylamine (0.744 mL, 4.268 mmol, 3 equiv.) at 0° C. The reaction mixture was warmed to room temperature and stirred for another 1 hr. The reaction was quenched by saturated NaHCO₃ aqueous solution (10 mL) and the product was extracted with ethyl acetate (3×20 mL). The organic phase was combined, dried over Na₂SO₄, and concentrated. The product was purified by CombiFlash® using silica gel as the stationary phase and was eluted with 3-4% methanol in DCM. The yield was 96.23%. LC-MS: calculated [M+H]+ 745.35, found 746.08.

171

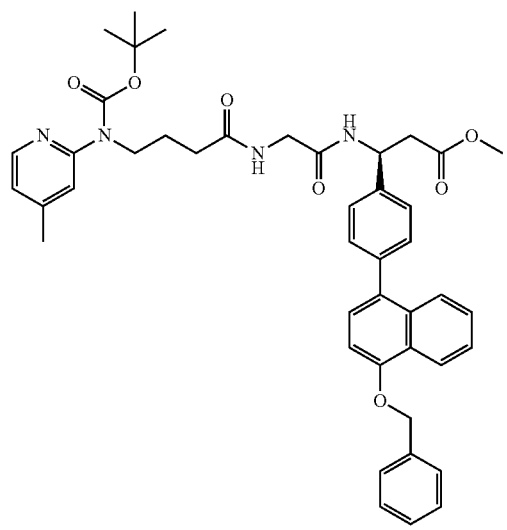

68

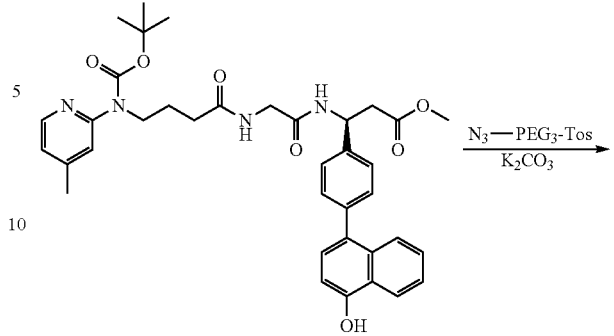

69

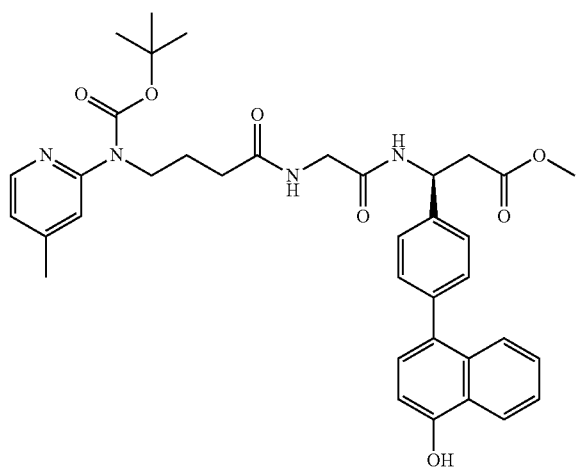

69

172

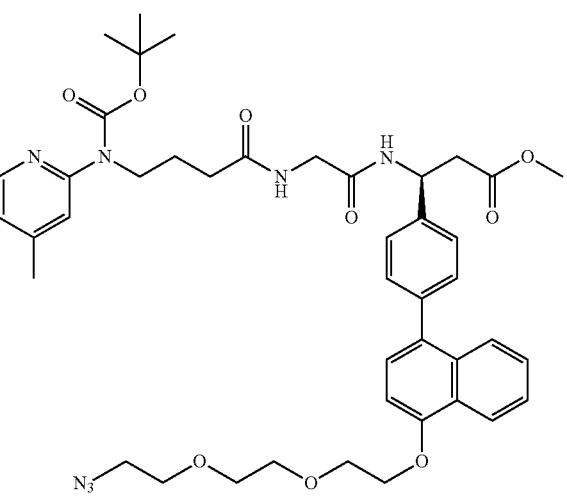

70

To a solution of compound 68 (1.02 g, 1.369 mmol, 1 equiv.) in ethyl acetate (10 mL) was added 10% Pd/C (0.15 g, 50% H₂O) at room temperature. The reaction mixture was warmed to room temperature and the reaction was monitored by LC-MS. The reaction was kept at room temperature overnight. The solids were filtered through Celite® and the solvent was removed by rotary evaporator. The product was directly used without further purification. LC-MS: [M+H]+ 655.31, found 655.87.

To a solution of compound 69 (100 mg, 0.152 mmol, 1 equiv.) and azido-PEG₃-OTs (100 mg, 0.305 mmol, 2 equiv.) in anhydrous DMF (2 mL) was added K₂CO₃ (42 mg, 0.305 mmol, 2 equiv.) at 0° C. The reaction mixture was stirred for 6 hours at 80° C. The reaction was quenched by saturated NaHCO₃ solution and the aqueous layer was extracted with ethyl acetate (3×10 mL). The organic phase was combined, dried over Na₂SO₄, and concentrated. The product was separated by CombiFlash® using silica gel as the stationary phase. LC-MS: calculated [M+H]+ 812.39, found 813.14.

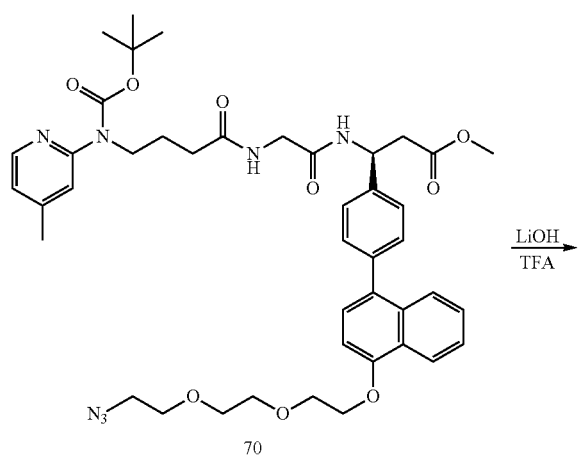

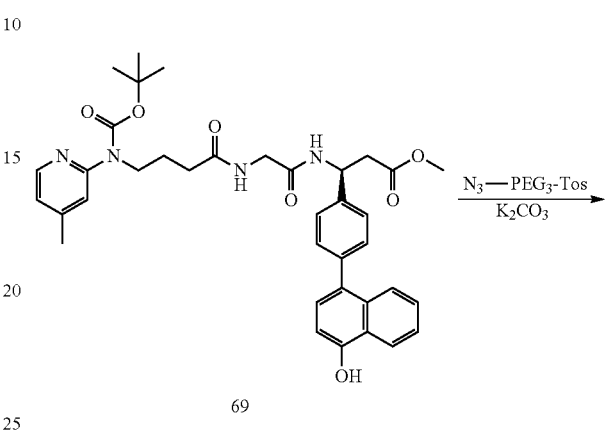

Structure 6.1b ((S)-3-(4-(4-((14-azido-3,6,9,12-tetraoxatetradecyl)oxy)naphthalen-1-yl)phenyl)-3-(2-(4-((4-methylpyridin-2-yl)amino)butanamido)acetamido)propanoic Acid)

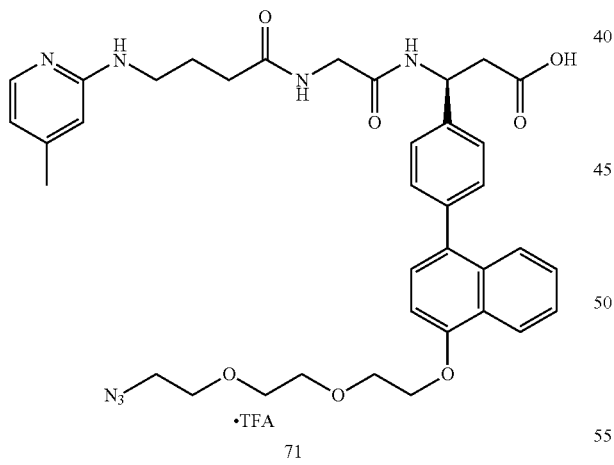

To a solution of compound 70 (77 mg, 0.0948 mmol, 1.0 equiv.) in THF (2 mL) and water (2 mL) was added lithium hydroxide (7 mg, 0.284 mmol, 3.0 equiv.) at room temperature. The mixture was stirred at room temperature for another 2 hours. The pH was adjusted to 3.0 by HCl (6N) and the aqueous phase was extracted with EtOAc (3×10 mL). The organic phase was combined, dried over $Na_2SO_4$, and concentrated. TFA (0.5 mL) and DCM (0.5 mL) was added into the residue and the mixture was stirred at room temperature for another 3 hours. The solvent was removed by rotary evaporator. LC-MS: calculated [M+H]+ 698.32, found 698.81.

To a solution of compound 69 (100 mg, 0.152 mmol, 1 equiv.) and azido-$PEG_5$-OTs (128 mg, 0.305 mmol, 2 equiv.) in anhydrous DMF (2 mL) was added $K_2CO_3$ (42 mg, 0.305 mmol, 2 equiv.) at 0° C. The reaction mixture was stirred for 6 hours at 80° C. The reaction was quenched by saturated $NaHCO_3$ solution and the aqueous layer was extracted with ethyl acetate (3×10 mL). The organic phase was combined, dried over $Na_2SO_4$, and concentrated. LC-MS: calculated [M+H]+ 900.40, found 901.46.

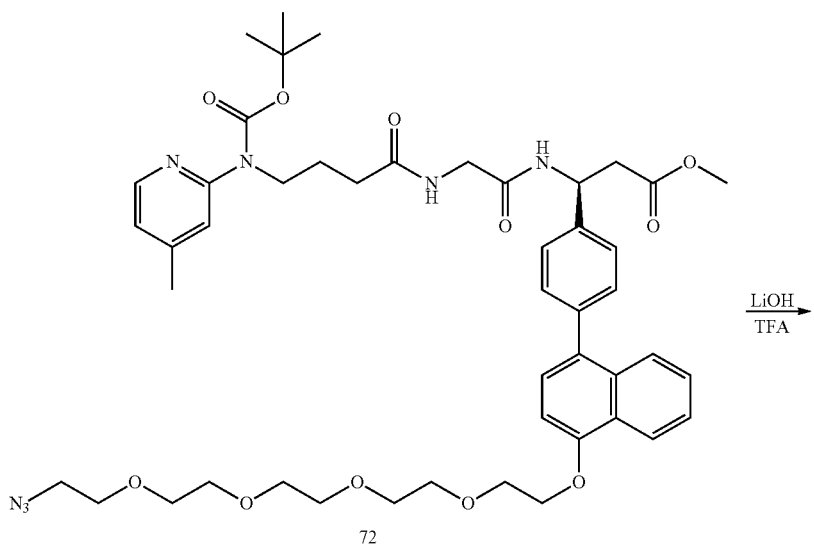

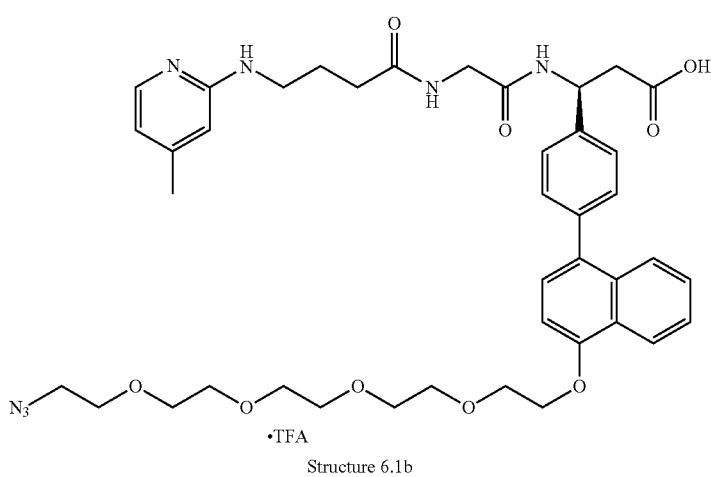

Structure 6.1b

To a solution of compound 72 (59 mg, 0.0656 mmol, 1.0 equiv.) in THF (2 mL) and water (2 mL) was added lithium hydroxide (5 mg, 0.197 mmol, 3.0 equiv.) at room temperature. The mixture was stirred at room temperature for another 1 hr. The pH was adjusted to 3.0 by HCl (6N) and the aqueous phase was extracted with EtOAc (3×10 mL). The organic phase was combined, dried over $Na_2SO_4$, and concentrated. TFA (0.5 mL) and DCM (0.5 mL) was added into the residue and the mixture was stirred at room temperature for another 3 hr. The solvent was removed by rotary evaporator. LC-MS: calculated [M+H]+ 786.37, found 786.95.

Structure 6.2b ((S)-3-(4-(4-((8-azidooctyl)oxy)naph-thalen-1-yl)phenyl)-3-(2-(4-((4-methylpyridin-2-yl)amino)butanamido)acetamido)propanoic Acid)

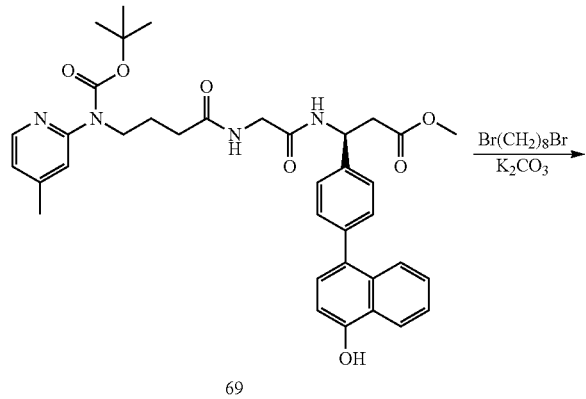

69

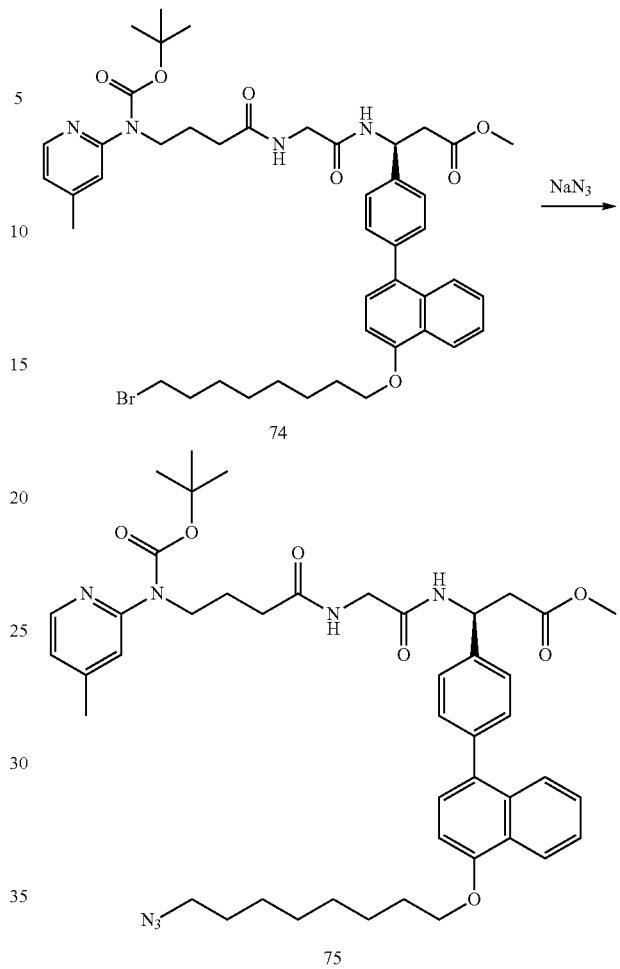

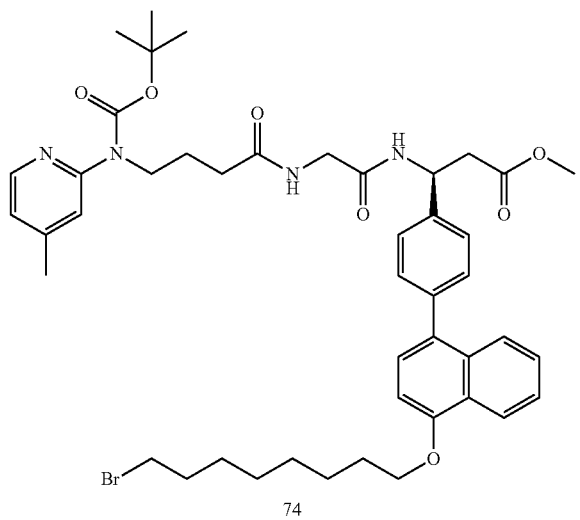

74

To a solution of compound 69 (150 mg, 0.229 mmol, 1 equiv.) and 1,8-dibromooctane (127 uL, 0.687 mmol, 3 equiv.) in acetone (2 mL) was added K₂CO₃ (95 mg, 0.687 mmol, 3 equiv.) at room temperature. The reaction mixture was stirred for overnight at 55° C. The reaction was quenched by saturated NaHCO₃ solution and the aqueous layer was extracted with ethyl acetate (3×10 mL). The organic phase was combined, dried over Na₂SO₄, and concentrated. LC-MS: calculated [M+H]+ 845.34, found 845.91.

To a solution of compound 74 (97 mg, 0.114 mmol, 1 equiv.) in anhydrous DMF (2 mL) was added sodium azide (15 mg, 0.229 mmol, 2 equiv.) at room temperature. The reaction mixture was stirred for 2 hours at 80° C. The reaction was quenched by water and the aqueous layer was extracted with ethyl acetate (3×10 mL). The organic phase was combined, dried over Na₂SO₄, and concentrated. LC-MS: calculated [M+H]+ 808.43, found 809.00.

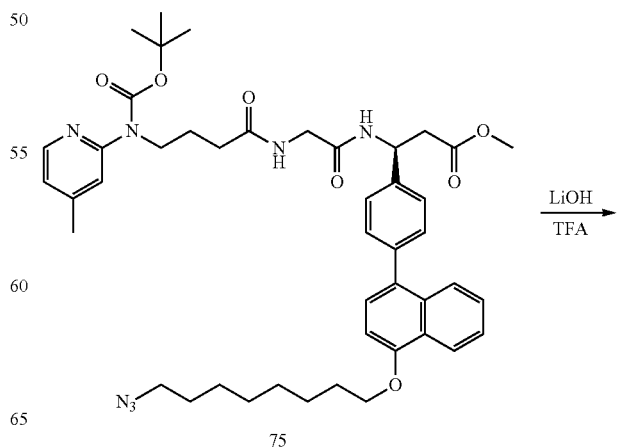

75

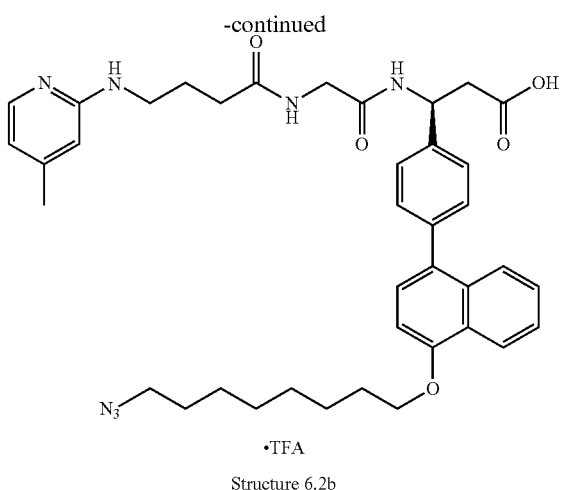

·TFA

Structure 6.2b

To a solution of compound 75 (92 mg, 0.114 mmol, 1.0 equiv.) in THF (2 mL) and water (2 mL) was added lithium hydroxide (8 mg, 0.342 mmol, 3.0 equiv.) at room temperature. The mixture was stirred at room temperature for another 1 hr. The pH was adjusted to 3.0 by HCl (6N) and the aqueous phase was extracted with EtOAc (3×10 mL). The organic phase was combined, dried over Na₂SO₄, and concentrated. TFA (0.5 mL) and DCM (0.5 mL) was added into the residue and the mixture was stirred at room temperature for another 3 hr. The solvent was removed by rotary evaporator. LC-MS: calculated [M+H]+ 694.36, found 694.94.

Structure 6.3b ((S)-3-(4-(4-((20-azido-3,6,9,12,15,18-hexaoxaicosyl)oxy)naphthalen-1-yl)phenyl)-3-(2-(4-((4-methylpyridin-2-yl)amino)butanamido)acetamido)propanoic Acid)

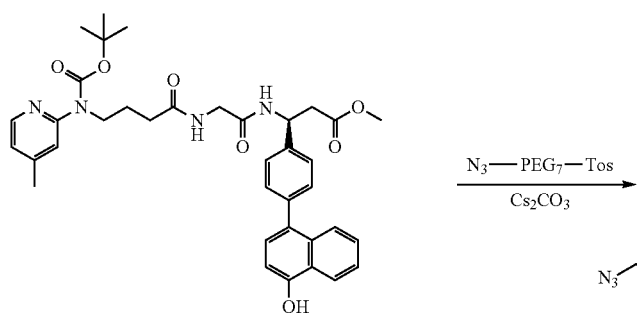

69 as the stationary phase, and the product was eluted with 2-3% methanol in DCM. LC-MS: calculated [M+H]+ 988.50, found 989.14.

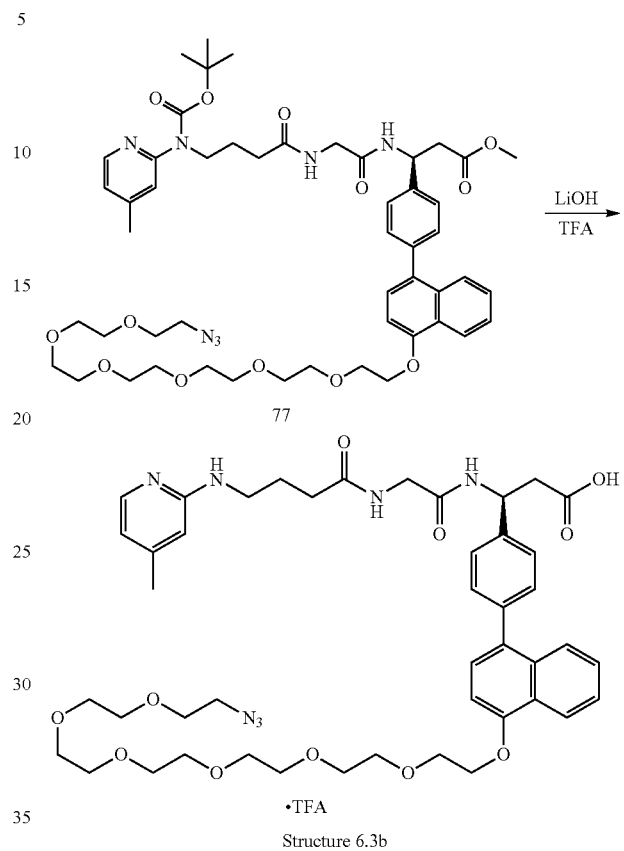

·TFA

Structure 6.3b

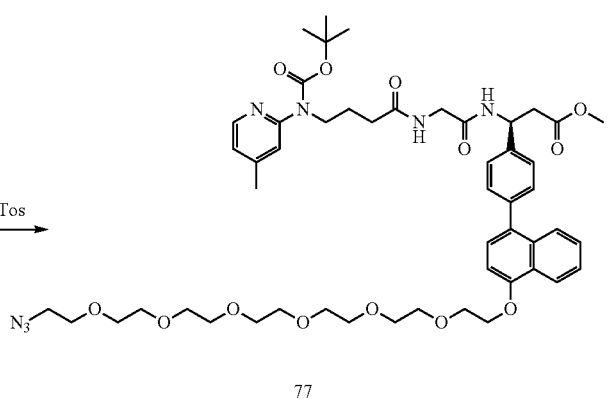

77

To a solution of compound 21 (112 mg, 0.113 mmol, 1.0 equiv.) in THF (2 mL) and water (2 mL) was added lithium hydroxide (8 mg, 0.340 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over Na₂SO₄, and concentrated. TFA (4 mL) and DCM (2 mL) was added into the residue and the mixture was stirred at room tem- To a solution of compound 69 (100 mg, 0.152 mmol, 1 equiv.) and azido-PEG₇-OTs (154 mg, 0.305 mmol, 2 equiv.) in anhydrous DMF (2 mL) was added Cs₂CO₃ (100 mg, 0.305 mmol, 2 equiv.) at 0° C. The reaction mixture was stirred at 40° C. overnight. The reaction was quenched by saturated NaHCO₃ solution (10 mL) and the aqueous layer was extracted with ethyl acetate (3×10 mL). The organic phase was combined, dried over Na₂SO₄, and concentrated. The product was separated by CombiFlash® using silica gel perature for another 3 hours. The solvent was removed by rotary evaporator. LC-MS: calculated [M+H]+ 874.43, found 875.08.

Structure 6.4b ((S)-3-(4-(4-(4-((35-azido-3,6,9,12,15,18,21,24,27,30,33-undecaoxapentatriacontyl)oxy)naphthalen-1-yl)phenyl)-3-(2-(4-((4-methylpyridin-2-yl)amino)butanamido)acetamido)propanoic Acid)

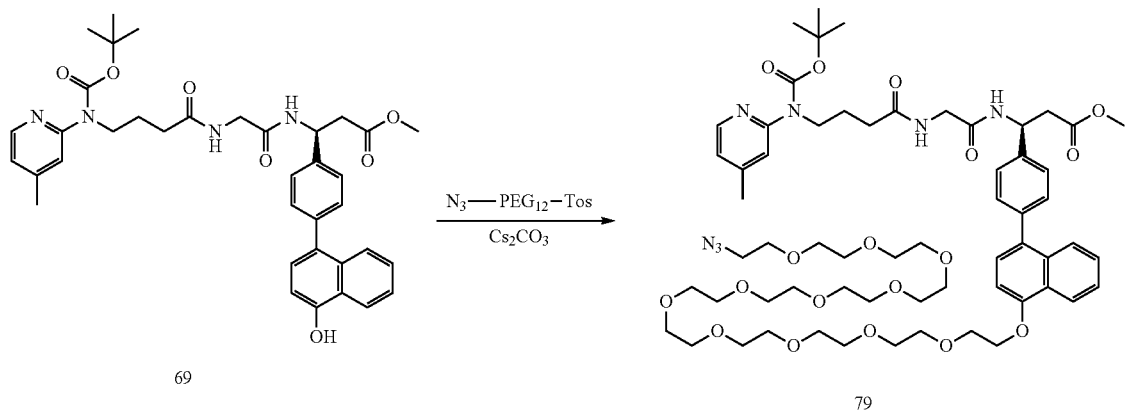

To a solution of compound 69 (80 mg, 0.122 mmol, 1 equiv.) and azido-PEG$_{12}$-OTs (184 mg, 0.244 mmol, 2 equiv.) in anhydrous DMF (2 mL) was added Cs$_2$CO$_3$ (80 mg, 0.244 mmol, 2 equiv.) at 0° C. The reaction mixture was stirred at 40° C. for 5 hours. The reaction was quenched by saturated NaHCO$_3$ solution (10 mL) and the aqueous layer was extracted with ethyl acetate (3×10 mL). The organic phase was combined, dried over Na$_2$SO$_4$, and concentrated. The product was separated by CombiFlash® using silica gel as the stationary phase and eluted with 2-3% methanol in DCM. LC-MS: calculated [M+H]+ 1208.63, found 1209.21.

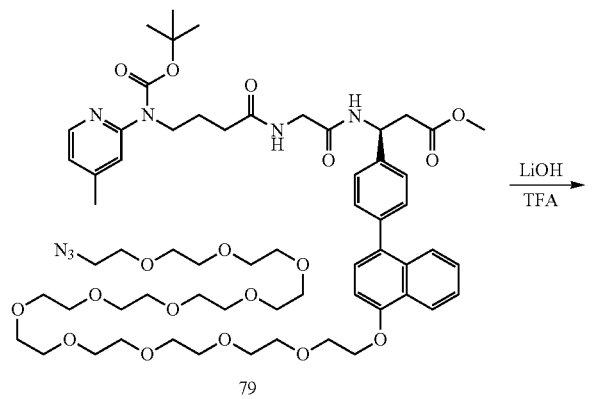

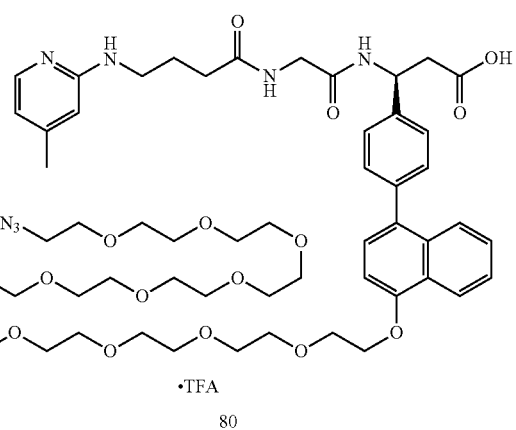

To a solution of compound 82 (100 mg, 0.0972 mmol, 1.0 equiv.) in THF (2 mL) and water (2 mL) was added lithium hydroxide (7 mg, 0.292 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over Na$_2$SO$_4$, and concentrated. TFA (4 mL) and DCM (2 mL) was added into the residue and the mixture was stirred at room temperature for another 3 hr. The solvent was removed by rotary evaporator. LC-MS: calculated [M+H]+ 1094.56, 1095.05.

Synthesis of Structure 7b ((R)-3-(4-(4-(2-(2-(2-azidoethoxy)ethoxy)ethoxy)naphthalen-1-yl)phenyl)-3-(2-(4-((4-methylpyridin-2-yl)amino)butanamido)acetamido)propanoic Acid)

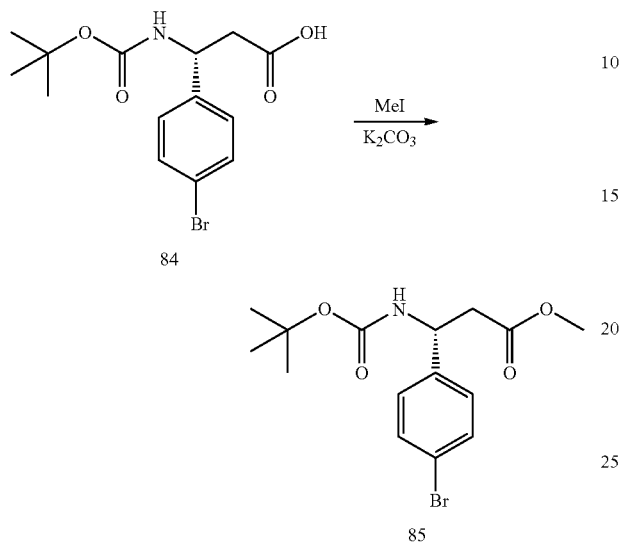

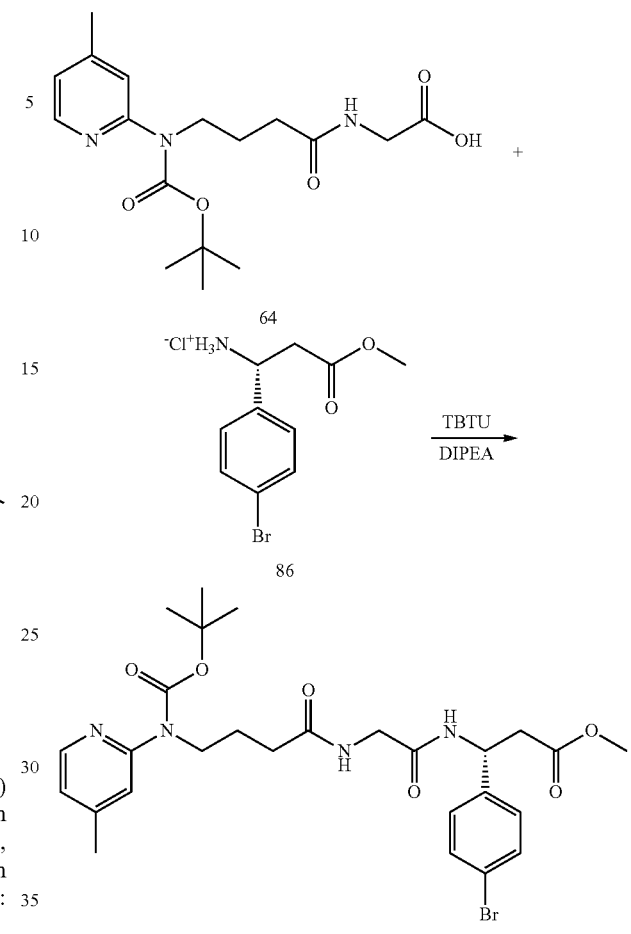

To a solution of compound 84 (1.0 g, 2.90 mmol, 1 equiv.) and potassium carbonate (0.60 g, 4.36 mmol, 1.5 equiv.) in anhydrous DMF (10 mL) was added methyl iodide (362 uL, 5.81 mmol, 2.0 equiv.) at room temperature. The reaction mixture was stirred at room temperature 1 hr. LC-MS: calculated [M+H]+ 358.06, found 358.34.

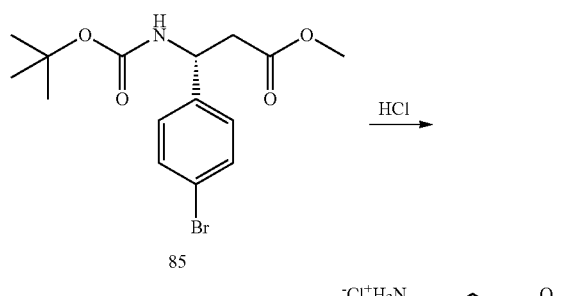

Compound 85 (1.0 g, 2.791 mmol, 1.0 equiv.) was cooled by ice bath. HCl in dioxane (7.0 mL, 27.91 mmol, 10 equiv.) was added into the flask. The reaction was warmed to room temperature and stirred for another 1 hour. The solvent was removed by rotary evaporator and the product was directly used without further purification. LC-MS: calculated [M+H]+ 258.01, found 257.97.

To a solution of compound 64 (790 mg, 2.248 mmol, 1 equiv.), compound 86 (728 mg, 2.473 mmol, 1.10 equiv.), and TBTU (866 mg, 2.698 mmol, 1.20 equiv.) in anhydrous DMF (15 mL) was added diisopropylethylamine (1.175 mL, 6.744 mmol, 3 equiv.) at 0° C. The reaction mixture was warmed to room temperature and stirred for another 1 hr. The reaction was quenched by saturated NaHCO₃ aqueous solution (10 mL) and the product was extracted with ethyl acetate (3×20 mL). The organic phase was combined, dried over Na₂SO₄, and concentrated. The product was purified by CombiFlash® using silica gel as the stationary phase and was eluted with 34% methanol in DCM. LC-MS: calculated [M+H]+ 591.17, found 591.49.

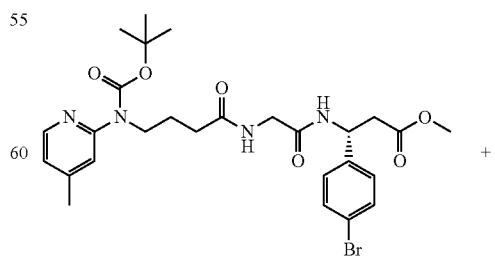

87

-continued

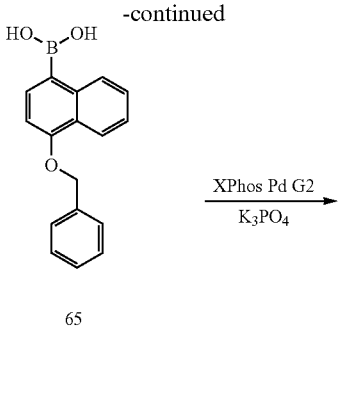

65

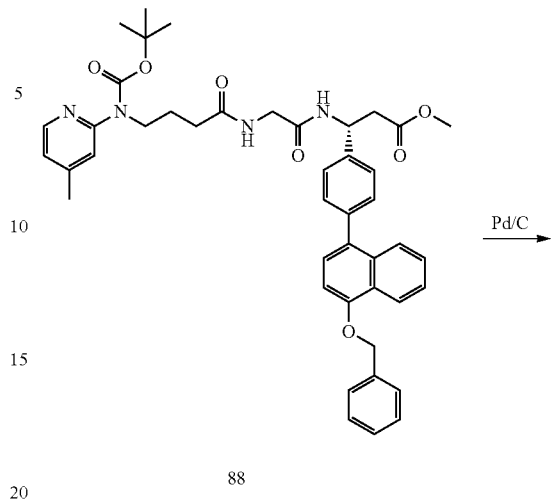

88

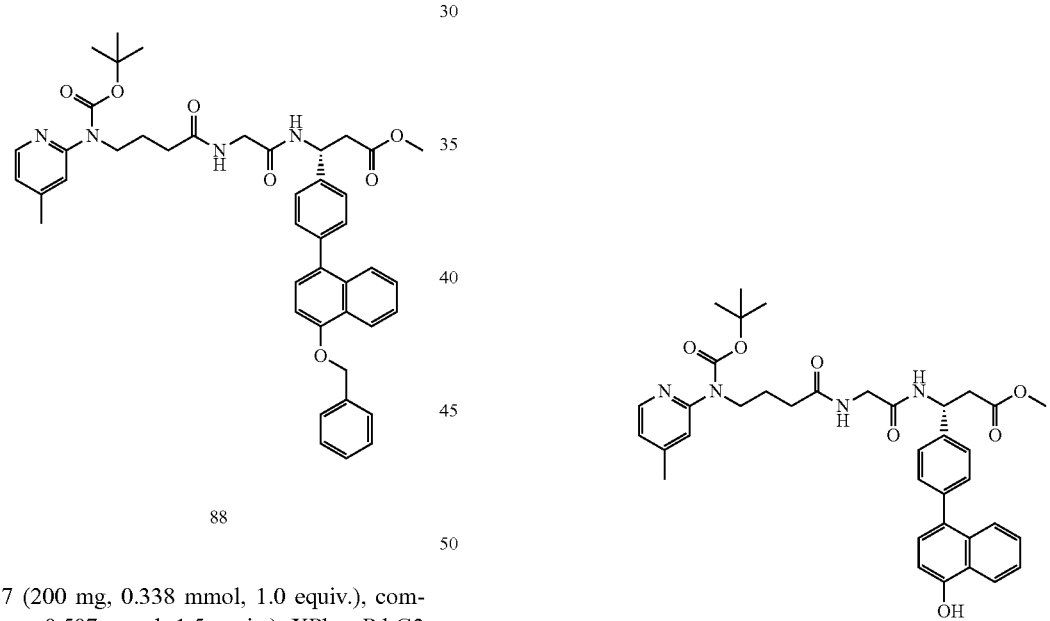

88

Compound 87 (200 mg, 0.338 mmol, 1.0 equiv.), compound 65 (141 mg, 0.507 mmol, 1.5 equiv.), XPhos Pd G2 (5.3 mg, 0.068 mmol, 0.02 equiv.), and $K_3PO_4$ (143 mg, 0.676 mmol, 2.0 equiv.) were mixed in a round-bottom flask. The flask was sealed with a screw-cap septum, and then evacuated and backfilled with nitrogen (this process was repeated a total of 3 times). Then, THF (8 mL) and water (2 mL) were added via syringe. The mixture was bubbled with nitrogen for 20 min and the reaction was kept at room temperature for overnight. The reaction was quenched with water (10 mL), and the aqueous phase was extracted with ethyl acetate (3×10 mL). The organic phase was dried over $Na_2SO_4$ and concentrated. LC-MS: calculated [M+H]+ 745.35, found 746.08.

To a solution of compound 88 (0.247 g, 0.331 mmol, 1 equiv.) in ethyl acetate (10 mL) was added 10% Pd/C (100 mg) at room temperature. The reaction mixture was stirred at room temperature for overnight. The catalyst was removed by filtration through Celite® and the product was used directly without further purification. LC-MS: calculated [M+H]+ 655.31, found 655.96.

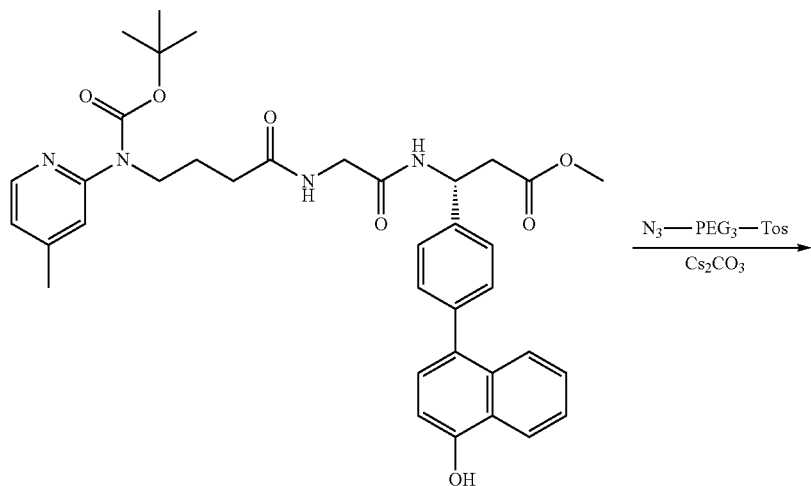

89

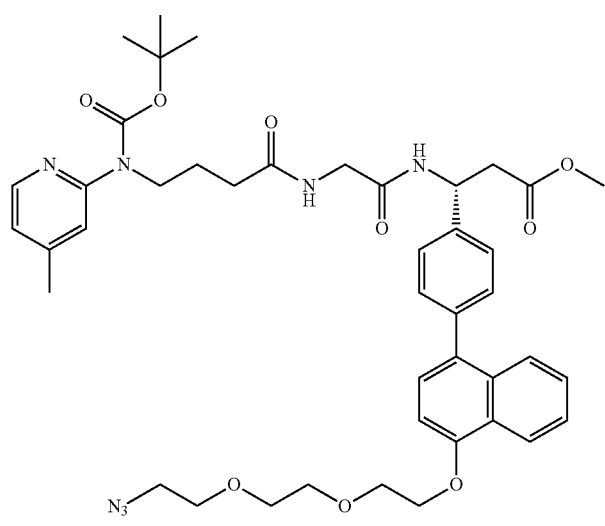

90

To a solution of compound 89 (50 mg, 0.076 mmol, 1 equiv.) and azido-PEG$_3$-OTs (50 mg, 0.152 mmol, 2 equiv.) in anhydrous DMF (2 mL) was added Cs$_2$CO$_3$ (50 mg, 0.152 mmol, 2 equiv.) at 0° C. The reaction mixture was stirred for 72 hr at room temperature. The reaction was quenched by saturated NaHCO$_3$ solution (10 mL) and the aqueous layer was extracted with ethyl acetate (3×10 mL). The organic phase was combined, dried over Na$_2$SO$_4$, and concentrated. The product was separated by CombiFlash® using silica gel as the stationary phase and was eluted with 4% MeOH in DCM. LC-MS: calculated [M+H]+ 812.39, found 813.14.

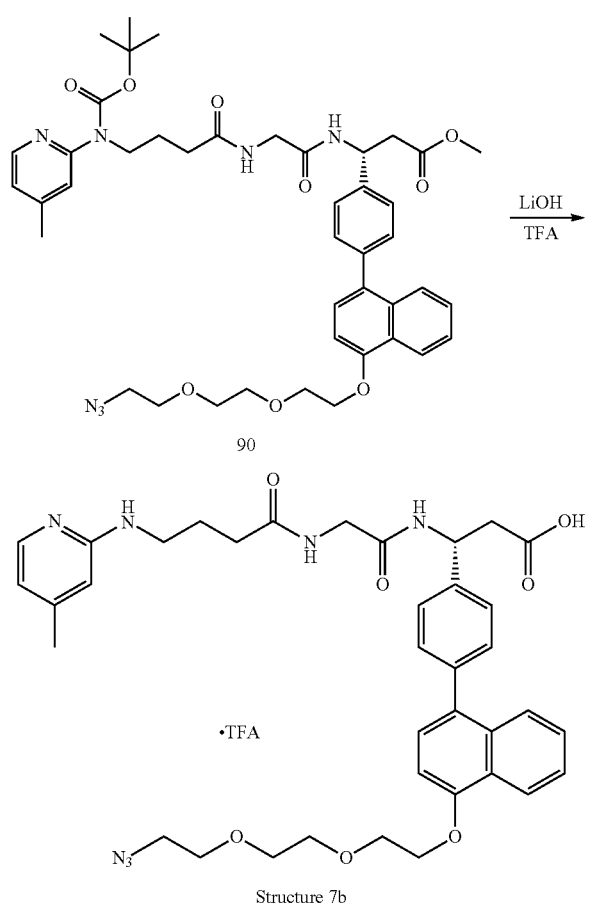

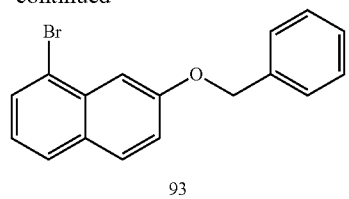

To a solution of compound 92 (1.0 g, 4.48 mmol, 1 equiv.), and compound 62 (1.06 mL, 8.96 mmol, 2 equiv.) in anhydrous DMF (10 mL) was added $K_2CO_3$ (1.24 g, 8.96 mmol, 2 equiv.) at room temperature. The reaction mixture was stirred at 80° C. overnight. The reaction was quenched by saturated $NaHCO_3$ solution (10 mL) and the aqueous phase was extracted with ethyl acetate (3×10 mL). The organic phase was combined, dried over $Na_2SO_4$, and concentrated. The product was separated by CombiFlash® using silica gel as the stationary phase and was eluted with 5% ethyl acetate in hexane.

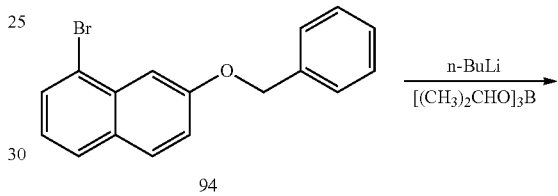

To a solution of compound 90 (36 mg, 0.0443 mmol, 1.0 equiv.) in THF (2 mL) and water (2 mL) was added lithium hydroxide (3 mg, 0.133 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over $Na_2SO_4$, and concentrated. TFA (0.5 mL) and DCM (0.5 mL) was added into the residue and the mixture was stirred at room temperature for another 3 hr. The solvent was removed by rotary evaporator. LC-MS: calculated [M+H]+ 698.32, found 698.90.

Synthesis of Structure 8b ((S)-3-(4-(7-(2-(2-(2-azidoethoxy)ethoxy)ethoxy)naphthalen-1-yl)phenyl)-3-(2-(4-((4-methylpyridin-2-yl)amino)butanamido)acetamido)propanoic Acid)

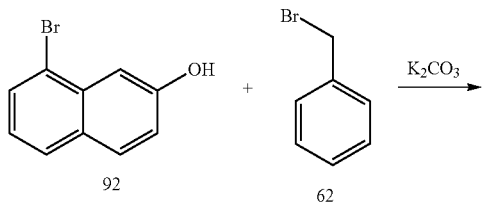

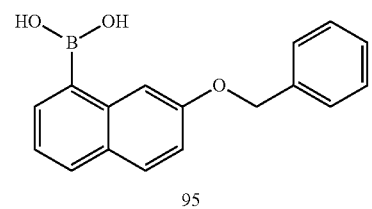

To a solution of compound 94 (0.5 g, 1.596 mmol, 1.0 equiv.) in anhydrous THF (10 mL) was added n-BuLi in hexane (0.96 mL, 2.394 mmol, 1.5 equiv.) drop-wise at −78° C. The reaction was kept at −78° C. for another 1 hour. Triisopropylborate (0.553 mL, 2.394 mmol, 1.5 equiv.) was then added into the mixture at −78° C. The reaction was then warmed up to room temperature and stirred for another 1 hour. The reaction was quenched by saturated $NH_4Cl$ solution (20 mL) and the pH was adjusted to 3. The aqueous phase was extracted with EtOAc (3×20 mL) and the organic phase was combined, dried over $Na_2SO_4$, and concentrated. The solid was triturated with hexane and filtered. The product was used directly without further purification. LC-MS: calculated [M−H]−277.11, found 277.35.

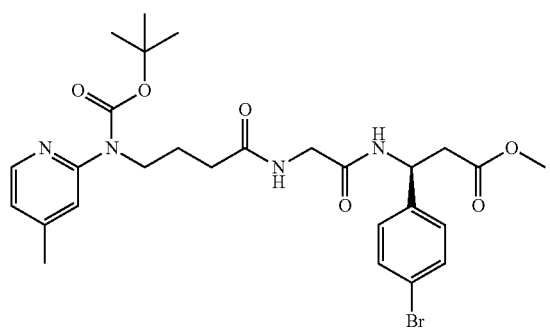

96

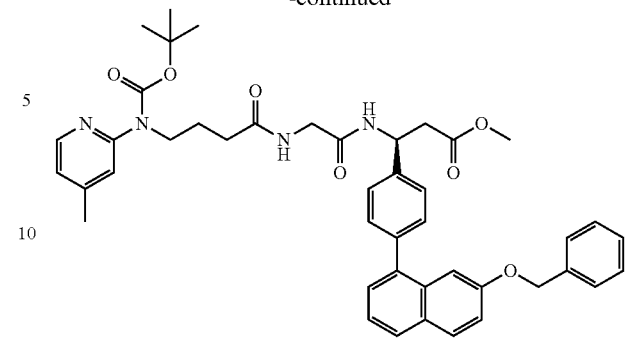

97

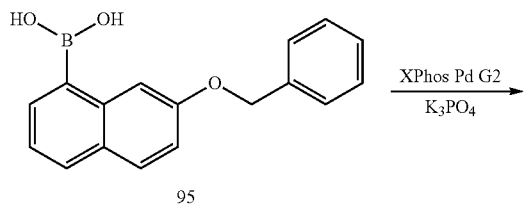

95

Compound 96 (100 mg, 0.169 mmol, 1.0 equiv.), compound 95 (70 mg, 0.253 mmol, 1.5 equiv.), XPhos Pd G2 (2.7 mg, 0.0034 mmol, 0.02 equiv.), and $K_3PO_4$ (72 mg, 0.338 mmol, 2.0 equiv.) were mixed in a round-bottom flask. The flask was sealed with a screw-cap septum, and then evacuated and backfilled with nitrogen (this process was repeated a total of 3 times). Then, THF (8 mL) and water (2 mL) were added via syringe. The mixture was bubbled with nitrogen for 20 min and the reaction was kept at room temperature for overnight. The reaction was quenched with water (10 mL), and the aqueous phase was extracted with ethyl acetate (3×10 mL). The organic phase was combined, dried over $Na_2SO_4$, and concentrated. The compound was separated by CombiFlash® using silica gel as the stationary phase and was eluted with 3% methanol in DCM.

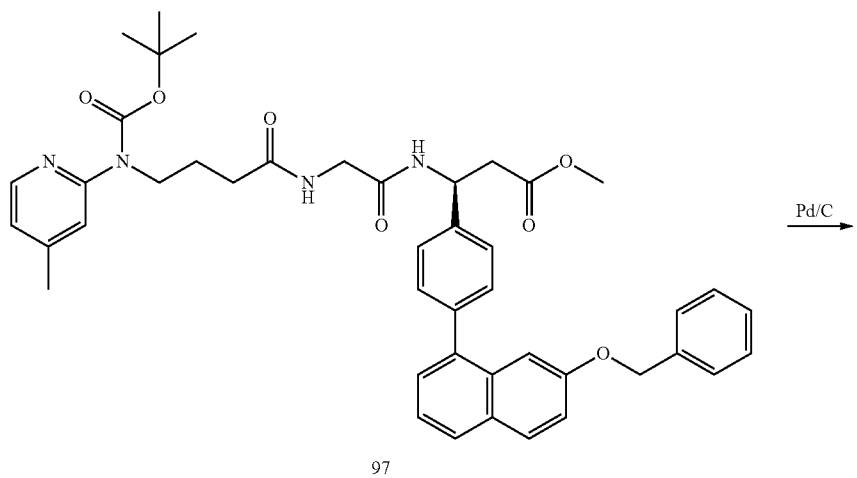

97

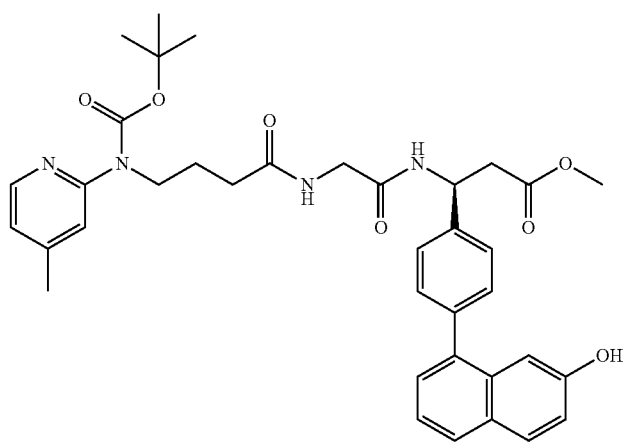
98
To a solution of compound 97 (0.116 g, 0.157 mmol, 1 equiv.) in ethyl acetate (10 mL) was added 10% Pd/C (100 mg) at room temperature. The reaction mixture was stirred at room temperature for overnight. The catalyst was removed by filtration through Celite® and the product was used directly without further purification. LC-MS: calculated [M+H]+ 655.31, found 655.87.
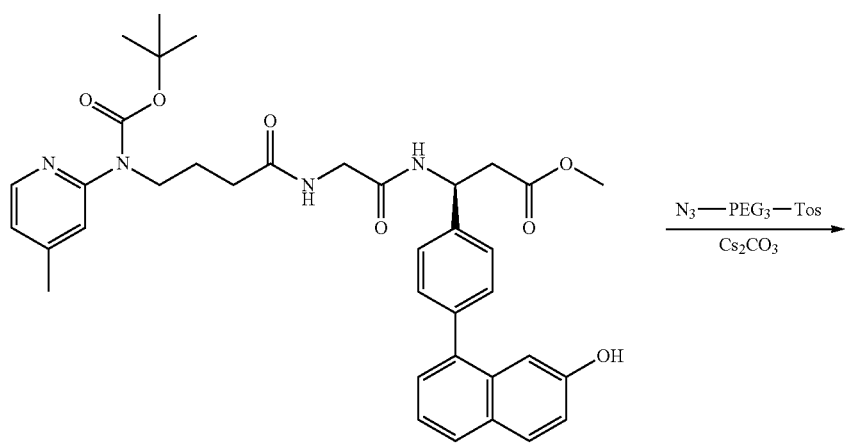
98

-continued

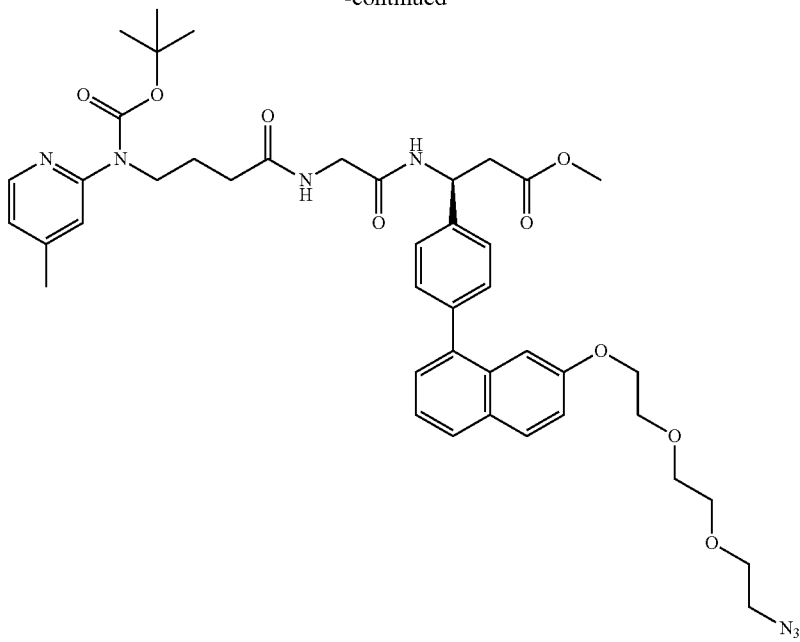

99

To a solution of compound 98 (87 mg, 0.133 mmol, 1 equiv.) and azido-PEG₃-OTs (87 mg, 0.266 mmol, 2 equiv.) in anhydrous DMF (2 mL) was added Cs₂CO₃ (87 mg, 0.266 mmol, 2 equiv.) at room temperature. The reaction mixture was stirred at 40° C. for 6 hours. The reaction was quenched by saturated NaHCO₃ solution (10 mL) and the aqueous layer was extracted with ethyl acetate (3×10 mL). The organic phase was combined, dried over Na₂SO₄, and concentrated. The product was separated by CombiFlash® using silica gel as the stationary phase and was eluted with 34% MeOH in DCM. LC-MS: calculated [M+H]+ 812.39, found 813.05.

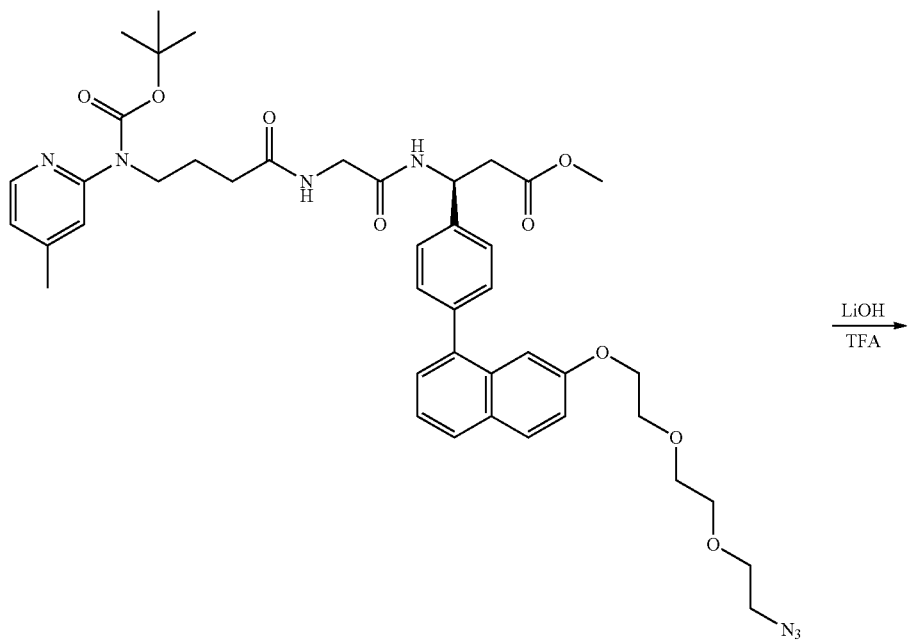

99

-continued

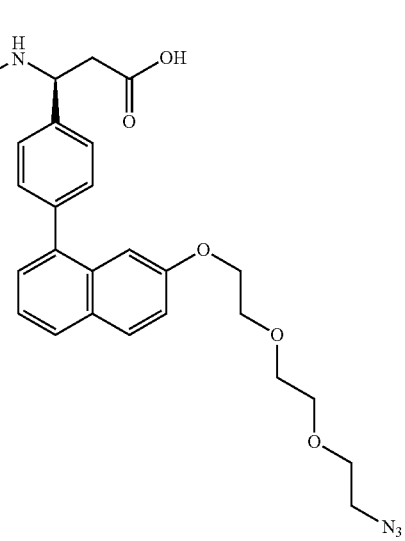

Structure 8b

To a solution of compound 99 (65 mg, 0.0801 mmol, 1.0 equiv.) in THF (2 mL) and water (2 mL) was added lithium hydroxide (6 mg, 0.240 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over Na$_2$SO$_4$, and concentrated. TFA (0.5 mL) and DCM (0.5 mL) was added into the residue and the mixture was stirred at room temperature for another 3 hr. The solvent was removed by rotary evaporator. LC-MS: calculated [M+H]+ 698.32, found 698.99.

Synthesis of Structure 9b (((14S,17R)-1-azido-14-(4-((4-methylpyridin-2-yl)amino)butanamido)-17-(4-(naphthalen-1-yl)phenyl)-15-oxo-3,6,9,12-tetraoxa-16-azanonadecan-19-oic Acid)

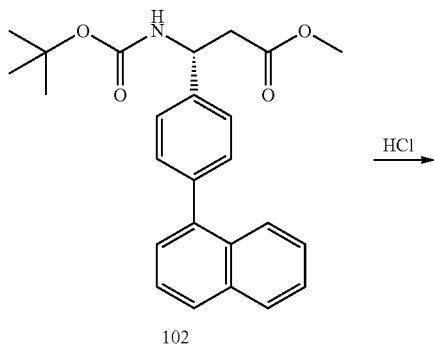

102

HCl ⟶

-continued

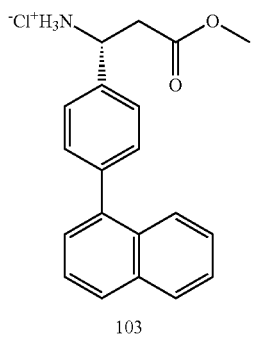

103

Compound 102 (0.19 g, 0.468 mmol, 1.0 equiv.) was cooled by ice bath. HCl in dioxane (2.35 mL, 9.37 mmol, 20 equiv.) was added into the flask. The reaction was warmed to room temperature and stirred for another 1 hr. The solvent was removed by rotary evaporator and the product was directly used without further purification. LC-MS: calculated [M+H]+ 306.14, found 306.51.

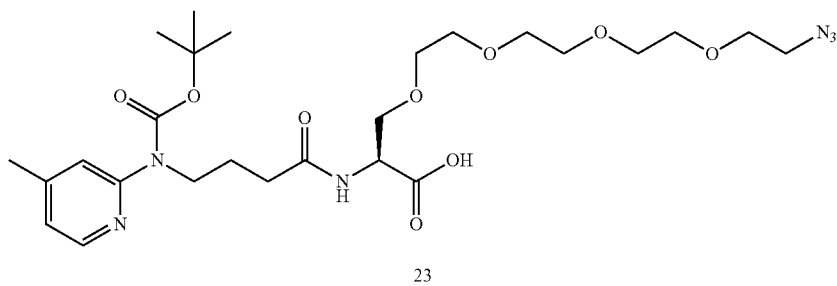

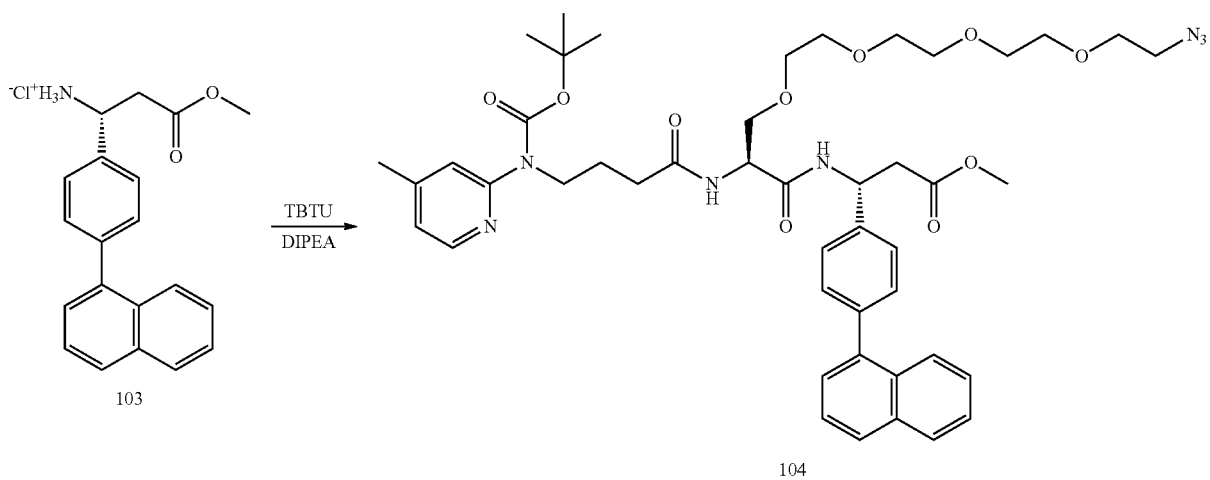

To a solution of compound 23 (110 mg, 0.188 mmol, 1 equiv.), compound 103 (71 mg, 0.207 mmol, 1.10 equiv.), and TBTU (72.7 mg, 0.226 mmol, 1.20 equiv.) in anhydrous DMF (2 mL) was added diisopropylethylamine (0.1 mL, 0.566 mmol, 3 equiv.) at 0° C. The reaction mixture was warmed to room temperature and stirred for another 1 hour. The reaction was quenched by saturated NaHCO$_3$ aqueous solution (10 mL) and the product was extracted with ethyl acetate (3×10 mL). The organic phase was combined, dried over Na$_2$SO$_4$, and concentrated. The product was purified by CombiFlash® using silica gel as the stationary phase and was eluted with 34% methanol in DCM. LC-MS: calculated [M+H]+ 870.43, found 871.12.

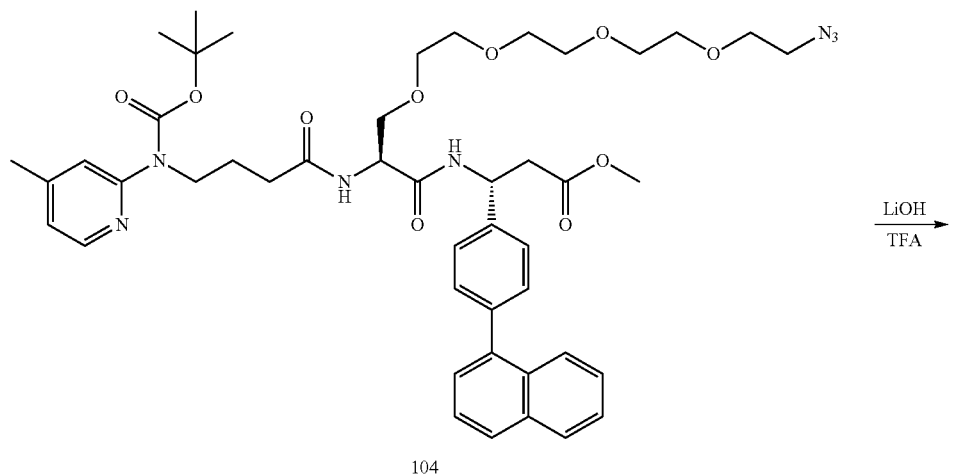

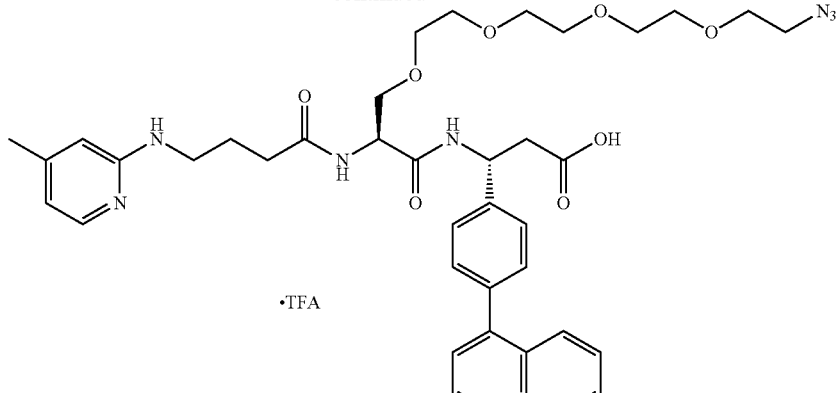

Structure 9b

To a solution of compound 104 (110 mg, 0.126 mmol, 1.0 equiv.) in THF (2 mL) and water (2 mL) was added lithium hydroxide (9 mg, 0.379 mmol, 3.0 equiv.) at room temperature. The mixture was stirred at room temperature for another 1 hour. The pH was adjusted to 3.0 by HCl (6N) and the aqueous phase was extracted with EtOAc (3×10 mL). The organic phase was combined, dried over $Na_2SO_4$, and concentrated. TFA (4 mL) and DCM (2 mL) was added into the residue and the mixture was stirred at room temperature for another 3 hours. The solvent was removed by rotary evaporator. LC-MS: calculated [M+H]+ 756.36, found 756.88.

Synthesis of Structure 10b ((S)-3-(4-(5-((14-azido-3,6,9,12-tetraoxatetradecyl)oxy)naphthalen-1-yl)phenyl)-3-(2-(4-((4-methylpyridin-2-yl)amino)butanamido)acetamido)propanoic Acid)

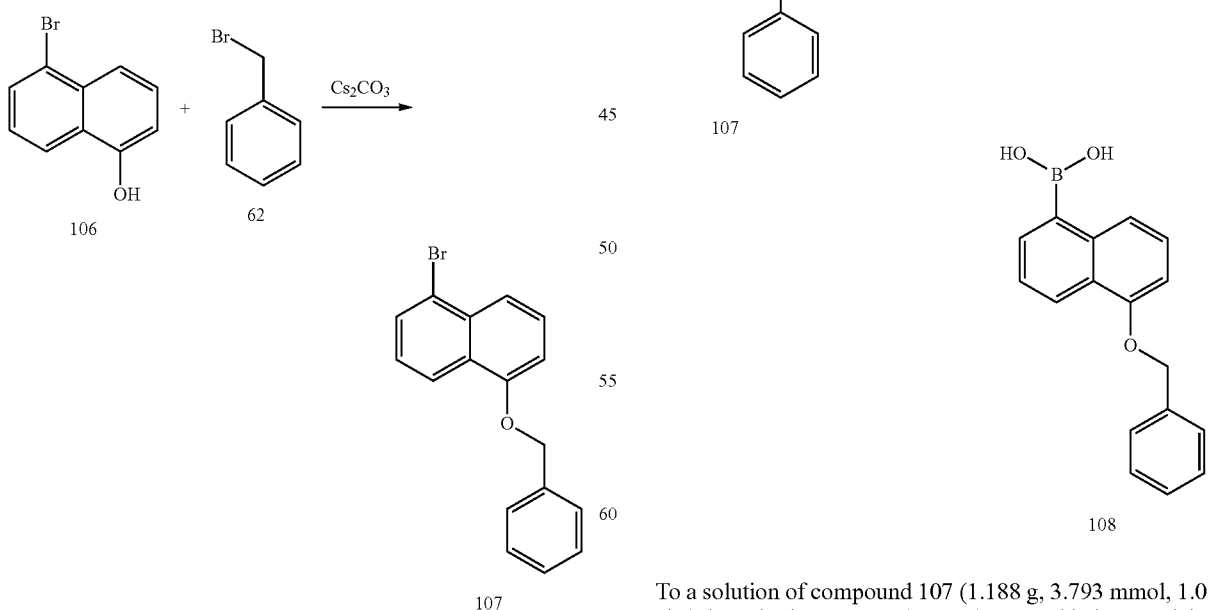

To a solution of compound 106 (1.0 g, 4.48 mmol, 1 equiv.), and compound 62 (1.06 mL, 8.96 mmol, 2 equiv.) in anhydrous DMF (10 mL) was added $Cs_2CO_3$ (2.92 g, 8.96 mmol, 2 equiv.) at room temperature. The reaction mixture was stirred at room temperature overnight. The reaction was quenched by water solution (20 mL) and the aqueous phase was extracted with ethyl acetate (3×10 mL). The organic phase was combined, dried over $Na_2SO_4$, and concentrated. The product was separated by CombiFlash® using silica gel as the stationary phase and was eluted with 5% ethyl acetate in hexane.

To a solution of compound 107 (1.188 g, 3.793 mmol, 1.0 equiv.) in anhydrous THF (10 mL) was added n-BuLi in hexane (2.27 mL, 5.689 mmol, 1.5 equiv.) drop-wise at −78° C. The reaction was kept at −78° C. for another 1 hour. Triisopropylborate (1.31 mL, 5.689 mmol, 1.5 equiv.) was then added into the mixture at −78° C. The reaction was then warmed up to room temperature and stirred for another 1 hour. The reaction was quenched by saturated NH$_4$Cl solution (20 mL) and the pH was adjusted to 3. The aqueous phase was extracted with EtOAc (3×20 mL) and the organic phase was combined, dried over Na$_2$SO$_4$, and concentrated. The solid was triturated with hexane and filtered. The product was used directly without further purification. LC-MS: calculated [M−H]−, 277.11, found 277.26.

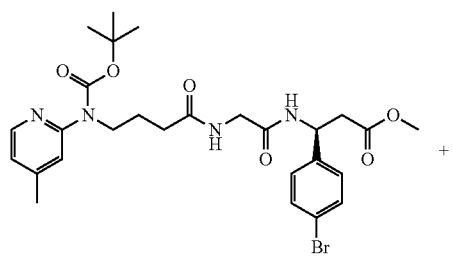

96

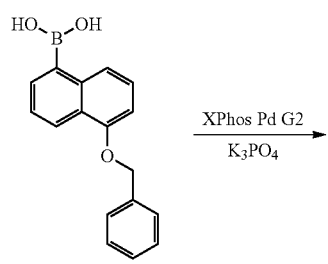

108

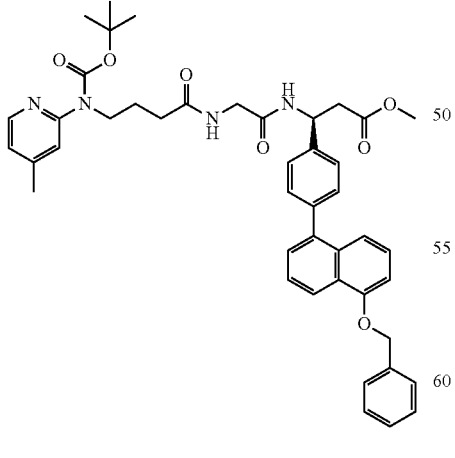

109

Compound 96 (100 mg, 0.169 mmol, 1.0 equiv.), compound 108 (70 mg, 0.253 mmol, 1.5 equiv.), XPhos Pd G2 (2.7 mg, 0.0034 mmol, 0.02 equiv.), and K$_3$PO$_4$ (72 mg, 0.338 mmol, 2.0 equiv.) were mixed in a round-bottom flask. The flask was sealed with a screw-cap septum, and then evacuated and backfilled with nitrogen (this process was repeated a total of 3 times). Then, THF (8 mL) and water (2 mL) were added via syringe. The mixture was bubbled with nitrogen for 20 min and the reaction was kept at room temperature for overnight. The reaction was quenched with water (10 mL), and the aqueous phase was extracted with ethyl acetate (3×10 mL). The organic phase was combined, dried over Na$_2$SO$_4$, and concentrated. The compound was separated by CombiFlash® using silica gel as the stationary phase and was eluted with 3% methanol in DCM. LC-MS: calculated [M+H]+ 745.35, found 745.99.

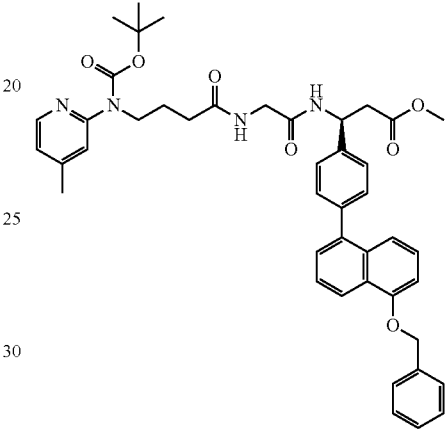

109

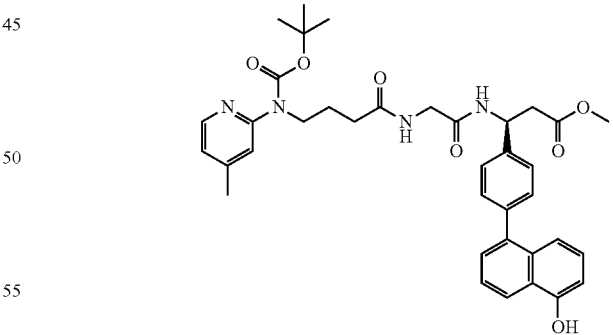

110

To a solution of compound 109 (0.135 g, 0.181 mmol, 1 equiv.) in ethyl acetate (10 mL) was added 10% Pd/C (100 mg) at room temperature. The reaction mixture was stirred at room temperature for overnight. The catalyst was removed by filtration through Celite® and the product was used directly without further purification. LC-MS: calculated [M+H]+ 655.31, found 655.87.

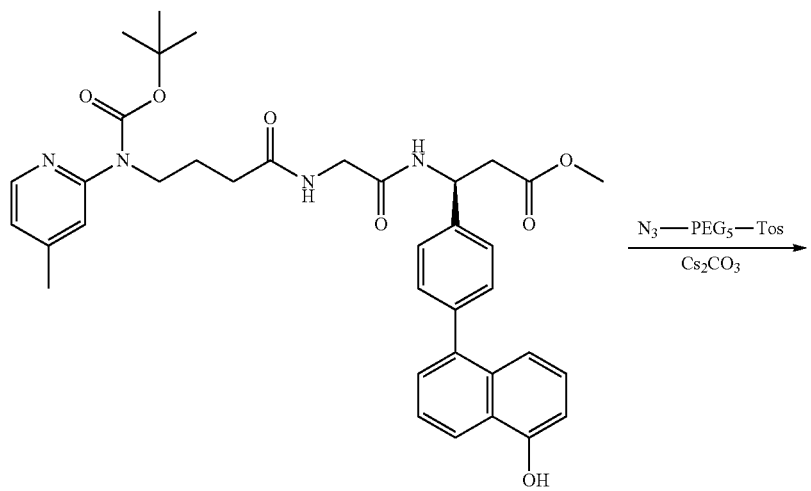

110

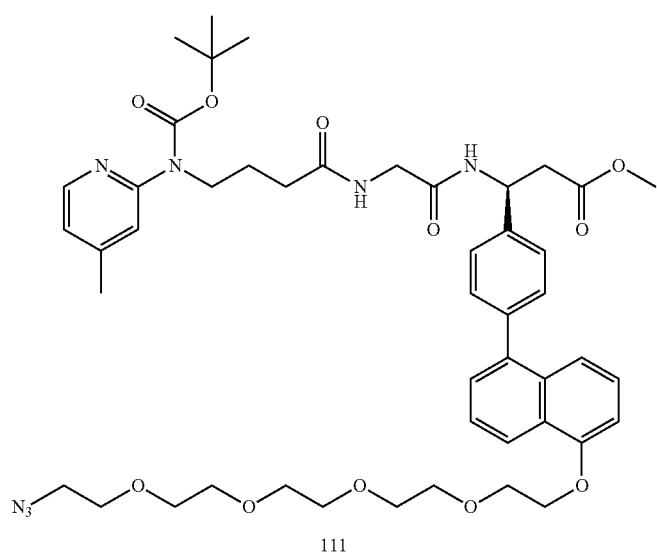

111

To a solution of compound 110 (50 mg, 0.0764 mmol, 1 equiv.) and azido-PEG5-OTs (64 mg, 0.152 mmol, 2 equiv.) in anhydrous DMF (2 mL) was added Cs$_2$CO$_3$ (50 mg, 0.152 mmol, 2 equiv.) at room temperature. The reaction mixture was stirred for 3 hours at 40° C. The reaction was quenched by saturated NaHCO$_3$ solution (10 mL) and the aqueous layer was extracted with ethyl acetate (3×10 mL). The organic phase was combined, dried over Na$_2$SO$_4$, and concentrated. The product was purified by CombiFlash® using silica gel as the stationary phase and was eluted with 4% methanol in DCM. The yield is 62%. LC-MS: calculated [M+H]+ 900.44, found 901.19.

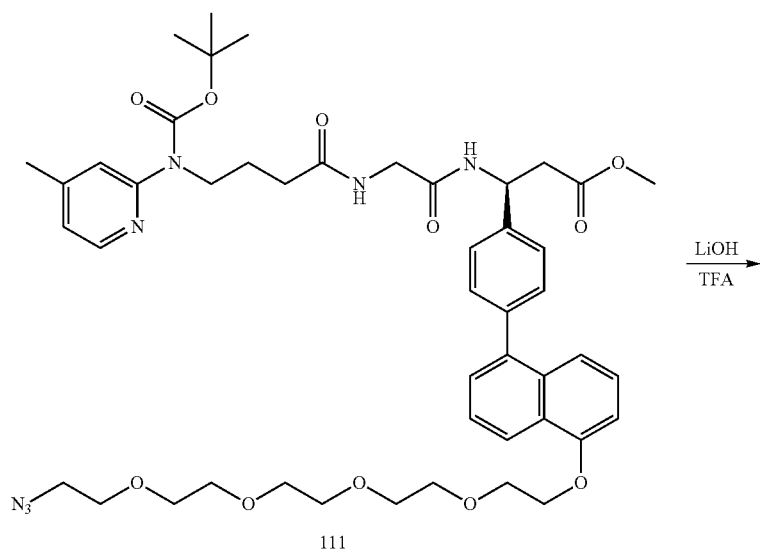

111

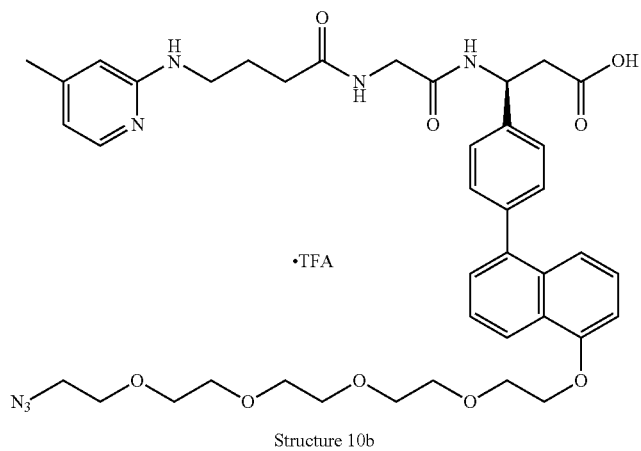

Structure 10b

To a solution of compound 111 (43 mg, 0.0478 mmol, 1.0 equiv.) in THF (2 mL) and water (2 mL) was added lithium hydroxide (3.4 mg, 0.143 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over $Na_2SO_4$, and concentrated. TFA (4 mL) and DCM (2 mL) was added into the residue and the mixture was stirred at room temperature for another 3 hr. The solvent was removed by rotary evaporator. LC-MS: calculated [M+H]+ 786.37, found 787.04.

209

Synthesis of Structure 11b ((S)-3-(4-(4-((14-azido-3,6,9,12-tetraoxatetradecyl)oxy)naphthalen-1-yl)phenyl)-3-((S)-1-(4-((4-methylpyridin-2-yl)amino)butanoyl)pyrrolidine-2-carboxamido)propanoic Acid)

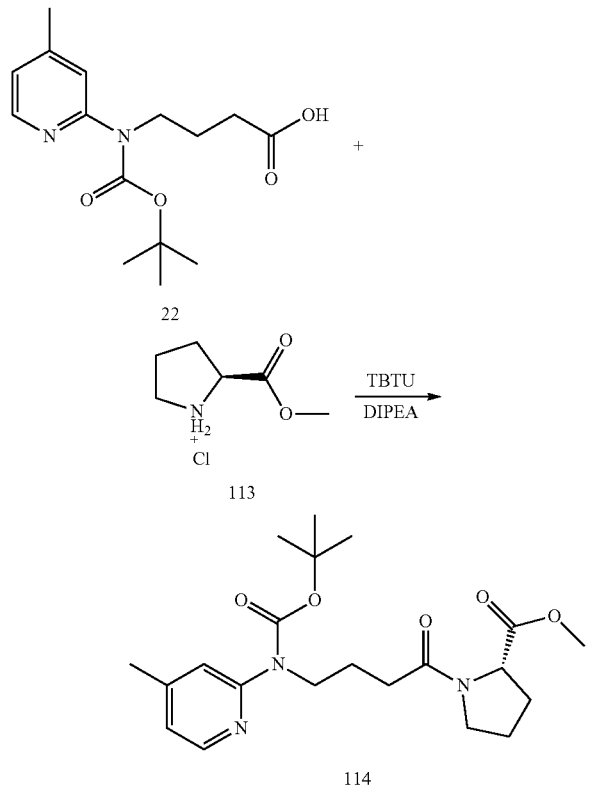

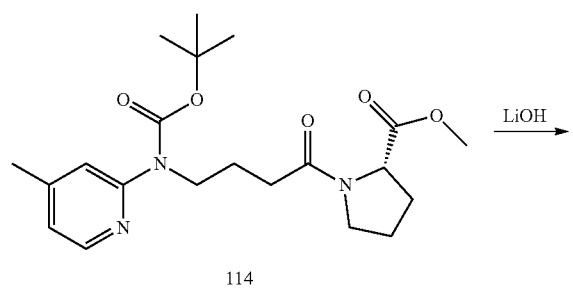

To a solution of compound 22 (500 mg, 1.698 mmol, 1 equiv.), compound 113 (295 mg, 1.783 mmol, 1.05 equiv.), and TBTU (654 mg, 2.038 mmol, 1.2 equiv.) in anhydrous DMF (10 mL) was added diisopropylethylamine (0.888 mL, 5.096 mmol, 3 equiv.) at 0° C. The reaction mixture was warmed to room temperature and stirred for another 1 hr. The reaction was quenched by saturated NaHCO₃ aqueous solution (10 mL) and the product was extracted with ethyl acetate (3×10 mL). The organic phase was combined, dried over Na₂SO₄, and concentrated. The product was purified by CombiFlash® using silica gel as the stationary phase and was eluted with 2-3% methanol in DCM. The yield is 98.72%. LC-MS: calculated [M+H]+ 406.23, found 406.07.

210

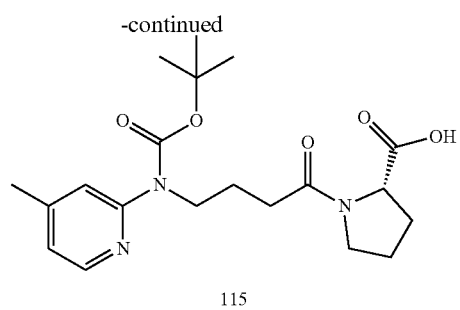

To a solution of compound 114 (0.68 g, 1.676 mmol, 1 equiv.) in THF (5 mL) and H₂O (5 mL) was added lithium hydroxide (0.12 g, 5.030 mmol, 3 equiv.) portion-wise at 0° C. The reaction mixture was warmed to room temperature. After stirring at room temperature for 1 hr, the reaction mixture was acidified by HCl (6 N) to pH 3.0. The aqueous phase was extracted with ethyl acetate (3×10 mL) and the organic layer was combined, dried over Na₂SO₄, and concentrated. The product was used without further purification. LC-MS: calculated [M+H]+ 392.21, found 392.39.

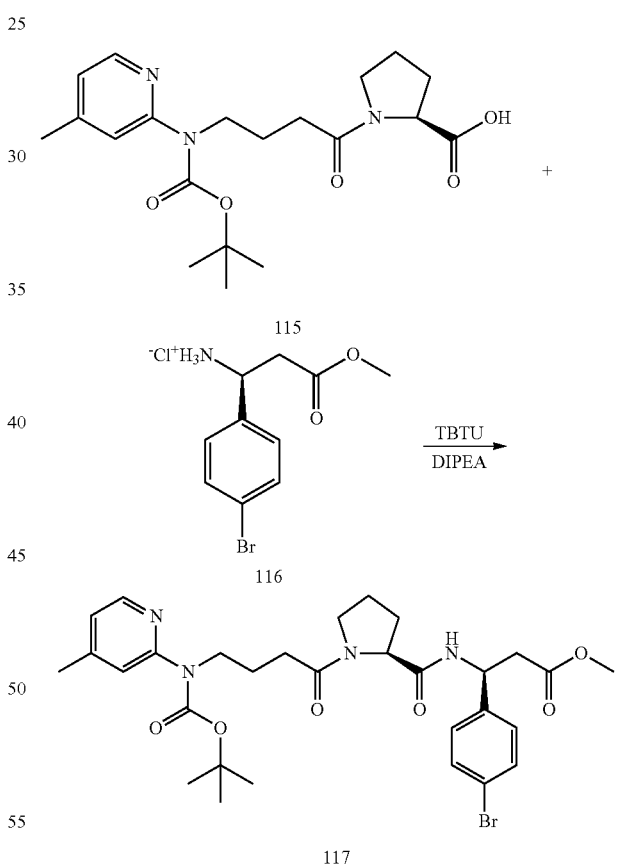

To a solution of compound 115 (300 mg, 0.766 mmol, 1 equiv.), compound 116 (237 mg, 0.804 mmol, 1.05 equiv.), and TBTU (295 mg, 0.919 mmol, 1.2 equiv.) in anhydrous DMF (10 mL) was added diisopropylethylamine (0.400 mL, 2.299 mmol, 3 equiv.) at 0° C. The reaction mixture was warmed to room temperature and stirred for another 1 hr. The reaction was quenched by saturated NaHCO₃ aqueous solution (10 mL) and the product was extracted with ethyl acetate (3×10 mL). The organic phase was combined, dried over Na$_2$SO$_4$, and concentrated. The product was purified by CombiFlash® using silica gel as the stationary phase and was eluted with 34% methanol in DCM. The yield is 83%. LC-MS: calculated [M+H]+ 631.21, found 631.46.

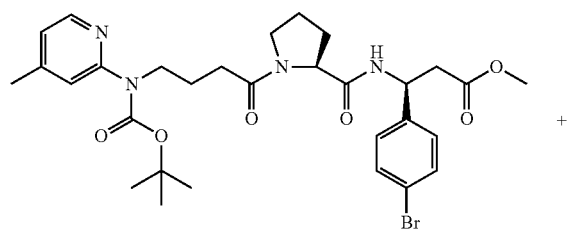

118

+

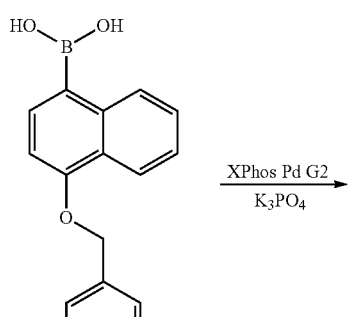

65

XPhos Pd G2
K$_3$PO$_4$
→

The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 20 min and the reaction was kept at 40° C. for 1 hr. The reaction was quenched with water (10 mL), and the aqueous phase was extracted with ethyl acetate (3×10 mL). The organic phase was combined, dried over Na$_2$SO$_4$, and concentrated. The compound was separated by Combi-Flash® using silica gel as the stationary phase and was eluted with 3% methanol in DCM. The yield was 96%. LC-MS: calculated [M+H]+ 78538, found 78569.

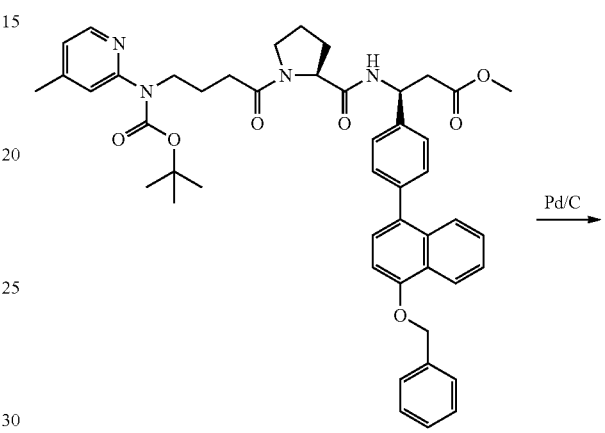

119

Pd/C →

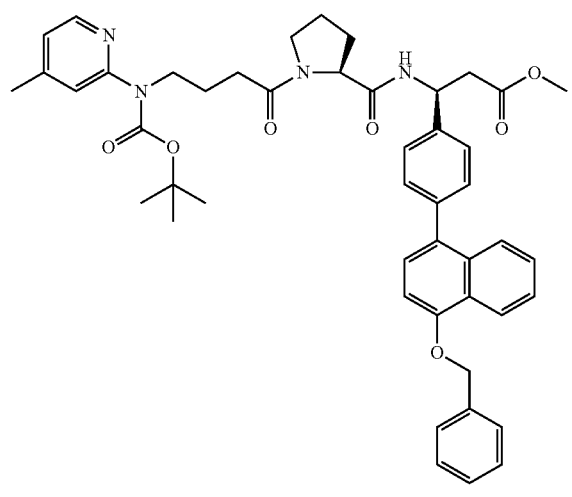

119

Compound 118 (100 mg, 0.158 mmol, 1.0 equiv.), compound 65 (66 mg, 0.237 mmol, 1.5 equiv.), XPhos Pd G2 (2.5 mg, 0.0032 mmol, 0.02 equiv.), and K$_3$PO$_4$ (67 mg, 0.316 mmol, 2.0 equiv.) were mixed in a round-bottom flask.

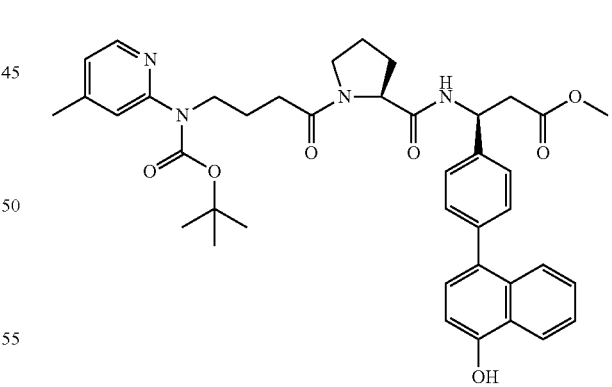

120

To a solution of compound 119 (0.120 g, 0.153 mmol, 1 equiv.) in ethyl acetate (10 mL) was added 10% Pd/C (100 mg) at room temperature. The reaction mixture was stirred at room temperature for overnight. The catalyst was removed by filtration through Celite® and the product was used directly without further purification. LC-MS: calculated [M+H]+ 695.34, found 695.66.

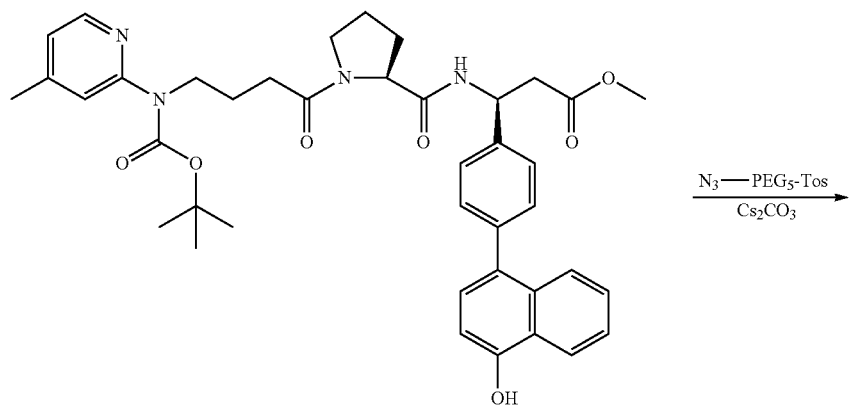

120

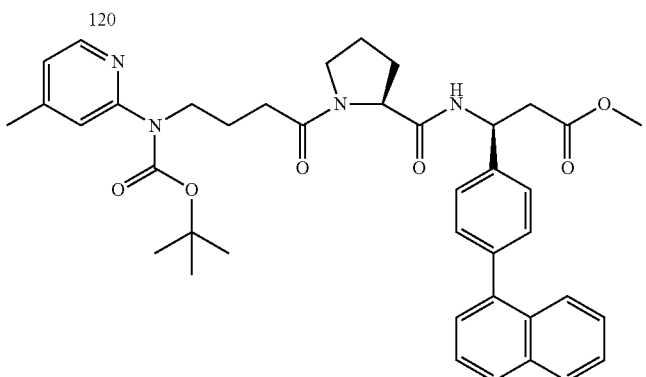

121

To a solution of compound 120 (83 mg, 0.119 mmol, 1 equiv.) and azido-PEG$_5$-OTs (100 mg, 0.239 mmol, 2 equiv.) in anhydrous DMF (2 mL) was added Cs$_2$CO$_3$ (78 mg, 0.239 mmol, 2 equiv.) at room temperature. The reaction mixture was stirred for 3 hours at 40° C. The reaction was quenched by saturated NaHCO$_3$ solution (10 mL) and the aqueous layer was extracted with ethyl acetate (3×10 mL). The organic phase was combined, dried over Na$_2$SO$_4$, and concentrated. The product was purified by CombiFlash® using silica gel as the stationary phase and was eluted with 4% methanol in DCM. The yield was 79%. LC-MS: calculated 940.47, found 941.16.

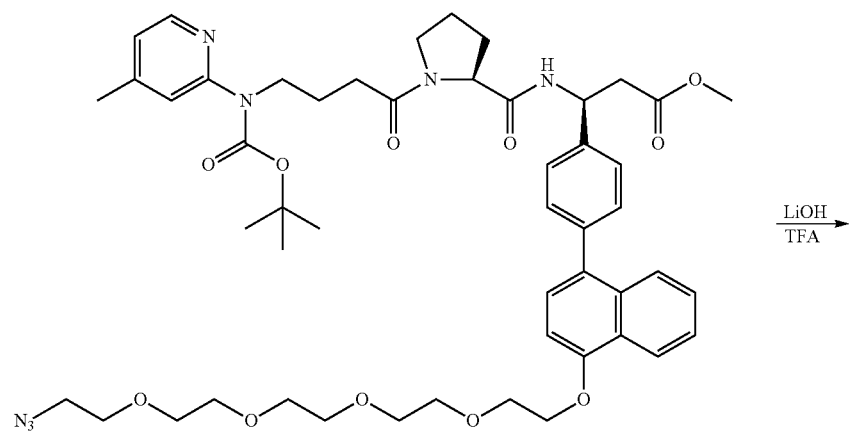

121

-continued

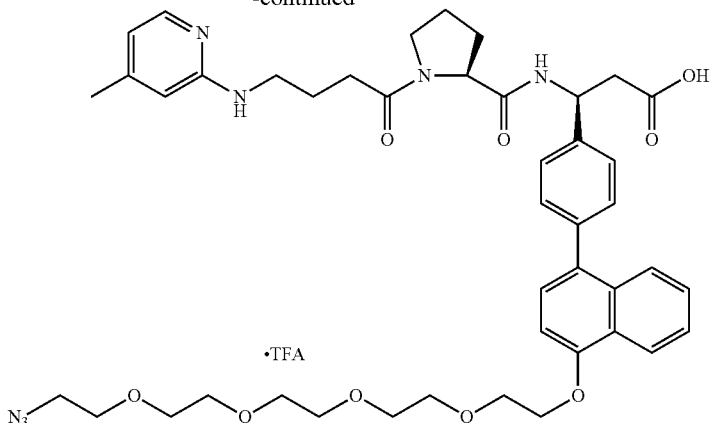

Structure 11b

To a solution of compound 121 (89 mg, 0.0947 mmol, 1.0 equiv.) in THF (2 mL) and water (2 mL) was added lithium hydroxide (6.8 mg, 0.284 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over $Na_2SO_4$, and concentrated. TFA (4 mL) and DCM (2 mL) was added into the residue and the mixture was stirred at room temperature for another 3 hr. The solvent was removed by rotary evaporator. LC-MS: calculated [M+H]+ 826.41, found 827.10.

Synthesis of Structure 12b ((S)-3-(4-(4-((14-azido-3,6,9,12-tetraoxatetradecyl)oxy)benzo[d]oxazol-7-yl)phenyl)-3-(2-(4-((4-methylpyridin-2-yl)amino)butanamido)acetamido)propanoic Acid)

To a solution of compound 123 (1.0 g, 7.40 mmol, 1 equiv.), and compound 62 (1.32 mL, 11.10 mmol, 1.5 equiv.) in anhydrous DMF (10 mL) was added $Cs_2CO_3$ (3.62 g, 11.10 mmol, 1.5 equiv.) at 0° C. The reaction mixture was warmed to room temperature and stirred overnight. The reaction was quenched by water (10 mL). The aqueous phase was extracted with ethyl acetate (3×10 mL) and the organic phase was combined, dried over anhydrous $Na_2SO_4$, and concentrated. The product was separated by Combi-Flash® using silica gel as the stationary phase and was eluted with 5-7% ethyl acetate in hexane. 85% yield.

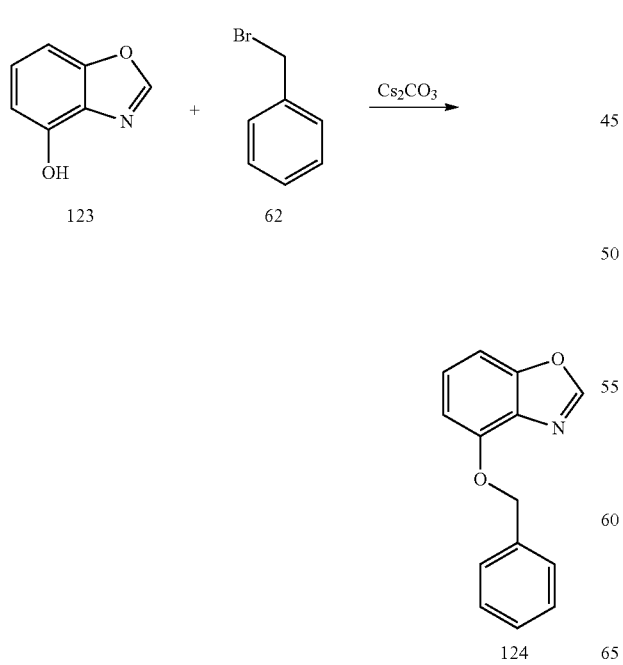

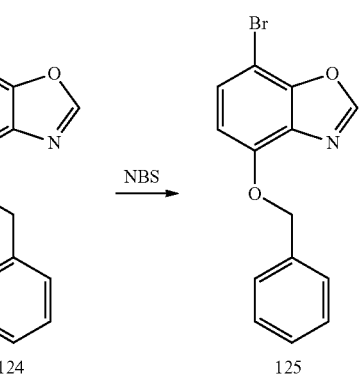

To a solution of compound 124 (1.425 g, 6.326 mmol, 1 equiv.) in anhydrous acetonitrile (20 mL) was added N-bromosuccinimide (1.216 g, 6.832 mmol, 1.08 equiv.) at 0° C. portion-wise. The reaction mixture was kept at 0° C. for another 30 min and then allowed to warm to room temperature and stirred overnight. The solvent was removed under reduced pressure and the residue was purified by Combi-Flash® using silica gel as the stationary phase. The product was eluted with 4-5% ethyl acetate in hexane. 65% yield. LC-MS: calculated [M+H]+ 303.99. found 304.08.

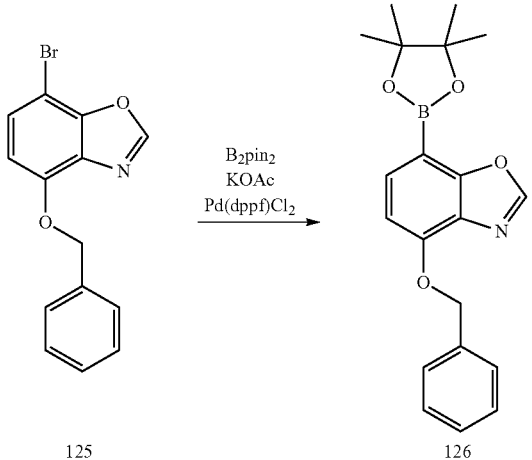 [SMILES: Brc1ccc(OCc2ccccc2)c2ncoc12 ; "B2pin2KOAcPd(dppf)Cl2" ; CC1(C)OB(c2ccc(OCc3ccccc3)c3ncoc23)OC1(C)C]

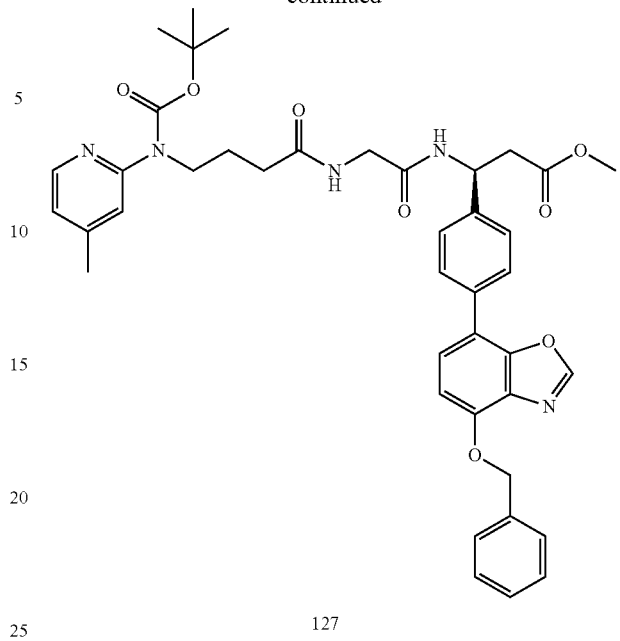

The mixture of compound 125 (1.339 g, 4.402 mmol, 1 equiv.), bis(pinacolato)diboron (2.236 g, 8.805 mmol, 2 equiv.), potassium acetate (0.864 g, 8.805 mmol, 2 equiv.) and Pd(dppf)Cl₂ (161 mg, 0.220 mmol, 0.05 equiv.) in 15 mL of anhydrous 1,4-dioxane was stirred at 100° C. under nitrogen for 8 hours. After concentration, the residue was partitioned between H₂O and DCM, the aqueous phase was extracted with DCM, and the combined organic layer was washed with brine, dried over Na₂SO₄, and concentrated. The product was purified by CombiFlash® using silica gel as the stationary phase and was eluted with 15-20% ethyl acetate in hexane. LC-MS: calculated [M+H]+ 352.16, found 352.06.

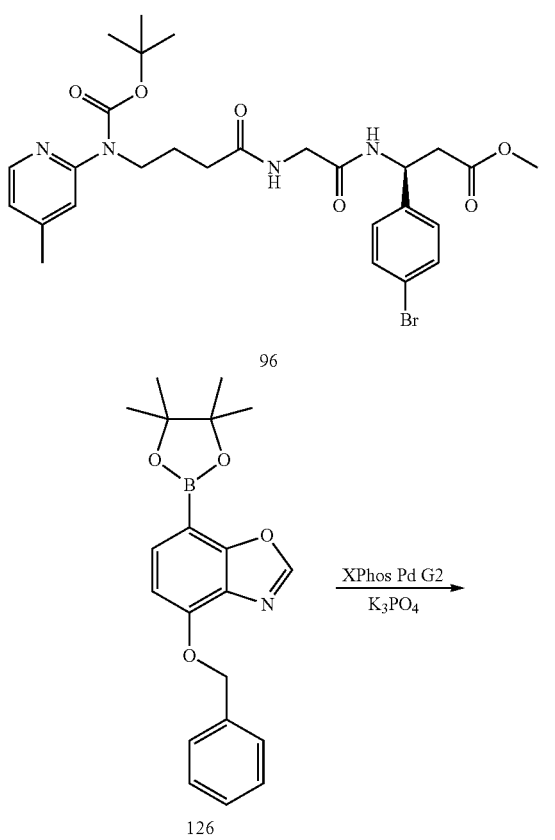

Compound 96 (200 mg, 0.338 mmol, 1.0 equiv.), compound 126 (178 mg, 0.507 mmol, 1.5 equiv.), XPhos Pd G2 (5.3 mg, 0.0068 mmol, 0.02 equiv.), and K₃PO₄ (143 mg, 0.676 mmol, 2.0 equiv.) were mixed in a round-bottom flask. The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 20 min and the reaction was kept at 40° C. for 1 hr. The reaction was quenched with saturated NaHCO₃ (10 mL), and the aqueous phase was extracted with ethyl acetate (3×10 mL). The organic phase was combined, dried over Na₂SO₄, and concentrated. The compound was separated by CombiFlash® using silica gel as the stationary phase and was eluted with 2-3% methanol in DCM. LC-MS: calculated [M+H]+ 736.33, found 736.89.

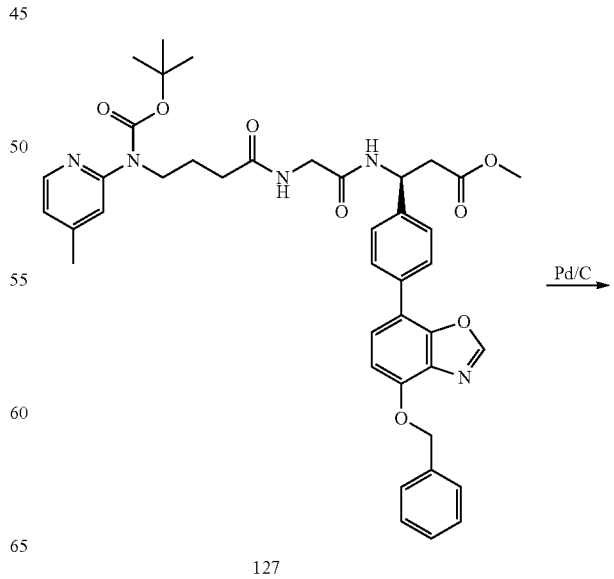

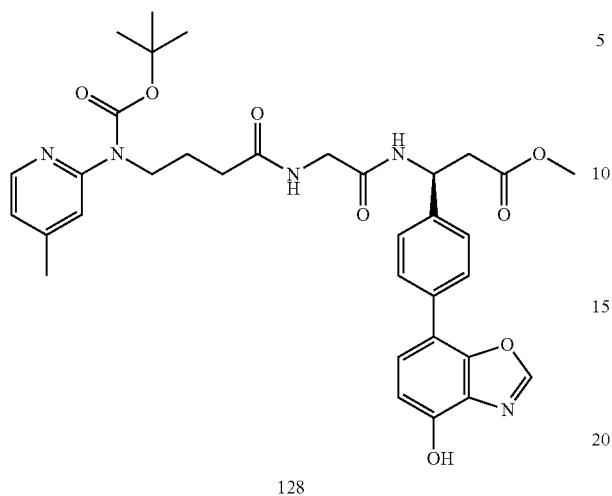
128
To a solution of compound 127 (0.219 g, 0.297 mmol, 1 equiv.) in ethyl acetate (10 mL) was added 10% Pd/C (100 mg) at room temperature. The reaction mixture was stirred at room temperature overnight. The catalyst was removed by filtration through Celite® and the product was used directly without further purification. LC-MS: calculated [M+H]+ 646.28, found 646.78.
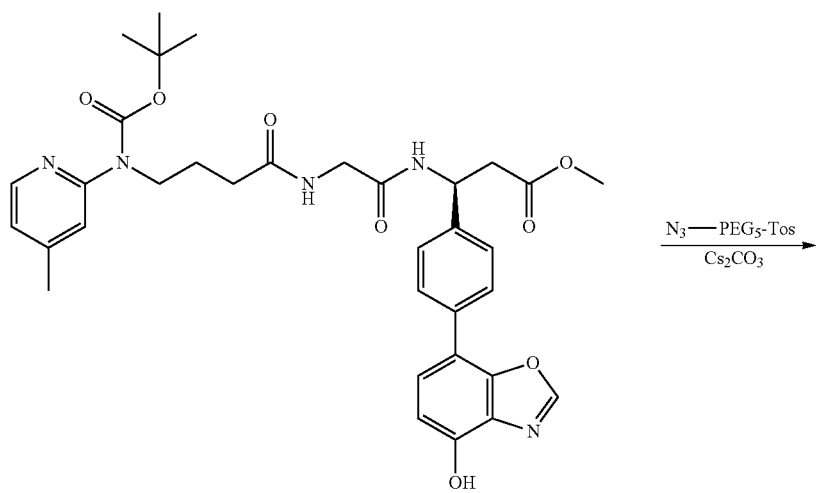
128

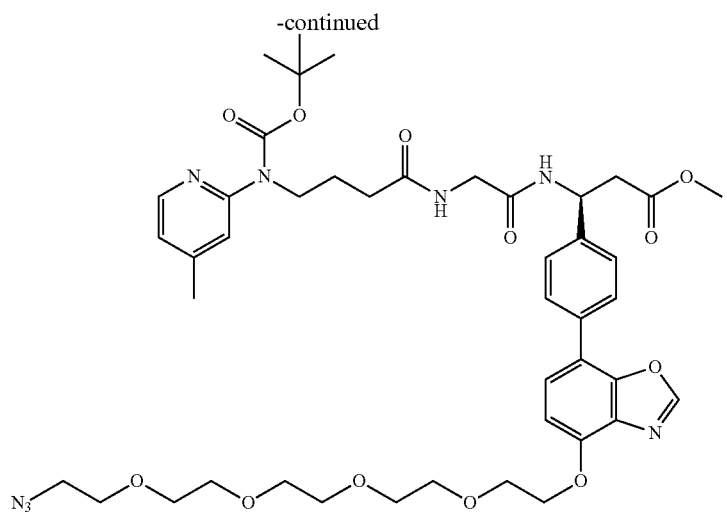

129

To a solution of compound 128 (73 mg, 0.113 mmol, 1 equiv.) and azido-PEG₅-OTs (94 mg, 0.226 mmol, 2 equiv.) in anhydrous DMF (2 mL) was added Cs₂CO₃ (74 mg, 0.226 mmol, 2 equiv.) at room temperature. The reaction mixture was stirred for 3 hours at 40° C. The reaction was quenched by saturated NaHCO₃ solution (10 mL) and the aqueous layer was extracted with ethyl acetate (3×10 mL). The organic phase was combined, dried over Na₂SO₄, and concentrated. The product was purified by CombiFlash® using silica gel as the stationary phase and was eluted with 4% methanol in DCM. The yield is 80%. LC-MS: calculated [M+H]+ 891.42, found 892.00.

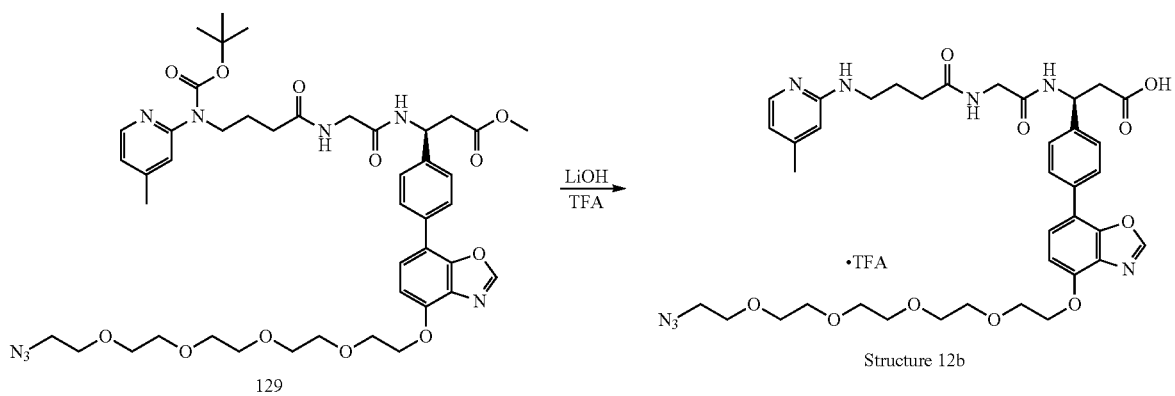 [SMILES: COC(=O)C[C@H](NC(=O)CNC(=O)CCCN(C(=O)OC(C)(C)C)c1cc(C)ccn1)c1ccc(-c2ccc(OCCOCCOCCOCCOCCN=[N+]=[N-])c3ncoc23)cc1 ; "LiOH" ; Cc1ccnc(NCCCC(=O)NCC(=O)N[C@@H](CC(=O)O)c2ccc(-c3ccc(OCCOCCOCCOCCOCCN=[N+]=[N-])c4ncoc34)cc2)c1 ; "TFA"]

To a solution of compound 129 (43 mg, 0.0478 mmol, 1.0 equiv.) in THF (2 mL) and water (2 mL) was added lithium hydroxide (3.4 mg, 0.143 mmol, 3.0 equiv.) at room temperature. The mixture was stirred at room temperature for 1 hour. The pH was adjusted to 3.0 by HCl (6N) and the aqueous phase was extracted with EtOAc (3×10 mL). The organic phase was combined, dried over Na₂SO₄, and concentrated. TFA (4 mL) and DCM (2 mL) was added into the residue and the mixture was stirred at room temperature for another 3 hr. The solvent was removed by rotary evaporator. LC-MS: calculated [M+H]+ 777.35, found 777.94.

223

Synthesis of Structure 13b ((S)-3-(4-(4-((14-azido-3,6,9,12-tetraoxatetradecyl)oxy)-5,6,7,8-tetrahydronaphthalen-1-yl)phenyl)-3-(2-(4-((4-methylpyridin-2-yl)amino)butanamido)acetamido)propanoic Acid)

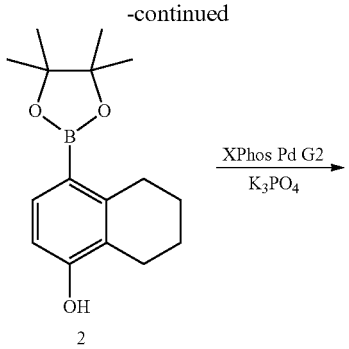

2

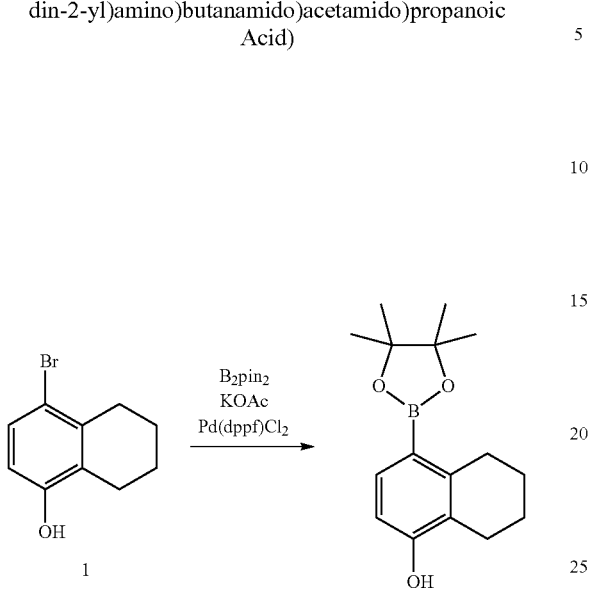

The mixture of compound 1 (300 mg, 1.321 mmol, 1 equiv.), bis(pinacolato)diboron (671 mg, 2.642 mmol, 2 equiv.), potassium acetate (389 mg, 3.963 mmol, 2 equiv.) and Pd(dppf)Cl$_2$ (48 mg, 0.066 mmol, 0.05 equiv.) in 10 mL of anhydrous 1,4-dioxane was stirred at 80° C. under nitrogen overnight. After concentration, the residue was partitioned between H$_2$O and DCM, the aqueous phase was extracted with DCM, and the combined organic layer was washed with brine, dried over Na$_2$SO$_4$, and concentrated. The product was purified by CombiFlash® using silica gel as the stationary phase and was eluted with 10% ethyl acetate in hexane. LC-MS: calculated [M−H]− 273.17, found 273.29.

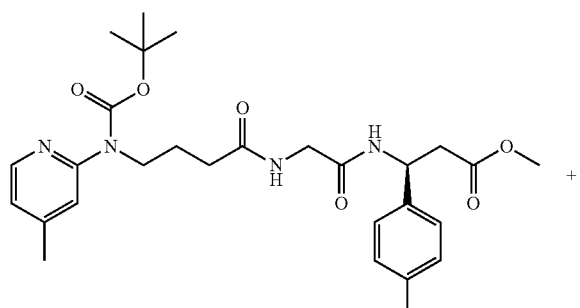

1

Compound 1 (100 mg, 0.169 mmol, 1.0 equiv.), compound 2 (70 mg, 0.253 mmol, 1.5 equiv.), XPhos Pd G2 (2.7 mg, 0.0034 mmol, 0.02 equiv.), and K$_3$PO$_4$ (72 mg, 0.338 mmol, 2.0 equiv.) were mixed in a round-bottom flask. The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 20 min and the reaction was kept at 40° C. for 3 hr. The reaction was then cooled to room temperature and left overnight. The reaction was quenched with saturated NaHCO$_3$ (10 mL), and the aqueous phase was extracted with ethyl acetate (3×10 mL). The organic phase was combined, dried over Na$_2$SO$_4$, and concentrated. The compound was separated by CombiFlash® using silica gel as the stationary phase and was eluted with 4-5% methanol in DCM. LC-MS: calculated [M+H]+ 659.34, found 659.57.

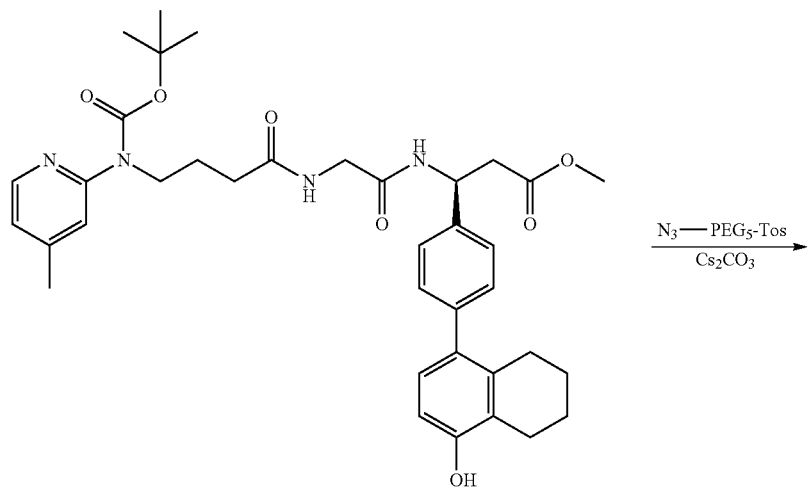

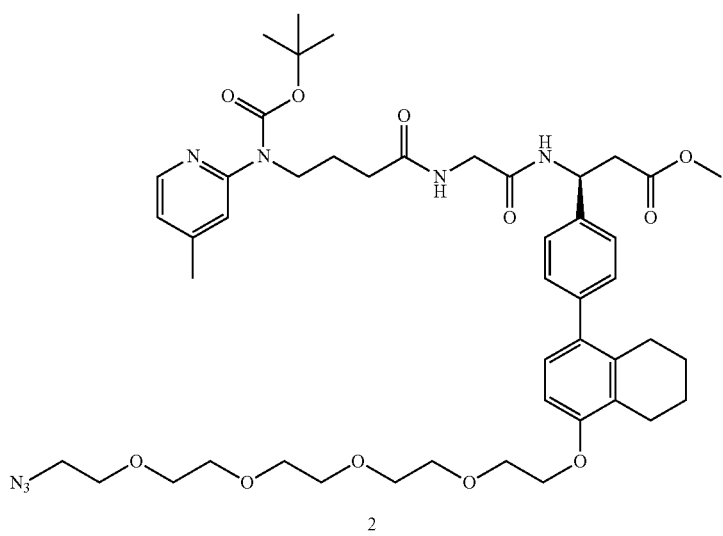

To a solution of compound 1 (30 mg, 0.0455 mmol, 1 equiv.) and azido-PEG$_5$-OTs (38 mg, 0.0911 mmol, 2 equiv.) in anhydrous DMF (2 mL) was added Cs$_2$CO$_3$ (30 mg, 0.0911 mmol, 2 equiv.) at room temperature. The reaction mixture was stirred for 3 hours at 40° C. The reaction was quenched by saturated NaHCO$_3$ solution (10 mL) and the aqueous layer was extracted with ethyl acetate (3×10 mL). The organic phase was combined, dried over Na$_2$SO$_4$, and concentrated. The product was purified by CombiFlash® using silica gel as the stationary phase and was eluted with 4% methanol in DCM. The yield is 70%. LC-MS: calculated [M+H]+ 904.47, found 904.88.

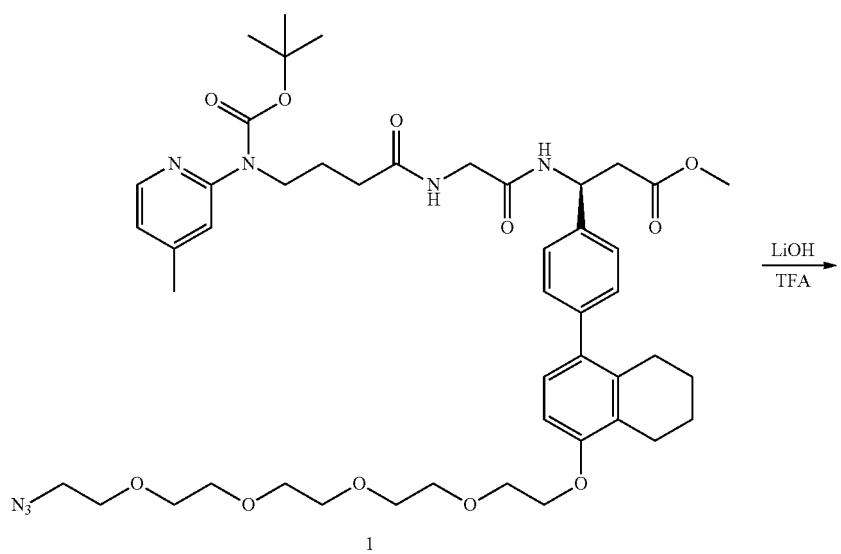

1

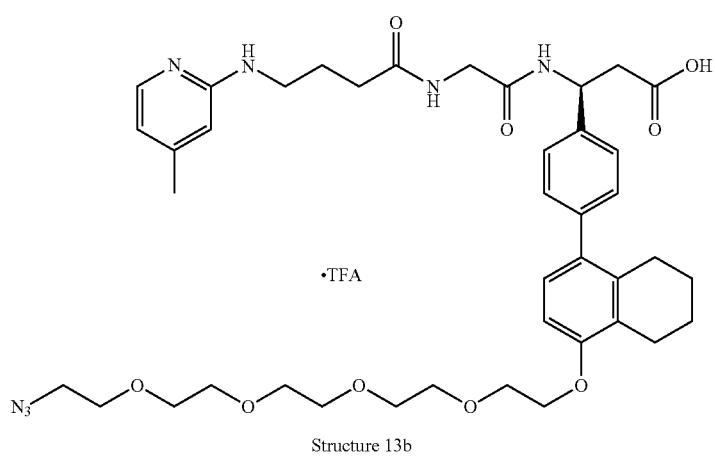

Structure 13b

To a solution of compound 1 (29 mg, 0.0321 mmol, 1.0 equiv.) in THF (2 mL) and water (2 mL) was added lithium hydroxide (2.3 mg, 0.0962 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over $Na_2SO_4$, and concentrated. TFA (4 mL) and DCM (2 mL) were added into the residue and the mixture was stirred at room temperature for another 3 hr. The solvent was removed by rotary evaporator. LC-MS: calculated [M+H]+ 790.41, found 790.64.

229

Synthesis of Structure 14b ((S)-3-(4'-((14-azido-3,6,9,12-tetraoxatetradecyl)oxy)-2'-(trifluoromethoxy)-[1,1'-biphenyl]-4-yl)-3-(2-(4-((4-methylpyridin-2-yl)amino)butanamido)acetamido)propanoic Acid)

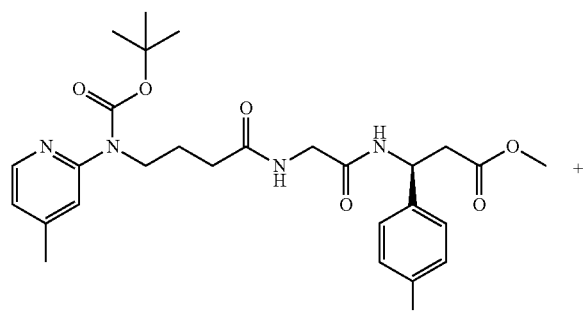

1

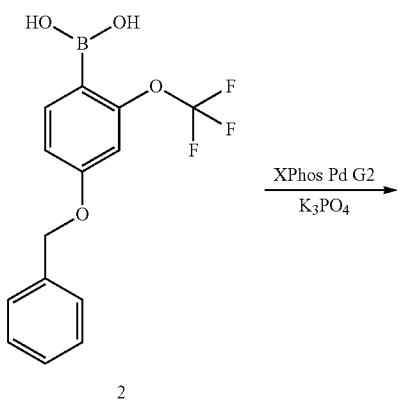

2

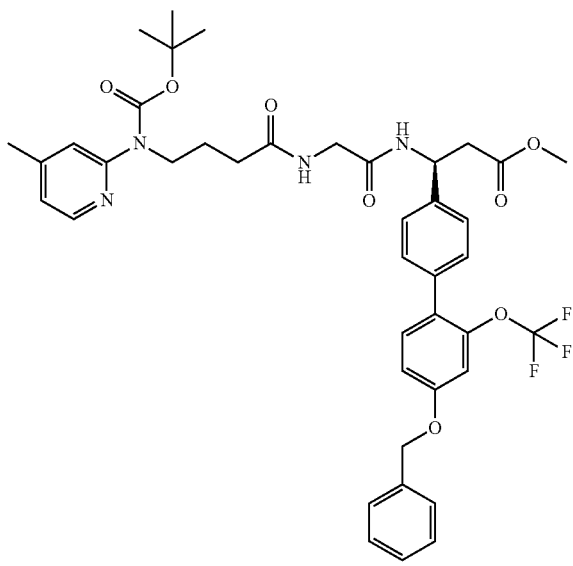

1

Compound 1 (150 mg, 0.253 mmol, 1.0 equiv.), compound 2 (118 mg, 0.380 mmol, 1.5 equiv.), XPhos Pd G2 (4 mg, 0.0051 mmol, 0.02 equiv.), and K₃PO₄ (107 mg, 0.507 mmol, 2.0 equiv.) were mixed in a round-bottom flask. The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 10 min and the reaction was kept at 40° C. for overnight. The reaction was quenched with water (10 mL), and the aqueous phase was extracted with ethyl acetate (3×10 mL). The organic phase was combined, dried over Na₂SO₄, and concentrated. The compound was separated by CombiFlash® using silica gel as the stationary phase and was eluted with 24% methanol in DCM. LC-MS: calculated [M+H]+ 779.32, found 779.65.

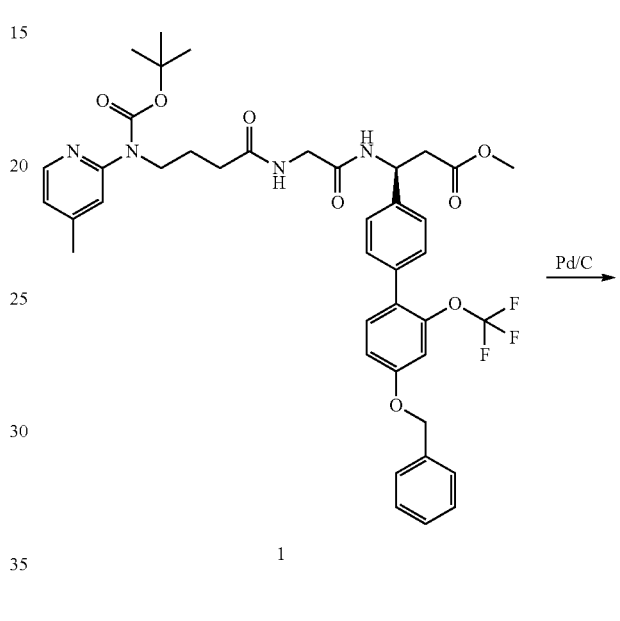

1

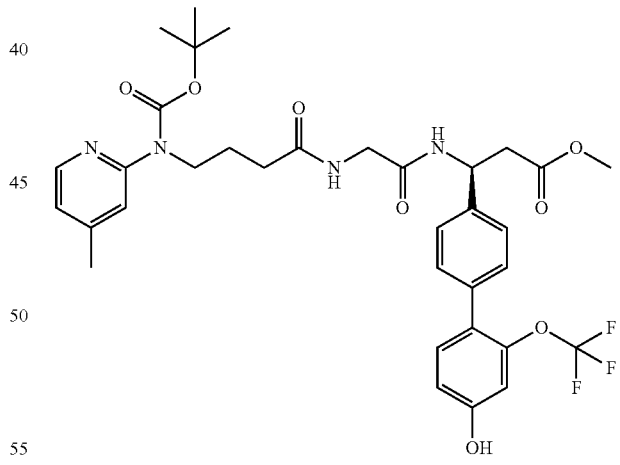

2

To a solution of compound 1 (0.19 g, 0.244 mmol, 1 equiv.) in ethyl acetate (10 mL) was added 10% Pd/C (100 mg) at room temperature. The reaction was evacuated and backfilled with hydrogen (this process was repeated for 3 times.). The reaction mixture was stirred at room temperature for overnight. The catalyst was removed by filtration through Celite® and the product was used directly without further purification. LC-MS: calculated [M+H]+ 689.27, found 689.54.

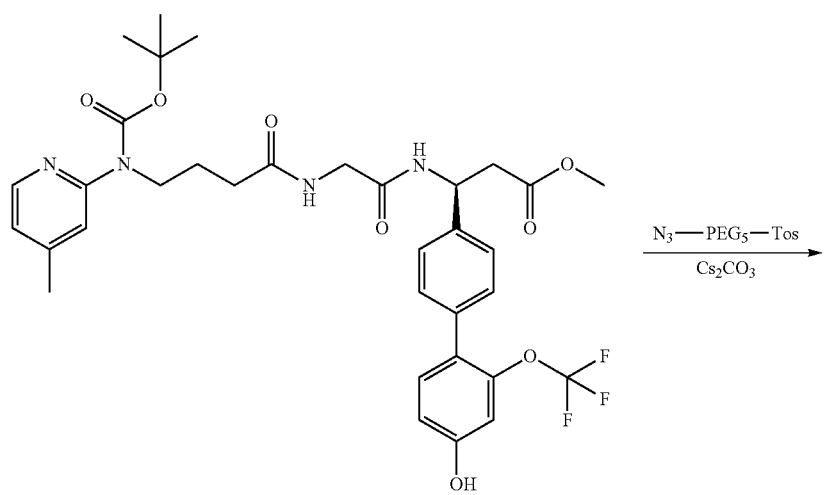

1

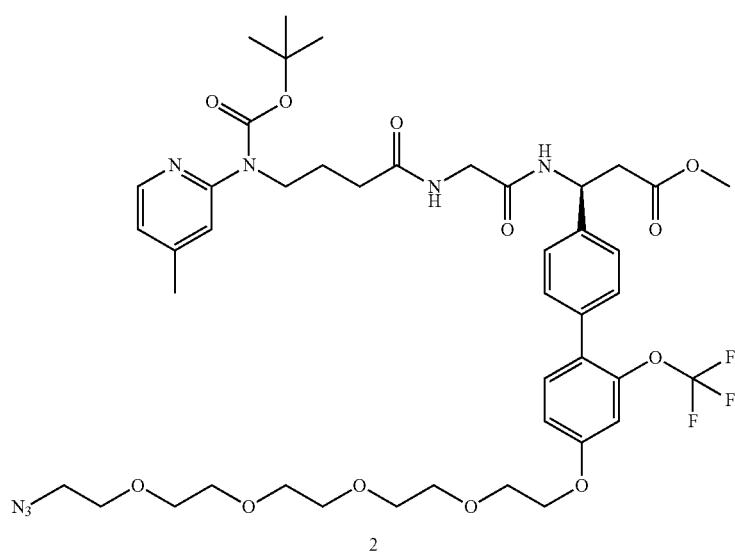

2

To a solution of compound 1 (80 mg, 0.116 mmol, 1 equiv.) an azido-PEG$_5$-OTs (97 mg, 0.232 mmol, 2 equiv.) in anhydrous DMF (2 mL) was added Cs$_2$CO$_3$ (76 mg, 0.232 mmol, 2 equiv.) at room temperature. The reaction mixture was stirred for 3 hours at 40° C. The reaction was quenched by saturated NaHCO$_3$ solution (10 mL) and the aqueous layer was extracted with ethyl acetate (3×5 mL). The organic phase was combined, dried over Na$_2$SO$_4$, and concentrated. The product was purified by CombiFlash® using silica gel as the stationary phase and was eluted with 3-4% methanol in DCM. The yield was 82%. LC-MS: calculated [M+H]+ 934.41, found 935.04.

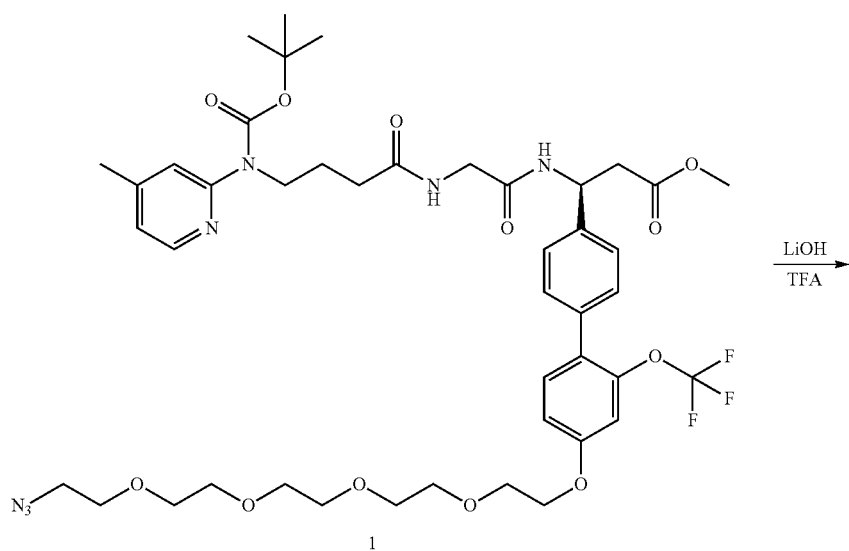

1

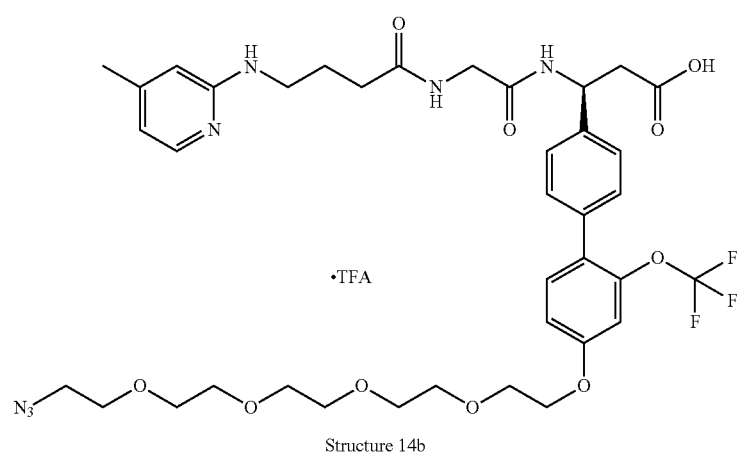

Structure 14b

To a solution of compound 1 (90 mg, 0.0964 mmol, 1.0 equiv.) in THF (2 mL) and water (2 mL) was added lithium hydroxide (7 mg, 0.289 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over $Na_2SO_4$, and concentrated. TFA (4 mL) and DCM (2 mL) was added into the residue and the mixture was stirred at room temperature for another 3 hr. The solvent was removed by rotary evaporator. LC-MS: calculated [M+H]+ 820.34, found 820.89.

235

Synthesis of Structure 15b ((S)-3-(3-(5-((14-azido-3,6,9,12-tetraoxatetradecyl)oxy)naphthalen-1-yl)phenyl)-3-(2-(4-((4-methylpyridin-2-yl)amino)butanamido)acetamido)propanoic Acid)

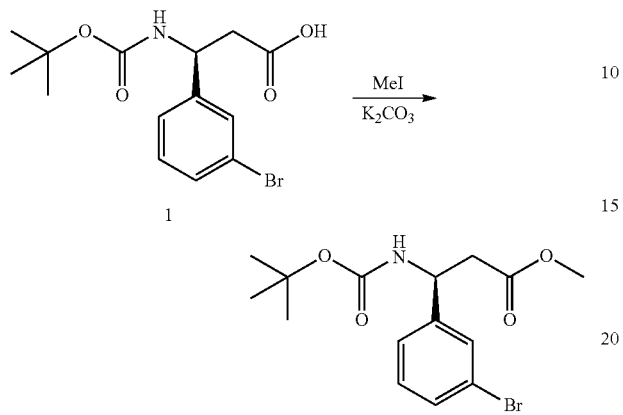

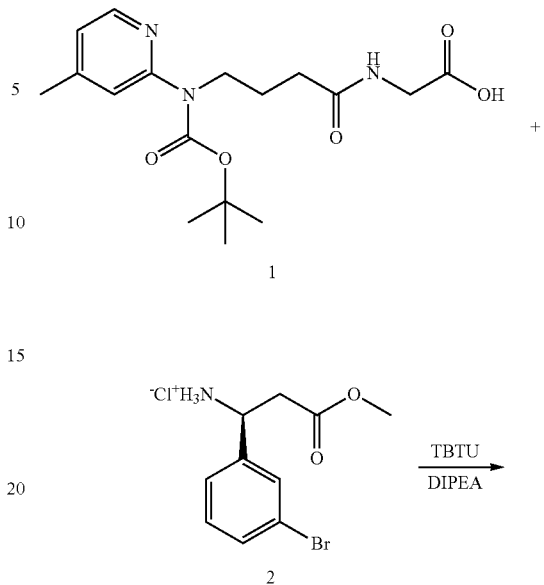

To a solution of compound 1 (1.0 g, 2.90 mmol, 1 equiv.) and potassium carbonate (0.60 g, 4.36 mmol, 1.5 equiv.) in anhydrous DMF (10 mL) was added methyl iodide (362 uL, 5.81 mmol, 2.0 equiv.) at room temperature. The reaction mixture was stirred at room temperature for 1 hr. The reaction was then quenched with water (20 mL) and the aqueous phase was extracted with ethyl acetate (3×10 mL). The organic phase was combined, dried over anhydrous $Na_2SO_4$, and concentrated. The product was separated by CombiFlash® using silica gel as the stationary phase and was eluted with 15% ethyl acetate in hexane. LC-MS: calculated [M+H]+ 358.06, found 358.18.

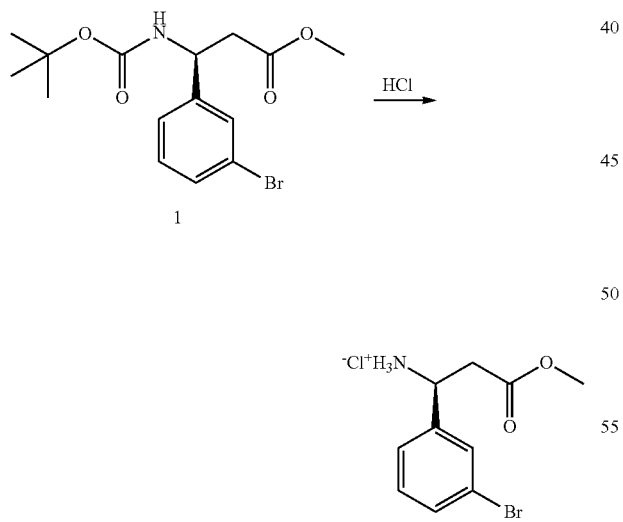

Compound 1 (858 mg, 1.677 mmol, 1.0 equiv.) was cooled by ice bath. HCl in dioxane (8.4 mL, 33.54 mmol, 20 equiv.) was added into the flask. The reaction was warmed to room temperature and stirred for another 1 hr. The solvent was removed by rotary evaporator and the product was directly used without further purification. LC-MS: calculated [M+H]+ 258.01, found 258.08.

To a solution of compound 1 (640 mg, 1.821 mmol, 1 equiv.), compound 2 (590 mg, 2.003 mmol, 1.10 equiv.), and TBTU (702 mg, 2.185 mmol, 1.20 equiv.) in anhydrous DMF (10 mL) was added diisopropylethylamine (0.952 mL, 5.464 mmol, 3 equiv.) at 0° C. The reaction mixture was warmed to room temperature and stirred for another 1 hr. The reaction was quenched by saturated $NaHCO_3$ aqueous solution (10 mL) and the product was extracted with ethyl acetate (3×10 mL). The organic phase was combined, dried over $Na_2SO_4$, and concentrated. The product was purified by CombiFlash® using silica gel as the stationary phase and was eluted with 34% methanol in DCM. LC-MS: calculated [M+H]+ 591.17, found 591.40.

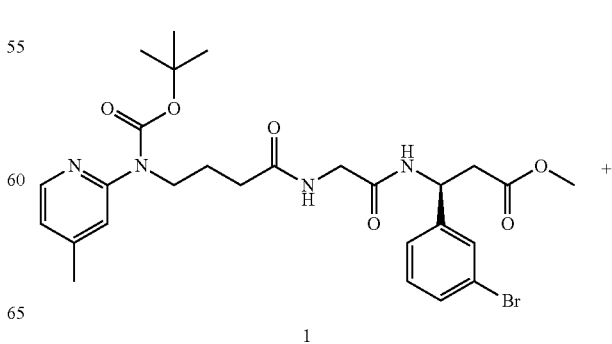

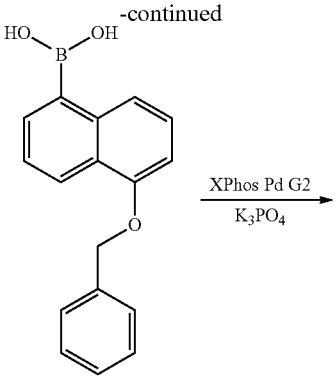

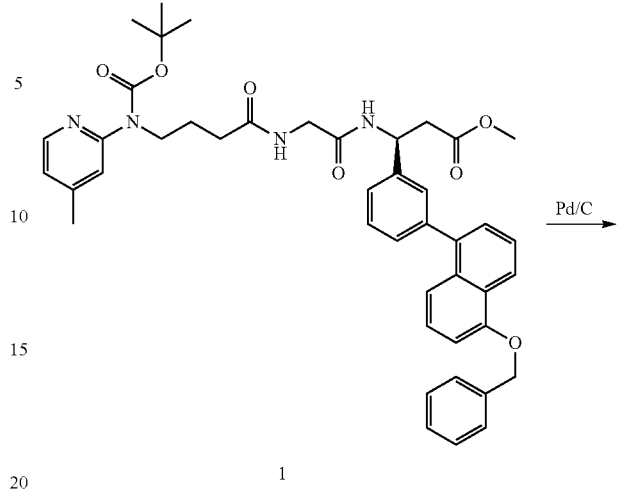

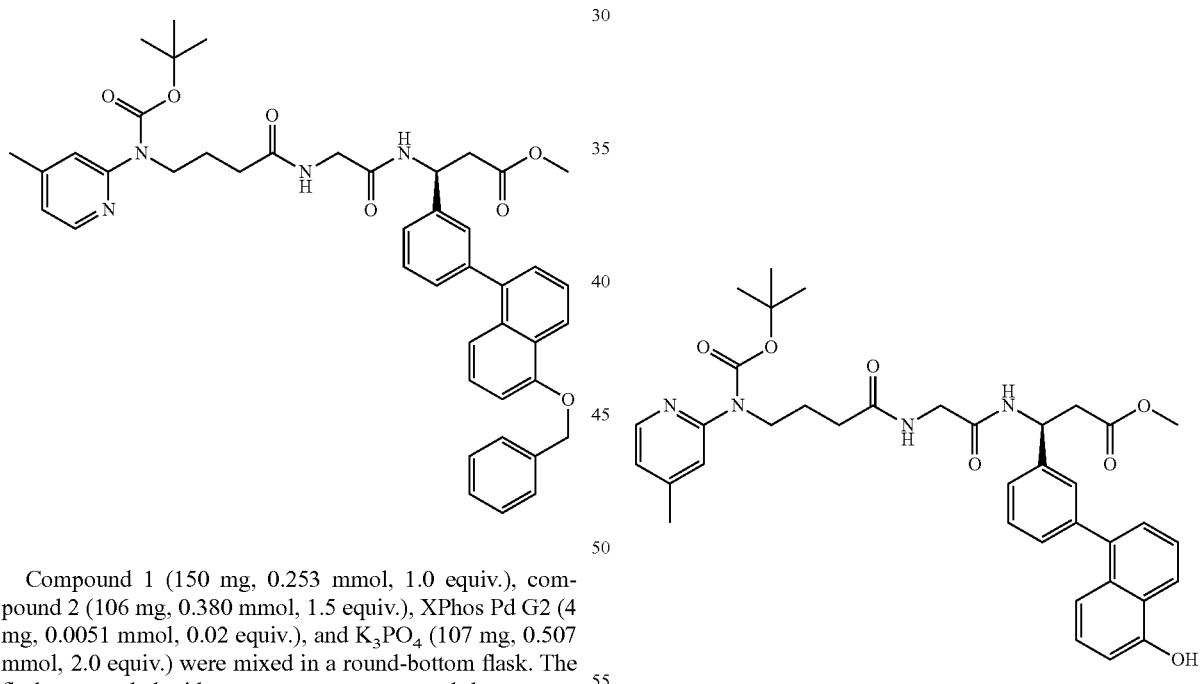

Compound 1 (150 mg, 0.253 mmol, 1.0 equiv.), compound 2 (106 mg, 0.380 mmol, 1.5 equiv.), XPhos Pd G2 (4 mg, 0.0051 mmol, 0.02 equiv.), and $K_3PO_4$ (107 mg, 0.507 mmol, 2.0 equiv.) were mixed in a round-bottom flask. The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 10 min and the reaction was kept at 40° C. for 2 hours. The reaction was quenched with water (10 mL), and the aqueous phase was extracted with ethyl acetate (3×10 mL). The organic phase was combined, dried over $Na_2SO_4$, and concentrated. The compound was separated by Combi-Flash® using silica gel as the stationary phase and was eluted with 34% methanol in DCM. LC-MS: calculated [M+H]+ 745.35, found 745.99.

To a solution of compound 1 (0.189 g, 0.253 mmol, 1 equiv.) in ethyl acetate (10 mL) was added 10% Pd/C (100 mg) at room temperature. The reaction was evacuated and backfilled with hydrogen (this process was repeated for 3 times.). The reaction mixture was stirred at room temperature for overnight. The catalyst was removed by filtration through Celite® and the product was used directly without further purification. LC-MS: calculated [M+H]+ 655.31, found 655.42.

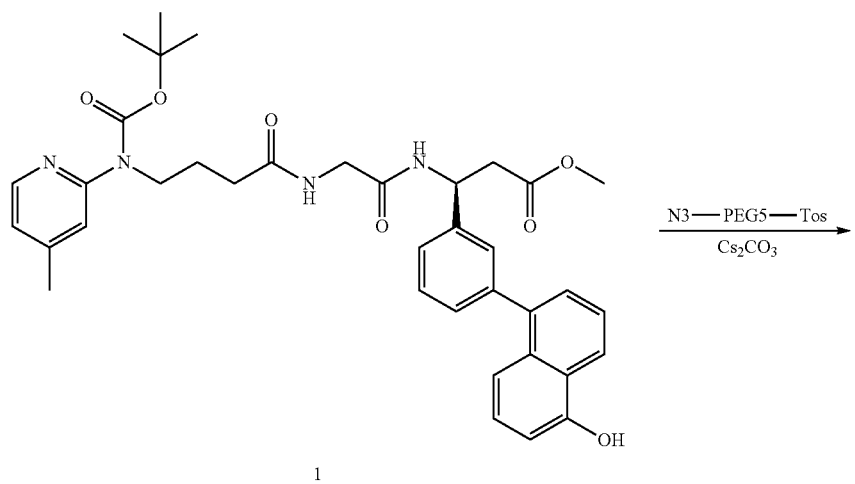

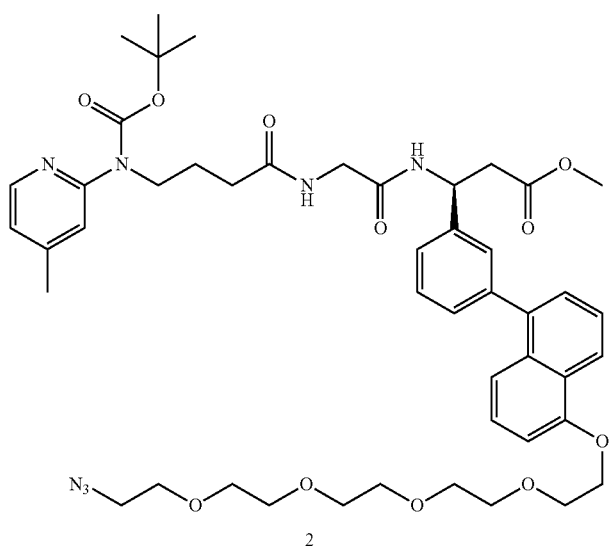

To a solution of compound 1 (80 mg, 0.122 mmol, 1 equiv.) and azido-PEG$_5$-OTs (102 mg, 0.244 mmol, 2 equiv.) in anhydrous DMF (2 mL) was added Cs$_2$CO$_3$ (80 mg, 0.244 mmol, 2 equiv.) at room temperature. The reaction mixture was stirred for 3 hours at 40° C. The reaction was quenched by saturated NaHCO$_3$ solution (10 mL) and the aqueous layer was extracted with ethyl acetate (3×5 mL). The organic phase was combined, dried over Na$_2$SO$_4$, and concentrated. The product was purified by CombiFlash® using silica gel as the stationary phase and was eluted with 1-2% methanol in DCM. The yield is 90%. LC-MS: calculated 900.44, found 901.10.

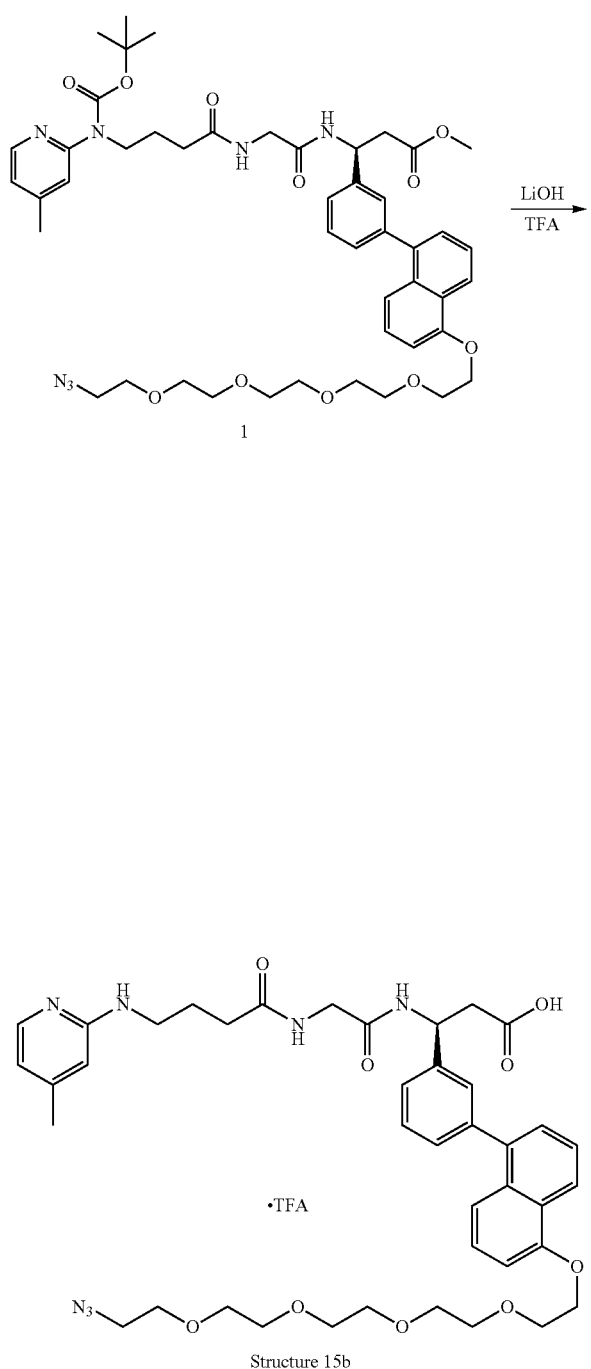

Structure 15b

To a solution of compound 1 (100 mg, 0.111 mmol, 1.0 equiv.) in THF (2 mL) and water (2 mL) was added lithium hydroxide (8 mg, 0.333 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over $Na_2SO_4$, and concentrated. TFA (4 mL) and DCM (2 mL) was added into the residue and the mixture was stirred at room temperature for another 3 hr. The solvent was removed by rotary evaporator. LC-MS: calculated [M+H]+ 786.37, found 786.95.

Synthesis of Structure 16b ((S)-3-(4-(4-((14-azido-3,6,9,12-tetraoxatetradecyl)oxy)naphthalen-1-yl)phenyl)-3-((R)-1-(4-((4-methylpyridin-2-yl)amino)butanoyl)pyrrolidine-2-carboxamido)propanoic Acid)

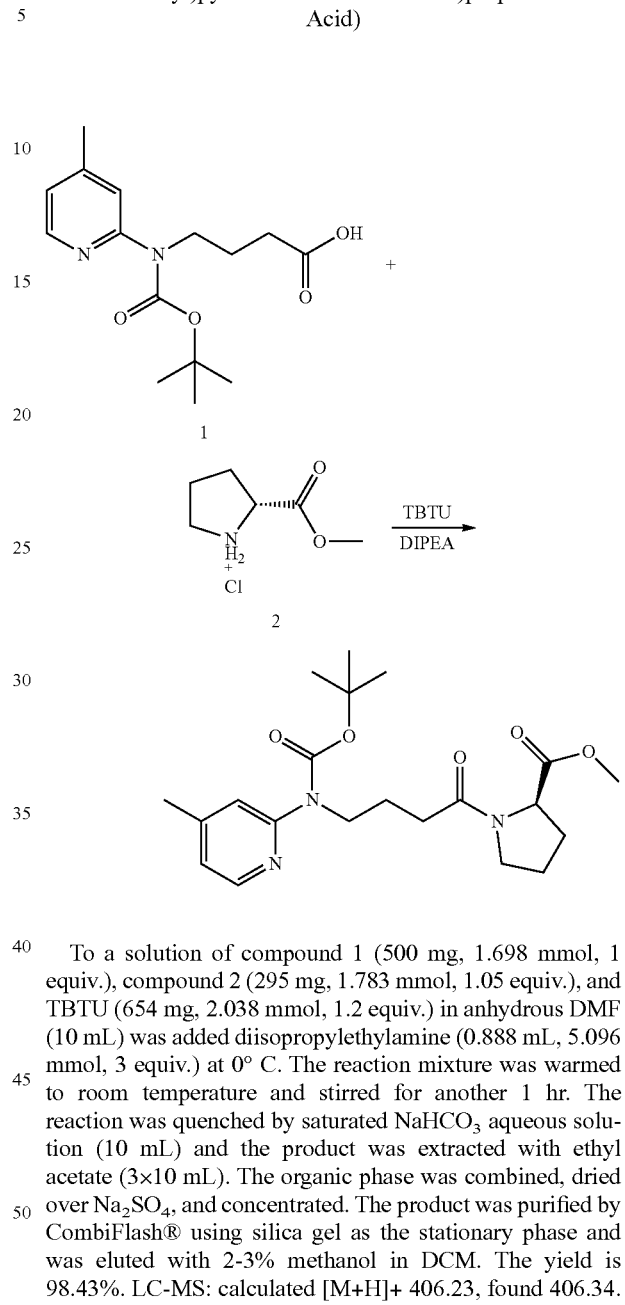

To a solution of compound 1 (500 mg, 1.698 mmol, 1 equiv.), compound 2 (295 mg, 1.783 mmol, 1.05 equiv.), and TBTU (654 mg, 2.038 mmol, 1.2 equiv.) in anhydrous DMF (10 mL) was added diisopropylethylamine (0.888 mL, 5.096 mmol, 3 equiv.) at 0° C. The reaction mixture was warmed to room temperature and stirred for another 1 hr. The reaction was quenched by saturated $NaHCO_3$ aqueous solution (10 mL) and the product was extracted with ethyl acetate (3×10 mL). The organic phase was combined, dried over $Na_2SO_4$, and concentrated. The product was purified by CombiFlash® using silica gel as the stationary phase and was eluted with 2-3% methanol in DCM. The yield is 98.43%. LC-MS: calculated [M+H]+ 406.23, found 406.34.

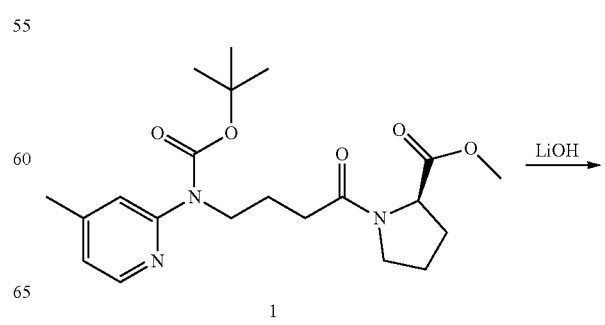

243

-continued

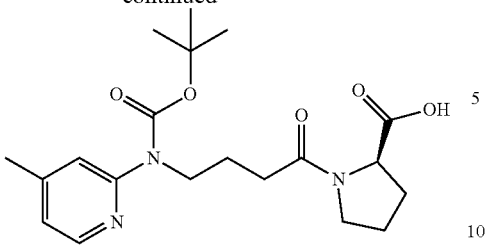

To a solution of compound 1 (0.678 g, 1.672 mmol, 1 equiv.) in THF (10 mL) and H₂O (10 mL) was added lithium hydroxide (0.12 g, 5.016 mmol, 3 equiv.) portion-wise at 0° C. The reaction mixture was warmed to room temperature. After stirring at room temperature for 1 hr, the reaction mixture was acidified by HCl (6 N) to pH 3.0. The aqueous phase was extracted with ethyl acetate (3×10 mL) and the organic layer was combined, dried over Na₂SO₄, and concentrated. The product was used without further purification. LC-MS: calculated [M+H]+ 392.21, found 392.39.

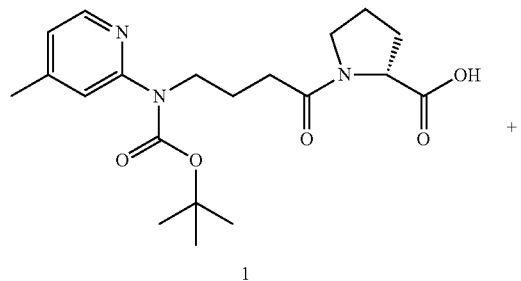

1

244

-continued

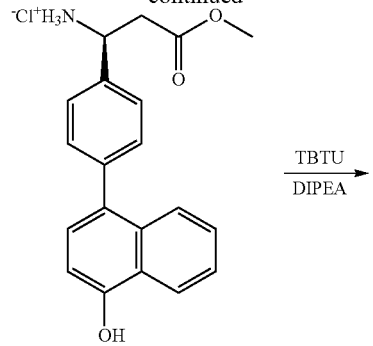

2

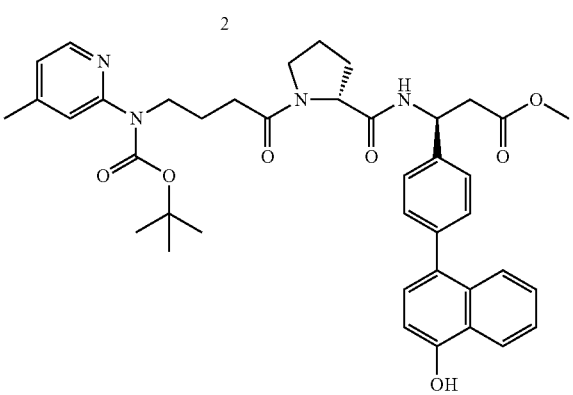

To a solution of compound 1 (130 mg, 0.332 mmol, 1 equiv.), compound 2 (125 mg, 0.348 mmol, 1.05 equiv.), and TBTU (128 mg, 0.398 mmol, 1.2 equiv.) in anhydrous DMF (5 mL) was added diisopropylethylamine (0.174 mL, 0.996 mmol, 3 equiv.) at 0° C. The reaction mixture was warmed to room temperature and stirred for another 1 hr. The reaction was quenched by saturated NaHCO₃ aqueous solution (10 mL) and the product was extracted with ethyl acetate (3×10 mL). The organic phase was combined, dried over Na₂SO₄, and concentrated. The product was purified by CombiFlash® using silica gel as the stationary phase and was eluted with 34% methanol in DCM. The yield is 86%. LC-MS: calculated [M+H]+ 695.34, found 695.93.

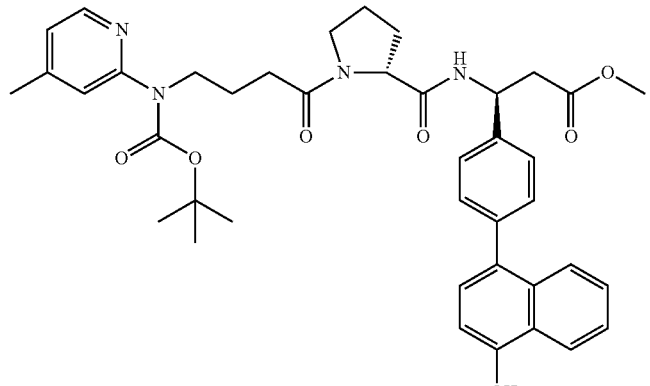

1

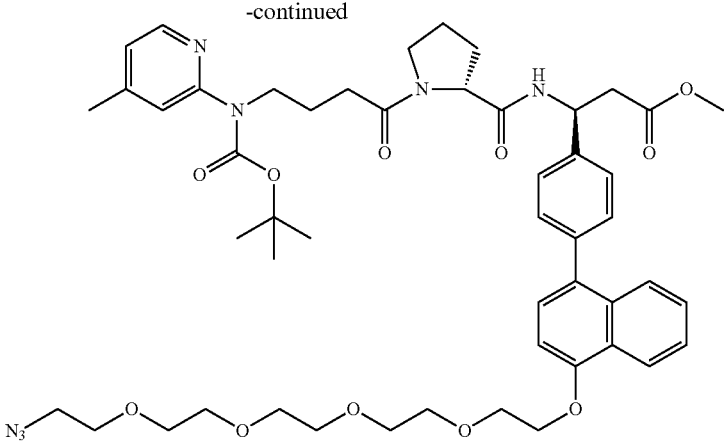

2

To a solution of compound 1 (80 mg, 0.115 mmol, 1 equiv.) and azido-PEG5-OTs (96 mg, 0.230 mmol, 2 equiv.) in anhydrous DMF (2 mL) was added $Cs_2CO_3$ (75 mg, 0.230 mmol, 2 equiv.) at room temperature. The reaction mixture was stirred for 3 hours at 40° C. The reaction was quenched by saturated $NaHCO_3$ solution (10 mL) and the aqueous layer was extracted with ethyl acetate (3×10 mL). The organic phase was combined, dried over $Na_2SO_4$, and concentrated. The product was purified by CombiFlash® using silica gel as the stationary phase and was eluted with 4-5% methanol in DCM. The yield is 60%.

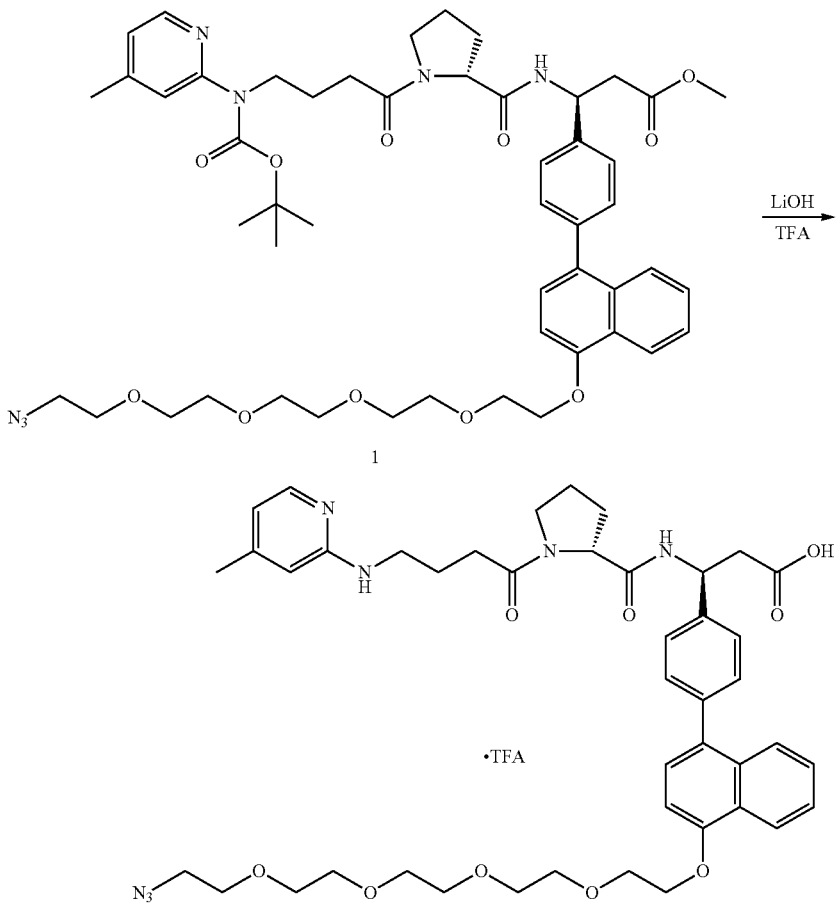

Structure 16b

To a solution of compound 1 (65 mg, 0.0691 mmol, 1.0 equiv.) in THF (2 mL) and water (2 mL) was added lithium hydroxide (5 mg, 0.207 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over Na₂SO₄, and concentrated. TFA (4 mL) and DCM (2 mL) was added into the residue and the mixture was stirred at room temperature for another 3 hr. The solvent was removed by rotary evaporator. LC-MS: calculated [M+H]+ 826.41, found 827.01.

Synthesis of Structure 17b ((S)-3-(4-(7-((14-azido-3,6,9,12-tetraoxatetradecyl)oxy)benzo[b]thiophen-4-yl)phenyl)-3-(2-(4-((4-methylpyridin-2-yl)amino)butanamido)acetamido)propanoic Acid)

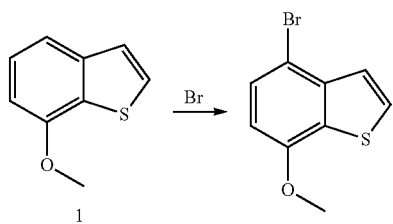

A solution of bromine (1.877 g, 11.745 mmol, 1.05 equiv.) in dry tetrachloromethane (20 mL) was added dropwise during 1.5 hours to a stirred solution of compound 1 (1.837 g, 11.186 mmol, 1 equiv.) in tetrachloromethane (20 mL) at 0° C. After a further hour at 0° C., the organic layer was washed with water and brine, dried over Na₂SO₄, concentrated to give a residue, which was purified by CombiFlash® using silica gel as the stationary phase. The product was eluted with pure hexane with impurities.

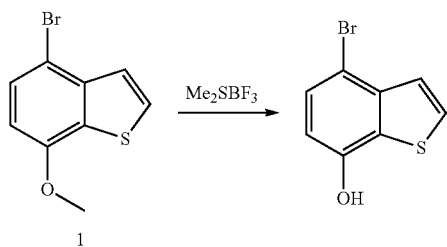

To a dichloromethane (20 ml) solution of compound 1 (2.70 g, 11.105 mmol, 1.0 equiv.), under nitrogen atmosphere, at 0° C., boron trifluoride dimethyl sulfide complex (3.5 mL, 33.317 mmol, 3.0 equiv.) was added and stirred at room temperature for 20 hours. The reaction mixture was cooled to 0° C. and quenched with saturated NH₄Cl solution (20 mL). The aqueous phase was extracted with ethyl acetate (3×20 mL) and the organic phase was combined, dried over Na₂SO₄, and concentrated. The product was separated by CombiFlash® using silica gel as the stationary phase and was eluted with 5% ethyl acetate in hexane. LC-MS: calculated [M−H]− 226.92, found 227.03.

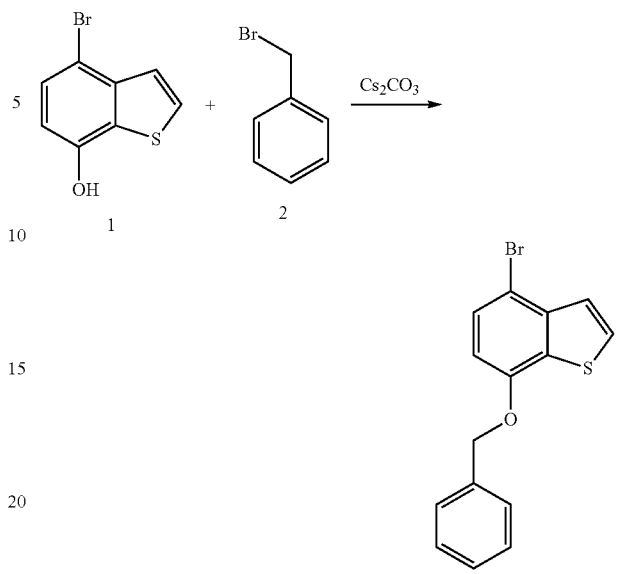

To a solution of compound 1 (1.838 g, 8.023 mmol, 1 equiv.), and compound 2 (1.906 mL, 16.04 mmol, 2 equiv.) in anhydrous DMF (10 mL) was added Cs₂CO₃ (5.228 g, 16.04 mmol, 2 equiv.) at room temperature. The reaction mixture was stirred at room temperature overnight. The reaction was quenched by water (20 mL) and the aqueous phase was extracted with ethyl acetate (3×10 mL). The organic phase was combined, dried over Na₂SO₄, and concentrated. The product was separated by CombiFlash® using silica gel as the stationary phase and was eluted with 2-3% ethyl acetate in hexane.

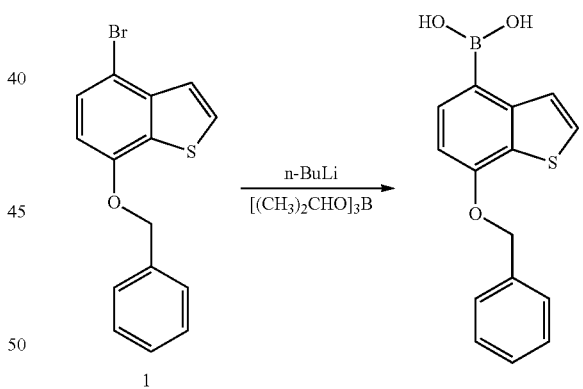

To a solution of compound 1 (2.22 g, 6.954 mmol, 1.0 equiv.) in anhydrous THF (20 mL) was added n-BuLi in hexane (4.17 mL, 10.43 mmol, 1.5 equiv.) drop-wise at −78° C. The reaction was kept at −78° C. for another 1 hr. Triisopropylborate (2.40 mL, 10.43 mmol, 1.5 equiv.) was then added into the mixture at −78° C. The reaction was then warmed up to room temperature and stirred for another 1 hr. The reaction was quenched by saturated NH₄Cl solution (20 mL) and the pH was adjusted to 3. The aqueous phase was extracted with EtOAc (3×20 mL) and the organic phase was combined, dried over Na₂SO₄, and concentrated. The product was separated by CombiFlash® using silica gel as the stationary phase and was eluted with 4-6% methanol in DCM. LC-MS: calculated [M−H]− 283.07, found 283.20.

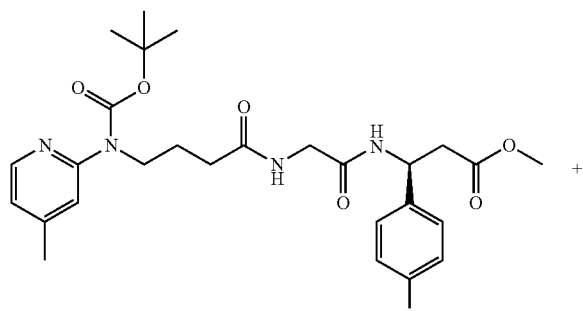

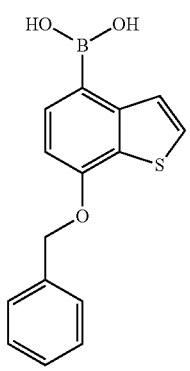

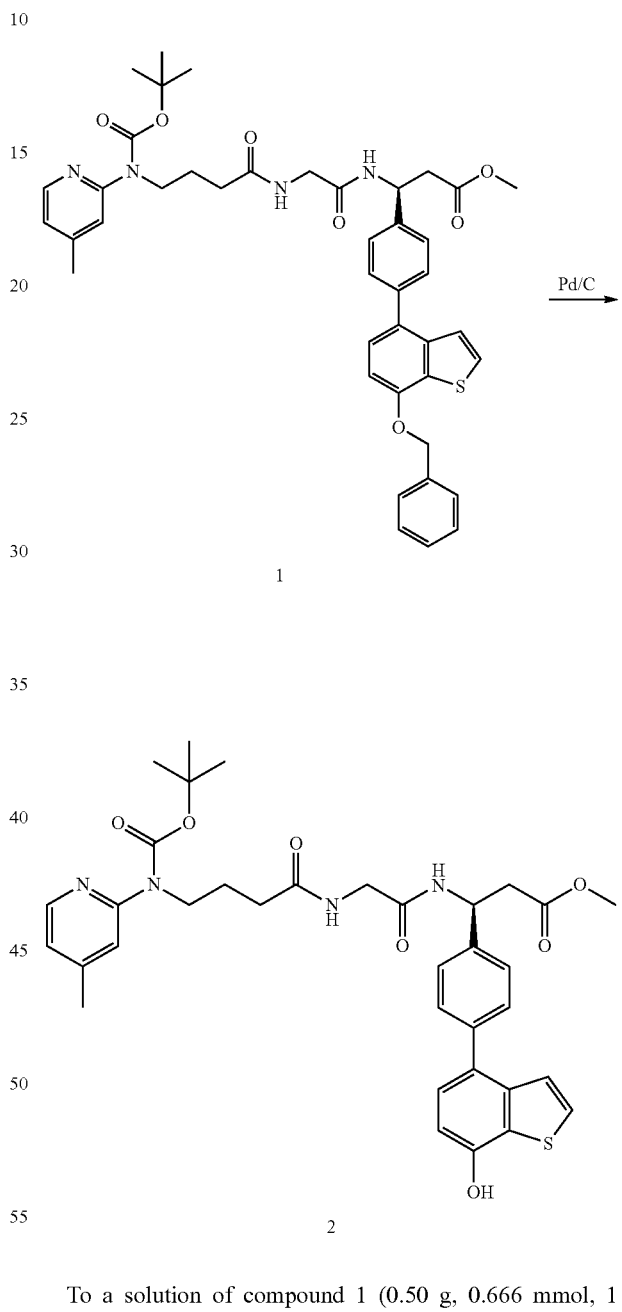

Compound 1 (400 mg, 0.676 mmol, 1.0 equiv.), compound 2 (288 mg, 1.01 mmol, 1.5 equiv.), XPhos Pd G2 (10 mg, 0.0135 mmol, 0.02 equiv.), and K₃PO₄ (287 mg, 1.352 mmol, 2.0 equiv.) were mixed in a round-bottom flask. The flask was sealed with a screw-cap septum, and then evacuated and backfilled with nitrogen (this process was repeated a total of 3 times). Then, THF (8 mL) and water (2 mL) were added via syringe. The mixture was bubbled with nitrogen for 10 min and the reaction was kept at 40° C. for 2 hours. The reaction was quenched with saturated NaHCO₃ solution (10 mL), and the aqueous phase was extracted with ethyl acetate (3×10 mL). The organic phase was combined, dried over Na₂SO₄, and concentrated. The compound was separated by CombiFlash® using silica gel as the stationary phase and was eluted with 34% methanol in DCM. LC-MS: calculated [M+H]+ 751.31, found 751.84.

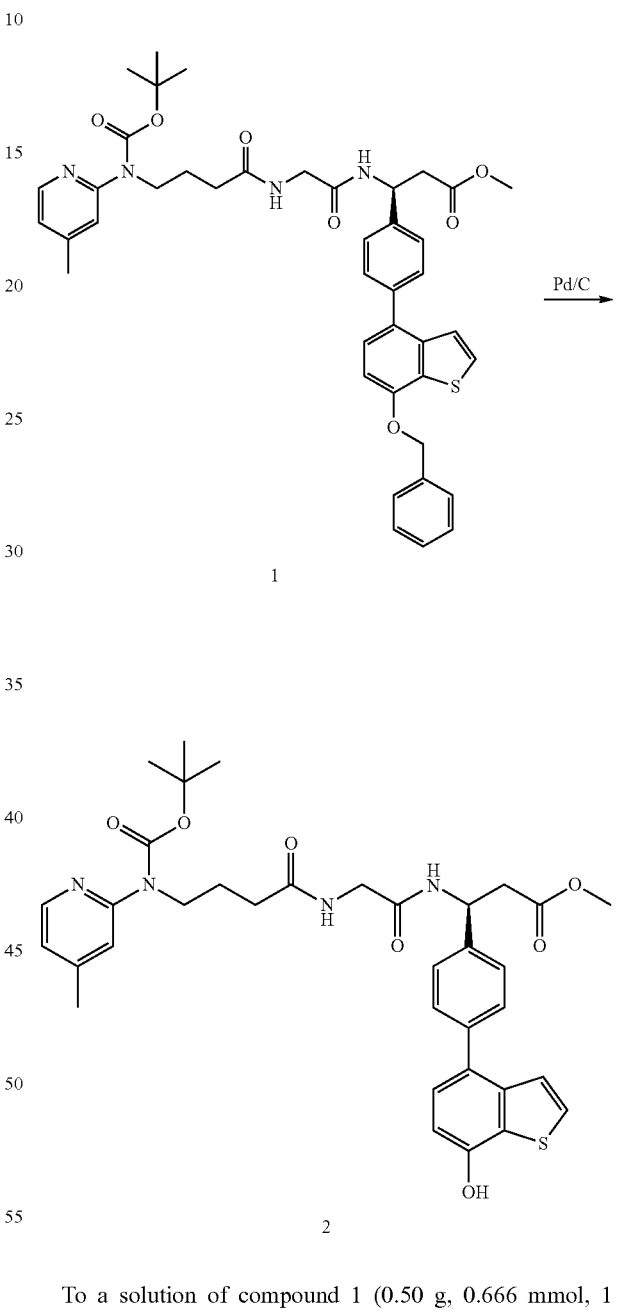

To a solution of compound 1 (0.50 g, 0.666 mmol, 1 equiv.) in ethyl acetate (10 mL) was added 10% Pd/C (100 mg) at room temperature. The reaction was evacuated and backfilled with hydrogen (this process was repeated for 3 times.). The reaction mixture was stirred at room temperature for overnight. The catalyst was removed by filtration through Celite® and the product was separated by CombiFlash® using silica gel as the stationary phase and was eluted with 5% methanol in DCM. LC-MS: calculated [M+H]+ 661.26, found 661.73.

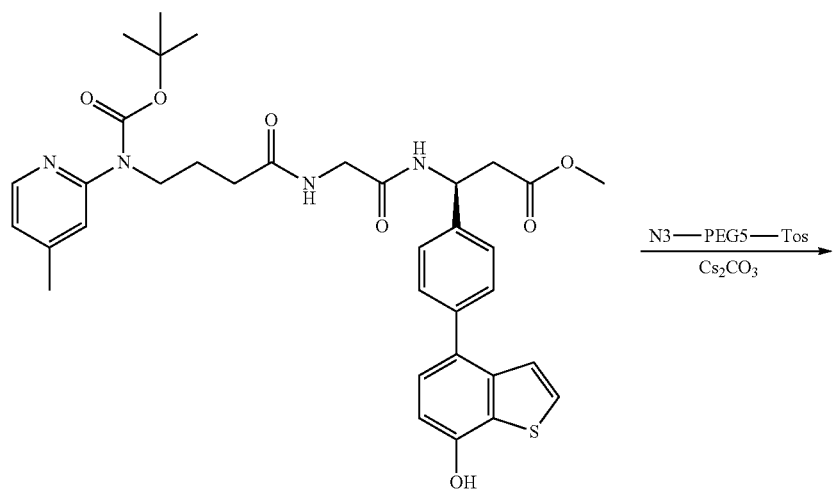

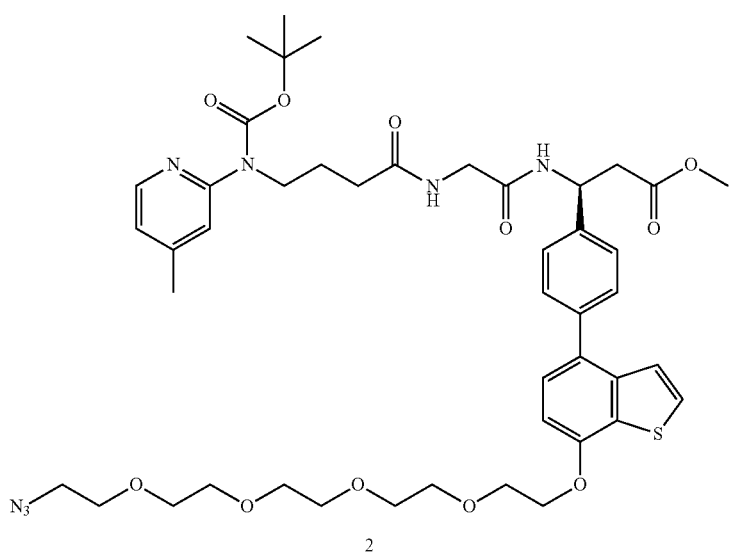

To a solution of compound 1 (130 mg, 0.196 mmol, 1 equiv.) and azido-PEG5-OTs (164 mg, 0.393 mmol, 2 equiv.) in anhydrous DMF (2 mL) was added Cs$_2$CO$_3$ (128 mg, 0.393 mmol, 2 equiv.) at room temperature. The reaction mixture was stirred for 3 hours at 40° C. The reaction was quenched by saturated NaHCO$_3$ solution (10 mL) and the aqueous layer was extracted with ethyl acetate (3×5 mL). The organic phase was combined, dried over Na$_2$SO$_4$, and concentrated. The product was purified by CombiFlash® using silica gel as the stationary phase and was eluted with 3-4% methanol in DCM. The yield is 82%. LC-MS: calculated [M+H]+ 906.40, found 906.95.

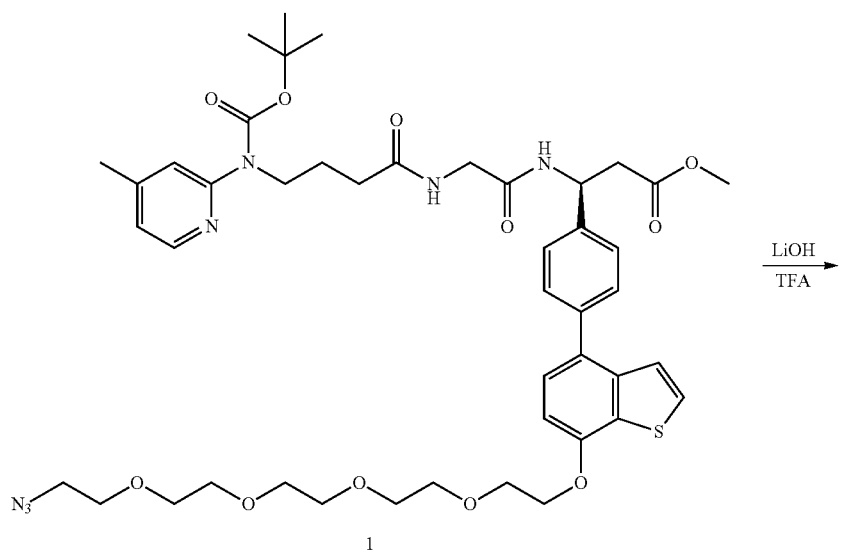

1

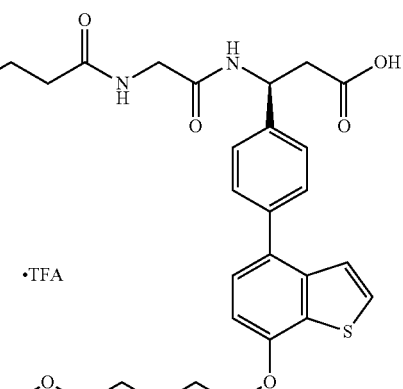

Structure 17b

To a solution of compound 1 (147 mg, 0.162 mmol, 1.0 equiv.) in THF (2 mL) and water (2 mL) was added lithium hydroxide (12 mg, 0.486 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over $Na_2SO_4$, and concentrated. TFA (2 mL) and DCM (2 mL) was added into the residue and the mixture was stirred at room temperature for another 3 hr. The solvent was removed by rotary evaporator and the product was separated by CombiFlash® using silica gel as the stationary phase. LC-MS: calculated [M+H]+ 792.33, found 792.89.

Synthesis of Structure 18b ((S)-3-(4-(6-((14-azido-3,6,9,12-tetraoxatetradecyl)oxy)naphthalen-2-yl)phenyl)-3-(2-(4-((4-methylpyridin-2-yl)amino)butanamido)acetamido)propanoic Acid)

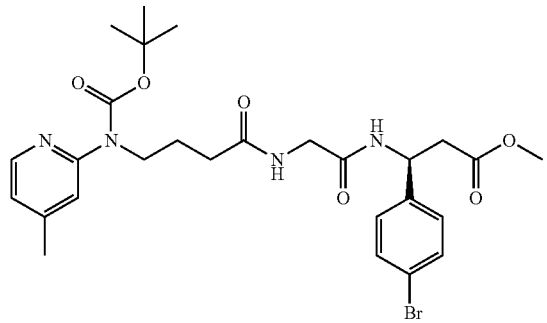

1

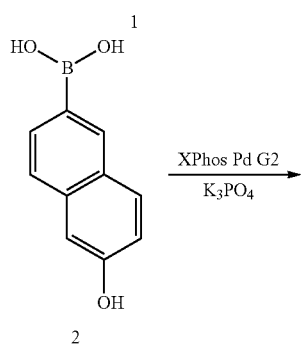

2

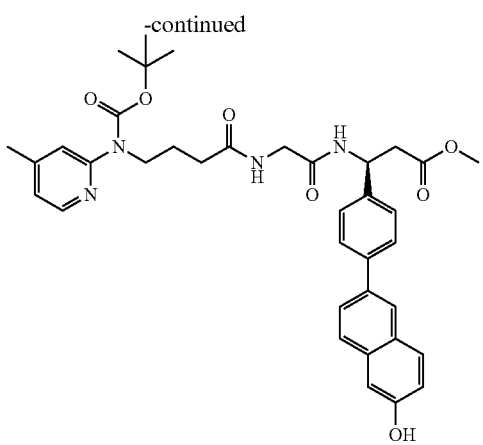

Compound 1 (150 mg, 0.253 mmol, 1.0 equiv.), compound 2 (71.5 mg, 0.380 mmol, 1.5 equiv.), XPhos Pd G2 (4 mg, 0.0051 mmol, 0.02 equiv.), and $K_3PO_4$ (107 mg, 0.507 mmol, 2.0 equiv.) were mixed in a round-bottom flask. The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 10 min and the reaction was kept at 40° C. for 2 hours. The reaction was quenched with water (10 mL), and the aqueous phase was extracted with ethyl acetate (3×10 mL). The organic phase was combined, dried over $Na_2SO_4$, and concentrated. The compound was separated by Combi-Flash® using silica gel as the stationary phase and was eluted with 2-3% methanol in DCM. LC-MS: calculated [M+H]+ 655.31, found 655.87.

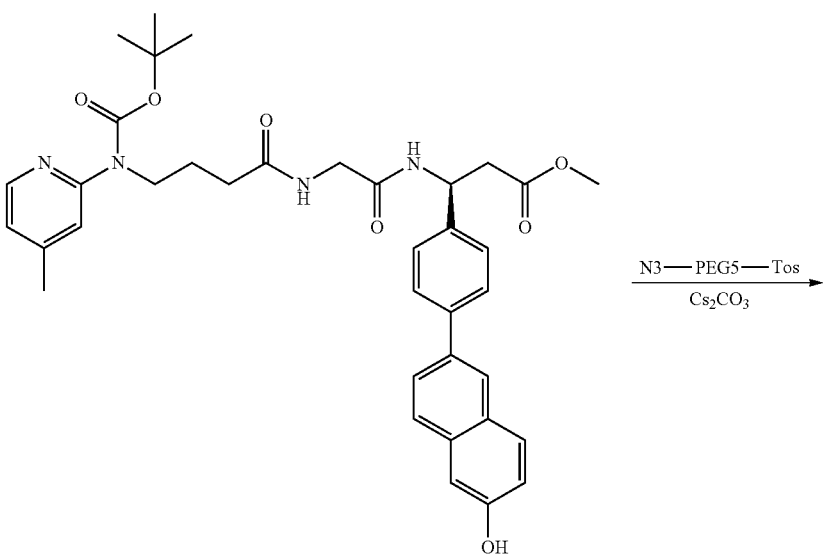

1

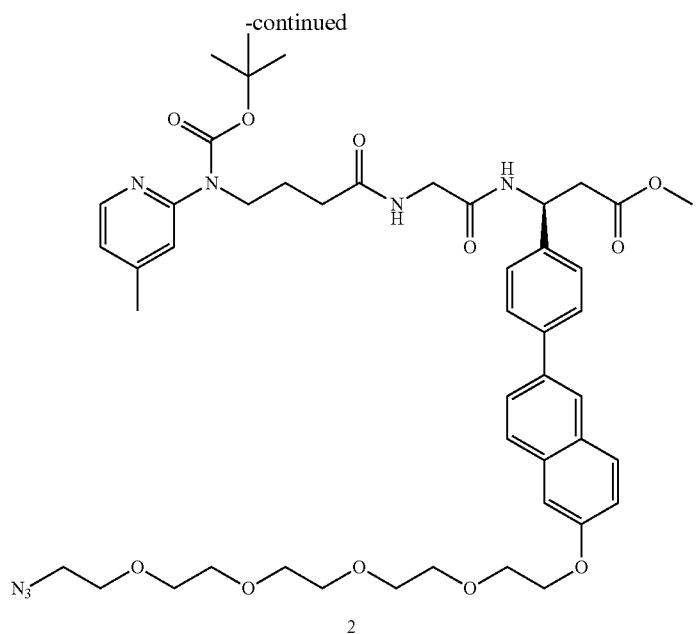

2

To a solution of compound 1 (160 mg, 0.244 mmol, 1 equiv.) and azido-PEG5-OTs (204 mg, 0.488 mmol, 2 equiv.) in anhydrous DMF (2 mL) was added $Cs_2CO_3$ (160 mg, 0.488 mmol, 2 equiv.) at room temperature. The reaction mixture was stirred for 3 hours at 60° C. The reaction was quenched by saturated $NaHCO_3$ solution (10 mL) and the aqueous layer was extracted with ethyl acetate (3×5 mL). The organic phase was combined, dried over $Na_2SO_4$, and concentrated. The product was purified by CombiFlash® using silica gel as the stationary phase and was eluted with 3-4% methanol in DCM. The yield was 30%. LC-MS: calculated [M+H]+ 900.44, found 901.01.

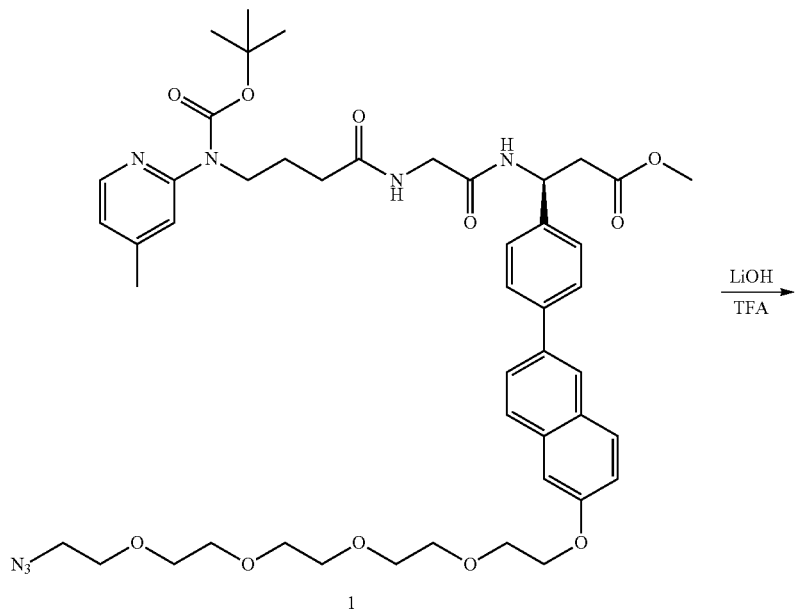

1

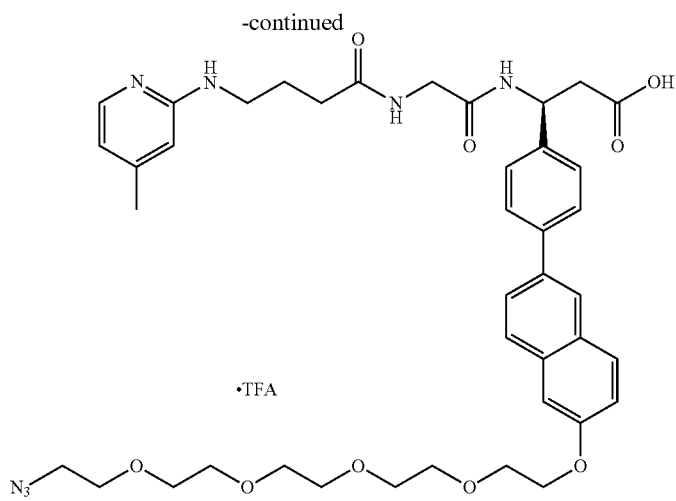

To a solution of compound 1 (67 mg, 0.0744 mmol, 1.0 equiv.) in THF (2 mL) and water (2 mL) was added lithium hydroxide (5 mg, 0.223 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over Na$_2$SO$_4$, and concentrated. TFA (2 mL) and DCM (2 mL) was added into the residue and the mixture was stirred at room temperature for another 3 hr. The solvent was removed by rotary evaporator and the product was separated by CombiFlash® using silica gel as the stationary phase and eluted with 10% methanol in DCM. LC-MS: calculated [M+H]+ 786.37, found 786.86.

Synthesis of Structure 19b ((S)-3-(3-(6-((14-azido-3,6,9,12-tetraoxatetradecyl)oxy)naphthalen-2-yl)phenyl)-3-(2-(4-((4-methylpyridin-2-yl)amino)butanamido)acetamido)propanoic Acid)

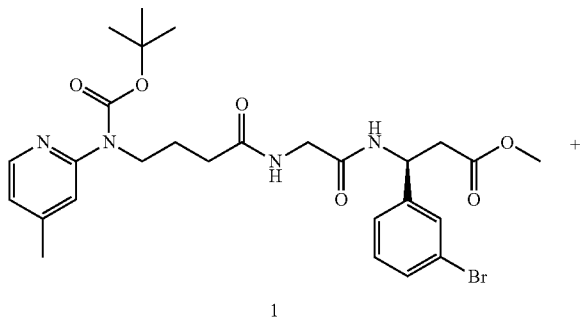

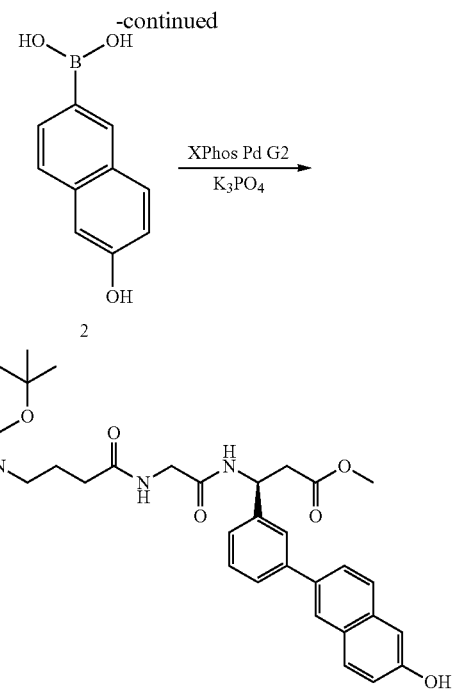

Compound 1 (150 mg, 0.253 mmol, 1.0 equiv.), compound 2 (71.5 mg, 0.380 mmol, 1.5 equiv.), XPhos Pd G2 (4 mg, 0.0051 mmol, 0.02 equiv.), and K$_3$PO$_4$ (107 mg, 0.507 mmol, 2.0 equiv.) were mixed in a round-bottom flask. The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 10 min and the reaction was kept at 40° C. for 2 hours. The reaction was quenched with water (10 mL), and the aqueous phase was extracted with ethyl acetate (3×10 mL). The organic phase was combined, dried over Na$_2$SO$_4$, and concentrated. The compound was separated by CombiFlash® using silica gel as the stationary phase and was eluted with 2-3% methanol in DCM. LC-MS: calculated [M+H]+ 655.31, found 655.78.

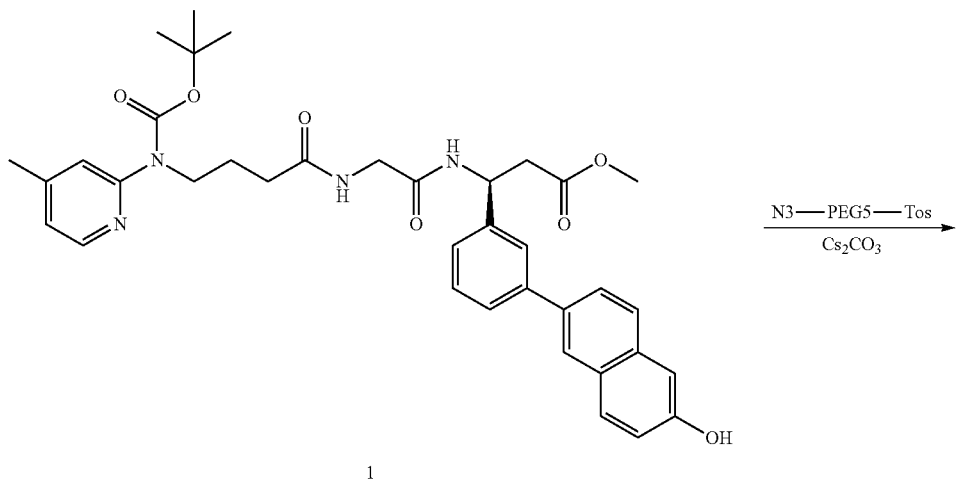

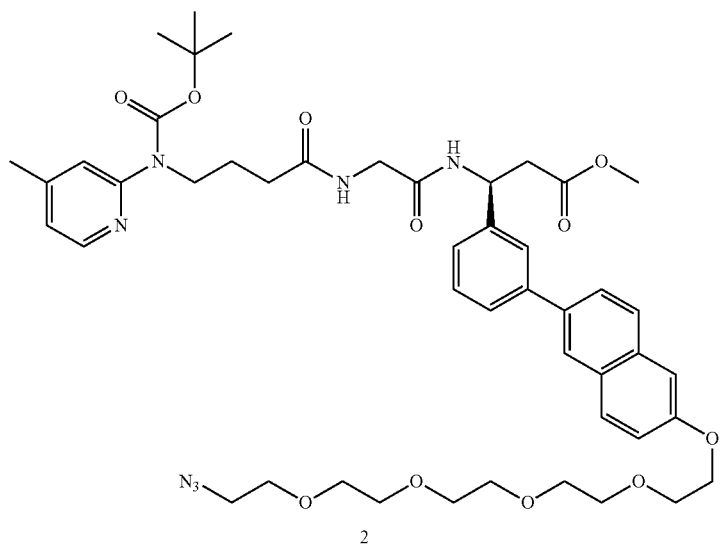

To a solution of compound 1 (104 mg, 0.158 mmol, 1 equiv.) and azido-PEG$_5$-OTs (132 mg, 0.317 mmol, 2 equiv.) in anhydrous DMF (2 mL) was added Cs$_2$CO$_3$ (103 mg, 0.317 mmol, 2 equiv.) at room temperature. The reaction mixture was stirred for 3 hours at 60° C. The reaction was quenched by saturated NaHCO$_3$ solution (10 mL) and the aqueous layer was extracted with ethyl acetate (3×5 mL). The organic phase was combined, dried over Na$_2$SO$_4$, and concentrated. The product was purified by CombiFlash® using silica gel as the stationary phase and was eluted with 3-4% methanol in DCM. LC-MS: calculated [M+H]+ 900.44, found 901.01.

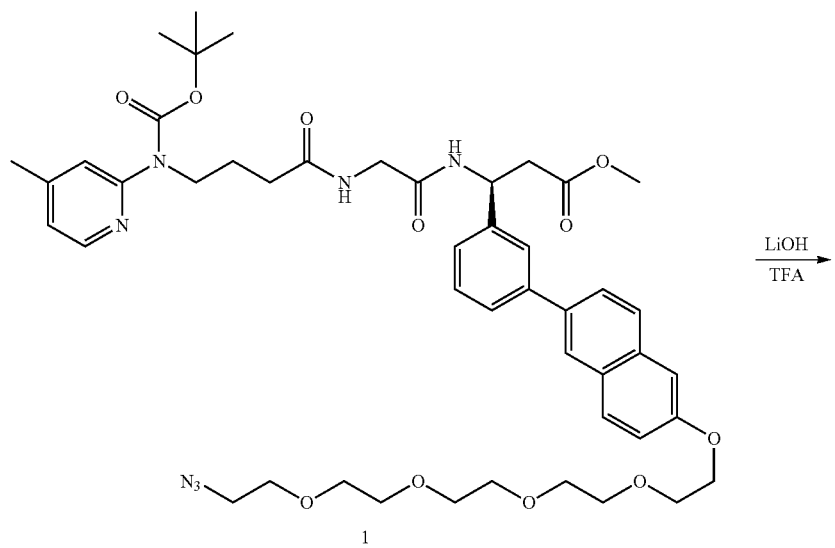

1

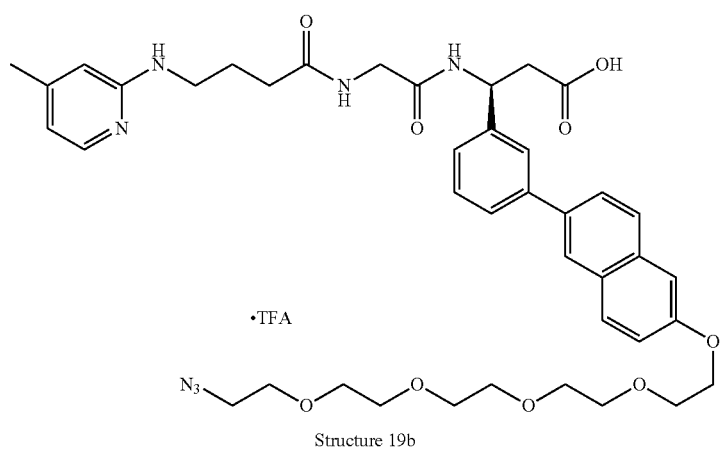

Structure 19b

To a solution of compound 1 (125 mg, 0.138 mmol, 1.0 equiv.) in THF (2 mL) and water (2 mL) was added lithium hydroxide (10 mg, 0.416 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over $Na_2SO_4$, and concentrated. TFA (4 mL) and DCM (2 mL) was added into the residue and the mixture was stirred at room temperature for another 3 hr. The solvent was removed by rotary evaporator and the product was separated by CombiFlash® using silica gel as the stationary phase and eluted with 12% methanol in DCM. LC-MS: calculated [M+H]+ 786.37, found 786.86.

265

Synthesis of Structure 20b ((S)-3-(3-(4-((14-azido-3,6,9,12-tetraoxatetradecyl)oxy)naphthalen-1-yl)phenyl)-3-(2-(4-((4-methylpyridin-2-yl)amino)butanamido)acetamido)propanoic Acid)

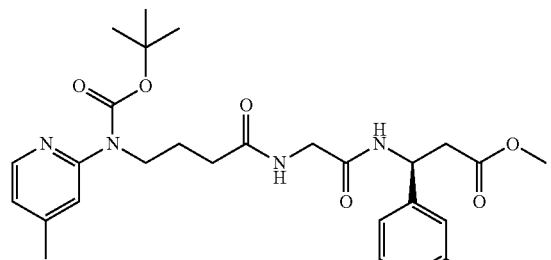

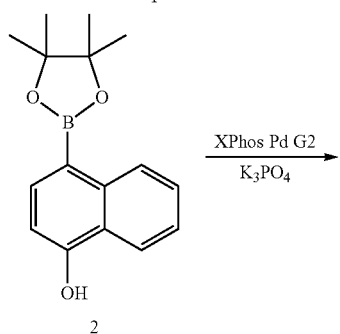

266

-continued

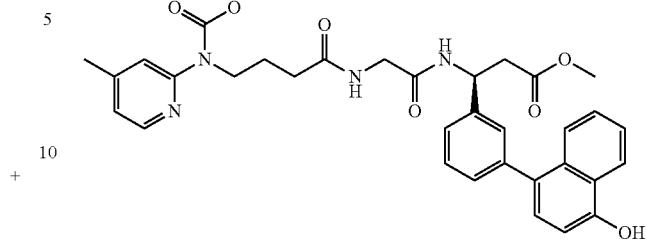

Compound 1 (150 mg, 0.253 mmol, 1.0 equiv.), compound 2 (102 mg, 0.380 mmol, 1.5 equiv.), XPhos Pd G2 (4 mg, 0.0051 mmol, 0.02 equiv.), and K$_3$PO$_4$ (107 mg, 0.507 mmol, 2.0 equiv.) were mixed in a round-bottom flask. The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 10 min and the reaction was kept at 40° C. for 2 hours. The reaction was quenched with water (10 mL), and the aqueous phase was extracted with ethyl acetate (3×10 mL). The organic phase was combined, dried over Na$_2$SO$_4$, and concentrated. The compound was separated by Combi-Flash® using silica gel as the stationary phase and was eluted with 2-3% methanol in DCM. LC-MS: calculated [M+H]+ 655.31, found 655.78.

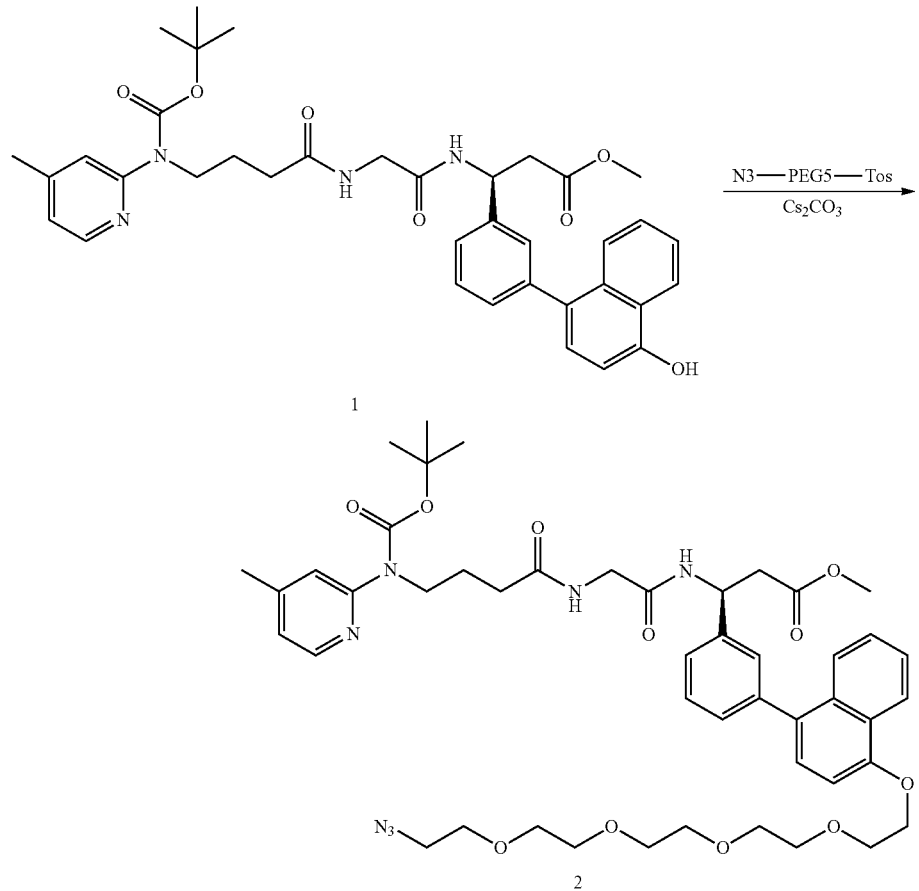

To a solution of compound 1 (160 mg, 0.244 mmol, 1 equiv.) and azido-PEG$_5$-OTs (204 mg, 0.488 mmol, 2 equiv.) in anhydrous DMF (2 mL) was added Cs$_2$CO$_3$ (159 mg, 0.488 mmol, 2 equiv.) at room temperature. The reaction mixture was stirred for 3 hours at 60° C. The reaction was quenched by saturated NaHCO$_3$ solution (10 mL) and the aqueous layer was extracted with ethyl acetate (3×5 mL). The organic phase was combined, dried over Na$_2$SO$_4$, and concentrated. The product was purified by CombiFlash® using silica gel as the stationary phase and was eluted with 3-4% methanol in DCM. LC-MS: calculated [M+H]+ 900.44, found 901.01.

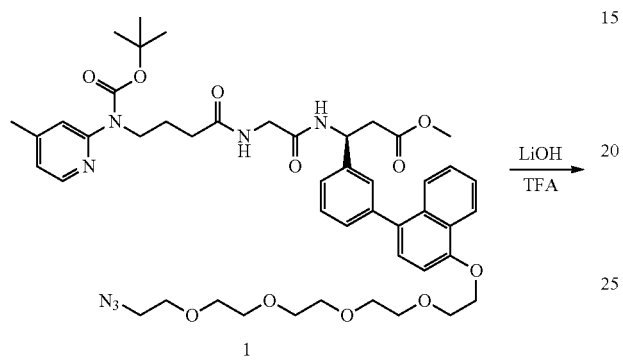

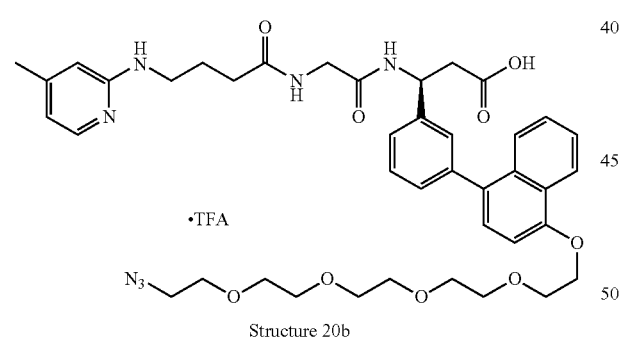

Structure 20b

To a solution of compound 1 (125 mg, 0.138 mmol, 1.0 equiv.) in THF (2 mL) and water (2 mL) was added lithium hydroxide (10 mg, 0.416 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over Na$_2$SO$_4$, and concentrated. TFA (4 mL) and DCM (2 mL) was added into the residue and the mixture was stirred at room temperature for another 3 hr. The solvent was removed by rotary evaporator and the product was separated by CombiFlash® using silica gel as the stationary phase and eluted with 8-12% methanol in DCM. LC-MS: calculated [M+H]+ 786.37, found 786.86.

Synthesis of Structure 22b ((S)-3-(4-(4-((14-azido-3,6,9,12-tetraoxatetradecyl)oxy)naphthalen-1-yl) phenyl)-3-((S)-2-(4-((4-methylpyridin-2-yl)amino) butanamido)propanamido)propanoic Acid)

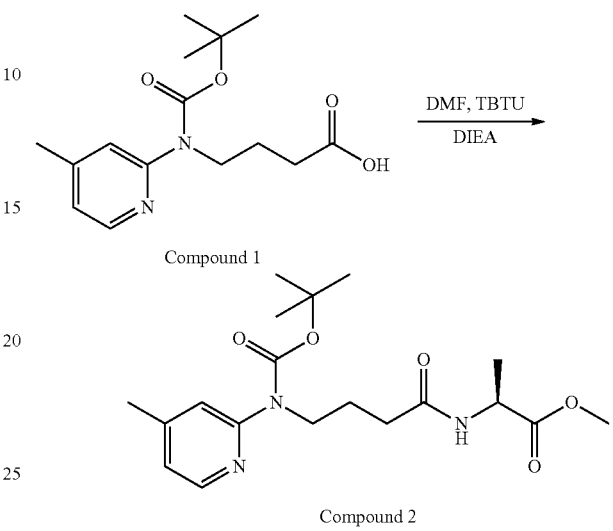

To a solution of compound 1 (250 mg, 0.85 mmol), L-alanine methyl ester hydrochloride salt (130 mg, 0.93 mmol), and TBTU (327 mg, 1.02 mmol) in DMF (2 mL) was added DIPEA (329 mg, 444 µL, 2.55 mmol) at 0° C. The reaction mixture was warmed to room temperature and stirred for 1 hour. The reaction was quenched with sat. NH$_4$Cl (aq) solution (0.75 mL) and deionized water (1 mL) then extracted with ethyl acetate (3 mL). The aqueous layer was further extracted with ethyl acetate (2×3 mL). The combined organic phase was washed with sat. NaHCO$_3$(aq) solution (2 mL). The organic layer was dried over Na$_2$SO$_4$, filtered, and concentrated. The crude mixture was separated by CombiFlash® using silica gel as the stationary phase with 0-5% methanol in DCM. Yield of compound 2: 294 mg (91%). [M+H] calculated for C$_{19}$H$_{29}$N$_3$O$_5$: 380.46, found: 380.33.

To a solution of compound 2 (294 mg, 0.77 mmol) in THF (4.5 mL) and deionized water (3 mL) at 0° C. was added a solution of lithium hydroxide (56 mg, 2.32 mmol) in deionized water (1 mL). The reaction was warmed to room temperature and stirred for 40 minutes. The reaction mixture was acidified to pH=3 with 6 M HCl (aq). The aqueous phase was extracted with ethyl acetate (3×10 mL). The combined organic phase was dried over $Na_2SO_4$, filtered, and concentrated. Compound 3 was used without further purification. Yield of compound 3: 267 mg (94%). [M+H] calculated for $C_{18}H_{27}N_3O_5$: 366.43, found: 366.19.

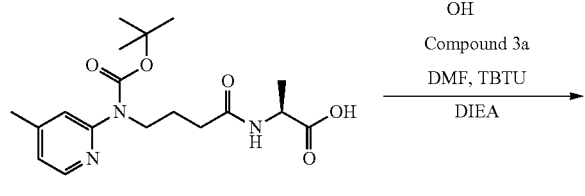

Compound 3

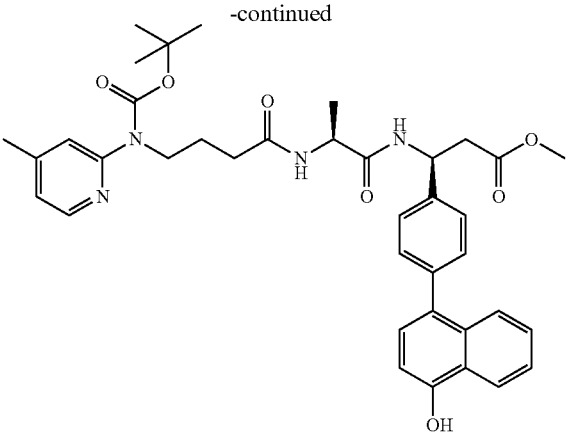

Compound 4

To a solution of compound 3 (267 mg, 0.73 mmol), compound 3a (288 mg, 0.80 mmol), and TBTU (282 mg, 0.88 mmol) in DMF (3 mL) was added DIPEA (283 mg, 382 µL, 2.19 mmol) at 0° C. The reaction mixture was warmed to room temperature and stirred for 1 hour. The reaction mixture was quenched with sat. $NH_4Cl$ (aq) solution (1.5 mL) and deionized water (1.5 mL) then extracted with ethyl acetate (12 mL). The aqueous layer was further extracted with ethyl acetate (2×12 mL). The combined organic phase was washed with half sat. $NH_4Cl$ (aq) solution (10 mL), half sat. $NaHCO_3$(aq) solution (10 mL), and sat. NaCl (aq) solution (10 mL). The organic layer was dried over $Na_2SO_4$, filtered, and concentrated. The crude mixture was separated by CombiFlash® using silica gel as the stationary phase with 0-5% methanol in DCM. Yield of compound 4: 342 mg (70%). [M+H] calculated for $C_{38}H_{44}N_4O_7$: 669.79, found: 669.74.

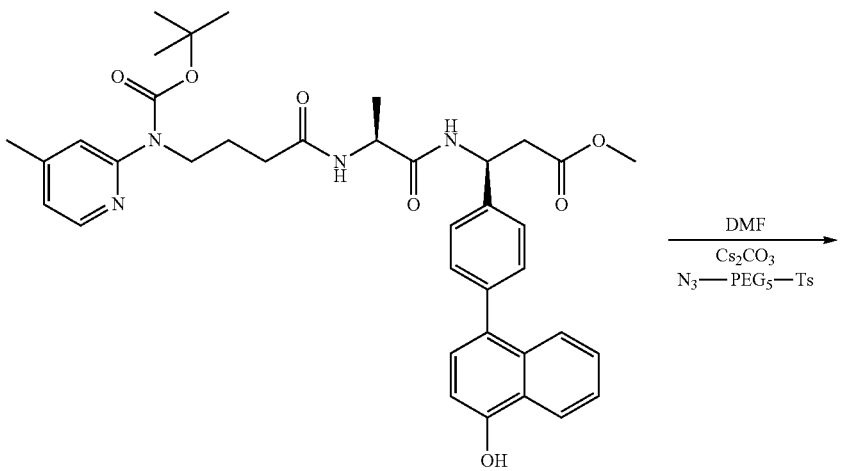

Compound 4

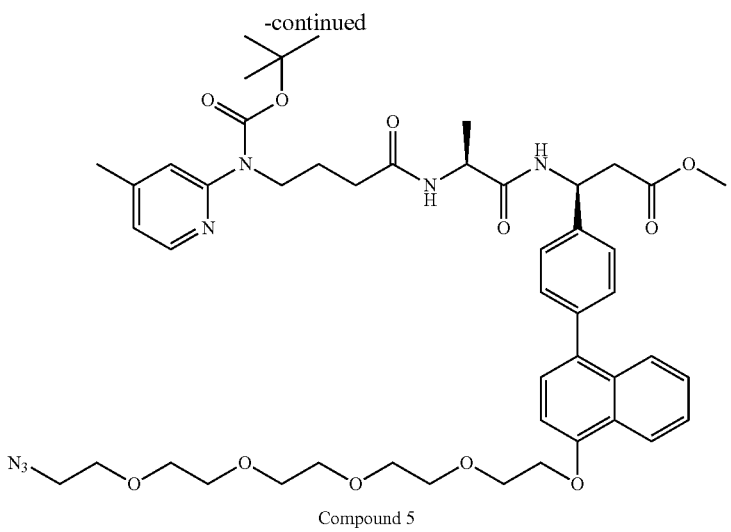
Compound 5

To a solution of compound 4 (150 mg, 0.22 mmol) and azido-PEG$_5$-OTs (187 mg, 0.49 mmol) in anhydrous DMF (1.2 mL) was added Cs$_2$CO$_3$ (146 mg, 0.49 mmol). The reaction mixture was stirred at 60° C. for 3 hours. The reaction mixture was quenched with sat. NaHCO$_3$(aq) solution (10 mL) and deionized water (5 mL) then extracted with ethyl acetate (7.5 mL). The aqueous layer was further extracted with ethyl acetate (2×7.5 mL). The combined organic phase was dried over Na$_2$SO$_4$, filtered, and concentrated. The crude mixture was separated by CombiFlash® using silica gel as the stationary phase with 0-4% methanol in DCM. Yield of compound 5: 142 mg (69%). [M+H] calculated for C$_{48}$H$_{63}$N$_7$O$_{11}$: 915.06, found: 914.96.

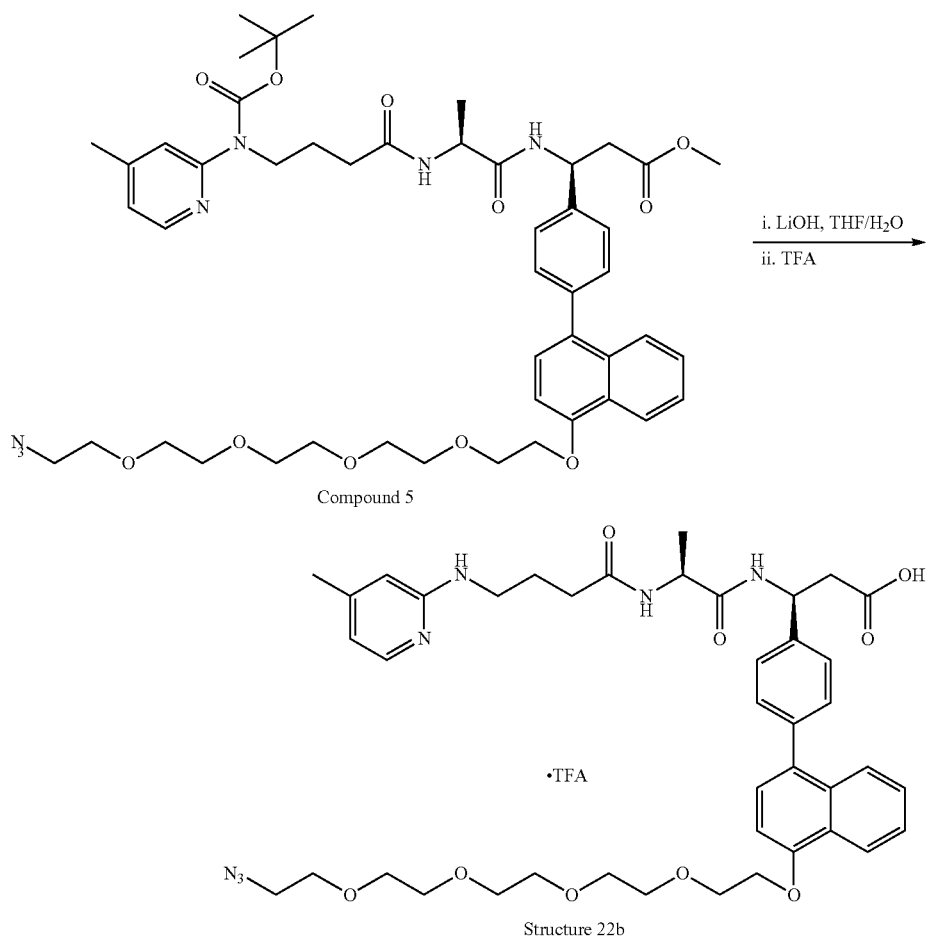

To a solution of compound 5 (142 mg, 0.16 mmol) in THF (2 mL) and deionized water (1.5 mL) at 0° C. was added a solution of lithium hydroxide (11 mg, 0.47 mmol) in deionized water (0.5 mL). The reaction was warmed to room temperature and stirred for 1 hour. The reaction mixture was acidified to pH=3 with 6 M HCl (aq). The aqueous phase was extracted with ethyl acetate (3×8 mL). The combined organic phase was dried over Na₂SO₄, filtered, and concentrated. To the crude residue was added TFA (2.0 mL) and water (100 µL). The reaction mixture was stirred for 1.5 hours at room temperature. The solvent was removed under reduced pressure, and the residue was coevaporated with acetonitrile:toluene [1:1] (2×20 mL). The crude mixture was separated by CombiFlash® using silica gel as the stationary phase with 0-13% methanol in DCM. Yield of Structure 22b: 100 mg (80%). [M+H] calculated for $C_{42}H_{53}N_7O_9$: 800.92, found: 800.81.

Synthesis of Structure 23b ((S)-3-(4-(4-((14-azido-3,6,9,12-tetraoxatetradecyl)oxy)naphthalen-1-yl)phenyl)-3-((S)-3-methyl-2-(4-((4-methylpyridin-2-yl)amino)butanamido)butanamido)propanoic Acid)

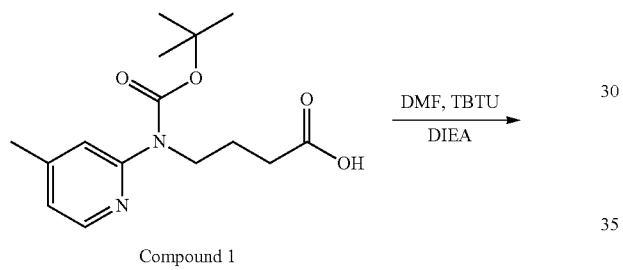

Compound 1

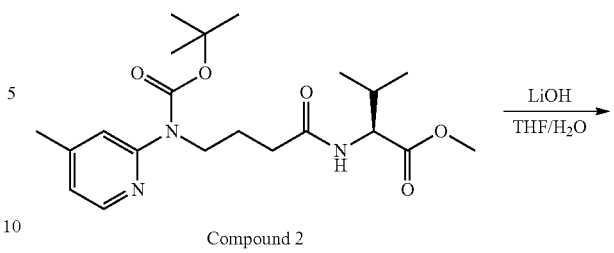

Compound 2

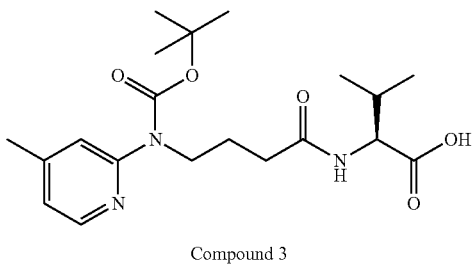

Compound 3

To a solution of compound 2 (297 mg, 0.73 mmol) in THF (4.5 mL) and deionized water (3 mL) at 0° C. was added a solution of lithium hydroxide (52 mg, 2.19 mmol) in deionized water (1 mL). The reaction was warmed to room temperature and stirred for 40 minutes. The reaction mixture was acidified to pH=3 with 6 M HCl (aq). The aqueous phase was extracted with ethyl acetate (3×10 mL). The combined organic phase was dried over Na₂SO₄, filtered, and concentrated. Compound 3 was used without further purification assuming 100% yield. [M+H] calculated for $C_{20}H_{31}N_3O_5$: 394.49, found: 393.83.

To a solution of compound 1 (250 mg, 0.85 mmol), L-valine methyl ester hydrochloride salt (157 mg, 0.93 mmol), and TBTU (327 mg, 1.02 mmol) in DMF (2 mL) was added DIPEA (329 mg, 444 µL, 2.55 mmol) at 0° C. The reaction mixture was warmed to room temperature and stirred for 1 hour. The reaction was quenched with sat. NH₄Cl (aq) solution (0.75 mL) and deionized water (1 mL) then extracted with ethyl acetate (3 mL). The aqueous layer was further extracted with ethyl acetate (2×3 mL). The combined organic phase was washed with sat. NaHCO₃(aq) solution (2 mL). The organic layer was dried over Na₂SO₄, filtered, and concentrated. The crude mixture was separated by CombiFlash® using silica gel as the stationary phase with 0-5% methanol in DCM. Yield of compound 2: 297 mg (86%). [M+H] calculated for $C_{21}H_{33}N_3O_5$: 408.51, found: 407.87.

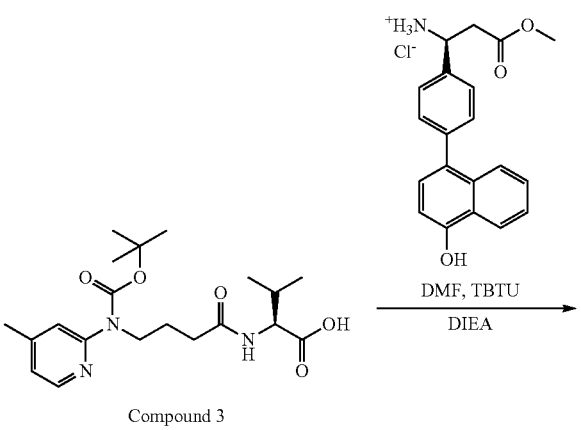

Compound 3

-continued

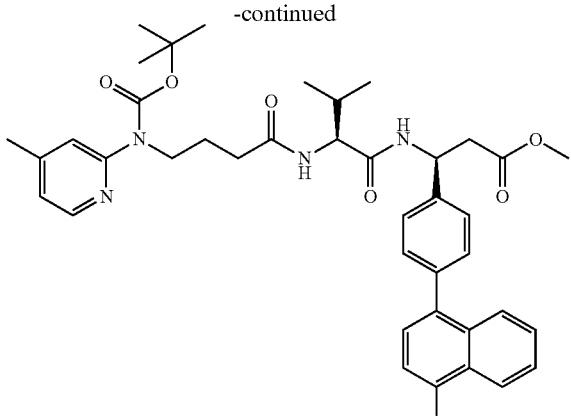

Compound 4

To a solution of compound 3 (287 mg, 0.73 mmol), compound 3a (287 mg, 0.80 mmol), and TBTU (281 mg, 0.88 mmol) in DMF (3 mL) was added DIPEA (283 mg, 382 µL, 2.19 mmol) at 0° C. The reaction mixture was warmed to room temperature and stirred for 1 hour. The reaction mixture was quenched with sat. NH$_4$Cl (aq) solution (2.5 mL) and deionized water (2.5 mL) then extracted with ethyl acetate (12 mL). The aqueous layer was further extracted with ethyl acetate (2×12 mL). The combined organic phase was washed with half sat. NH$_4$Cl (aq) solution (10 mL), half sat. NaHCO$_3$(aq) solution (10 mL), and sat. NaCl (aq) solution (10 mL). The organic layer was dried over Na$_2$SO$_4$, filtered, and concentrated. The crude mixture was separated by CombiFlash® using silica gel as the stationary phase with 0-5% methanol in DCM. Yield of compound 4: 374 mg (74%). [M+H] calculated for C$_4$H$_{48}$N$_4$O$_7$: 697.84, found: 697.46.

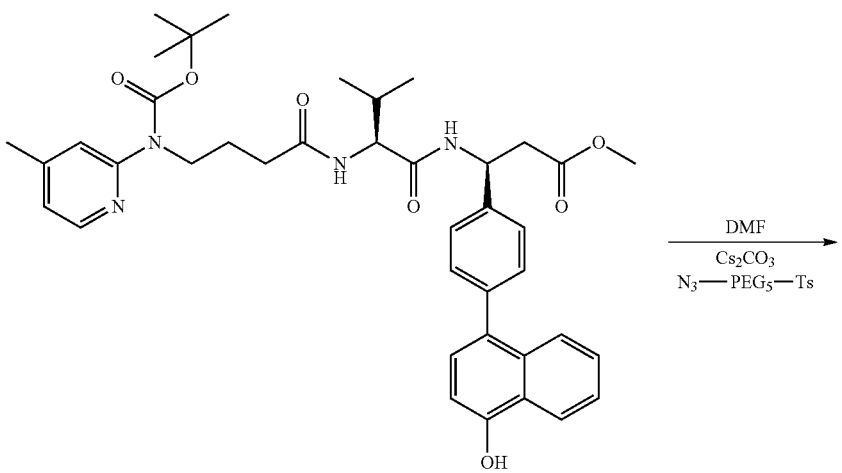

Compound 4

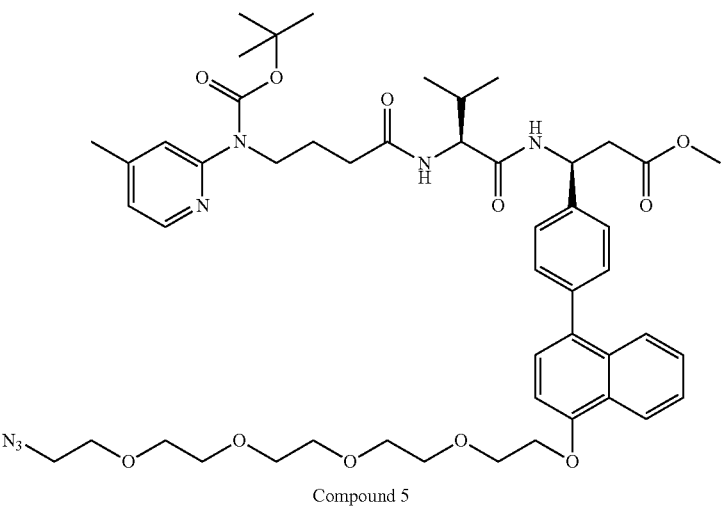

Compound 5

To a solution of compound 4 (150 mg, 0.215 mmol) and azido-PEG$_5$-OTs (180 mg, 0.43 mmol) in anhydrous DMF (1.2 mL) was added Cs$_2$CO$_3$ (140 mg, 0.43 mmol). The reaction mixture was stirred at 60° C. for 3 hours. The reaction mixture was quenched with sat. NaHCO$_3$(aq) solution (10 mL) and deionized water (5 mL) then extracted with ethyl acetate (7.5 mL). The aqueous layer was further extracted with ethyl acetate (2×7.5 mL). The combined organic phase was dried over Na$_2$SO$_4$, filtered, and concentrated. The crude mixture was separated by CombiFlash® using silica gel as the stationary phase with 04% methanol in DCM. Yield of compound 5: 134 mg (66%). [M+H] calculated for C$_{50}$H$_{67}$N$_7$O$_{11}$: 943.12, found: 942.96.

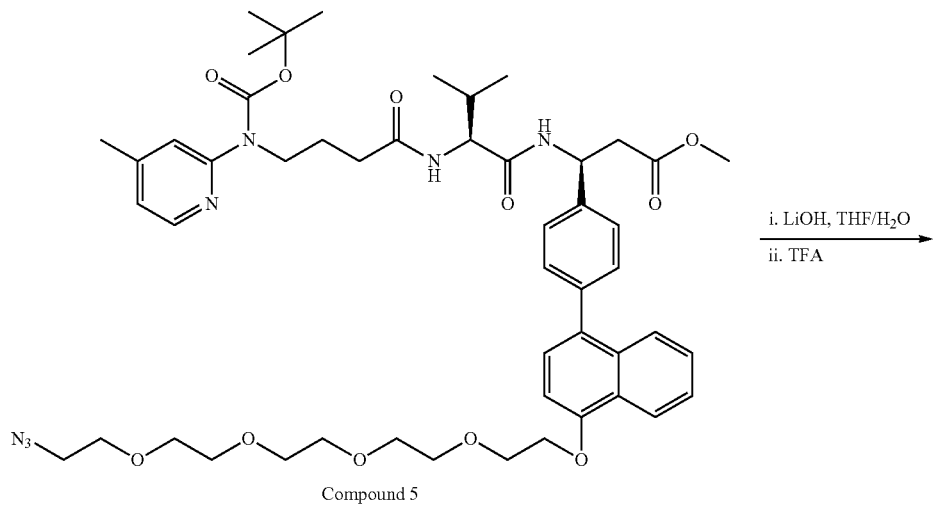

Compound 5 i. LiOH, THF/H$_2$O
ii. TFA

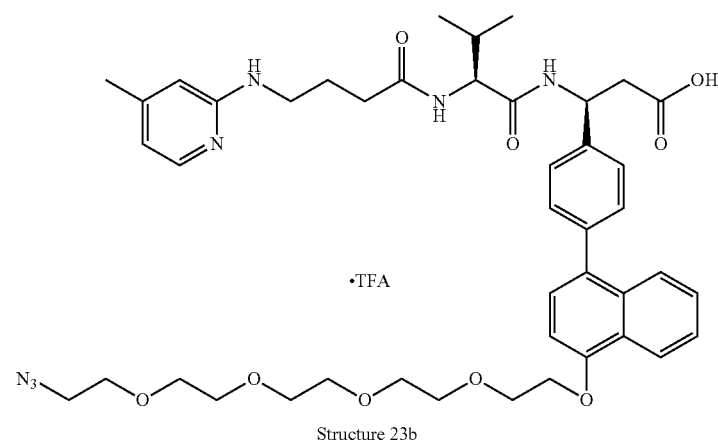 [SMILES: Cc1ccnc(NCCCC(=O)N[C@@H](C(=O)N[C@@H](CC(=O)O)c2ccc(-c3ccc(OCCOCCOCCOCCOCCN=[N+]=[N-])c4ccccc34)cc2)C(C)C)c1]

Structure 23b

To a solution of compound 5 (134 mg, 0.14 mmol) in THF (2 mL) and deionized water (1.5 mL) at 0° C. was added a solution of lithium hydroxide (10 mg, 0.43 mmol) in deionized water (0.5 mL). The reaction was warmed to room temperature and stirred for 1 hour. The reaction mixture was acidified to pH=3 with 6 M HCl (aq). The aqueous phase was extracted with ethyl acetate (3×8 mL). The combined organic phase was dried over $Na_2SO_4$, filtered, and concentrated. To the crude residue was added TFA (1.9 mL) and water (95 μL). The reaction mixture was stirred for 1.5 hours at room temperature. The solvent was removed under reduced pressure, and the residue was coevaporated with acetonitrile:toluene [1:1] (2×20 mL). The crude mixture was separated by CombiFlash® using silica gel as the stationary phase with 0-10% methanol in DCM. Yield of Structure 23b: 36 mg (30.5%). [M+H] calculated for $C_{44}H_{57}N_7O_9$: 828.97, found 828.90.

Synthesis of Structure 24b ((S)-3-(4-(4-((14-azido-3,6,9,12-tetraoxatetradecyl)oxy)naphthalen-1-yl)phenyl)-3-((S)-2-(4-((4-methylpyridin-2-yl)amino)butanamido)-3-phenylpropanamido)propanoic Acid)

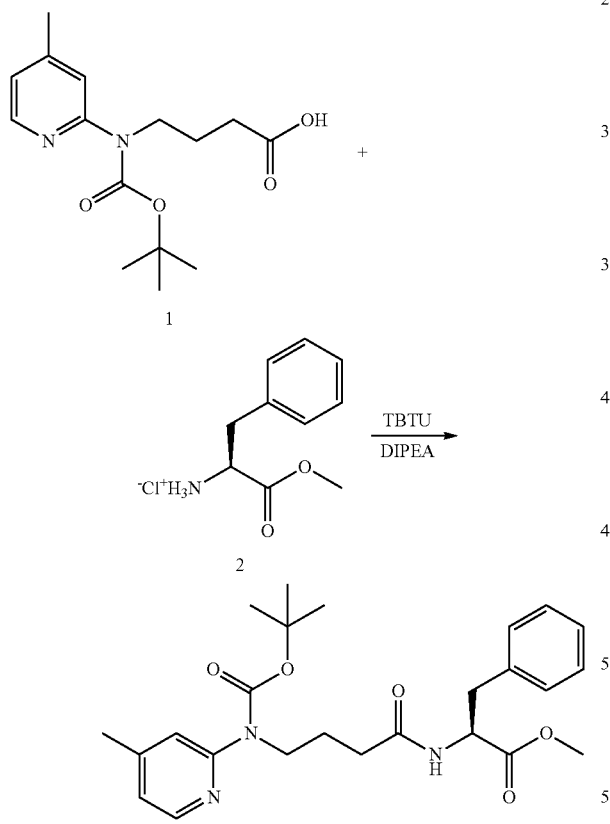

CombiFlash® using silica gel as the stationary phase and was eluted with 2-3% methanol in DCM. LC-MS: calculated [M+H]+ 456.24, found 456.12.

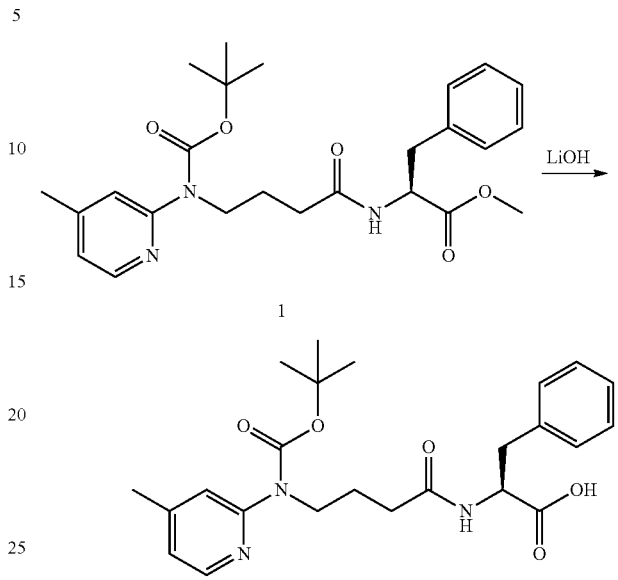

To a solution of compound 1 (300 mg, 0.658 mmol, 1 equiv.) in THF (5 mL) and $H_2O$ (5 mL) was added lithium hydroxide (47 mg, 1.975 mmol, 3 equiv.) portion-wise at 0° C. The reaction mixture was warmed to room temperature. After stirring at room temperature for 1 hr, the reaction mixture was acidified by HCl (6 N) to pH 3.0. The aqueous phase was extracted with ethyl acetate (3×10 mL) and the organic layer was combined, dried over $Na_2SO_4$, and concentrated. The product was used without further purification. LC-MS: calculated [M+H]+ 442.23, found 442.08.

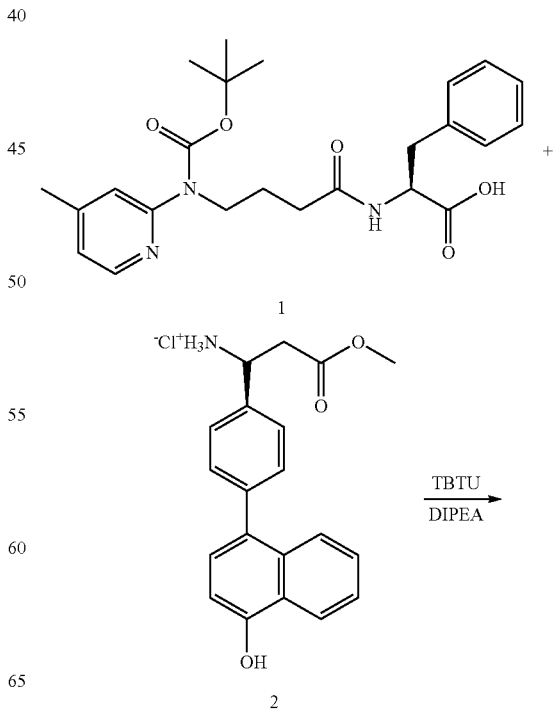

-continued

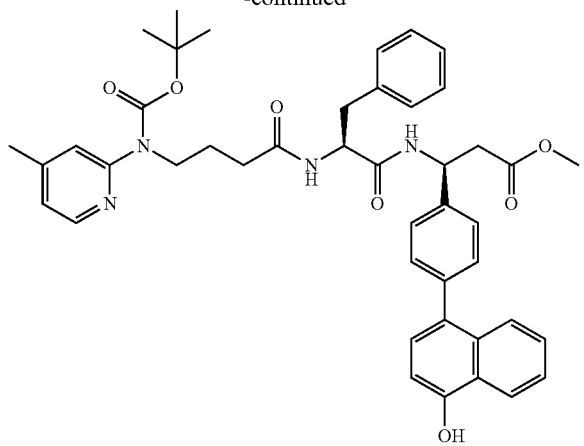

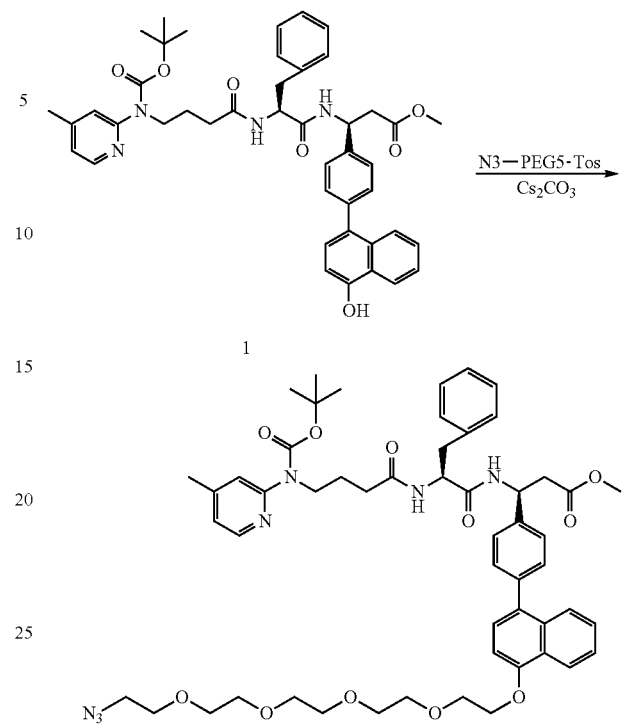

To a solution of compound 1 (290 mg, 0.656 mmol, 1 equiv.), compound 2 (258 mg, 0.722 mmol, 1.1 equiv.), and TBTU (253 mg, 0.788 mmol, 1.2 equiv.) in anhydrous DMF (5 mL) was added diisopropylethylamine (0.343 mL, 1.970 mmol, 3 equiv.) at 0° C. The reaction mixture was warmed to room temperature and stirred for another 1 hr. The reaction was quenched with saturated NaHCO$_3$ solution (10 mL) and the aqueous phase was extracted with ethyl acetate (3×10 mL). The organic phase was combined, dried over Na$_2$SO$_4$, and concentrated. The product was separated by CombiFlash® using silica gel as the stationary phase and was eluted with 3-4% methanol in DCM. LC-MS: calculated [M+H]+ 745.35, found 745.63.

To a solution of compound 1 (113 mg, 0.151 mmol, 1 equiv.) and azido-PEG5-OTs (126 mg, 0.303 mmol, 2 equiv.) in anhydrous DMF (2 mL) was added Cs$_2$CO$_3$ (99 mg, 0.303 mmol, 2 equiv.) at room temperature. The reaction mixture was stirred for 3 hours at 40° C. The reaction was quenched by saturated NaHCO$_3$ solution (10 mL) and the aqueous layer was extracted with ethyl acetate (3×5 mL). The organic phase was combined, dried over Na$_2$SO$_4$, and concentrated. The product was purified by CombiFlash® using silica gel as the stationary phase and was eluted with 3-4% methanol in DCM. LC-MS: calculated [M+H]+ 990.49, found 990.87.

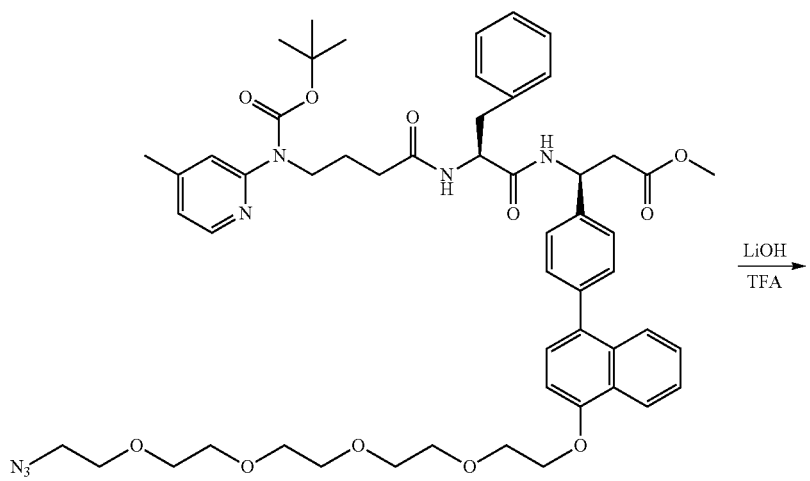

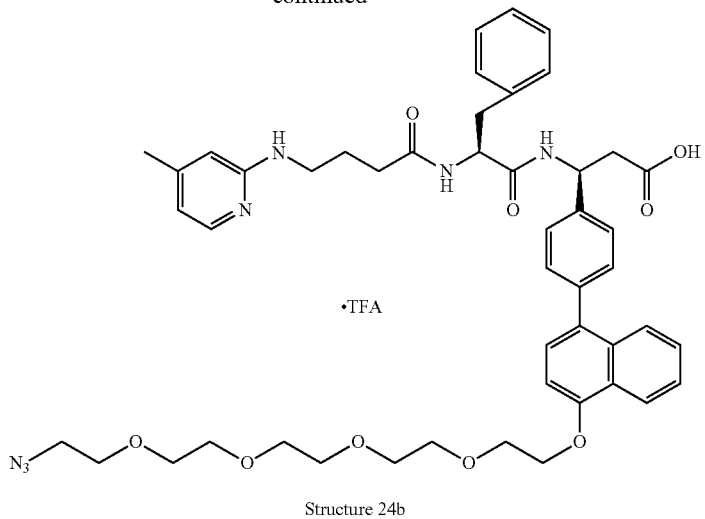

Structure 24b

To a solution of compound 1 (140 mg, 0.141 mmol, 1.0 equiv.) in THF (2 mL) and water (2 mL) was added lithium hydroxide (10 mg, 0.424 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over Na$_2$SO$_4$, and concentrated. TFA (4 mL) and DCM (2 mL) was added into the residue and the mixture was stirred at room temperature for another 3 hr. The solvent was removed by rotary evaporator and the product was separated by CombiFlash® using silica gel as the stationary phase and eluted with 6-10% methanol in DCM. LC-MS: calculated [M+H]+ 876.42, found 876.88.

Synthesis of Structure 25b ((S)-3-(4-(4-((14-azido-3,6,9,12-tetraoxatetradecyl)oxy)naphthalen-1-yl)phenyl)-3-((S)-3-(benzyloxy)-2-(4-((4-methylpyridin-2-yl)amino)butanamido)propanamido)propanoic Acid)

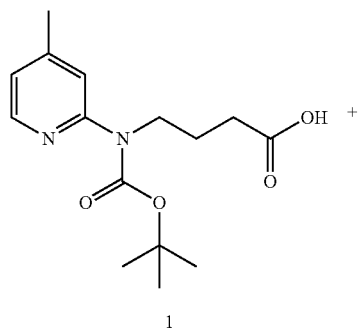

1

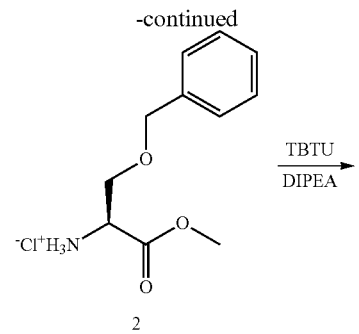

2

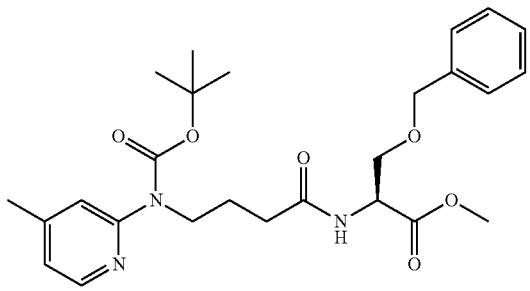

To a solution of compound 1 (100 mg, 0.339 mmol, 1 equiv.), compound 2 (92 mg, 0.373 mmol, 1.1 equiv.), and TBTU (131 mg, 0.407 mmol, 1.2 equiv.) in anhydrous DMF (4 mL) was added diisopropylethylamine (0.178 mL, 1.019 mmol, 3 equiv.) at 0° C. The reaction mixture was warmed to room temperature and stirred for another 1 hr. The reaction was quenched with saturated NaHCO$_3$ solution (10 mL) and the aqueous phase was extracted with ethyl acetate (3×10 mL). The organic phase was combined, dried over Na$_2$SO$_4$, and concentrated. The product was separated by CombiFlash® using silica gel as the stationary phase and was eluted with 2-4% methanol in DCM. LC-MS: calculated [M+H]+ 486.25, found 486.37.

285

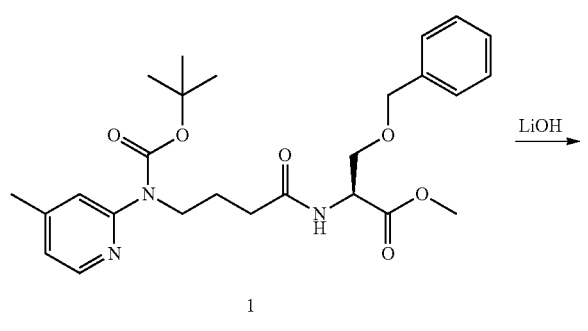

1

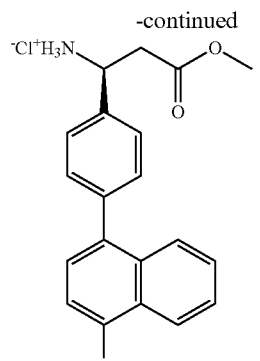

2

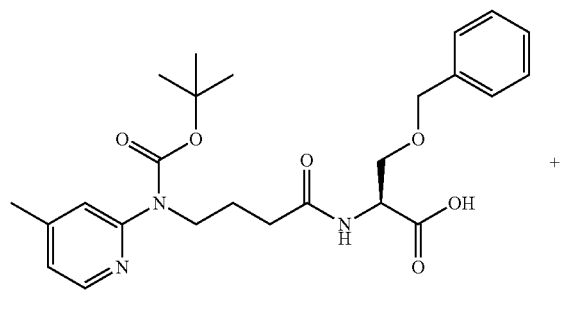

1

To a solution of compound 1 (160 mg, 0.329 mmol, 1 equiv.) in THF (5 mL) and H₂O (5 mL) was added lithium hydroxide (23 mg, 0.988 mmol, 3 equiv.) portion-wise at 0° C. The reaction mixture was warmed to room temperature. After stirring at room temperature for 1 hr, the reaction mixture was acidified by HCl (6 N) to pH 3.0. The aqueous phase was extracted with ethyl acetate (3×10 mL) and the organic layer was combined, dried over Na₂SO₄, and concentrated. The product was used without further purification. LC-MS: calculated [M+H]+ 472.24, found 472.32.

286

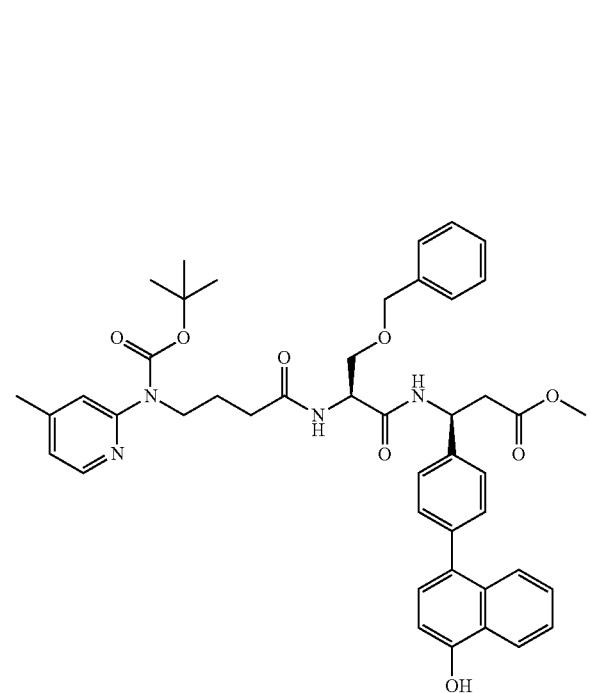

To a solution of compound 1 (1600 mg, 0.339 mmol, 1 equiv.), compound 2 (133 mg, 0.373 mmol, 1.1 equiv.), and TBTU (130 mg, 0.815 mmol, 1.2 equiv.) in anhydrous DMF (3 mL) was added diisopropylethylamine (0.177 mL, 1.018 mmol, 3 equiv.) at 0° C. The reaction mixture was warmed to room temperature and stirred for another 1 hr. The reaction was quenched with saturated NaHCO₃ solution (10 mL) and the aqueous phase was extracted with ethyl acetate (3×10 mL). The organic phase was combined, dried over Na₂SO₄, and concentrated. The product was separated by CombiFlash® using silica gel as the stationary phase and was eluted with 2-3% methanol in DCM. LC-MS: calculated [M+H]+ 775.36, found 775.87.

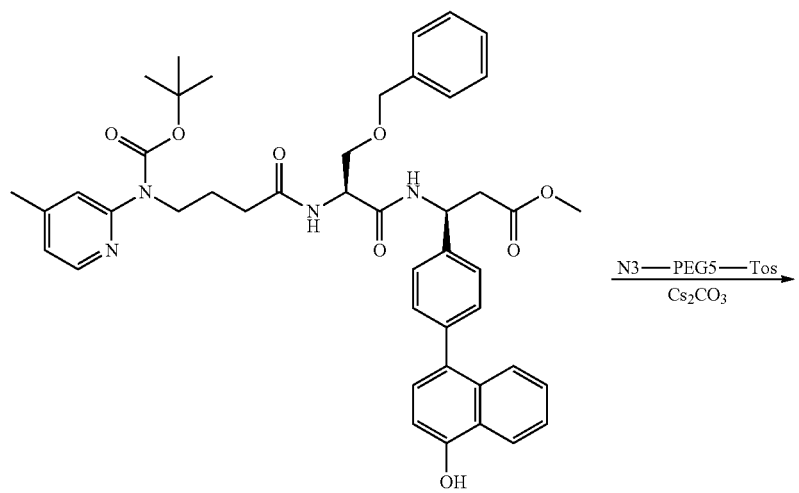

1

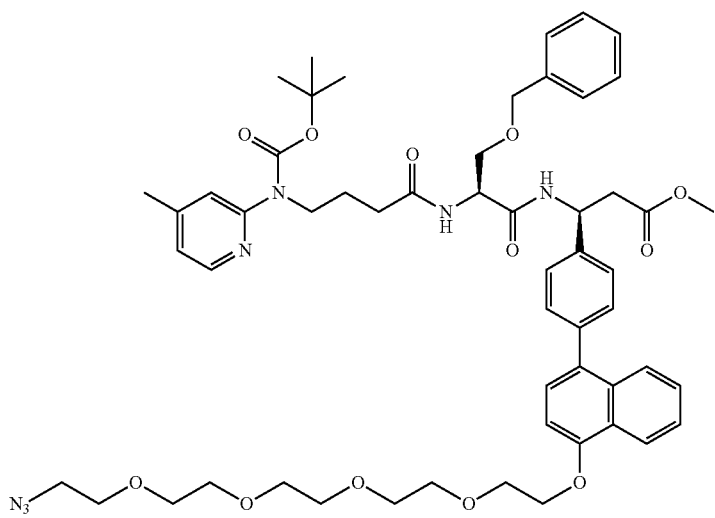

To a solution of compound 1 (140 mg, 0.180 mmol, 1 equiv.) and azido-PEG5-OTs (150 mg, 0.361 mmol, 2 equiv.) in anhydrous DMF (2 mL) was added Cs$_2$CO$_3$ (117 mg, 0.361 mmol, 2 equiv.) at room temperature. The reaction mixture was stirred for 3 hours at 40° C. The reaction was quenched by saturated NaHCO$_3$ solution (10 mL) and the aqueous layer was extracted with ethyl acetate (3×5 mL). The organic phase was combined, dried over Na$_2$SO$_4$, and concentrated. The product was purified by CombiFlash® using silica gel as the stationary phase and was eluted with 3-4% methanol in DCM. LC-MS: calculated [M+H]+ 1020.50, found 1020.88.

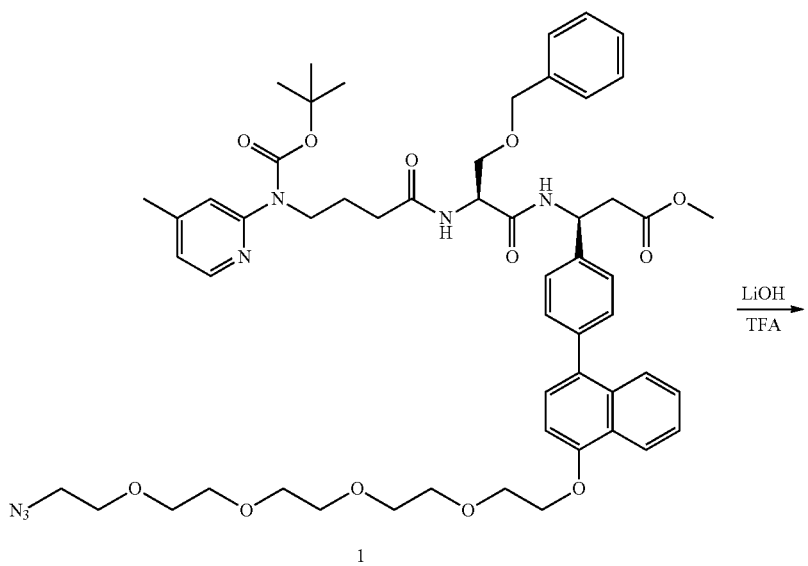

1

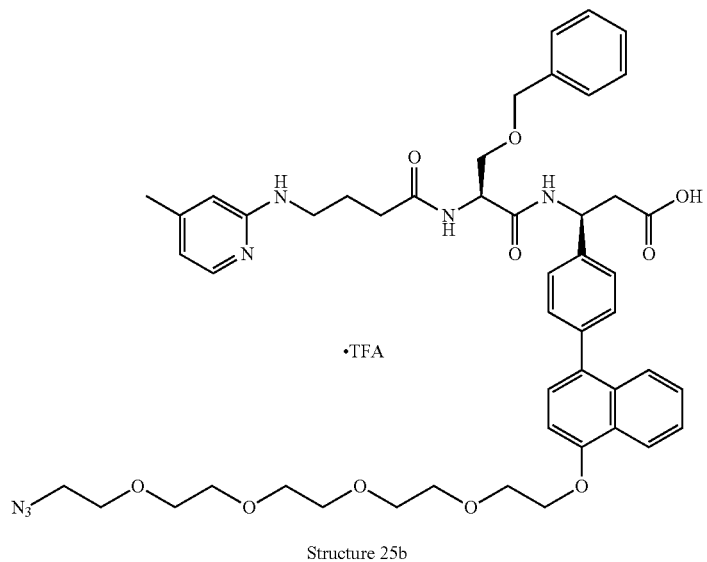

Structure 25b

To a solution of compound 1 (170 mg, 0.166 mmol, 1.0 equiv.) in THF (2 mL) and water (2 mL) was added lithium hydroxide (12 mg, 0.499 mmol, 3.0 equiv.) at room temperature. The mixture was stirred at room temperature for another 1 hours. The pH was adjusted to 3.0 by HCl (6N) and the aqueous phase was extracted with EtOAc (3×10 mL). The organic phase was combined, dried over Na$_2$SO$_4$, and concentrated. TFA (4 mL) and DCM (2 mL) was added into the residue and the mixture was stirred at room temperature for another 3 hr. The solvent was removed by rotary evaporator and the product was separated by CombiFlash® using silica gel as the stationary phase and eluted with 6-10% methanol in DCM. LC-MS: calculated [M+H]+ 906.43, found 906.95.

Synthesis of Structure 27b ((S)-3-(3-(4-((14-azido-3,6,9,12-tetraoxatetradecyl)oxy)-3,5-dimethyl-1H-pyrazol-1-yl)phenyl)-3-(2-(4-((4-methylpyridin-2-yl)amino)butanamido)acetamido)propanoic Acid)

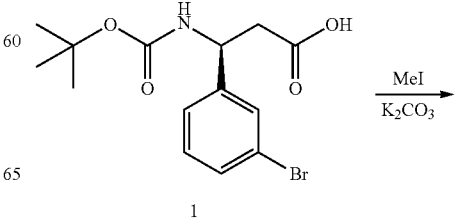

1

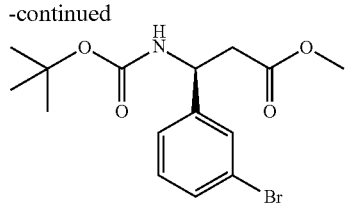

To a solution of compound 1 (3.0 g, 8.71 mmol, 1 equiv.) and potassium carbonate (1.806 g, 13.073 mmol, 1.5 equiv.) in anhydrous DMF (10 mL) was added methyl iodide (1.085 mL, 17.431 mmol, 2.0 equiv.) at room temperature. The reaction mixture was stirred at room temperature for 1 hr. The reaction was then quenched with water (20 mL) and the aqueous phase was extracted with ethyl acetate (3×10 mL). The organic phase was combined, dried over anhydrous Na$_2$SO$_4$, and concentrated. The product was separated by CombiFlash® using silica gel as the stationary phase and was eluted with 15% ethyl acetate in hexane. LC-MS: calculated [M+H]+ 358.06, found 358.15.

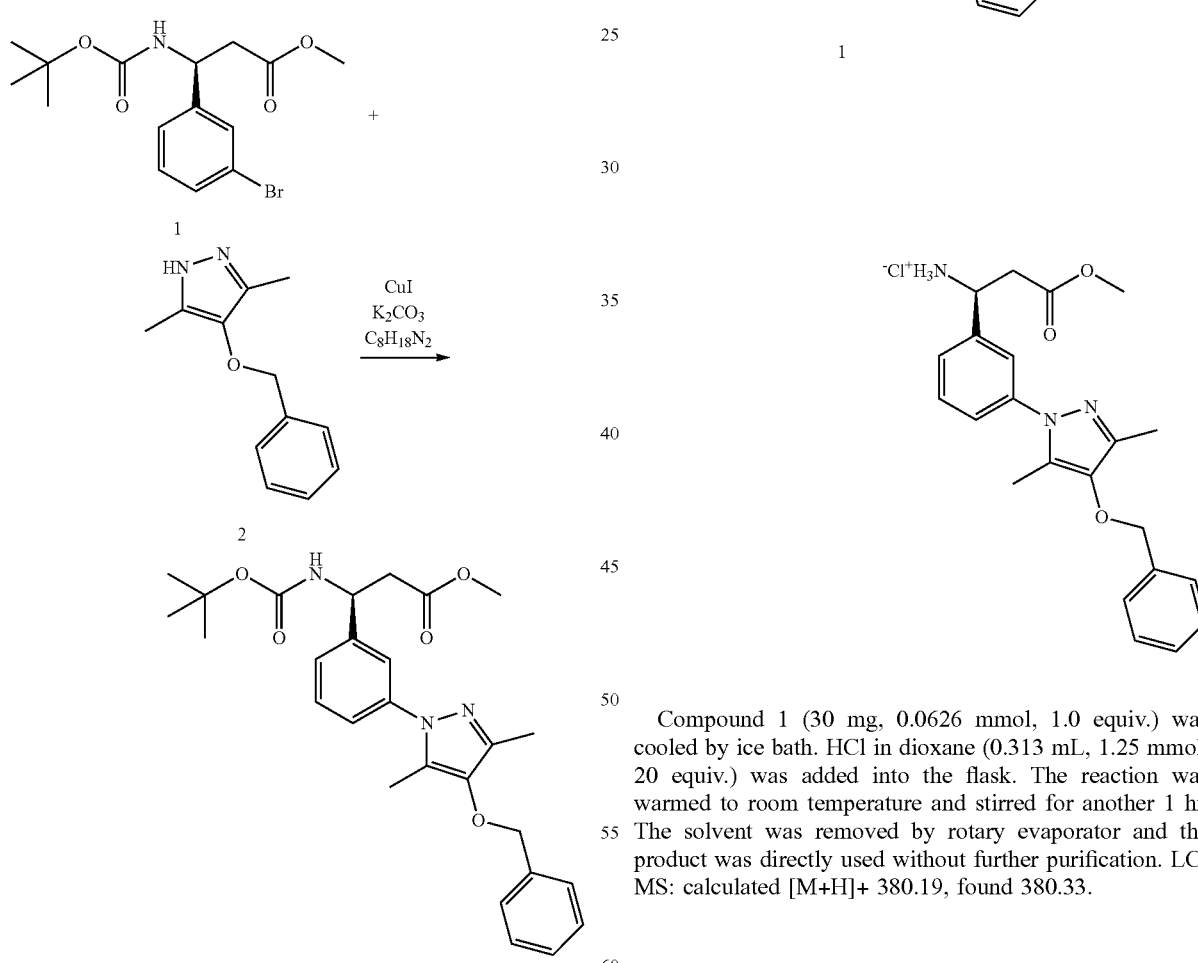

The mixture of compound 1 (200 mg, 0.558 mmol, 1 equiv.), compound 2 (169 mg, 0.837 mmol, 1.5 equiv.), copper (I) iodide (106 mg, 0.558 mmol, 1.0 equiv.), potassium carbonate (154 mg, 1.116 mmol, 2.0 equiv.) and trans-N,N'-dimethylcyclohexane-1,2-diamine (88 μL, 0.558 mmol, 1.0 equiv.) in anhydrous DMF (5 mL) was backfilled with nitrogen 3 times. The mixture was stirred at 120° C. for 24 hrs. The mixture was cooled to room temperature and was concentrated. The product was separated by CombiFlash® using silica gel as the stationary phase and was eluted with 30-40% ethyl acetate in hexane. LC-MS: calculated [M+H]+ 480.24, found 480.43.

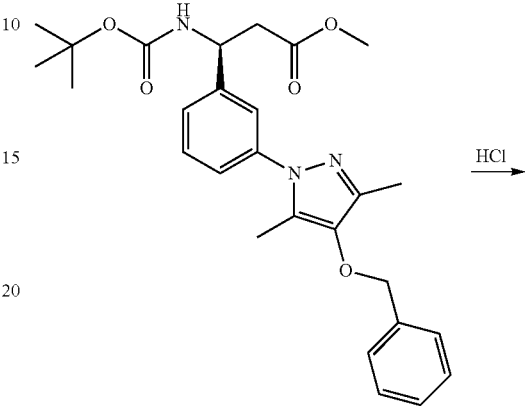

Compound 1 (30 mg, 0.0626 mmol, 1.0 equiv.) was cooled by ice bath. HCl in dioxane (0.313 mL, 1.25 mmol, 20 equiv.) was added into the flask. The reaction was warmed to room temperature and stirred for another 1 hr. The solvent was removed by rotary evaporator and the product was directly used without further purification. LC-MS: calculated [M+H]+ 380.19, found 380.33.

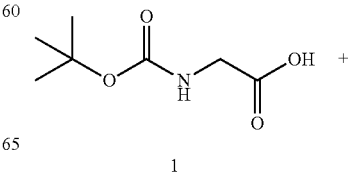

293

-continued

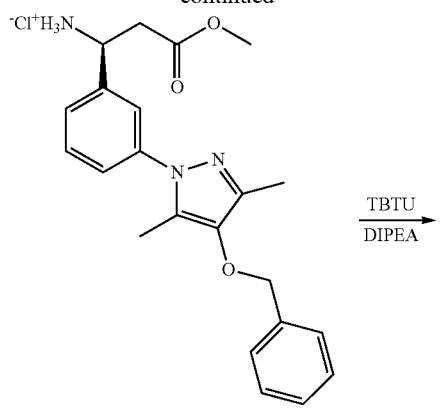

2

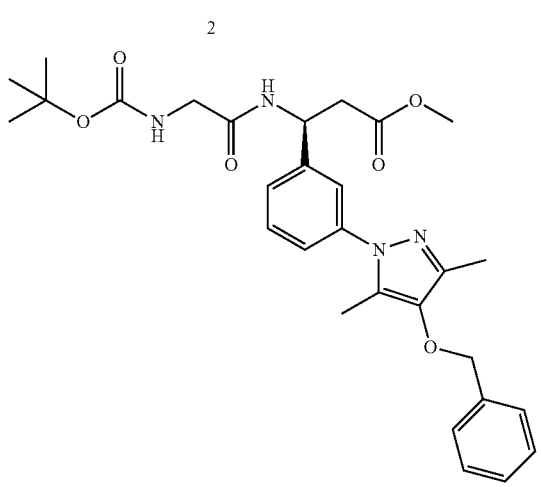

To a solution of compound 1 (10 mg, 0.0571 mmol, 1 equiv.), compound 2 (26 mg, 0.0628 mmol, 1.1 equiv.), and TBTU (22 mg, 0.0685 mmol, 1.2 equiv.) in anhydrous DMF (1 mL) was added diisopropylethylamine (0.030 mL, 0.171 mmol, 3 equiv.) at 0° C. The reaction mixture was warmed to room temperature and stirred for another 1 hr. The reaction was quenched with saturated NaHCO₃ solution (5 mL) and the aqueous phase was extracted with ethyl acetate (3×5 mL). The organic phase was combined, dried over Na₂SO₄, and concentrated. The product was separated by CombiFlash® using silica gel as the stationary phase and was eluted with 3-4% methanol in DCM. LC-MS: calculated [M+H]+ 537.26, found 537.41.

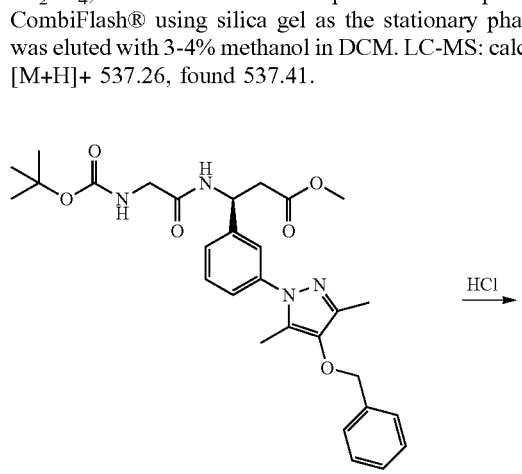

1

294

-continued

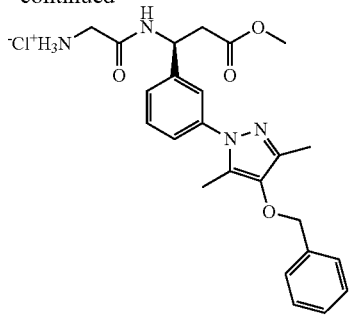

Compound 1 (30 mg, 0.0626 mmol, 1.0 equiv.) was cooled by ice bath. HCl in dioxane (0.313 mL, 1.25 mmol, 20 equiv.) was added into the flask. The reaction was warmed to room temperature and stirred for another 1 hr. The solvent was removed by rotary evaporator and the product was directly used without further purification. LC-MS: calculated [M+H]+ 437.21, found 437.31.

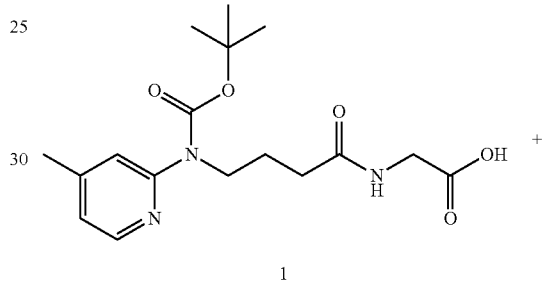

1

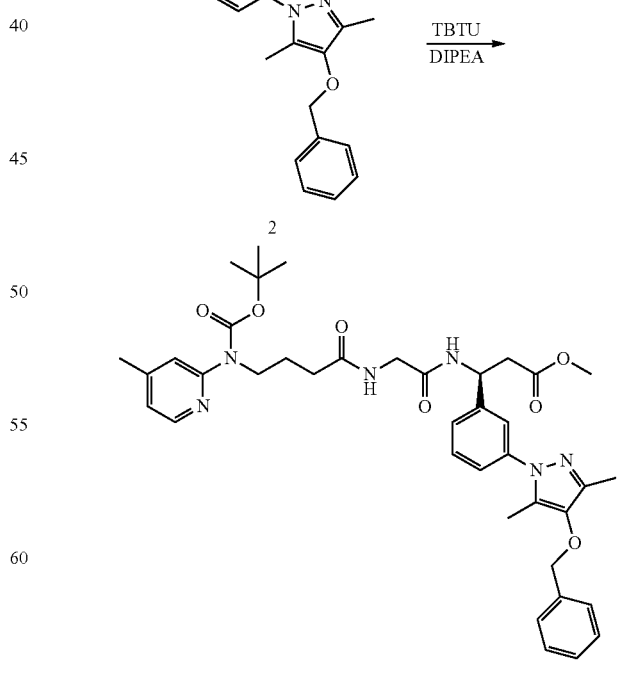

2

To a solution of compound 1 (20 mg, 0.0569 mmol, 1 equiv.), compound 2 (26 mg, 0.0626 mmol, 1.1 equiv.), and TBTU (22 mg, 0.0683 mmol, 1.2 equiv.) in anhydrous DMF (2 mL) was added diisopropylethylamine (0.03 mL, 0.170 mmol, 3 equiv.) at 0° C. The reaction mixture was warmed to room temperature and stirred for another 1 hr. The reaction was quenched with saturated NaHCO$_3$ solution (5 mL) and the aqueous phase was extracted with ethyl acetate (3×5 mL). The organic phase was combined, dried over Na$_2$SO$_4$, and concentrated. The product was separated by CombiFlash® using silica gel as the stationary phase and was eluted with 4-5% methanol in DCM. LC-MS: calculated [M+H]+ 713.36, found 713.85.

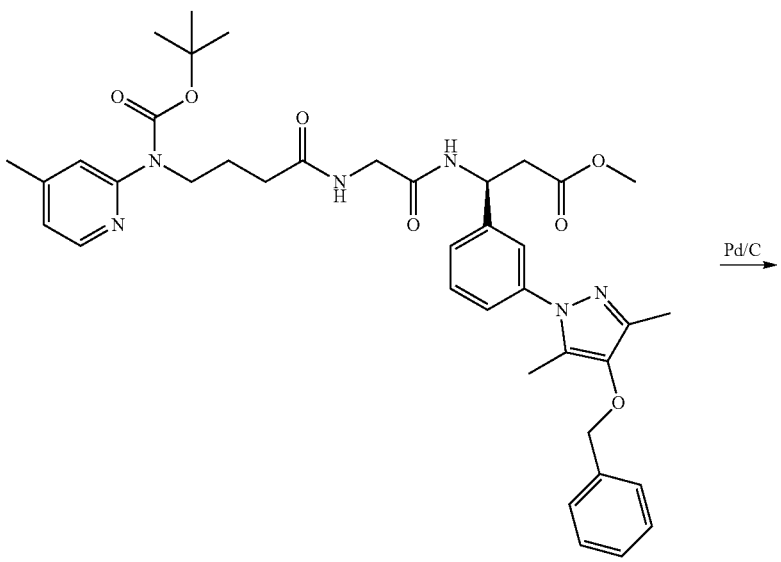

1

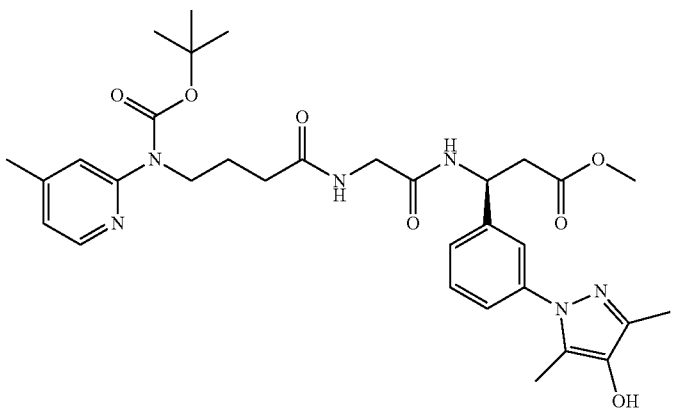

To a solution of compound 1 (0.033 g, 0.0463 mmol, 1 equiv.) in ethyl acetate (10 mL) was added 10% Pd/C (20 mg) at room temperature. The reaction mixture was stirred with hydrogen gas at room temperature for overnight. The catalyst was removed by filtration through Celite® and the product was used directly without further purification. LC-MS: calculated [M+H]+ 623.31, found 623.56.

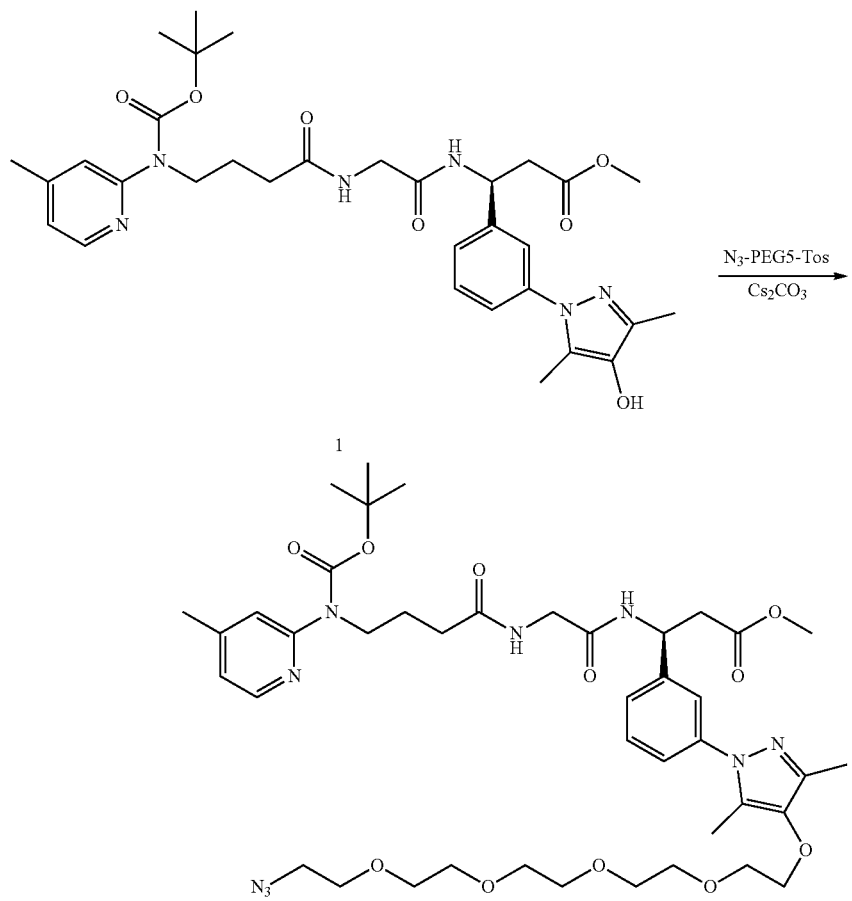

To a solution of compound 1 (16 mg, 0.0257 mmol, 1 equiv.) and azido-PEG5-OTs (22 mg, 0.0514 mmol, 2 equiv.) in anhydrous DMF (2 mL) was added $Cs_2CO_3$ (17 mg, 0.0514 mmol, 2 equiv.) at room temperature. The reaction mixture was stirred for 3 hrs at 40° C. The reaction was quenched by saturated $NaHCO_3$ solution (10 mL) and the aqueous layer was extracted with ethyl acetate (3×5 mL). The organic phase was combined, dried over $Na_2SO_4$, and concentrated. The product was purified by CombiFlash® using silica gel as the stationary phase and was eluted with 34% methanol in DCM. LC-MS: calculated [M+H]+ 868.45, found 868.96.

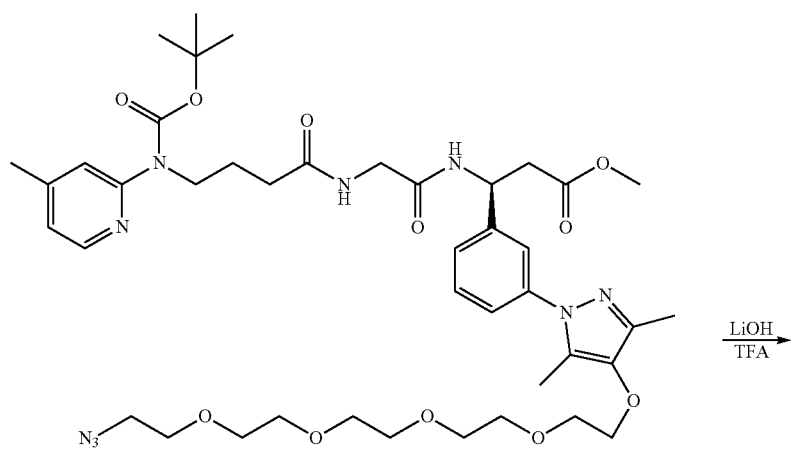

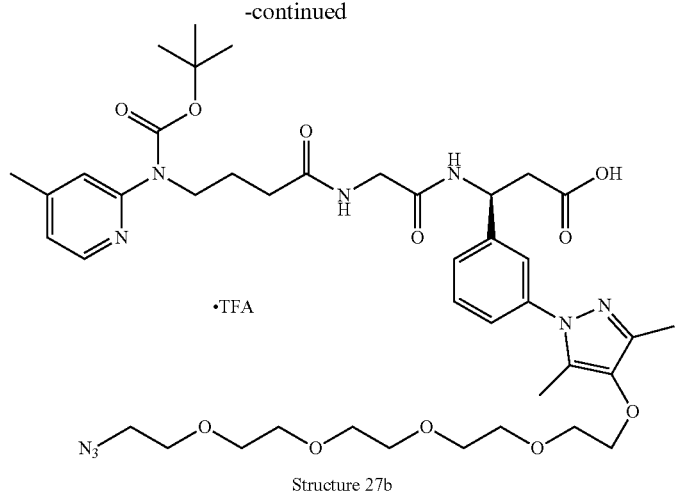

Structure 27b

To a solution of compound 1 (5 mg, 0.0058 mmol, 1.0 equiv.) in THF (1 mL) and water (1 mL) was added lithium hydroxide (1 mg, 0.0346 mmol, 6.0 equiv.) at room temperature. The mixture was stirred at room temperature for another 1 hrs. The pH was adjusted to 3.0 by HCl (6N) and the aqueous phase was extracted with EtOAc (3×10 mL). The organic phase was combined, dried over $Na_2SO_4$, and concentrated. TFA (1 mL) and DCM (1 mL) was added into the residue and the mixture was stirred at room temperature for another 3 hr. The solvent was removed by rotary evaporator. LC-MS: calculated [M+H]+ 754.38, found 755.

Synthesis of Structure 29b ((S)-3-(4-(3-((14-azido-3,6,9,12-tetraoxatetradecyl)oxy)naphthalen-1-yl)phenyl)-3-(2-(4-((4-methylpyridin-2-yl)amino)butanamido)acetamido)propanoic Acid)

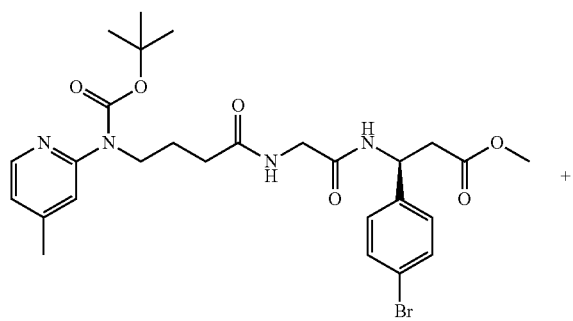

1

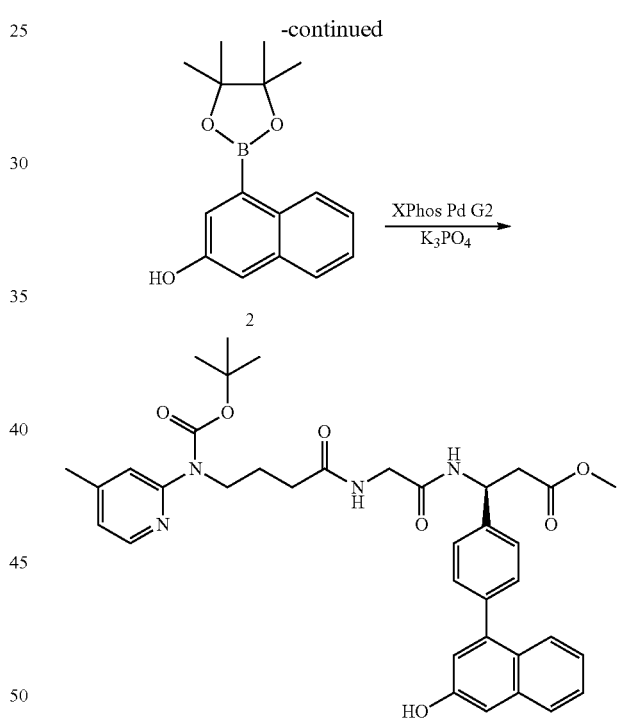

Compound 1 (100 mg, 0.169 mmol, 1.0 equiv.), compound 2 (68 mg, 0.253 mmol, 1.5 equiv.), XPhos Pd G2 (3 mg, 0.0034 mmol, 0.02 equiv.), and $K_3PO_4$ (72 mg, 0.338 mmol, 2.0 equiv.) were mixed in a round-bottom flask. The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 10 min and the reaction was kept at 40° C. for 2 hrs. The reaction was quenched with water (10 mL), and the aqueous phase was extracted with ethyl acetate (3×10 mL). The organic phase was combined, dried over $Na_2SO_4$, and concentrated. The compound was separated by CombiFlash®using silica gel as the stationary phase and was eluted with 4% methanol in DCM. LC-MS: calculated [M+H]+ 655.31, found 656.

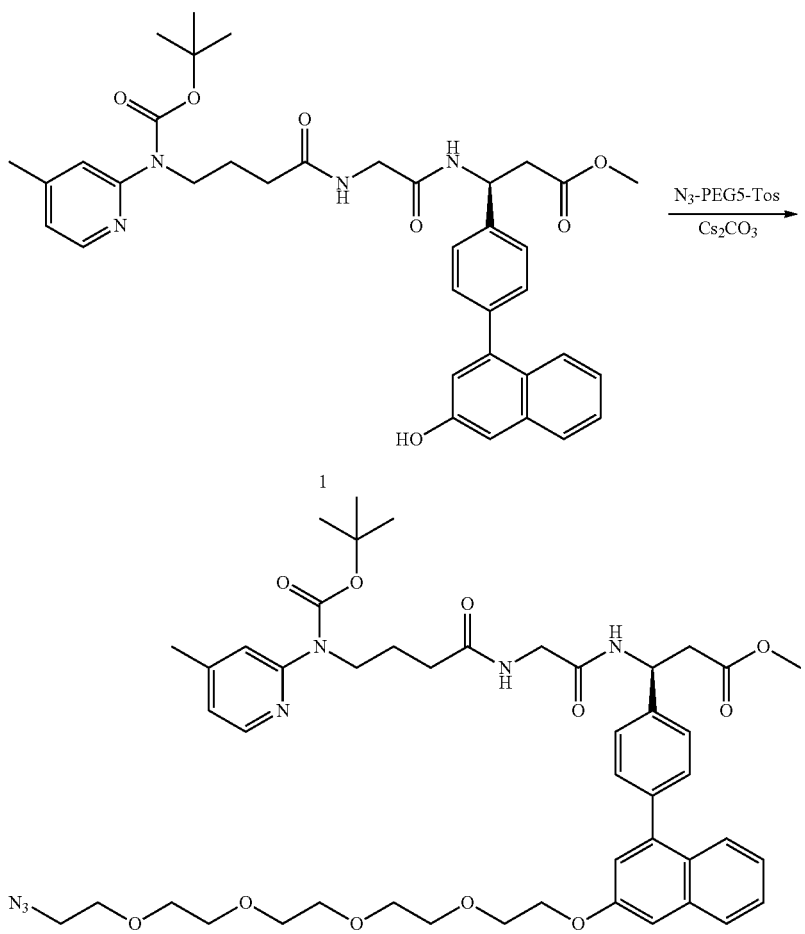

To a solution of compound 1 (100 mg, 0.152 mmol, 1 equiv.) and azido-PEG5-OTs (127 mg, 0.305 mmol, 2 equiv.) in anhydrous DMF (2 mL) was added $Cs_2CO_3$ (100 mg, 0.305 mmol, 2 equiv.) at room temperature. The reaction mixture was stirred for 3 hrs at 40° C. The reaction was quenched by saturated $NaHCO_3$ solution (10 mL) and the aqueous layer was extracted with ethyl acetate (3×5 mL). The organic phase was combined, dried over $Na_2SO_4$, and concentrated. The product was purified by CombiFlash® using silica gel as the stationary phase and was eluted with 34% methanol in DCM. LC-MS: calculated [M+H]+ 900.44, found 901.

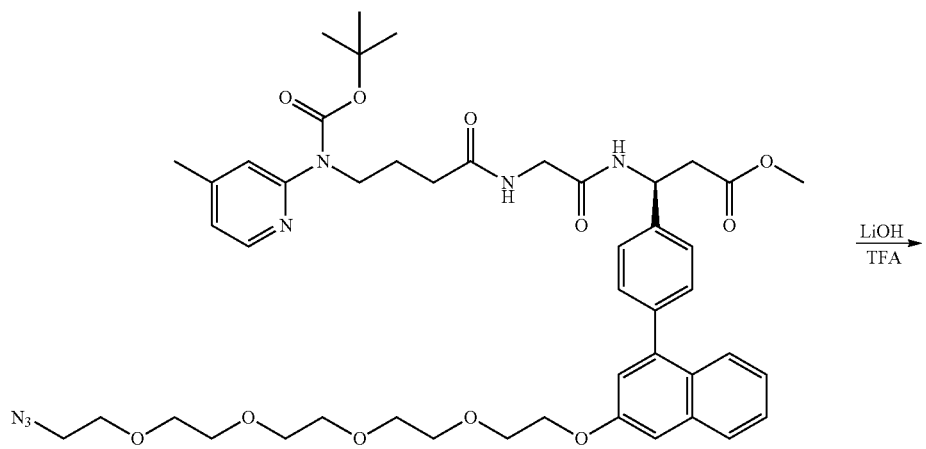

-continued

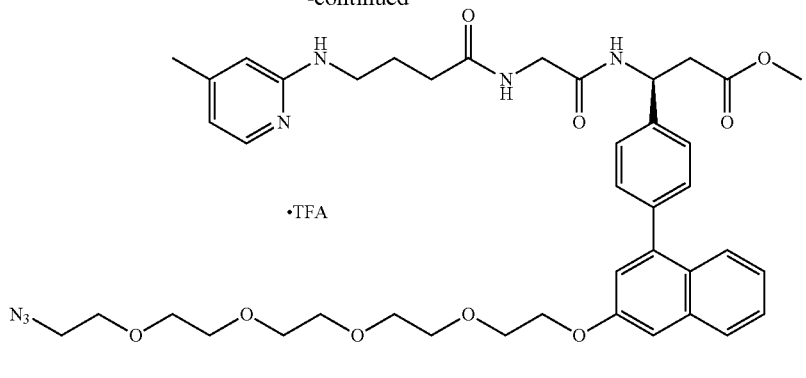

Structure 29b

To a solution of compound 1 (125 mg, 0.138 mmol, 1.0 equiv.) in THF (1 mL) and water (1 mL) was added lithium hydroxide (10 mg, 0.416 mmol, 3.0 equiv.) at room temperature. The mixture was stirred at room temperature for another 1 hrs. The pH was adjusted to 3.0 by HCl (6N) and the aqueous phase was extracted with EtOAc (3×10 mL). The organic phase was combined, dried over $Na_2SO_4$, and concentrated. TFA (3 mL) and DCM (2 mL) was added into the residue and the mixture was stirred at room temperature for another 3 hr. The solvent was removed by rotary evaporator. The product was used directly without further purification. LC-MS: calculated [M+H]+ 786.37, found 787.

Synthesis of Structure 30b ((S)—N-(1-azido-21-(4-(naphthalen-1-yl)phenyl)-19,23-dioxo-3,6,9,12,15-pentaoxa-18,22-diazatetracosan-24-yl)-4-((4-methylpyridin-2-yl)amino)butanamide)

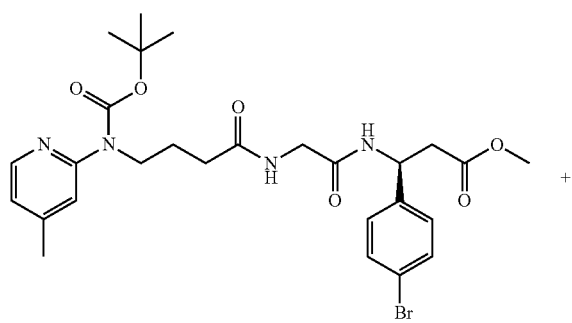

1

+

-continued

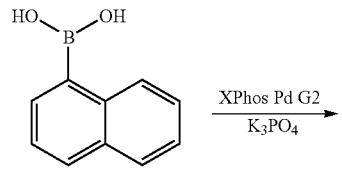

2

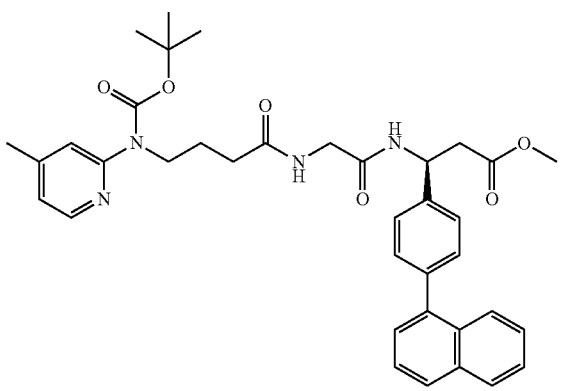

Compound 1 (100 mg, 0.169 mmol, 1.0 equiv.), compound 2 (43 mg, 0.253 mmol, 1.5 equiv.), XPhos Pd G2 (3 mg, 0.0034 mmol, 0.02 equiv.), and $K_3PO_4$ (72 mg, 0.338 mmol, 2.0 equiv.) were mixed in a round-bottom flask. The flask was sealed with a screw-cap septum, and then evacuated and backfilled with nitrogen (this process was repeated a total of 3 times). Then, THF (5 mL) and water (1 mL) were added via syringe. The mixture was bubbled with nitrogen for 10 min and the reaction was kept at 40° C. for 2 hrs. The reaction was quenched with water (10 mL), and the aqueous phase was extracted with ethyl acetate (3×10 mL). The organic phase was combined, dried over Na$_2$SO$_4$, and concentrated. The compound was separated by CombiFlash® using silica gel as the stationary phase and was eluted with 34% methanol in DCM. LC-MS: calculated [M+H]+ 639.31, found 640.

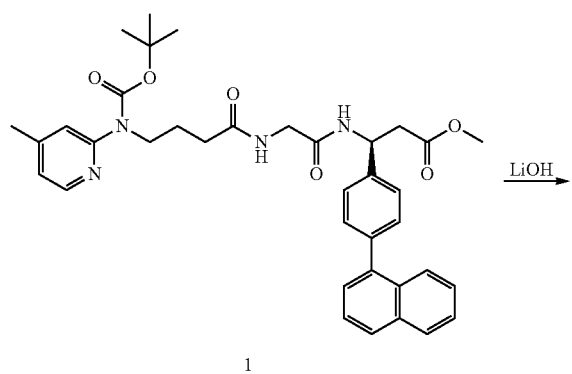

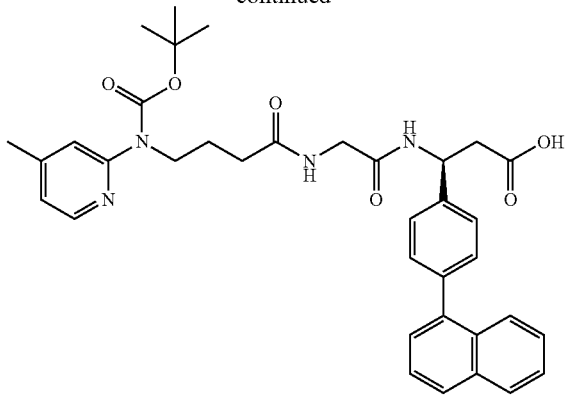

To a solution of compound 1 (90 mg, 0.140 mmol, 1 equiv.) in THF (5 mL) and H$_2$O (5 mL) was added lithium hydroxide (10 mg, 0.422 mmol, 3 equiv.) portion-wise at 0° C. The reaction mixture was warmed to room temperature. After stirring at room temperature for 1 hr, the reaction mixture was acidified by HCl (6 N) to pH 3.0. The aqueous phase was extracted with ethyl acetate (3×10 mL) and the organic layer was combined, dried over Na$_2$SO$_4$, and concentrated. The product was used without further purification. LC-MS: calculated [M+H]+ 625.29, found 625.36.

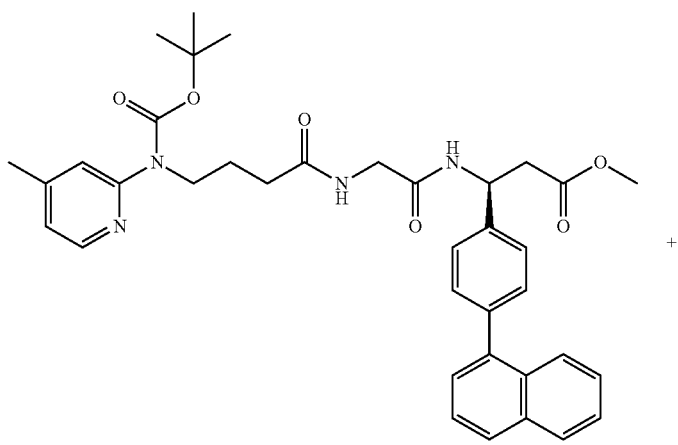

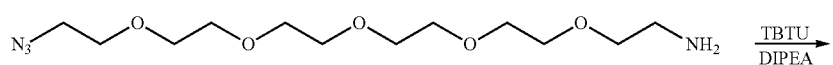

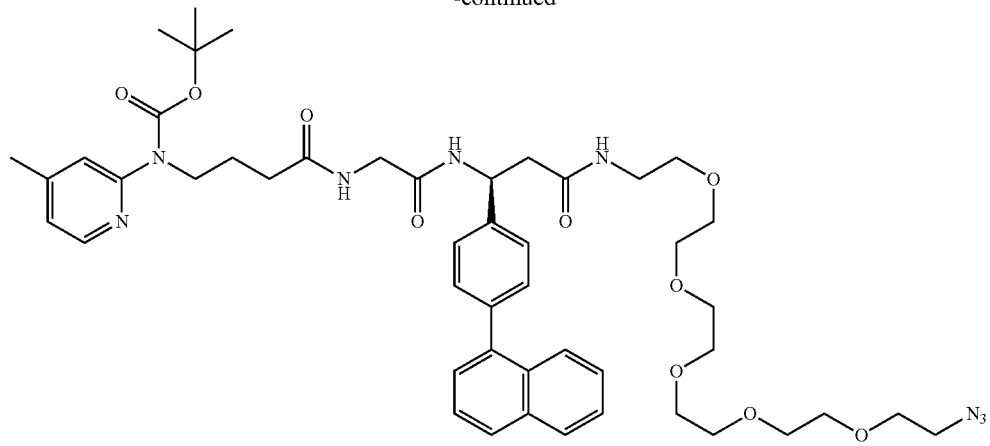

To a solution of compound 1 (88 mg, 0.140 mmol, 1 equiv.), compound 2 (48 mg, 0.154 mmol, 1.1 equiv.), and TBTU (54 mg, 0.169 mmol, 1.2 equiv.) in anhydrous DMF (3 mL) was added diisopropylethylamine (0.074 mL, 0.422 mmol, 3 equiv.) at 0° C. The reaction mixture was warmed to room temperature and stirred for another 1 hr. The reaction was quenched with saturated NaHCO₃ solution (10 mL) and the aqueous phase was extracted with ethyl acetate (3×5 mL). The organic phase was combined, dried over Na₂SO₄, and concentrated. The product was separated by CombiFlash® using silica gel as the stationary phase and was eluted with 4-6% methanol in DCM. LC-MS: calculated [M+H]+ 913.47, found 913.70.

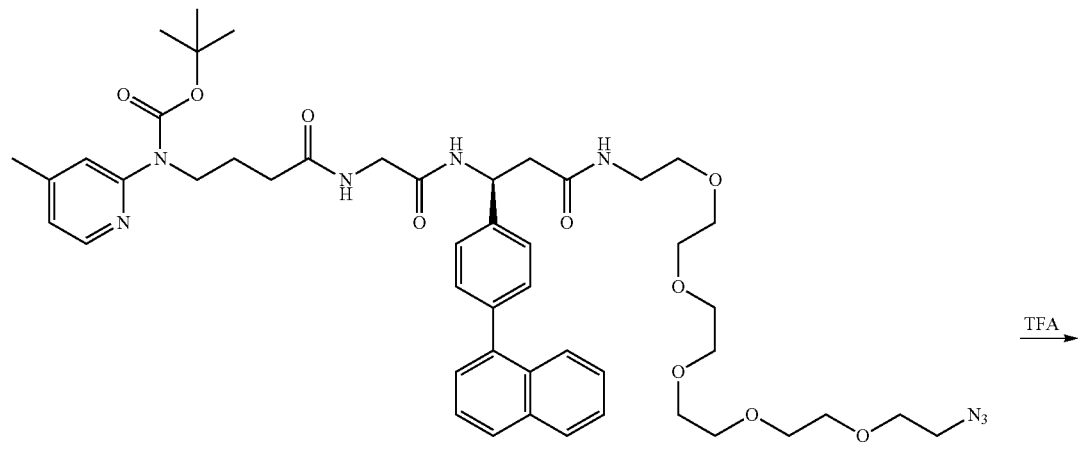

1

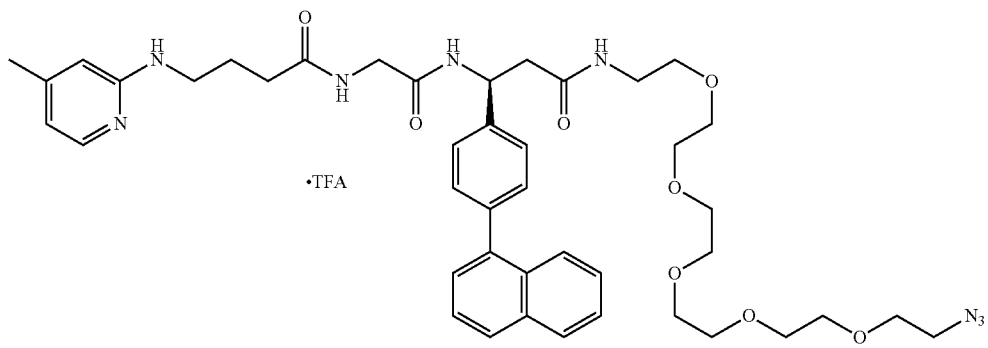

Structure 30b

To a solution of compound 1 (93 mg, 0.101 mmol, 1.0 equiv.) in DCM (2 mL) was added TFA (3 mL) and the mixture was stirred at room temperature for another 3 hr. The solvent was removed by rotary evaporator and the product was separated by CombiFlash® using silica gel as the stationary phase. The product was eluted with 10-12% methanol in dichloromethane. LC-MS: calculated [M+H]+ 813.42, found 813.68.

Synthesis of Structure 31b ((S)-3-(4-(4-((14-azido-3,6,9,12-tetraoxatetradecyl)oxy)naphthalen-1-yl)phenyl)-3-((S)-3-hydroxy-2-(4-((4-methylpyridin-2-yl)amino)butanamido)propanamido)propanoic Acid)

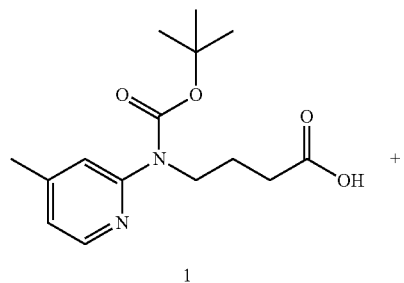

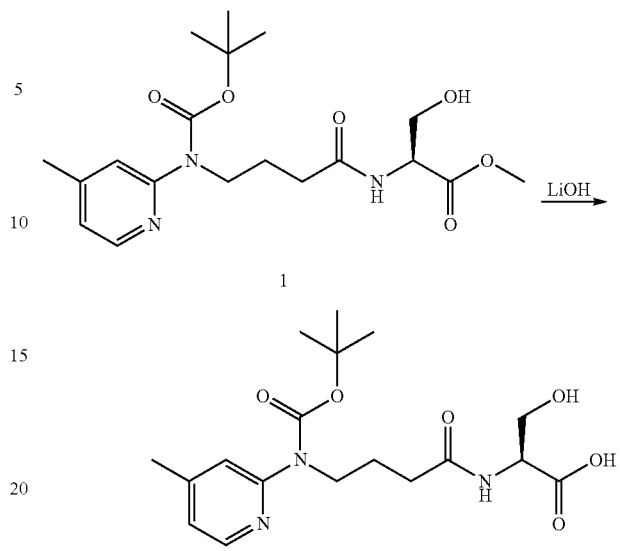

To a solution of compound 1 (196 mg, 0.495 mmol, 1 equiv.) in THF (5 mL) and H₂O (5 mL) was added lithium hydroxide (35 mg, 1.486 mmol, 3 equiv.) portion-wise at 0° C. The reaction mixture was warmed to room temperature. After stirring at room temperature for 1 hr, the reaction mixture was acidified by HCl (6 N) to pH 3.0. The aqueous phase was extracted with ethyl acetate (3×10 mL) and the organic layer was combined, dried over Na₂SO₄, and concentrated. The product was used without further purification. LC-MS: calculated [M+H]+ 382.19, found 382.13.

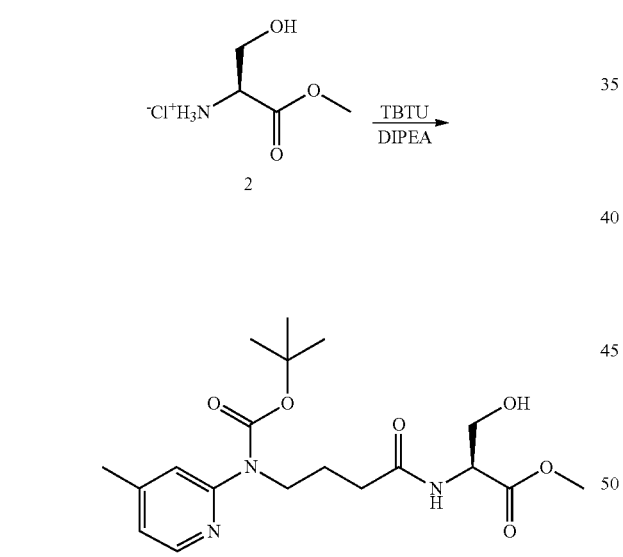

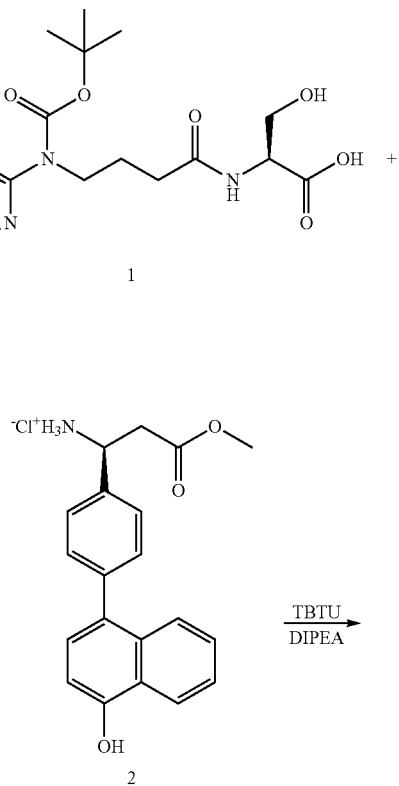

To a solution of compound 1 (150 mg, 0.509 mmol, 1 equiv.), compound 2 (87 mg, 0.560 mmol, 1.1 equiv.), and TBTU (196 mg, 0.196 mmol, 1.2 equiv.) in anhydrous DMF (3 mL) was added diisopropylethylamine (0.074 mL, 0.422 mmol, 3 equiv.) at 0° C. The reaction mixture was warmed to room temperature and stirred for another 1 hr. The reaction was quenched with saturated NaHCO₃ solution (10 mL) and the aqueous phase was extracted with ethyl acetate (3×5 mL). The organic phase was combined, dried over Na₂SO₄, and concentrated. The product was separated by CombiFlash® using silica gel as the stationary phase and was eluted with 4-6% methanol in DCM. LC-MS: calculated [M+H]+ 396.21, found 396.17.

-continued

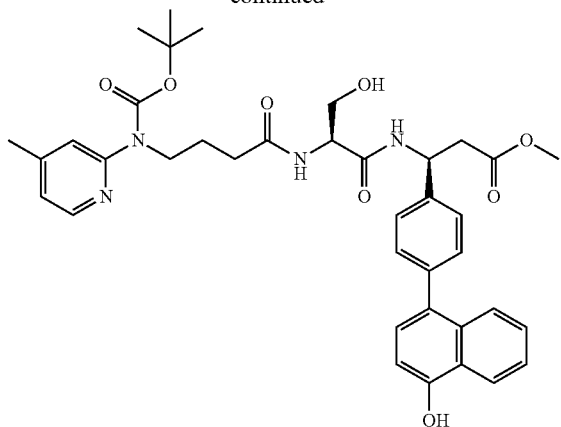

[0479] To a solution of compound 1 (189 mg, 0.495 mmol, 1 equiv.), compound 2 (195 mg, 0.545 mmol, 1.1 equiv.), and TBTU (190 mg, 0.595 mmol, 1.2 equiv.) in anhydrous DMF (5 mL) was added diisopropylethylamine (0.259 mL, 1.486 mmol, 3 equiv.) at 0° C. The reaction mixture was warmed to room temperature and stirred for another 1 hr. The reaction was quenched with saturated $NaHCO_3$ solution (10 mL) and the aqueous phase was extracted with ethyl acetate (3×10 mL). The organic phase was combined, dried over $Na_2SO_4$, and concentrated. The product was separated by CombiFlash® using silica gel as the stationary phase and was eluted with 4-6% methanol in DCM. LC-MS: calculated [M+H]+ 685.32, found 685.58.

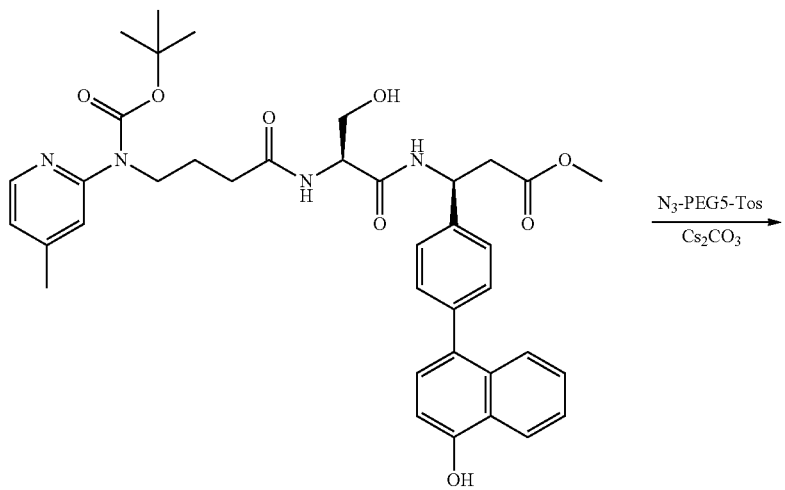

1

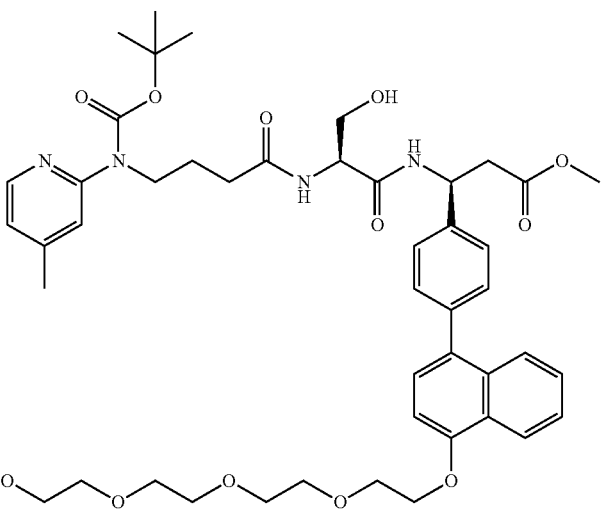

To a solution of compound 1 (75 mg, 0.109 mmol, 1 equiv.) and azido-PEG5-OTs (91 mg, 0.219 mmol, 2 equiv.) in anhydrous DMF (2 mL) was added $Cs_2CO_3$ (71 mg, 0.219 mmol, 2 equiv.) at room temperature. The reaction mixture was stirred overnight at 40° C. The reaction was quenched by saturated $NaHCO_3$ solution (10 mL) and the aqueous layer was extracted with ethyl acetate (3×10 mL). The organic phase was combined, dried over $Na_2SO_4$, and concentrated. The product was purified by CombiFlash® using silica gel as the stationary phase and was eluted with 4% methanol in DCM. The yield is 29%. LC-MS: calculated [M+H]+ 930.45, found 930.90.

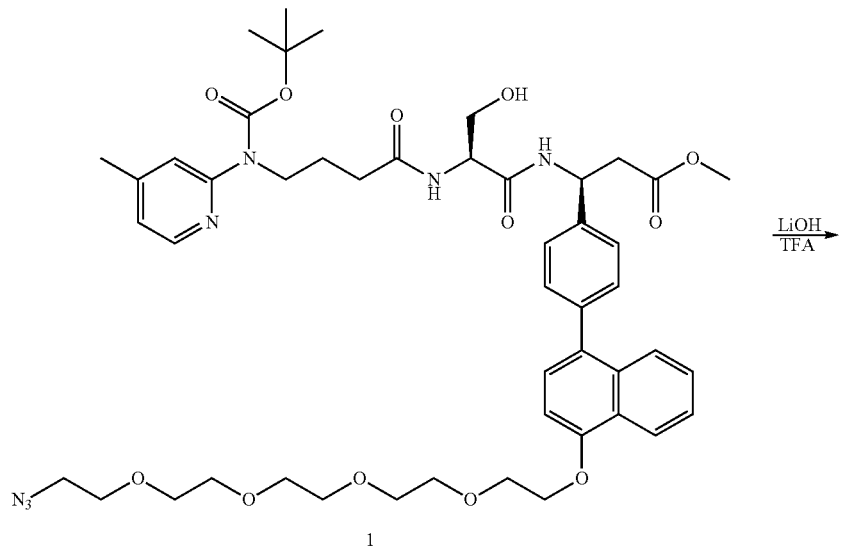

1

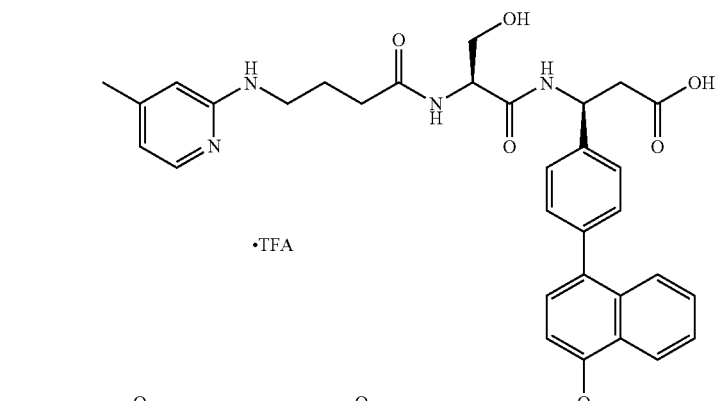

Structure 31b

To a solution of compound 1 (30 mg, 0.0323 mmol, 1.0 equiv.) in THF (1 mL) and water (1 mL) was added lithium hydroxide (2.3 mg, 0.0968 mmol, 3.0 equiv.) at room temperature. The mixture was stirred at room temperature for another 1 hrs. The pH was adjusted to 3.0 by HCl (6N) and the aqueous phase was extracted with EtOAc (3×10 mL). The organic phase was combined, dried over $Na_2SO_4$, and concentrated. TFA (2 mL) and DCM (1 mL) was added into the residue and the mixture was stirred at room temperature for another 3 hr. The solvent was removed by rotary evaporator and the product was separated by CombiFlash® using silica gel as the stationary phase. The product was eluted with 12-15% methanol in dichloromethane. LC-MS: calculated [M+H]+ 816.39, found 816.92.

315

Synthesis of Structure 32b ((S)-4-(((S)-1-(4-(4-((14-azido-3,6,9,12-tetraoxatetradecyl)oxy)naphthalen-1-yl)phenyl)-2-carboxyethyl)amino)-3-(4-((4-methylpyridin-2-yl)amino)butanamido)-4-oxobutanoic Acid)

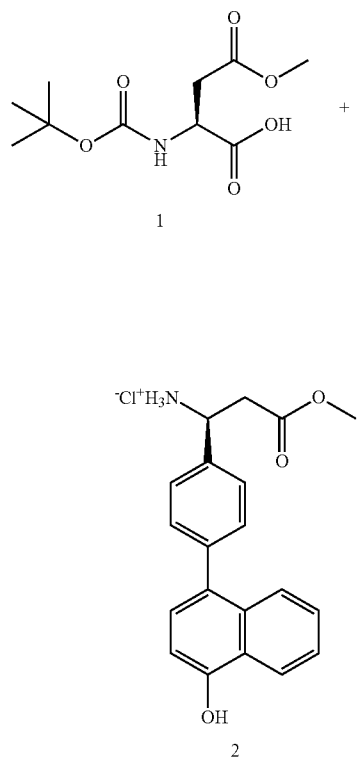

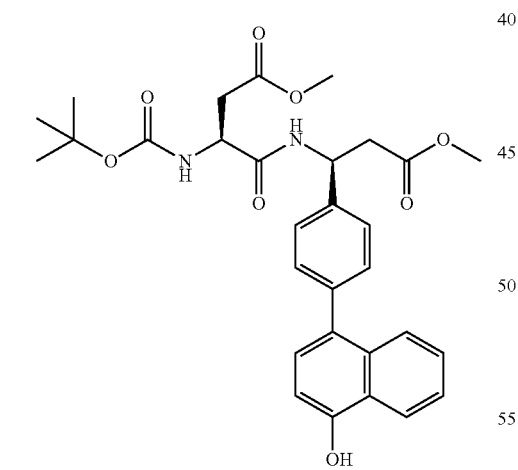

To a solution of compound 1 (100 mg, 0.404 mmol, 1 equiv.), compound 2 (160 mg, 0.444 mmol, 1.1 equiv.), and TBTU (155 mg, 0.485 mmol, 1.2 equiv.) in anhydrous DMF (2 mL) was added diisopropylethylamine (0.211 mL, 1.213 mmol, 3 equiv.) at 0° C. The reaction mixture was warmed to room temperature and stirred for another 1 hr. The reaction was quenched with saturated NaHCO₃ solution (10 mL) and the aqueous phase was extracted with ethyl acetate (3×5 mL). The organic phase was combined, dried over Na₂SO₄, and concentrated. The product was separated by CombiFlash® using silica gel as the stationary phase and was eluted with 2-3% methanol in DCM. LC-MS: calculated [M+H]+ 551.23, found 551.45.

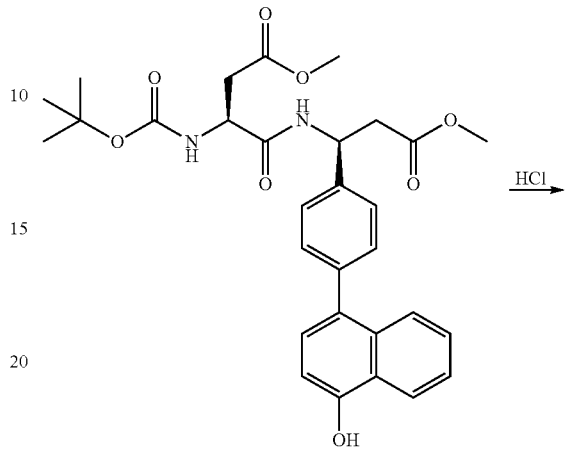

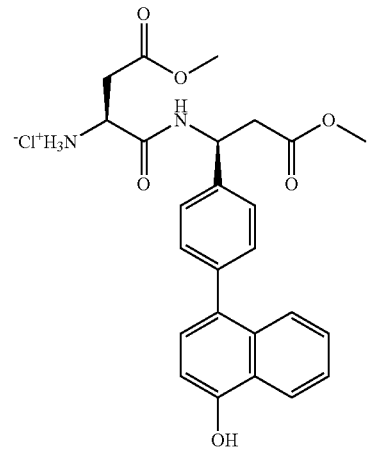

Compound 1 (0.164 g, 0.297 mmol, 1.0 equiv.) was cooled by ice bath. HCl in dioxane (0.745 mL, 2.978 mmol, 10 equiv.) was added into the flask. The reaction was warmed to room temperature and stirred for another 1 hr. The solvent was removed by rotary evaporator and the product was directly used without further purification. LC-MS: calculated [M+H]+ 451.18, found 451.35.

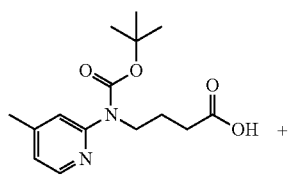

1

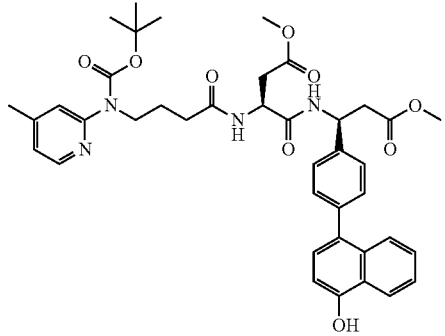

5

10

15

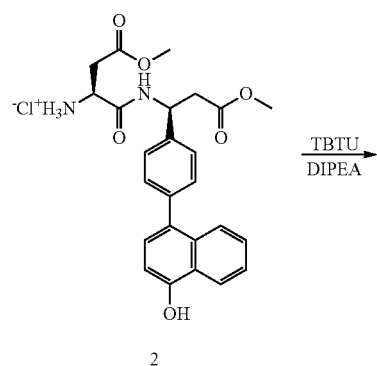

2

To a solution of compound 1 (100 mg, 0.404 mmol, 1 equiv.), compound 2 (160 mg, 0.444 mmol, 1.1 equiv.), and TBTU (155 mg, 0.485 mmol, 1.2 equiv.) in anhydrous DMF (2 mL) was added diisopropylethylamine (0.211 mL, 1.213 mmol, 3 equiv.) at 0° C. The reaction mixture was warmed to room temperature and stirred for another 1 hr. The reaction was quenched with saturated NaHCO$_3$ solution (10 mL) and the aqueous phase was extracted with ethyl acetate (3×5 mL). The organic phase was combined, dried over Na$_2$SO$_4$, and concentrated. The product was separated by CombiFlash® using silica gel as the stationary phase and was eluted with 3-5% methanol in DCM. LC-MS: calculated [M+H]+ 727.33, found 727.53.

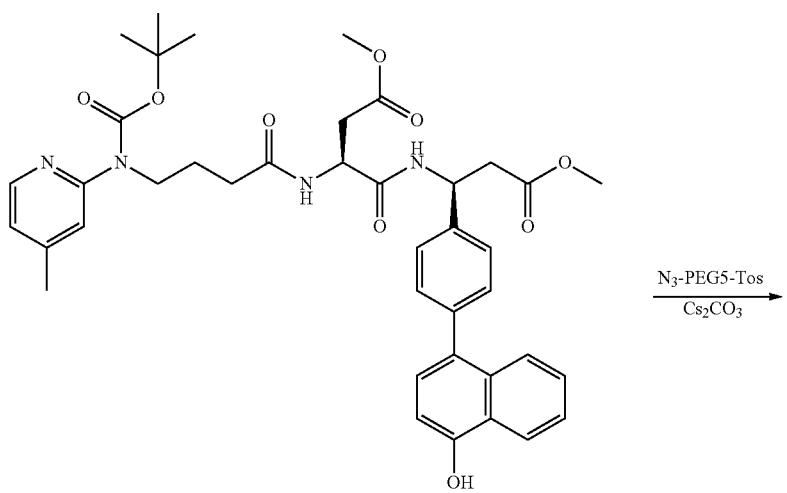

1

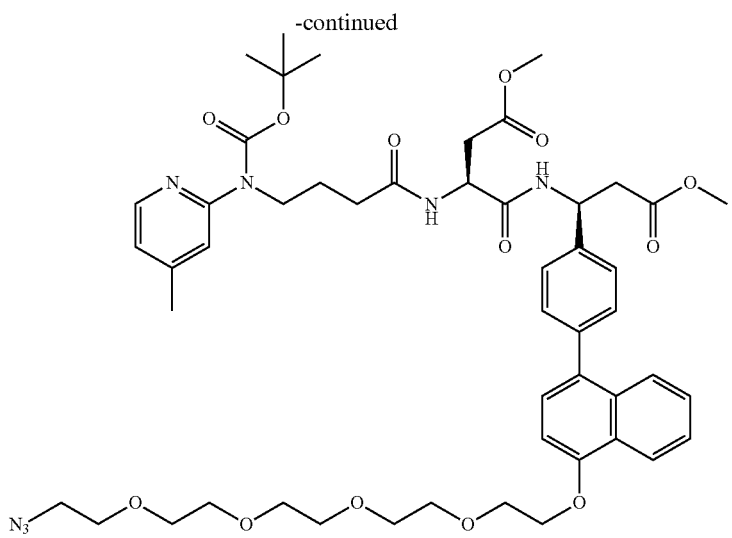

To a solution of compound 1 (150 mg, 0.206 mmol, 1 equiv.) and azido-PEG5-OTs (172 mg, 0.412 mmol, 2 equiv.) in anhydrous DMF (2 mL) was added Cs$_2$CO$_3$ (134 mg, 0.412 mmol, 2 equiv.) at room temperature. The reaction mixture was stirred overnight at room temperature. The reaction was quenched by saturated NaHCO$_3$ solution (10 mL) and the aqueous layer was extracted with ethyl acetate (3×10 mL). The organic phase was combined, dried over Na$_2$SO$_4$, and concentrated. The product was purified by CombiFlash® using silica gel as the stationary phase and was eluted with 4% methanol in DCM. The yield is 29%. LC-MS: calculated [M+H]+ 940.45, found 940.71.

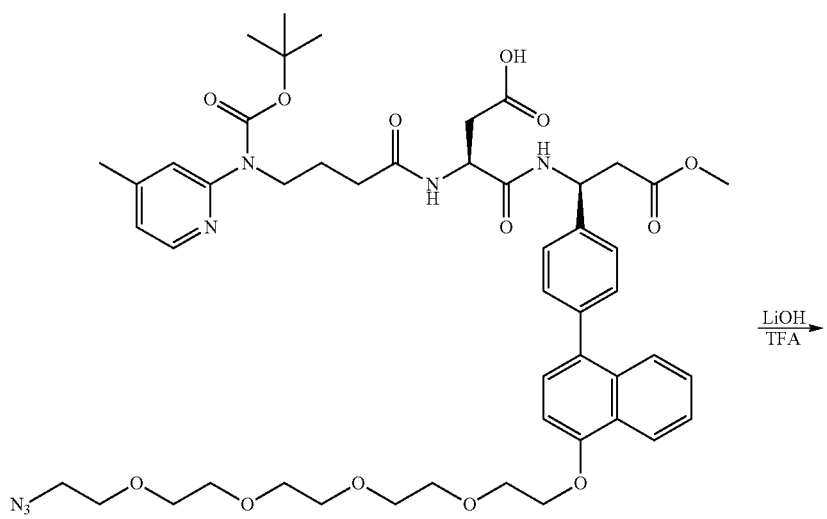

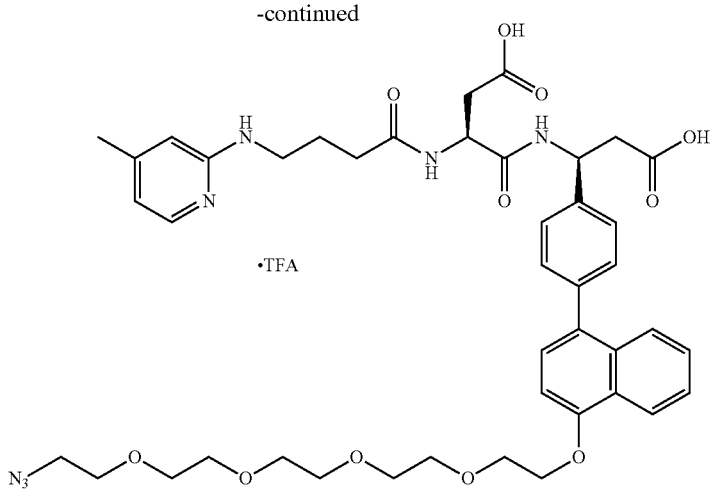

Structure 32b

To a solution of compound 1 (30 mg, 0.0344 mmol, 1.0 equiv.) in THF (1 mL) and water (1 mL) was added lithium hydroxide (2.5 mg, 0.103 mmol, 3.0 equiv.) at room temperature. The mixture was stirred at room temperature for another 1 hrs. The pH was adjusted to 3.0 by HCl (6N) and the aqueous phase was extracted with EtOAc (3×10 mL). The organic phase was combined, dried over $Na_2SO_4$, and concentrated. TFA (2 mL) and DCM (1 mL) was added into the residue and the mixture was stirred at room temperature for another 3 hr. The solvent was removed by rotary evaporator and the product was separated by CombiFlash® using silica gel as the stationary phase. The product was eluted with 20% methanol in dichloromethane. LC-MS: calculated [M+H]+ 844.38, found 844.56.

Synthesis of Structure 33b ((S)-3-((S)-6-amino-2-(4-((4-methylpyridin-2-yl)amino)butanamido)hexanamido)-3-(4-(4-((14-azido-3,6,9,12-tetraoxatetradecyl)oxy)naphthalen-1-yl)phenyl)propanoic Acid)

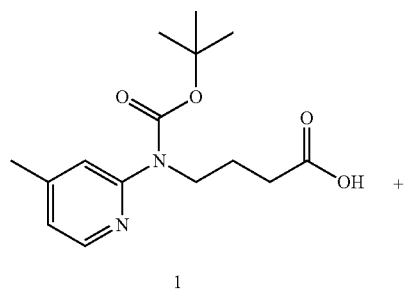

1

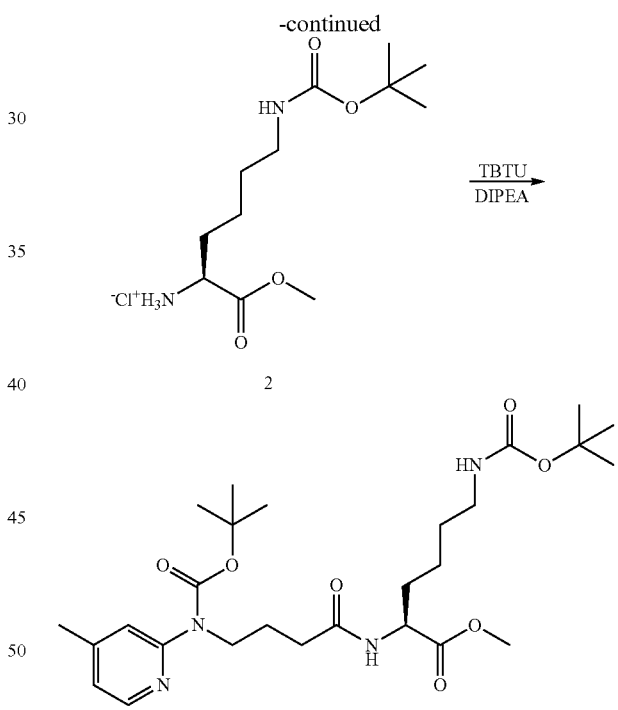

To a solution of compound 1 (150 mg, 0.509 mmol, 1 equiv.), compound 2 (166 mg, 0.560 mmol, 1.1 equiv.), and TBTU (196 mg, 0.611 mmol, 1.2 equiv.) in anhydrous DMF (3 mL) was added diisopropylethylamine (0.266 mL, 1.528 mmol, 3 equiv.) at 0° C. The reaction mixture was warmed to room temperature and stirred for another 1 hr. The reaction was quenched with saturated $NaHCO_3$ solution (10 mL) and the aqueous phase was extracted with ethyl acetate (3×5 mL). The organic phase was combined, dried over $Na_2SO_4$, and concentrated. The product was separated by CombiFlash® using silica gel as the stationary phase and was eluted with 3-5% methanol in DCM. LC-MS: calculated [M+H]+ 537.32, found 537.23.

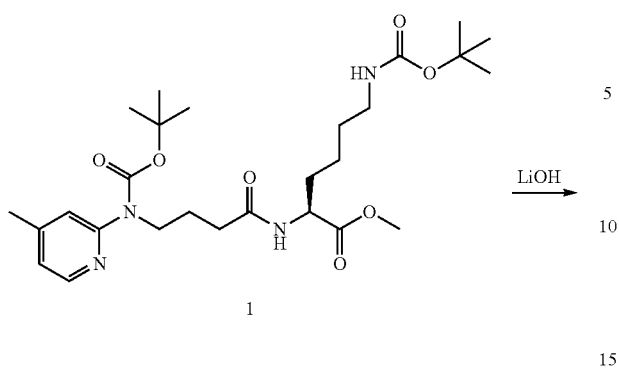

1

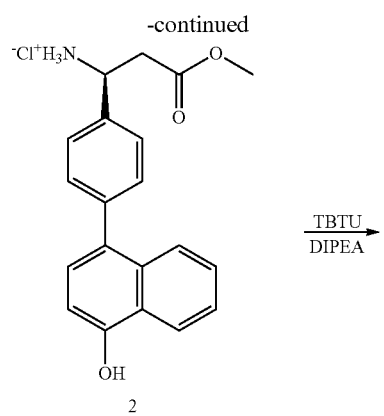

2

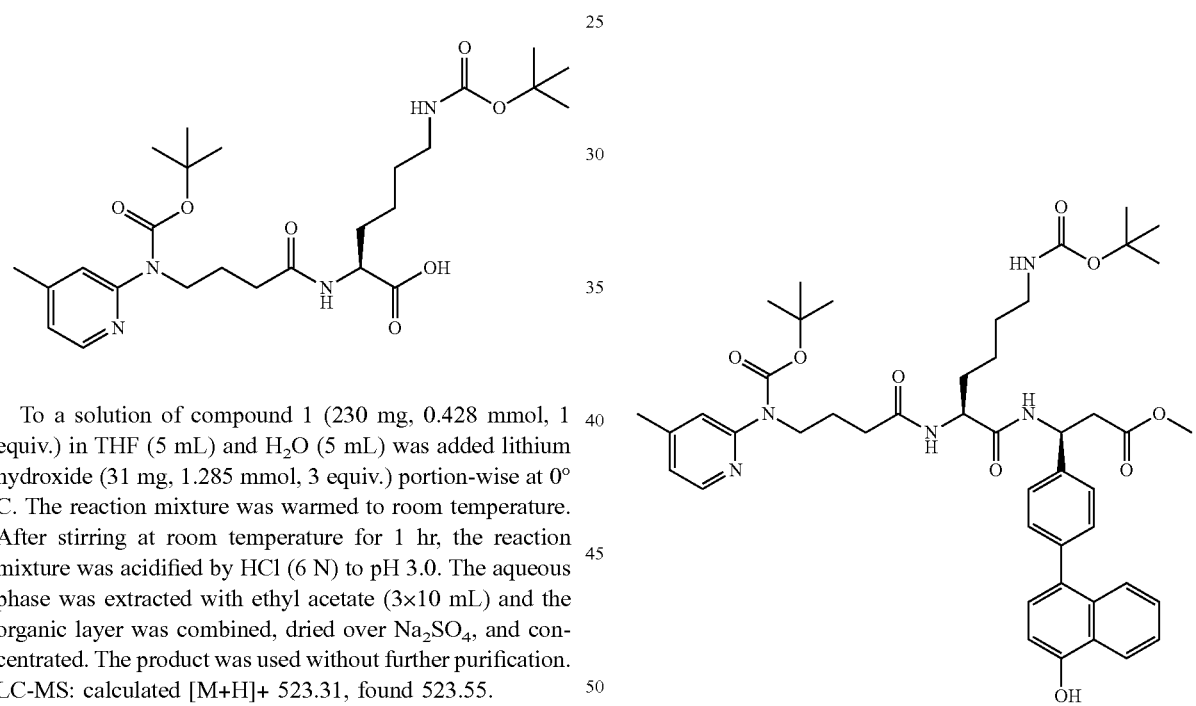

To a solution of compound 1 (230 mg, 0.428 mmol, 1 equiv.) in THF (5 mL) and H₂O (5 mL) was added lithium hydroxide (31 mg, 1.285 mmol, 3 equiv.) portion-wise at 0° C. The reaction mixture was warmed to room temperature. After stirring at room temperature for 1 hr, the reaction mixture was acidified by HCl (6 N) to pH 3.0. The aqueous phase was extracted with ethyl acetate (3×10 mL) and the organic layer was combined, dried over Na₂SO₄, and concentrated. The product was used without further purification. LC-MS: calculated [M+H]+ 523.31, found 523.55.

To a solution of compound 1 (230 mg, 0.440 mmol, 1 equiv.), compound 2 (173 mg, 0.484 mmol, 1.1 equiv.), and TBTU (170 mg, 0.528 mmol, 1.2 equiv.) in anhydrous DMF (2 mL) was added diisopropylethylamine (0.230 mL, 1.320 mmol, 3 equiv.) at 0° C. The reaction mixture was warmed to room temperature and stirred for another 1 hr. The reaction was quenched with saturated NaHCO₃ solution (10 mL) and the aqueous phase was extracted with ethyl acetate (3×5 mL). The organic phase was combined, dried over Na₂SO₄, and concentrated. The product was separated by CombiFlash® using silica gel as the stationary phase and was eluted with 4-6% methanol in DCM. LC-MS: calculated [M+H]+ 826.43, found 826.65.

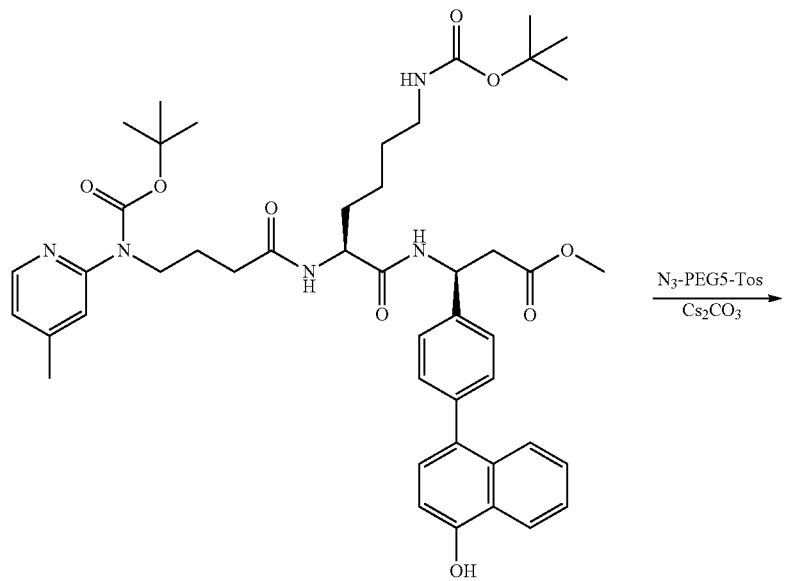

1

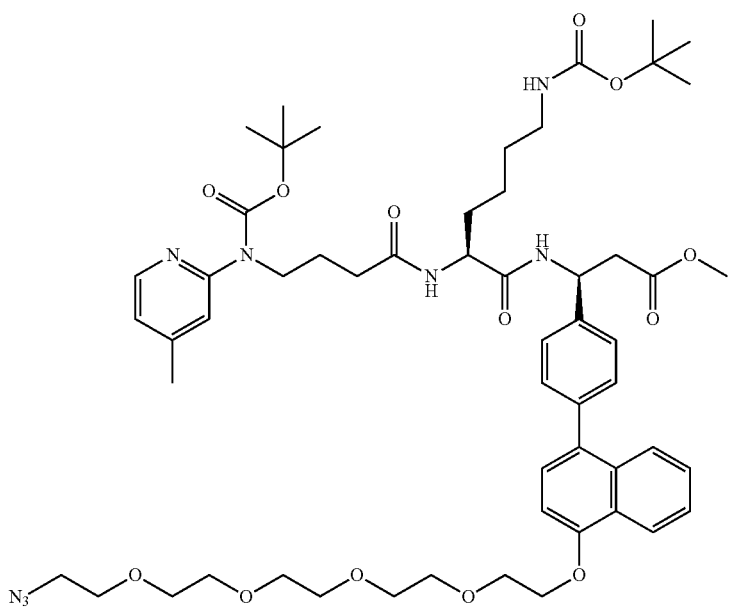

To a solution of compound 1 (150 mg, 0.181 mmol, 1 equiv.) and azido-PEG5-OTs (113 mg, 0.272 mmol, 1.5 equiv.) in anhydrous DMF (2 mL) was added Cs$_2$CO$_3$ (118 mg, 0.363 mmol, 2 equiv.) at room temperature. The reaction mixture was stirred at 40° C. for 3 hrs. The reaction was quenched by saturated NaHCO$_3$ solution (5 mL) and the aqueous layer was extracted with ethyl acetate (3×5 mL). The organic phase was combined, dried over Na$_2$SO$_4$, and concentrated. The product was purified by CombiFlash® using silica gel as the stationary phase and was eluted with 4% methanol in DCM. The yield is 66%. LC-MS: calculated [M+H]+ 1071.57, found 1071.89.

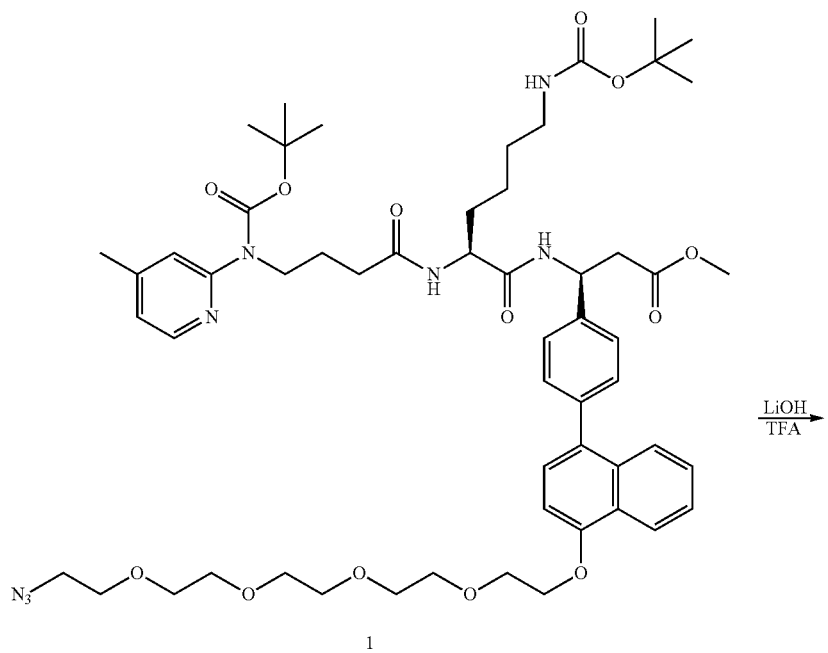

1

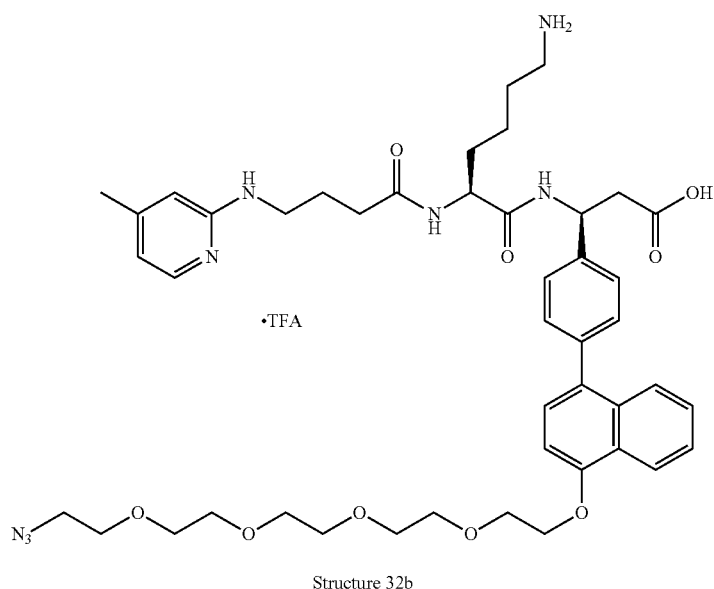

Structure 32b

To a solution of compound 1 (130 mg, 0.121 mmol, 1.0 equiv.) in THF (2 mL) and water (2 mL) was added lithium hydroxide (8.7 mg, 0.364 mmol, 3.0 equiv.) at room temperature. The mixture was stirred at room temperature for another 1 hrs. The pH was adjusted to 3.0 by HCl (6N) and the aqueous phase was extracted with EtOAc (3×10 mL). The organic phase was combined, dried over $Na_2SO_4$, and concentrated. TFA (3 mL) and DCM (2 mL) was added into the residue and the mixture was stirred at room temperature for another 3 hr. The solvent was removed by rotary evaporator and the product was separated by CombiFlash® using silica gel as the stationary phase. The product was eluted with 20% methanol in dichloromethane. LC-MS: calculated [M+H]+ 857.45, found 857.64.

Synthesis of Structure 34b ((S)-3-(4-(4-((14-azido-3,6,9,12-tetraoxatetradecyl)oxy)naphthalen-1-yl)phenyl)-3-((S)-4-methyl-2-(4-((4-methylpyridin-2-yl)amino)butanamido)pentanamido)propanoic Acid)

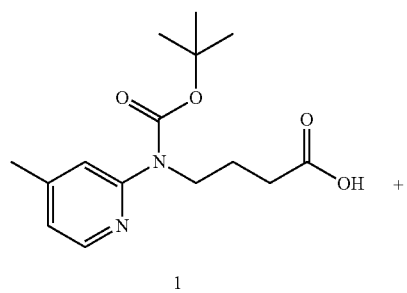

1

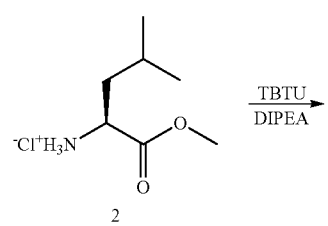

2

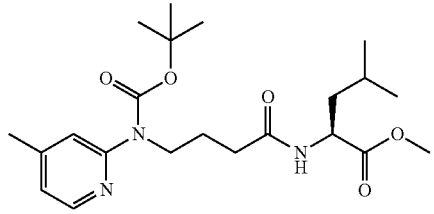

1

To a solution of compound 1 (150 mg, 0.509 mmol, 1 equiv.), compound 2 (101 mg, 0.560 mmol, 1.1 equiv.), and TBTU (196 mg, 0.611 mmol, 1.2 equiv.) in anhydrous DMF (3 mL) was added diisopropylethylamine (0.266 mL, 1.528 mmol, 3 equiv.) at 0° C. The reaction mixture was warmed to room temperature and stirred for another 1 hr. The reaction was quenched with saturated NaHCO₃ solution (5 mL) and the aqueous phase was extracted with ethyl acetate (3×5 mL). The organic phase was combined, dried over Na₂SO₄, and concentrated. The product was separated by CombiFlash® using silica gel as the stationary phase and was eluted with 3-5% methanol in DCM. LC-MS: calculated [M+H]+ 422.26, found 422.36.

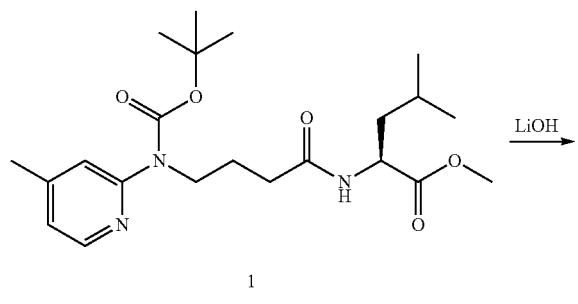

1

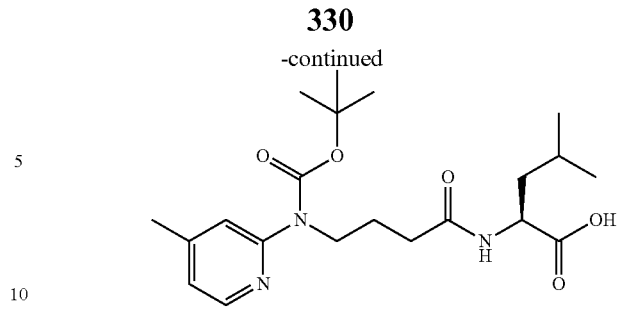

To a solution of compound 1 (186 mg, 0.441 mmol, 1 equiv.) in THF (3 mL) and H₂O (3 mL) was added lithium hydroxide (31 mg, 1.323 mmol, 3 equiv.) portion-wise at 0° C. The reaction mixture was warmed to room temperature. After stirring at room temperature for 1 hr, the reaction mixture was acidified by HCl (6 N) to pH 3.0. The aqueous phase was extracted with ethyl acetate (3×10 mL) and the organic layer was combined, dried over Na₂SO₄, and concentrated. The product was used without further purification. LC-MS: calculated [M+H]+ 408.24, found 408.23.

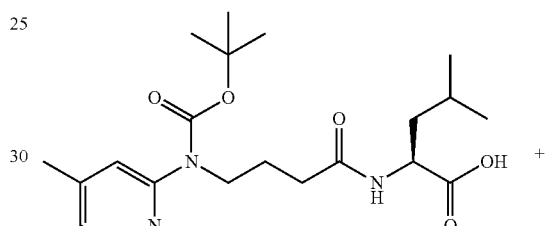

1

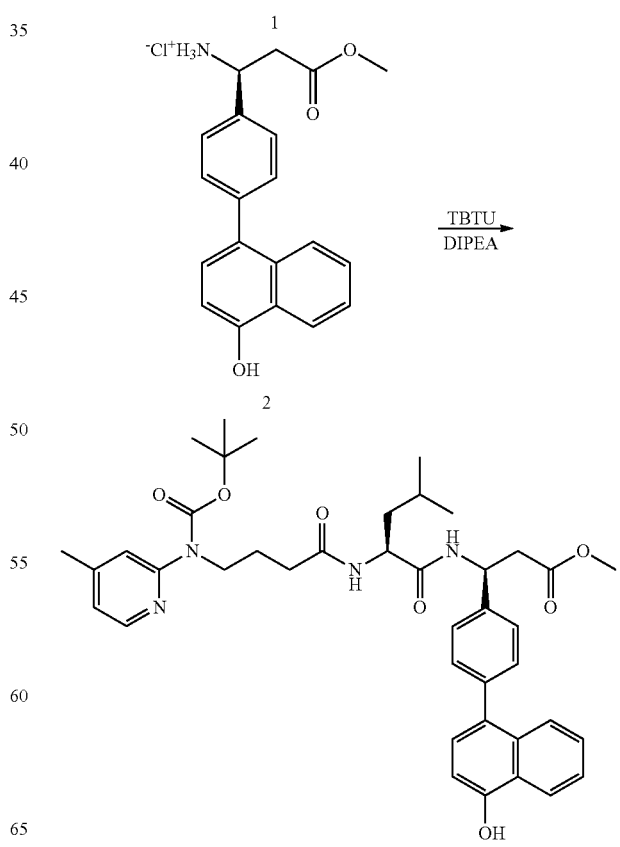

2

To a solution of compound 1 (168 mg, 0.412 mmol, 1 equiv.), compound 2 (162 mg, 0.453 mmol, 1.1 equiv.), and TBTU (159 mg, 0.494 mmol, 1.2 equiv.) in anhydrous DMF (2 mL) was added diisopropylethylamine (0.215 mL, 1.237 mmol, 3 equiv.) at 0° C. The reaction mixture was warmed to room temperature and stirred for another 1 hr. The reaction was quenched with saturated NaHCO$_3$ solution (10 mL) and the aqueous phase was extracted with ethyl acetate (3×5 mL). The organic phase was combined, dried over Na$_2$SO$_4$, and concentrated. The product was separated by CombiFlash® using silica gel as the stationary phase and was eluted with 2-4% methanol in DCM. LC-MS: calculated [M+H]+ 711.37, found 711.69.

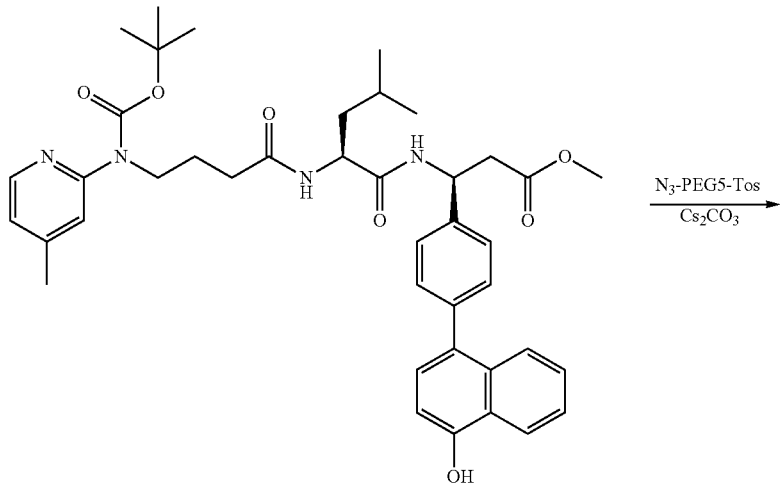

1

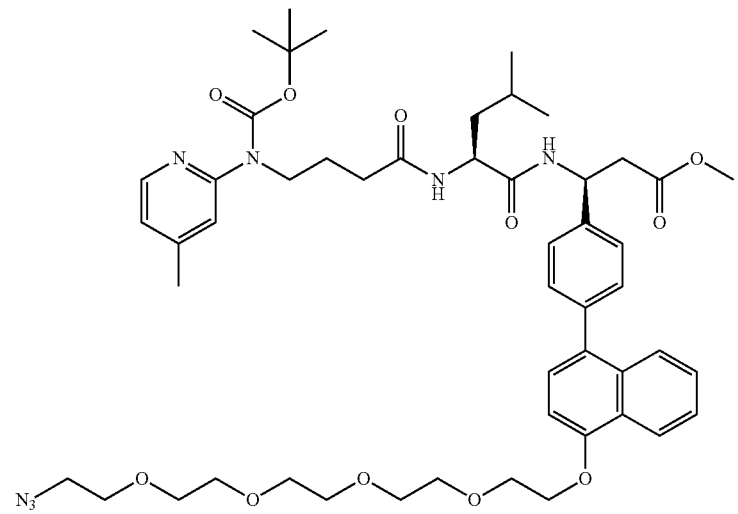

To a solution of compound 1 (150 mg, 0.206 mmol, 1 equiv.) and azido-PEG5-OTs (132 mg, 0.317 mmol, 1.5 equiv.) in anhydrous DMF (2 mL) was added Cs$_2$CO$_3$ (137 mg, 0.422 mmol, 2 equiv.) at room temperature. The reaction mixture was stirred at 40° C. for 3 hrs. The reaction was quenched by saturated NaHCO$_3$ solution (10 mL) and the aqueous layer was extracted with ethyl acetate (3×10 mL). The organic phase was combined, dried over Na$_2$SO$_4$, and concentrated. The product was purified by CombiFlash® using silica gel as the stationary phase and was eluted with 3-4% methanol in DCM. The yield is 82%. LC-MS: calculated [M+H]+ 956.51, found 956.64.

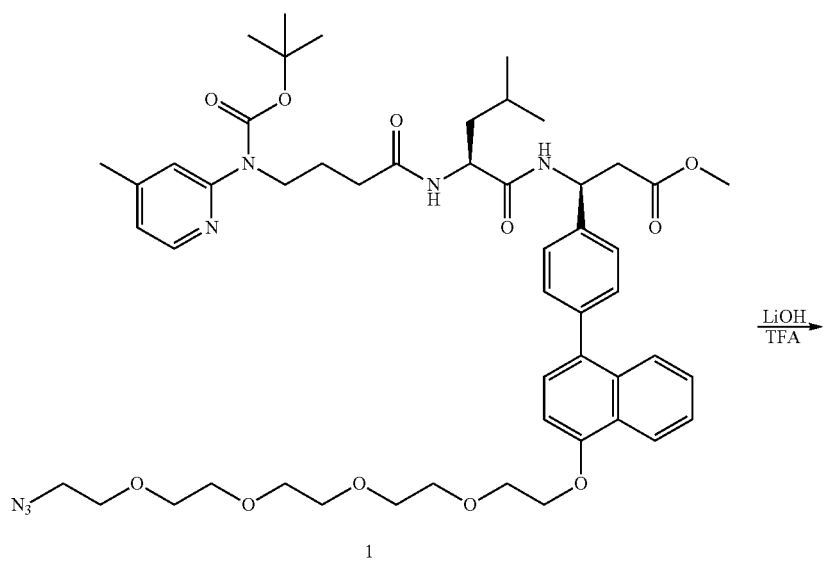

1

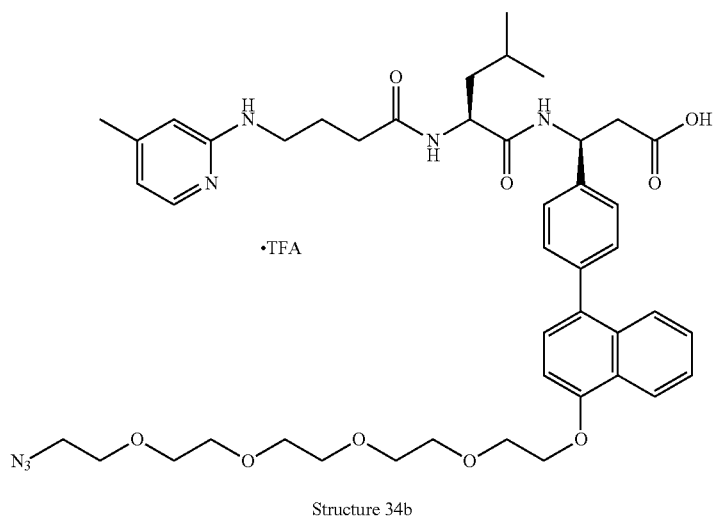

Structure 34b

To a solution of compound 1 (160 mg, 0.167 mmol, 1.0 equiv.) in THF (2 mL) and water (2 mL) was added lithium hydroxide (12 mg, 0.502 mmol, 3.0 equiv.) at room temperature. The mixture was stirred at room temperature for another 1 hrs. The pH was adjusted to 3.0 by HCl (6N) and the aqueous phase was extracted with EtOAc (3×10 mL). The organic phase was combined, dried over $Na_2SO_4$, and concentrated. TFA (3 mL) and DCM (2 mL) was added into the residue and the mixture was stirred at room temperature for another 3 hr. The solvent was removed by rotary evaporator and the product was separated by CombiFlash® using silica gel as the stationary phase. The product was eluted with 8-10% methanol in dichloromethane. LC-MS: calculated [M+H]+ 842.44, found 842.67.

Synthesis of Structure 35b ((S)-3-(4-(4-((14-azido-3,6,9,12-tetraoxatetradecyl)oxy)naphthalen-1-yl)phenyl)-3-((2S,3R)-3-hydroxy-2-(4-((4-methylpyridin-2-yl)amino)butanamido)butanamido)propanoic Acid)

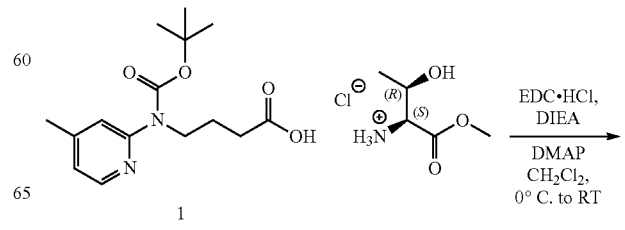

1

335

-continued

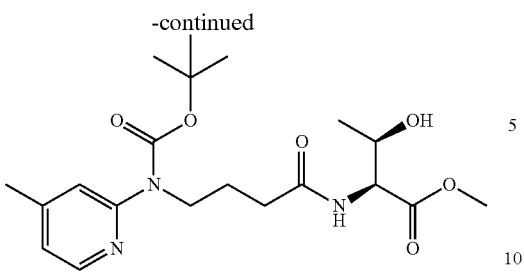

5

To a vial containing L-threonine-OMe HCl (1.000 g, 5.896 mmol, 1.3 eq) was added compound 1 (1.335 g, 4.535 mmol, 1 eq), dimethylaminopyridine (0.277 g, 2.268 mmol, 0.5 eq), and $CH_2Cl_2$ (13.3 mL). To the mixture was added diisopropylamine (2.054 mL, 11.792 mmol, 2.6 eq) and the resulting solution was cooled to 0° C. EDC.HCl (1.130 g, 5.896 mmol, 1.3 eq) was added and the reaction was allowed to stir at 0° C. for 30 minutes before warming to room temperature. The reaction was determined to be complete after 16 hours by HPLC and was transferred to a separatory funnel, washed with 66% saturated $NH_4Cl$ (4×20 mL) and saturated $NH_4Cl$ (20 mL). The organic layer was dried over $Na_2SO_4$ and concentrated to yield a viscous oil (1.7588 g, 94.7%) which was carried directly into the next step. LC-MS: calculated $[M+H]^+$: 410.22, found 410.03.

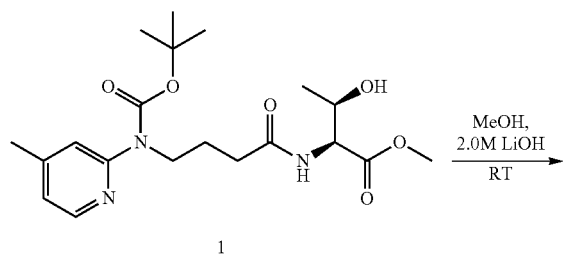

336

-continued

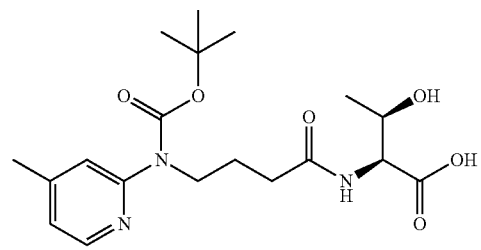

3

Compound 1 was dissolved in MeOH (4.5 mL) and to the mixture was added a 2.0 M solution of LiOH (9.1 mL). The reaction was stirred for 1.5 h and concentrated to remove MeOH. The mixture was then acidified to pH=4 with 20% $KHSO_4$ and extracted with EtOAc (3×15 mL). The combined organic was washed with brine (20 mL), dried over $Na_2SO_4$, and concentrated to obtain 3 as a solid (1.5095 g, 88.9% yield). LC-MS: calculated $[M-H]^-$: 394.21, found 394.37. $^1$H NMR (400 MHz, Chloroform-d) δ 8.26 (d, 1H), 7.27-7.24 (m, 1H), 7.23 (s, 1H), 6.95 (ddd, 1H), 4.60 (dd, 1H), 4.39 (qd, 1H), 3.97-3.77 (m, 2H), 2.36 (s, 3H), 2.41-2.23 (m, 2H), 1.98-1.84 (m, 2H), 1.45 (s, 9H), 1.19 (d, 3H).

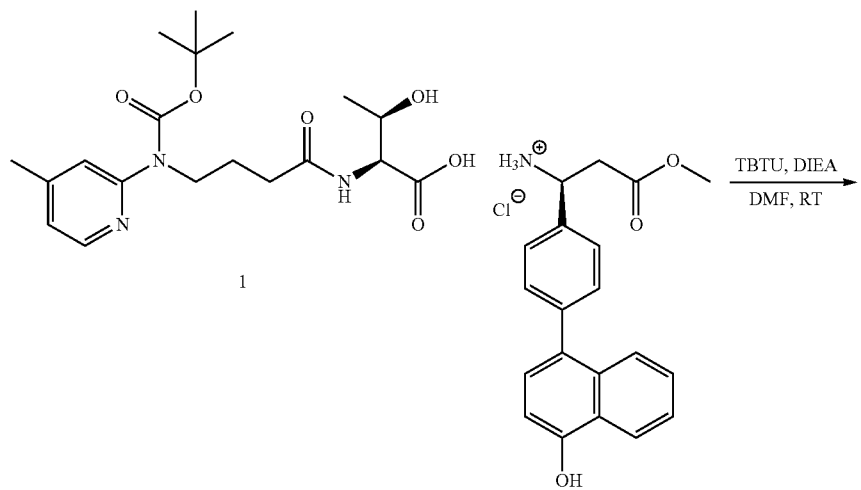

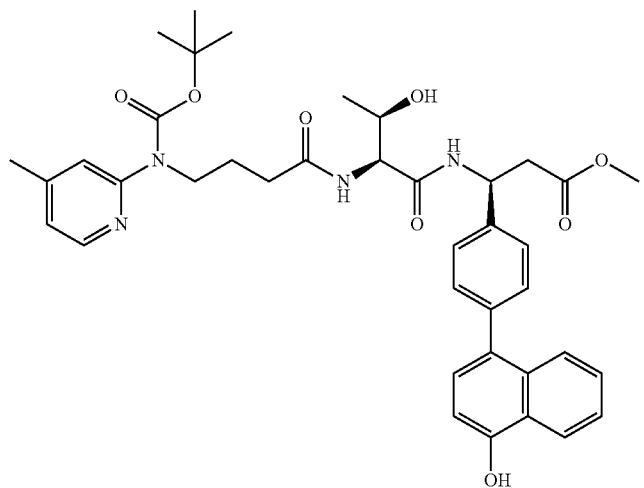

A vial was changed with compound 1 (0.200 g, 0.506 mmol, 1 eq), TBTU (0.195 g, 0.607 mmol, 1.2 eq), DMF (2.0 mL) and DIEA (0.264 mL, 1.517 mmol, 3.0 eq). The reaction was stirred for 2 minutes before the addition of 2 (0.253 g, 0.708 mmol, 1.4 eq). After completion, the reaction was diluted with sat. aq. NaHCO$_3$ (10 mL), extracted with EtOAc (3×5 mL). The combined organic layers were washed with brine (10 mL), dried over Na$_2$SO$_4$, and concentrated. The crude material was purified via column chromatography, eluting with 0-20% MeOH in CH$_2$Cl$_2$ to obtain the product (150.8 mg, 42.7% yield). LC-MS: calculated [M+H]$^+$: 699.33, found 699.53.

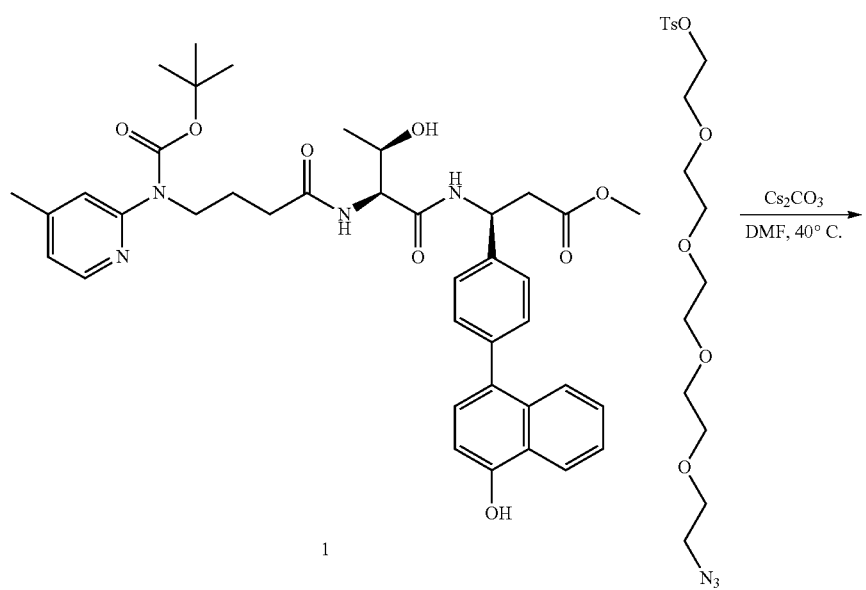

-continued

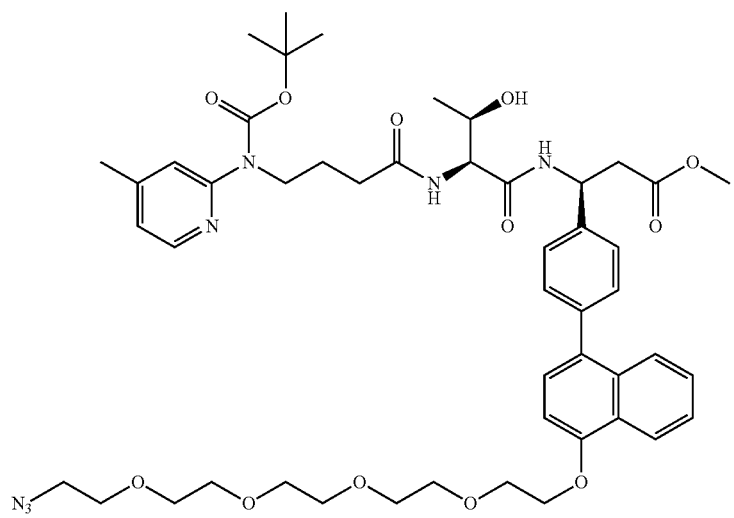

To a vial containing compound 1 (0.151 g, 0.216 mmol, 1 eq) was added $Cs_2CO_3$ (0.106 g, 0.324 mmol, 1.5 eq) and DMF (1.9 mL). $N_3$-PEG5-OTs (0.135 g, 0.324 mmol, 1.5 eq) was added to the mixture, and the reaction stirred at 40° C. After completion, the reaction was diluted with EtOAc (10 mL), sat. aq. $NaHCO_3$ (5 mL) and water (5 mL). The layers were separated and aqueous extracted a total of 3×10 mL with EtOAc. The combined organic layers were dried over $Na_2SO_4$ and concentrated. The crude material was purified via column chromatography, eluting with 0-20% MeOH in $CH_2Cl_2$ to obtain the product (103 mg, 50.4% yield). LC-MS: calculated $[M+H]^+$: 944.47, found 944.56.

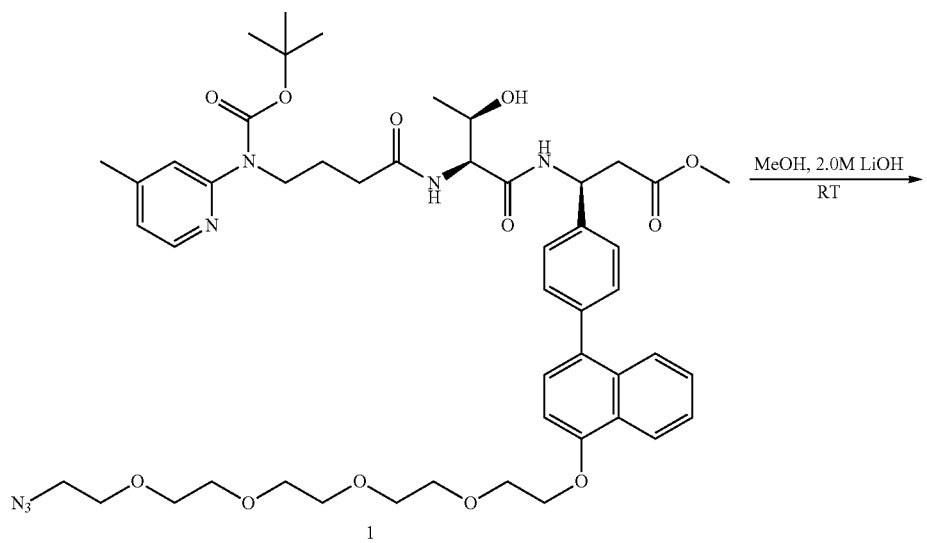

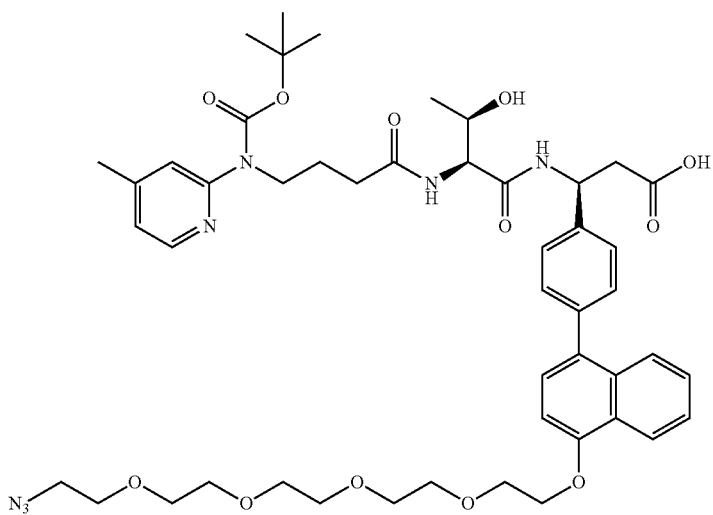

To a vial containing compound 1 (0.103 g, 0.109 mmol, 1 eq) was added MeOH (1.5 mL) and 2.0 M LiOH (2.0 mL). The reaction was stirred at room temperature, then concentrated to remove MeOH, acidified with 20% KHSO$_4$ to pH=2. To the mixture was added EtOAc (5 mL) and water (4 mL). The aqueous layer was extracted with EtOAc (3×5 mL). The combined organic layers were washed with brine (10 mL), dried over Na$_2$SO$_4$, and concentrated to yield the product (0.0879 g, 86.9%). LC-MS: calculated [M+H]$^+$: 930.45, found 930.56.

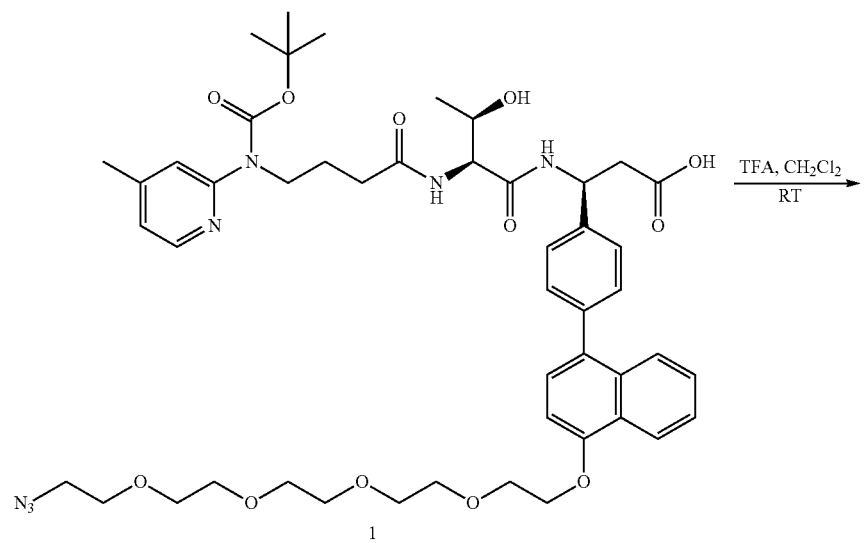

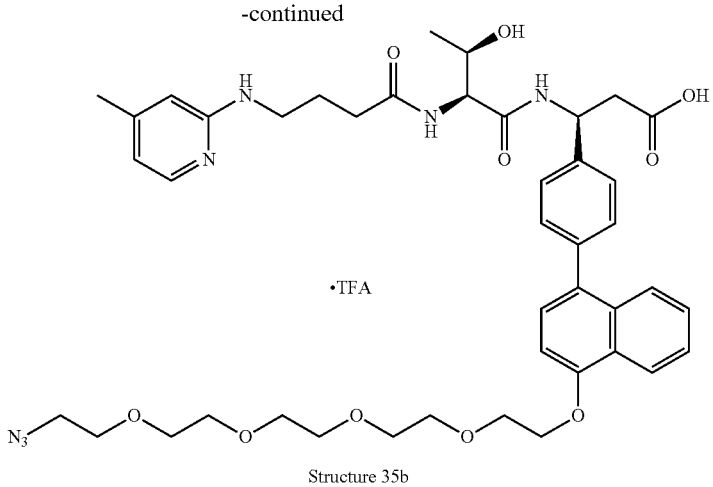

Structure 35b

To a vial containing compound 1 (0.0879 g, 0.0945 mmol, 1 eq) was added CH$_2$Cl$_2$ (0.3 mL) and trifluoroacetic acid (0.64 mL). The solution was stirred at room temperature. After completion (>97% product), the reaction was concentrated, co-evaporating with toluene (3 mL) and then acetonitrile (2×3 mL). The product was obtained with additional TFA present (115.6 mg).

Synthesis of Structure 36b ((S)-3-(4-(4-((14-azido-3,6,9,12-tetraoxatetradecyl)oxy)naphthalen-1-yl)phenyl)-3-((2S,3S)-3-methyl-2-(4-((4-methylpyridin-2-yl)amino)butanamido)pentanamido)propanoic Acid)

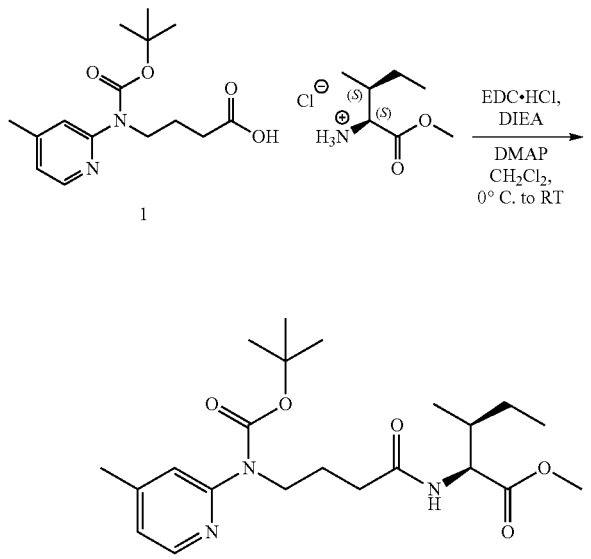

To a vial containing L-isoleucine-OMe HCl (1.000 g, 5.505 mmol, 1.3 eq) was added compound 1 (1.246 g, 4.234 mmol, 1 eq), dimethylaminopyridine (0.259 g, 2.117 mmol, 0.5 eq), and CH$_2$Cl$_2$ (12.5 mL). To the mixture was added diisopropylamine (2.054 mL, 11.792 mmol, 2.6 eq) and the resulting solution was cooled to 0° C. EDC.HCl (1.055 g, 5.505 mmol, 1.3 eq) was added and the reaction was allowed to stir at 0° C. for 30 minutes before warming to room temperature. The reaction was determined to be complete after 16 hours by HPLC and was transferred to a separatory funnel, washed with 66% saturated NH$_4$Cl (4×20 mL) and saturated NH$_4$Cl (1×20 mL). The organic layer was dried over Na$_2$SO$_4$ and concentrated to yield a viscous oil (1.8634 g, wet with CH$_2$Cl$_2$) which was carried directly into the next step. LC-MS: calculated [M+H]$^+$: 422.26, found 422.00.

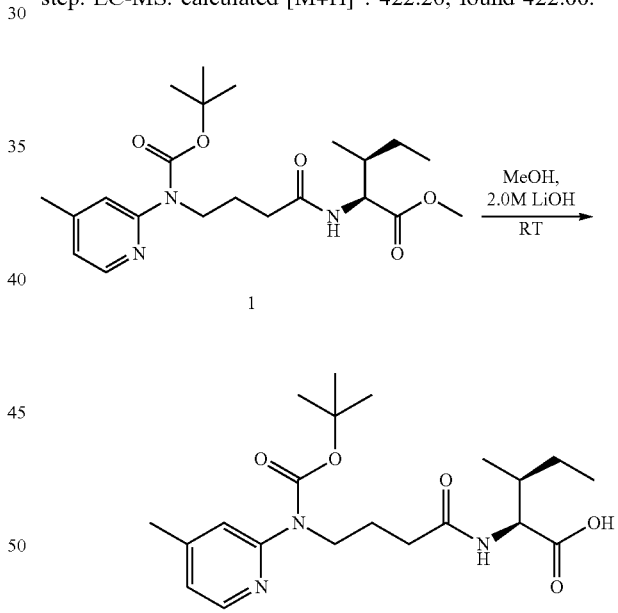

Compound 1 was dissolved in MeOH (4.2 mL) and to the mixture was added a 2.0 mL solution of LiOH (8.5 mL). The reaction was stirred for 1.5 h and concentrated to remove MeOH. The mixture was then acidified to pH=4 with 20% KHSO$_4$ and extracted with EtOAc (3×15 mL). The combined organic was washed with brine (20 mL), dried over Na$_2$SO$_4$, and concentrated to obtain the product as a viscous oil (1.6123 g, 93.4% yield across two steps). LC-MS: calculated [M−H]$^-$: 406.24, found 406.43. $^1$H NMR (400 MHz, Chloroform-d) δ 8.23 (d, 1H), 7.12 (d, 1H), 6.95-6.88 (m, 1H), 4.58 (dd, 1H), 3.99-3.83 (m, 2H), 2.35-2.34 (s, 3H), 2.30 (hept, 2H), 2.00-1.84 (m, 4H), 1.45 (s, 9H), 0.91 (m, 6H).

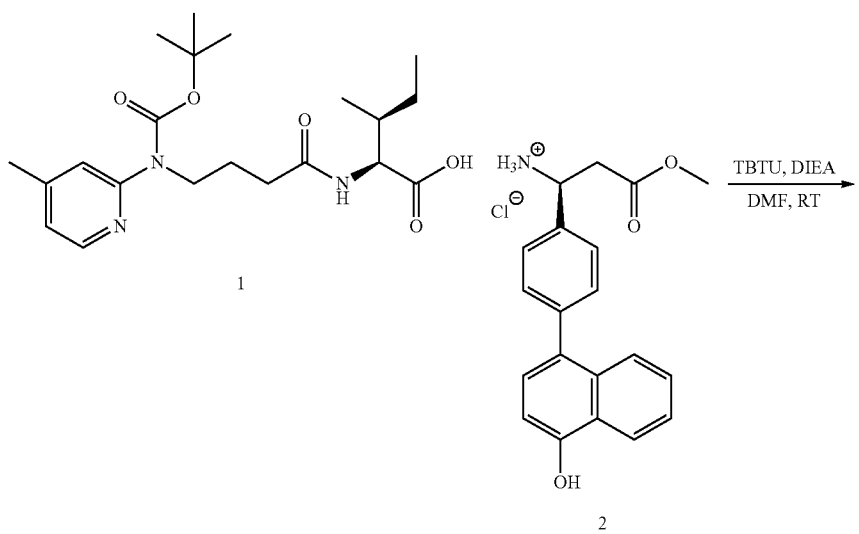

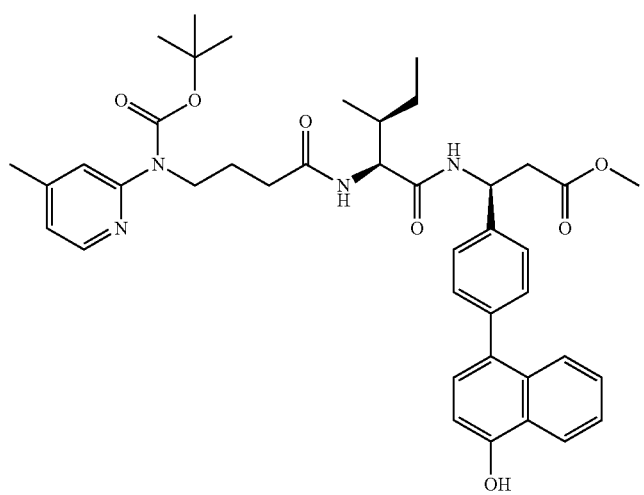

A vial was changed with compound 1 (0.200 g, 0.491 mmol, 1 eq), TBTU (0.189 g, 0.589 mmol, 1.2 eq), DMF (2.0 mL) and DIEA (0.256 mL, 1.472 mmol, 3.0 eq). The reaction was stirred for 2 minutes before the addition of 2 (0.246 g, 0.687 mmol, 1.4 eq). After completion, the reaction was diluted with sat. aq. NaHCO$_3$ (10 mL), extracted with EtOAc (3×5 mL). The combined organic layers were washed with brine (10 mL), dried over Na$_2$SO$_4$, and concentrated. The crude material was purified via column chromatography, eluting with 0-20% MeOH in CH$_2$Cl$_2$ to obtain the product (0.3024 mg, 86.7% yield). LC-MS: calculated [M+H]$^+$: 711.37, found 711.51.

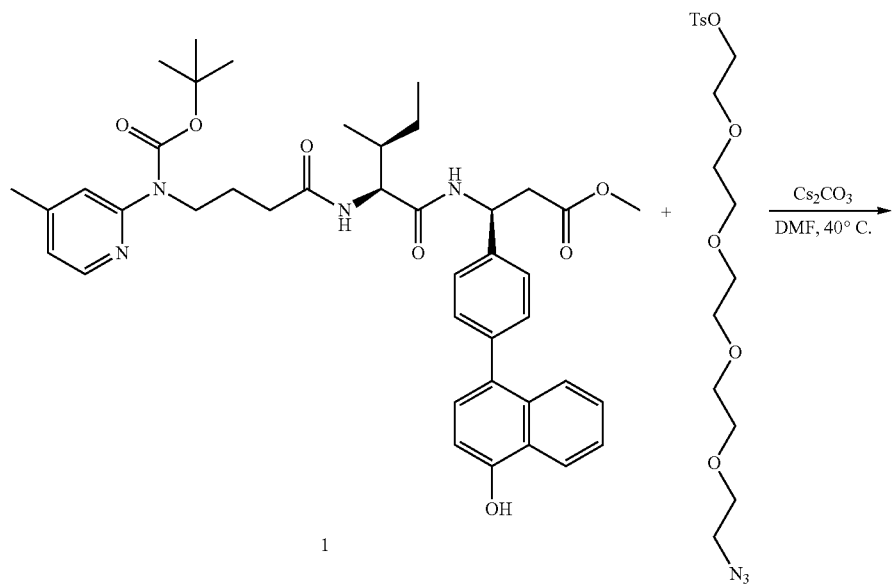

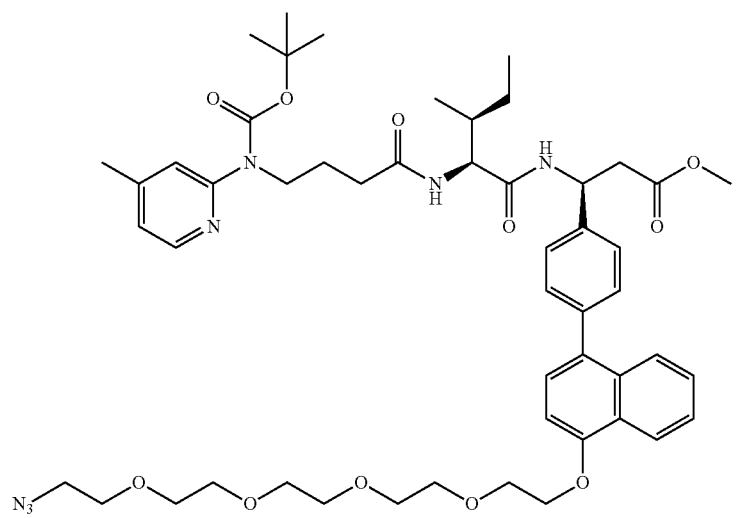

To a vial containing compound 1 (0.170 g, 0.238 mmol, 1 eq) was added Cs$_2$CO$_3$ (0.116 g, 0.358 mmol, 1.5 eq) and DMF (2.1 mL). N$_3$-PEG5-OTs (0.149 g, 0.358 mmol, 1.5 eq) was added to the mixture, and the reaction stirred at 40° C. After completion, the reaction was diluted with EtOAc (10 mL), sat. aq. NaHCO$_3$ (5 mL) and water (5 mL). The layers were separated and aqueous extracted a total of 3×10 mL with EtOAc. Combined organic layers were dried over Na$_2$SO$_4$ and concentrated. The crude material was purified via column chromatography, eluting with 0-20% MeOH in CH$_2$Cl$_2$ to obtain the product (0.1645 g, 72.1% yield). LC-MS: calculated [M+H]$^+$: 956.51, found 956.78.

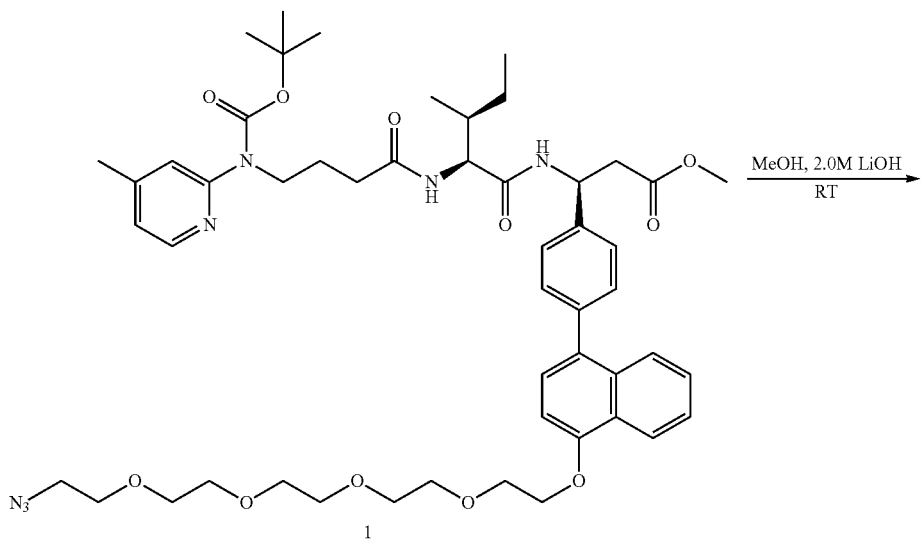

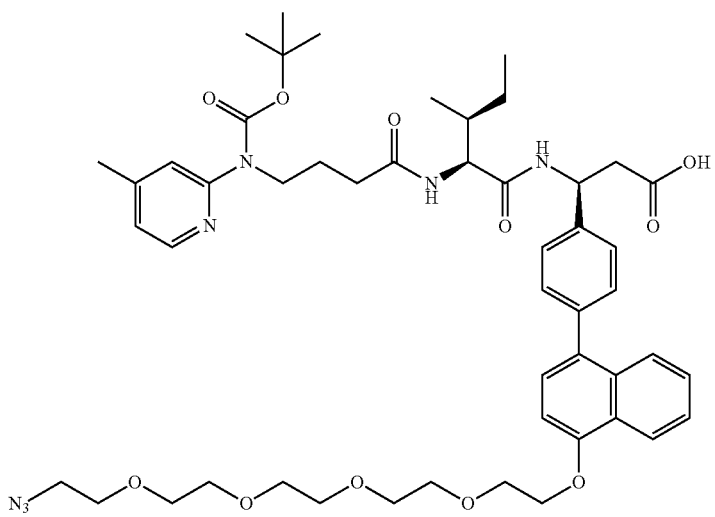

To a vial containing compound 1 (0.164 g, 0.172 mmol, 1 eq) was added MeOH (2.0 mL) and 2.0 M LiOH (3.0 mL). The reaction was stirred at room temperature and monitored by HPLC. Additional LiOH (33 mg, 1.38 mmol, 8 eq), water (5 mL) and MeOH (4 mL) was required to dissolve the material and drive the reaction. HPLC revealed the formation of two new peaks, thought to be diastereomers. Upon reaching >94% conversion, the reaction was concentrated to remove MeOH, acidified with 20% $KHSO_4$ to pH=2. To the mixture was added EtOAc (5 mL) and water (4 mL). The aqueous layer was extracted with EtOAc (4×5 mL). The combined organic layers were washed with brine (10 mL), dried over $Na_2SO_4$, and concentrated to yield the product (0.1417 g, 87.4%). LC-MS: calculated $[M+H]^+$: 942.49, found 942.56.

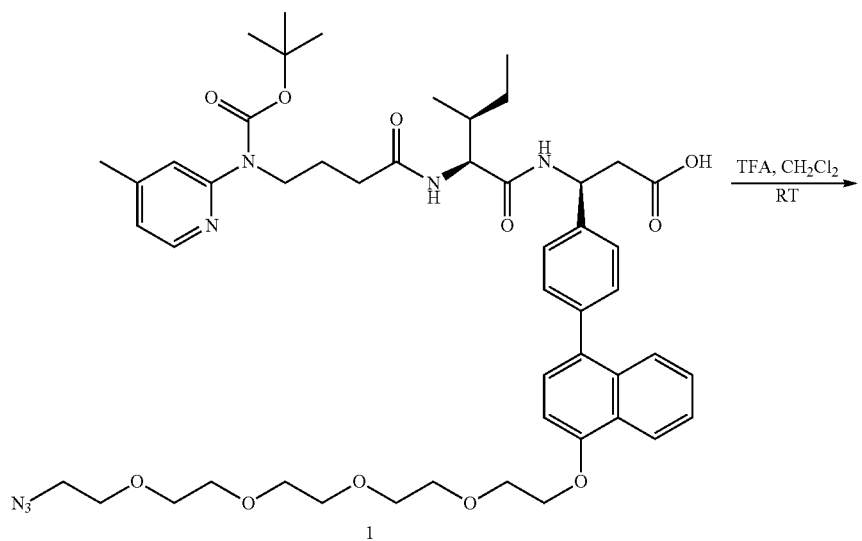

1

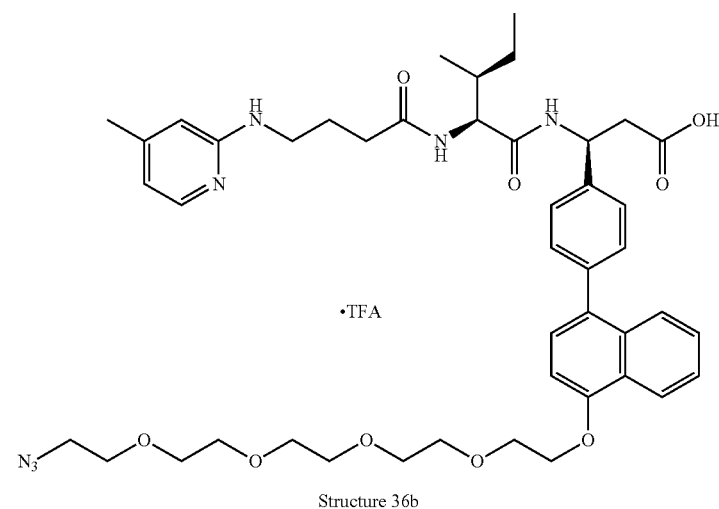

Structure 36b

To a vial containing compound 1 (0.1417 g, 0.1504 mmol, 1 eq) was added CH₂Cl₂ (0.5 mL) and trifluoroacetic acid (1.0 mL). The solution was stirred at room temperature. After completion (>97% product), the reaction was concentrated, co-evaporating with toluene (3 mL) and then acetonitrile (2×3 mL). The product was obtained with additional TFA present (150.3 mg). Two peaks were present through the reaction for both starting material and product. LC-MS: calculated [M+H]$^+$: 842.44, found 842.56. Both product peaks were found to have the same mass, indicating the presence of diastereomers.

Synthesis of Structure 37b ((S)-3-(4-(4-((14-azido-3,6,9,12-tetraoxatetradecyl)oxy)naphthalen-1-yl)phenyl)-3-((R)-3-methyl-2-(4-((4-methylpyridin-2-yl)amino)butanamido)butanamido)propanoic Acid)

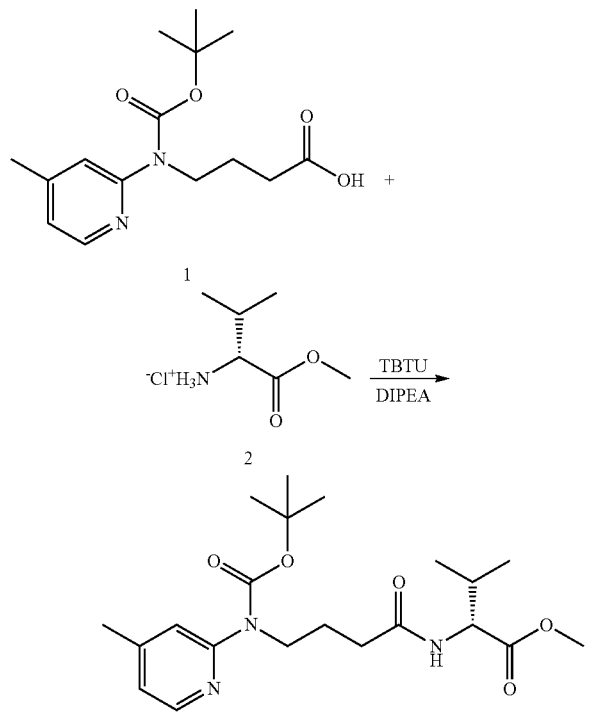

To a solution of compound 1 (150 mg, 0.509 mmol, 1 equiv.), compound 2 (94 mg, 0.560 mmol, 1.1 equiv.), and TBTU (196 mg, 0.611 mmol, 1.2 equiv.) in anhydrous DMF (3 mL) was added diisopropylethylamine (0.266 mL, 1.528 mmol, 3 equiv.) at 0° C. The reaction mixture was warmed to room temperature and stirred for another 1 hr. The reaction was quenched with saturated NaHCO$_3$ solution (10 mL) and the aqueous phase was extracted with ethyl acetate (3×5 mL). The organic phase was combined, dried over Na$_2$SO$_4$, and concentrated. The product was separated by CombiFlash and was eluted with 2-3% methanol in DCM. Yield: 205 mg (99%).

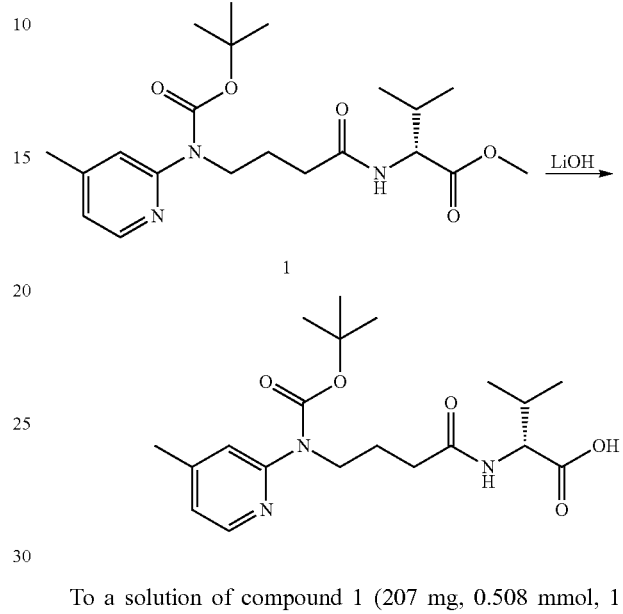

To a solution of compound 1 (207 mg, 0.508 mmol, 1 equiv.) in THF (5 mL) and H$_2$O (5 mL) was added lithium hydroxide (36 mg, 1.523 mmol, 3 equiv.) portion-wise at 0° C. The reaction mixture was warmed to room temperature. After stirring at room temperature for 1 hr, the reaction mixture was acidified by HCl (6 N) to pH 3.0. The aqueous phase was extracted with ethyl acetate (3×10 mL) and the organic layer was combined, dried over Na$_2$SO$_4$, and concentrated. The product was used without further purification. Yield: 180 mg (91%).

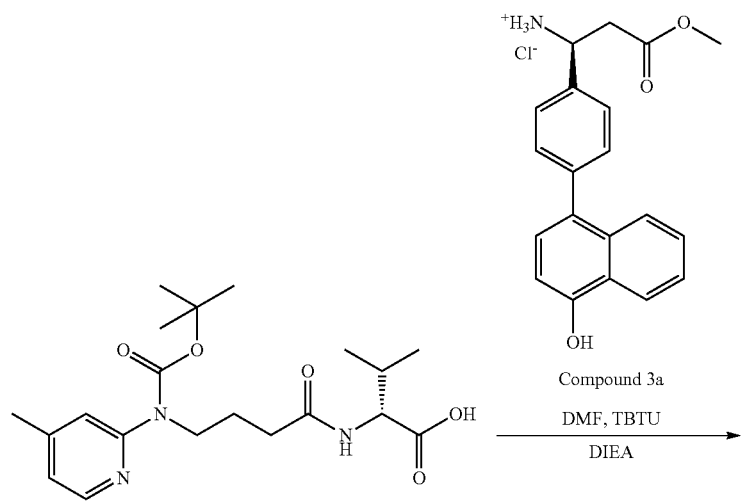

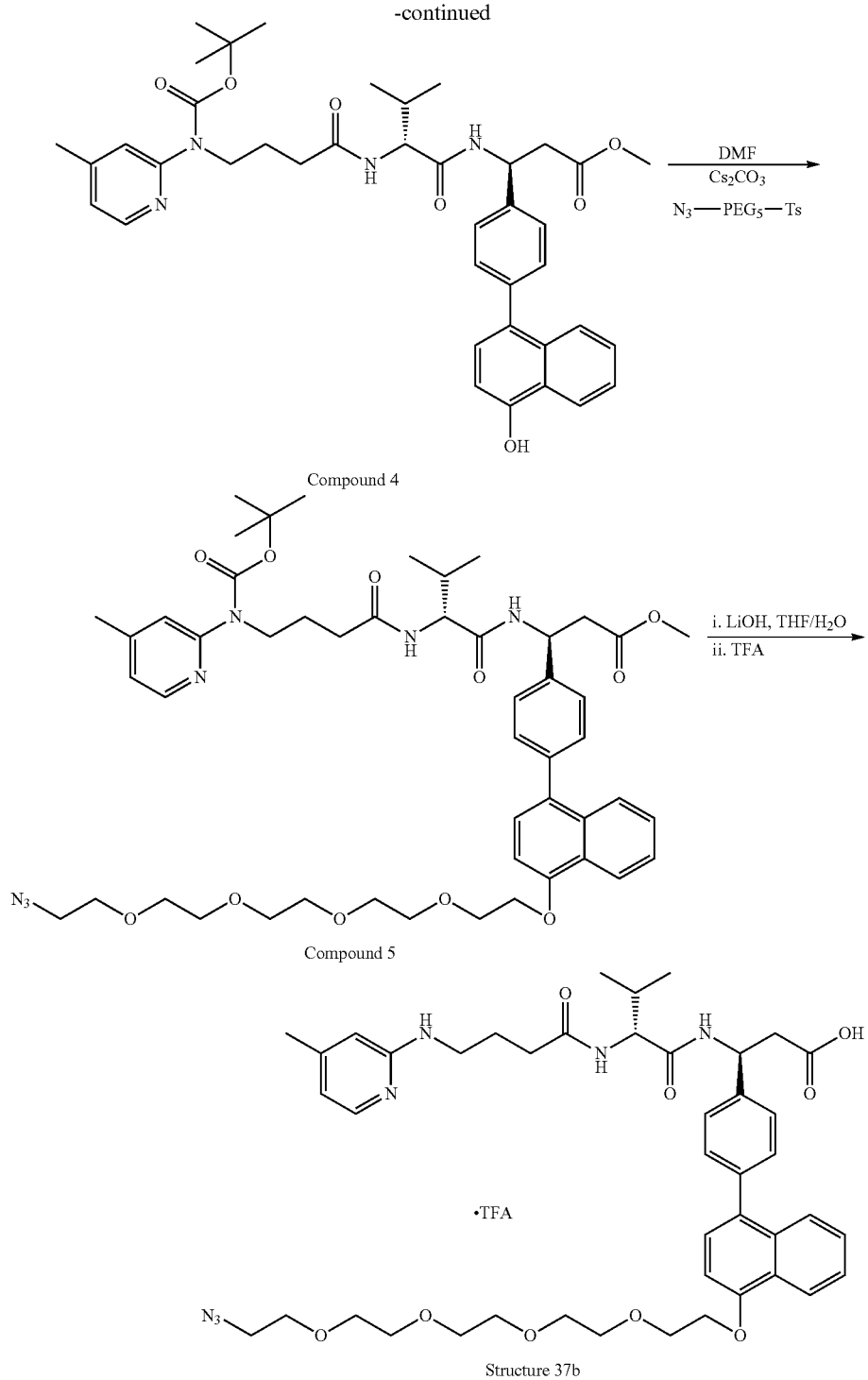

Compound 4

Compound 5

Structure 37b

To a solution of compound 3 (180 mg, 0.46 mmol), compound 3a (180 mg, 0.50 mmol), and TBTU (176 mg, 0.55 mmol) in DMF (2.5 mL) was added DIPEA (177 mg, 239 μL, 1.37 mmol) at 0° C. The reaction mixture was warmed to room temperature and stirred for 1 hour. The reaction mixture was quenched with sat. NH$_4$Cl (aq) solution (1.75 mL) and deionized water (1.75 mL) then extracted with ethyl acetate (8 mL). The aqueous layer was further extracted with ethyl acetate (2×8 mL). The combined organic phase was washed with half sat. NH$_4$Cl (aq) solution (6 mL) and half sat. NaHCO$_3$(aq) solution (6 mL). The organic layer was dried over Na$_2$SO$_4$, filtered, and concentrated. The crude mixture was separated by CombiFlash using silica gel as the stationary phase with 0-5% methanol in DCM. Yield of compound 4: 295 mg (92%). [M+H]+ calculated for C$_{40}$H$_{48}$N$_4$O$_7$: 697.84, found: 697.82.

To a solution of compound 4 (200 mg, 0.29 mmol) and azido-PEG$_5$-OTs (240 mg, 0.57 mmol) in anhydrous DMF (2.5 mL) was added Cs$_2$CO$_3$ (187 mg, 0.57 mmol). The reaction mixture was stirred at 60° C. for 2 hours. The reaction mixture was quenched with sat. NaHCO$_3$(aq) solution (15 mL) and deionized water (7.5 mL) then extracted with ethyl acetate (10 mL). The aqueous layer was further extracted with ethyl acetate (2×10 mL). The combined organic phase was dried over Na$_2$SO$_4$, filtered, and concentrated. The crude mixture was separated by CombiFlash using silica gel as the stationary phase with 0-5% methanol in DCM. Yield of compound 5: 97 mg (36%). [M+H]+ calculated for C$_{50}$H$_{67}$N$_7$O$_{11}$: 943.15, found: 942.96.

To a solution of compound 5 (94 mg, 0.10 mmol) in THF (1.5 mL) and deionized water (1 mL) was added a solution of lithium hydroxide (7.2 mg, 0.30 mmol) in deionized water (0.5 mL). The reaction mixture was stirred for 1 hour then acidified to pH=3 with 6 M HCl (aq). The aqueous phase was extracted with ethyl acetate (3×5 mL). The combined organic phase was dried over Na$_2$SO$_4$, filtered, and concentrated. To the crude residue was added TFA (1.34 mL) and water (67 µL). The reaction mixture was stirred for 1.5 hours at room temperature. The solvent was removed under reduced pressure, and the residue was coevaporated with acetonitrile:toluene [1:1] (2×20 mL). The crude mixture was separated by CombiFlash using silica gel as the stationary phase with 0-10% methanol in DCM. Yield of Structure 37b: 44 mg (53%). [M+H]+ calculated for C$_{44}$H$_{57}$N$_7$O$_9$: 828.97, found: 828.63.

Example 2. Syntheses of Tridentate αvβ6 Integrin Ligands and Conjugation of αvβ6 Integrin Ligands to Cargo Molecules (RNAi Agents)

The αvβ6 integrin ligands can be conjugated to one or more RNAi agents useful for inhibiting the expression of one or more targeted genes. The αvβ6 integrin ligands facilitate the delivery of the RNAi agents to the targeted cells and/or tissues. Example 1, above, described the synthesis of certain αvβ6 integrin ligands disclosed herein. The following describes the general procedures for the syntheses of certain αvβ6 integrin ligand-RNAi agent conjugates that are illustrated in the non-limiting Examples set forth herein.

A. Synthesis of RNAi Agents

RNAi agents can be synthesized using methods generally known in the art. For the synthesis of the RNAi agents illustrated in the Examples set forth herein, the sense and antisense strands of the RNAi agents were synthesized according to phosphoramidite technology on solid phase used in oligonucleotide synthesis. Depending on the scale, a MerMade96E® (Bioautomation), a MerMadel2® (Bioautomation), or an OP Pilot 100 (GE Healthcare) was used. Syntheses were performed on a solid support made of controlled pore glass (CPG, 500 Å or 600 Å, obtained from Prime Synthesis, Aston, Pa., USA). All RNA and 2'-modified RNA phosphoramidites were purchased from Thermo Fisher Scientific (Milwaukee, Wis., USA). Specifically, the following 2'-O-methyl phosphoramidites were used: (5'-O-dimethoxytrityl-N$^6$-(benzoyl)-2'-O-methyl-adenosine-3'-O-(2-cyanoethyl-N,N-diisopropylamino) phosphoramidite, 5'-O-dimethoxy-trityl-N$^4$-(acetyl)-2'-O-methyl-cytidine-3'-O-(2-cyanoethyl-N,N-diisopropyl-amino) phosphoramidite, (5'-O-dimethoxytrityl-N$^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl RNA amidites. 5'-di-methoxytrityl-2'-O-methyl-inosine-3'-O-(2-cyanoethyl-N, N-diisopropylamino) phosphoramidites were purchased from Glen Research (Virginia). The inverted abasic (3'-O-dimethoxytrityl-2'-deoxyribose-5'-O-(2-cyanoethyl-N,N-diisopropylamino) phosphoramidites were purchased from ChemGenes (Wilmington, Mass., USA). The following UNA phosphoramidites were used: 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diiso-propyl)]-phosphoramidite. TFA aminolink phosphoramidites were also commercially purchased (ThermoFisher).

In some examples, the αvβ6 integrin ligands disclosed herein are conjugated to the RNAi agents by linking the components to a scaffold that includes a tri-alkyne group. In some examples, the tri-alkyne group is added by using a tri-alkyne-containing phosphoramidite, which can be added at the 5' terminal end of the sense strand of an RNAi agent. When used in connection with the RNAi agents presented in certain Examples herein, tri-alkyne-containing phosphoramidites were dissolved in anhydrous dichloromethane or anhydrous acetonitrile (50 mM), while all other amidites were dissolved in anhydrous acetonitrile (50 mM), and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 90 sec (2' O-Me), and 60 sec (2' F). In order to introduce phosphorothioate linkages, a 100 mM solution of 3-phenyl 1,2,4-dithiazoline-5-one (POS, obtained from PolyOrg, Inc., Leominster, Mass., USA) in anhydrous acetonitrile was employed.

Alternatively, where the αvβ6 integrin ligands are conjugated to the RNAi agents via a tri-alkyne scaffold, instead of using a phosphoramidite approach, tri-alkyne-containing compounds can be introduced post-synthetically (see, for example, section E, below). When used in connection with the RNAi agents presented in certain Examples set forth herein, when attaching a tri-alkyne group post-synthetically to the 5' end of the sense strand the 5' terminal nucleotide of the sense strand was functionalized with a nucleotide that included a primary amine at the 5' end to facilitate attachment to the tri-alkyne-containing scaffold. TFA aminolink phosphoramidite was dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 90 sec (2' O-Me), and 60 sec (2' F). In order to introduce phosphorothioate linkages, a 100 mM solution of 3-phenyl 1,2,4-dithiazoline-5-one (POS, obtained from PolyOrg, Inc., Leominster, Mass., USA) in anhydrous acetonitrile was employed.

B. Cleavage and Deprotection of Support Bound Oligomer.

After finalization of the solid phase synthesis, the dried solid support was treated with a 1:1 volume solution of 40 wt. % methylamine in water and 28% to 31% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 fine with a running buffer of 100 mM ammonium bicarbonate, pH 6.7 and 20% Acetonitrile or filtered water.

D. Annealing.

Complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor and the dilution factor to determine the duplex concentration. The conversion factor used was either 0.037 mg/(mL-cm), or, alternatively for some experiments, a conversion factor was calculated from an experimentally determined extinction coefficient.

E. Conjugation of Tri-Alkyne Scaffold.

Either prior to or after annealing, the 5' or 3' amine functionalized sense strand of an RNAi agent can be conjugated to a tri-alkyne scaffold. Example tri-alkyne scaffold structures that can be used in forming the constructs disclosed herein include the following:

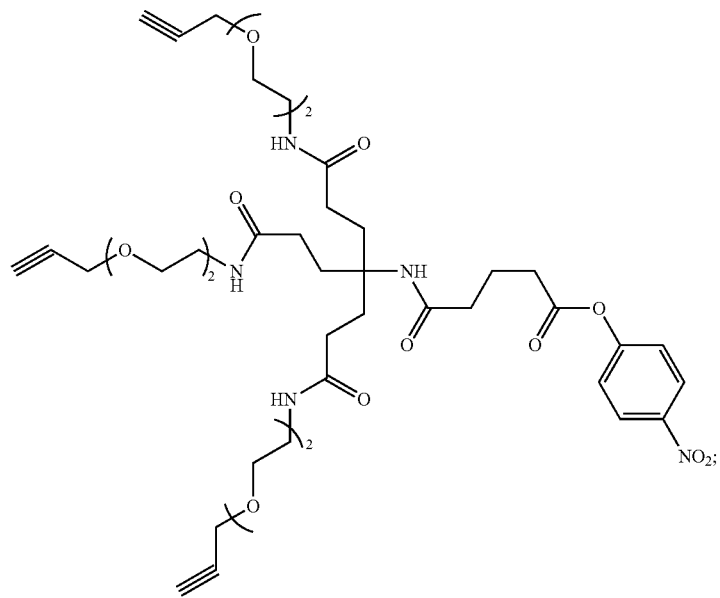

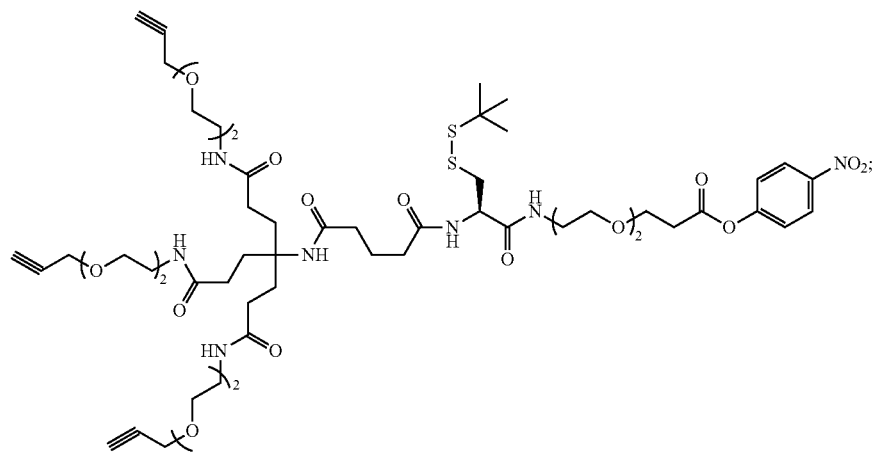

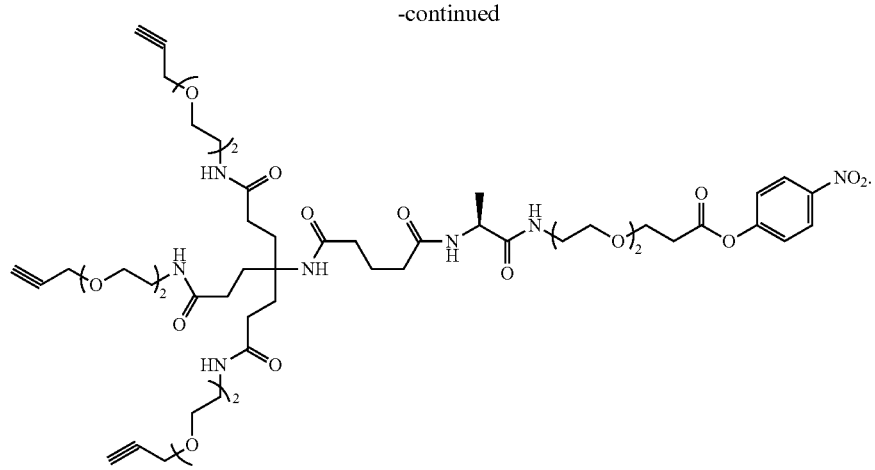

The following describes the conjugation of tri-alkyne scaffold to the annealed duplex: Amine functionalized duplex was dissolved in 90% DMSO/10% H₂O, at ~50-70 mg/mL. 40 eq triethylamine was added, followed by 3 eq tri-alkyne-PNP. Once complete, the conjugate was precipitated twice in a solvent system of 1× phosphate buffered saline/acetonitrile (1:14 ratio), and dried.

F. Conjugation of αvβ6 Integrin Ligands.

Either prior to or after annealing, the 5' or 3' tridentate alkyne functionalized sense strand is conjugated to the αvβ6 Integrin Ligands. The following example describes the conjugation of αvβ6 integrin ligands to the annealed duplex: Stock solutions of 0.5M Tris(3-hydroxypropyltriazolylmethyl)amine (THPTA), 0.5M of Cu(II) sulfate pentahydrate (Cu(II)SO₄.5H₂O) and 2M solution of sodium ascorbate were prepared in deionized water. A 75 mg/mL solution in DMSO of αvβ6 integrin ligand was made. In a 1.5 mL centrifuge tube containing tri-alkyne functionalized duplex (3 mg, 75 μL, 40 mg/mL in deionized water, ~15,000 g/mol), 25 μL of 1M Hepes pH 8.5 buffer is added. After vortexing, 35 μL of DMSO was added and the solution is vortexed. αvβ6 integrin ligand was added to the reaction (6 eq/duplex, 2 eq/alkyne, ~15 μL) and the solution is vortexed. Using pH paper, pH was checked and confirmed to be pH ~8. In a separate 1.5 mL centrifuge tube, 50 μL of 0.5M THPTA was mixed with 10 uL of 0.5M Cu(II)SO₄.5 H₂O, vortexed, and incubated at room temp for 5 min. After 5 min, THPTA/Cu solution (7.2 μL, 6 eq 5:1 THPTA:Cu) was added to the reaction vial, and vortexed. Immediately afterwards, 2M ascorbate (5 μL, 50 eq per duplex, 16.7 per alkyne) was added to the reaction vial and vortexed. Once the reaction was complete (typically complete in 0.5-1 h), the reaction was immediately purified by non-denaturing anion exchange chromatography.

G. Functionalization of Thiol group on Cysteine Linker.

In some examples, a cysteine linker can be used to facilitate conjugation of the αvβ6 integrin ligands to the RNAi agent. Either prior to or after annealing, the 5' or 3' tridentate alkyne-Cys(Stbu)-PEG₂ functionalized sense strand is functionalized with a maleimide-containing moiety, or can be reduced and left as the free thiol, as shown in the following structure:

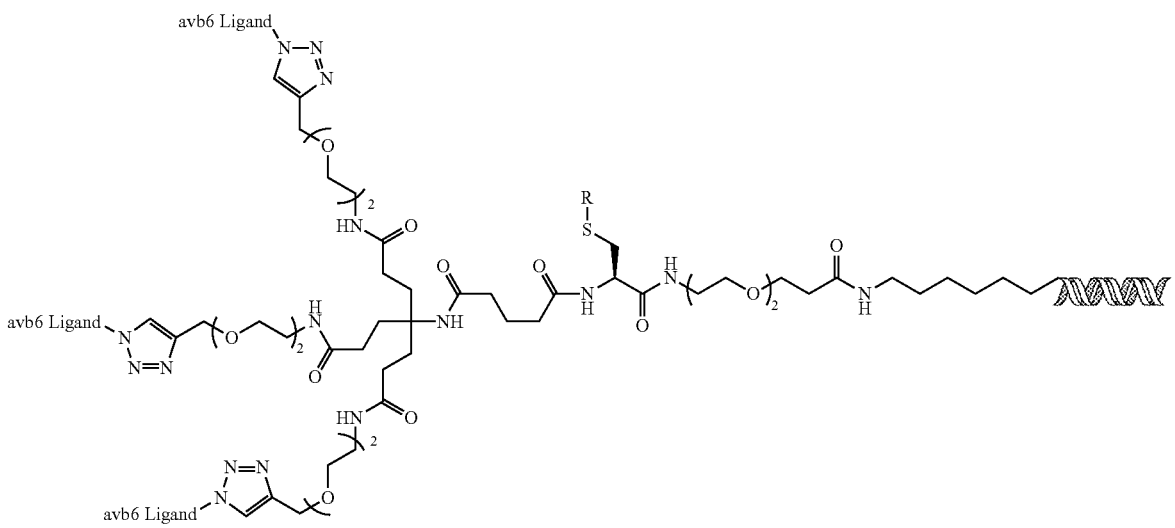

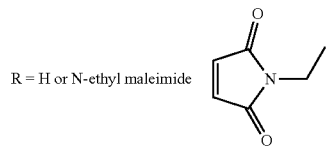

R = H or N-ethyl maleimide

The following example describes the modification of the tri-alkyne-Cys(Stbu)-PEG₂-duplex with N-ethyl maleimide: Tri-alkyne-Cys(Stbu)-PEG₂-duplex (35 mg) was dissolved in 500 µL deionized H₂O. HEPES buffer (1M, pH 8.5, 82 µL), was added to the reaction, and the solution was vortexed. A solution of 1 M Dithiothreitol (DTT, 100 eq, 236 µL) was added and the solution was placed on a vortex shaker for 3 h. After confirmation of reduction of the disulfide by denaturing RP-HPLC, the conjugate was precipitated three times in a solvent system of 1× phosphate buffered saline/acetonitrile (1:14 ratio). The precipitated pellet was reconstituted in 0.5 mL of 0.1 M HEPES, pH 6.5, and N-ethyl maleimide (3 mg, 10 eq) was added to the solution, and placed on a vortex mixer for 15 min. After completion of the reaction, the conjugate was precipitated three times in a solvent system of 1× phosphate buffered saline/acetonitrile (1:14 ratio), desalted, and dried.

Example 3. αvβ6 Integrin Ligand Binding Activity

As reported in the following Table 1, IC50 binding data was obtained for the αvβ6 integrin ligands of Structures 1 and 2:

TABLE 1

IC50 Binding Activity.

| Group | αvβ3 | αvβ5 | αvβ6 |
| --- | --- | --- | --- |
| | IC50 (nM) | | |
| Structure 1 | not active | not active | 13 |
| Structure 2 | not active | not active | 129 |

Azide-functionalized structures (i.e., Structures 1b and 2b) were examined for IC50 under conditions typically used and known in the art. As shown in Table 1, above, Structures 1 and 2 showed selective binding to αvβ6 integrin.

Example 4. In Vivo Intratracheal Administration of RNAi Agents Targeting Alpha-ENaC Conjugated to αvβ6 Integrin Ligands in Rats RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents included an antisense strand having a nucleobase sequence at least partially complementary to the gene expressing the alpha subunit of the amiloride-sensitive epithelial sodium channel (commonly referred to as alpha-ENaC or SCNN1A). The alpha-ENaC RNAi agents were designed to be capable of degrading or inhibiting translation of messenger RNA (mRNA) transcripts of alpha-ENaC in a sequence specific manner, thereby inhibiting expression of the alpha-ENaC gene. The RNAi agent used in this Example (AD04835) was comprised of modified nucleotides and more than one non-phosphodiester linkage, and included the following nucleotide sequences:

```
Sense strand sequence (5' → 3'):
                                           (SEQ ID NO: 1)
(NH₂-C₆)sgscugugcaAfCfCfagaacaaauas(invAb)

Antisense strand sequence (5' → 3')
                                           (SEQ ID NO: 2)
cPrpusAfsusUfuGfuUfcUfgGfuUfgCfaCfaGfsc,
``` wherein (invAb) represents an inverted (3'-3' linked) abasic deoxyribonucleotide; s represents a phosphorothioate linkage; a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; cPrpu represents a 5'-cyclopropyl phosphonate-2'-O-methyl uridine (see, e.g., Table A); and (NH₂—C₆) represents a C₆ terminal amine to facilitate targeting ligand conjugation as desired (see, e.g., Table A).

As the person of ordinary skill in the art would clearly understand, the nucleotide monomers are linked by standard phosphodiester linkages except where inclusion of a phosphorothioate linkage, as shown in the modified nucleotide sequences disclosed herein, replaces the phosphodiester linkage typically present in an oligonucleotide.

On study day 1 and day 2, male Sprague-Dawley rats were administered a dose of 200 microliters intratracheally via a microsprayer device (Penn Century, Philadelphia, Pa.), which included the following dosing groups:

(1) 5% dextrose in water vehicle (D5W);

(2) 3.0 mg/kg of an alpha-ENaC RNAi agent (AD04835) without a ligand ("naked RNAi agent"), formulated in 5% dextrose in water (d5w); or (3) 3.0 mg/kg of an alpha-ENaC RNAi agent (AD04835) conjugated to a tridentate αvβ6 integrin ligand of Structure 1, formulated in d5w.

The same alpha-ENaC RNAi agent was used in Groups 2 and 3. For Group 3, the terminal amine (NH₂—C₆) present on the 5' terminal end of the sense strand of the RNAi agent was then conjugated to a scaffold that included three terminal alkyne groups. The alkyne groups were then conjugated to the azide functional group present on Structure 1b, thereby forming a tridentate αvβ6 integrin ligand of Structure 1. General synthetic procedures are described in Example 2, above.

Four (4) rats were dosed per group. Rats were euthanized on study day 5, and total RNA was isolated from both lungs following collection and homogenization. mRNA abundance of alpha-ENaC was quantitated by probe-based quantitative PCR, normalized to GAPDH expression and expressed as fraction of vehicle control group (geometric mean, +/−95% confidence interval).

TABLE 2

Relative alpha-ENaC Expression of mRNA Normalized to Control of Example 4.

| Group | Relative Expression (Geometric Mean) | Lower/Upper 95% Confidence Interval |
|---|---|---|
| (1) 5% dextrose vehicle | 1.000 | 0.81/1.23 |
| (2) Naked RNAi agent (no ligand) | 0.36 | 0.07/1.79 |
| (3) tridentate αvβ6 integrin ligand Structure 1 [(αvβ6 integrin ligand Structure 1)₃-RNAi agent] | 0.19 | 0.05/0.59 |

As shown in Table 2 above, the αvβ6 integrin ligand of Structure 1 in tridentate form conjugated to the alpha-ENaC RNAi agent (i.e., Group 3) showed increased relative knockdown of alpha-ENaC mRNA (approximately 81% knockdown), compared to naked RNAi agent (64% knockdown) without any ligand (i.e., Group 2) and the vehicle control, in vivo.

Example 5. In Vivo Oropharyngeal Aspiration Administration of RNAi Agents Targeting Alpha-ENaC Conjugated to αvβ6 Integrin Ligands in Rats In the following examples, various RNAi agents are used as cargo molecules to test the delivery of a cargo molecule via an αvβ6 integrin to a cell of interest. Certain of the RNAi agents used herein are described in U.S. 62/679,549, which is incorporated herein by reference in its entirety.

On study day 1, male Sprague Dawley rats were dosed via oropharyngeal ("OP") aspiration administration with 200 microliters using a pipette, according to the following dosing Groups:

TABLE 3

Dosing Groups of Rats in Example 5.

| Group | RNAi Agent and Dose | Dosing Regimen |
|---|---|---|
| 1 | Isotonic saline (no RNAi agent) | Single OP dose on day 1 |
| 2 | 0.5 mg/kg of alpha-ENaC double-stranded RNAi agent (AD04835) conjugated to the tridentate αvβ6 integrin ligand of Structure 2, formulated in isotonic saline. | Single OP dose on day 1 |
| 3 | 0.5 mg/kg of alpha-ENaC double-stranded RNAi agent (AD04835) conjugated to the tridentate αvβ6 integrin ligand of Structure 5.1, formulated in isotonic saline. | Single OP dose on day 1 |
| 4 | 0.5 mg/kg of alpha-ENaC double-stranded RNAi agent (AD04835) conjugated to the tridentate αvβ6 integrin ligand of Structure 5.2, formulated in isotonic saline. | Single OP dose on day 1 |
| 5 | 0.5 mg/kg of alpha-ENaC double-stranded RNAi agent (AD04835) conjugated to the tridentate αvβ6 integrin ligand of Structure 6, formulated in isotonic saline. | Single OP dose on day 1 |
| 6 | 0.5 mg/kg of alpha-ENaC double-stranded RNAi agent (AD04835) conjugated to the tridentate αvβ6 integrin ligand of Structure 6.1, formulated in isotonic saline. | Single OP dose on day 1 |
| 7 | 0.5 mg/kg of alpha-ENaC double-stranded RNAi agent (AD04835) conjugated to the tridentate αvβ6 integrin ligand of Structure 6.2, formulated in isotonic saline. | Single OP dose on day 1 |

The RNAi agents were synthesized having nucleotide sequences directed to target the human alpha-ENaC gene, and included a functionalized amine reactive group (NH₂—C₆) at the 5' terminal end of the sense strand to facilitate conjugation to the αvβ6 integrin ligands. The respective αvβ6 integrin ligands were then conjugated to the RNAi agents via a tridentate scaffold that included a cysteine-n-ethyl-maleimide linker. For the RNAi agent-αvβ6 integrin ligand conjugates of Example 5, the RNAi agent as well as the scaffold/linker structures, were consistent for each of the Groups 2-7. Thus, the only variable for Groups 2 through 7 was the specific αvβ6 integrin ligand (each in tridentate form) that was used. The RNAi agent-αvβ6 integrin ligand conjugates of Example 5 had structures represented by the following:

wherein ⋙ represents the RNAi agent, and "avb6 Ligand" represents the respective ligand Structure. The structure of the RNAi agent used in this Example (AD04835) is set forth in Example 4, above.

Five (5) rats were dosed in each Group (n=5). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 4

Average Relative rENaC mRNA Expression at Sacrifice (Day 9) in Example 5.

| Group ID | Average Relative rENaC mRNA expression | Low (error) | High (error) |
|---|---|---|---|
| Group 1 (isotonic saline) | 1.000 | 0.195 | 0.243 |
| Group 2 (RNAi agent-Cys-(n-ethyl-Mal)-PEG$_2$-tridentate αvβ6 integrin ligand Structure 2) | 0.543 | 0.114 | 0.145 |
| Group 3 (RNAi agent-Cys-(n-ethyl-Mal)-PEG$_2$-tridentate αvβ6 integrin ligand Structure 5.1) | 0.541 | 0.138 | 0.185 |
| Group 4 (RNAi agent-Cys-(n-ethyl-Mal)-PEG$_2$-tridentate αvβ6 integrin ligand Structure 5.2) | 0.522 | 0.151 | 0.212 |
| Group 5 (RNAi agent-Cys-(n-ethyl-Mal)-PEG$_2$-tridentate αvβ6 integrin ligand Structure 6) | 0.399 | 0.108 | 0.148 |
| Group 6 (RNAi agent-Cys-(n-ethyl-Mal)-PEG$_2$-tridentate αvβ6 integrin ligand Structure 6.1) | 0.351 | 0.100 | 0.139 |
| Group 7 (RNAi agent-Cys-(n-ethyl-Mal)-PEG$_2$-tridentate αvβ6 integrin ligand Structure 6.2) | 0.568 | 0.061 | 0.068 |

As shown in Table 4 above, each of the alpha-ENaC RNAi agents showed a reduction in mRNA expression in rats compared to control. For example, Group 6 (AD04835-tridentate-Structure 6.1) showed approximately a 65% reduction (0.351) in average rENaC mRNA expression compared to control; Group 2 (AD04835-tridentate-Structure 2) showed approximately a 46% reduction (0.543) in average rENaC mRNA expression compared to control; and Group 4 (AD04835-tridentate-Structure 5.2) showed approximately a 48% reduction (0.522) in average rENaC mRNA expression compared to control.

Example 6. In Vivo Oropharyngeal Aspiration Administration of RNAi Agents Targeting Alpha-ENaC Conjugated to αvβ6 Integrin Ligands in Rats On study day 1, male Sprague Dawley rats were dosed via oropharyngeal ("OP") aspiration administration with 200 microliters using a pipette, according to the following dosing Groups:

TABLE 5

Dosing Groups of Rats in Example 6.

| Group | RNAi Agent and Dose | Dosing Regimen |
|---|---|---|
| 1 | Isotonic saline (no RNAi agent) | Single OP dose on day 1 |
| 2 | 0.5 mg/kg of alpha-ENaC double-stranded RNAi agent (AD05347), conjugated to a tridentate αvβ6 integrin ligand of Structure 2 that included a glutaric linker (i.e., having the structure represented in Structure 300a), formulated in isotonic saline. | Single OP dose on day 1 |
| 3 | 0.5 mg/kg of alpha-ENaC double-stranded RNAi agent (AD05453), conjugated to a tridentate αvβ6 integrin ligand of Structure 2 that included a glutaric linker (i.e., having the structure represented in Structure 300a), formulated in isotonic saline. | Single OP dose on day 1 |
| 4 | 0.5 mg/kg of alpha-ENaC double-stranded RNAi agent (AD05453), conjugated to a tridentate αvβ6 integrin ligand of Structure 6 that included a glutaric linker (i.e., having the structure represented in Structure 300a), formulated in isotonic saline. | Single OP dose on day 1 |
| 5 | 0.5 mg/kg of alpha-ENaC double-stranded RNAi agent (AD05453), conjugated to a tridentate αvβ6 integrin ligand of Structure 6.1 that included a glutaric linker (i.e., having the structure represented in Structure 300a), formulated in isotonic saline. | Single OP dose on day 1 |
| 6 | 0.5 mg/kg of alpha-ENaC double-stranded RNAi agent (AD05453), conjugated to a tridentate αvβ6 integrin ligand of Structure 7 that included a glutaric linker (i.e., having the structure represented in Structure 300a), formulated in isotonic saline. | Single OP dose on day 1 |

The RNAi agents were synthesized having nucleotide sequences directed to target the human alpha-ENaC gene, and included a functionalized amine reactive group ($NH_2$—$C_6$) at the 5' terminal end of the sense strand to facilitate conjugation to the αvβ6 integrin ligands. The RNAi agents used in this Example were comprised of modified nucleotides and more than one non-phosphodiester linkage, and included the following nucleotide sequences:

AD05347:

Sense strand sequence (5' → 3'):

(SEQ ID NO: 3)

($NH_2$-$C_6$) cscugugcaAfCfCfagaacaaauas (invAb)

Antisense strand sequence (5' → 3')

(SEQ ID NO: 2)

cPrpusAfsusUfuGfuUfcUfgGfuUfgCfaCfaGfsc, and

AD05453:

Sense strand sequence (5' → 3'):

-continued (SEQ ID NO: 3)

($NH_2$-$C_6$) cscugugcaAfCfCfagaacaaauas (invAb)

Antisense strand sequence (5' → 3')

(SEQ ID NO: 4)

usAfsusUfuGfuUfcUfgGfuUfgCfaCfaGfsg, wherein (invAb) represents an inverted (3'-3' linked) abasic deoxyribonucleotide; s represents a phosphorothioate linkage; a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; cPrpu represents a 5'-cyclopropyl phosphonate-2'-O-methyl uridine (see, e.g., Table A); and ($NH_2$—$C_6$) represents a $C_6$ terminal amine to facilitate targeting ligand conjugation as desired (see, e.g., Table A).

For Groups 2, 3, 4, 5, and 6, the respective αvβ6 integrin ligands were conjugated to the RNAi agents via a tridentate scaffold/linker structure that included a glutaric linker (via addition of glutaric acid), as depicted in the following Structure 300a:

(Structure 300a)

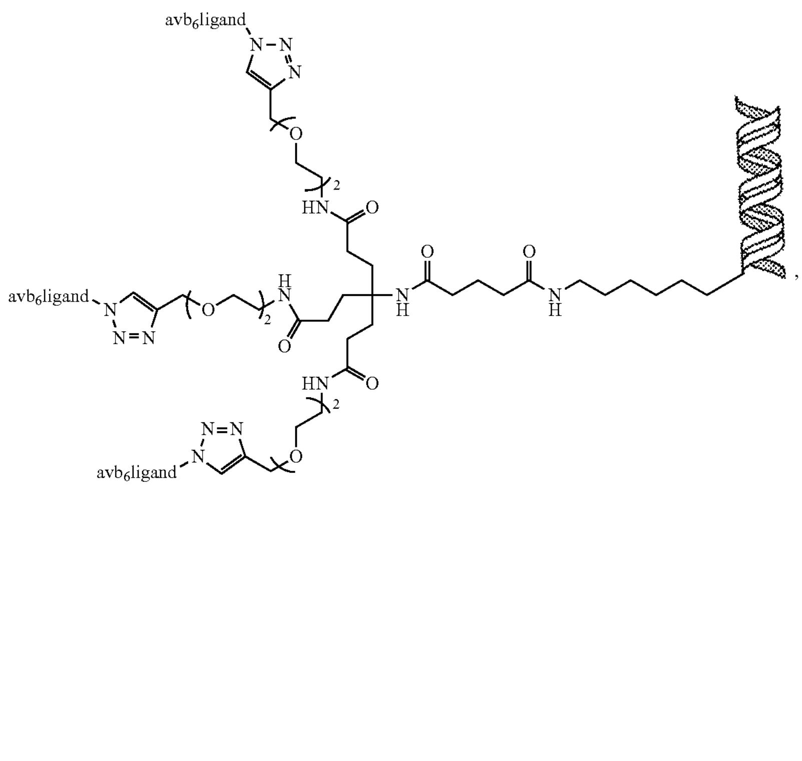

wherein  represents the RNAi agent, and "avb6 Ligand" represents the respective ligand structure.

For Groups 7 and 8, the respective αvβ6 integrin ligands were conjugated to the RNAi agents via a tridentate scaffold/linker structure having the structure depicted in Structure 330a:

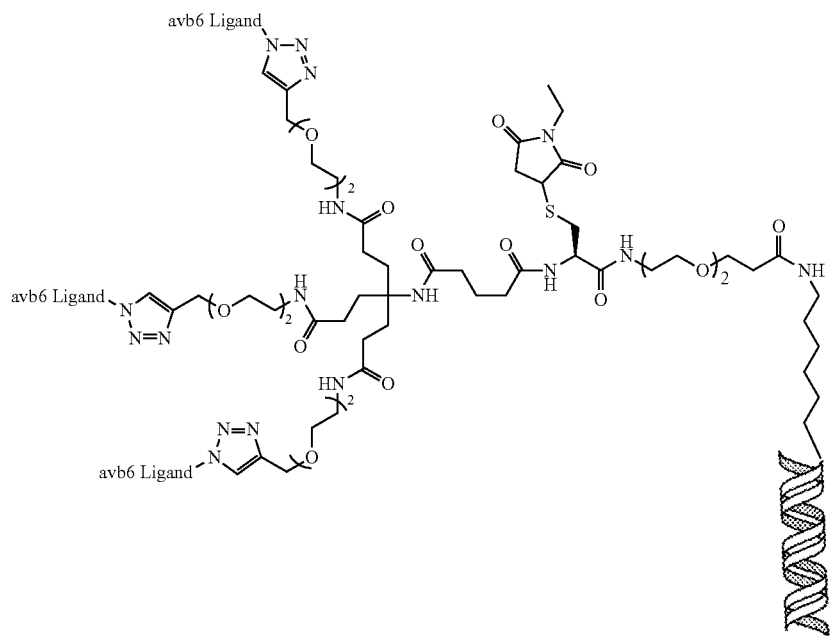

(Structure 330a), wherein ⟋⟋⟍⟍ represents the RNAi agent, and "avb6 Ligand" represents the respective ligand structure.

Four (4) rats were dosed in Groups 1, 3, 4, 6, and 7 (n=4); five (5) rats were dosed in Groups 5 and 8 (n=5); and three (3) rats were dosed in Group 2 (n=3). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 6

Average Relative rENaC mRNA Expression at Sacrifice (Day 9) in Example 6.

| Group ID | Number of animals (n=) | Average Relative rENaC mRNA expression | Low (error) | High (error) |
| --- | --- | --- | --- | --- |
| Group 1 (isotonic saline) | 4 | 1.000 | 0.137 | 0.159 |
| Group 2 (0.5 mg/kg AD05347-glutaric-tridentate αvβ6 integrin ligand Structure 2) | 3 | 0.486 | 0.090 | 0.110 |
| Group 3 (0.5 mg/kg AD05453-glutaric-tridentate αvβ6 integrin ligand Structure 2) | 4 | 0.615 | 0.066 | 0.074 |
| Group 4 (0.5 mg/kg AD05453-glutaric-tridentate αvβ6 integrin ligand Structure 6) | 4 | 0.512 | 0.119 | 0.156 |
| Group 5 (0.5 mg/kg AD05453-glutaric-tridentate αvβ6 integrin ligand Structure 6.1) | 5 | 0.494 | 0.101 | 0.127 |
| Group 6 (0.5 mg/kg AD05453-glutaric-tridentate αvβ6 integrin ligand Structure 7) | 4 | 0.743 | 0.104 | 0.121 |

As shown in Table 6 above, each of the alpha-ENaC RNAi agents showed a reduction in mRNA expression in rats compared to control. For example, Group 5 (AD05453-tridentate αvβ6 integrin ligand Structure 6.1) showed approximately a 51% reduction (0.494) in average rENaC mRNA expression compared to control, and Group 3 (AD05453-tridentate αvβ6 integrin ligand Structure 2) showed approximately a 38% reduction (0.615) in average rENaC mRNA expression compared to control. Further, Group 5 (which included αvβ6 integrin ligand Structure 6.1) showed improvement over Group 6 (which included αvβ6 integrin ligand Structure 7), indicating a chirality dependence of (s), as found in Structure 6.1, over (r) as found in Structure 7, for the αvβ6 integrin ligands.

Example 7. In Vivo Oropharyngeal Aspiration Administration of RNAi Agents Targeting Alpha-ENaC Conjugated to αvβ6 Integrin Ligands in Rats On study day 1, male Sprague Dawley rats were dosed via oropharyngeal ("OP") aspiration administration with 200 microliters using a pipette, according to the following dosing Groups:

The RNAi agents were synthesized having nucleotide sequences directed to target the human alpha-ENaC gene, and included a functionalized amine reactive group ($NH_2$—$C_6$) at the 5' terminal end of the sense strand to facilitate conjugation to the αvβ6 integrin ligands. The nucleotide sequences for the RNAi agents used in this Example are set forth in Example 6, above. For Groups 2, 3, 4, 5, 6, 7, 8, 9, and 10, the respective αvβ6 integrin ligands were conjugated to the RNAi agents via a tridentate scaffold/linker structure that included a glutaric linker as depicted in Structure 300a, shown in Example 6, above. For Group 11, the epithelial cell targeting ligands were comprised of RGD-mimetic peptides that are known to bind to αvβ6 integrin and included a 20 kDa PEG moiety as a pharmacokinetic (PK) modulator.

Four (4) rats were dosed in each Group (n=4). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 7

Dosing Groups of Rats in Example 7.

| Group | RNAi Agent and Dose | Dosing Regimen |
|---|---|---|
| 1 | Isotonic saline (no RNAi agent) | Single OP dose on day 1 |
| 2 | 0.5 mg/kg of alpha-ENaC RNAi agent AD05347 conjugated to a tridentate αvβ6 integrin ligand of Structure 2 that included a glutaric linker (i.e., having the structure represented in Structure 300a), formulated in isotonic saline. | Single OP dose on day 1 |
| 3 | 0.5 mg/kg of alpha-ENaC RNAi agent AD05347 conjugated to a tridentate αvβ6 integrin ligand of Structure 6.1 that included a glutaric linker (i.e., having the structure represented in Structure 300a), formulated in isotonic saline. | Single OP dose on day 1 |
| 4 | 0.5 mg/kg of alpha-ENaC RNAi agent AD05453 conjugated to a tridentate αvβ6 integrin ligand of Structure 2 that included a glutaric linker (i.e., having the structure represented in Structure 300a), formulated in isotonic saline. | Single OP dose on day 1 |
| 5 | 0.5 mg/kg of alpha-ENaC RNAi agent AD05453 conjugated to a tridentate αvβ6 integrin ligand of Structure 9 that included a glutaric linker (i.e., having the structure represented in Structure 300a), formulated in isotonic saline. | Single OP dose on day 1 |
| 6 | 0.5 mg/kg of alpha-ENaC RNAi agent AD05453 conjugated to a tridentate αvβ6 integrin ligand of Structure 6 that included a glutaric linker (i.e., having the structure represented in Structure 300a), formulated in isotonic saline. | Single OP dose on day 1 |
| 7 | 0.5 mg/kg of alpha-ENaC RNAi agent AD05453 conjugated to a tridentate αvβ6 integrin ligand of Structure 8 that included a glutaric linker (i.e., having the structure represented in Structure 300a), formulated in isotonic saline. | Single OP dose on day 1 |
| 8 | 0.5 mg/kg of alpha-ENaC RNAi agent AD05453 conjugated to a tridentate αvβ6 integrin ligand of Structure 6.1 that included a glutaric linker (i.e., having the structure represented in Structure 300a), formulated in isotonic saline. | Single OP dose on day 1 |
| 9 | 0.5 mg/kg of alpha-ENaC RNAi agent AD05453 conjugated to a tridentate αvβ6 integrin ligand of Structure 10 that included a glutaric linker (i.e., having the structure represented in Structure 300a), formulated in isotonic saline. | Single OP dose on day 1 |
| 10 | 0.5 mg/kg of alpha-ENaC RNAi agent AD05453 conjugated to a tridentate αvβ6 integrin ligand of Structure 11 that included a glutaric linker (i.e., having the structure represented in Structure 300a), formulated in isotonic saline. | Single OP dose on day 1 |
| 11 | 0.5 mg/kg of alpha-ENaC RNAi agent AD05453 conjugated to a tridentate peptide-based epithelial cell targeting ligand via the amine ($NH_2$—$C_6$) linkage on the 5' terminal end of the sense strand that further included a 20 kilodalton (kDa) PEG moiety, formulated in isotonic saline. | Single OP dose on day 1 |

TABLE 8

Average Relative rENaC mRNA Expression at Sacrifice (Day 9) in Example 7.

| Group ID | Average Relative rENaC mRNA expression | Low (error) | High (error) |
|---|---|---|---|
| Group 1 (isotonic saline) | 1.000 | 0.162 | 0.193 |
| Group 2 (0.5 mg/kg AD05347-glutaric-tridentate αvβ6 integrin ligand Structure 2) | 0.469 | 0.101 | 0.129 |
| Group 3 (0.5 mg/kg AD05347-glutaric-tridentate αvβ6 integrin ligand Structure 6.1) | 0.358 | 0.078 | 0.100 |
| Group 4 (0.5 mg/kg AD05453-glutaric-tridentate αvβ6 integrin ligand Structure 2) | 0.562 | 0.086 | 0.102 |
| Group 5 (0.5 mg/kg AD05453-glutaric-tridentate αvβ6 integrin ligand Structure 9) | 0.620 | 0.168 | 0.230 |
| Group 6 (0.5 mg/kg AD05453-glutaric-tridentate αvβ6 integrin ligand Structure 6) | 0.559 | 0.099 | 0.120 |
| Group 7 (0.5 mg/kg AD05453-glutaric-tridentate αvβ6 integrin ligand Structure 8) | 0.691 | 0.072 | 0.081 |
| Group 8 (0.5 mg/kg AD05453-glutaric-tridentate αvβ6 integrin ligand Structure 6.1) | 0.454 | 0.055 | 0.063 |
| Group 9 (0.5 mg/kg AD05453-glutaric-tridentate αvβ6 integrin ligand Structure 10) | 0.454 | 0.080 | 0.097 |
| Group 10 (0.5 mg/kg AD05453-glutaric- tridentate αvβ6 integrin ligand Structure 11) | 0.577 | 0.113 | 0.140 |
| Group 11 (0.5 mg/kg AD05453-tridentate peptide-based epithelial cell targeting ligand-20 kDa PEG) | 0.558 | 0.057 | 0.064 |

As shown in Table 8 above, each of the alpha-ENaC RNAi agents showed a reduction in mRNA expression in rats compared to control. For example, Group 3 (AD05347-glutaric-tridentate αvβ6 integrin ligand Structure 6.1) showed approximately a 64% reduction (0.358) in average rENaC mRNA expression compared to control, and Group 8 (AD05453-glutaric-tridentate αvβ6 integrin ligand Structure 6.1) showed approximately a 55% reduction (0.454) in average rENaC mRNA expression compared to control. Further, the αvβ6 integrin ligands in Example 7 (i.e., Structure 2, Structure 6, Structure 6.1, Structure 8, Structure 9, Structure 10, and Structure 11) all showed comparable knockdown levels to the tridentate peptide-based epithelial cell targeting ligand that further included a relatively bulky 20 kilodalton PEG moiety to enhance the pharmacokinetic effect of Group 11.

Example 8. In Vivo Intratracheal Administration of RNAi Agents Targeting Alpha-ENaC Conjugated to αvβ6 Integrin Ligands in Rats On study day 1 and day 2, male Sprague-Dawley rats were administered a dose of 200 microliters intratracheally via a microsprayer device (Penn Century, Philadelphia, Pa.), which included the following dosing Groups:

TABLE 9

Dosing Groups of Rats in Example 8.

| Group | RNAi Agent and Dose | Dosing Regimen |
|---|---|---|
| 1 | Isotonic saline (no RNAi agent) | IT dose on day 1 and day 2 |
| 2 | 1.5 mg/kg of alpha-ENaC RNAi agent AD04835 conjugated to a monodentate peptide-based epithelial cell targeting ligand via the amine ($NH_2$—$C_6$) linkage on the 5' terminal end of the sense strand that further included a 20 kilodalton (kDa) PEG moiety, a cysteine linker, and an FCFP peptide linker, formulated in isotonic saline. | IT dose on day 1 and day 2 |
| 3 | 0.5 mg/kg of alpha-ENaC RNAi agent AD04835 conjugated to a tridentate αvβ6 integrin ligand of Structure 1 that included a cysteine linker (i.e., having the structure represented in Structure 331a), formulated in isotonic saline. | IT dose on day 1 and day 2 |
| 4 | 1.5 mg/kg of alpha-ENaC RNAi agent AD04835 conjugated to a tridentate αvβ6 integrin ligand of Structure 1 that included a cysteine linker (i.e., having the structure represented in Structure 331a), formulated in isotonic saline. | IT dose on day 1 and day 2 |
| 5 | 1.5 mg/kg of alpha-ENaC RNAi agent AD04835 conjugated to a tridentate αvβ6 integrin ligand of Structure 1 that included a cysteine-n-ethyl-maleimide linker (i.e., having the structure represented in Structure 330a), formulated in isotonic saline. | IT dose on day 1 and day 2 |
| 6 | 1.5 mg/kg of alpha-ENaC RNAi agent AD04835 conjugated to a tridentate peptide-based epithelial cell targeting ligand via the amine ($NH_2$—$C_6$) linkage on the 5' terminal end of the sense strand that further included a 20 kDa PEG moiety and a cysteine linker, formulated in isotonic saline | IT dose on day 1 and day 2 |
| 7 | 1.5 mg/kg of alpha-ENaC RNAi agent AD04835 conjugated to a tridentate αvβ6 integrin ligand of Structure 1 that included a glutaric linker (i.e., having the structure represented in Structure 300a), formulated in isotonic saline. | IT dose on day 1 and day 2 |

The RNAi agents were synthesized having nucleotide sequences directed to target the human alpha-ENaC gene, and included a functionalized amine reactive group ($NH_2$—$C_6$) at the 5' terminal end of the sense strand to facilitate conjugation to the αvβ6 integrin ligands. The nucleotide sequences for the RNAi agents used in this Example are set forth in Example 4, above.

For Groups 3 and 4, the αvβ6 integrin ligand of Structure 1 was conjugated to the RNAi agents via a tridentate scaffold and linker structure that included a cysteine linker as depicted in the following Structure 331a:

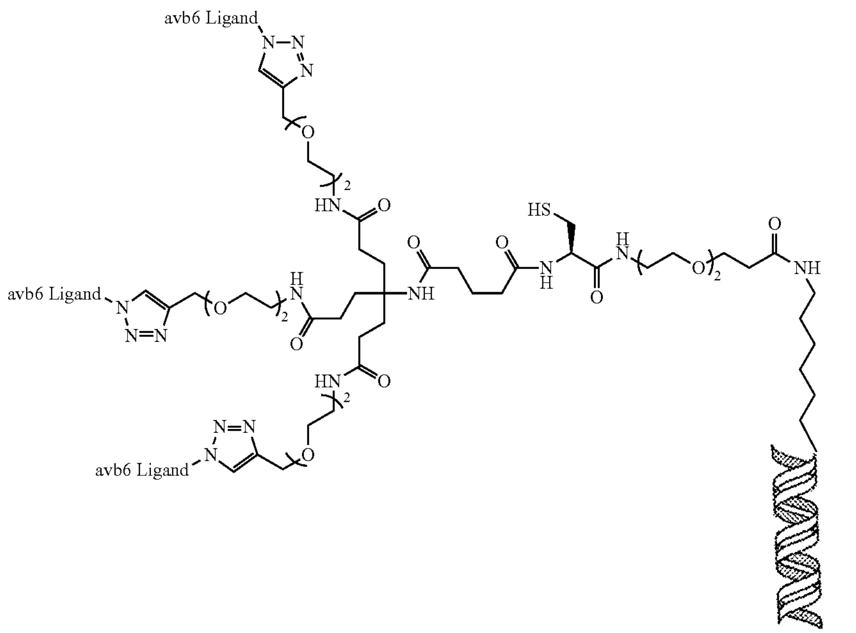

(Structure 331a), wherein  represents the RNAi agent, and "avb6 Ligand" represents the respective ligand structure.

For Group 5, the αvβ6 integrin ligands were conjugated to the RNAi agents via a tridentate scaffold and linker structure that included a cysteine-n-ethyl-maleimide linker as depicted in Structure 330a, shown in Example 6, above. For Group 7, the αvβ6 integrin ligands were conjugated to the RNAi agents via a tridentate scaffold and linker structure that included a glutaric acid linker as depicted in Structure 300a, shown in Example 6, above. For Groups 2 and 6, the peptide-based epithelial cell targeting ligands were comprised of RGD-mimetic peptides and included a 20 kDa PEG moiety as a pharmacokinetic (PK) modulator.

The same alpha-ENaC RNAi agent was used in each of Groups 2 through 7.

Five (5) rats were dosed in each of Groups 1, 2, 3, 4, 5, and 6 (n=5), and four (4) rats were dosed in Group 7 (n=4). Rats were sacrificed on study day 8, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 10

Average Relative rENaC mRNA Expression at Sacrifice (Day 8) in Example 8.

| Group ID | Average Relative rENaC mRNA expression | Low (error) | High (error) |
|---|---|---|---|
| Group 1 (isotonic saline) | 1.000 | 0.143 | 0.167 |
| Group 2 (1.5 mg/kg AD04835-Cys-FCFP-monodentate peptide-based ligand-PEG20 kDa) | 0.354 | 0.078 | 0.100 |
| Group 3 (0.5 mg/kg AD04835-Cys-tridentate αvβ6 integrin ligand of Structure 1) | 0.695 | 0.215 | 0.312 |
| Group 4 (1.5 mg/kg AD04835-Cys-tridentate αvβ6 integrin ligand of Structure 1) | 0.438 | 0.077 | 0.093 |
| Group 5 (1.5 mg/kg AD04835-Cys-(n-ethyl-Mal)-tridentate αvβ6 integrin ligand of Structure 1) | 0.349 | 0.083 | 0.108 |
| Group 6 (1.5 mg/kg AD04835-Cys-PEG20k-tridentate peptide-based ligand) | 0.643 | 0.070 | 0.079 |
| Group 7 (1.5 mg/kg AD04835-glutaric-tridentate αvβ6 integrin ligand of Structure 1) | 0.648 | 0.184 | 0.256 |

As shown in Table 10 above, each of the alpha-ENaC RNAi agents showed a reduction in mRNA expression in rats compared to control. For example, Group 5 (comprising AD04835-Cys-(n-ethyl-Mal)-tridentate αvβ6 integrin ligand Structure 1) showed approximately a 65% reduction (0.358) in average rENaC mRNA expression compared to control, which was comparable to the level of knockdown achieved in Group 2, which had a peptide-based epithelial cell targeting ligand that also included a 20 kDa PEG moiety as a pharmacokinetic modulator.

Example 9. In Vivo Intratracheal Administration of RNAi Agents Targeting Alpha-ENaC Conjugated to αvβ6 Integrin Ligands in Rats On study day 1 and day 2, male Sprague-Dawley rats were administered a dose of 200 microliters intratracheally via a microsprayer device (Penn Century, Philadelphia, Pa.), which included the following dosing Groups:

TABLE 11

Dosing Groups of Rats in Example 9.

| Group | RNAi Agent and Dose | Dosing Regimen |
|---|---|---|
| 1 | Isotonic saline (no RNAi agent) | IT dose on day 1 and day 2 |
| 2 | 1.5 mg/kg of alpha-ENaC RNAi agent AD04835 conjugated to a tridentate αvβ6 integrin ligand of Structure 1 that included a glutaric linker (i.e., having the structure represented in Structure 300a), formulated in isotonic saline. | IT dose on day 1 and day 2 |
| 3 | 1.5 mg/kg of alpha-ENaC RNAi agent AD04835 conjugated to a tridentate αvβ6 integrin ligand of Structure 2 that included a glutaric linker (i.e., having the structure represented in Structure 300a), formulated in isotonic saline. | IT dose on day 1 and day 2 |
| 6 | 1.5 mg/kg of alpha-ENaC RNAi agent AD04835 conjugated to a tridentate αvβ6 integrin ligand of Structure 2 that included a cysteine linker (i.e., having the structure represented in Structure 331a). formulated in isotonic saline. | IT dose on day 1 and day 2 |

The RNAi agents were synthesized having nucleotide sequences directed to target the human alpha-ENaC gene, and included a functionalized amine reactive group ($NH_2$—$C_6$) at the 5' terminal end of the sense strand to facilitate conjugation to the αvβ6 integrin ligands. The nucleotide sequences for the RNAi agents used in this Example are set forth in Example 4, above. For Groups 2 and 3, the respective αvβ6 integrin ligands were conjugated to the RNAi agents via a tridentate scaffold/linker structure that included a glutaric linker as depicted in Structure 300a, shown in Example 6, above. For Group 6 the respective αvβ6 integrin ligands were conjugated to the RNAi agents via a tridentate scaffold/linker structure that included a cysteine linker as depicted in Structure 331a, shown in Example 8, above.

The same alpha-ENaC RNAi agent was used in each of Groups 2 through 8.

Five (5) rats were dosed in Group 1 (n=5), and four (4) rats were dosed in each of Groups 2 and 3 (n=4). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 12

Average Relative rENaC mRNA Expression at Sacrifice (Day 9) in Example 9.

| Group ID | Average Relative rENaC mRNA expression | Low (error) | High (error) |
|---|---|---|---|
| Group 1 (isotonic saline) | 1.000 | 0.165 | 0.197 |
| Group 2 (1.5 mg/kg AD04835-glutaric-tridentate αvβ6 integrin ligand Structure 1) | 0.545 | 0.121 | 0.156 |
| Group 3 (1.5 mg/kg AD04835-glutaric-tridentate αvβ6 integrin ligand Structure 2) | 0.483 | 0.038 | 0.041 |

TABLE 12-continued

Average Relative rENaC mRNA Expression at Sacrifice (Day 9) in Example 9.

| Group ID | Average Relative rENaC mRNA expression | Low (error) | High (error) |
|---|---|---|---|
| Group 6 (1.5 mg/kg AD04835-Cys-tridentate αvβ6 integrin ligand Structure 2) | 0.237 | 0.125 | 0.267 |

As shown in Table 12 above, each of the alpha-ENaC RNAi agents showed a reduction in mRNA expression in rats compared to control. For example, Group 3 (RNAi agent-glutaric-tridentate αvβ6 integrin ligand Structure 2) showed approximately a 52% reduction (0.483) in average rENaC mRNA expression compared to control, and Group 6 (RNAi agent-Cys-tridentate αvβ6 integrin ligand Structure 2) showed approximately a 76% reduction (0.237) in average rENaC mRNA expression compared to control.

Example 10. In Vivo Intratracheal Administration of RNAi Agents Targeting Alpha-ENaC Conjugated to αvβ6 Integrin Ligands in Rats On study day 1 and day 2, male Sprague-Dawley rats were administered a dose of 200 microliters intratracheally via a microsprayer device (Penn Century, Philadelphia, Pa.), which included the following dosing Groups:

TABLE 13

Dosing Groups of Rats in Example 10.

| Group | RNAi Agent and Dose | Dosing Regimen |
|---|---|---|
| 1 | Isotonic saline (no RNAi agent) | IT dose on day 1 and day 2 |
| 2 | 1.0 mg/kg of alpha-ENaC RNAi agent AD04835 conjugated to a monodentate peptide-based epithelial cell targeting ligand via the amine ($NH_2$-$C_6$) linkage on the 5' terminal end of the sense strand that further included a 20 kDa PEG moiety, a cysteine linker, and an FCFP peptide linker, formulated in isotonic saline. | IT dose on day 1 and day 2 |
| 3 | 1.5 mg/kg of alpha-ENaC RNAi agent AD04835 conjugated to a tridentate αvβ6 integrin ligand of Structure 1 that included a cysteine linker (i.e., having the structure represented in Structure 331a), formulated in isotonic saline. | IT dose on day 1 and day 2 |
| 4 | 1.5 mg/kg of alpha-ENaC RNAi agent AD04835 conjugated to a tridentate αvβ6 integrin ligand of Structure 2 that included a cysteine linker (i.e., having the structure represented in Structure 331a), formulated in isotonic saline. | IT dose on day 1 and day 2 |
| 5 | 1.0 mg/kg of alpha-ENaC RNAi agent AD04835 conjugated to a tridentate αvβ6 integrin ligand of Structure 2 that included a cysteine linker (i.e., having the structure represented in Structure 331a), formulated in isotonic saline. | IT dose on day 1 and day 2 |
| 6 | 0.50 mg/kg of alpha-ENaC RNAi agent AD04835 conjugated to a tridentate αvβ6 integrin ligand of Structure 2 that included a cysteine linker (i.e., having the structure represented in Structure 331a), formulated in isotonic saline. | IT dose on day 1 and day 2 |
| 7 | 0.10 mg/kg of alpha-ENaC RNAi agent AD04835 conjugated to a tridentate αvβ6 integrin ligand of Structure 2 that included a cysteine linker (i.e., having the structure represented in Structure 331a), formulated in isotonic saline. | IT dose on day 1 and day 2 |

The RNAi agents were synthesized having nucleotide sequences directed to target the human alpha-ENaC gene, and included a functionalized amine reactive group ($NH_2$—$C_6$) at the 5' terminal end of the sense strand to facilitate conjugation to the αvβ6 integrin ligands. The nucleotide sequences for the RNAi agents used in this Example are set forth in Example 4, above. For Groups 3, 4, 5, and 6, the respective αvβ6 integrin ligands were conjugated to the RNAi agents via a tridentate scaffold/linker structure that included a cysteine linker as depicted in Structure 331a, shown in Example 8, above. For Group 2, the targeting ligands were comprised of RGD-mimetic peptides and included a 20 kDa PEG moiety as a pharmacokinetic (PK) modulator and an FCFP peptide linker.

The same alpha-ENaC RNAi agent was used in each of Groups 2 through 7.

Five (5) rats were dosed in each Group (n=5). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 14

Average Relative rENaC mRNA Expression at Sacrifice (Day 8) in Example 10.

| Group ID | Average Relative rENaC mRNA expression | Low (error) | High (error) |
|---|---|---|---|
| Group 1 (isotonic saline) | 1.000 | 0.164 | 0.196 |
| Group 2 (1.0 mg/kg AD04835-Cys-PEG20 kDa-FCFP-PEG$_{20}$-peptide-based epithelial cell targeting ligand) | 0.531 | 0.132 | 0.176 |
| Group 3 (1.5 mg/kg AD04835-Cys-tridentate αvβ6 integrin ligand Structure 1) | 0.451 | 0.156 | 0.238 |
| Group 4 (1.5 mg/kg AD04835-Cys-tridentate αvβ6 integrin ligand Structure 2) | 0.418 | 0.077 | 0.094 |
| Group 5 (1.0 mg/kg AD04835-Cys-tridentate αvβ6 integrin ligand Structure 2) | 0.436 | 0.043 | 0.048 |
| Group 6 (0.5 mg/kg AD04835-Cys-tridentate αvβ6 integrin ligand Structure 2) | 0.537 | 0.049 | 0.054 |
| Group 7 (0.1 mg/kg AD04835-Cys-tridentate αvβ6 integrin ligand Structure 2) | 0.616 | 0.069 | 0.078 |

As shown in Table 14 above, each of the alpha-ENaC RNAi agents showed a reduction in mRNA expression in rats compared to control. Notably, Group 5 (1.0 mg/kg AD04835-Cys-tridentate αvβ6 integrin ligand Structure 2) showed a numerically superior level of inhibition of alpha-ENaC expression compared to Group 2 (1.0 mg/kg AD04835-Cys-PEG20 kDa-FCFP-PEG20-peptide-based epithelial cell targeting ligand), despite not including a large 20 kilodalton PEG moiety as pharmacokinetic modulator (Group 5=approximately 56% knockdown (0.436); Group 2=approximately 47% knockdown (0.531)).

Example 11. In Vivo Oropharyngeal Aspiration Administration of RNAi Agents Targeting Alpha-ENaC Conjugated to αvβ6 Integrin Ligands in Rats On study day 1, day 2, and day 3, male Sprague Dawley rats were dosed via oropharyngeal ("OP") aspiration administration with 200 microliters using a pipette, according to the following dosing Groups:

TABLE 15

Dosing Groups of Rats in Example 11.

| Group | RNAi Agent and Dose | Dosing Regimen |
|---|---|---|
| 1 | Isotonic saline (no RNAi agent) | OP dose administered on each of days 1, 2, and 3 |
| 2 | 0.01 mg/kg of AD05453 ("naked RNAi agent"), formulated in isotonic saline. | OP dose administered on each of days 1, 2, and 3 |
| 3 | 0.05 mg/kg of AD05453 ("naked RNAi agent"), formulated in isotonic saline | OP dose administered on each of days 1, 2, and 3 |
| 4 | 0.15 mg/kg of AD05453 ("naked RNAi agent"), formulated in isotonic saline | OP dose administered on each of days 1, 2, and 3 |
| 5 | 0.50 mg/kg of AD05453 ("naked RNAi agent"), formulated in isotonic saline | OP dose administered on each of days 1, 2, and 3 |
| 6 | 0.01 mg/kg of AD05453 conjugated to a tridentate αvβ6 integrin ligand of Structure 6.1, formulated in isotonic saline. | OP dose administered on each of days 1, 2, and 3 |
| 7 | 0.05 mg/kg of AD05453 conjugated to a tridentate αvβ6 integrin ligand of Structure 6.1, formulated in isotonic saline. | OP dose administered on each of days 1, 2, and 3 |
| 8 | 0.15 mg/kg of AD05453 conjugated to a tridentate αvβ6 integrin ligand of Structure 6.1, formulated in isotonic saline. | OP dose administered on each of days 1, 2, and 3 |
| 9 | 0.50 mg/kg of AD05453 conjugated to a tridentate αvβ6 integrin ligand of Structure 6.1, formulated in isotonic saline. | OP dose administered on each of days 1, 2, and 3 |

The RNAi agents were synthesized having nucleotide sequences directed to target the human alpha-ENaC gene, and included a functionalized amine reactive group ($NH_2$—$C_6$) at the 5' terminal end of the sense strand to facilitate conjugation to the αvβ6 integrin ligands. The nucleotide sequences for the RNAi agents used in this Example are set forth in Example 6, above. The respective αvβ6 integrin ligands were conjugated to the RNAi agents via a tridentate scaffold/linker structure that included a glutaric linker as depicted in Structure 300a, shown in Example 6, above.

Five (5) rats were dosed in each of Groups 1, 3, 4, 5, 8, and 9 (n=5), and six (6) rats were dosed in Groups 2, 6, and 7 (n=6). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 16

Average Relative rENaC mRNA Expression at Sacrifice (Day 9) in Example 11.

| Group ID | Average Relative rENaC mRNA expression | Low (error) | High (error) |
|---|---|---|---|
| Group 1 (isotonic saline) | 1.000 | 0.199 | 0.249 |
| Group 2 (0.01 mg/kg AD05347 (naked)) | 1.016 | 0.219 | 0.279 |
| Group 3 (0.05 mg/kg AD05347 (naked)) | 0.881 | 0.157 | 0.192 |
| Group 4 (0.15 mg/kg AD05347 (naked)) | 0.638 | 0.179 | 0.250 |
| Group 5 (0.50 mg/kg AD05347 (naked)) | 0.354 | 0.076 | 0.097 |
| Group 6 (0.01 mg/kg AD05453-glutaric-tridentate αvβ6 integrin ligand Structure 6.1) | 0.646 | 0.058 | 0.063 |
| Group 7 (0.05 mg/kg AD05453-glutaric-tridentate αvβ6 integrin ligand Structure 6.1) | 0.432 | 0.044 | 0.049 |
| Group 8 (0.15 mg/kg AD05453-glutaric-tridentate αvβ6 integrin ligand Structure 6.1) | 0.319 | 0.034 | 0.038 |
| Group 9 (0.50 mg/kg AD05453-glutaric-tridentate αvβ6 integrin ligand Structure 6.1) | 0.254 | 0.043 | 0.052 |

As shown in Table 16 above, each of the alpha-ENaC RNAi agents conjugated to the avb6 integrin ligand having Structure 6.1 (in tridentate form) showed a reduction in mRNA expression in rats compared to control. Further, at each dosage level, the alpha-ENaC RNAi agents conjugated to the avb6 integrin ligand having Structure 6.1 outperformed the alpha-ENaC RNAi agents administered naked, showing a ligand effect on delivery of the RNAi agent. (e.g., compare Groups 2 and 6; Groups 3 and 7; Groups 4 and 8; and Groups 5 and 9).

Example 12. Additional αvβ6 Integrin Ligand Binding Activity

As reported in the following Table 17, additional IC50 binding data was obtained for the αvβ6 integrin ligands of Structures 2, 6.1, 7, and 23 used in certain Examples herein:

TABLE 17

IC50 Binding Activity.

| Group | IC50 (nM) αvβ6 |
|---|---|
| Structure 2 | 205.4 |
| Structure 6.1 | 1.6 |
| Structure 7 | 381.5 |
| Structure 23 | 759.7 |

Azide-functionalized structures (i.e., Structures 2b and 6.1b, 7b, and 23b) were examined for IC50 under conditions typically used and known in the art. As shown in Table 17, above, Structure 6.1 showed potent binding activity to αvβ6 integrin (IC50=1.6 nM).

Example 13. In Vivo Oropharyngeal Aspiration Administration of RNAi Agents Targeting Alpha-ENaC Conjugated to αvβ6 Integrin Ligands in Rats On study day 1, male Sprague Dawley rats were dosed via oropharyngeal ("OP") aspiration administration with 200 microliters using a pipette, according to the following dosing Groups:

TABLE 18

Dosing Groups of Rats in Example 13.

| Group | RNAi Agent and Dose | Dosing Regimen |
|---|---|---|
| 1 | Isotonic saline (no RNAi agent) | Single OP dose administered on day 1 |
| 5 | (0.5 mg/kg AD05347 tridentate αvβ6 integrin ligand Structure 1) | Single OP dose administered on day 1 |
| 6 | (0.5 mg/kg AD05347 tridentate αvβ6 integrin ligand Structure 2) | Single OP dose administered on day 1 |
| 7 | (0.5 mg/kg AD05347 tridentate αvβ6 integrin ligand Structure 5) | Single OP dose administered on day 1 |

The RNAi agents were synthesized having nucleotide sequences directed to target the human alpha-ENaC gene, and those including the AD05347 duplex included a functionalized amine reactive group ($NH_2$—$C_6$) at the 5' terminal end of the sense strand to facilitate conjugation to the αvβ6 integrin ligands. The nucleotide sequences for RNAi agent AD05347 is set forth in Example 6, above. The respective αvβ6 integrin ligands were conjugated to the RNAi agents via a tridentate scaffold/linker structure that included a glutaric linker as depicted in Structure 300a, shown in Example 6, above.

Five (5) rats were dosed in each group (n=5). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 19

Average Relative rENaC mRNA Expression at Sacrifice (Day 9) in Example 13.

| Group ID | Average Relative rENaC mRNA expression | Low (error) | High (error) |
|---|---|---|---|
| Group 1 (isotonic saline) | 1.000 | 0.044 | 0.046 |
| Group 5 (0.5 mg/kg AD05347 tridentate αvβ6 integrin ligand Structure 1) | 0.449 | 0.088 | 0.109 |
| Group 6 (0.5 mg/kg AD05347 tridentate αvβ6 integrin ligand Structure 2) | 0.487 | 0.049 | 0.055 |
| Group 7 (0.5 mg/kg AD05347 tridentate αvβ6 integrin ligand Structure 5) | 0.715 | 0.078 | 0.087 |

Example 14. In Vivo Oropharyngeal Aspiration Administration of RNAi Agents Targeting Alpha-ENaC Conjugated to αvβ6 Integrin Ligands in Rats On study day 1, male Sprague Dawley rats were dosed via oropharyngeal ("OP") aspiration administration with 200 microliters using a pipette, according to the following dosing Groups:

TABLE 20

Dosing Groups of Rats in Example 14.

| Group | RNAi Agent and Dose | Dosing Regimen |
|---|---|---|
| 1 | Isotonic saline (no RNAi agent) | Single OP dose administered on day 1 |
| 2 | (0.5 mg/kg AD05347- tridentate αvβ6 integrin ligand Structure 2) | Single OP dose administered on day 1 |
| 3 | (0.5 mg/kg AD05453- tridentate αvβ6 integrin ligand Structure 6.1) | Single OP dose administered on day 1 |
| 4 | (0.5 mg/kg AD05453- tridentate αvβ6 integrin ligand Structure 6.3) | Single OP dose administered on day 1 |
| 5 | (0.5 mg/kg AD05453- tridentate αvβ6 integrin ligand Structure 6.4) | Single OP dose administered on day 1 |

The RNAi agents were synthesized having nucleotide sequences directed to target the human alpha-ENaC gene, and those including the AD05347 and AD05453 duplex included a functionalized amine reactive group ($NH_2$—$C_6$) at the 5' terminal end of the sense strand to facilitate conjugation to the αvβ6 integrin ligands. The nucleotide sequences for the RNAi agents used in this Example are set forth in Example 6, above. The respective αvβ6 integrin ligands were conjugated to the RNAi agents via a tridentate scaffold/linker structure that included a glutaric linker as depicted in Structure 300a, shown in Example 6, above.

Four (4) rats were dosed in each group (n=4). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 21

Average Relative rENaC mRNA Expression at Sacrifice (Day 9) in Example 14.

| Group ID | Average Relative rENaC mRNA expression | Low (error) | High (error) |
|---|---|---|---|
| Group 1 (isotonic saline) | 1.000 | 0.164 | 0.197 |
| Group 2 (0.5 mg/kg AD05347- tridentate αvβ6 integrin ligand Structure 2) | 0.418 | 0.051 | 0.058 |
| Group 3 (0.5 mg/kg AD05453- tridentate αvβ6 integrin ligand Structure 6.1) | 0.472 | 0.071 | 0.084 |
| Group 4 (0.5 mg/kg AD05453- tridentate αvβ6 integrin ligand Structure 6.3) | 0.534 | 0.059 | 0.066 |
| Group 5 (0.5 mg/kg AD05453- tridentate αvβ6 integrin ligand Structure 6.4) | 0.620 | 0.105 | 0.127 |

Example 15. In Vivo Oropharyngeal Aspiration Administration of RNAi Agents Targeting Alpha-ENaC Conjugated to αvβ6 Integrin Ligands in Rats On study day 1, male Sprague Dawley rats were dosed via oropharyngeal ("OP") aspiration administration with 200 microliters using a pipette, according to the following dosing Groups:

TABLE 22

Dosing Groups of Rats in Example 15.

| Group | RNAi Agent and Dose | Dosing Regimen |
|---|---|---|
| 1 | Isotonic saline (no RNAi agent) | Single OP dose administered on day 1 |
| 4 | (0.5 mg/kg AD05453-tridentate αvβ6 integrin ligand Structure 6.1) | Single OP dose administered on day 1 |
| 9 | (0.5 mg/kg AD05453-tridentate αvβ6 integrin ligand Structure 2) | Single OP dose administered on day 1 |
| 11 | (0.5 mg/kg AD05453-tridentate αvβ6 integrin ligand Structure 12) | Single OP dose administered on day 1 |
| 12 | (0.5 mg/kg AD05453-tridentate αvβ6 integrin ligand Structure 13) | Single OP dose administered on day 1 |

The RNAi agents were synthesized having nucleotide sequences directed to target the human alpha-ENaC gene, the RNAi agents including a functionalized amine reactive group ($NH_2$—$C_6$) at the 5' terminal end of the sense strand to facilitate conjugation to the αvβ6 integrin ligands. The nucleotide sequences for RNAi agent AD05453 is set forth in Example 6, above. The respective αvβ6 integrin ligands were conjugated to the RNAi agents via a tridentate scaffold/linker structure that included a glutaric linker as depicted in Structure 300a, shown in Example 6, above.

Four (4) rats were dosed in each of groups 1-9 and 12 (n=4). Three (3) rats were dosed in groups 10 and 11 (n=3). Rats were sacrificed on study day 7, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 23

Average Relative rENaC mRNA Expression at Sacrifice (Day 7) in Example 15.

| Group ID | Average Relative rENaC mRNA expression | Low (error) | High (error) |
|---|---|---|---|
| Group 1 (isotonic saline) | 1.000 | 0.058 | 0.062 |
| Group 4 (0.5 mg/kg AD05453-tridentate αvβ6 integrin ligand Structure 6.1) | 0.606 | 0.217 | 0.338 |
| Group 9 (0.5 mg/kg AD05453-tridentate αvβ6 integrin ligand Structure 2) | 0.705 | 0.136 | 0.169 |
| Group 11 (0.5 mg/kg AD05453-tridentate αvβ6 integrin ligand Structure 12) | 0.703 | 0.093 | 0.108 |
| Group 12 (0.5 mg/kg AD05453-tridentate αvβ6 integrin ligand Structure 13) | 0.711 | 0.086 | 0.098 |

Example 16. In Vivo Oropharyngeal Aspiration Administration of RNAi Agents Targeting Alpha-ENaC Conjugated to αvβ6 Integrin Ligands in Rats On study day 1, male Sprague Dawley rats were dosed via oropharyngeal ("OP") aspiration administration with 200 microliters using a pipette, according to the following dosing Groups:

TABLE 24

Dosing Groups of Rats in Example 16.

| Group | RNAi Agent and Dose | Dosing Regimen |
|---|---|---|
| 1 | Isotonic saline (no RNAi agent) | Single OP dose administered on day 1 |
| 2 | (0.5 mg/kg AD05453 tridentate αvβ6 integrin ligand Structure 6.1) | Single OP dose administered on day 1 |
| 3 | (0.5 mg/kg AD05453 tridentate αvβ6 integrin ligand Structure 14) | Single OP dose administered on day 1 |
| 4 | (0.5 mg/kg AD05453 tridentate αvβ6 integrin ligand Structure 15) | Single OP dose administered on day 1 |

The RNAi agents were synthesized having nucleotide sequences directed to target the human alpha-ENaC gene, the RNAi agents including a functionalized amine reactive group ($NH_2$—$C_6$) at the 5' terminal end of the sense strand to facilitate conjugation to the αvβ6 integrin ligands. The nucleotide sequences for RNAi agent AD05453 is set forth in Example 6, above. The respective αvβ6 integrin ligands were conjugated to the RNAi agents via a tridentate scaffold/linker structure that included a glutaric linker as depicted in Structure 300a, shown in Example 6, above.

Four (4) rats were dosed in each group. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 25

Average Relative rENaC mRNA Expression at Sacrifice (Day 9) in Example 16.

| Group ID | Average Relative rENaC mRNA expression | Low (error) | High (error) |
|---|---|---|---|
| Group 1 (isotonic saline) | 1.000 | 0.084 | 0.092 |
| Group 2 (0.5 mg/kg AD05453 tridentate αvβ6 integrin ligand Structure 6.1) | 0.597 | 0.163 | 0.224 |
| Group 3 (0.5 mg/kg AD05453 tridentate αvβ6 integrin ligand Structure 14) | 0.674 | 0.115 | 0.139 |
| Group 4 (0.5 mg/kg AD05453 tridentate αvβ6 integrin ligand Structure 15) | 0.533 | 0.047 | 0.052 |

Example 17. In Vivo Oropharyngeal Aspiration Administration of RNAi Agents Targeting Alpha-ENaC Conjugated to αvβ6 Integrin Ligands in Rats On study day 1, male Sprague Dawley rats were dosed via oropharyngeal ("OP") aspiration administration with 200 microliters using a pipette, according to the following dosing Groups:

TABLE 26

Dosing Groups of Rats in Example 17.

| Group | RNAi Agent and Dose | Dosing Regimen |
|---|---|---|
| 1 | Isotonic saline (no RNAi agent) | Single OP dose administered on day 1 |

TABLE 26-continued

Dosing Groups of Rats in Example 17.

| Group | RNAi Agent and Dose | Dosing Regimen |
|---|---|---|
| 2 | (0.5 mg/kg AD05453 tridentate αvβ6 integrin ligand Structure 6.1) | Single OP dose administered on day 1 |
| 3 | (0.5 mg/kg AD05453 tridentate αvβ6 integrin ligand Structure 16) | Single OP dose administered on day 1 |
| 4 | (0.5 mg/kg AD05453 tridentate αvβ6 integrin ligand Structure 11) | Single OP dose administered on day 1 |

The RNAi agents were synthesized having nucleotide sequences directed to target the human alpha-ENaC gene, the RNAi agents including a functionalized amine reactive group (NH$_2$—C$_6$) at the 5' terminal end of the sense strand to facilitate conjugation to the αvβ6 integrin ligands. The nucleotide sequences for RNAi agent AD05453 is set forth in Example 6, above. The respective αvβ6 integrin ligands were conjugated to the RNAi agents via a tridentate scaffold/linker structure that included a glutaric linker as depicted in Structure 300a, shown in Example 6, above.

Five (5) rats were dosed in each group, except for group 4, which had four (4) rats dosed. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 27

Average Relative rENaC mRNA Expression at Sacrifice (Day 9) in Example 17.

| Group ID | Average Relative rENaC mRNA expression | Low (error) | High (error) |
|---|---|---|---|
| Group 1 (isotonic saline) | 1.000 | 0.195 | 0.242 |
| Group 2 (0.5 mg/kg AD05453 tridentate αvβ6 integrin ligand Structure 6.1) | 0.489 | 0.168 | 0.257 |
| Group 3 (0.5 mg/kg AD05453 tridentate αvβ6 integrin ligand Structure 16) | 0.872 | 0.104 | 0.118 |
| Group 4 (0.5 mg/kg AD05453 tridentate αvβ6 integrin ligand Structure 11) | 0.625 | 0.126 | 0.158 |

Example 18. In Vivo Oropharyngeal Aspiration Administration of RNAi Agents Targeting Alpha-ENaC Conjugated to αvβ6 Integrin Ligands in Rats On study day 1, male Sprague Dawley rats were dosed via oropharyngeal ("OP") aspiration administration with 200 microliters using a pipette, according to the following dosing Groups:

TABLE 28

Dosing Groups of Rats in Example 18.

| Group | RNAi Agent and Dose | Dosing Regimen |
|---|---|---|
| 1 | Isotonic saline (no RNAi agent) | Single OP dose administered on day 1 |

TABLE 28-continued

Dosing Groups of Rats in Example 18.

| Group | RNAi Agent and Dose | Dosing Regimen |
|---|---|---|
| 2 | (0.5 mg/kg AD05453 tridentate αvβ6 integrin ligand Structure 6.1) | Single OP dose administered on day 1 |
| 3 | (0.5 mg/kg AD05453 tridentate αvβ6 integrin ligand Structure 17) | Single OP dose administered on day 1 |
| 4 | (0.5 mg/kg AD05453 tridentate αvβ6 integrin ligand Structure 15) | Single OP dose administered on day 1 |

The RNAi agents were synthesized having nucleotide sequences directed to target the human alpha-ENaC gene, the RNAi agents including a functionalized amine reactive group (NH$_2$—C$_6$) at the 5' terminal end of the sense strand to facilitate conjugation to the αvβ6 integrin ligands. The nucleotide sequences for RNAi agent AD05453 is set forth in Example 6, above. The respective αvβ6 integrin ligands were conjugated to the RNAi agents via a tridentate scaffold/linker structure that included a glutaric linker as depicted in Structure 300a, shown in Example 6, above.

Four (4) rats were dosed in each group. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 29

Average Relative rENaC mRNA Expression at Sacrifice (Day 9) in Example 18.

| Group ID | Average Relative rENaC mRNA expression | Low (error) | High (error) |
|---|---|---|---|
| Group 1 (isotonic saline) | 1.000 | 0.140 | 0.162 |
| Group 2 (0.5 mg/kg AD05453 tridentate αvβ6 integrin ligand Structure 6.1) | 0.622 | 0.035 | 0.037 |
| Group 3 (0.5 mg/kg AD05453 tridentate αvβ6 integrin ligand Structure 17) | 0.818 | 0.101 | 0.116 |
| Group 4 (0.5 mg/kg AD05453 tridentate αvβ6 integrin ligand Structure 15) | 0.628 | 0.101 | 0.120 |

Example 19. In Vivo Oropharyngeal Aspiration Administration of RNAi Agents Targeting Alpha-ENaC Conjugated to αvβ6 Integrin Ligands in Rats On study day 1, male Sprague Dawley rats were dosed via oropharyngeal ("OP") aspiration administration with 200 microliters using a pipette, according to the following dosing Groups:

TABLE 30

Dosing Groups of Rats in Example 19.

| Group | RNAi Agent and Dose | Dosing Regimen |
|---|---|---|
| 1 | Isotonic saline (no RNAi agent) | Single OP dose administered on day 1 |

TABLE 30-continued

Dosing Groups of Rats in Example 19.

| Group | RNAi Agent and Dose | Dosing Regimen |
|---|---|---|
| 2 | (0.5 mg/kg AD05453 tridentate αvβ6 integrin ligand Structure 6.1) | Single OP dose administered on day 1 |
| 3 | (0.5 mg/kg AD05453 tridentate αvβ6 integrin ligand Structure 15) | Single OP dose administered on day 1 |
| 4 | (0.5 mg/kg AD05453 tridentate αvβ6 integrin ligand Structure 18) | Single OP dose administered on day 1 |
| 5 | (0.5 mg/kg AD05453 tridentate αvβ6 integrin ligand Structure 19) | Single OP dose administered on day 1 |
| 6 | (0.5 mg/kg AD05453 tridentate αvβ6 integrin ligand Structure 20) | Single OP dose administered on day 1 |

The RNAi agents were synthesized having nucleotide sequences directed to target the human alpha-ENaC gene, the RNAi agents including a functionalized amine reactive group ($NH_2$—$C_6$) at the 5' terminal end of the sense strand to facilitate conjugation to the αvβ6 integrin ligands. The nucleotide sequences for RNAi agent AD05453 is set forth in Example 6, above. The respective αvβ6 integrin ligands were conjugated to the RNAi agents via a tridentate scaffold/linker structure that included a glutaric linker as depicted in Structure 300a, shown in Example 6, above.

Four (4) rats were dosed in each group. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 31

Average Relative rENaC mRNA Expression at Sacrifice (Day 9) in Example 19.

| Group ID | Average Relative rENaC mRNA expression | Low (error) | High (error) |
|---|---|---|---|
| Group 1 (isotonic saline) | 1.000 | 0.121 | 0.138 |
| Group 2 (0.5 mg/kg AD05453 tridentate αvβ6 integrin ligand Structure 6.1) | 0.503 | 0.074 | 0.086 |
| Group 3 (0.5 mg/kg AD05453 tridentate αvβ6 integrin ligand Structure 15) | 0.700 | 0.079 | 0.089 |
| Group 4 (0.5 mg/kg AD05453 tridentate αvβ6 integrin ligand Structure 18) | 0.742 | 0.137 | 0.169 |
| Group 5 (0.5 mg/kg AD05453 tridentate αvβ6 integrin ligand Structure 19) | 0.837 | 0.186 | 0.239 |
| Group 6 (0.5 mg/kg AD05453 tridentate αvβ6 integrin ligand Structure 20) | 0.589 | 0.078 | 0.090 |

Example 20. In Vivo Oropharyngeal Aspiration Administration of RNAi Agents Targeting Alpha-ENaC Conjugated to αvβ6 Integrin Ligands in Rats On study days 1 and 2, male Sprague Dawley rats were dosed via oropharyngeal ("OP") aspiration administration with 200 microliters using a pipette, according to the following dosing Groups:

TABLE 32

Dosing Groups of Rats in Example 20.

| Group | RNAi Agent and Dose | Dosing Regimen |
|---|---|---|
| 1 | Isotonic saline (no RNAi agent) | OP dose administered on days 1 and 2 |
| 2 | (0.5 mg/kg AD05453 tridentate αvβ6 integrin ligand Structure 6.1) | OP dose administered on days 1 and 2 |
| 3 | (0.5 mg/kg AD05453 tridentate αvβ6 integrin ligand Structure 22) | OP dose administered on days 1 and 2 |
| 4 | (0.5 mg/kg AD05453 tridentate αvβ6 integrin ligand Structure 23) | OP dose administered on days 1 and 2 |
| 5 | (0.5 mg/kg AD05453 tridentate αvβ6 integrin ligand Structure 24) | OP dose administered on days 1 and 2 |
| 6 | (0.5 mg/kg AD05453 tridentate αvβ6 integrin ligand Structure 25) | OP dose administered on days 1 and 2 |
| 7 | (0.5 mg/kg AD05453 tridentate αvβ6 integrin ligand Structure 15) | OP dose administered on days 1 and 2 |

The RNAi agents were synthesized having nucleotide sequences directed to target the human alpha-ENaC gene, the RNAi agents including a functionalized amine reactive group ($NH_2$—$C_6$) at the 5' terminal end of the sense strand to facilitate conjugation to the αvβ6 integrin ligands. The nucleotide sequences for RNAi agent AD05453 is set forth in Example 6, above. The respective αvβ6 integrin ligands were conjugated to the RNAi agents via a tridentate scaffold/linker structure that included a glutaric linker as depicted in Structure 300a, shown in Example 6, above.

Four (4) rats were dosed in each group, except for group 1, which had three (3) rats dosed. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 33

Average Relative rENaC mRNA Expression at Sacrifice (Day 9) in Example 20.

| Group ID | Average Relative rENaC mRNA expression | Low (error) | High (error) |
|---|---|---|---|
| Group 1 (isotonic saline) | 1.000 | 0.164 | 0.197 |
| Group 2 (0.5 mg/kg AD05453 tridentate αvβ6 integrin ligand Structure 6.1) | 0.400 | 0.057 | 0.066 |
| Group 3 (0.5 mg/kg AD05453 tridentate αvβ6 integrin ligand Structure 22) | 0.483 | 0.170 | 0.263 |
| Group 4 (0.5 mg/kg AD05453 tridentate αvβ6 integrin ligand Structure 23) | 0.339 | 0.042 | 0.048 |
| Group 5 (0.5 mg/kg AD05453 tridentate αvβ6 integrin ligand Structure 24) | 0.493 | 0.125 | 0.168 |
| Group 6 (0.5 mg/kg AD05453 tridentate αvβ6 integrin ligand Structure 25) | 0.416 | 0.089 | 0.113 |
| Group 7 (0.5 mg/kg AD05453 tridentate αvβ6 integrin ligand Structure 15) | 0.473 | 0.052 | 0.058 |

Example 21. In Vivo Oropharyngeal Aspiration Administration of RNAi Agents Targeting Alpha-ENaC Conjugated to αvβ6 Integrin Ligands in Rats On study days 1 and 2, male Sprague Dawley rats were dosed via oropharyngeal ("OP") aspiration administration with 200 microliters using a pipette, according to the following dosing Groups:

TABLE 34

Dosing Groups of Rats in Example 21.

| Group | RNAi Agent and Dose | Dosing Regimen |
|---|---|---|
| 1 | Isotonic saline (no RNAi agent) | OP dose administered on days 1 and 2 |
| 2 | (0.5 mg/kg AD05453 tridentate αvβ6 integrin ligand Structure 6.1) | OP dose administered on days 1 and 2 |
| 4 | (0.5 mg/kg AD05453 tridentate αvβ6 integrin ligand Structure 27) | OP dose administered on days 1 and 2 |

The RNAi agents were synthesized having nucleotide sequences directed to target the human alpha-ENaC gene, the RNAi agents including a functionalized amine reactive group ($NH_2$—$C_6$) at the 5' terminal end of the sense strand to facilitate conjugation to the αvβ6 integrin ligands. The nucleotide sequences for RNAi agent AD05453 is set forth in Example 6, above. The respective αvβ6 integrin ligands were conjugated to the RNAi agents via a tridentate scaffold/linker structure that included a glutaric linker as depicted in Structure 300a, shown in Example 6, above.

Five (5) rats were dosed in each group, except group 2, which had six (6) rats dosed. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 35

Average Relative rENaC mRNA Expression at Sacrifice (Day 9) in Example 21.

| Group ID | Average Relative rENaC mRNA expression | Low (error) | High (error) |
|---|---|---|---|
| Group 1 (isotonic saline) | 1.000 | 0.150 | 0.176 |
| Group 2 (0.5 mg/kg AD05453 tridentate αvβ6 integrin ligand Structure 6.1) | 0.380 | 0.108 | 0.151 |
| Group 4 (0.5 mg/kg AD05453 tridentate αvβ6 integrin ligand Structure 27) | 0.411 | 0.051 | 0.058 |

Example 22. In Vivo Oropharyngeal Aspiration Administration of RNAi Agents Targeting Alpha-ENaC Conjugated to αvβ6 Integrin Ligands in Rats On study days 1 and 2, male Sprague Dawley rats were dosed via oropharyngeal ("OP") aspiration administration with 200 microliters using a pipette, according to the following dosing Groups:

TABLE 36

Dosing Groups of Rats in Example 22.

| Group | RNAi Agent and Dose | Dosing Regimen |
|---|---|---|
| 1 | Isotonic saline (no RNAi agent) | OP dose administered on days 1 and 2 |
| 2 | (0.5 mg/kg AD05453 tridentate αvβ6 integrin ligand Structure 6.1) | OP dose administered on days 1 and 2 |
| 3 | (0.5 mg/kg AD05453 tridentate αvβ6 integrin ligand Structure 29) | OP dose administered on days 1 and 2 |
| 4 | (0.5 mg/kg AD05453 tridentate αvβ6 integrin ligand Structure 30) | OP dose administered on days 1 and 2 |
| 5 | (0.5 mg/kg AD05453 tridentate αvβ6 integrin ligand Structure 31) | OP dose administered on days 1 and 2 |
| 6 | (0.5 mg/kg AD05453 tridentate αvβ6 integrin ligand Structure 32) | OP dose administered on days 1 and 2 |
| 7 | (0.5 mg/kg AD05453 tridentate αvβ6 integrin ligand Structure 33) | OP dose administered on days 1 and 2 |

The RNAi agents were synthesized having nucleotide sequences directed to target the human alpha-ENaC gene, the RNAi agents including a functionalized amine reactive group ($NH_2$—$C_6$) at the 5' terminal end of the sense strand to facilitate conjugation to the αvβ6 integrin ligands. The nucleotide sequences for RNAi agent AD05453 is set forth in Example 6, above. The respective αvβ6 integrin ligands were conjugated to the RNAi agents via a tridentate scaffold/linker structure that included a glutaric linker as depicted in Structure 300a, shown in Example 6, above.

Four (4) rats were dosed in each group. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 37

Average Relative rENaC mRNA Expression at Sacrifice (Day 9) in Example 22.

| Group ID | Average Relative rENaC mRNA expression | Low (error) | High (error) |
|---|---|---|---|
| Group 1 (isotonic saline) | 1.000 | 0.179 | 0.218 |
| Group 2 (0.5 mg/kg AD05453 tridentate αvβ6 integrin ligand Structure 6.1) | 0.511 | 0.132 | 0.178 |
| Group 3 (0.5 mg/kg AD05453 tridentate αvβ6 integrin ligand Structure 29) | 0.455 | 0.024 | 0.025 |
| Group 4 (0.5 mg/kg AD05453 tridentate αvβ6 integrin ligand Structure 30) | 0.637 | 0.047 | 0.050 |
| Group 5 (0.5 mg/kg AD05453 tridentate αvβ6 integrin ligand Structure 31) | 0.505 | 0.079 | 0.093 |
| Group 6 (0.5 mg/kg AD05453 tridentate αvβ6 integrin ligand Structure 32) | 0.534 | 0.135 | 0.181 |
| Group 7 (0.5 mg/kg AD05453 tridentate αvβ6 integrin ligand Structure 33) | 0.560 | 0.145 | 0.196 |

Example 23. In Vivo Oropharyngeal Aspiration Administration of RNAi Agents Targeting Alpha-ENaC Conjugated to αvβ6 Integrin Ligands in Rats On study days 1 and 2, male Sprague Dawley rats were dosed via oropharyngeal ("OP") aspiration administration with 200 microliters using a pipette, according to the following dosing Groups:

TABLE 38

Dosing Groups of Rats in Example 23.

| Group | RNAi Agent and Dose | Dosing Regimen |
|---|---|---|
| 1 | Isotonic saline (no RNAi agent) | OP dose administered on days 1 and 2 |
| 2 | (0.5 mg/kg AD05453 tridentate αvβ6 integrin ligand Structure 6.1) | OP dose administered on days 1 and 2 |
| 3 | (0.5 mg/kg AD05453 tridentate αvβ6 integrin ligand Structure 29) | OP dose administered on days 1 and 2 |
| 4 | (0.5 mg/kg AD05453 tridentate αvβ6 integrin ligand Structure 34) | OP dose administered on days 1 and 2 |
| 5 | (0.5 mg/kg AD05453 tridentate αvβ6 integrin ligand Structure 35) | OP dose administered on days 1 and 2 |
| 6 | (0.5 mg/kg AD05453 tridentate αvβ6 integrin ligand Structure 36) | OP dose administered on days 1 and 2 |
| 7 | (0.5 mg/kg AD05453 tridentate αvβ6 integrin ligand Structure 37) | OP dose administered on days 1 and 2 |

The RNAi agents were synthesized having nucleotide sequences directed to target the human alpha-ENaC gene, the RNAi agents including a functionalized amine reactive group ($NH_2$—$C_6$) at the 5' terminal end of the sense strand to facilitate conjugation to the αvβ6 integrin ligands. The nucleotide sequences for RNAi agent AD05453 is set forth in Example 6, above. The respective αvβ6 integrin ligands were conjugated to the RNAi agents via a tridentate scaffold/linker structure that included a glutaric linker as depicted in Structure 300a, shown in Example 6, above.

Four (4) rats were dosed in each group. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 39

Average Relative rENaC mRNA Expression at Sacrifice (Day 9) in Example 23.

| Group ID | Average Relative rENaC mRNA expression | Low (error) | High (error) |
|---|---|---|---|
| Group 1 (isotonic saline) | 1.000 | 0.117 | 0.132 |
| Group 2 (0.5 mg/kg AD05453 tridentate αvβ6 integrin ligand Structure 6.1) | 0.368 | 0.079 | 0.100 |
| Group 3 (0.5 mg/kg AD05453 tridentate αvβ6 integrin ligand Structure 29) | 0.429 | 0.033 | 0.036 |
| Group 4 (0.5 mg/kg AD05453 tridentate αvβ6 integrin ligand Structure 34) | 0.465 | 0.103 | 0.132 |
| Group 5 (0.5 mg/kg AD05453 tridentate αvβ6 integrin ligand Structure 35) | 0.449 | 0.053 | 0.060 |
| Group 6 (0.5 mg/kg AD05453 tridentate αvβ6 integrin ligand Structure 36) | 0.501 | 0.043 | 0.047 |
| Group 7 (0.5 mg/kg AD05453 tridentate αvβ6 integrin ligand Structure 37) | 0.443 | 0.049 | 0.055 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An αvβ6 integrin ligand having the structure:

2. The αvβ6 integrin ligand of claim 1, wherein the αvβ6 integrin ligand comprises a structure selected from the group consisting of:

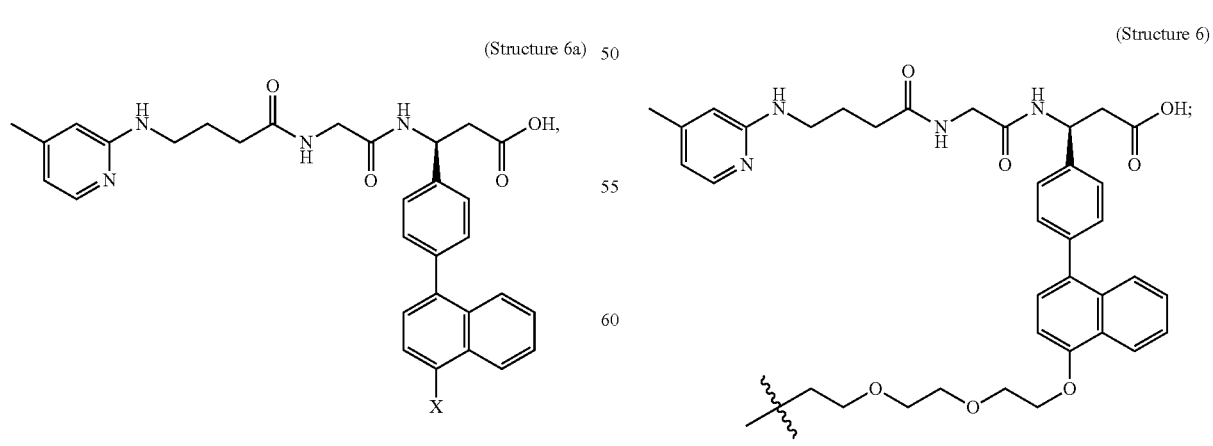

or a pharmaceutically acceptable salt thereof, wherein X comprises a cargo molecule.

(Structure 6.1)

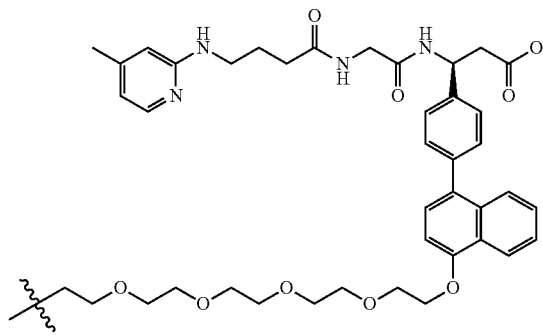

(Structure 6.2)

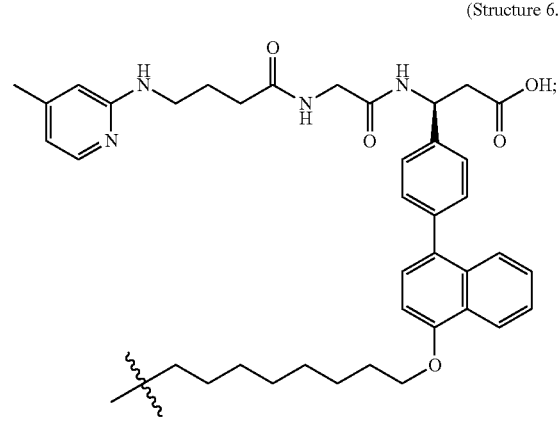

(Structure 6.3)

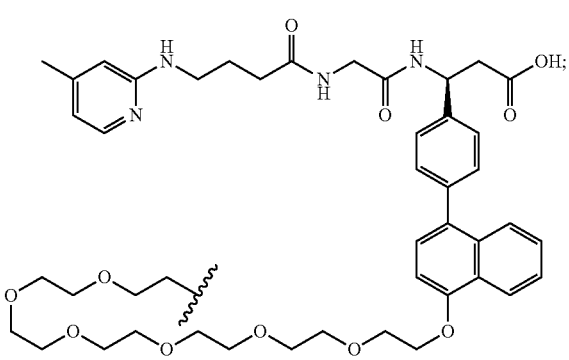

-continued and (Structure 6.4)

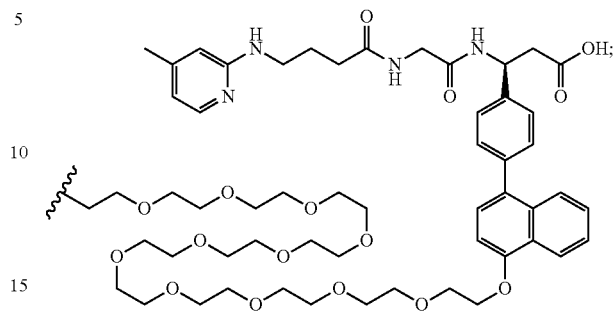

or a pharmaceutically acceptable salt thereof, wherein ⸹ indicates the point of connection to a moiety comprising a cargo molecule.

3. The αvβ6 integrin ligand of claim 1, wherein the cargo molecule is an active pharmaceutical ingredient or a prodrug.

4. The αvβ6 integrin ligand of claim 1, wherein the cargo molecule comprises a natural or modified nucleic acid oligonucleotide.

5. The αvβ6 integrin ligand of claim 1, wherein the cargo molecule comprises an RNAi agent.

6. The αvβ6 integrin ligand of claim 1, further comprising a polyethylene glycol linker having 2-20 ethylene oxide units.

7. A structure comprising the αvβ6 integrin ligand of claim 1, a linking group, and a scaffold, wherein the structure is bound to the cargo molecule.

8. The structure of claim 7, wherein the structure comprises the αvβ6 integrin ligand in monodentate form.

9. The structure of claim 7, wherein the structure comprises the αvβ6 integrin ligand in bidentate form.

10. The structure of claim 7, wherein the structure comprises the αvβ6 integrin ligand in tridentate form.

11. The structure of claim 7, wherein the structure comprises the αvβ6 integrin ligand in tetradentate form.

12. The structure of claim 7, wherein the structure has the formula:

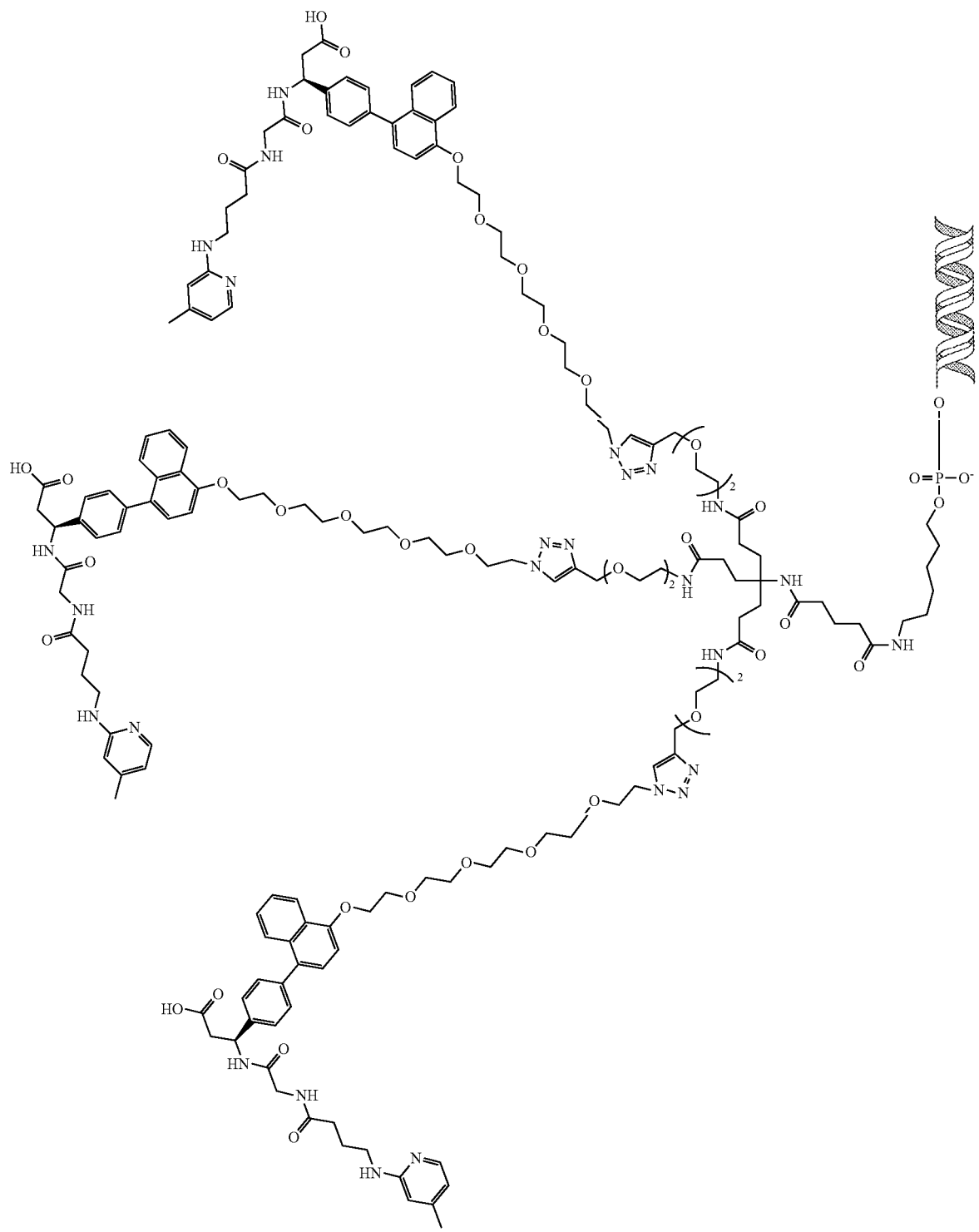

(Structure 701c), and wherein ⁓⁓⁓ represents an RNAi agent.

13. A composition comprising the αvβ6 integrin ligand of claim 1, and a pharmaceutically acceptable excipient.

14. The composition of claim 13, wherein the αvβ6 integrin ligand is conjugated to an oligonucleotide-based compound that is capable of inhibiting the expression of a target gene in an epithelial cell.

15. The composition of claim 13, wherein the αvβ6 integrin ligand is conjugated to an RNAi agent that is capable of inhibiting the expression of a target gene in an epithelial cell.

16. The composition of claim 13, wherein the αvβ6 integrin ligand is conjugated to an RNAi agent that is capable of inhibiting the expression of a target gene in a bronchiolar epithelial cell.

17. A method of delivering one or more cargo molecules to a cell, the method comprising administering to the cell an αvβ6 integrin ligand of claim 1.

18. A method of delivering one or more cargo molecules to a cell or tissue of a subject in vivo, the method comprising administering to the subject a composition of claim 13.

19. The method of claim 18, wherein the cell is selected from the group consisting of: type I and II alveolar epithelial cell, goblet cell, secretory epithelial cell, ciliated epithelial cell, corneal and conjunctival epithelial cell, dermal epithelial cell, cholangiocyte, enterocyte, ductal epithelial cell, glandular epithelial cell, and epithelial tumors (carcinomas).

20. The method of claim 18, wherein the one or more cargo molecules comprises an oligonucleotide-based compound.

21. The method of claim 20, wherein the oligonucleotide-based compound is an RNAi agent.

22. A method of inhibiting the expression of a target gene in a cell in vivo, the method comprising administering to the subject an effective amount of a composition that includes an oligonucleotide-based compound conjugated to an αvβ6 integrin ligand of claim claim 1.

23. The method of claim 22, wherein the cell is selected from the group consisting of: type I and II alveolar epithelial cell, goblet cell, secretory epithelial cell, ciliated epithelial cell, corneal and conjunctival epithelial cell, dermal epithelial cell, cholangiocyte, enterocyte, ductal epithelial cell, glandular epithelial cell, and epithelial tumors (carcinomas).

24. The method of claim 22 wherein the oligonucleotide-based compound is an RNAi agent.

* * * * *

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1
gcugugcaac cagaacaaau a                                              21

<210> SEQ ID NO 2
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 2
uauuuguucu gguugcacag c                                              21

<210> SEQ ID NO 3
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 3
ccugugcaac cagaacaaau a                                              21

<210> SEQ ID NO 4
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 4
uauuuguucu gguugcacag g                                              21
```